(12) United States Patent
Greenhalgh et al.

(10) Patent No.: US 12,245,953 B2
(45) Date of Patent: *Mar. 11, 2025

(54) BONE GRAFT DELIVERY SYSTEM AND METHOD FOR USING SAME

(71) Applicant: SurGenTec, LLC, Boca Raton, FL (US)

(72) Inventors: Travis Greenhalgh, Boca Raton, FL (US); Andrew Shoup, Boca Raton, FL (US); John Souza, Monroe, NC (US); Bryan Hellriegel, Boynton Beach, FL (US)

(73) Assignee: SurGenTec, LLC, Boca Raton, FL (US)

( * ) Notice: Subject to any disclaimer, the term of this patent is extended or adjusted under 35 U.S.C. 154(b) by 684 days.

This patent is subject to a terminal disclaimer.

(21) Appl. No.: 17/473,591

(22) Filed: Sep. 13, 2021

(65) Prior Publication Data

US 2022/0257387 A1 Aug. 18, 2022

Related U.S. Application Data

(63) Continuation of application No. 16/900,758, filed on Jun. 12, 2020, now Pat. No. 11,116,647, which is a continuation-in-part of application No. 16/384,826, filed on Apr. 15, 2019, now Pat. No. 10,687,828.

(60) Provisional application No. 62/802,624, filed on Feb. 7, 2019, provisional application No. 62/657,631, filed on Apr. 13, 2018.

(51) Int. Cl.
*A61F 2/46* (2006.01)

(52) U.S. Cl.
CPC .......... *A61F 2/4601* (2013.01); *A61F 2/4611* (2013.01)

(58) Field of Classification Search
CPC .............................. A61F 2/4601; A61F 2/4611
See application file for complete search history.

(56) References Cited

U.S. PATENT DOCUMENTS

| | | | |
|---|---|---|---|
| 2,316,095 A | 4/1943 | Mead, Jr. | |
| 4,277,184 A | 7/1981 | Solomon | |
| 4,338,925 A | 7/1982 | Miller | |
| 4,801,263 A | 1/1989 | Clark | |

(Continued)

FOREIGN PATENT DOCUMENTS

| | | |
|---|---|---|
| CA | 2656050 | 2/2015 |
| CH | 708198 A1 | 12/2014 |

(Continued)

OTHER PUBLICATIONS

Berkeley Advanced Biomaterials, Inc., 2014, Cem-Ostetic®, catalog, 3 pp.

(Continued)

*Primary Examiner* — Si Ming Ku
(74) *Attorney, Agent, or Firm* — Knobbe Martens Olson & Bear LLP

(57) ABSTRACT

A bone graft delivery system includes a rasp having an elongate body extending between a proximal end and a distal end, a lumen extending through the elongate body and configured to receive bone graft material, a rasping surface removably couplable to the distal end of the elongate body and configured to decorticate bone material of a patient, and one or more openings configured to deliver bone graft material from the lumen.

14 Claims, 192 Drawing Sheets

(56) References Cited

U.S. PATENT DOCUMENTS

| | | |
|---|---|---|
| 5,531,749 A | 7/1996 | Michelson |
| 5,733,288 A | 3/1998 | Allen |
| 5,861,176 A | 1/1999 | Ducheyne et al. |
| 6,187,047 B1 | 2/2001 | Kwan et al. |
| 6,224,607 B1 | 5/2001 | Michelson |
| 6,331,312 B1 | 12/2001 | Lee et al. |
| 6,439,439 B1 | 8/2002 | Rickard et al. |
| 6,676,664 B1 | 1/2004 | Al-Assir |
| 6,696,073 B2 | 2/2004 | Boyce et al. |
| 6,767,550 B1 | 7/2004 | Génin et al. |
| 6,793,660 B2 | 9/2004 | Kerr et al. |
| 6,814,736 B2 | 11/2004 | Reiley et al. |
| 7,141,054 B2 | 11/2006 | Vandewalle |
| 7,150,879 B1 | 12/2006 | Lee et al. |
| 7,214,635 B2 | 5/2007 | Gonda et al. |
| 7,306,603 B2 | 12/2007 | Boehm, Jr. et al. |
| 7,513,901 B2 | 4/2009 | Scifert et al. |
| 7,517,539 B1 | 4/2009 | Lee et al. |
| 7,718,616 B2 | 5/2010 | Thorne |
| 7,799,033 B2 | 9/2010 | Assell et al. |
| 7,811,291 B2 | 10/2010 | Liu et al. |
| 7,887,543 B2 | 2/2011 | Sand et al. |
| 7,909,833 B2 | 3/2011 | Voellmicke |
| 7,964,206 B2 | 6/2011 | Suokas et al. |
| 8,109,961 B2 | 2/2012 | Deshmukh |
| 8,287,915 B2 | 10/2012 | Clineff et al. |
| 8,303,967 B2 | 11/2012 | Clineff et al. |
| 8,308,805 B2 | 11/2012 | Lynn et al. |
| 8,460,686 B2 | 6/2013 | Clineff et al. |
| 8,551,525 B2 | 10/2013 | Cook et al. |
| 8,613,938 B2 | 12/2013 | Akella et al. |
| 8,623,089 B2 | 1/2014 | Sharkey et al. |
| 8,628,536 B2 | 1/2014 | Walker et al. |
| 8,696,679 B2 | 4/2014 | Shadduck |
| 8,778,378 B2 | 7/2014 | Clineff et al. |
| 8,932,295 B1 | 1/2015 | Greenhalgh |
| 8,945,137 B1 | 2/2015 | Greenhalgh et al. |
| 9,005,286 B2 | 4/2015 | Giorno |
| 9,119,646 B2 | 9/2015 | Sharkey et al. |
| 9,138,187 B2 | 9/2015 | Sharkey et al. |
| 9,173,694 B2 | 11/2015 | Kleiner |
| 9,668,881 B1 | 6/2017 | Greenhalgh et al. |
| 10,123,849 B2 | 11/2018 | Greenhalgh |
| 10,238,507 B2 | 3/2019 | Greenhalgh et al. |
| 10,292,747 B2 | 5/2019 | Greenhalgh et al. |
| 10,405,905 B2 | 9/2019 | Greenhalgh |
| 10,543,105 B2 | 1/2020 | Greenhalgh |
| 10,687,828 B2 | 6/2020 | Greenhalgh et al. |
| 2002/0155167 A1 | 10/2002 | Lee et al. |
| 2003/0049328 A1 | 3/2003 | Dalal et al. |
| 2003/0049329 A1 | 3/2003 | Lee et al. |
| 2003/0055512 A1 | 3/2003 | Genin et al. |
| 2003/0129748 A1 | 7/2003 | Flake et al. |
| 2003/0158602 A1 | 8/2003 | Ting |
| 2003/0216777 A1 | 11/2003 | Tien et al. |
| 2004/0024409 A1 | 2/2004 | Sand et al. |
| 2004/0071668 A1 | 4/2004 | Bays et al. |
| 2004/0133211 A1 | 7/2004 | Raskin et al. |
| 2004/0215201 A1 | 10/2004 | Lieberman |
| 2005/0098915 A1 | 5/2005 | Long et al. |
| 2005/0107800 A1 | 5/2005 | Frankel et al. |
| 2005/0137604 A1 | 6/2005 | Assell et al. |
| 2005/0142164 A1 | 6/2005 | Lindholm et al. |
| 2005/0171549 A1 | 8/2005 | Boehm, Jr. et al. |
| 2005/0203523 A1 | 9/2005 | Wenstrom, Jr. et al. |
| 2006/0025861 A1 | 2/2006 | McKay |
| 2006/0293687 A1 | 12/2006 | Bogert |
| 2007/0005072 A1 | 1/2007 | Castillo et al. |
| 2007/0016163 A1 | 1/2007 | Santini et al. |
| 2007/0026030 A1 | 2/2007 | Gill et al. |
| 2007/0026069 A1 | 2/2007 | Shastri et al. |
| 2007/0040478 A1 | 2/2007 | Tofail et al. |
| 2007/0043376 A1 | 2/2007 | Leatherbury et al. |
| 2007/0190102 A1 | 8/2007 | Luo |
| 2007/0224245 A1 | 9/2007 | Ameer et al. |
| 2007/0233131 A1 | 10/2007 | Song |
| 2007/0276397 A1 | 11/2007 | Pacheco |
| 2007/0289998 A1 | 12/2007 | Keller |
| 2008/0033572 A1 | 2/2008 | D'Antonio et al. |
| 2008/0065082 A1 | 3/2008 | Chang et al. |
| 2008/0071284 A1 | 3/2008 | Lechmann |
| 2008/0125856 A1 | 5/2008 | Perez-Cruet et al. |
| 2008/0300684 A1 | 12/2008 | Shelokov |
| 2009/0024174 A1* | 1/2009 | Stark .................. A61B 17/7055 606/321 |
| 2009/0155332 A1 | 6/2009 | Sherry et al. |
| 2009/0216238 A1 | 8/2009 | Stark |
| 2009/0276056 A1 | 11/2009 | Bose et al. |
| 2009/0317447 A1 | 12/2009 | Hsiao et al. |
| 2009/0318925 A1 | 12/2009 | Campion et al. |
| 2009/0318982 A1 | 12/2009 | Genin et al. |
| 2009/0324683 A1 | 12/2009 | Evans et al. |
| 2009/0325775 A1 | 12/2009 | Yeh |
| 2010/0021518 A1 | 1/2010 | Scifert |
| 2010/0036381 A1 | 2/2010 | Vanleeuwen |
| 2010/0057087 A1 | 3/2010 | Cha |
| 2010/0114317 A1 | 5/2010 | Lambrecht et al. |
| 2010/0121459 A1 | 5/2010 | Garigapati et al. |
| 2010/0174286 A1 | 7/2010 | Truckai et al. |
| 2010/0178278 A1 | 7/2010 | Luo et al. |
| 2010/0179556 A1 | 7/2010 | Scribner |
| 2010/0204702 A1 | 8/2010 | Lechot et al. |
| 2010/0222750 A1 | 9/2010 | Cheng |
| 2010/0226959 A1 | 9/2010 | Mckay |
| 2010/0262146 A1 | 10/2010 | Tulkis |
| 2010/0297082 A1 | 11/2010 | Guelcher et al. |
| 2011/0071527 A1 | 3/2011 | Nelson et al. |
| 2011/0071536 A1 | 3/2011 | Kleiner et al. |
| 2011/0117165 A1 | 5/2011 | Melican et al. |
| 2011/0165199 A1 | 7/2011 | Thorne |
| 2011/0196492 A1 | 8/2011 | Lambrecht et al. |
| 2011/0218513 A1 | 9/2011 | Walker et al. |
| 2011/0237704 A1 | 9/2011 | Guelcher et al. |
| 2011/0243913 A1 | 10/2011 | Antonio |
| 2011/0276147 A1 | 11/2011 | Cook et al. |
| 2011/0280924 A1 | 11/2011 | Lin et al. |
| 2012/0100225 A1 | 4/2012 | McKay |
| 2012/0107383 A1 | 5/2012 | McKay |
| 2012/0253316 A1 | 10/2012 | Oktavec et al. |
| 2013/0131683 A1 | 3/2013 | Shah et al. |
| 2013/0090662 A1 | 4/2013 | Hanson et al. |
| 2013/0122057 A1 | 5/2013 | Garigapati et al. |
| 2013/0236513 A1 | 9/2013 | Guelcher et al. |
| 2013/0282128 A1 | 10/2013 | McKay |
| 2014/0039454 A1 | 2/2014 | Sharkey |
| 2014/0079753 A1 | 3/2014 | Darby et al. |
| 2014/0121781 A1 | 5/2014 | Tunc et al. |
| 2014/0200676 A1 | 7/2014 | Shimko et al. |
| 2014/0248372 A1 | 9/2014 | Boden et al. |
| 2014/0251438 A1 | 9/2014 | Gettings et al. |
| 2014/0252044 A1 | 9/2014 | Greter et al. |
| 2014/0255334 A1 | 9/2014 | Raynor et al. |
| 2014/0271779 A1 | 9/2014 | Bagga et al. |
| 2014/0271785 A1 | 9/2014 | Bagga et al. |
| 2014/0271786 A1 | 9/2014 | Bagga et al. |
| 2014/0271914 A1 | 9/2014 | Wagner |
| 2014/0277569 A1 | 9/2014 | Lange |
| 2014/0358188 A1 | 12/2014 | Larson et al. |
| 2015/0018886 A1 | 1/2015 | Ali |
| 2015/0054195 A1 | 2/2015 | Greyf |
| 2015/0071983 A1 | 3/2015 | Bagga et al. |
| 2015/0079146 A1 | 3/2015 | Pomrink et al. |
| 2015/0105748 A1 | 4/2015 | McBride et al. |
| 2015/0148292 A1 | 5/2015 | Boden et al. |
| 2015/0165092 A1 | 6/2015 | Kaplan et al. |
| 2015/0190148 A1 | 7/2015 | Greenhalgh |
| 2015/0209156 A1 | 7/2015 | Greenhalgh et al. |
| 2015/0283298 A1 | 10/2015 | Kaplan et al. |
| 2015/0283300 A1 | 10/2015 | Pomrink et al. |
| 2016/0296344 A1 | 10/2016 | Greenhalgh |
| 2017/0354514 A1 | 12/2017 | Greenhalgh |
| 2019/0247201 A1 | 8/2019 | Greenhalgh |
| 2020/0046377 A1 | 2/2020 | Woodard |
| 2020/0069352 A1 | 3/2020 | Greenhalgh |

(56) References Cited

U.S. PATENT DOCUMENTS

FOREIGN PATENT DOCUMENTS

| | | |
|---|---|---|
| CN | 1654543 | 8/2005 |
| CN | 101007183 | 8/2007 |
| CN | 101401966 | 4/2009 |
| CN | 101461963 | 6/2009 |
| CN | 101618230 | 1/2010 |
| CN | 104876439 | 9/2015 |
| DE | 10338634 | 3/2005 |
| EP | 0 287 584 | 3/1992 |
| EP | 0 891 421 | 1/1999 |
| EP | 0 741 785 | 11/1999 |
| EP | 1 018 978 | 7/2000 |
| EP | 1 051 205 | 11/2000 |
| EP | 1 121 072 | 8/2001 |
| EP | 1 263 353 | 12/2002 |
| EP | 1 311 656 | 5/2003 |
| EP | 1 233 794 | 9/2003 |
| EP | 1 344 538 | 9/2003 |
| EP | 1 348 453 | 10/2003 |
| EP | 1 359 951 | 11/2003 |
| EP | 1 363 551 | 11/2003 |
| EP | 1 365 792 | 12/2003 |
| EP | 1 377 236 | 1/2004 |
| EP | 1 383 509 | 1/2004 |
| EP | 1 410 810 | 4/2004 |
| EP | 1 140 239 | 7/2004 |
| EP | 0 883 410 | 8/2004 |
| EP | 1 194 518 | 9/2004 |
| EP | 1 464 345 | 10/2004 |
| EP | 1 250 163 | 12/2004 |
| EP | 1 137 448 | 1/2006 |
| EP | 1 085 842 | 3/2006 |
| EP | 1 152 777 | 5/2006 |
| EP | 1 624 904 | 1/2007 |
| EP | 1 094 851 | 2/2007 |
| EP | 1 753 396 | 2/2007 |
| EP | 0 874 601 | 3/2007 |
| EP | 1 778 760 | 5/2007 |
| EP | 1 781 319 | 5/2007 |
| EP | 1 804 814 | 7/2007 |
| EP | 1 824 530 | 8/2007 |
| EP | 1 909 860 | 4/2008 |
| EP | 1 976 459 | 10/2008 |
| EP | 1 981 440 | 10/2008 |
| EP | 1 988 940 | 11/2008 |
| EP | 1 996 114 | 12/2008 |
| EP | 2 007 317 | 12/2008 |
| EP | 2 010 104 | 1/2009 |
| EP | 2 037 973 | 3/2009 |
| EP | 1 210 092 | 4/2009 |
| EP | 2 127 689 | 12/2009 |
| EP | 2 131 851 | 12/2009 |
| EP | 1 399 199 | 2/2010 |
| EP | 2 182 886 | 5/2010 |
| EP | 2 271 378 | 1/2011 |
| EP | 2 272 470 | 1/2011 |
| EP | 1 778 306 | 6/2011 |
| EP | 2 358 408 | 8/2011 |
| EP | 2 448 607 | 5/2012 |
| EP | 2 456 389 | 5/2012 |
| EP | 2 344 081 | 1/2013 |
| EP | 2 542 187 | 1/2013 |
| EP | 2 588 154 | 5/2013 |
| EP | 2 600 912 | 6/2013 |
| EP | 2 585 124 | 1/2014 |
| EP | 2 678 050 | 1/2014 |
| EP | 2 678 052 | 1/2014 |
| EP | 1 677 846 | 8/2014 |
| EP | 2 771 041 | 9/2014 |
| EP | 2 793 915 | 10/2014 |
| EP | 1 945 132 | 12/2014 |
| EP | 2 823 829 | 1/2015 |
| EP | 2 826 495 | 1/2015 |
| EP | 1 528 894 | 6/2015 |
| EP | 2 897 560 | 7/2015 |
| EP | 2 512 537 | 8/2015 |
| EP | 2 903 657 | 8/2015 |
| EP | 2 904 094 | 8/2015 |
| EP | 2 934 394 | 10/2015 |
| EP | 1 986 712 | 12/2015 |
| EP | 1 404 346 | 3/2016 |
| EP | 1 638 621 | 3/2016 |
| EP | 1 148 847 | 7/2016 |
| EP | 2 605 804 | 3/2017 |
| EP | 2 381 970 | 4/2017 |
| GB | 2513599 | 6/2013 |
| IN | 2011DE01996 | 1/2013 |
| KR | 101427305 | 8/2014 |
| WO | WO 98/016267 | 4/1998 |
| WO | WO 00/027316 | 5/2000 |
| WO | WO 10/115138 | 10/2000 |
| WO | WO 05/102281 | 11/2005 |
| WO | WO 07/011172 | 1/2007 |
| WO | WO 08/049242 | 5/2008 |
| WO | WO 08/102985 | 8/2008 |
| WO | WO 09/101228 | 8/2009 |
| WO | WO 11/58443 | 5/2011 |
| WO | WO 11/084731 | 7/2011 |
| WO | WO 12/134540 | 10/2012 |
| WO | WO 14/32099 | 3/2014 |
| WO | WO 14/110284 | 7/2014 |
| WO | WO 14/124496 | 8/2014 |
| WO | WO 14/147622 | 9/2014 |
| WO | WO 14/152113 | 9/2014 |
| WO | WO 14/099967 | 6/2015 |
| WO | WO 15/123733 | 8/2015 |
| WO | WO 15/123734 | 8/2015 |
| WO | WO 15/147834 | 10/2015 |

OTHER PUBLICATIONS

Bioventus Surgical, 2017, OsteoPlus, product brochure, 5 pp.
Globus Medical Allocate product, http://www.globusmedical.com/portfolio/allocate/, 2014, 2 pp.
IFGL Bio Ceramics Ltd, Nov. 20, 2008, Bone regenerative solutions for advanced dental surgeries, 3 pp.
Kumar et al., Jun. 2013, Bone grafts in dentistry, J. Pharm Bioallied Sci, 5(Suppl1):S125-S127.
Maxigen Biotech Inc., 2010, Formagraft® Bone Graft Substitute, product brochure, 1 p.
Medtronic, 2005, Mastergraft®, product brochure, 12 pp.
RTI Surgical, Inc., 2017 NanOss® Loaded Advanced Bone Graft Substitute, product brochure, 3 pp.
Stryker Corporation 1998, Vitoss Bone Graft Substitute, product brochure, 2 pp.
Zimmer Biomet, 2017, CopiOs® Bone Void Filler, product brochure, 7 pp.
TranS1 Pylon, https://vimeo.com/318566244, dated as uploaded Feb. 20, 2019, site visited Feb. 4, 2021.

* cited by examiner

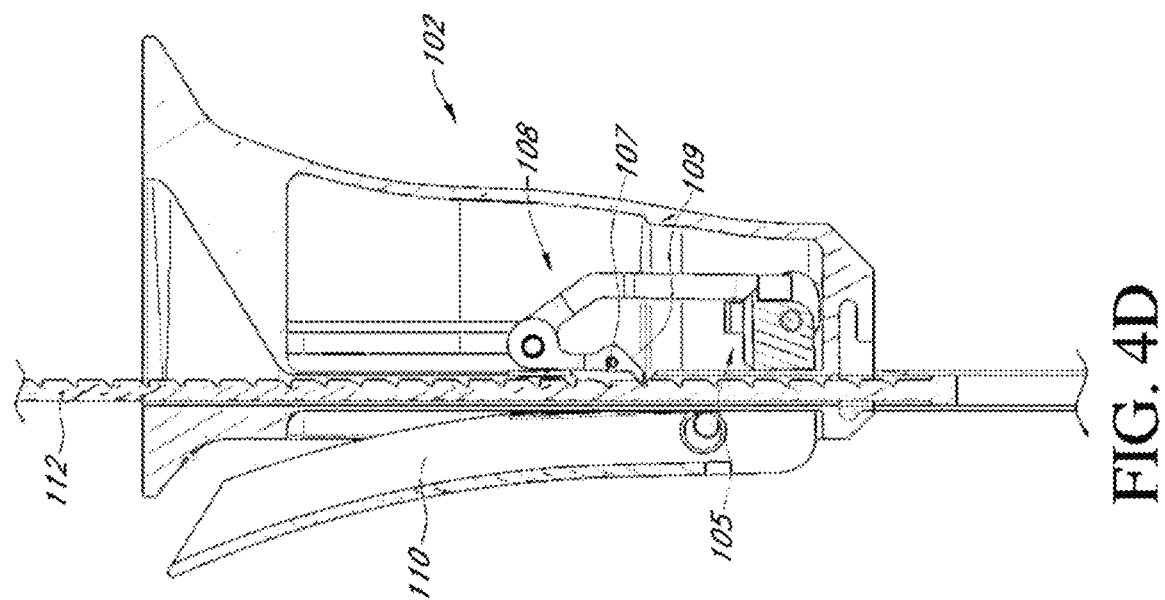

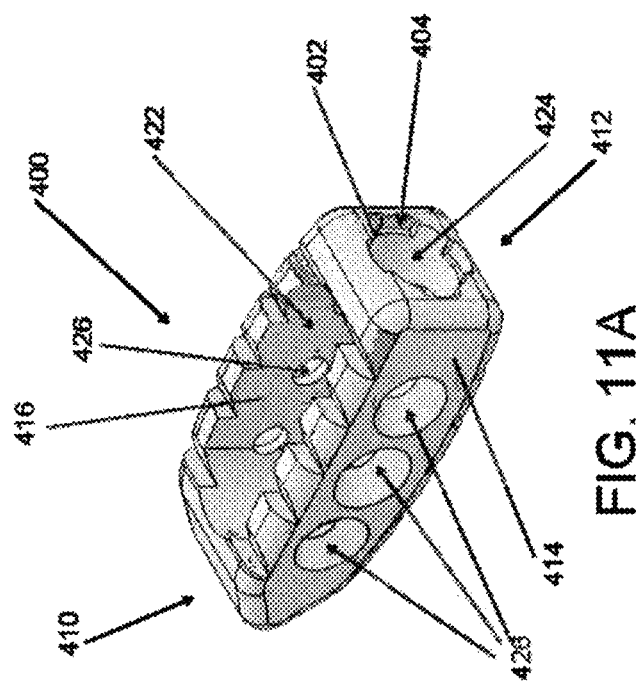
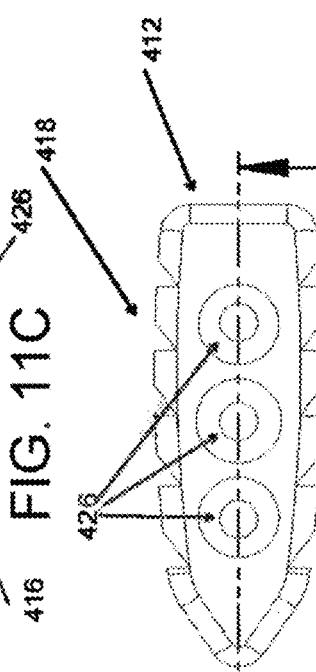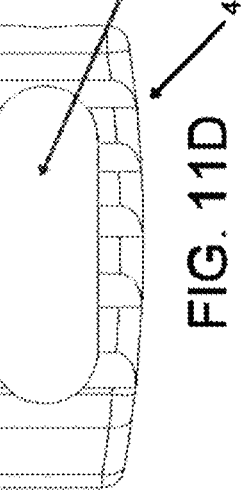

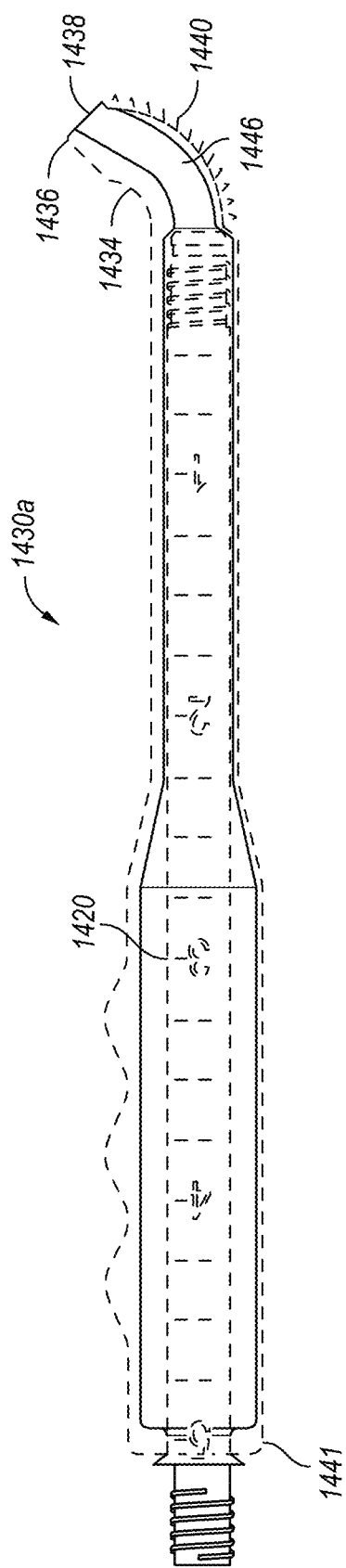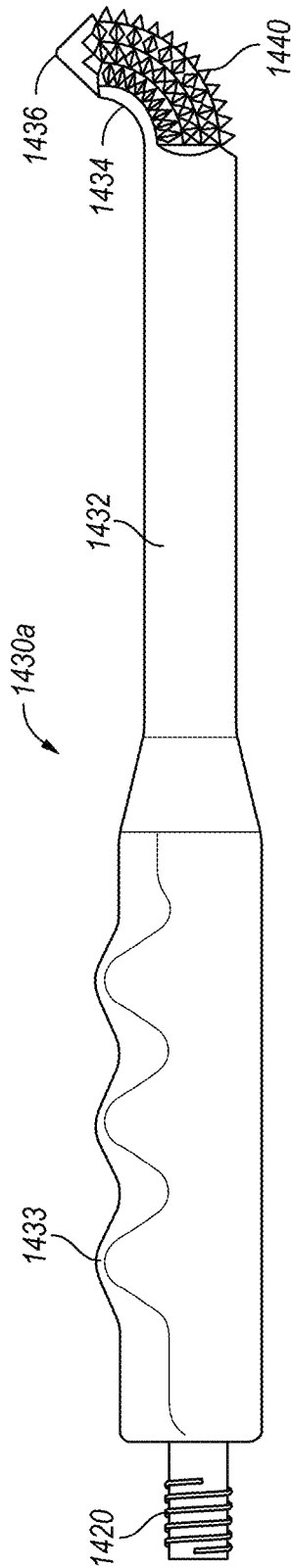
FIG. 29A
FIG. 29B

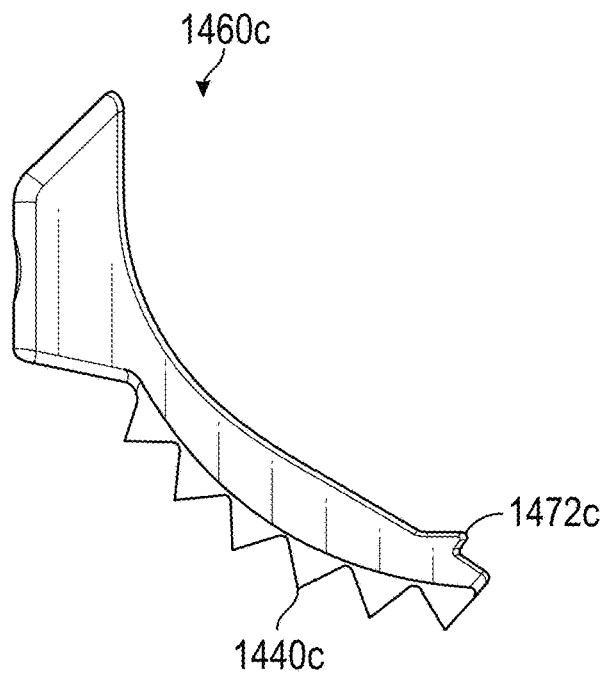
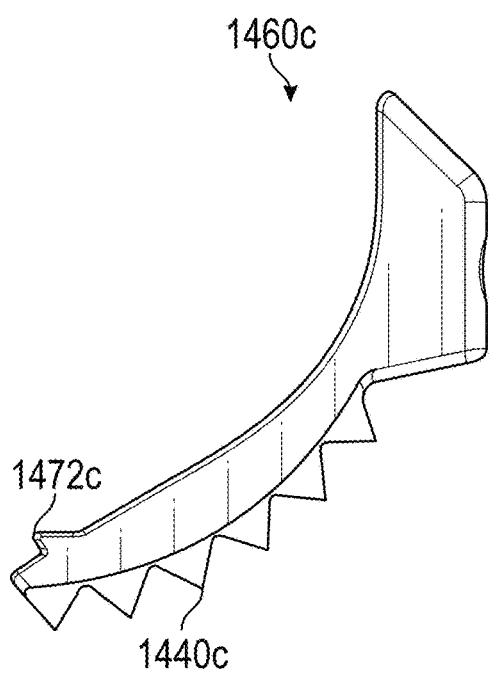
FIG. 54K  FIG. 54L
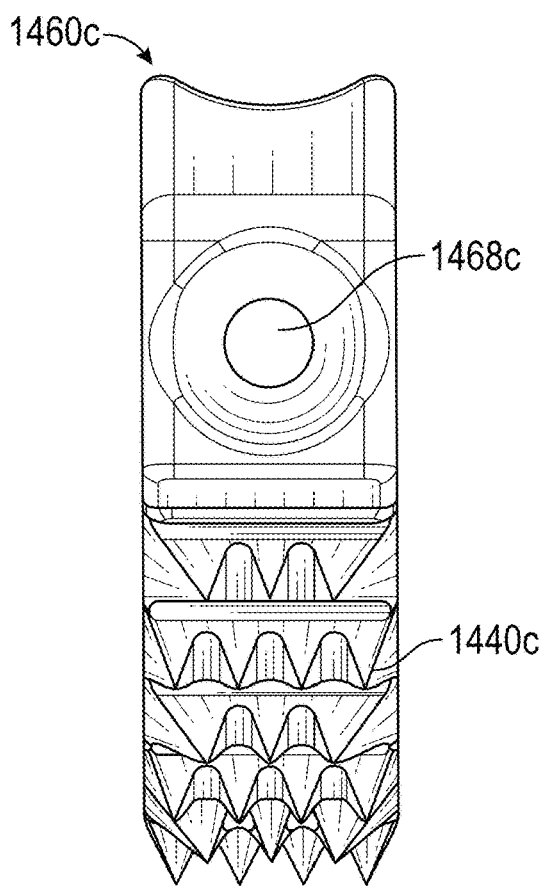
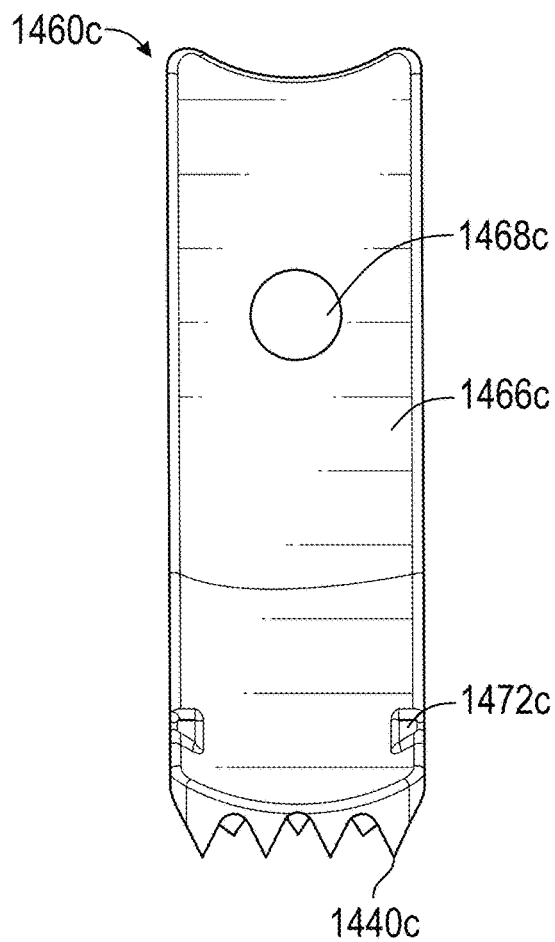
FIG. 54M  FIG. 54N

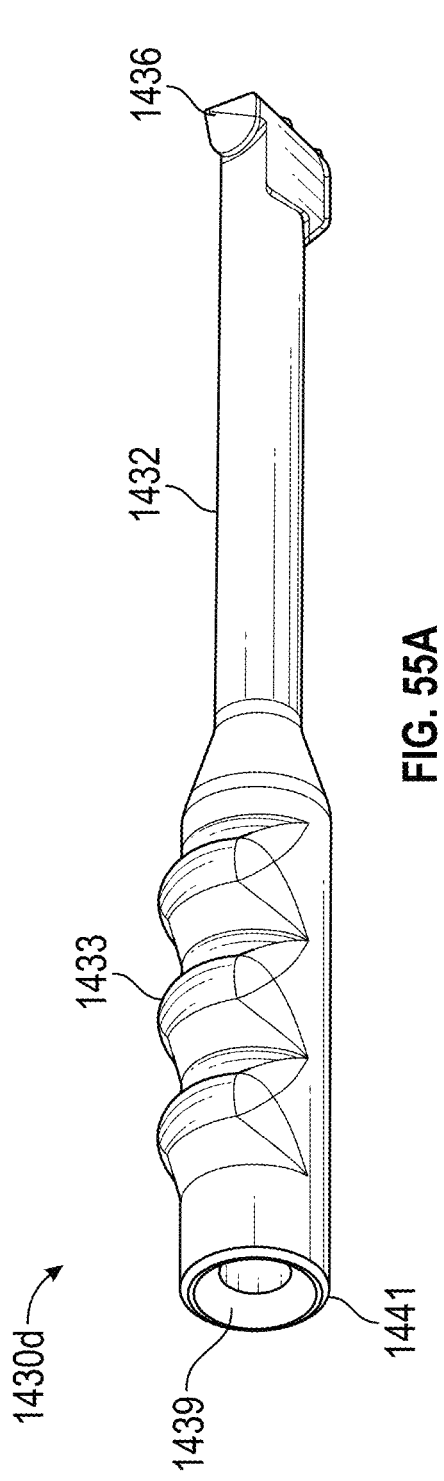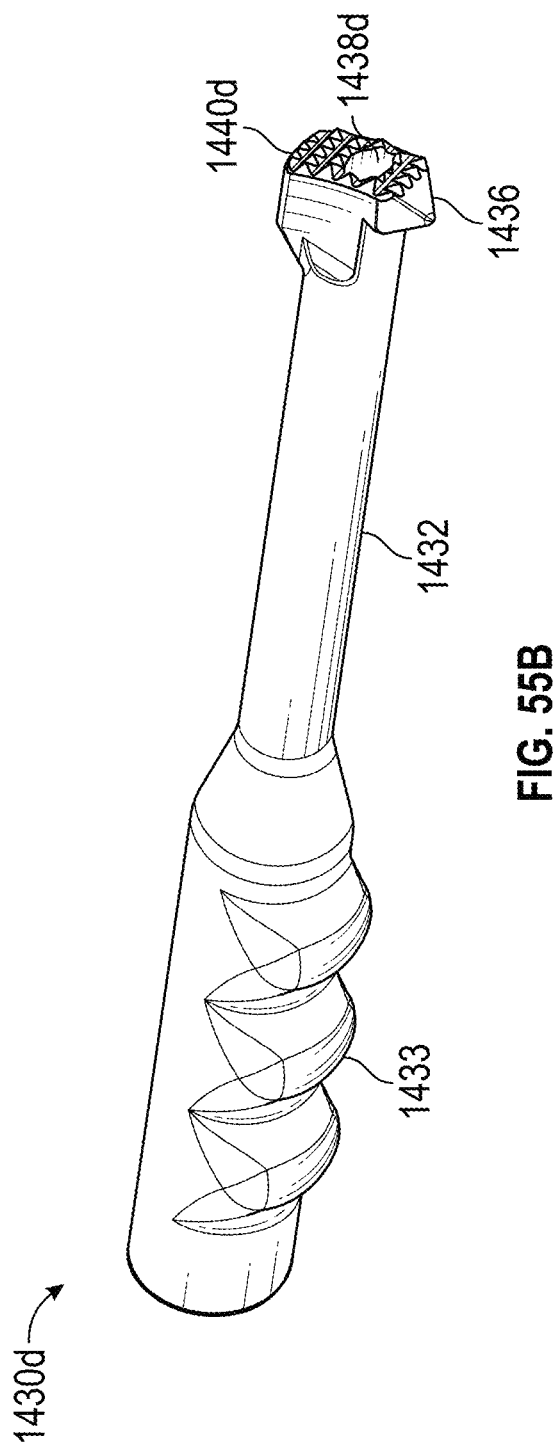
FIG. 55A
FIG. 55B

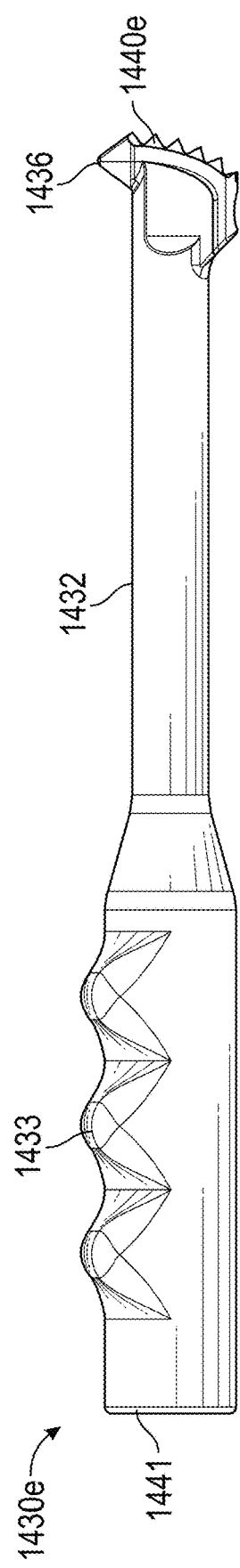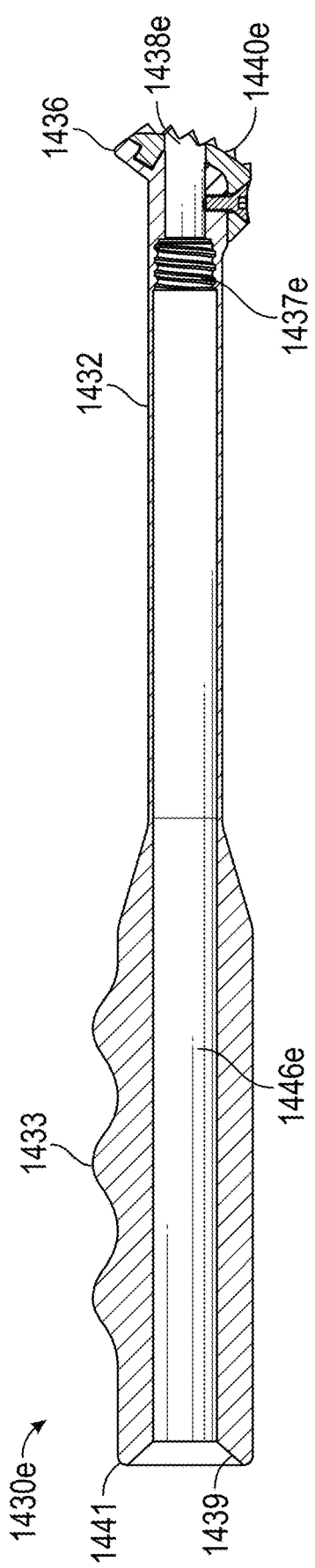

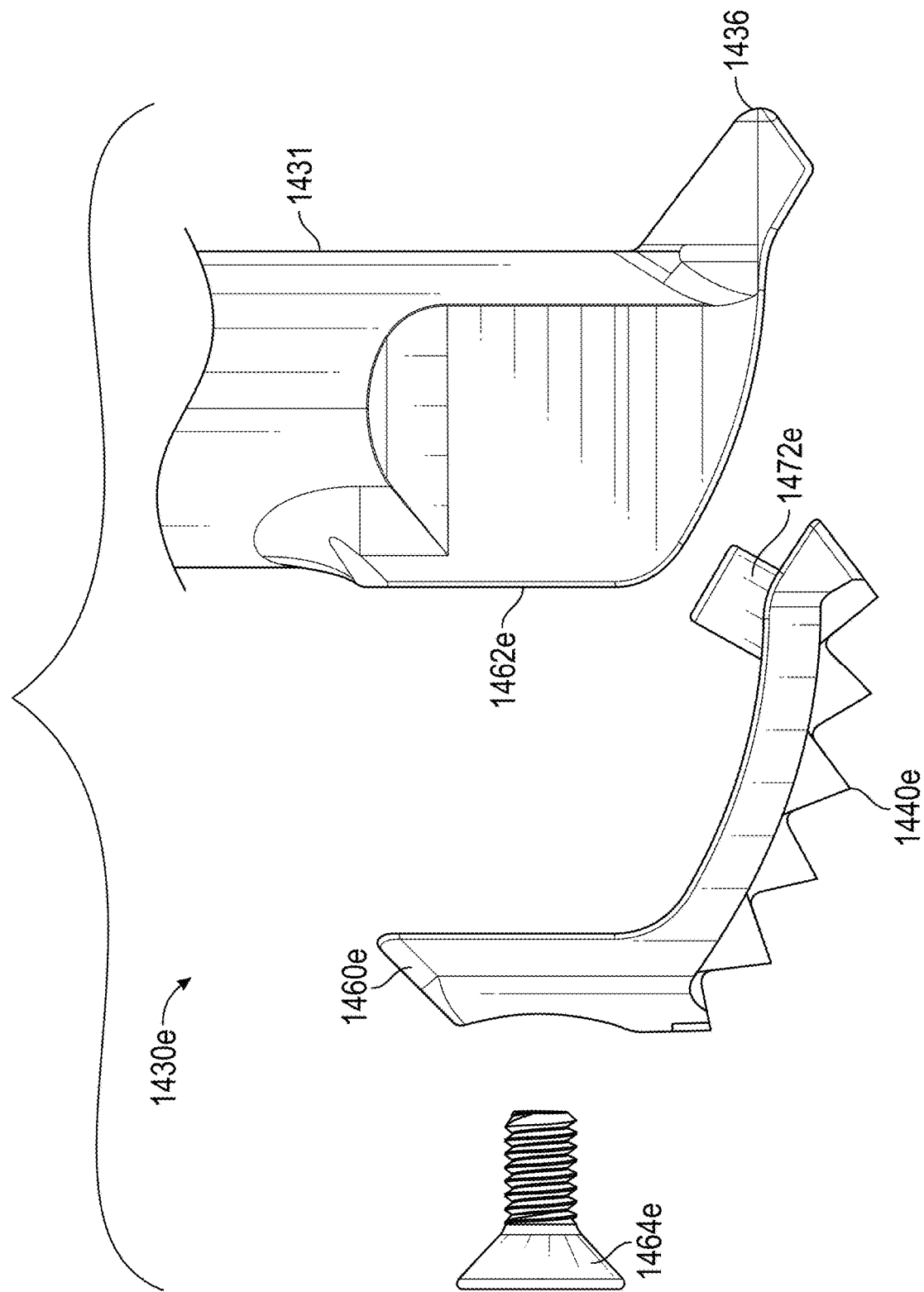

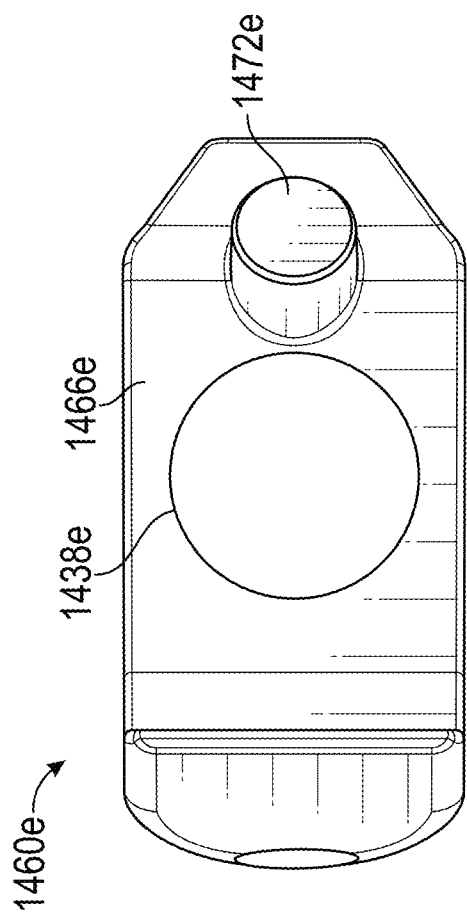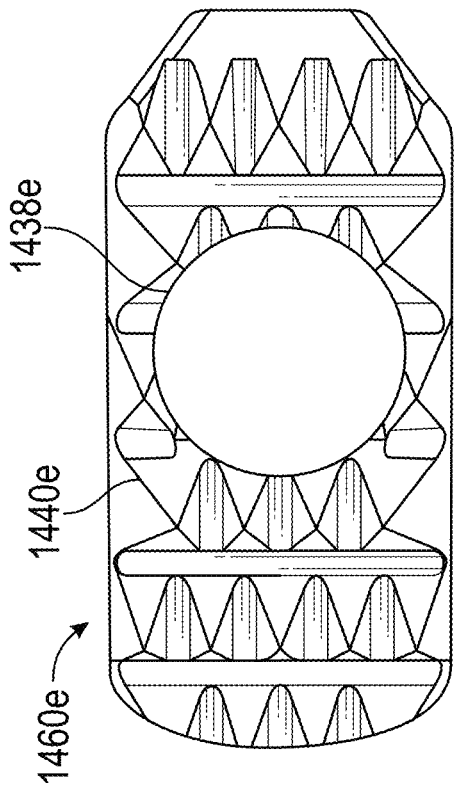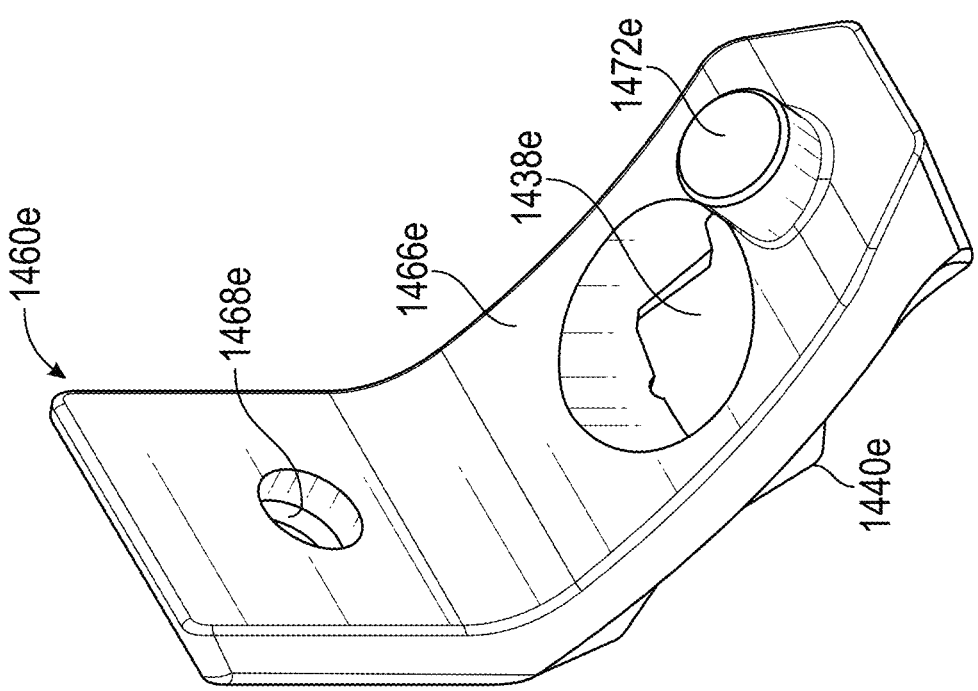
FIG. 56I
FIG. 56J
FIG. 56H

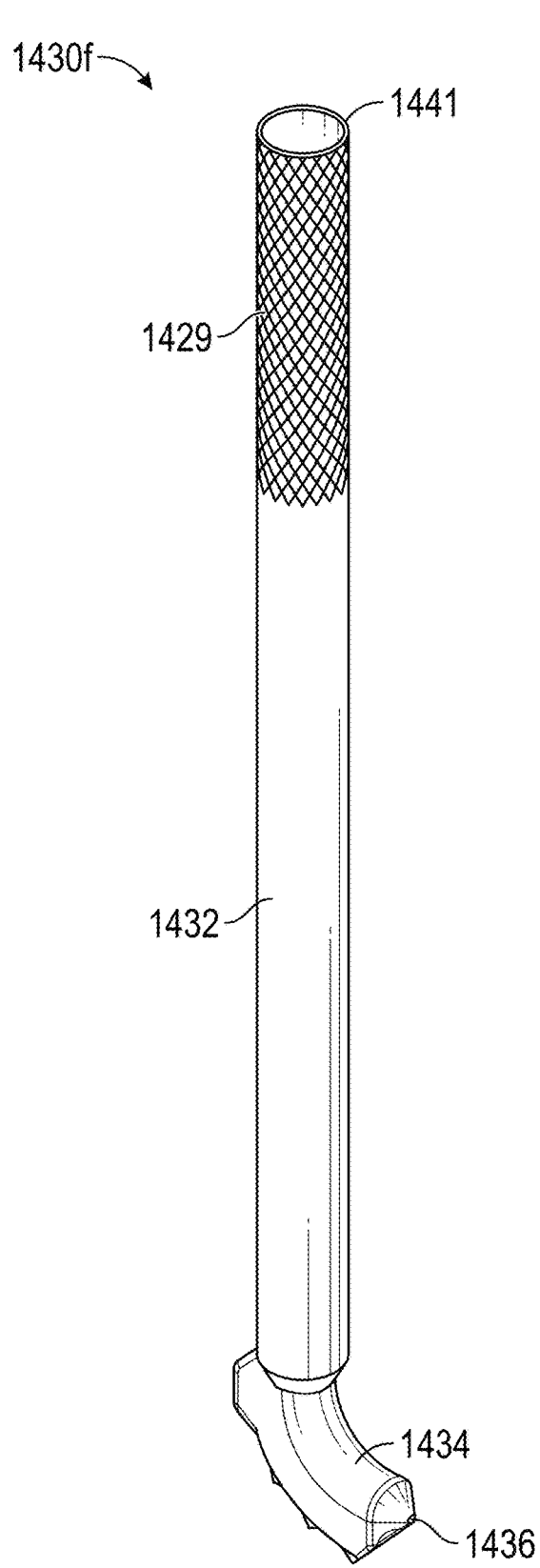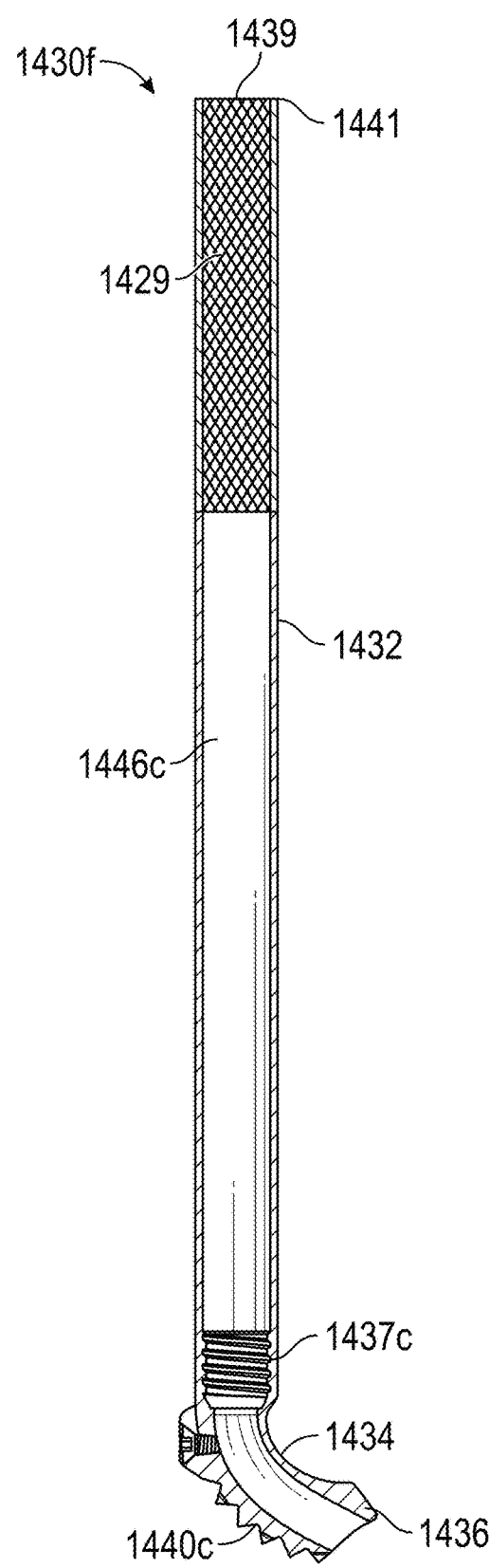
FIG. 58A
FIG. 58B

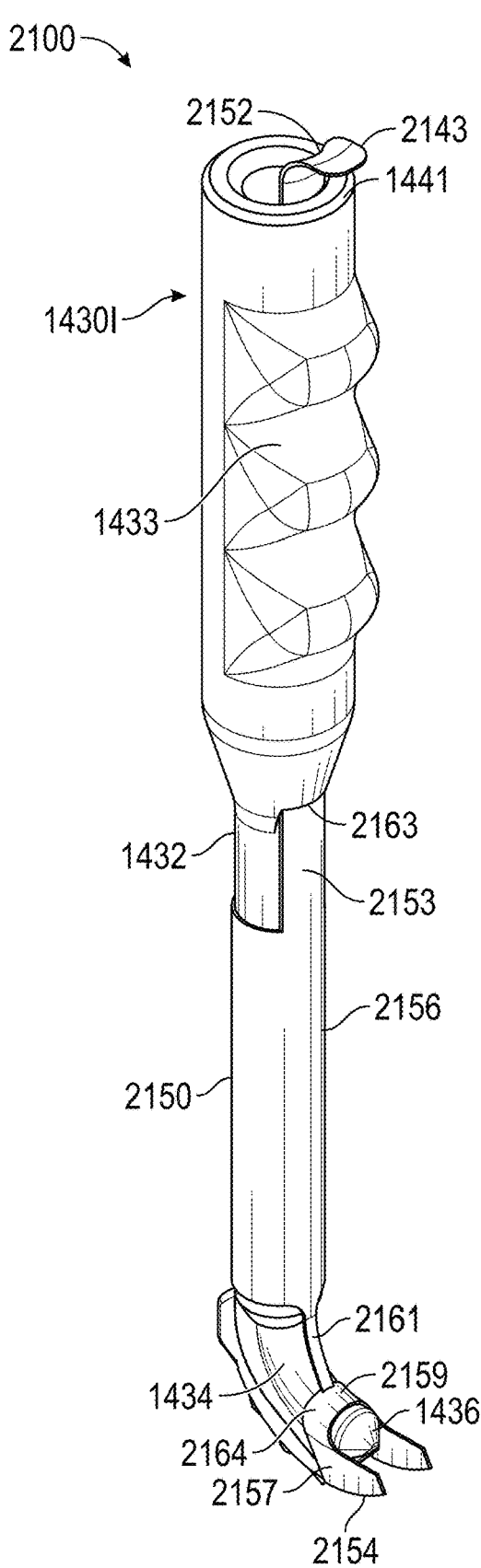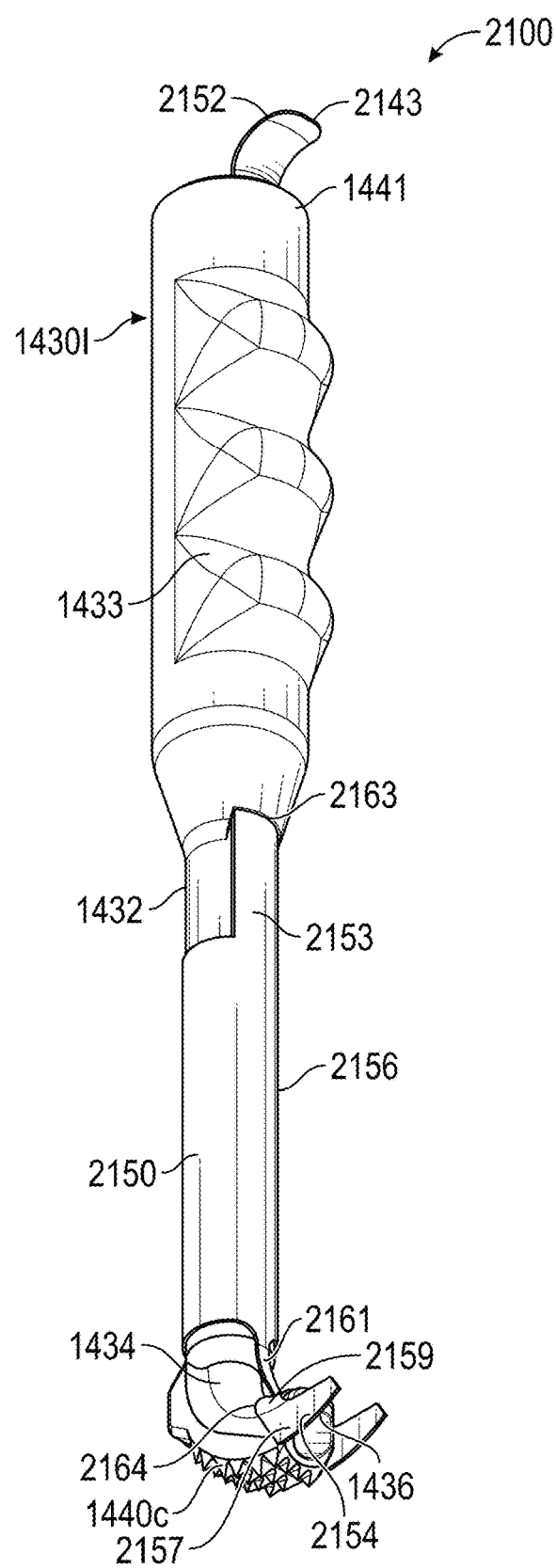
FIG. 68C
FIG. 68D

BONE GRAFT DELIVERY SYSTEM AND METHOD FOR USING SAME

CROSS-REFERENCE TO RELATED APPLICATIONS

The present application is a continuation of U.S. application Ser. No. 16/900,758, entitled "BONE GRAFT DELIVERY SYSTEM AND METHOD FOR USING SAME," filed Jun. 12, 2020, which is a continuation-in-part of U.S. application Ser. No. 16/384,826, entitled "BONE GRAFT DELIVERY SYSTEM AND METHOD FOR USING SAME," filed Apr. 15, 2019, now U.S. Pat. No. 10,687,828, which claims priority benefit of U.S. Provisional application Ser. No. 62/657,631, entitled "BONE GRAFT DELIVERY SYSTEM AND METHOD FOR USING SAME," filed Apr. 13, 2018, and U.S. Provisional application Ser. No. 62/802,624, entitled "BONE GRAFT DELIVERY SYSTEM AND METHOD FOR USING SAME," filed Feb. 7, 2019.

BACKGROUND

Field

The present application relates to orthopedic surgery in general, and more particularly, to bone graft delivery systems and methods.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can also be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein allow for delivery of bone graft material to a desired location in an open, mini-open, or minimally invasive procedure. In some embodiments, the devices, systems, and methods described herein also provide for bone decortication.

In some embodiments, a bone graft delivery system includes an elongated tube, a handle at a proximal end of the tube, and a tip at a distal end of the tube. The handle is configured to be actuated to deliver bone graft material through the tube. The tip includes one or more openings configured to deliver the bone graft material to a desired location and a surface suitable to serve as a rasp for scraping bone.

In some embodiments, the rasping surface of the tip includes jagged edges. The tip can be made of a metal, a radiopaque material, a durable medical plastic, a composite material, or another material or combination of materials. In some embodiments, the tip includes one or more radiopaque markers. The tip can have a sharp or blunt end. The tip can be removably attachable to the distal end of the tube. Alternatively, the tip can be integrally formed or permanently coupled to the distal end of the tube. In some embodiments the tube is rigid. In other embodiments the tube is at least somewhat bendable. In some embodiments the tube is straight, while in other embodiments the tube includes a permanent bend. The handle can include a trigger configured to be actuated to deliver the bone graft material through the tube. In some embodiments, the bone graft delivery system includes an endoscopic camera positioned adjacent the tip.

In some embodiments, a method for delivering bone graft material to a surgical location includes providing a bone graft delivery device and positioning the device adjacent the surgical location. The bone graft delivery device includes an elongate tube and a distal tip. The distal tip includes at least one opening for delivering the bone graft material to the surgical location. The method further includes decorticating bone with the distal tip and delivering bone graft material through the tube and out the at least one opening of the tip.

The bone graft material can be one or more autogenous, allogenic, cadaveric, and/or synthetic materials. In some embodiments, the bone graft delivery device is positioned at the surgical location through a minimally invasive opening in a patient's skin. In some embodiments, the surgical location is a portion of the patient's spine, so the bone graft delivery device is positioned adjacent to the spine and the distal tip decorticates a portion of the spine. In some embodiments, decorticating bone with the distal tip is accomplished by rasping bone with jagged edges of the distal tip. In some embodiments, bone is decorticated with the distal tip by actuating the distal tip with mechanical, battery powered, electric, pneumatic, or other means of force.

In some embodiments, a bone graft delivery system includes an elongate tube and a handle at a proximal end of the tube configured to be actuated to deliver bone graft material through the tube. The tube can be removably coupled to the handle. In some embodiments, a distal end of the tube can be configured to couple to an interbody device disposed within a disc space to deliver bone graft within the interbody device. In some embodiments, the handle includes a trigger configured to be actuated to deliver bone graft material through the tube. In some embodiments, the handle includes a funnel configured to receive bone graft material, a channel in fluid communication with the funnel and the proximal end of the tube, and a ratcheting mechanism configured to advance bone graft material distally through the tube. The bone graft delivery system can further include a plunger configured to be removably received in the channel and tube.

The channel can include a window along at least one side of the channel, and the handle can further include a sheath movably disposed within the channel and configured to selectively cover the window of the channel. The ratcheting mechanism can include a pawl operatively coupled to the trigger, the plunger can include a series of notches, and the pawl can be configured to engage the notches of the plunger through the window of the channel when the plunger is inserted into the channel and the window is at least partially uncovered.

In some embodiments, a bone graft delivery system kit includes a handle, one or more elongate tubes configured to be coupled to the handle, and one or more plungers configured to be removably received in the handle and tube. The kit can further include one or more tips configured to be coupled to a distal end of the tube and having one or more openings configured to deliver bone graft material to a desired location and a surface configured to decorticate bone.

In some embodiments, a method for delivering bone graft material to a surgical location includes providing a bone graft delivery device. The bone graft delivery device can include an elongate tube and a handle at a proximal end of the tube that includes a ratcheting mechanism, a trigger operatively coupled to the ratcheting mechanism, a proximal opening, and a lumen extending between and in fluid communication with the proximal opening and proximal end of the tube. The method further includes loading bone graft material into the bone graft delivery device, for example into the proximal opening, inserting a plunger into the lumen and tube, and manipulating the trigger so that the ratcheting mechanism engages the plunger. In some embodiments, the method further includes coupling a distal end of the elongate tube to an interbody implant positioned within a disc space and delivering bone graft material within the interbody implant.

In some embodiments, an interbody implant includes a leading end, a trailing end, first and second sidewalls extending between the leading end and the trailing end, and a central opening bounded by the leading end, trailing end, and first and second sidewalls. The trailing end includes a hole in fluid communication with the central opening, and a perimeter of the hole includes engagement features configured to mate with corresponding engagement features on a distal end of a tube of a bone graft delivery device. At least one of the first and second sidewalls can include at least one hold in fluid communication with the central opening. A perimeter of the at least one hole can be tapered outwardly from an inner surface to an outer surface of the at least one of the first and second sidewalls.

In some embodiments, a bone graft delivery system kit includes one or more elongate tubes configured to receive a bone graft material, one or more tips configured to couple to a distal end of one of the one or more tubes, and one or more dilators, wherein at least one of the one or more dilators includes a slot extending longitudinally along a body of the dilator.

In some embodiments, a bone graft delivery system kit includes one or more elongate tubes configured to receive a bone graft material, one or more rasps configured to decorticate bone, and one or more dilators, wherein at least one of the one or more dilators includes a slot extending longitudinally along a body of the dilator.

In some embodiments, a bone graft delivery system kit includes one or more elongate tubes configured to receive a bone graft material, one or more rasps configured to decorticate bone, and a bone graft material including demineralized cortical fibers.

In some embodiments, a bone graft delivery system kit includes one or more elongate tubes configured to receive a bone graft material, one or more tips, each tip including at least one opening for the delivery of bone graft material, and a bone graft material including demineralized cortical fibers.

In some embodiments, a bone graft delivery system kit includes one or more elongate tubes configured to receive a bone graft material, one or more plungers configured to be removably received in the one or more elongate tubes, and a bone graft material including demineralized cortical fibers.

In some embodiments, a bone graft delivery system kit includes a handle, one or more elongate tubes configured to be coupled to the handle, and a bone graft material including demineralized cortical fibers.

In some embodiments, a bone graft delivery system includes an elongate tube configured to receive a bone graft material and a rasp. The rasp includes a lumen configured to receive at least a portion of the elongate tube, a rasping surface configured to decorticate bone, one or more openings configured to deliver bone graft material from the elongate tube when the lumen receives at least a portion of the elongate tube, and a handle portion configured to be gripped in use to facilitate movement of the rasping surface to decorticate bone.

In some embodiments, a rasping system includes a rasp and a sheath coupled to the rasp and configured to slide over at least a portion of the rasp. The rasp includes a lumen configured to receive at least a portion of an elongate tube, a rasping surface configured to decorticate bone, one or more openings configured to deliver bone graft material from the elongate tube when the lumen receives at least a portion of the elongate tube, and a handle portion configured to be gripped in use to facilitate movement of the rasping surface to decorticate bone.

In some embodiments, a rasp includes a handle section at a proximal end of the rasp, a connection section distal to the handle section, a lumen extending through the handle section and the connection section configured to receive a bone graft delivery tube, a curved or angled section distal to the connection section, and a tip distal to the curved or angled section. The tip includes a rasping surface and one or more openings configured to deliver bone graft material from the bone graft delivery tube when received within the lumen.

In some embodiments, a guide is provided including one or more features described herein.

In some embodiments, a method of decorticating bone includes using a guide including one or more of the features described herein.

In some embodiments, a method for delivering bone graft material to a surgical location includes using a guide including one or more of the features described herein.

In some embodiments, a bone graft delivery system kit includes one or more of the features described herein.

In some embodiments, a rasping systems includes one or more of the features described herein.

In some embodiments, a rasp includes on or more of the features described herein.

In some embodiments, a method of decorticating bone includes using a rasp including one or more of the features described herein.

In some embodiments, a method of decorticating bone includes using a sheath including one or more of the features described herein.

In some embodiments, a method of decorticating bone includes using a rasping system including one or more of the features described herein.

In some embodiments, a method of delivering bone graft material includes using a rasp including one or more of the features described herein.

In some embodiments, a method of delivering bone graft material includes using a sheath including one or more of the features described herein.

In some embodiments, a method of delivering bone graft material includes using a rasping system including one or more of the features described herein.

In some embodiments, a bone graft delivery system is provided. The bone graft delivery system includes a rasp having an elongate body extending between a proximal end and a distal end, a lumen extending through the elongate body and configured to receive bone graft material, a rasping surface removably couplable to the distal end of the elongate body and configured to decorticate bone material of a patient, and one or more openings configured to deliver bone graft material from the lumen.

The lumen can extend along a straight axis between the proximal end and distal end of the elongate body. The system can further include a pusher having a shaft, the shaft having sufficient flexibility to extend through a curved portion of the elongate body. The elongate body can a curved portion, wherein the rasping surface is removably couplable to the curved portion. The rasping surface can be positioned on a cover having one or more prongs configured to be received in one or more recesses of the elongate body. The rasping surface can include a cover having one or more plugs configured to be received in one or more recesses of the elongate body. The system can further include a fastener configured to couple the rasping surface to the elongate body. The rasping surface can include a plurality of teeth arranged in a plurality of rows, wherein at least one row of the plurality of rows is offset from another row of the plurality of rows. The elongate body can include a threaded section configured to removably secure a corresponding threaded section of an elongate tube received within the lumen.

In some embodiments, a method for decorticating bone is provided. The method includes inserting a rasp into an incision, the rasp including an elongate body extending between a proximal end and a distal end, the elongate body including a curved portion, and a rasping surface positioned on the curved portion of the elongate body and configured to decorticate bone material of a patient. The method includes advancing the rasp through the incision to a first transverse process, decorticating the first transverse process using the rasp, advancing the rasp to a second transverse process using the incision, and decorticating the second transverse process using the rasp.

The method can include delivering bone graft material to one or both of the first transverse process and the second transverse process using the rasp. Delivering the bone graft material can include advancing a flexible portion of a pusher through the curved portion of the elongate body to advance the bone graft material through the curved portion of the elongate body. The rasping surface can be removably couplable to the elongate body. The rasping surface can be curved. The elongate body can include a straight portion extending between the proximal end and the curved portion, wherein the curved portion extends laterally relative to the straight portion beyond a diameter of the straight portion.

In some embodiments, a method for bone graft delivery is provided. The method includes making an incision, inserting an implant through the incision, advancing the implant through the incision to a facet joint, implanting the implant within the facet joint, inserting a rasp through the incision, advancing the rasp to a surgical location, and delivering bone graft material through the rasp to the surgical location.

The method can include decorticating bone using the rasp. Advancing the implant through the incision to the facet joint can include advancing the implant using an inserter coupled to the implant, the method further including delivering bone graft material to a channel within the implant through a lumen of the inserter. The implant can include an intrafacet screw comprising a head and a shank, the method further including countersinking the intrafacet screw within the facet joint. The surgical location can be a facet or a transverse process.

In some embodiments, a bone graft delivery system is provided. The system includes a funnel configured to receive a bone graft material and rasp. The rasp includes an elongate body extending between a proximal end and a distal end, a lumen extending through the elongate body and configured to receive at least a portion of the funnel, a rasping surface positioned at the distal end of the elongate body and configured to decorticate bone material of a patient, one or more openings configured to deliver bone graft material from lumen when the lumen receives bone graft material from the funnel, and a handle portion positioned at a proximal section of the elongate body and configured to be gripped in use to facilitate movement of the rasping surface to decorticate bone.

BRIEF DESCRIPTION OF THE DRAWINGS

FIGS. 4A-4E are section views illustrating operation of an example embodiment of a ratcheting mechanism in a handle of a bone graft delivery device;

FIG. 4O illustrates an exploded view of the bone graft delivery device of FIG. 4N;

FIG. 11A illustrates a perspective view of an example embodiment of an interbody device configured to be coupled to a bone graft delivery device;

FIG. 11B illustrates a side view of the interbody device of FIG. 11A;

FIG. 11C illustrates a section view of the interbody device of FIGS. 11A-11B taken along line 11C-11C in FIG. 11B;

FIG. 11D illustrates a top view of the interbody device of FIGS. 11A-11C;

FIG. 29A illustrates a side view of an embodiment of a tube and the rasp of FIG. 27A in which the rasp is shown as transparent.

FIG. 29B illustrates a side view of the tube and rasp of FIG. 29A.

FIG. 41A illustrates an example of bone graft material.

FIG. 41B illustrates an example of bone graft material.

FIG. 42A illustrates a perspective view of an embodiment of a bone graft delivery system.

FIG. 42B illustrates a front view of the bone graft delivery system of FIG. 42A.

FIG. 42C illustrates a front view of the bone graft delivery system of FIG. 42A.

FIG. 43A illustrates a perspective view of an embodiment of an applicator system of a bone graft delivery system.

FIG. 43B illustrates a perspective view of the applicator system of FIG. 43A.

FIG. 43C illustrates a bottom view of the applicator system of FIG. 43A.

FIG. 43D illustrates a top view of the applicator system of FIG. 43A

FIG. 43E illustrates a rear view of the applicator system of FIG. 43A.

FIG. 43F illustrates a front view of the applicator system of FIG. 43A.

FIG. 43G illustrates an exploded view of the applicator system of FIG. 43A.

Figure 43A:
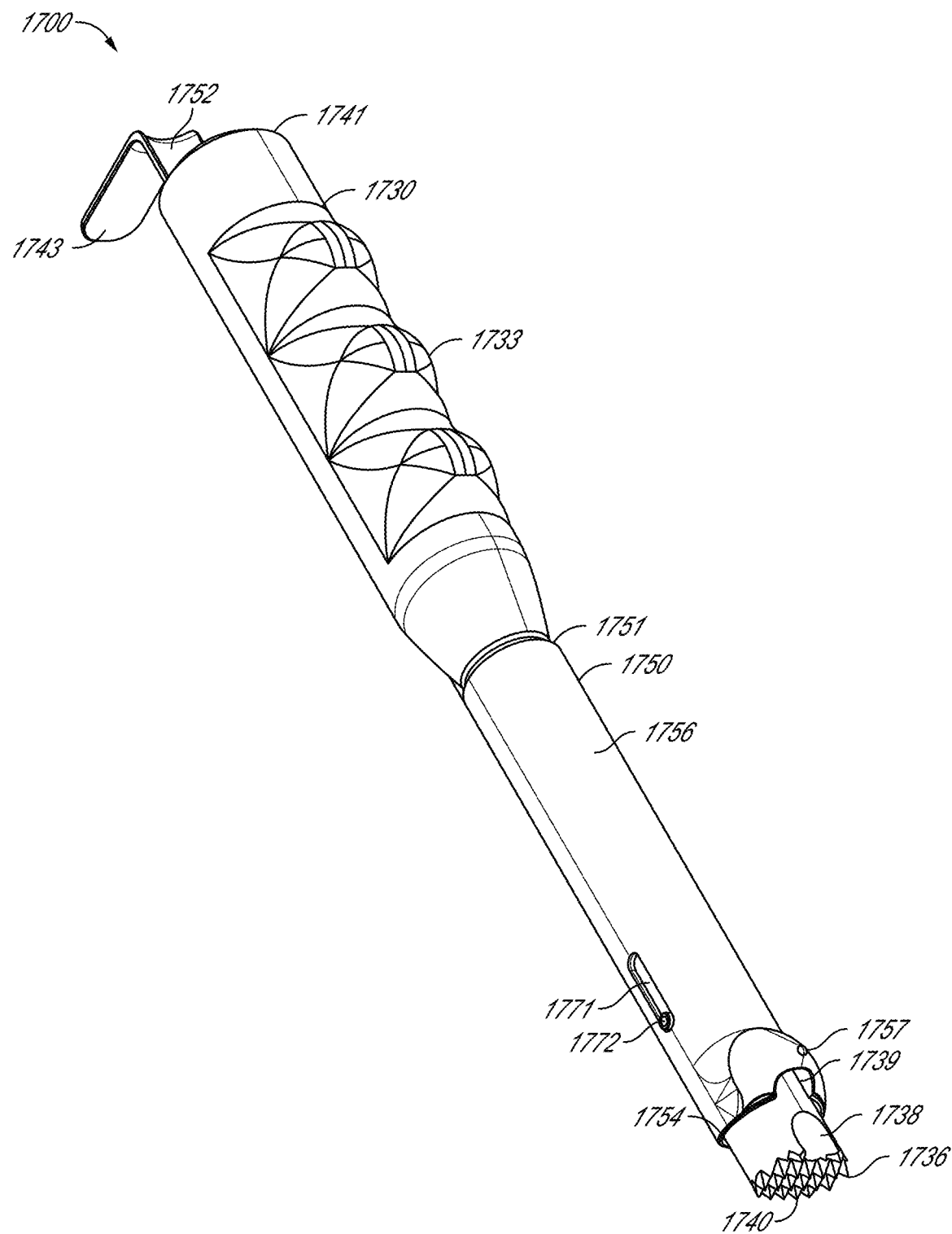
Figure 44A:
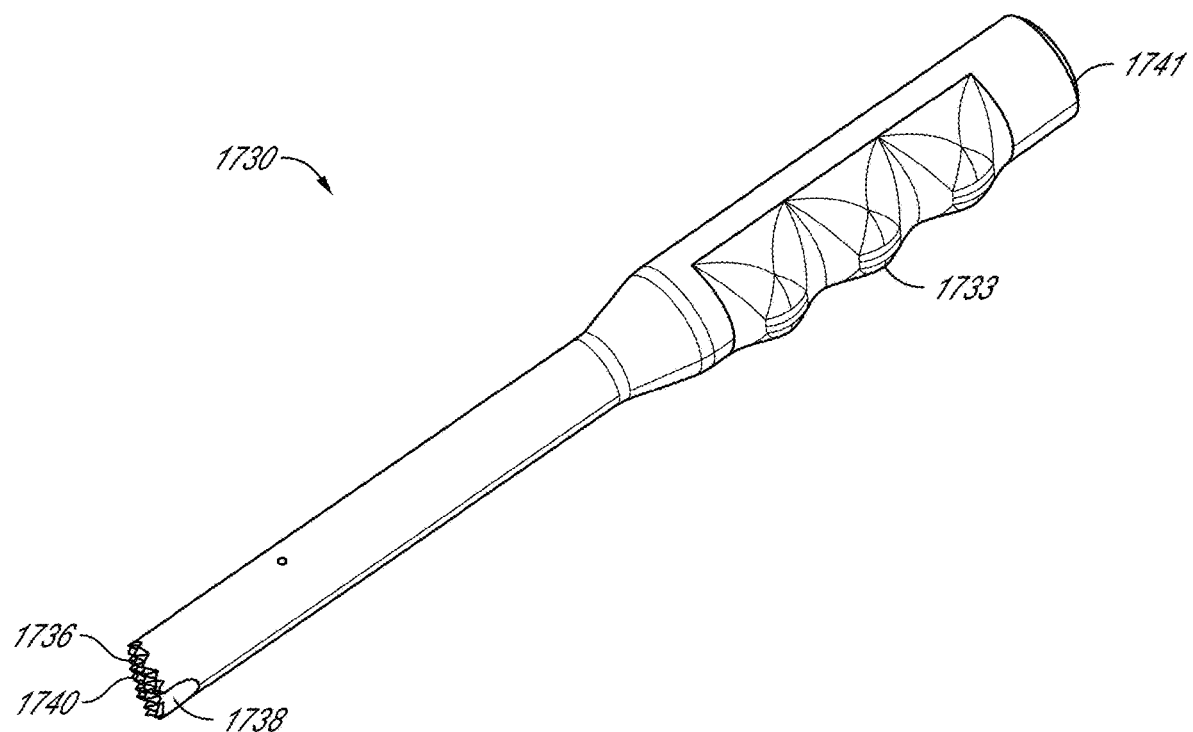

FIG. 44A illustrates a perspective view of an applicator of the applicator system of FIG. 43A.

Figure 44B:
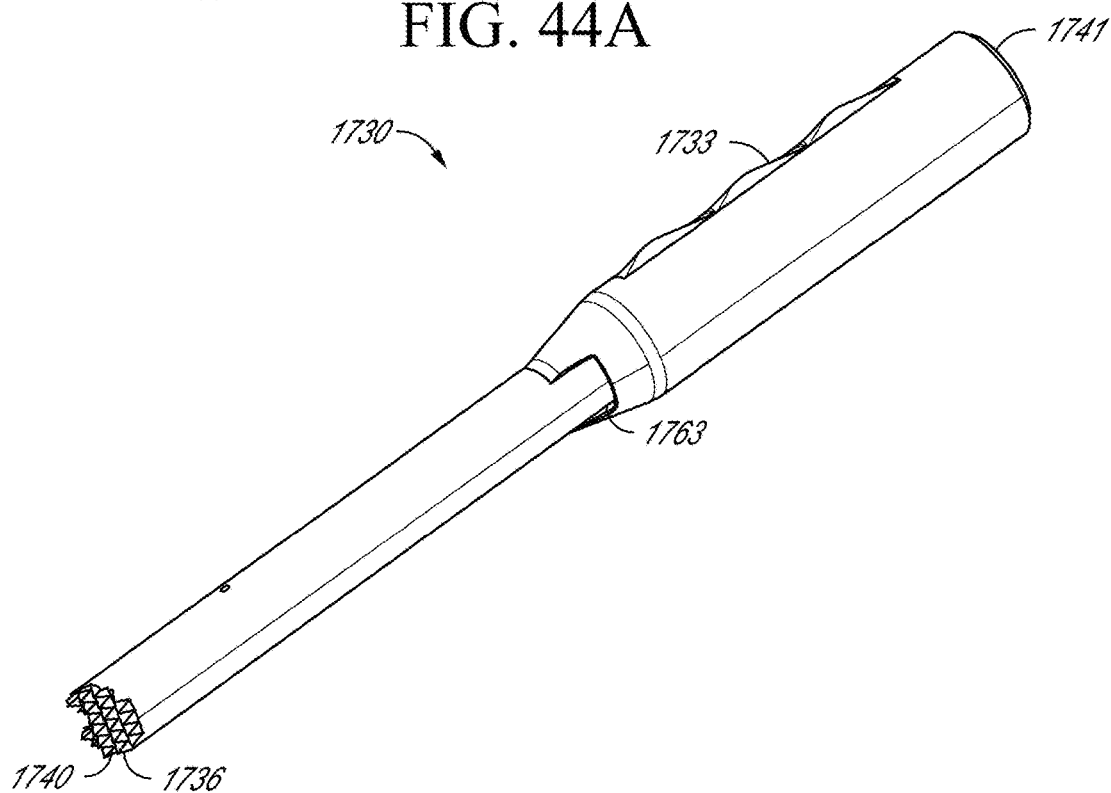

FIG. 44B illustrates a perspective view of the applicator of FIG. 44A.

Figure 45A:
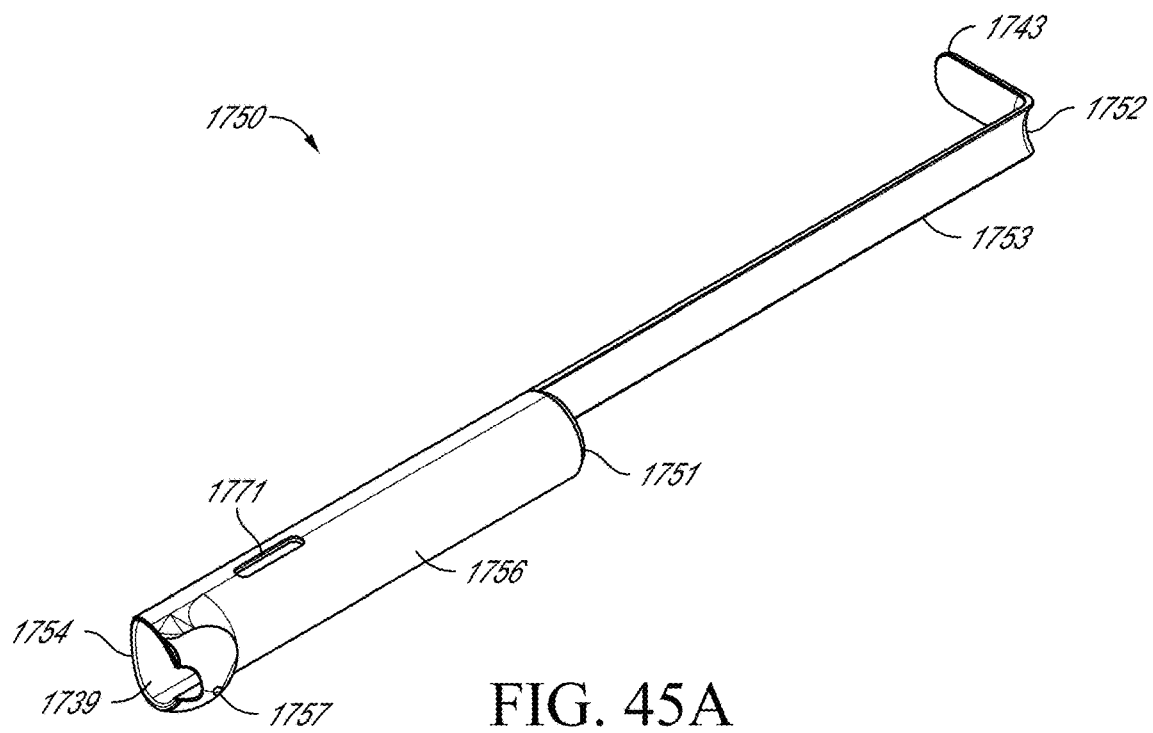

FIG. 45A illustrates a perspective view of a guide of the applicator system of FIG. 44A.

Figure 45B:
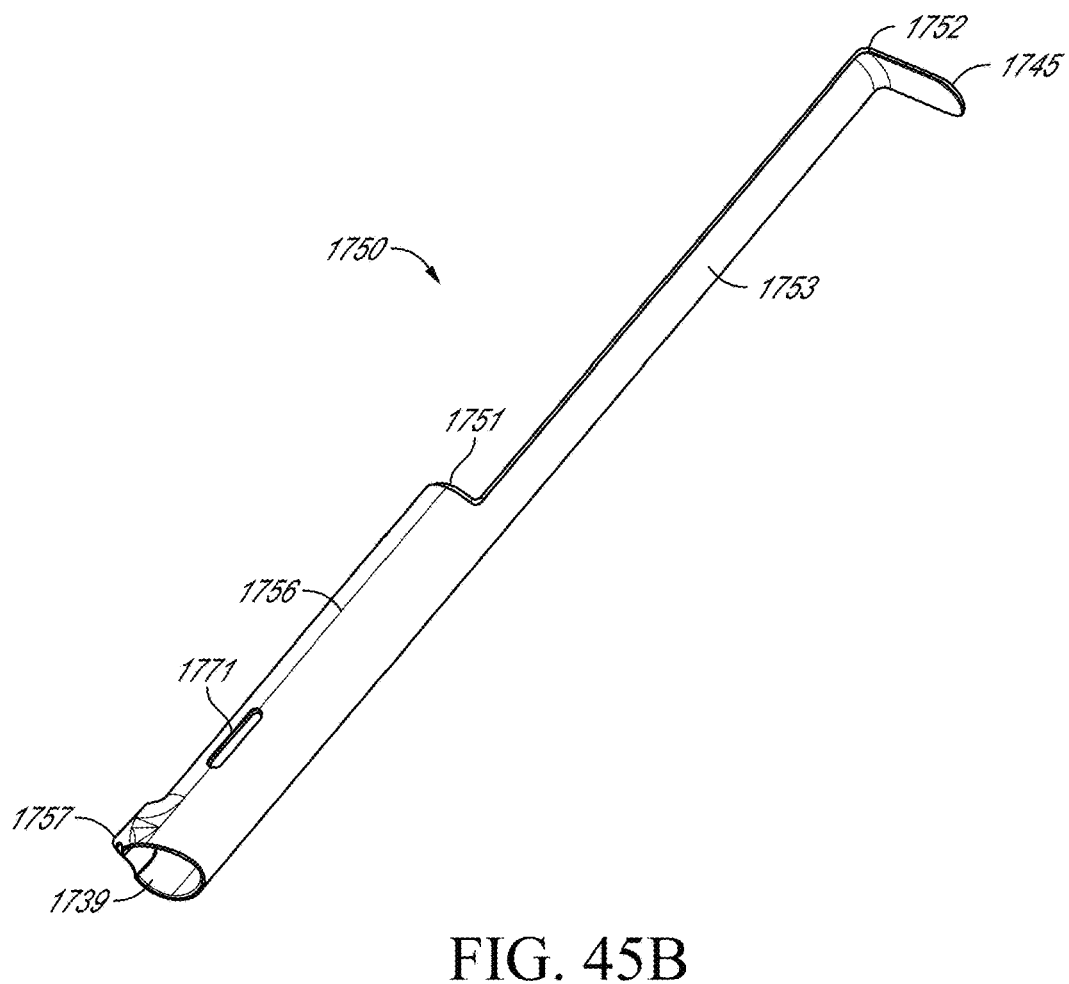

FIG. 45B illustrates a perspective view of the guide of FIG. 45A.

Figure 46:
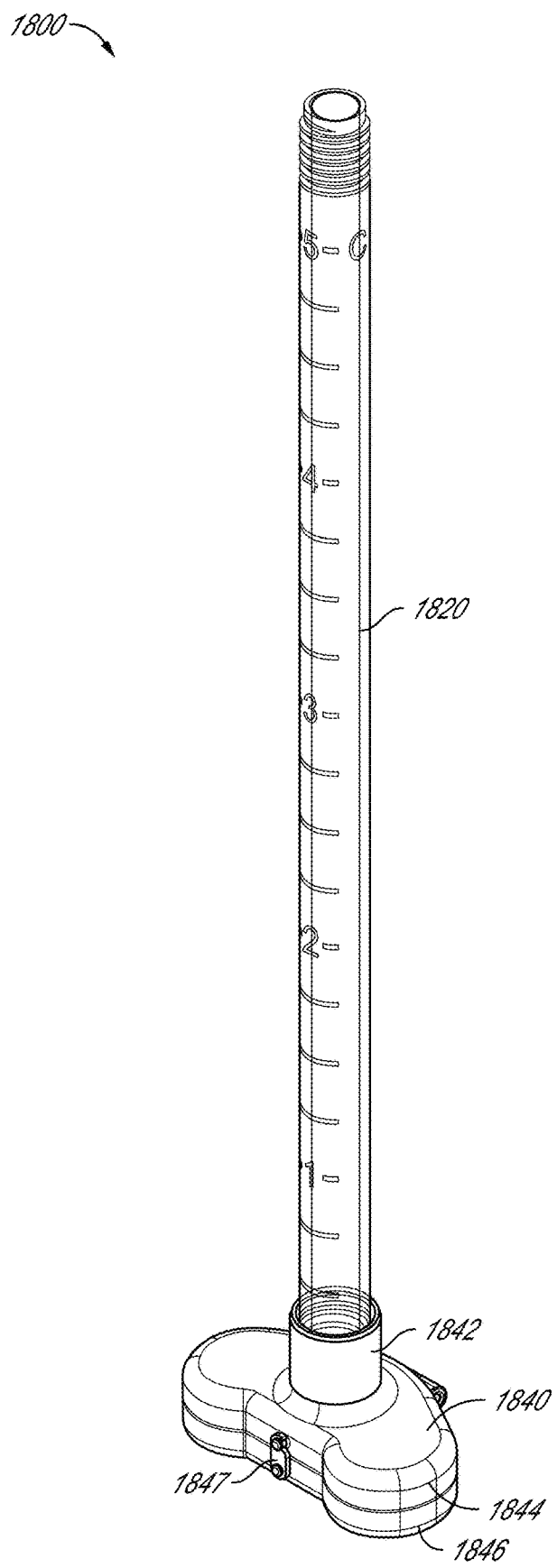

FIG. 46 illustrates a perspective view of an embodiment of a filling system.

Figure 47:
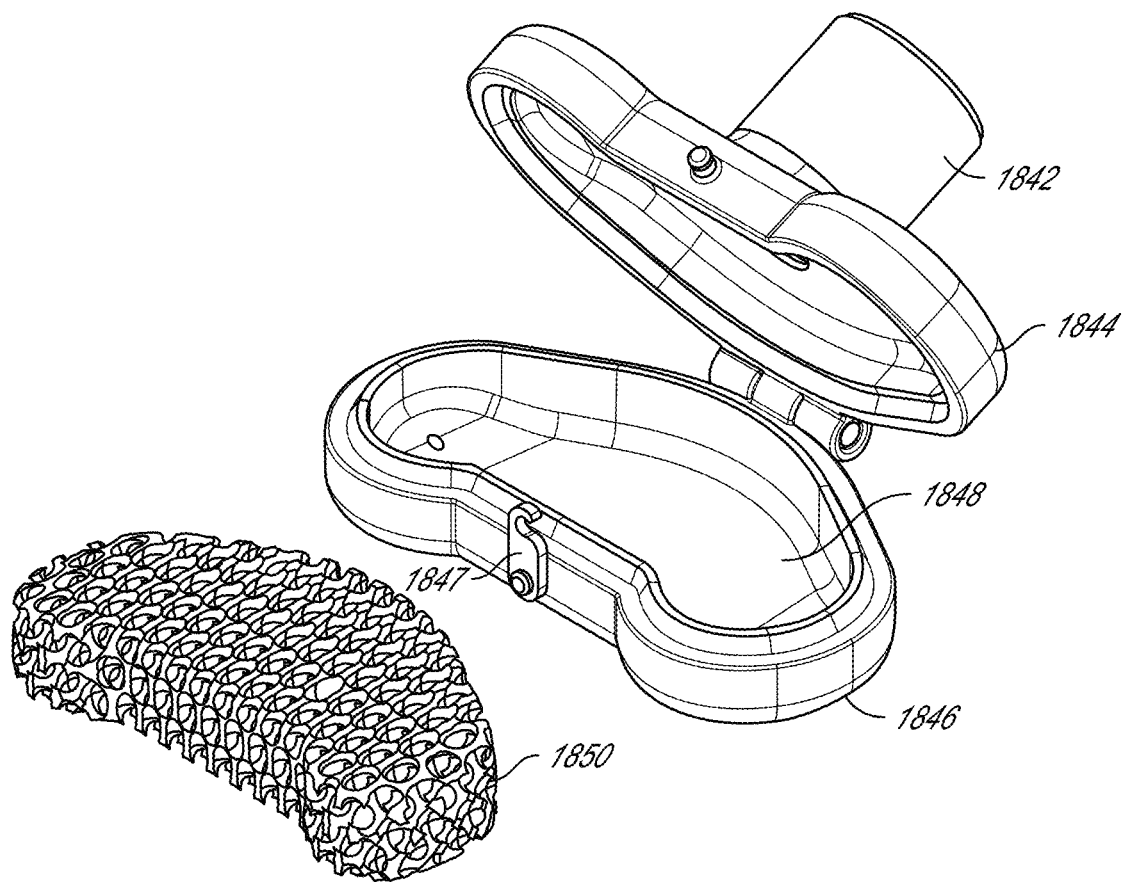

FIG. 47 illustrates a perspective view of a container and implant of the filling system of FIG. 46.

Figure 48:
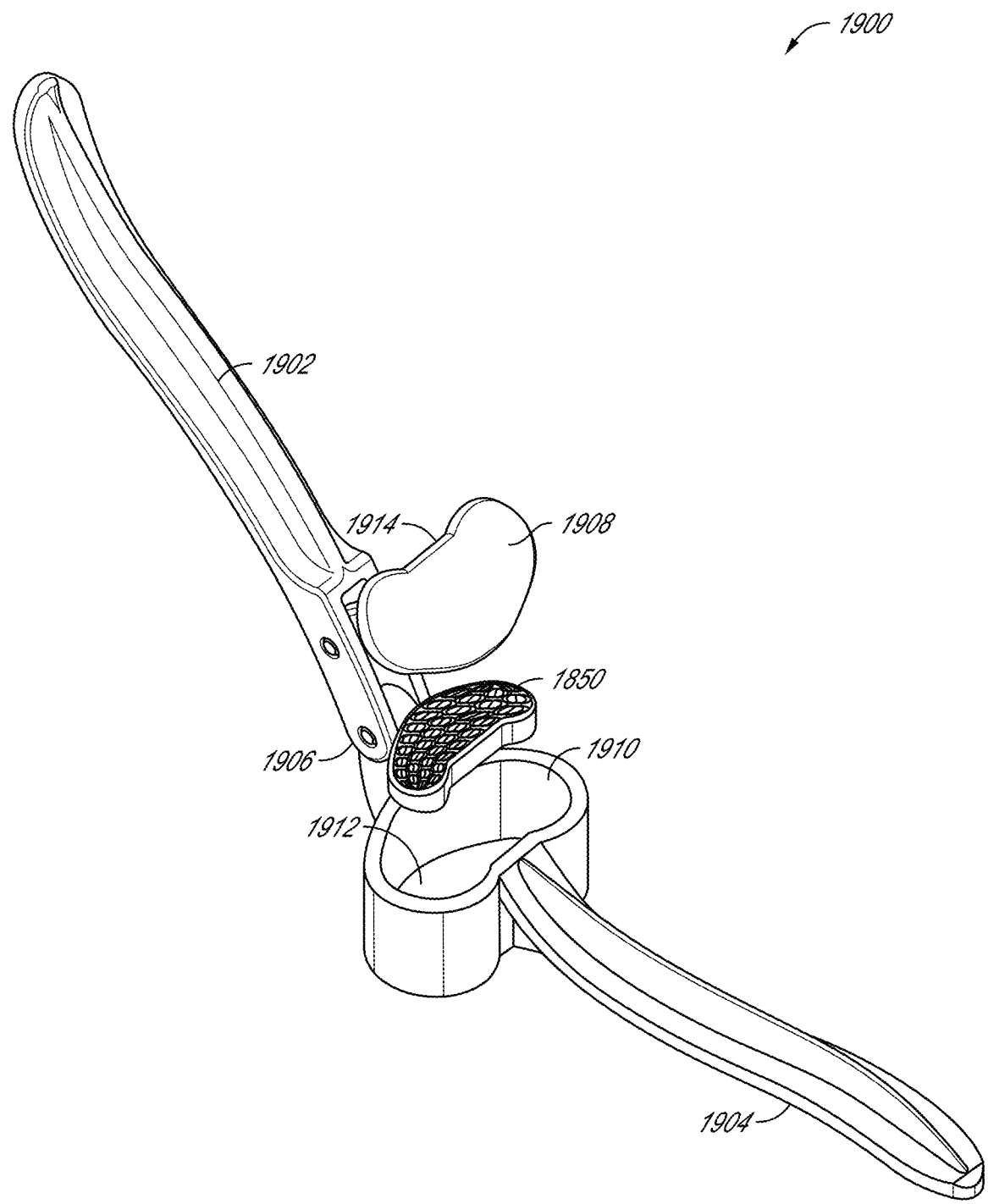

FIG. 48 illustrates a perspective view of an embodiment of a filling system.

Figure 49A:
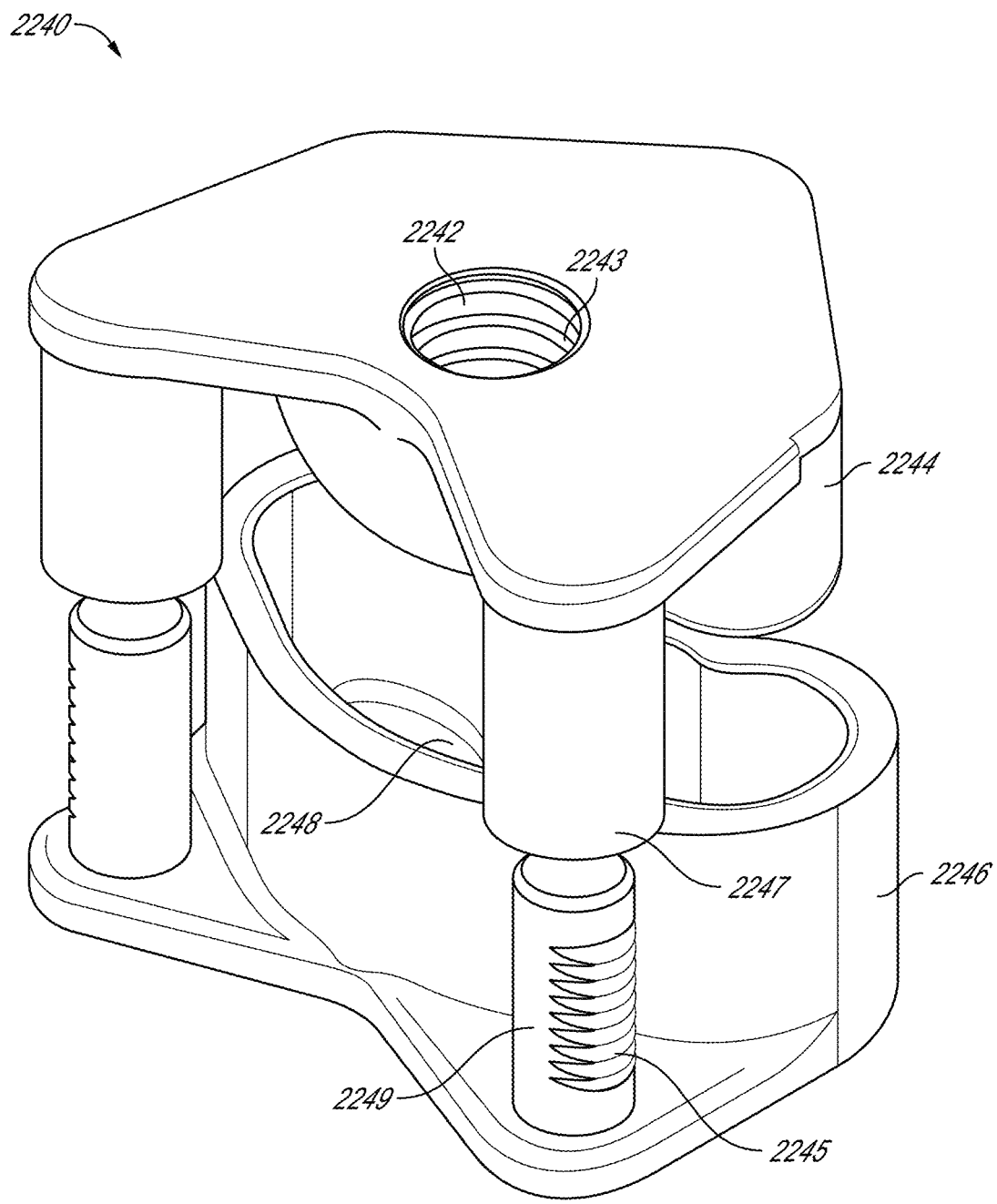

FIG. 49A illustrates a perspective view of an embodiment of a filling container.

Figure 49B:
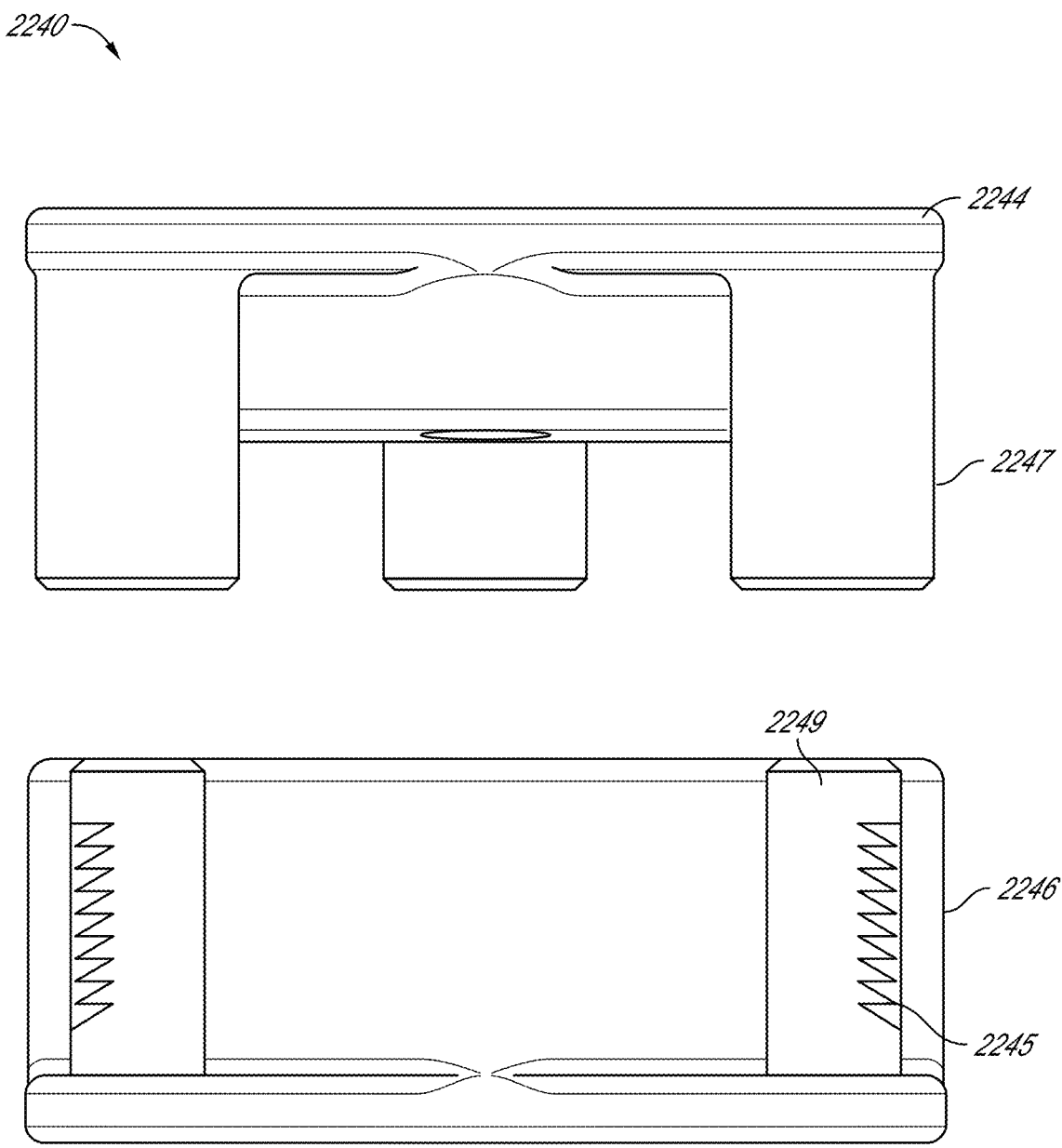

FIG. 49B illustrates a side view of the filling container of FIG. 49A.

Figure 49C:
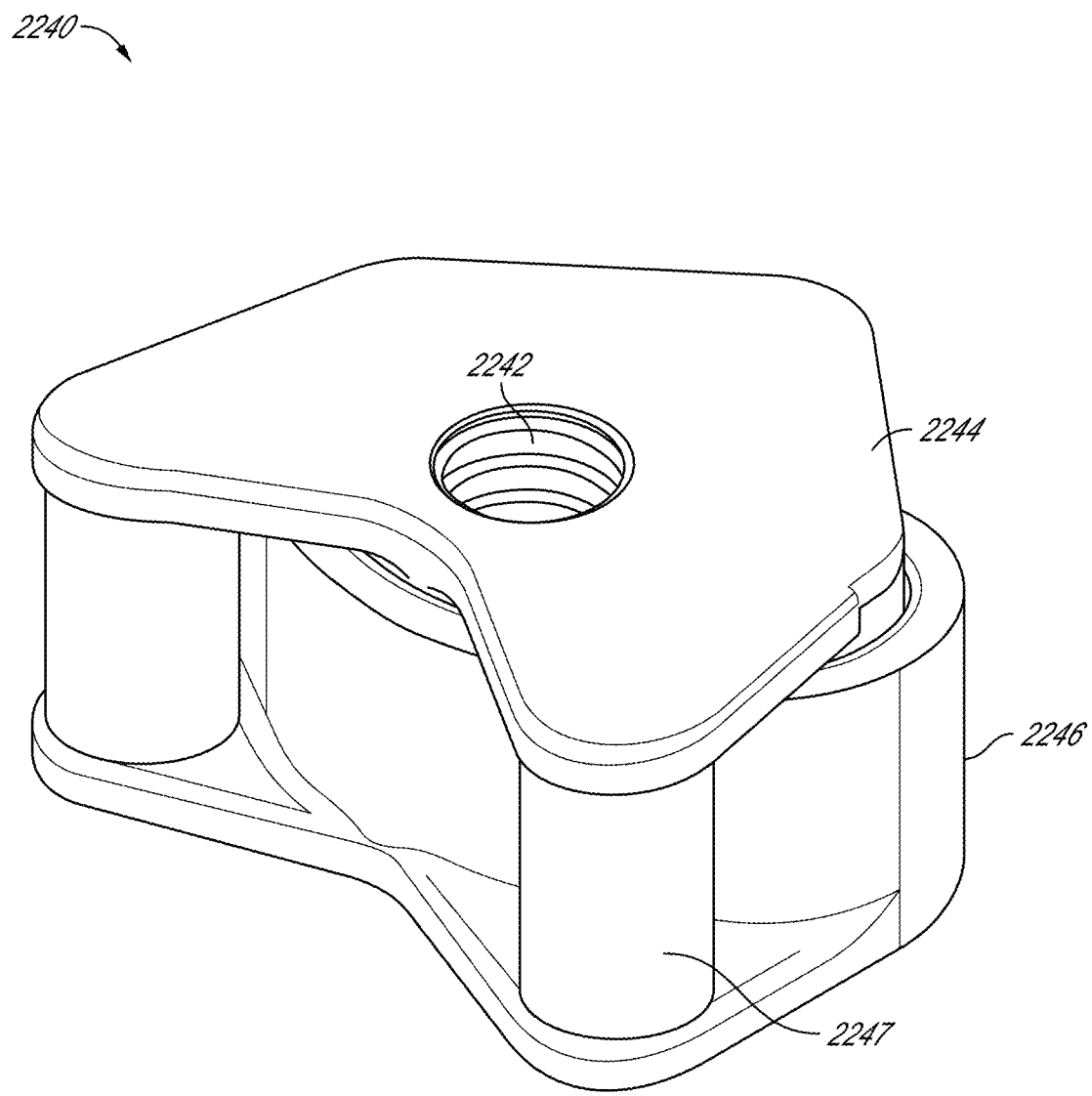

FIG. 49C illustrates a perspective view of the filling container of FIG. 49A.

Figure 49D:
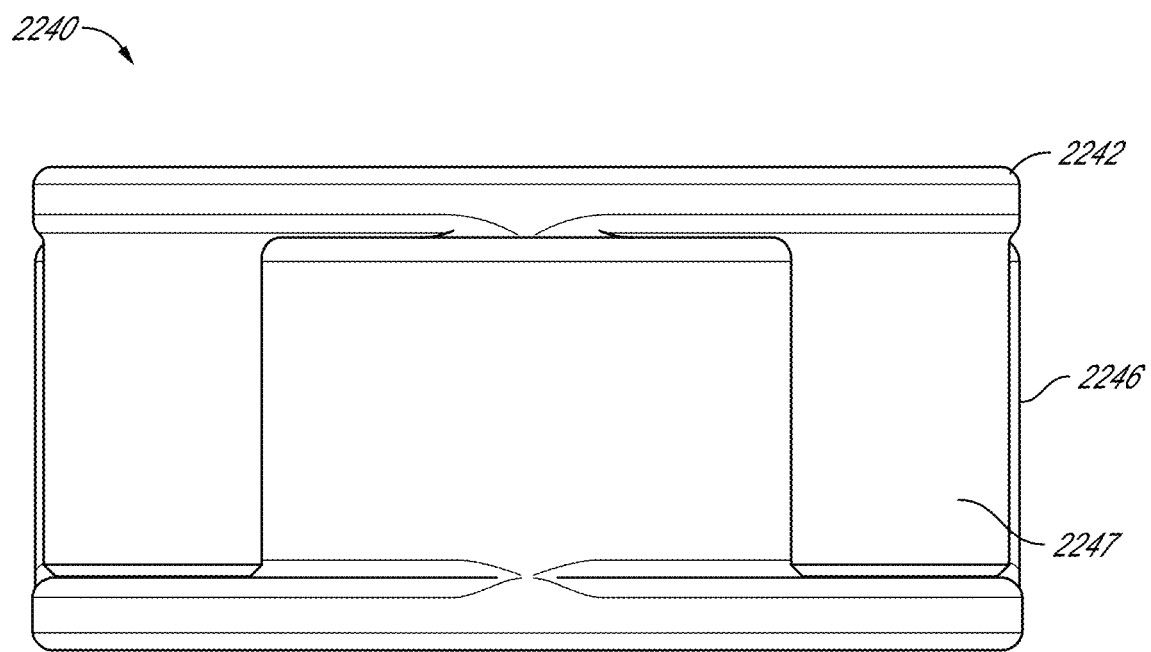

FIG. 49D illustrates a side view of the filling container of FIG. 49A.

Figure 50A:
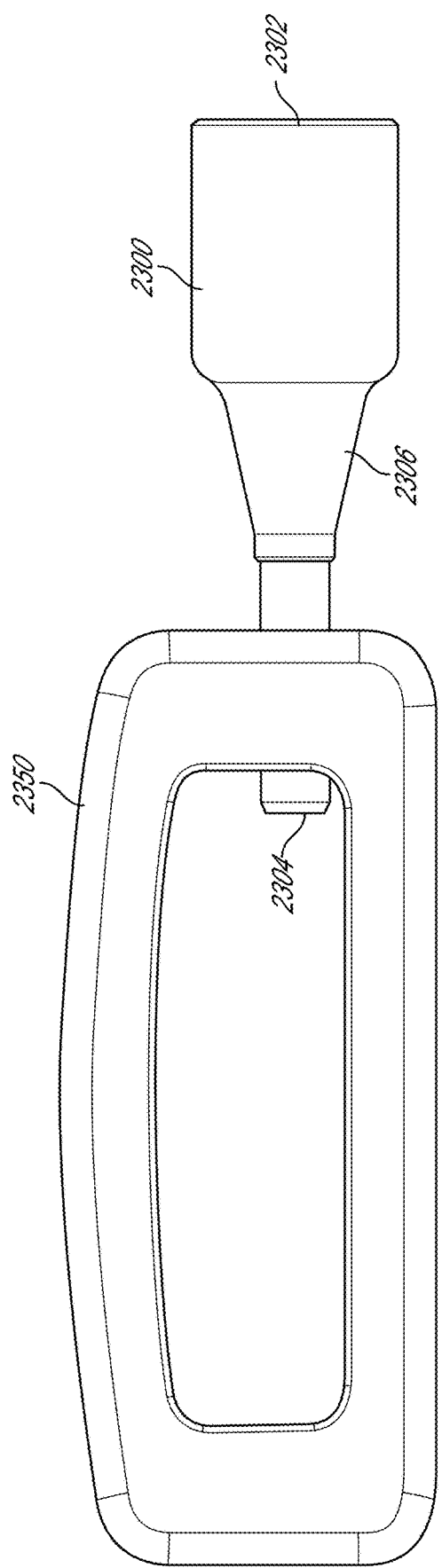

FIG. 50A illustrates a top view of an embodiment of an implant and an adapter for filling the implant with bone graft material.

Figure 50B:
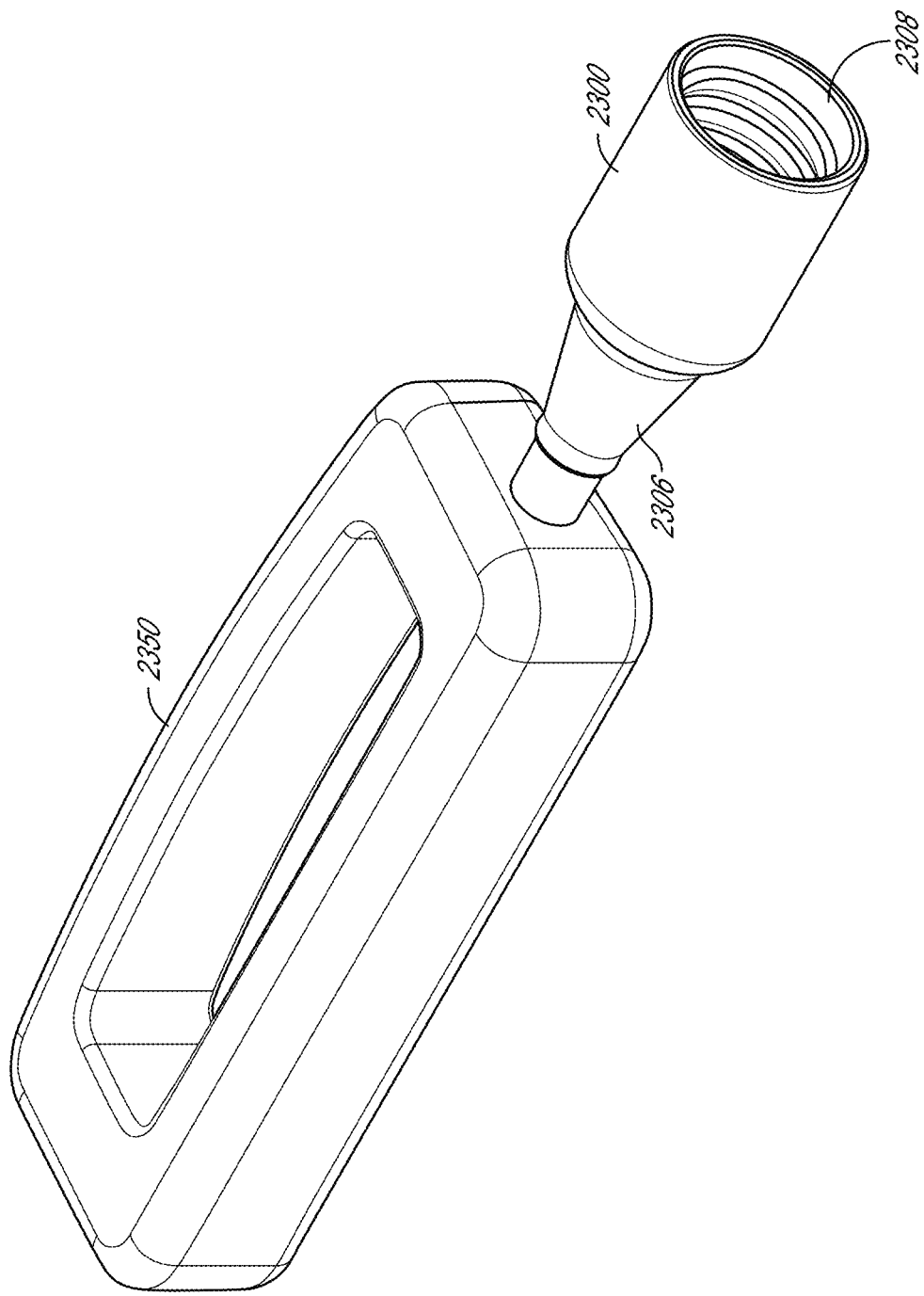

FIG. 50B illustrates a perspective view of the implant and adapter of FIG. 50A.

Figure 50C:
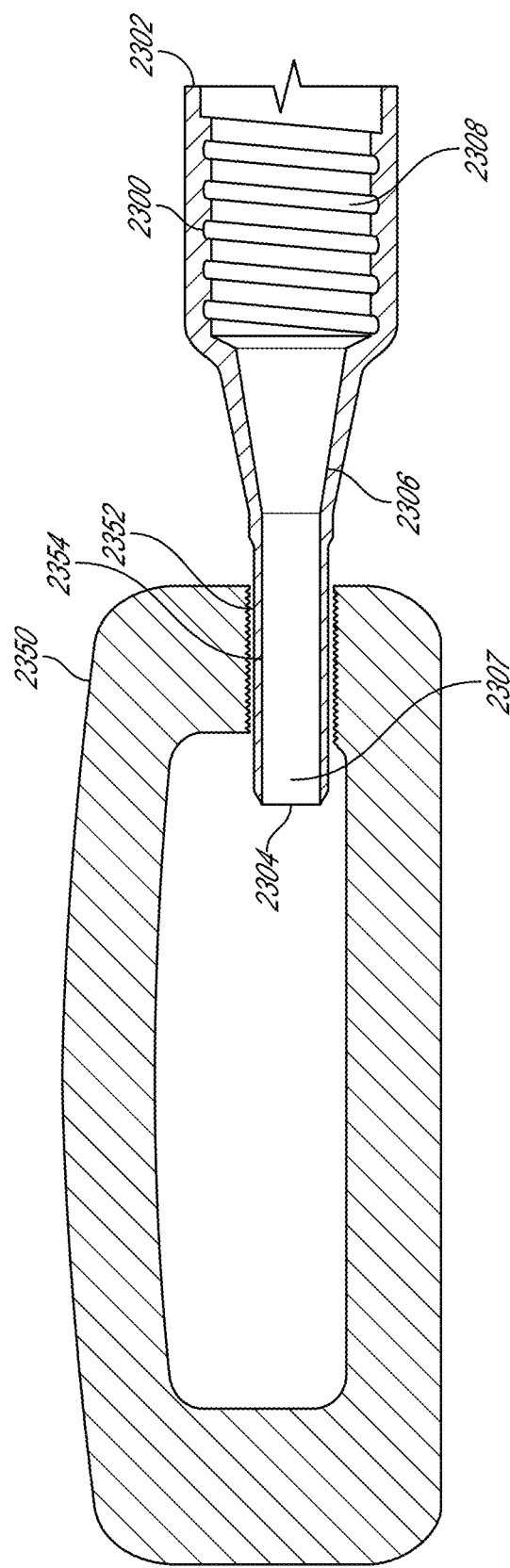

FIG. 50C illustrates a cross-sectional view of the implant and adapter of FIG. 50A.

Figure 50D:
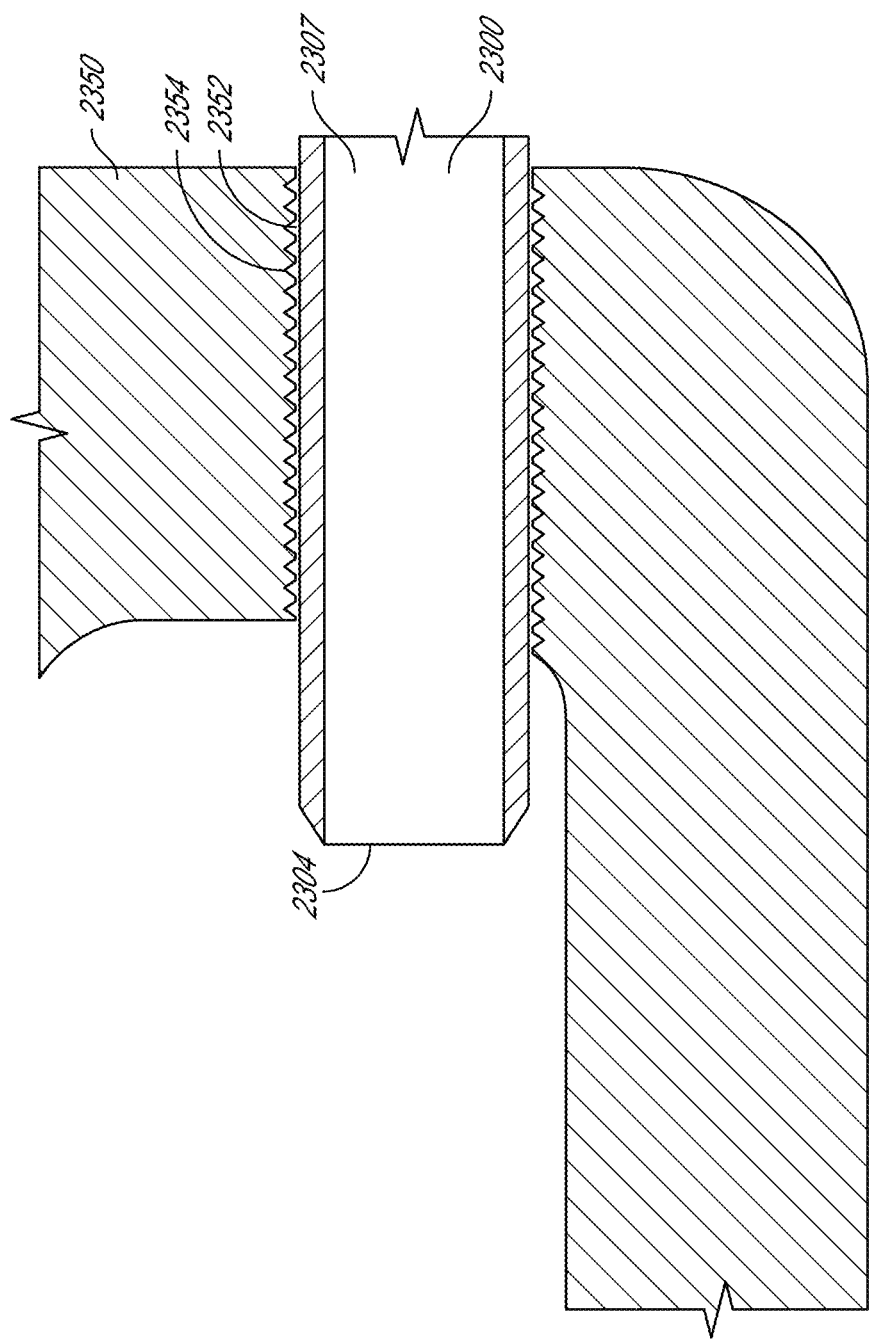

FIG. 50D illustrates an enlarged cross-section view of a section of the implant and adapter of FIG. 50A.

Figure 51A:
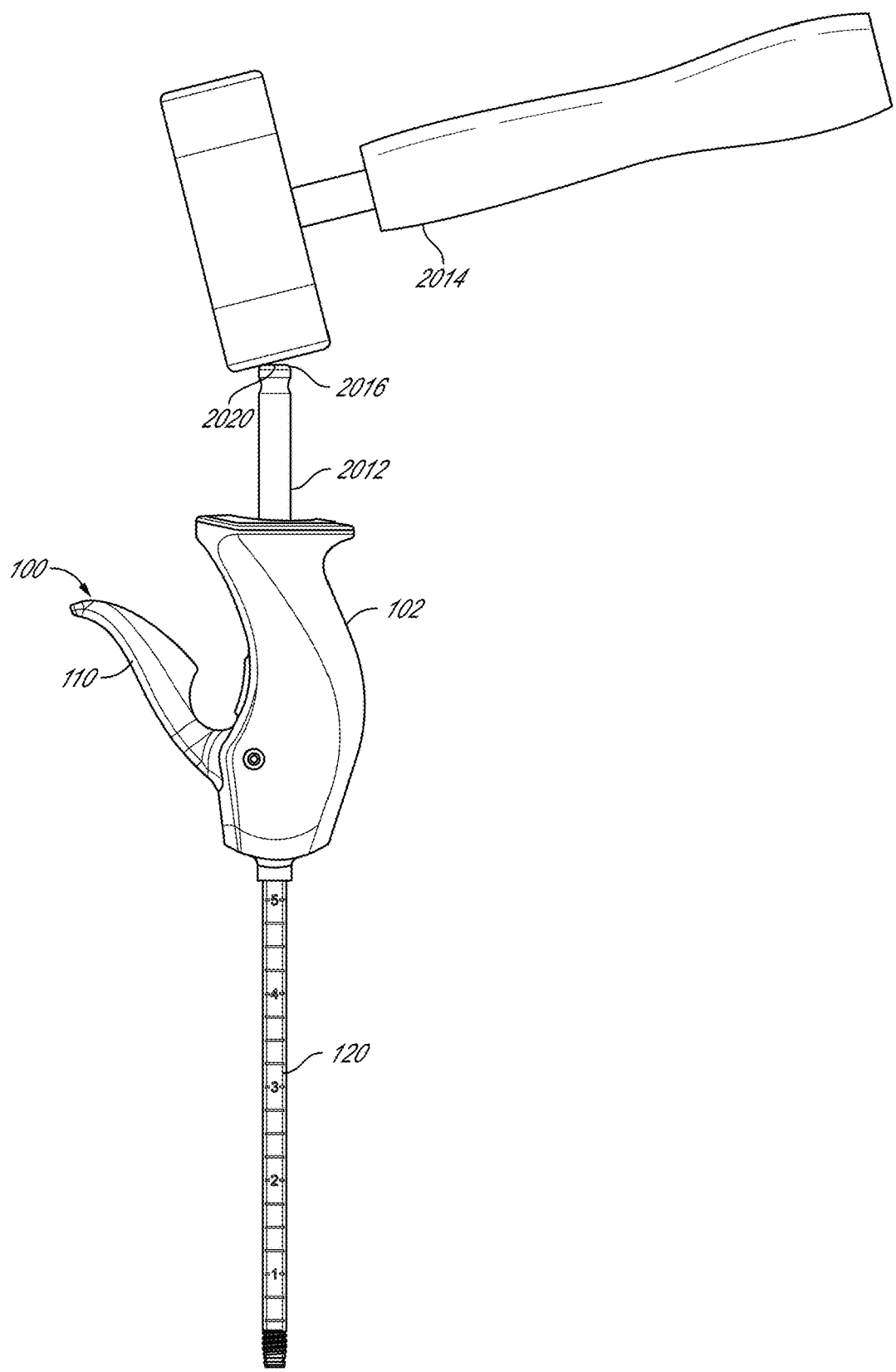

FIG. 51A illustrates a side view of a bone graft delivery system having a mallet and plunger.

Figure 51B:
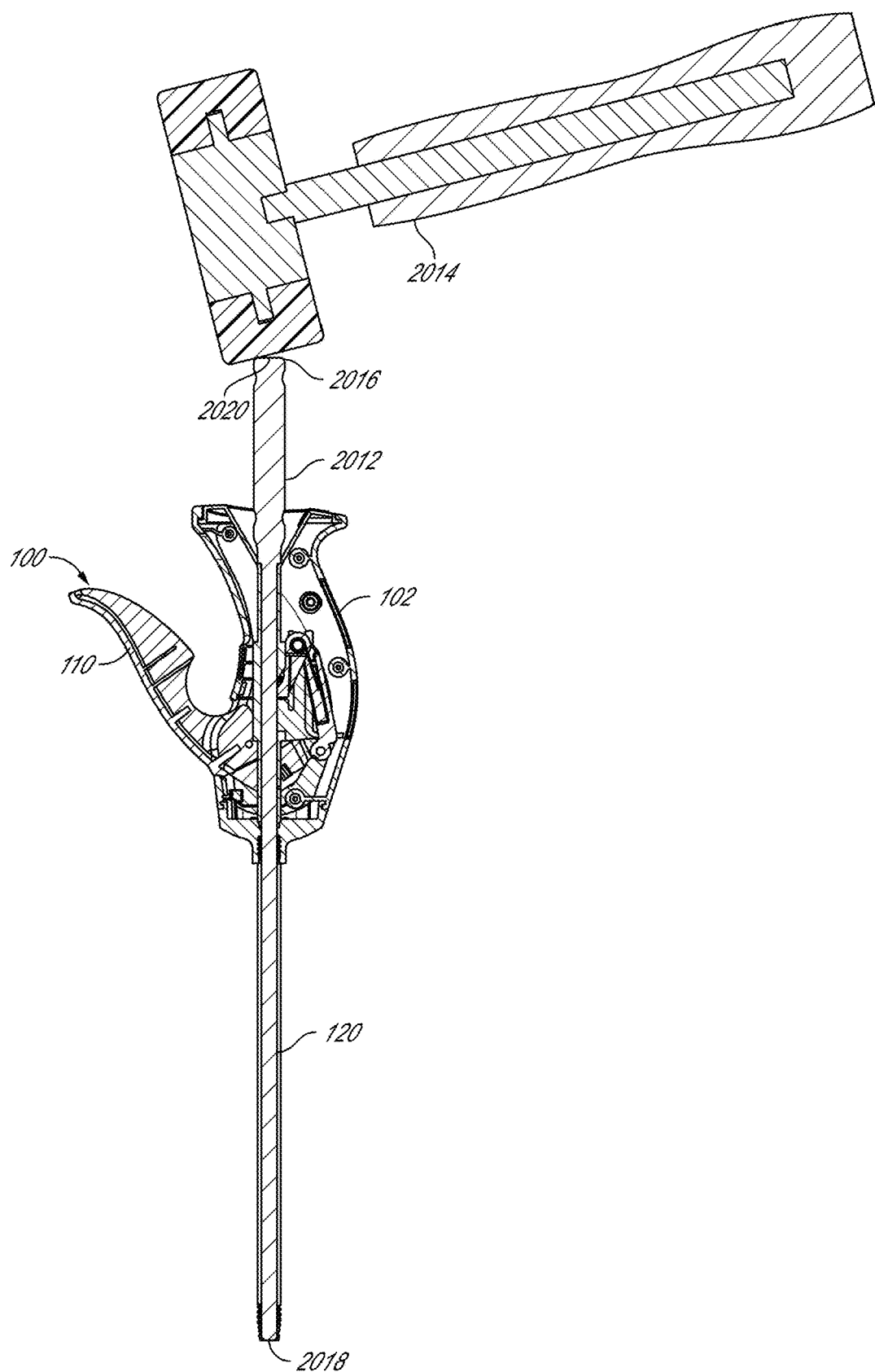

FIG. 51B illustrates a cross-sectional view of the bone graft delivery system of FIG. 51A.

Figure 52:
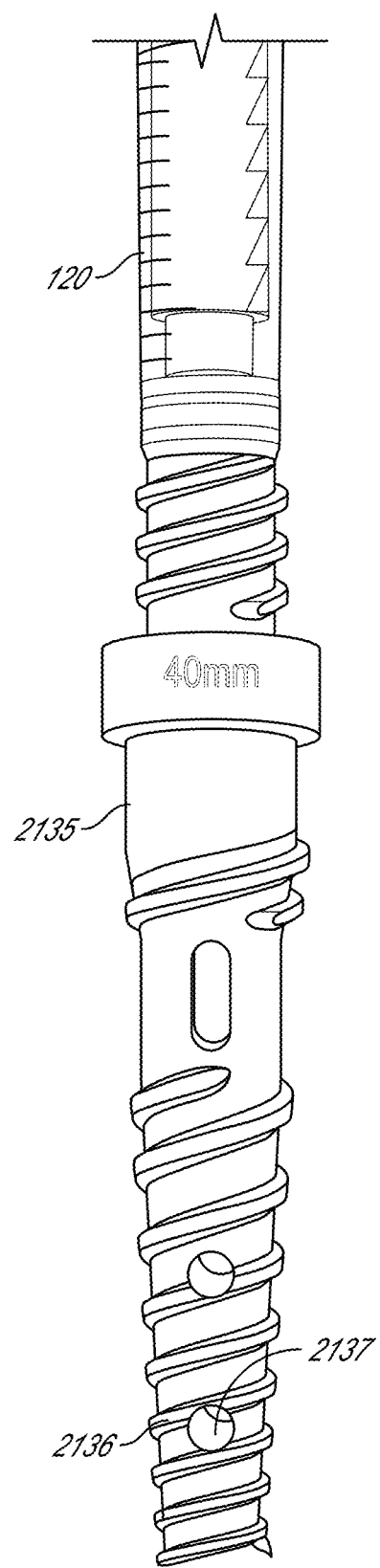

FIG. 52 illustrates a side view of a screw for use with a bone graft delivery system.

Figures 53A, 53B:
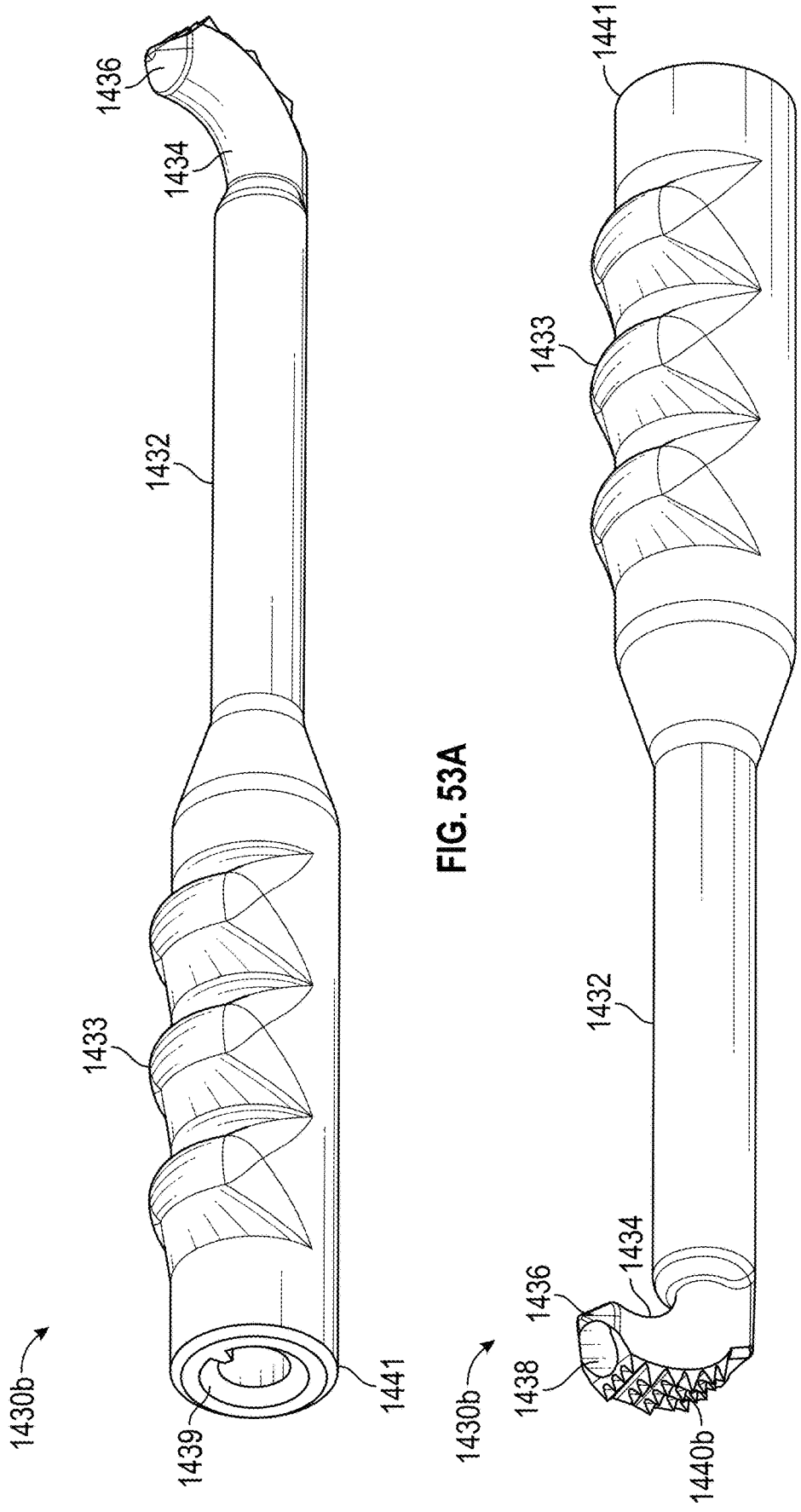

FIG. 53A illustrates a perspective view of an embodiment of a rasp.

FIG. 53B illustrates another perspective view of the rasp of FIG. 53A.

Figure 53C:
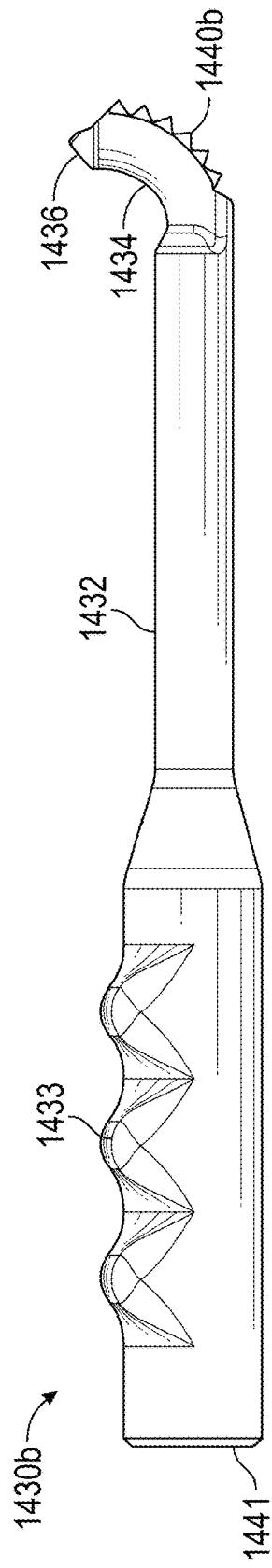

FIG. 53C illustrates a side view of the rasp of FIG. 53A.

Figure 53D:
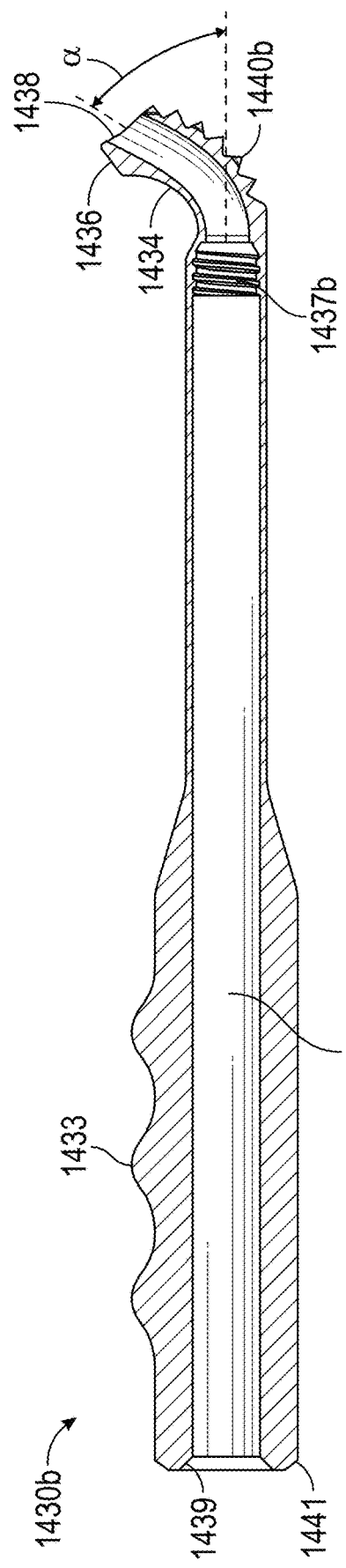

FIG. 53D illustrates a cross-sectional view of the rasp of FIG. 53A.

Figure 54A:
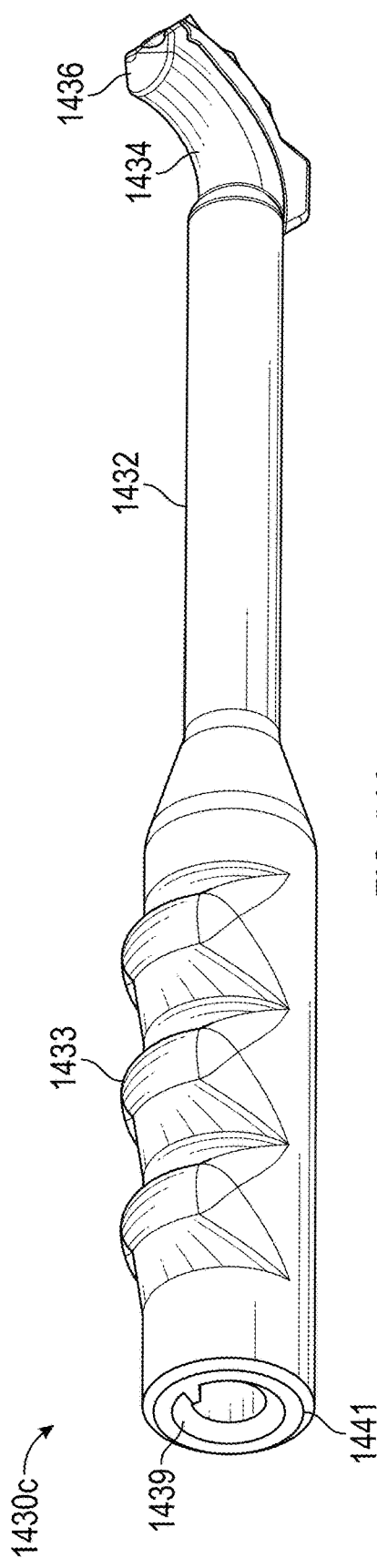

FIG. 54A illustrates a perspective view of an embodiment of a rasp.

Figure 54B:
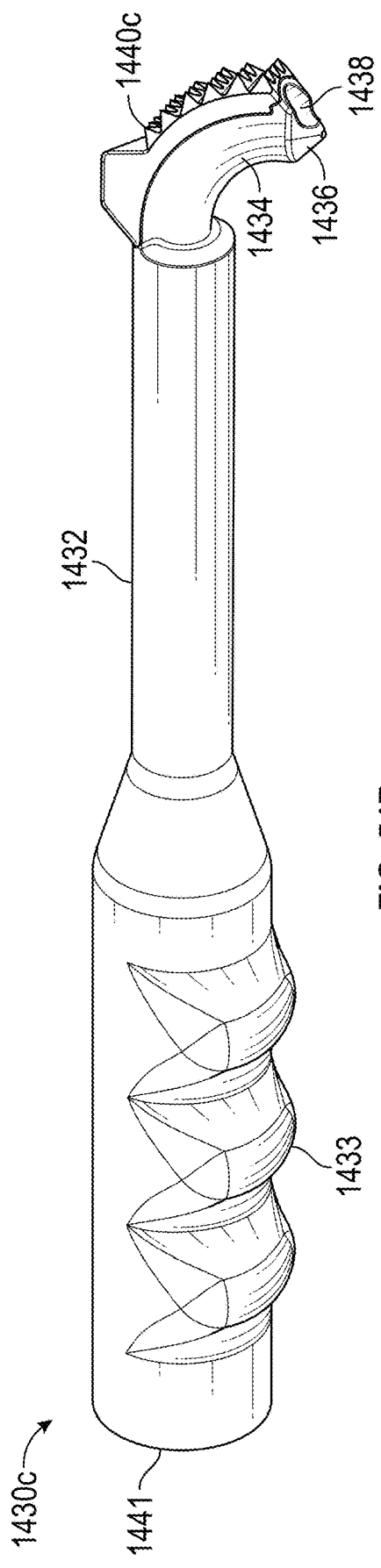

FIG. 54B illustrates another perspective view of the rasp of FIG. 54A.

Figure 54C:
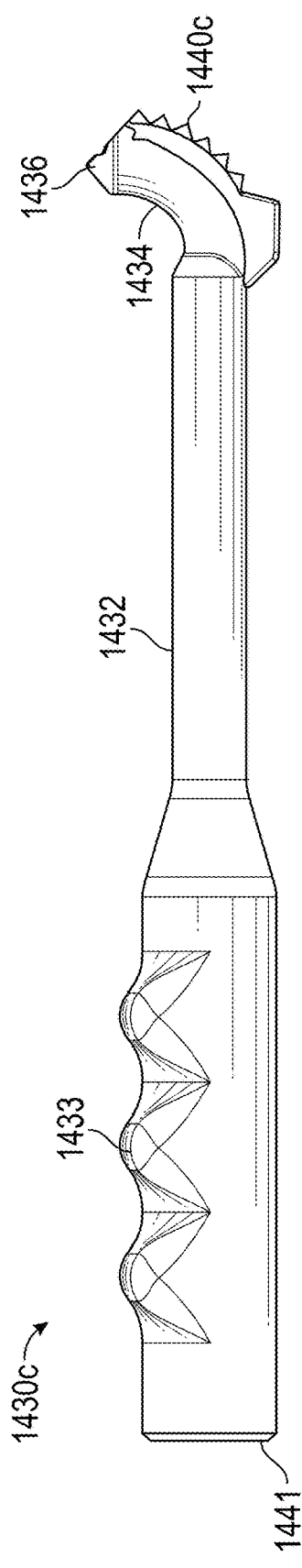

FIG. 54C illustrates a side view of the rasp of FIG. 54A.

Figure 54D:
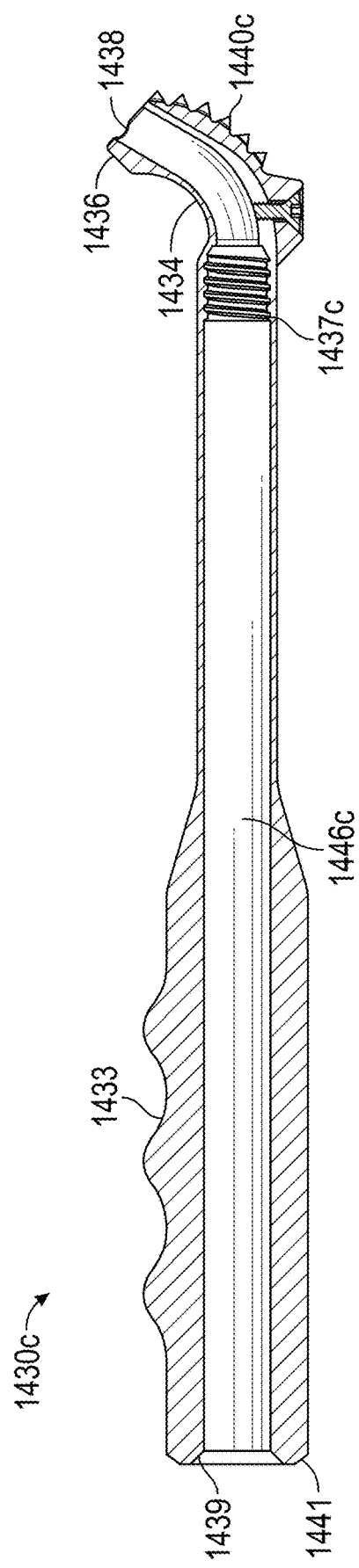

FIG. 54D illustrates a cross-sectional view of the rasp of FIG. 54A.

Figure 54E:
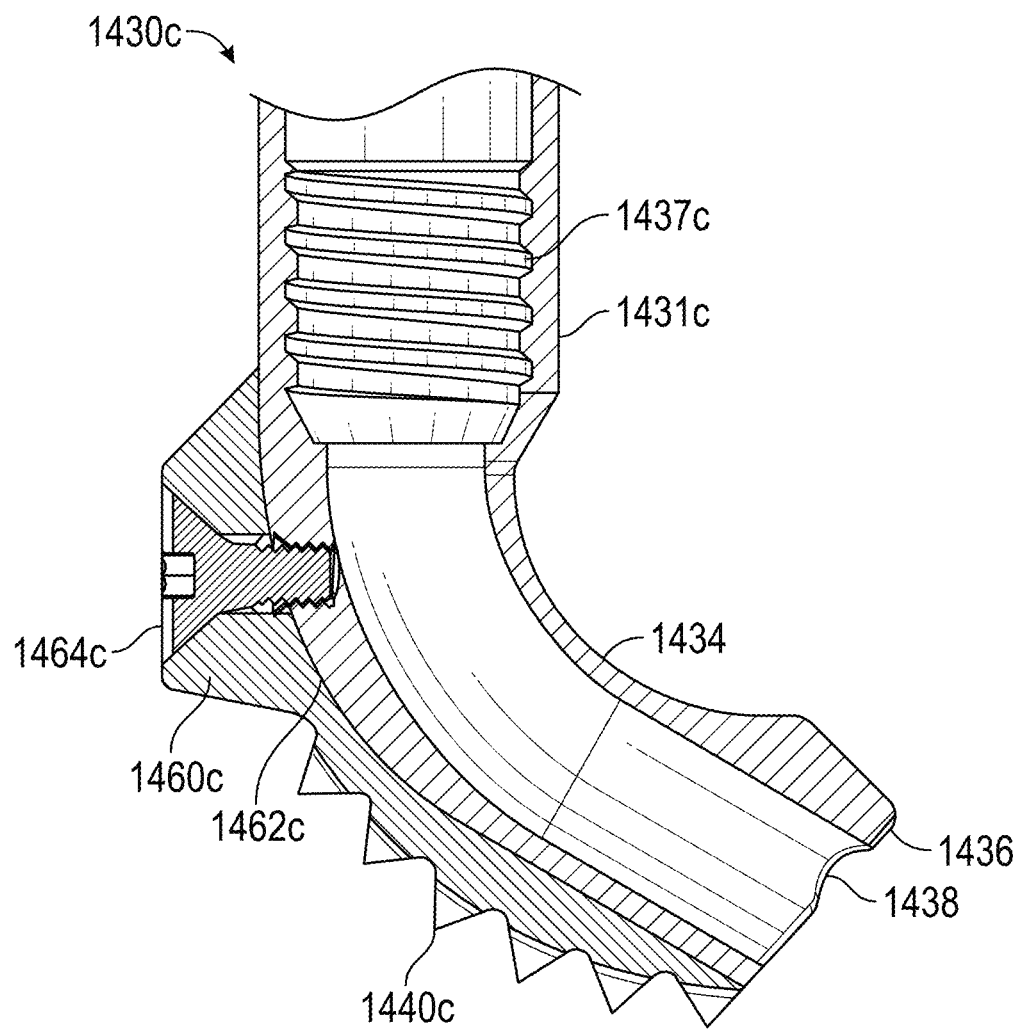

FIG. 54E illustrates an enlarged cross-sectional view of a portion of the rasp of FIG. 54A.

Figure 54F:
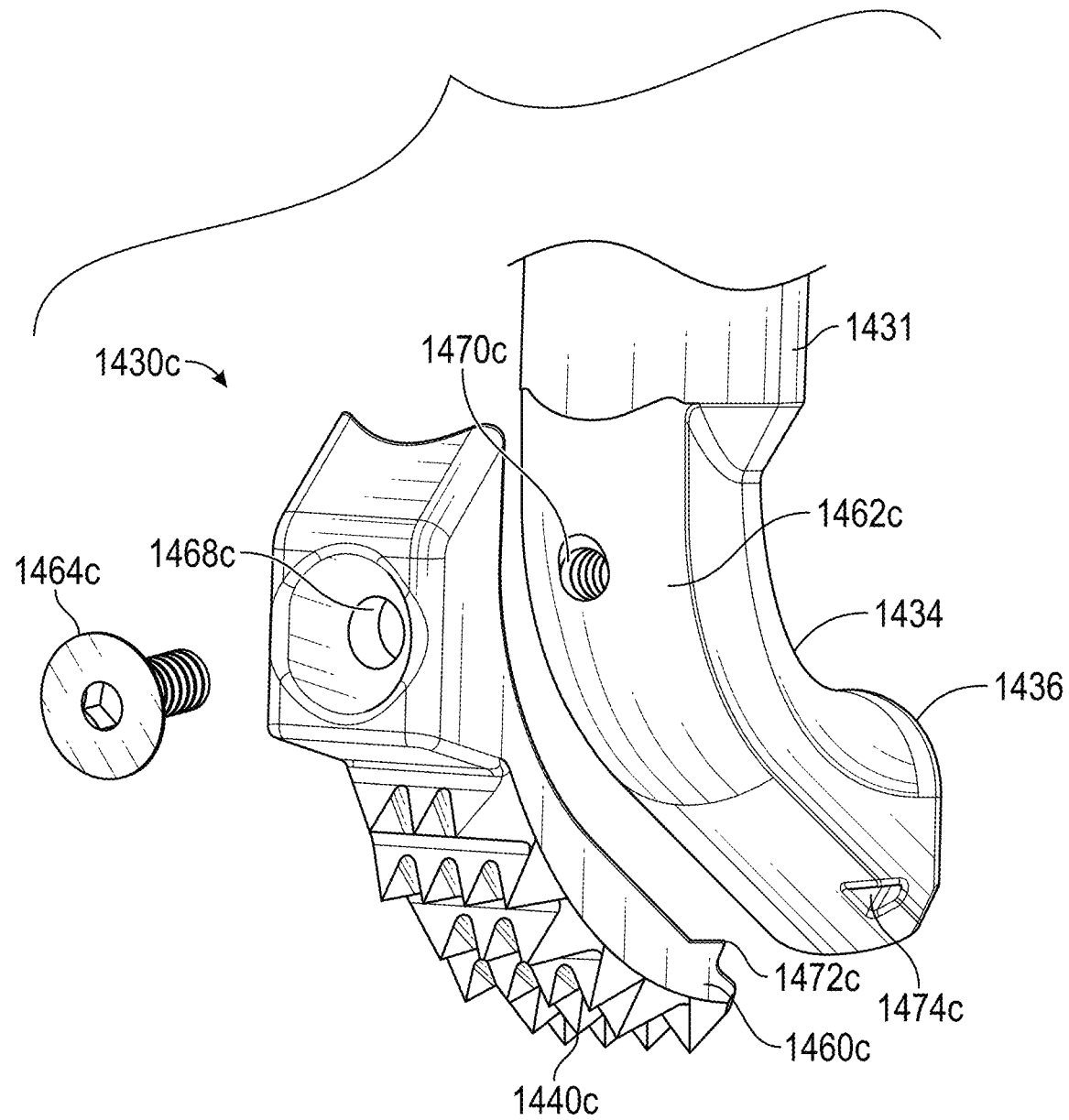

FIG. 54F illustrates an enlarged exploded perspective view of a portion of the rasp of FIG. 54A.

Figure 54G:
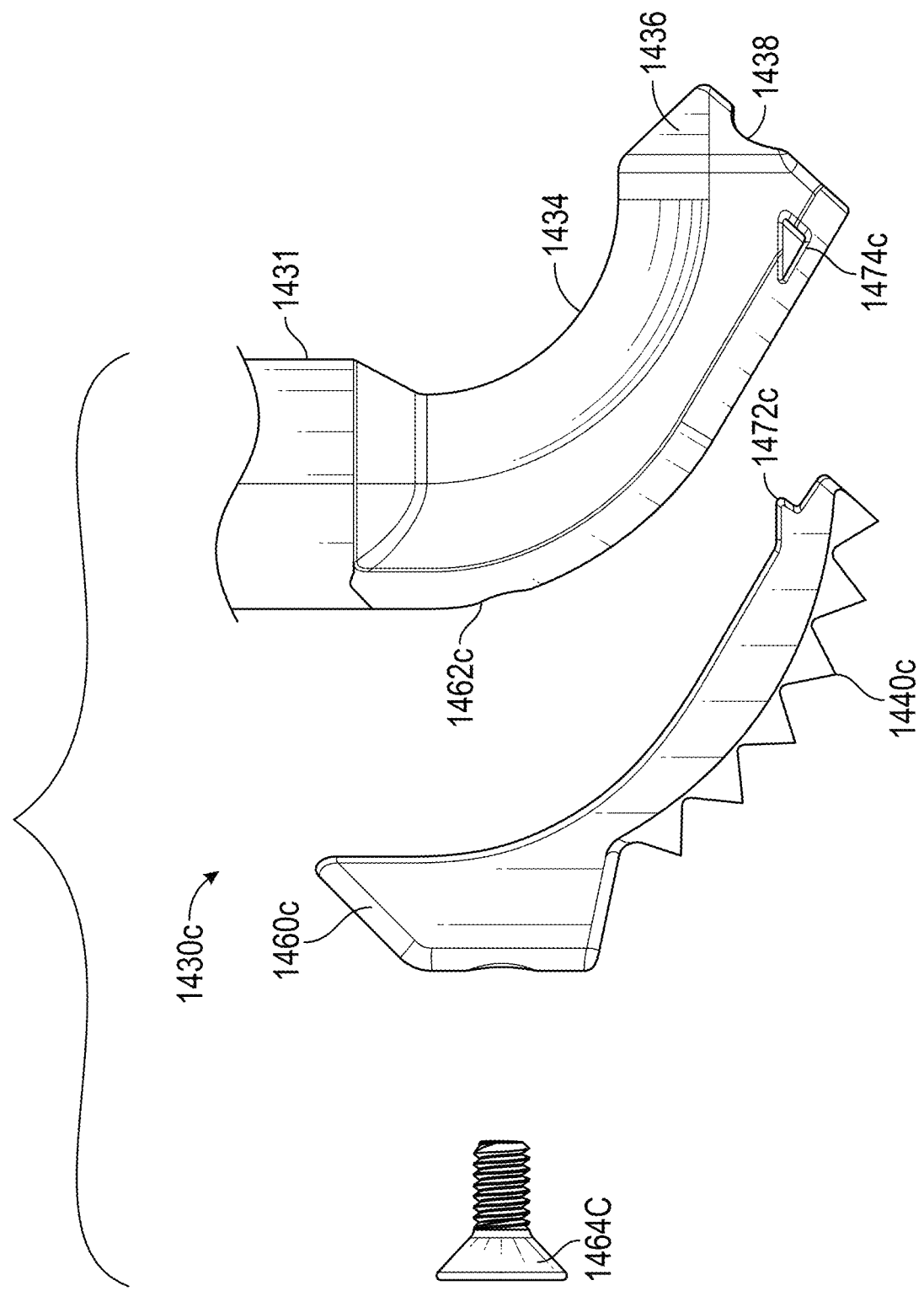

FIG. 54G illustrates an enlarged exploded view of a portion of the rasp of FIG. 54A.

Figure 54I:
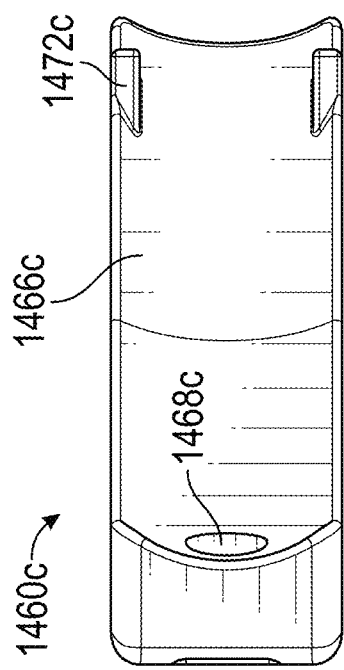
Figure 54J:
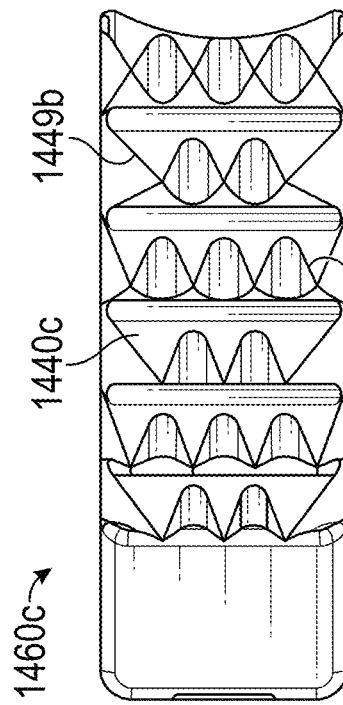
Figure 54H:
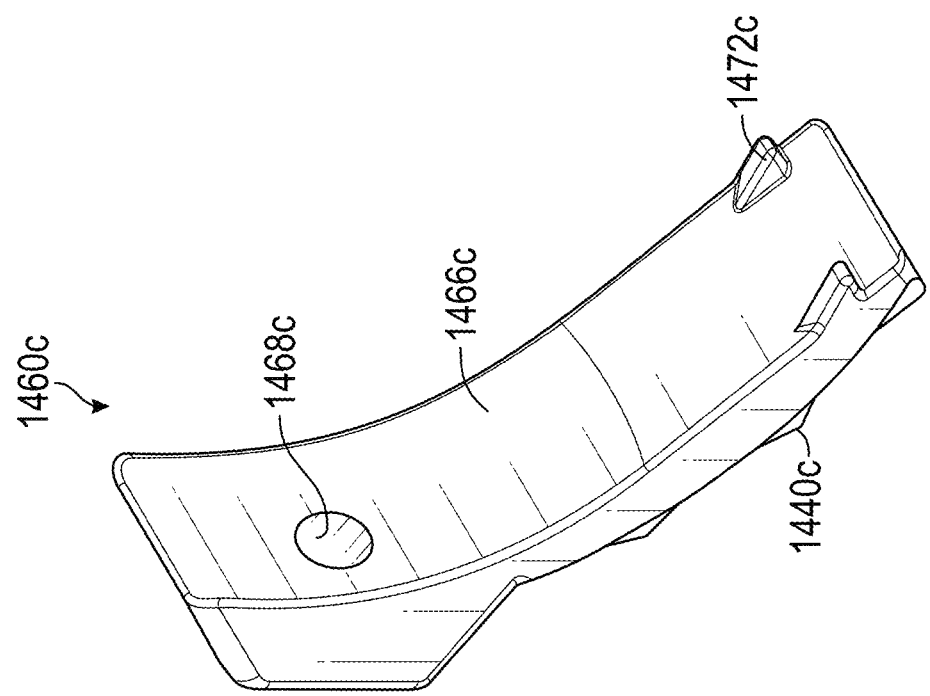

FIG. 54H illustrates a perspective view of a cover of the rasp of FIG. 54A.

FIG. 54I illustrates a top view of the cover of FIG. 54H.

FIG. 54J illustrates a bottom view of the cover of FIG. 54H.

FIG. 54K illustrates a first side view of the cover of FIG. 54H.

FIG. 54L illustrates a second side view of the of FIG. 54H.

FIG. 54M illustrates a front view of the cover of FIG. 54H.

FIG. 54N illustrates a rear view of the cover of FIG. 54H.

Figure 54O:
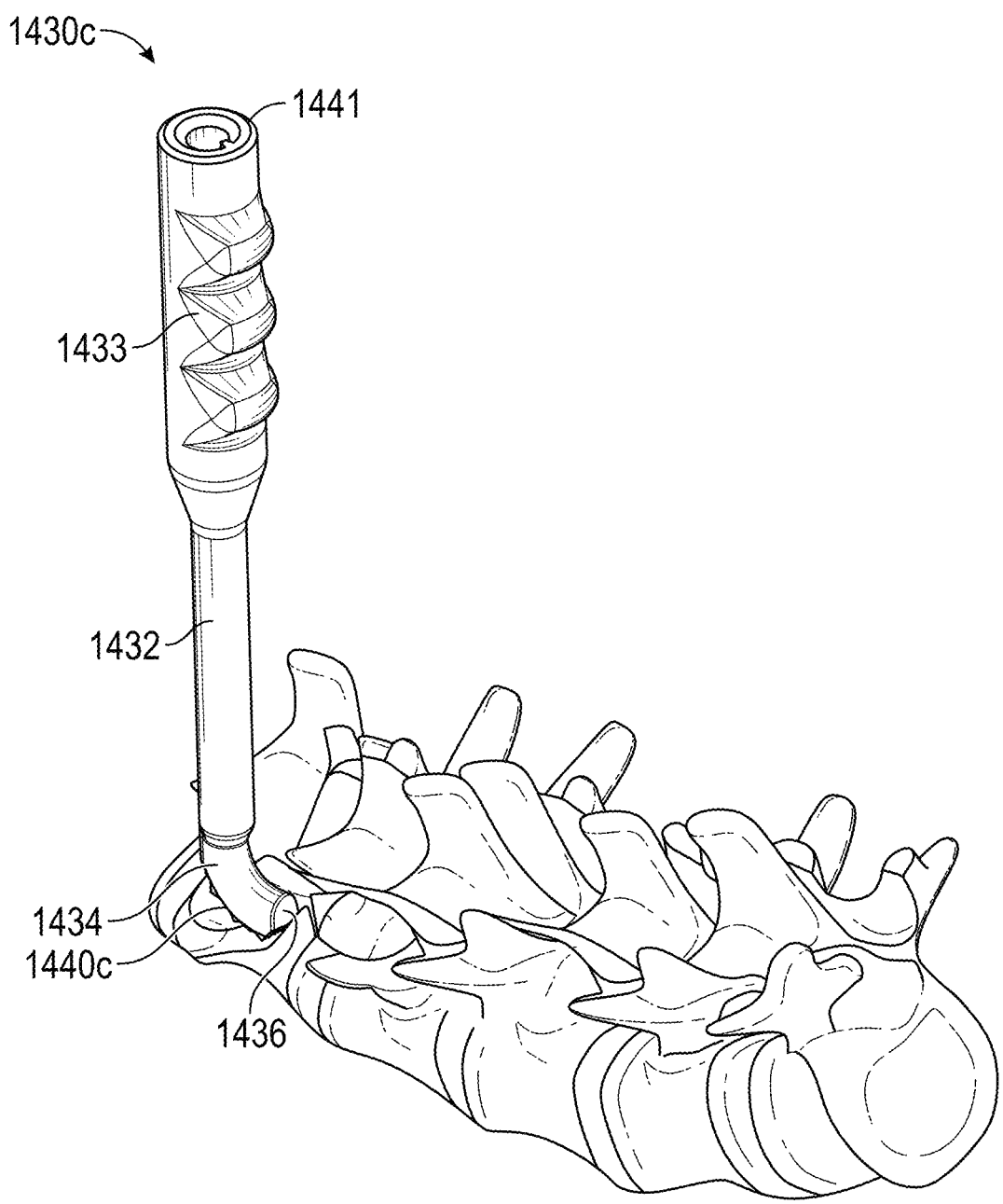

FIG. 54O illustrates a perspective view of the rasp of FIG. 54A positioned at a surgical location.

Figure 54P:
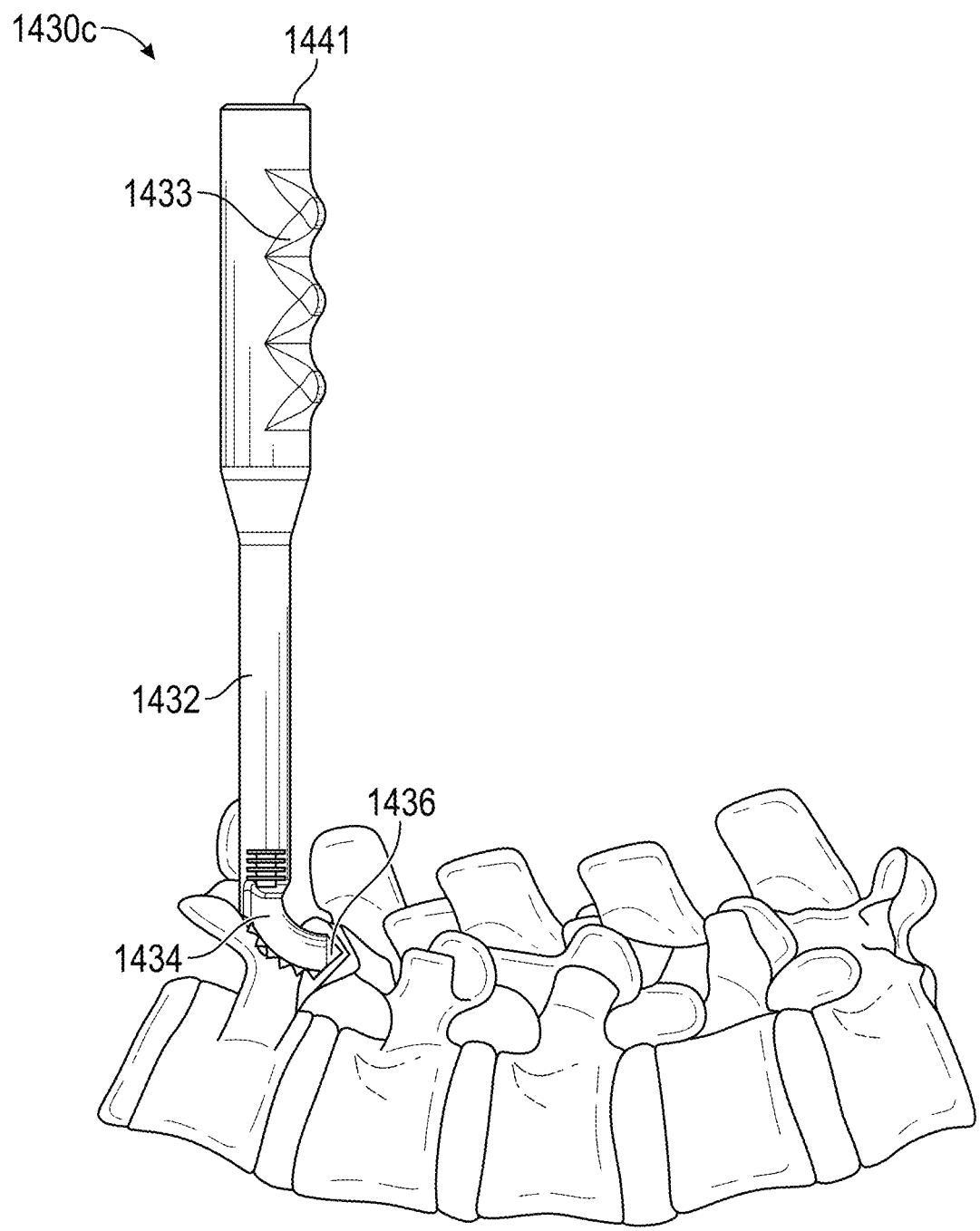

FIG. 54P illustrates a side view of the rasp of FIG. 54A positioned at a surgical location.

FIG. 55A illustrates a perspective view of an embodiment of a rasp.

FIG. 55B illustrates another perspective view of the rasp of FIG. 55A.

Figure 55C:
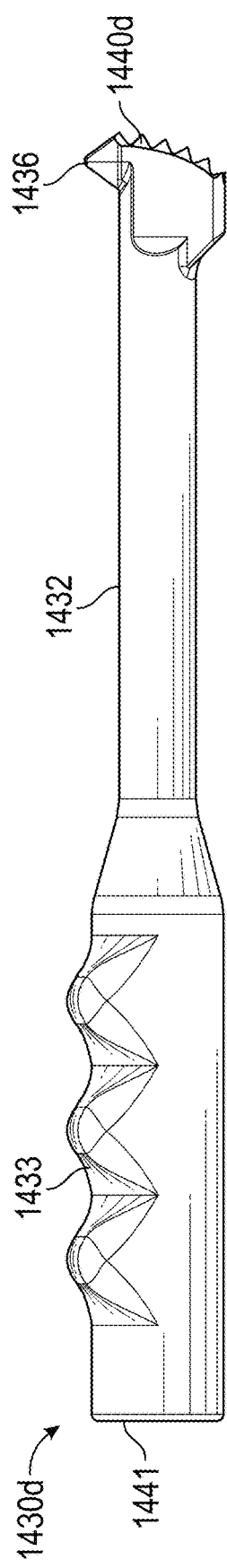

FIG. 55C illustrates a side view of the rasp of FIG. 55A.

Figure 55D:
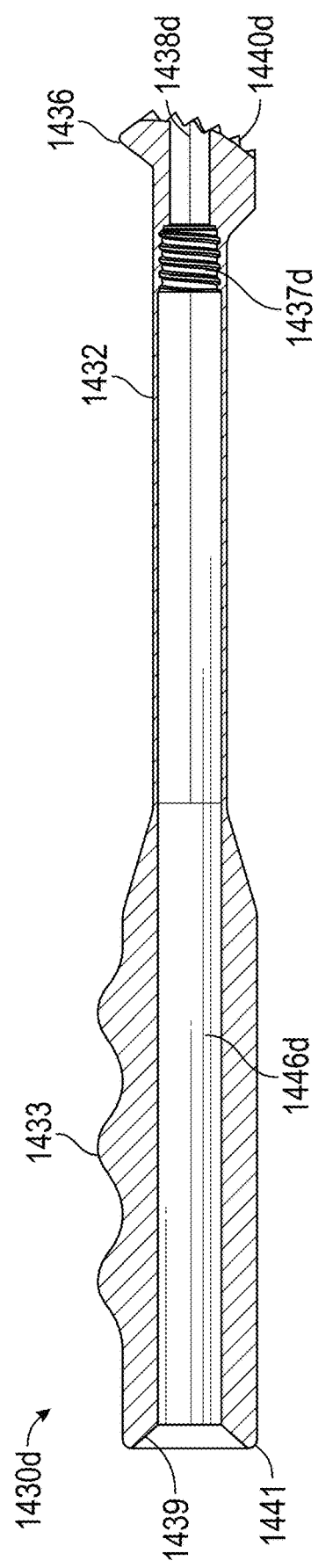

FIG. 55D illustrates a cross-sectional view of the rasp of FIG. 55A.

Figure 56A:
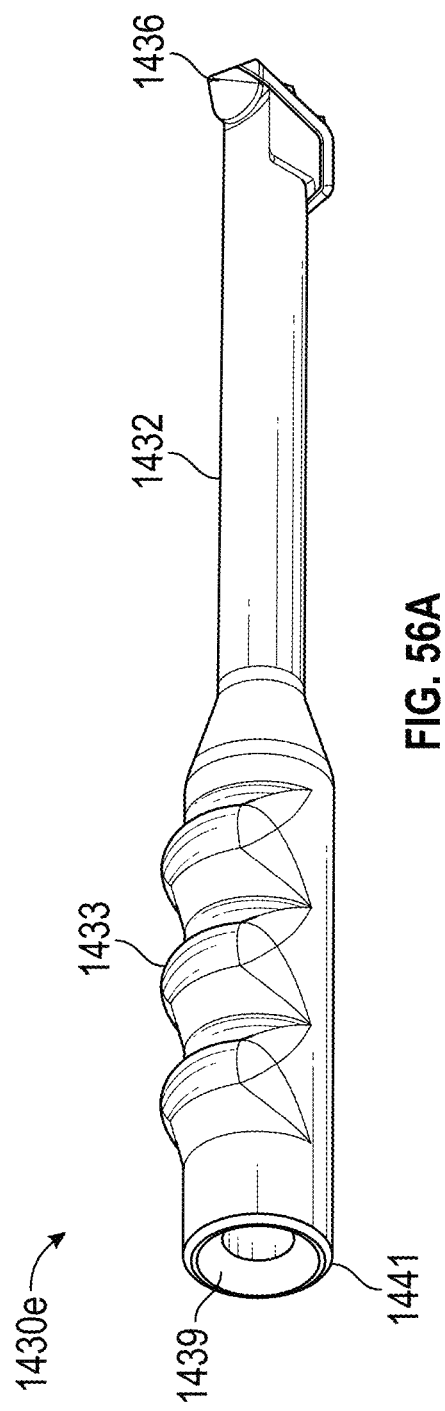

FIG. 56A illustrates a perspective view of an embodiment of a rasp.

Figure 56B:
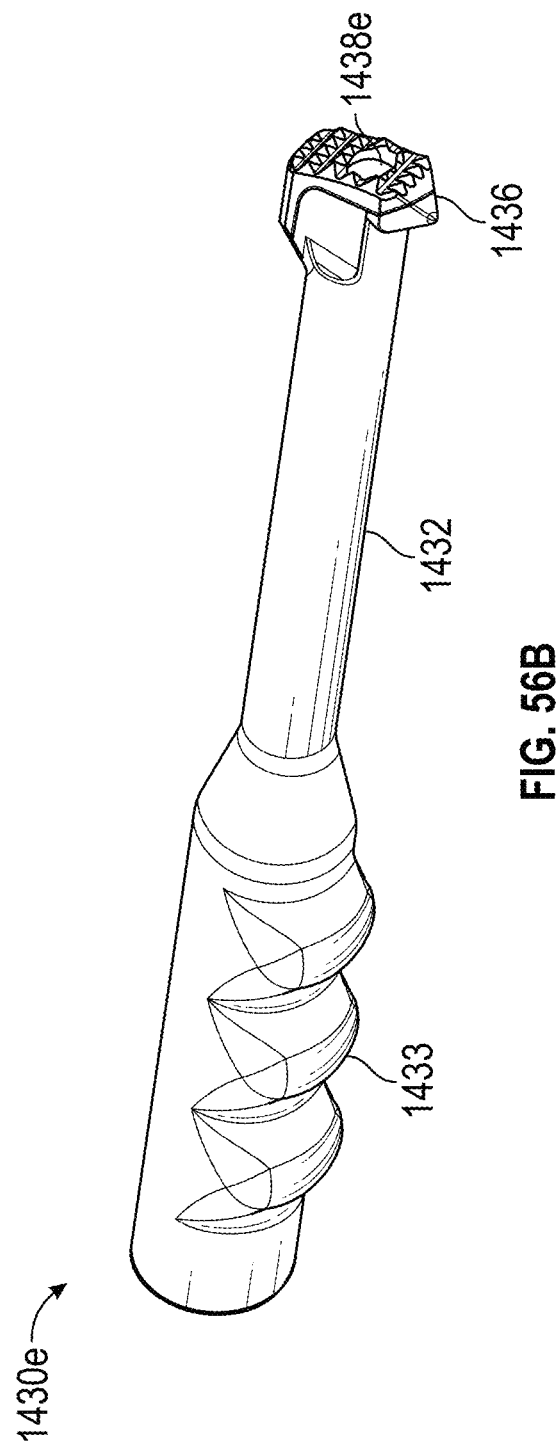

FIG. 56B illustrates another perspective view of the rasp of FIG. 56A.

FIG. 56C illustrates a side view of the rasp of FIG. 56A.

FIG. 56D illustrates a cross-sectional view of the rasp of FIG. 56A.

Figure 56E:
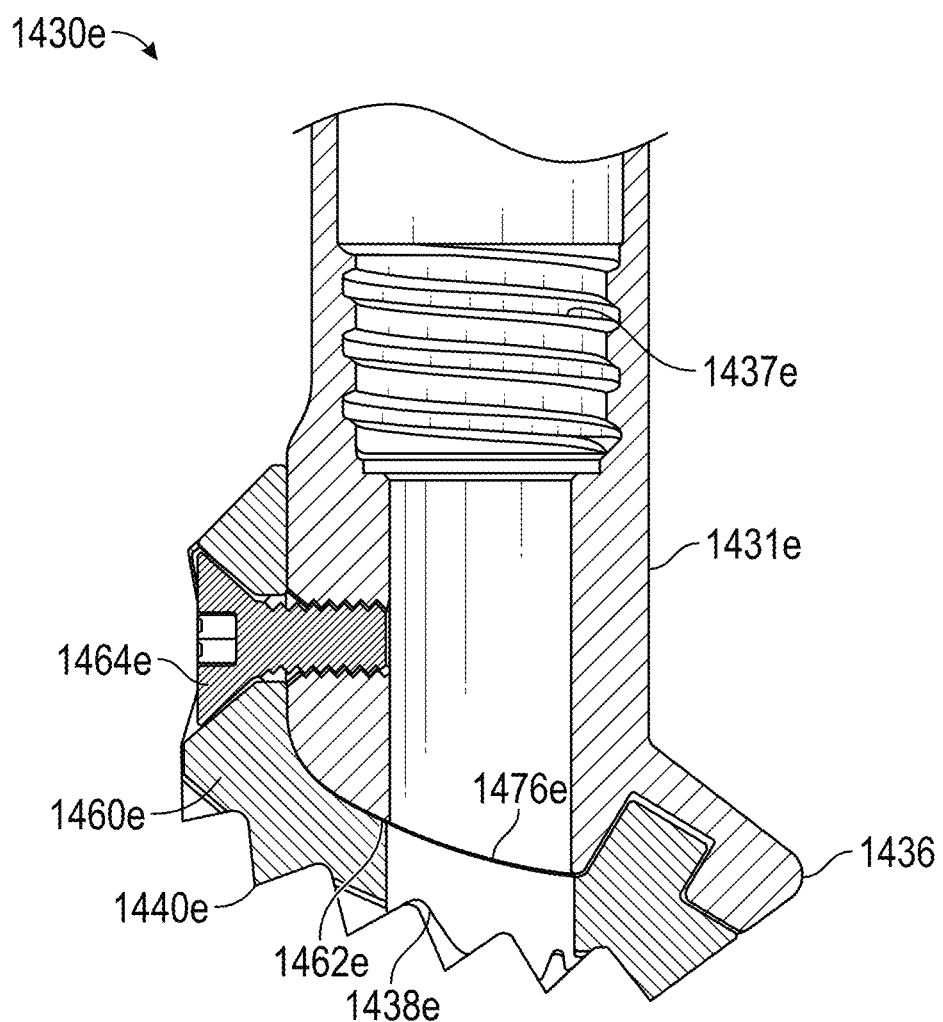

FIG. 56E illustrates an enlarged cross-sectional view of a portion of the rasp of FIG. 56A.

Figure 56F:
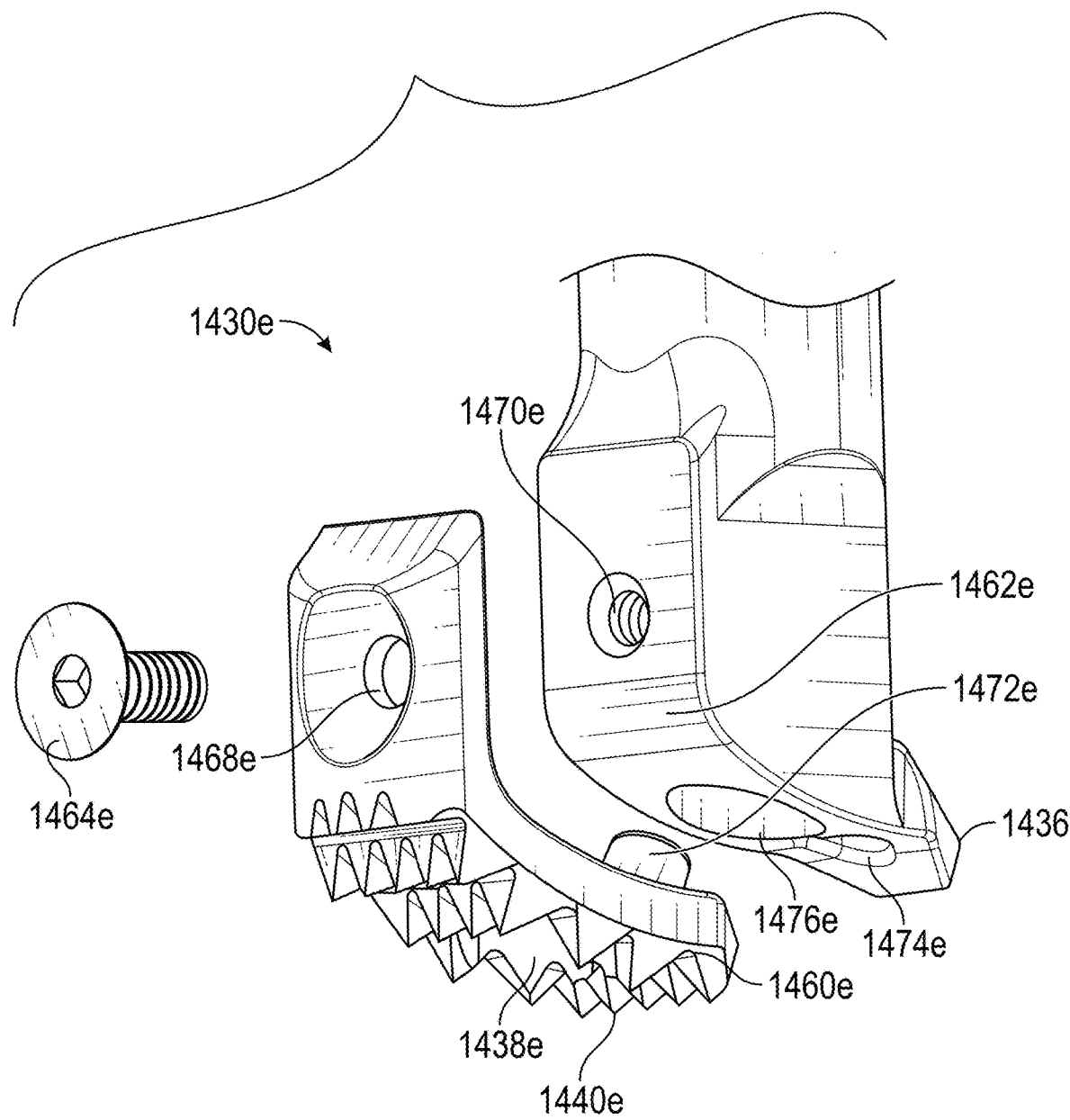

FIG. 56F illustrates an enlarged exploded perspective view of a portion of the rasp of FIG. 56A.

FIG. 56G illustrates an enlarged exploded view of a portion of the rasp of FIG. 56A.

FIG. 56H illustrates a perspective view of a cover of the rasp of FIG. 56A.

FIG. 56I illustrates a top view of the cover of FIG. 56H.

FIG. 56J illustrates a bottom view of the cover of FIG. 56H.

Figure 56K:
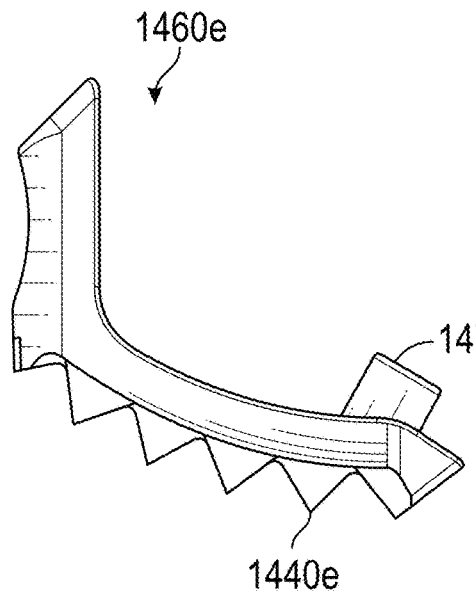

FIG. 56K illustrates a first side view of the cover of FIG. 56H.

Figure 56L:
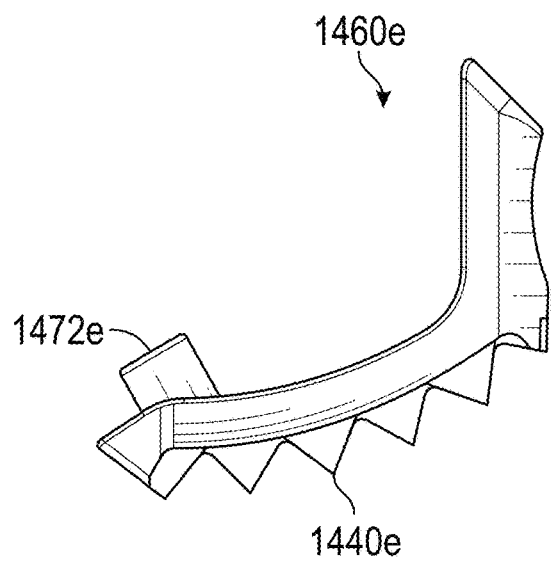

FIG. 56L illustrates a second side view of the of FIG. 56H.

Figure 56M:
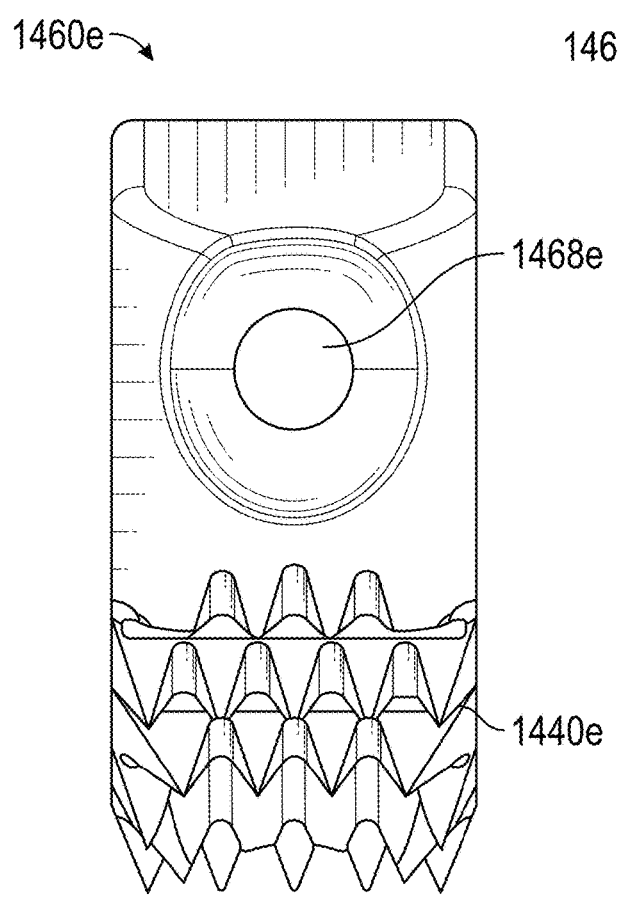

FIG. 56M illustrates a front view of the cover of FIG. 56H.

Figure 56N:
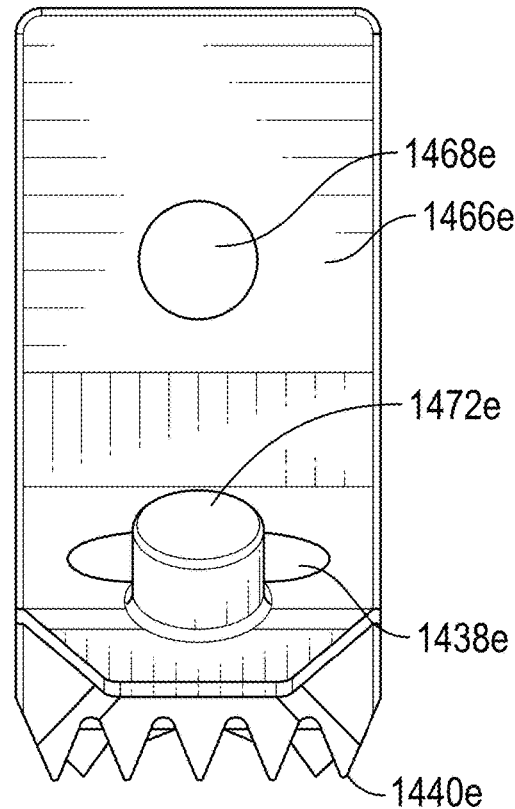

FIG. 56N illustrates a rear view of the cover of FIG. 56H.

Figure 57A:
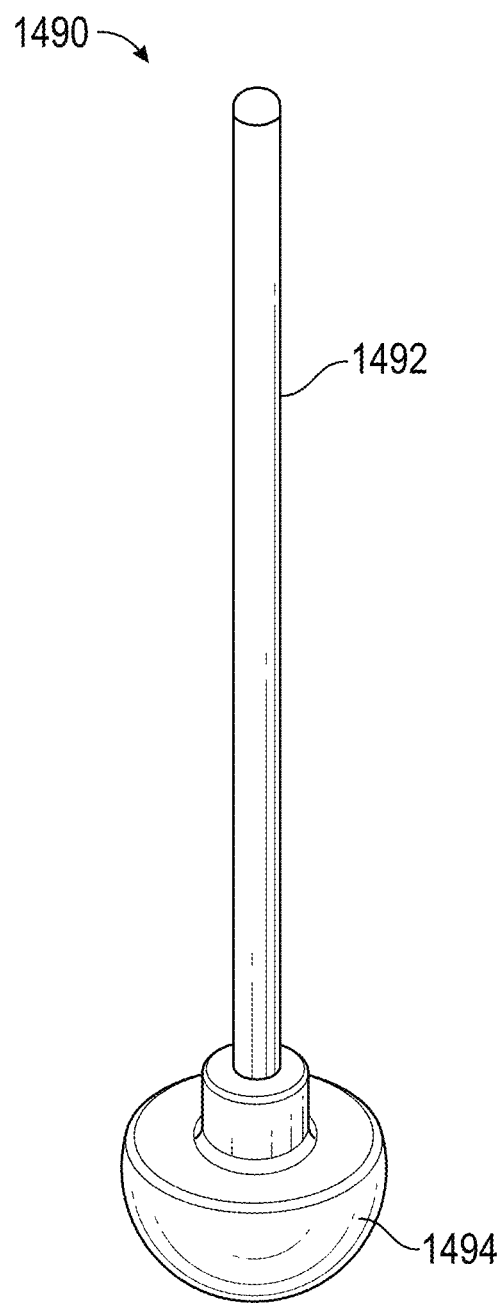

FIG. 57A illustrates a perspective view of an embodiment of an attachment for a pusher.

Figure 57B:
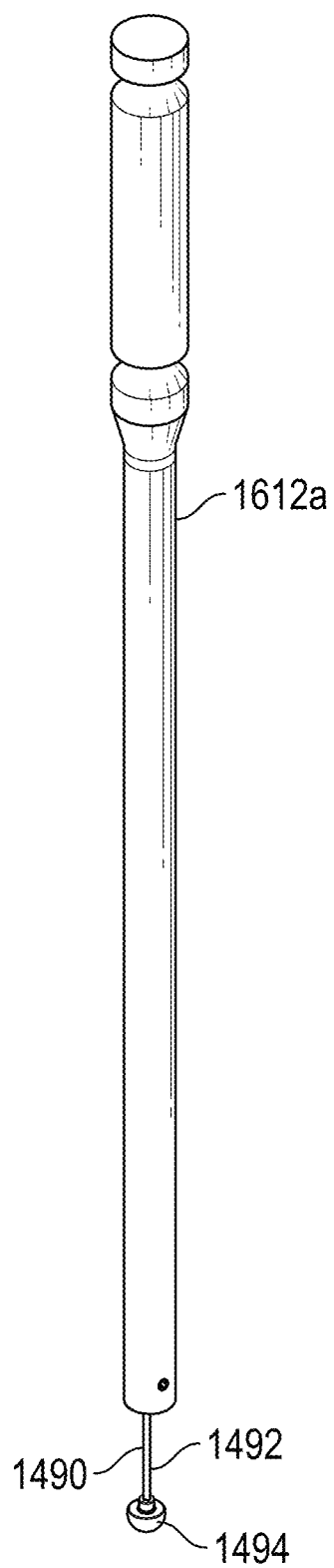

FIG. 57B illustrates a perspective view of the attachment of FIG. 57A coupled to a pusher.

Figure 57C:
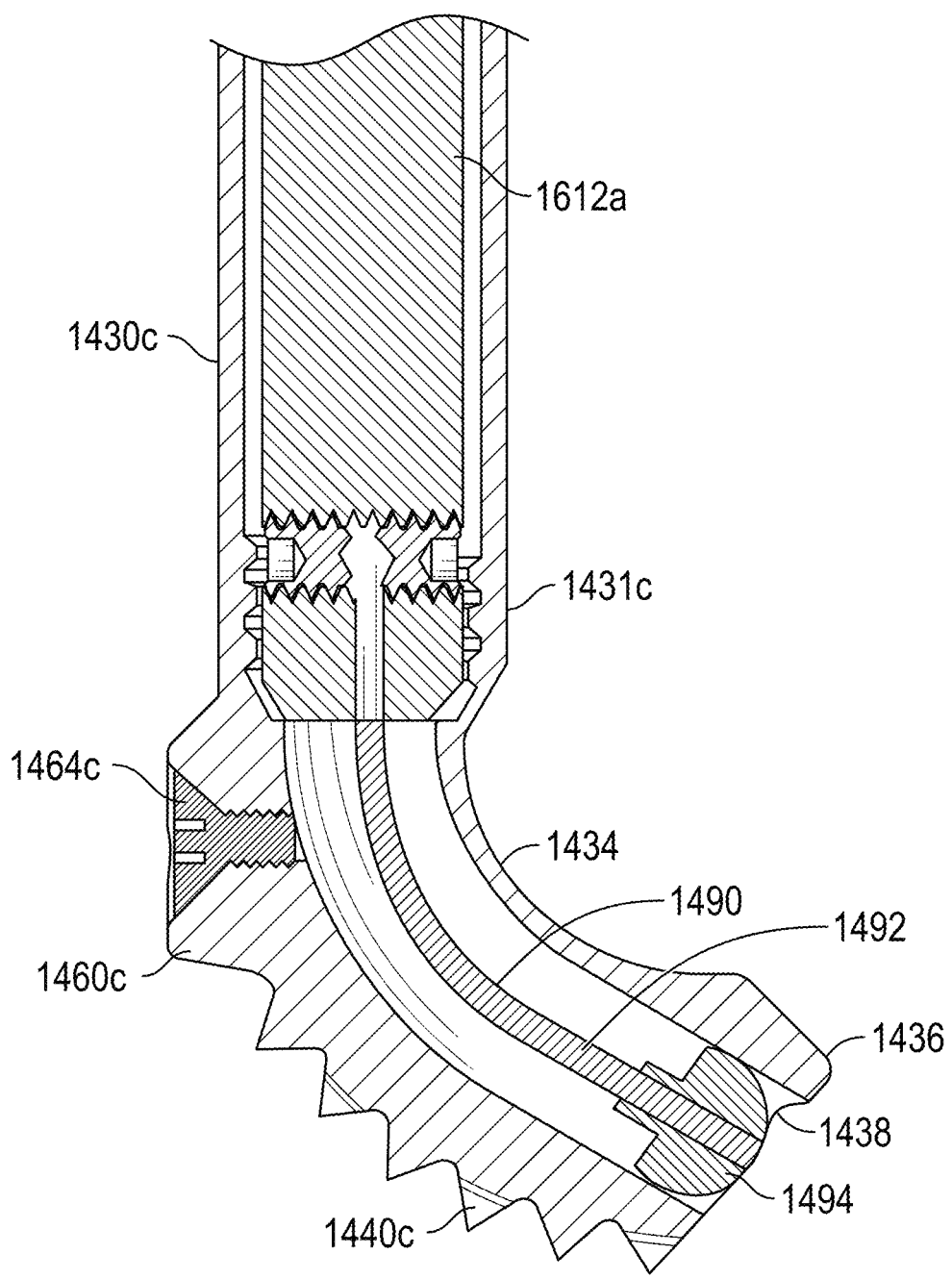

FIG. 57C illustrates an enlarged cross-sectional view of a portion of the pusher and attachment of FIG. 57B positioned within a portion of a rasp.

FIG. 58A illustrates a perspective view of an embodiment of a rasp.

FIG. 58B illustrates a cross-sectional view of the rasp of FIG. 58A.

Figure 59A:
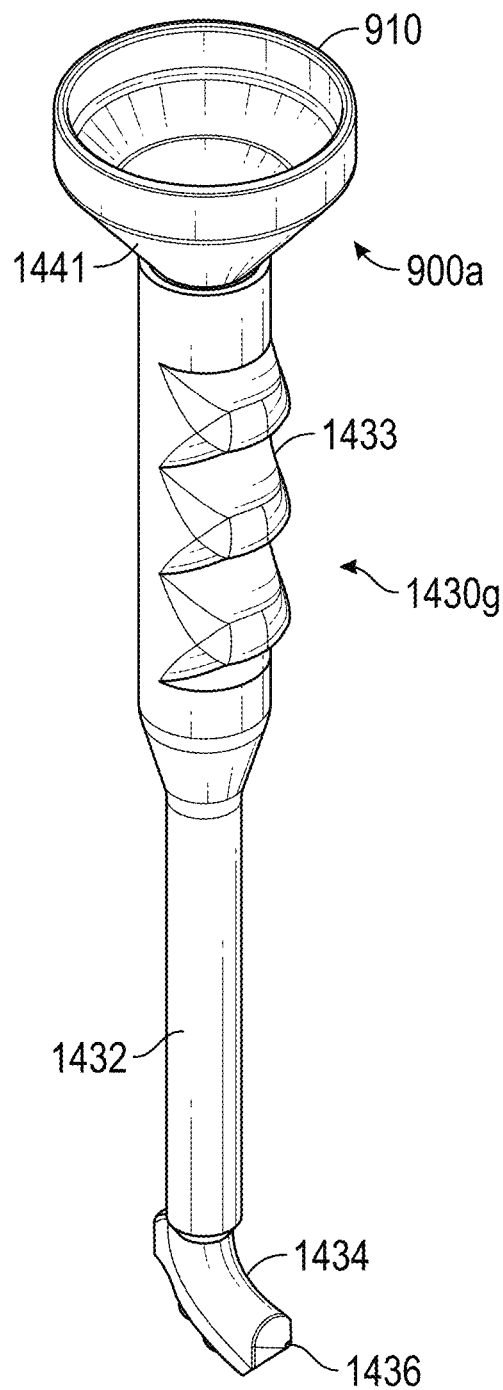

FIG. 59A illustrates a perspective view of an embodiment of a rasp.

Figure 59B:
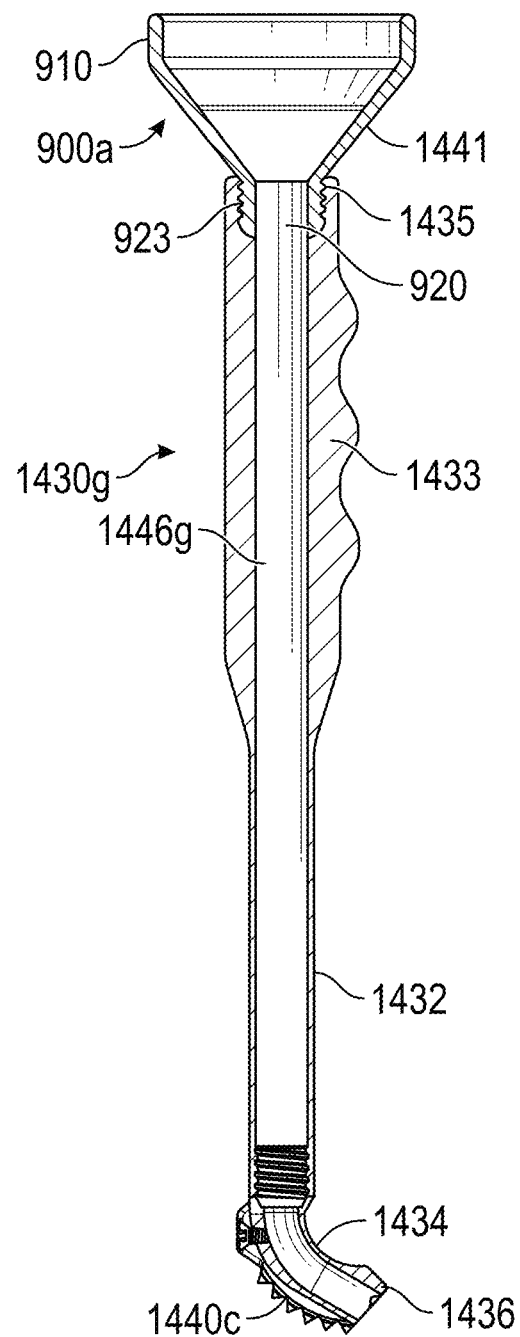

FIG. 59B illustrates a cross-sectional view of the rasp of FIG. 59A.

Figure 60A:
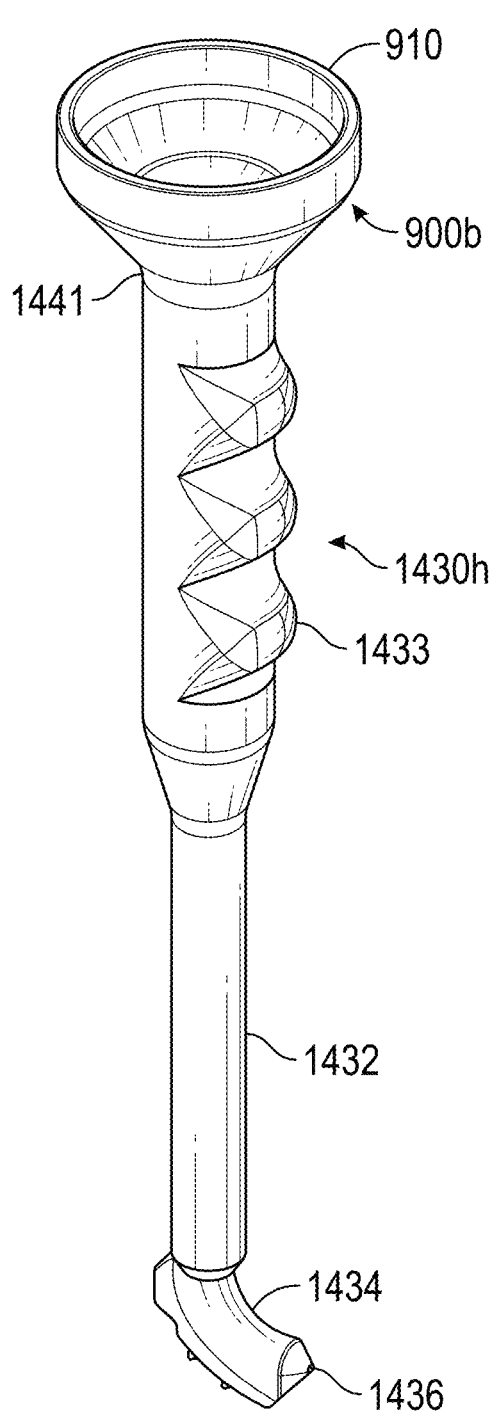

FIG. 60A illustrates a perspective view of an embodiment of a rasp.

Figure 60B:
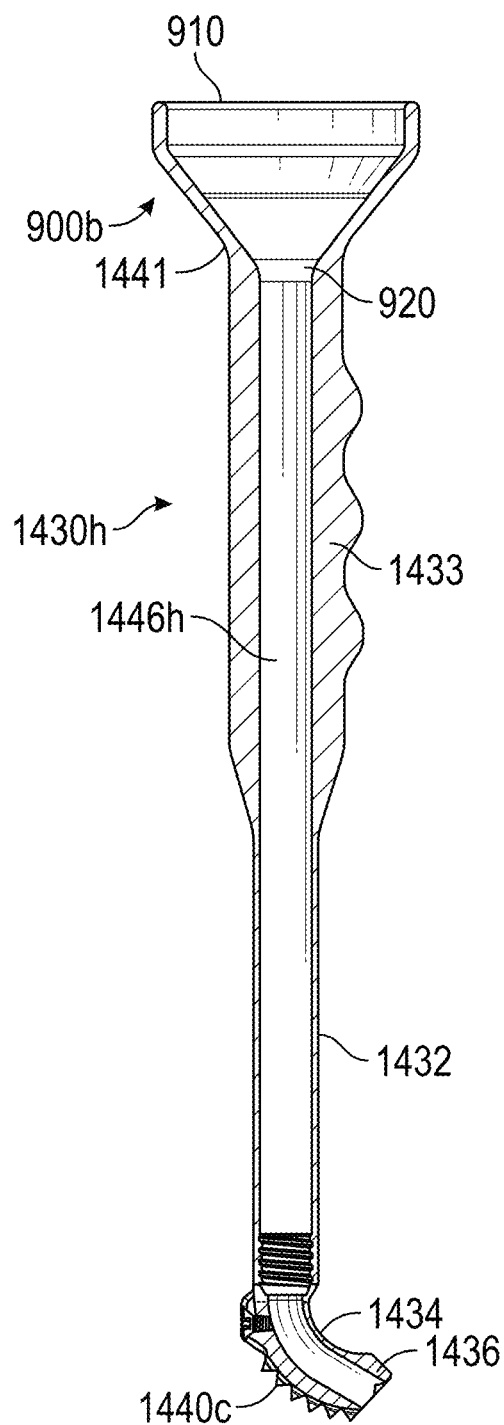

FIG. 60B illustrates a cross-sectional view of the rasp of FIG. 60A.

Figure 61A:
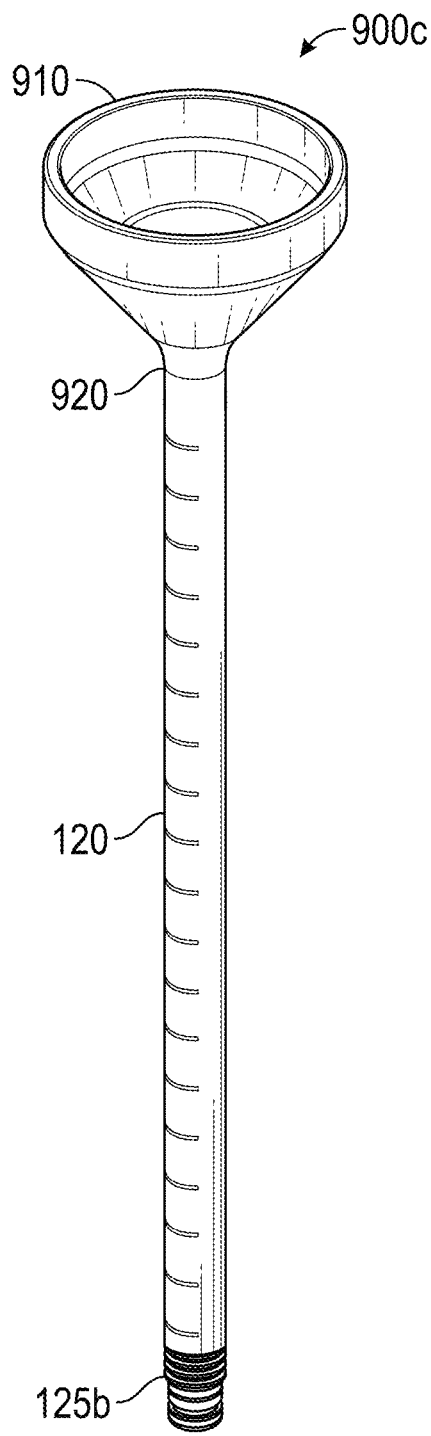

FIG. 61A illustrates a perspective view of an embodiment of a funnel coupled to a tube.

Figure 61B:
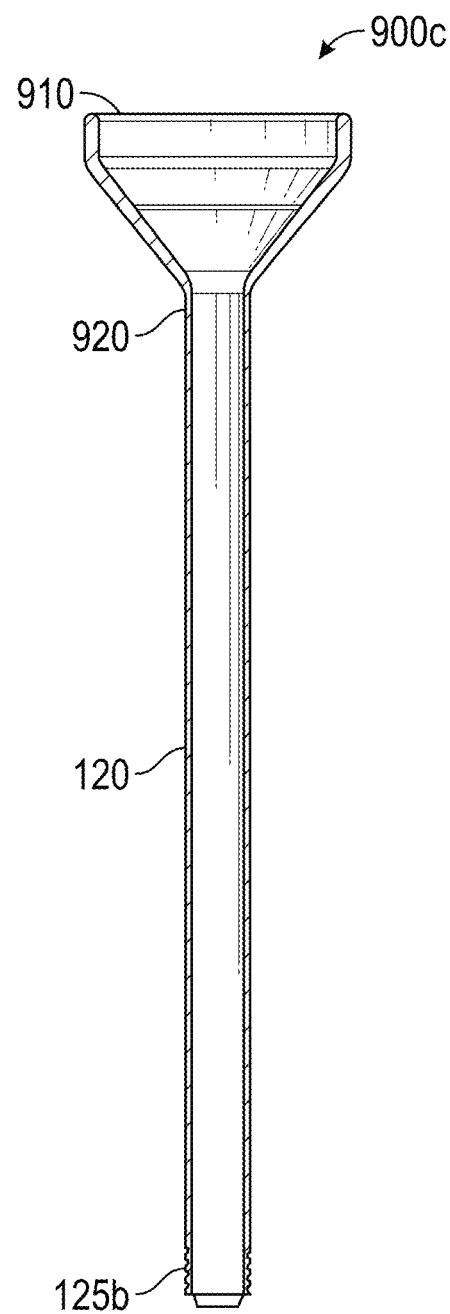

FIG. 61B illustrates a cross-sectional view of the funnel and tube of FIG. 61A.

Figure 62A:
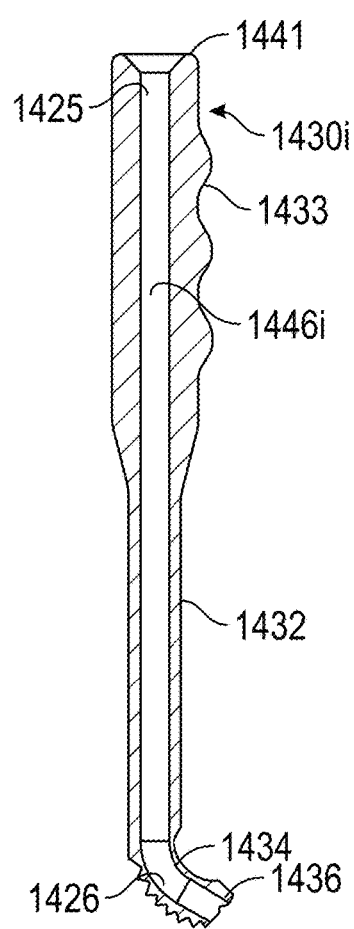

FIG. 62A illustrates a cross-sectional view of an embodiment of a rasp.

Figure 62B:
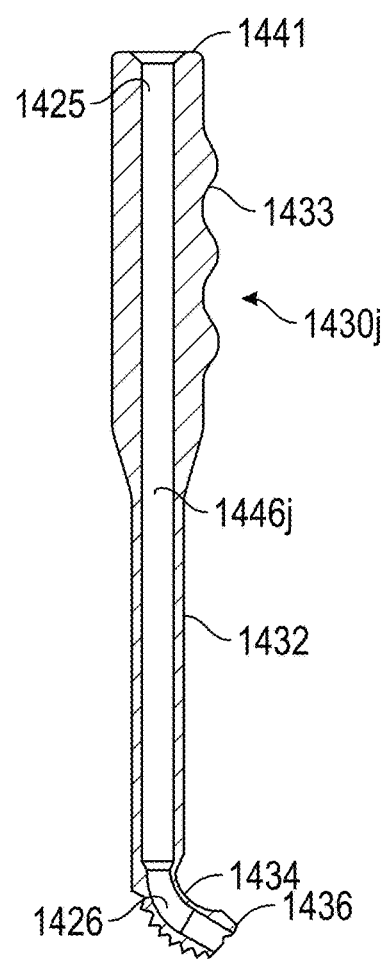

FIG. 62B illustrates a cross-sectional view of an embodiment of a rasp.

Figure 62C:
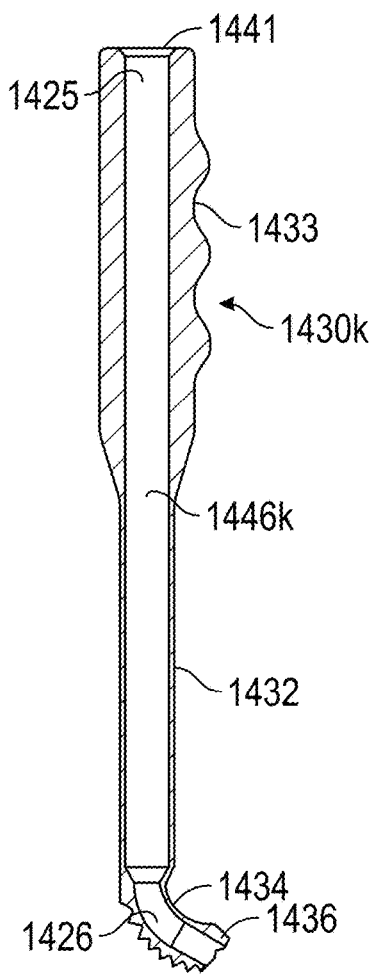

FIG. 62C illustrates a cross-sectional view of an embodiment of a rasp.

Figure 63A:
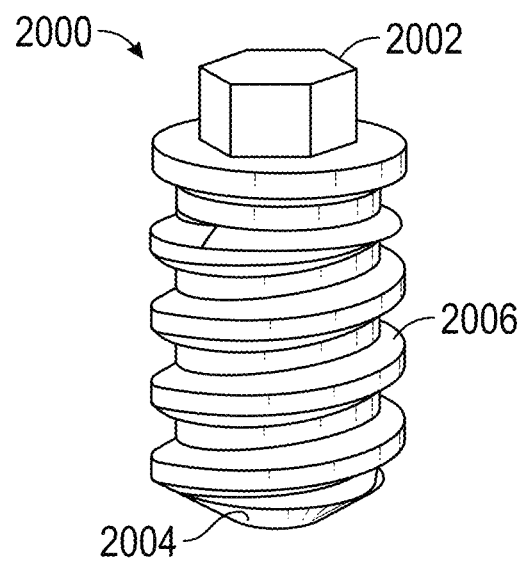

FIG. 63A illustrates a perspective view of an embodiment of an implant.

Figure 63B:
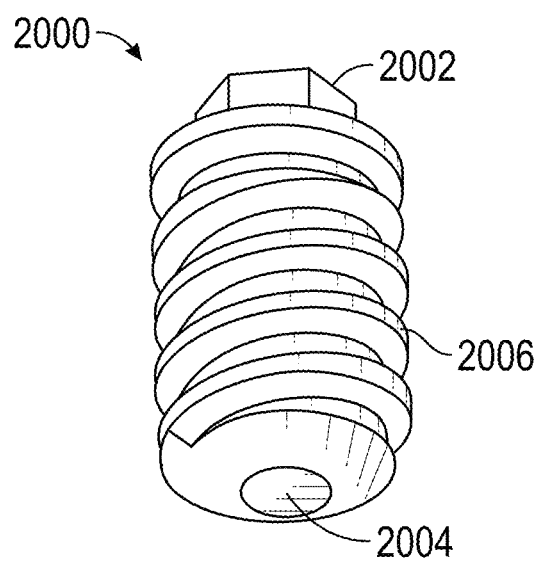

FIG. 63B illustrates another perspective view of the implant of FIG. 63A.

Figure 63C:
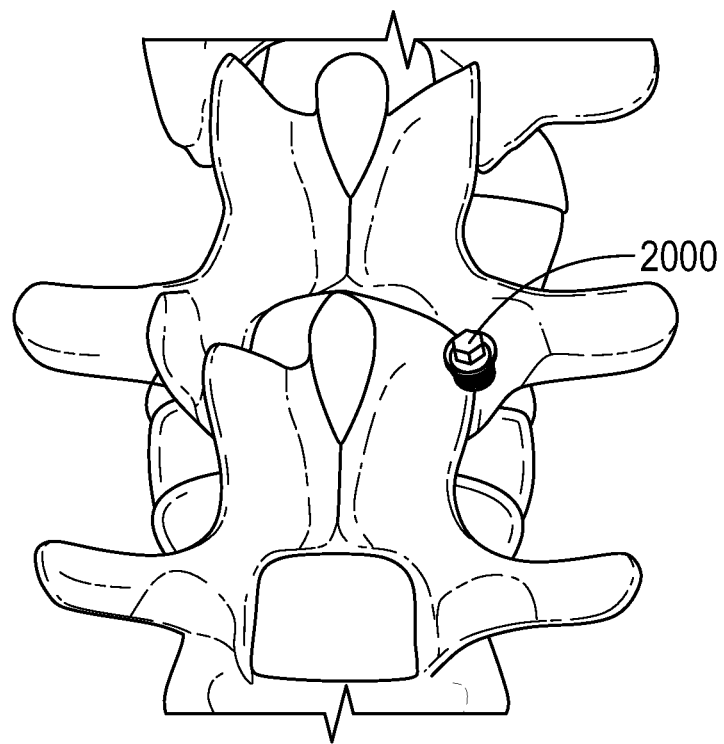

FIG. 63C illustrates a perspective view of the implant of FIG. 63A positioned in a surgical location.

Figure 64A:
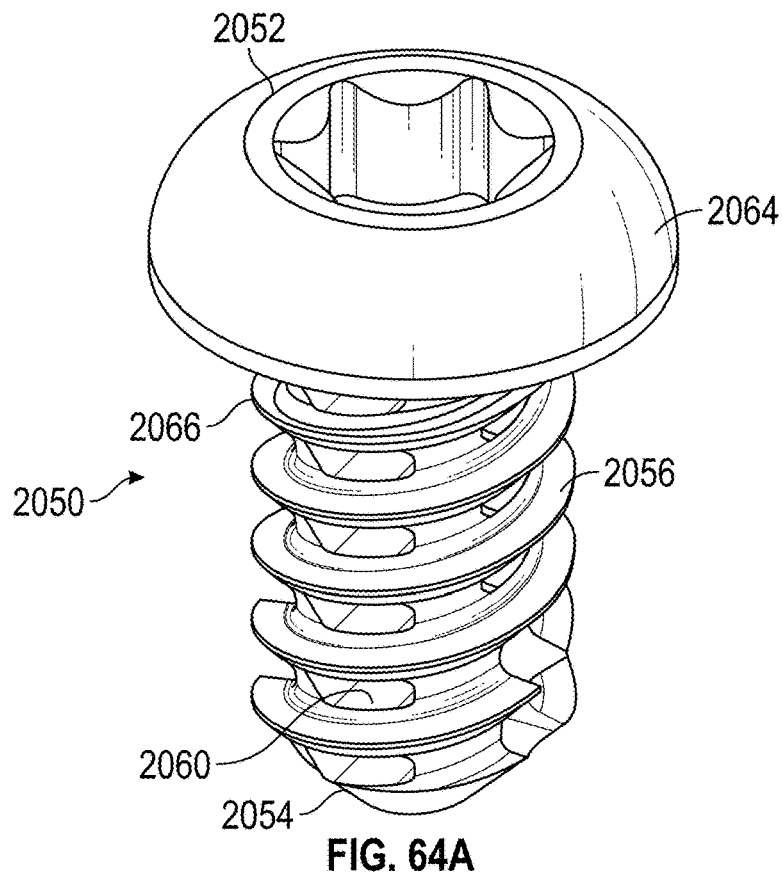

FIG. 64A illustrates a perspective view of an embodiment of an implant.

Figure 64B:
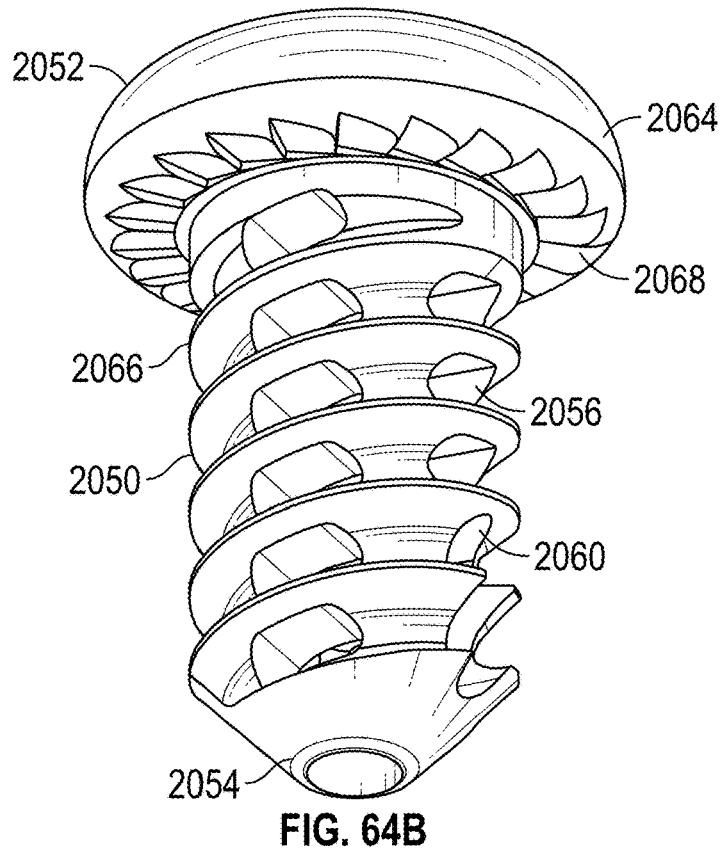

FIG. 64B illustrates another perspective view of the implant of FIG. 64A.

Figure 64C:
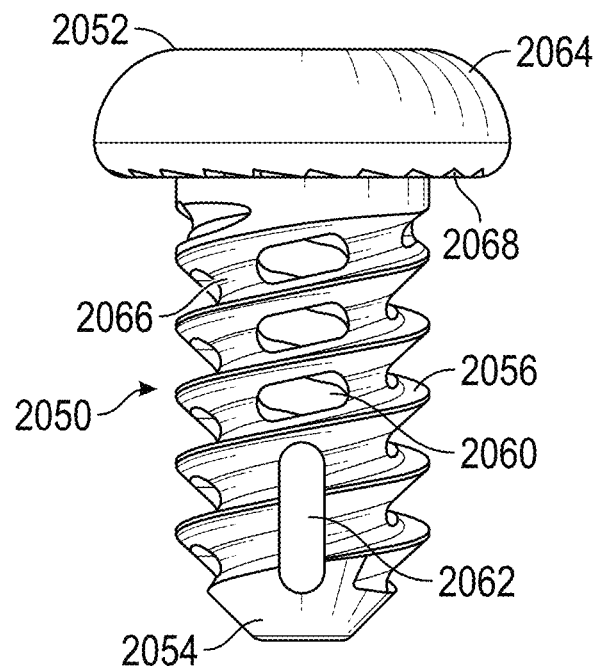

FIG. 64C illustrates a side view of the implant of FIG. 64A.

Figure 64D:
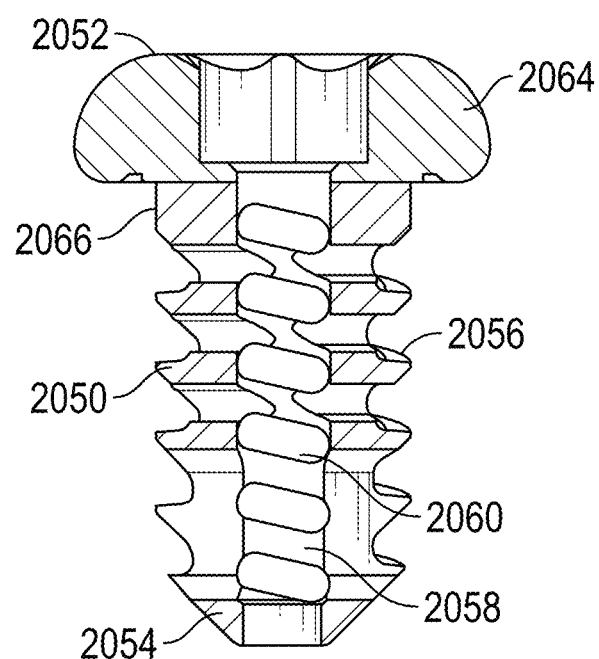

FIG. 64D illustrates a cross-sectional view of the implant of FIG. 64A.

Figure 64E:
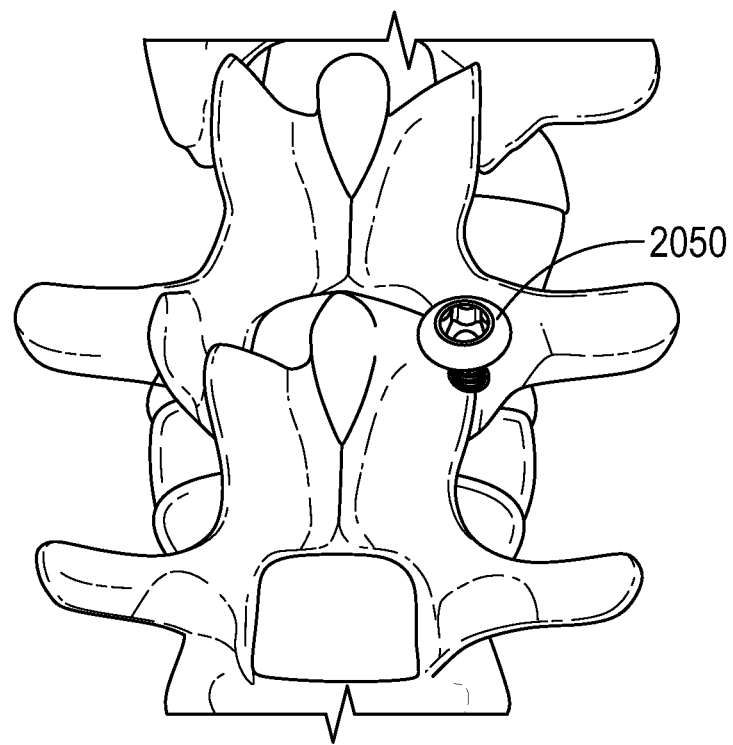

FIG. 64E illustrates a perspective view of the implant of FIG. 64A positioned in a surgical location.

Figure 65A:
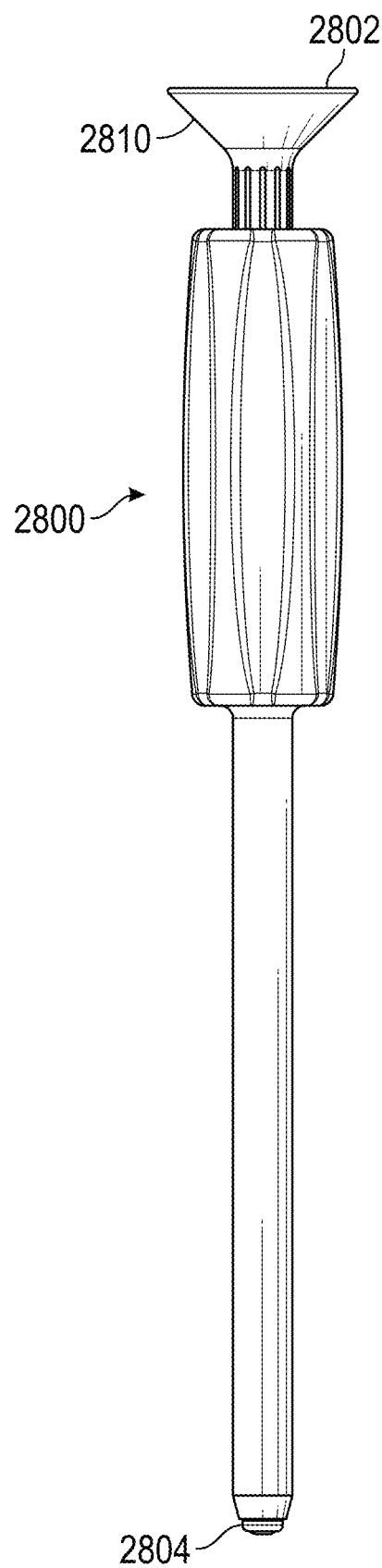

FIG. 65A illustrates a front view of an embodiment of an inserter.

Figure 65B:
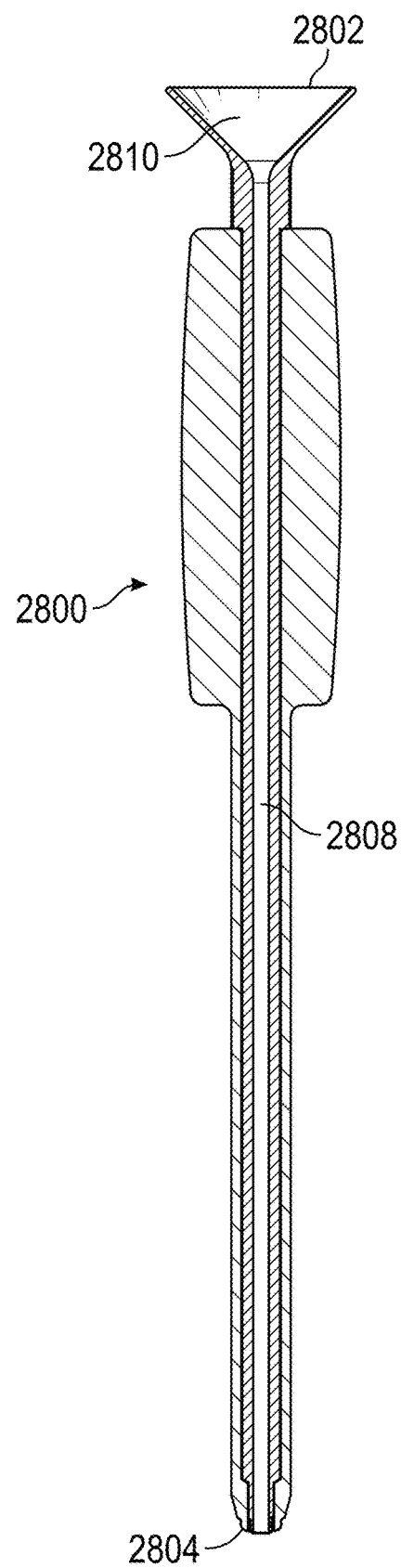

FIG. 65B illustrates a cross-sectional view of the inserter of FIG. 65A.

Figure 66A:
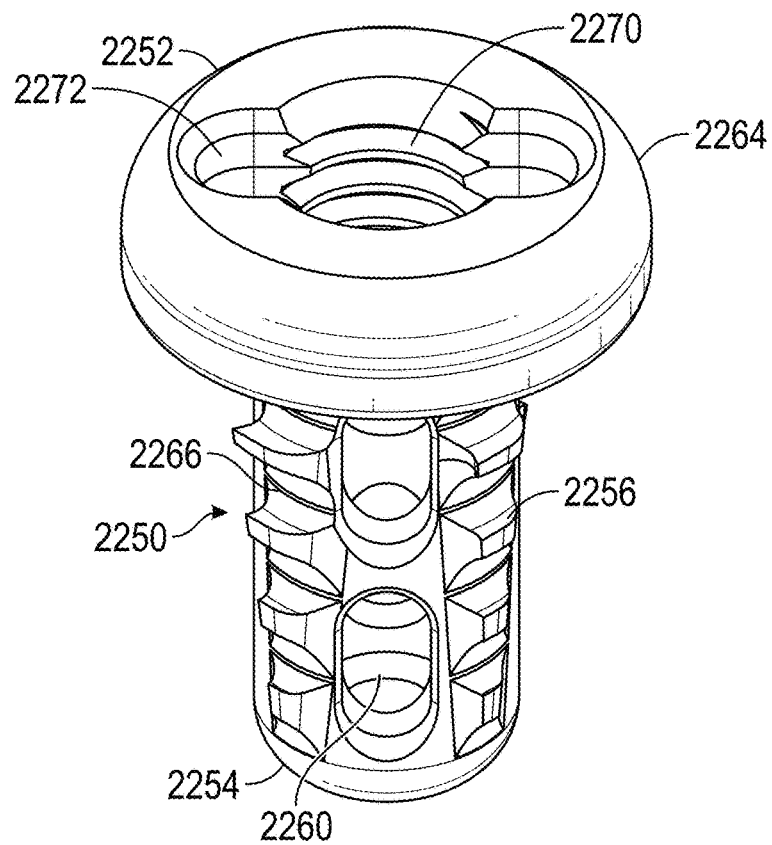

FIG. 66A illustrates a perspective view of an embodiment of an implant.

Figure 66B:
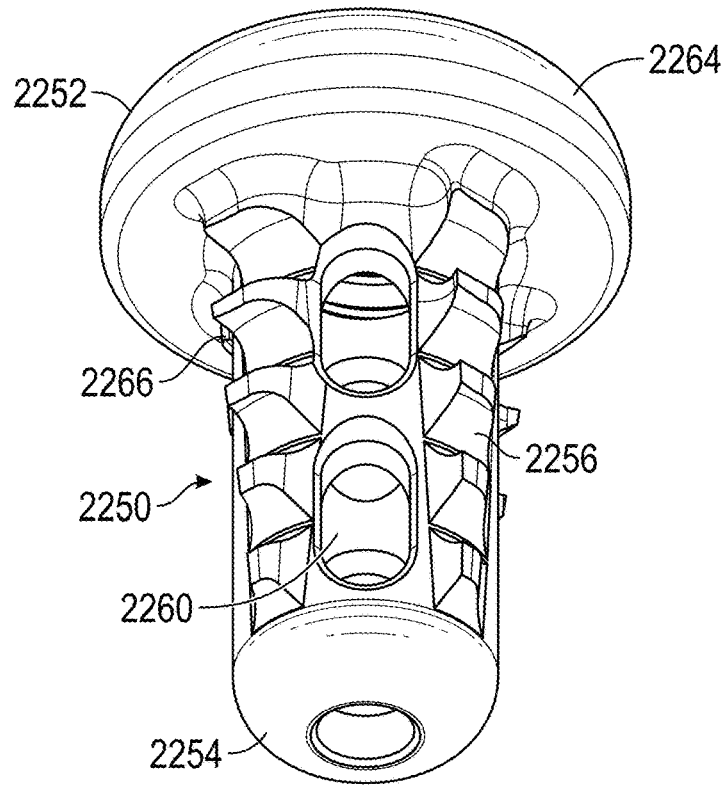

FIG. 66B illustrates another perspective view of the implant of FIG. 66A.

Figure 66C:
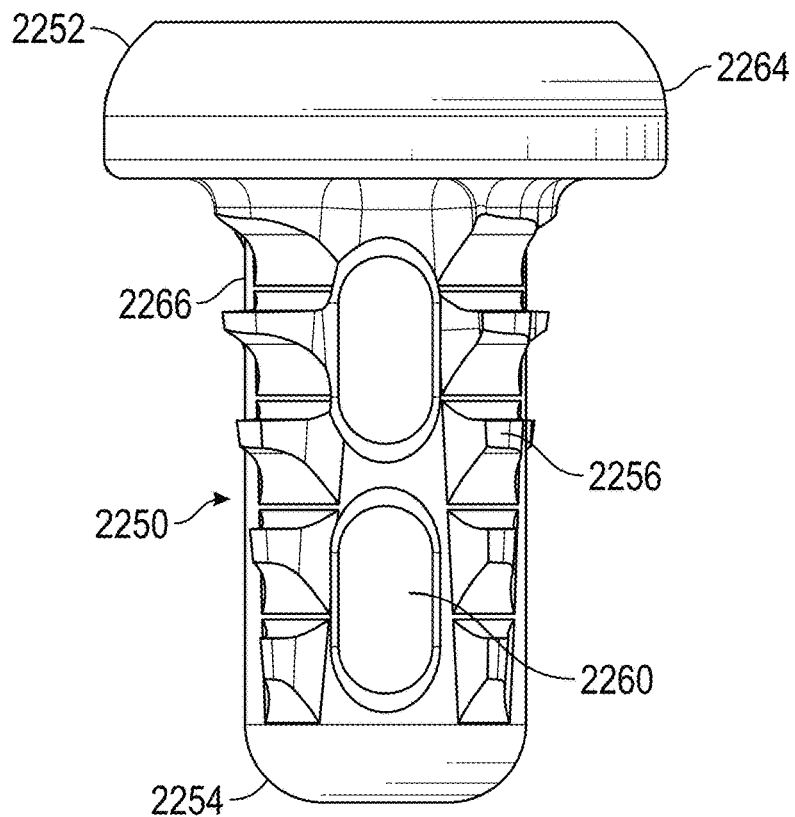

FIG. 66C illustrates a side view of the implant of FIG. 66A.

Figure 66D:
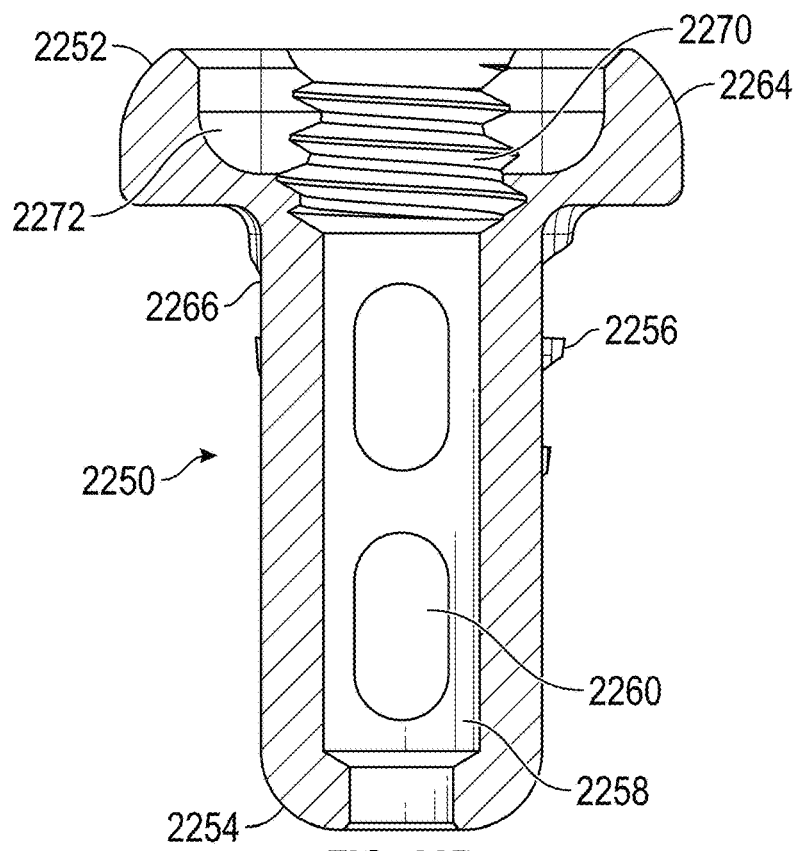

FIG. 66D illustrates a cross-sectional view of the implant of FIG. 66A.

Figure 66E:
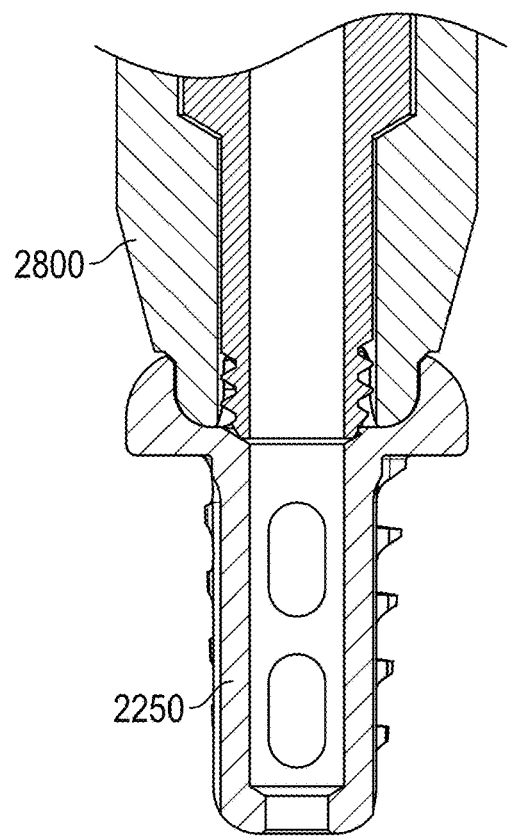

FIG. 66E illustrates a cross-sectional view of the implant of FIG. 66A coupled to the inserter of FIG. 65A.

Figure 67A:
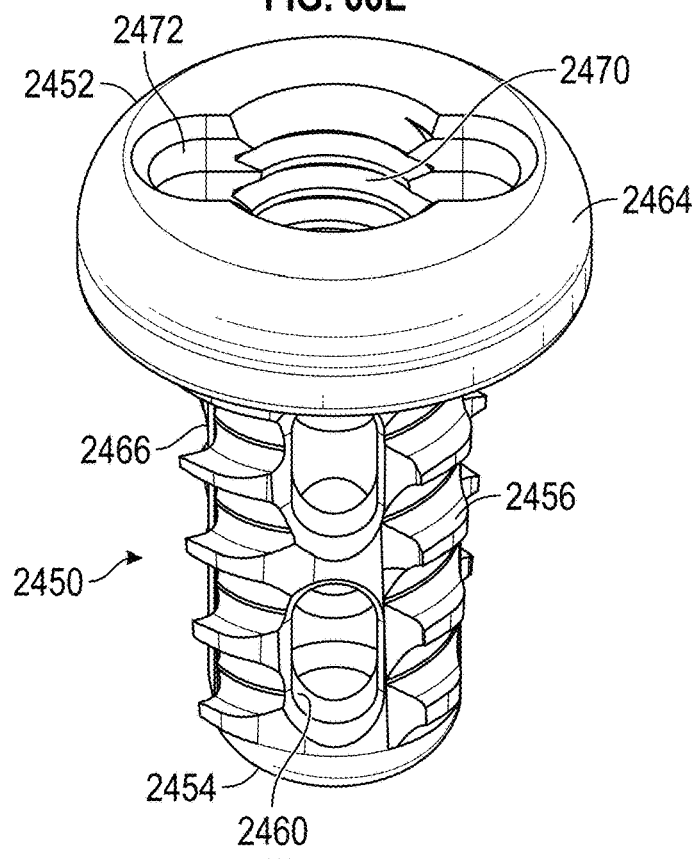

FIG. 67A illustrates a perspective view of an embodiment of an implant.

Figure 67B:
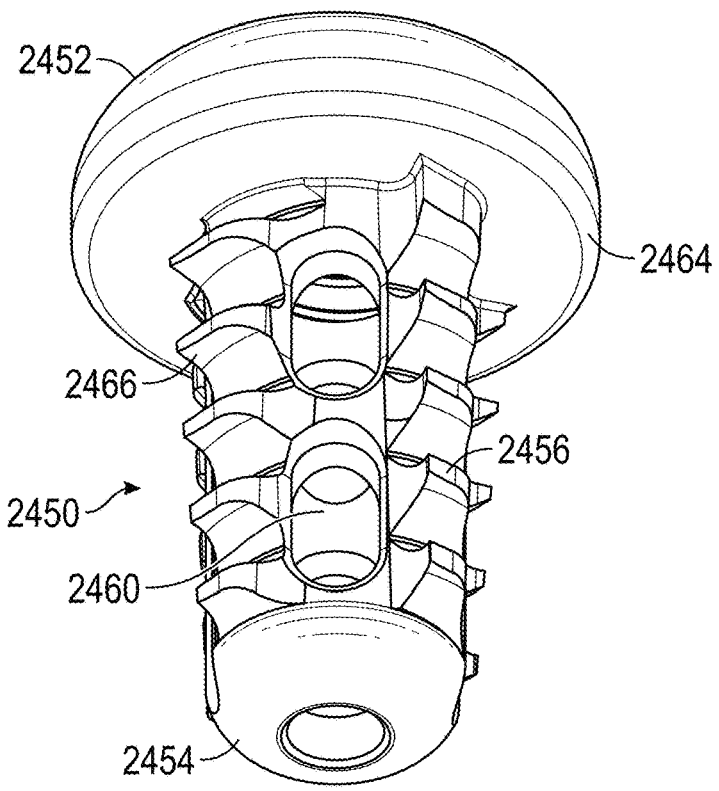

FIG. 67B illustrates another perspective view of the implant of FIG. 67A.

Figure 67C:
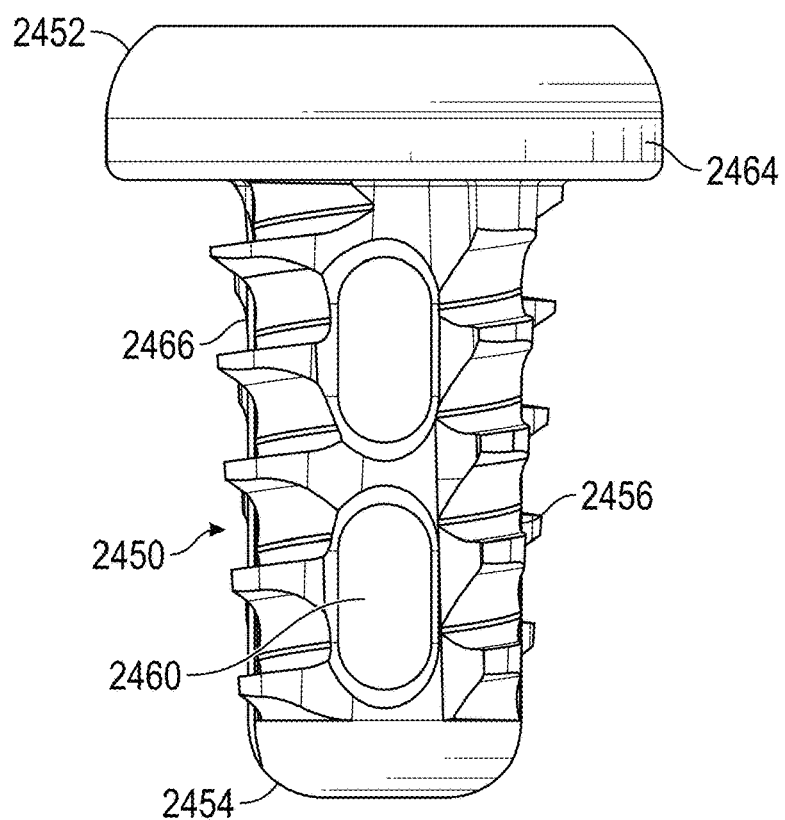

FIG. 67C illustrates a side view of the implant of FIG. 67A.

Figure 67D:
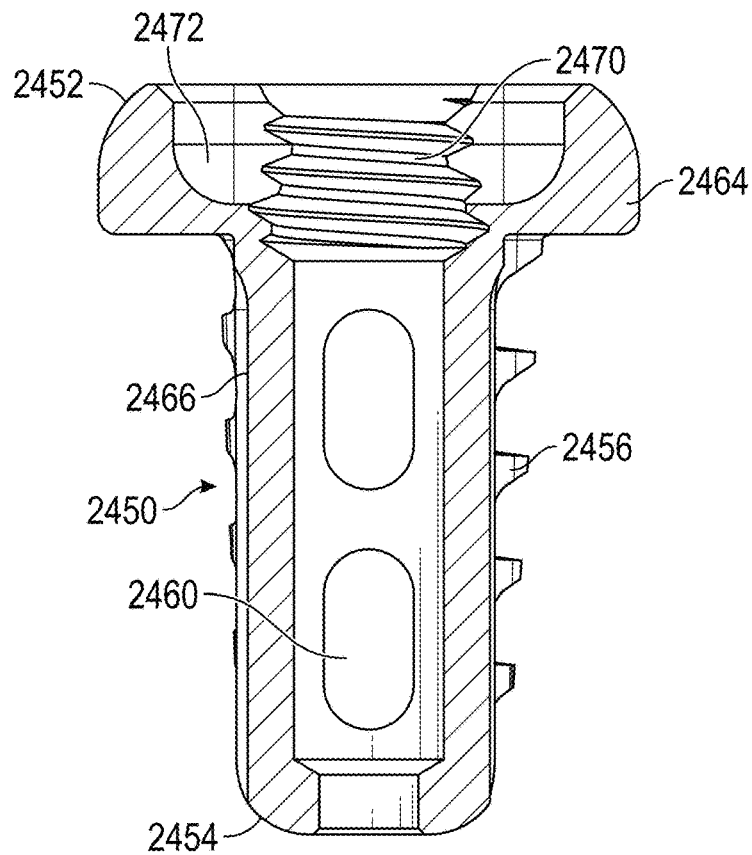

FIG. 67D illustrates a cross-sectional view of the implant of FIG. 67A.

Figure 67E:
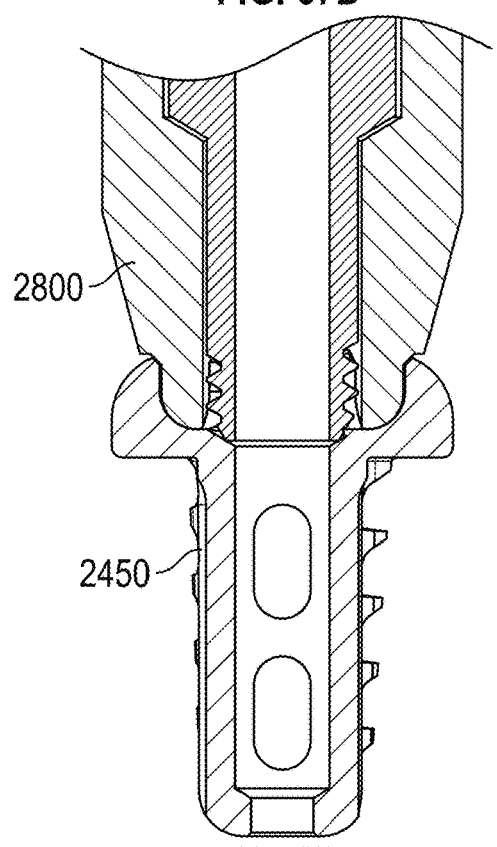

FIG. 67E illustrates a cross-sectional view of the implant of FIG. 67A coupled to the inserter of FIG. 65A.

Figure 68A:
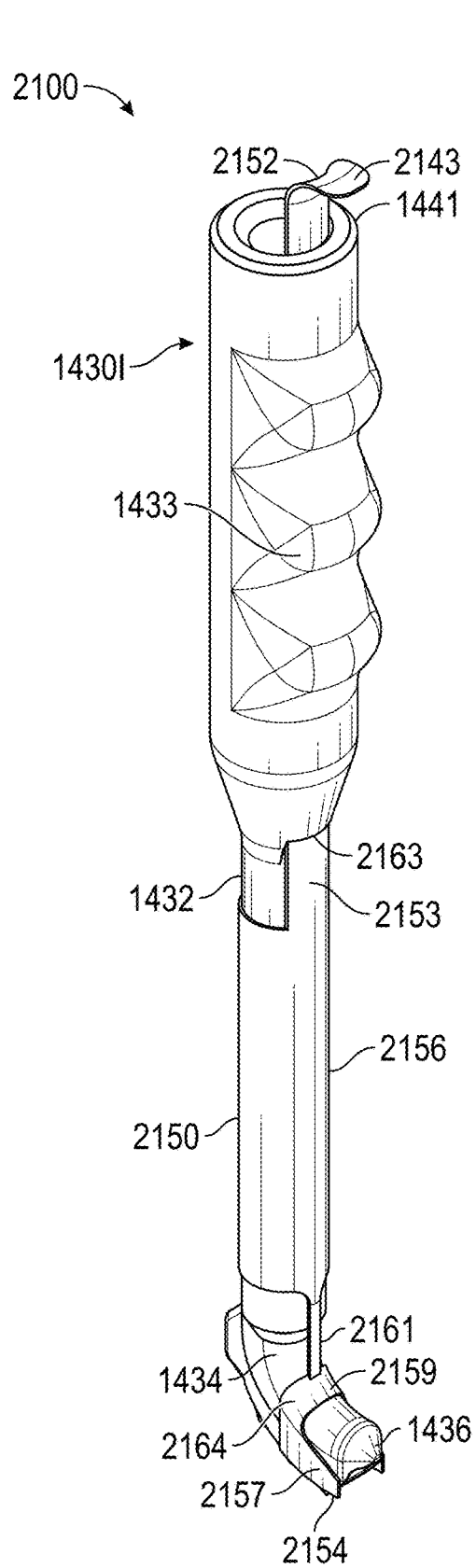

FIG. 68A illustrates a perspective view of an embodiment of a rasping system.

Figure 68B:
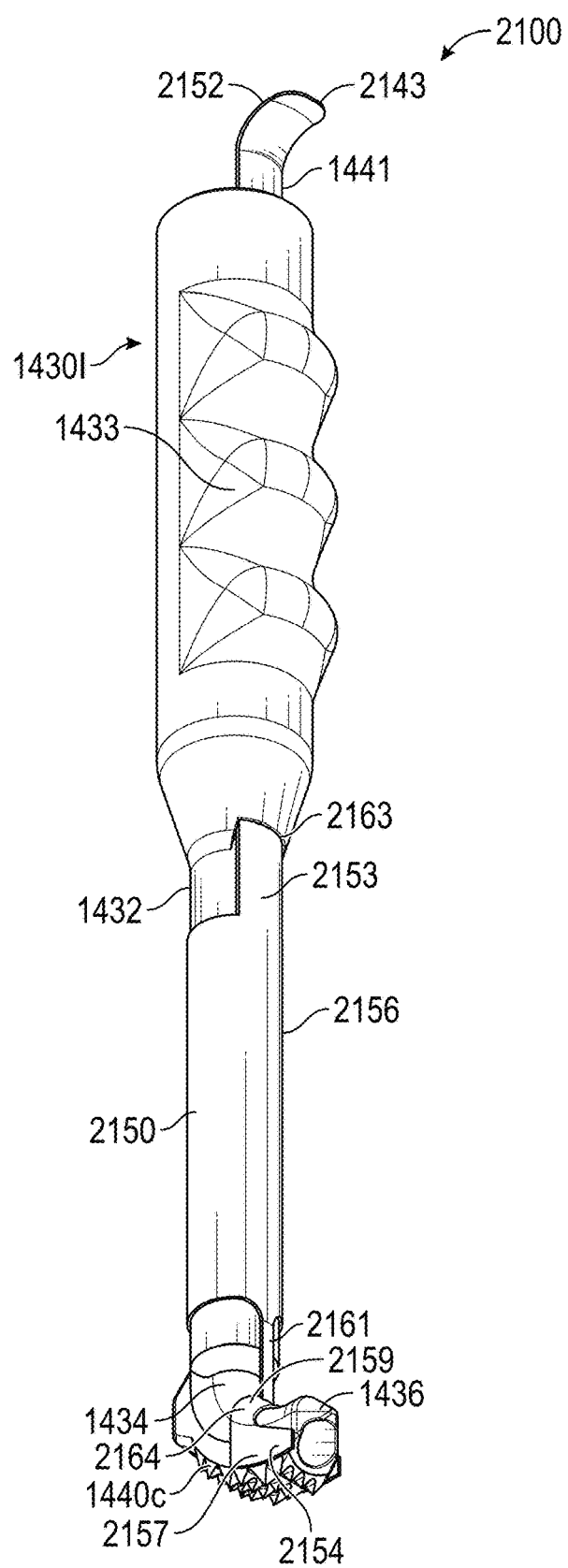

FIG. 68B illustrates another perspective view of the rasping system of FIG. 68A.

FIG. 68C illustrates another perspective view of the rasping system of FIG. 68A.

FIG. 68D illustrates another perspective view of the rasping system of FIG. 68A.

Figure 68E:
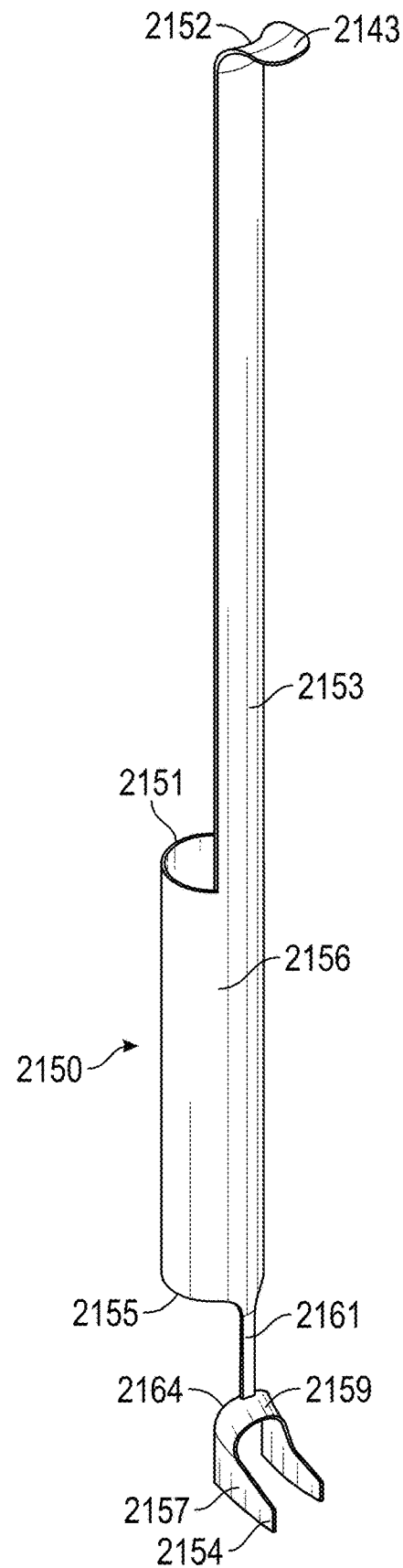

FIG. 68E illustrates a perspective view of a sheath of the rasping system of FIG. 68A.

Figure 69A:
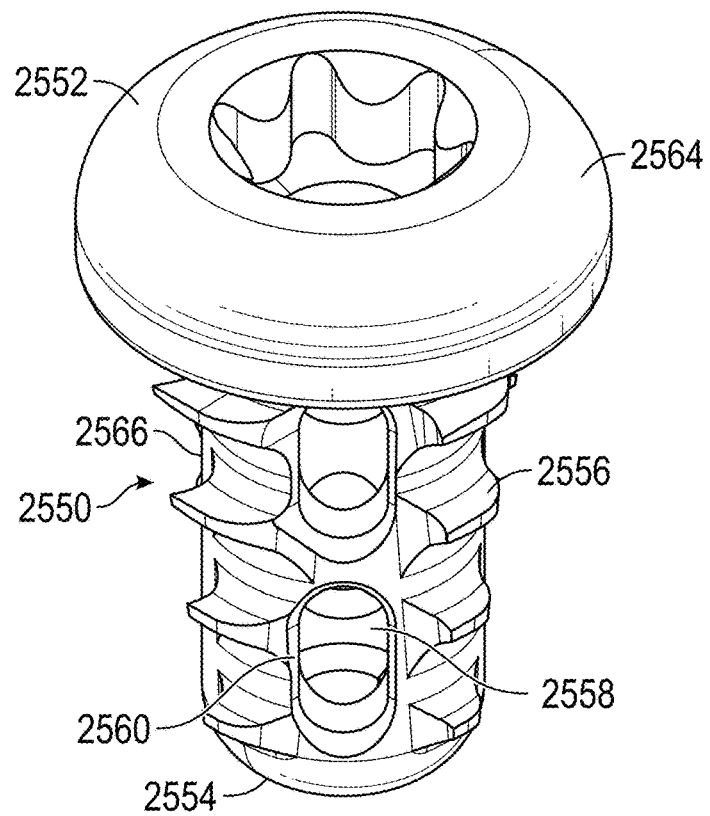

FIG. 69A illustrates a perspective of an embodiment of an implant.

Figure 69B:
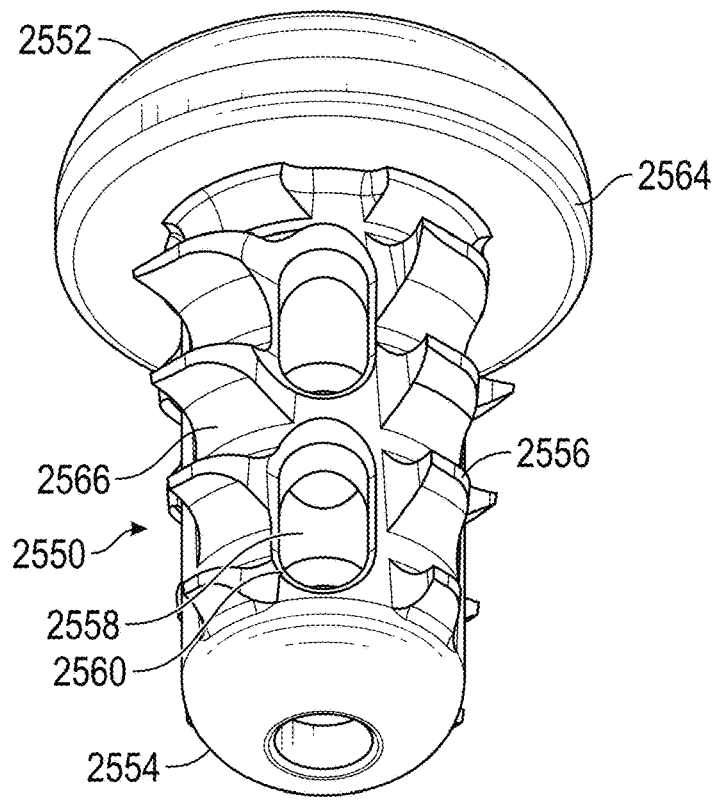

FIG. 69B illustrates another perspective view of the implant of FIG. 69A.

Figure 70A:
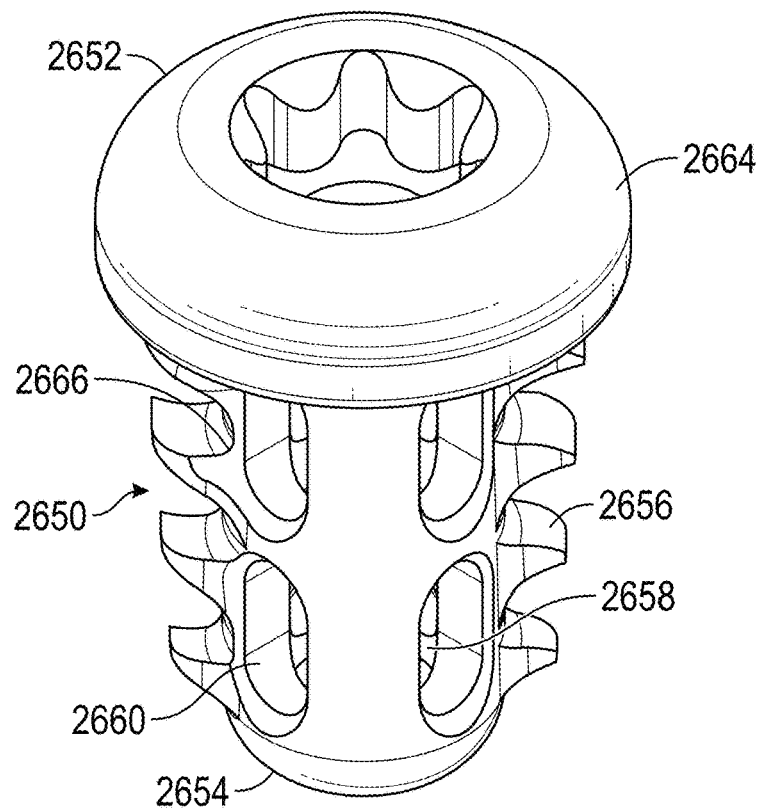

FIG. 70A illustrates a perspective of an embodiment of an implant.

Figure 70B:
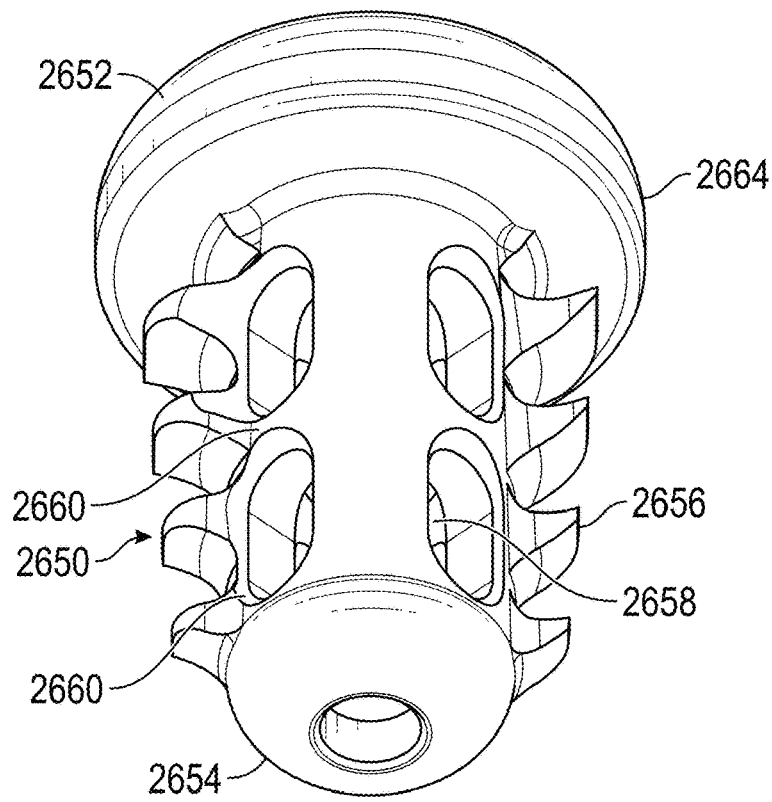

FIG. 70B illustrates another perspective view of the implant of FIG. 70A.

Figure 71A:
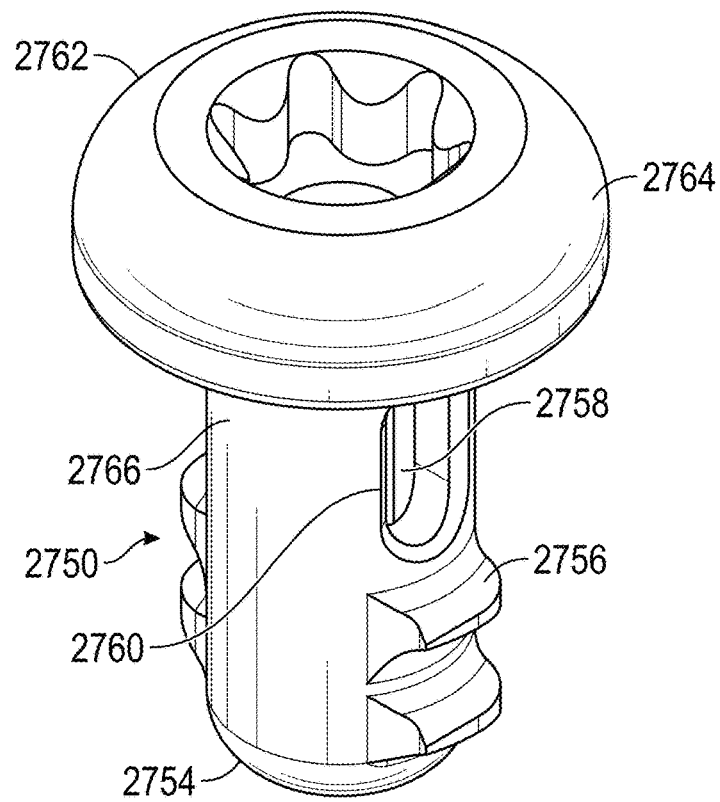

FIG. 71A illustrates a perspective of an embodiment of an implant.

Figure 71B:
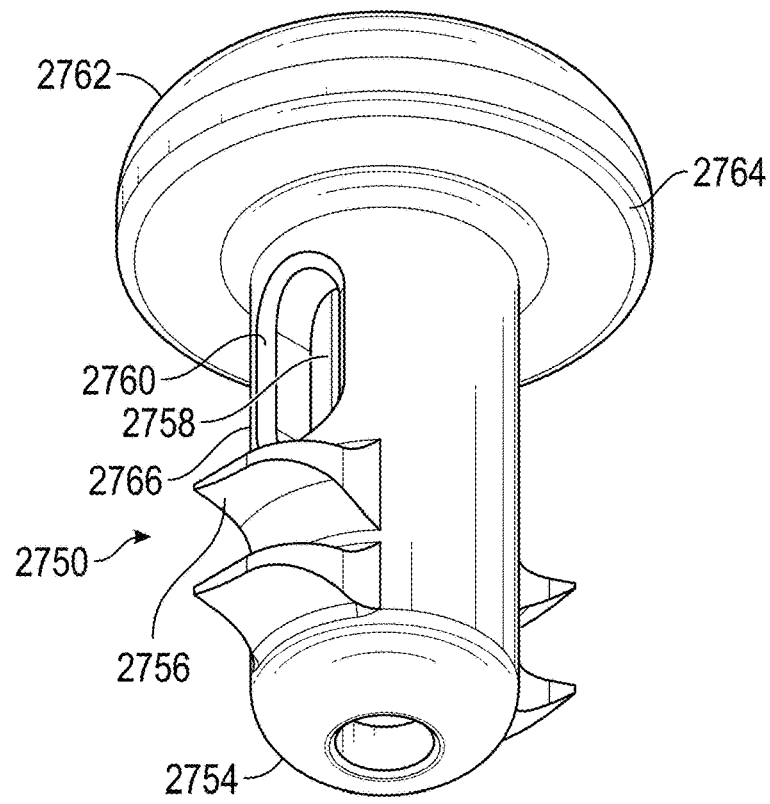

FIG. 71B illustrates another perspective view of the implant of FIG. 71A.

Figure 72A:
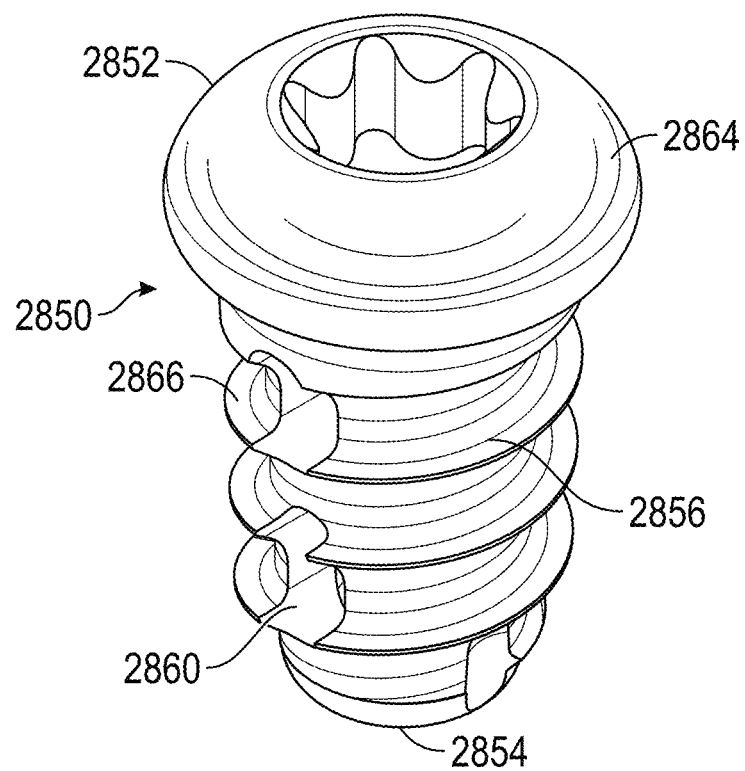

FIG. 72A illustrates a perspective of an embodiment of an implant.

Figure 72B:
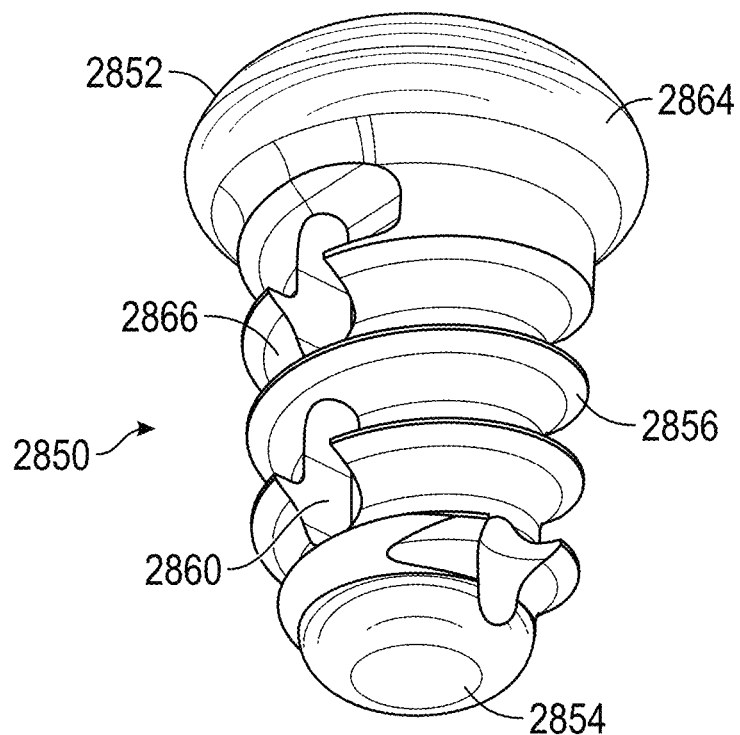

FIG. 72B illustrates another perspective view of the implant of FIG. 72A.

Figure 72C:
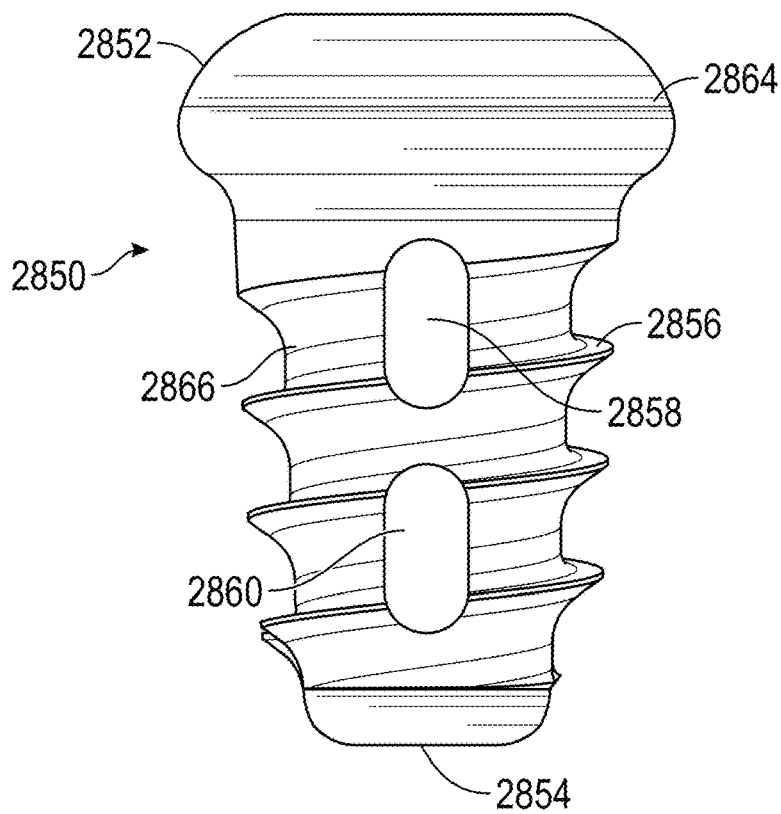

FIG. 72C illustrates a side view of the implant of FIG. 72A.

Figure 73A:
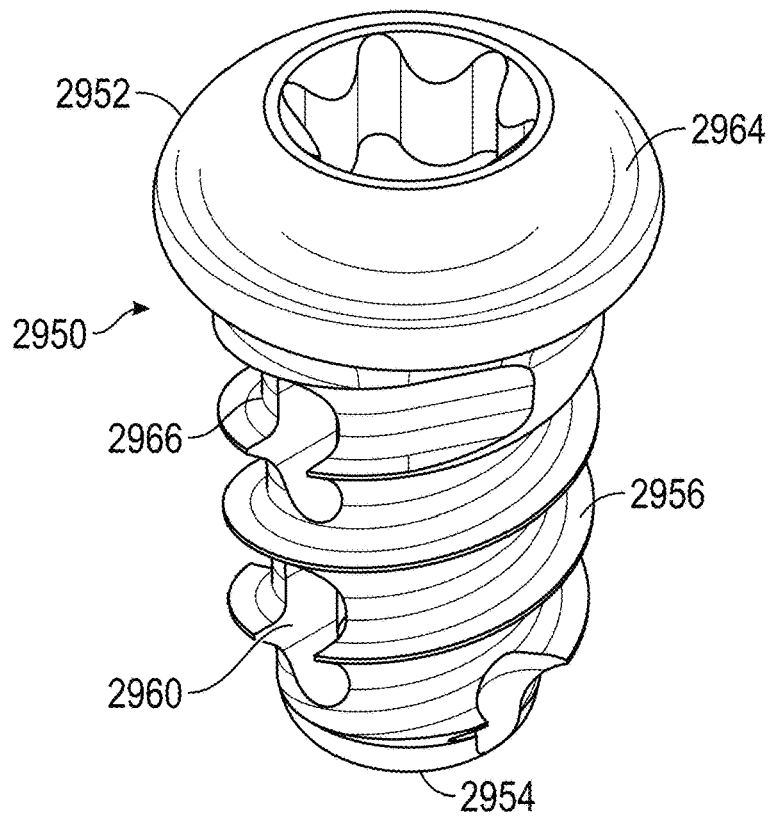

FIG. 73A illustrates a perspective of an embodiment of an implant.

Figure 73B:
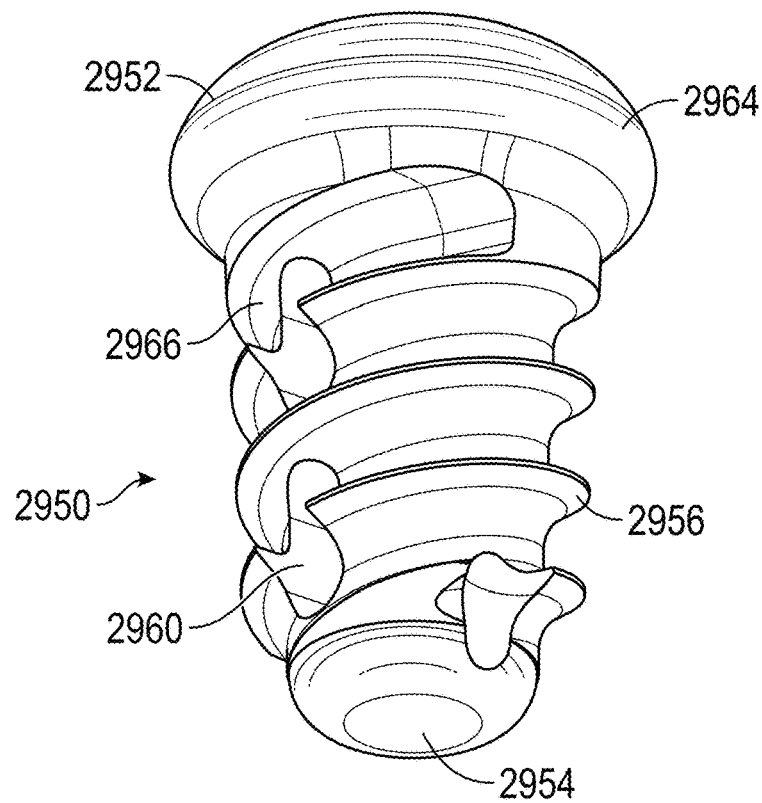

FIG. 73B illustrates another perspective view of the implant of FIG. 73A.

Figure 73C:
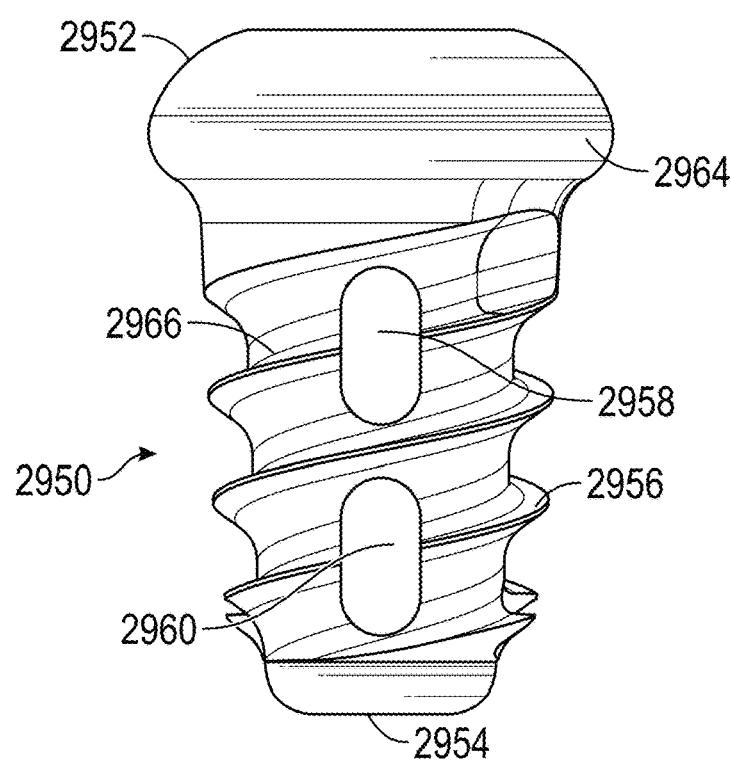

FIG. 73C illustrates a side view of the implant of FIG. 73A.

Figure 74A:
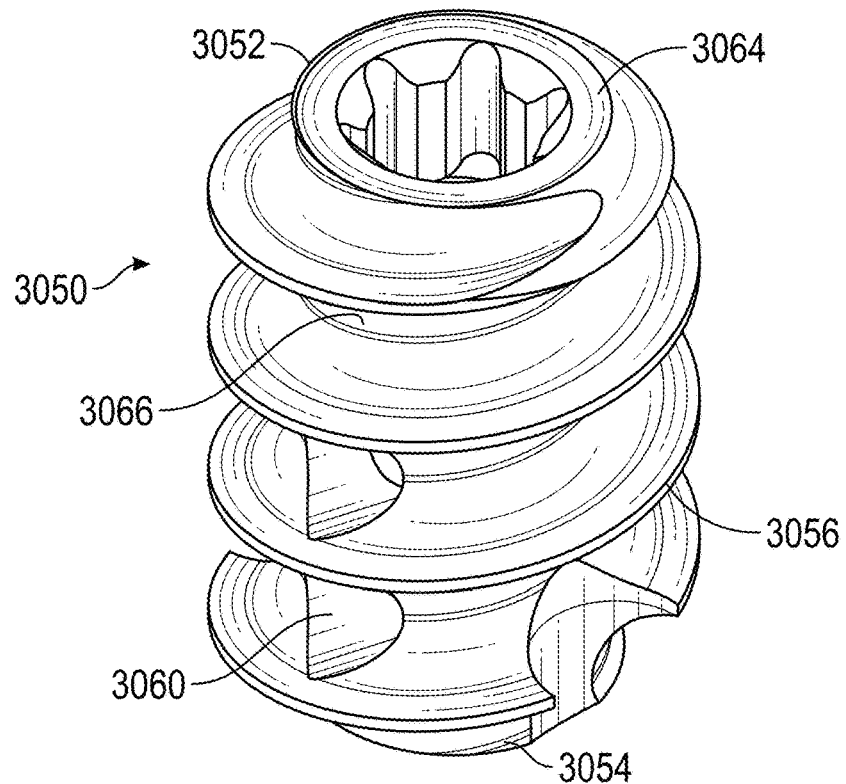

FIG. 74A illustrates a perspective of an embodiment of an implant.

Figure 74B:
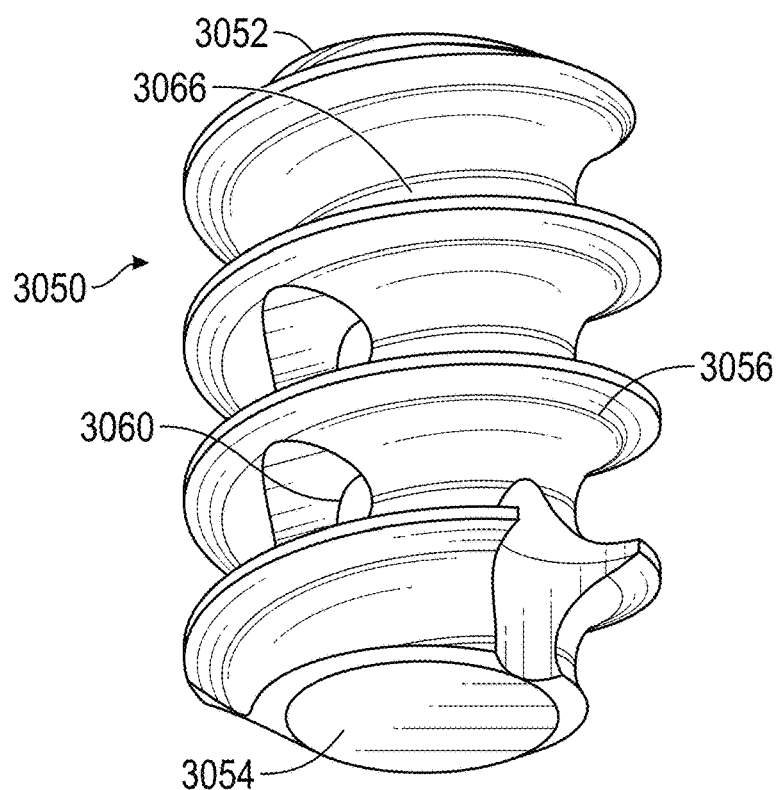

FIG. 74B illustrates another perspective view of the implant of FIG. 74A.

Figure 74C:
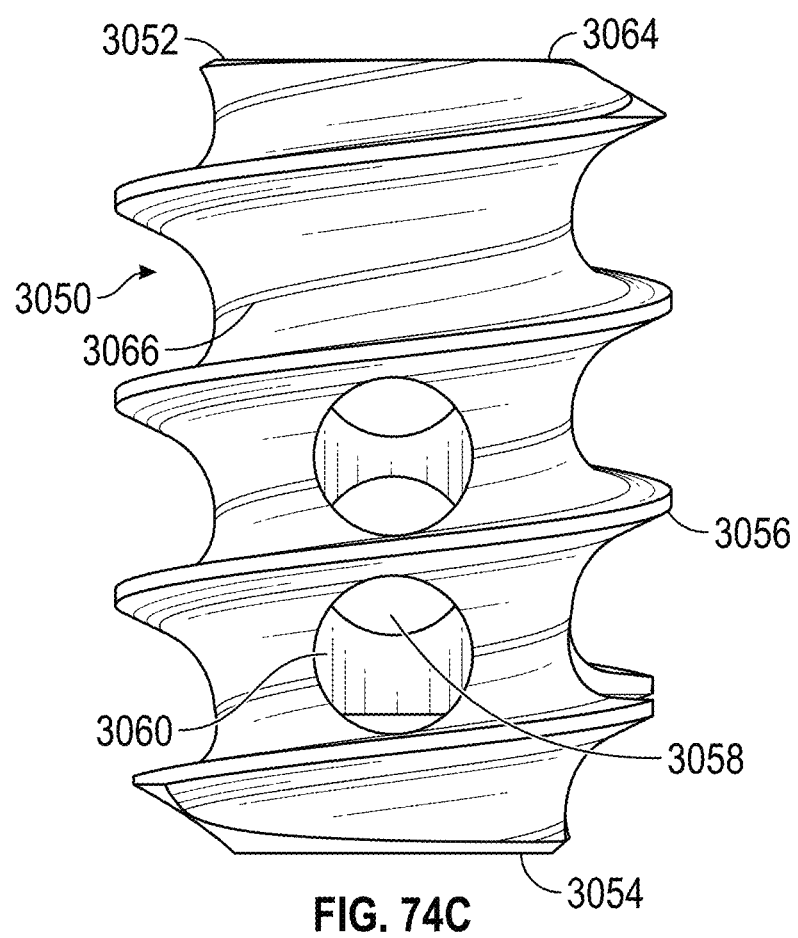

FIG. 74C illustrates a side view of the implant of FIG. 74A.

DETAILED DESCRIPTION

Figure 1A:
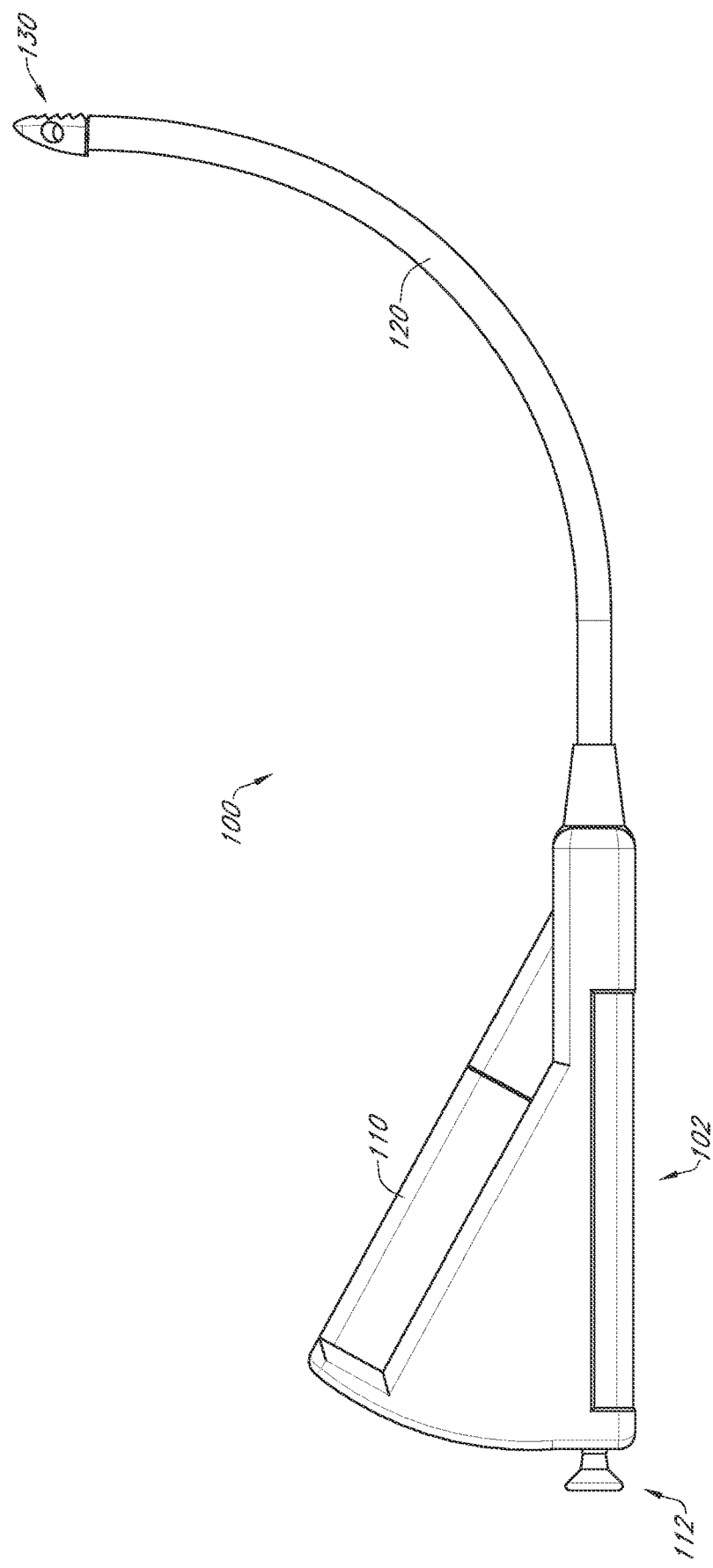
FIG. 1A illustrates a side view of an example embodiment of a bone graft delivery device.
Figure 1B:
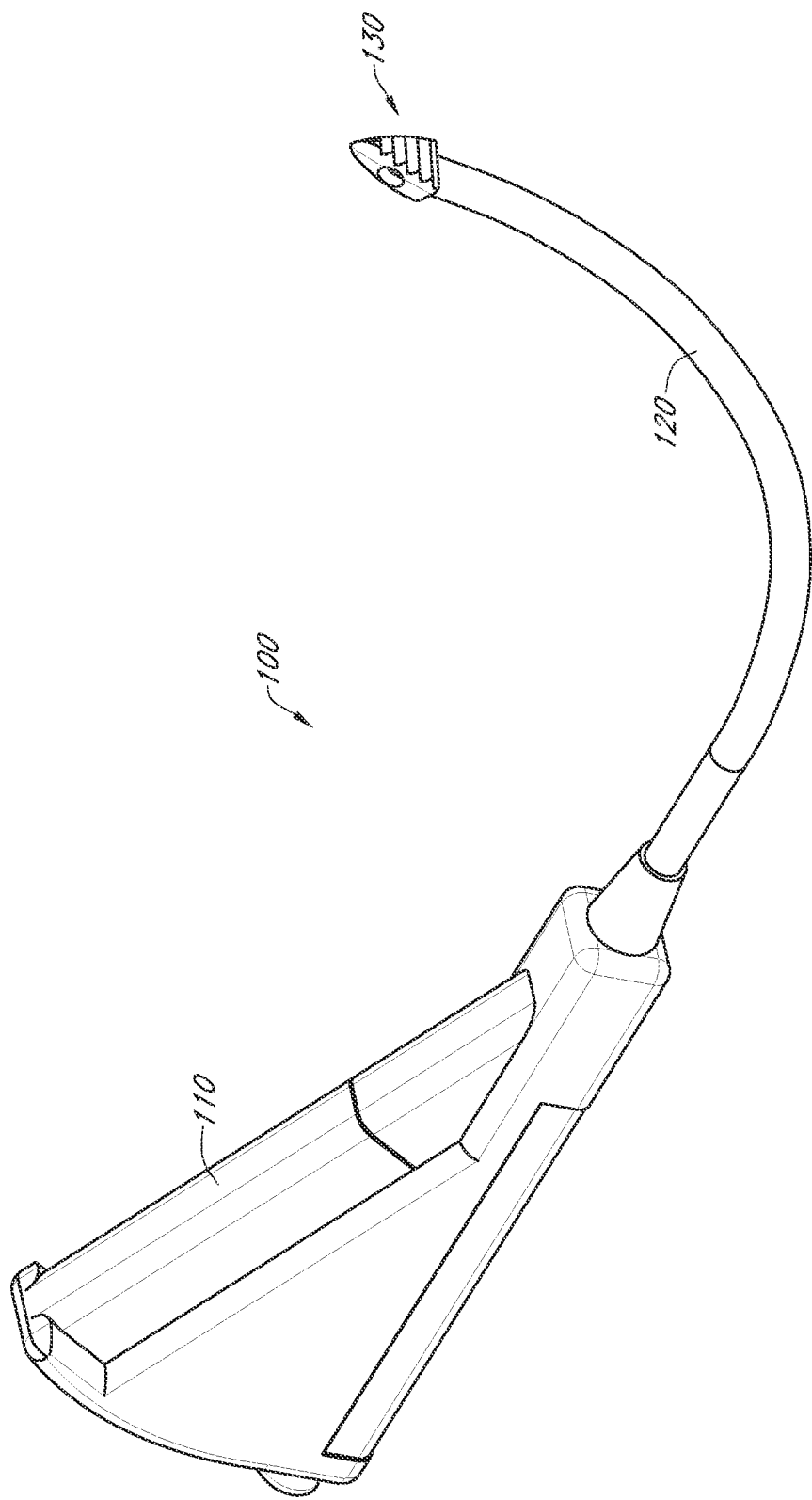
FIG. 1B illustrates a perspective view of the bone graft delivery device of FIG. 1A.

As shown in FIGS. 1A and 1B, an example embodiment of a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or tube 120 or can be supplied to the handle, for example, via a cartridge that can be removably coupled to the handle 102. In some embodiments, the device 100 can further include a plunger 112 that is retracted proximally to allow the handle to receive a cartridge or pre-loaded volume of bone graft material. In some embodiments, for example as shown in the example embodiment of FIGS. 2A and 2B, the bone graft delivery device 100 does not include a distal tip 130. In some embodiments, the bone graft delivery device does not include a rasping distal tip as described in greater detail herein.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

Figure 2A:
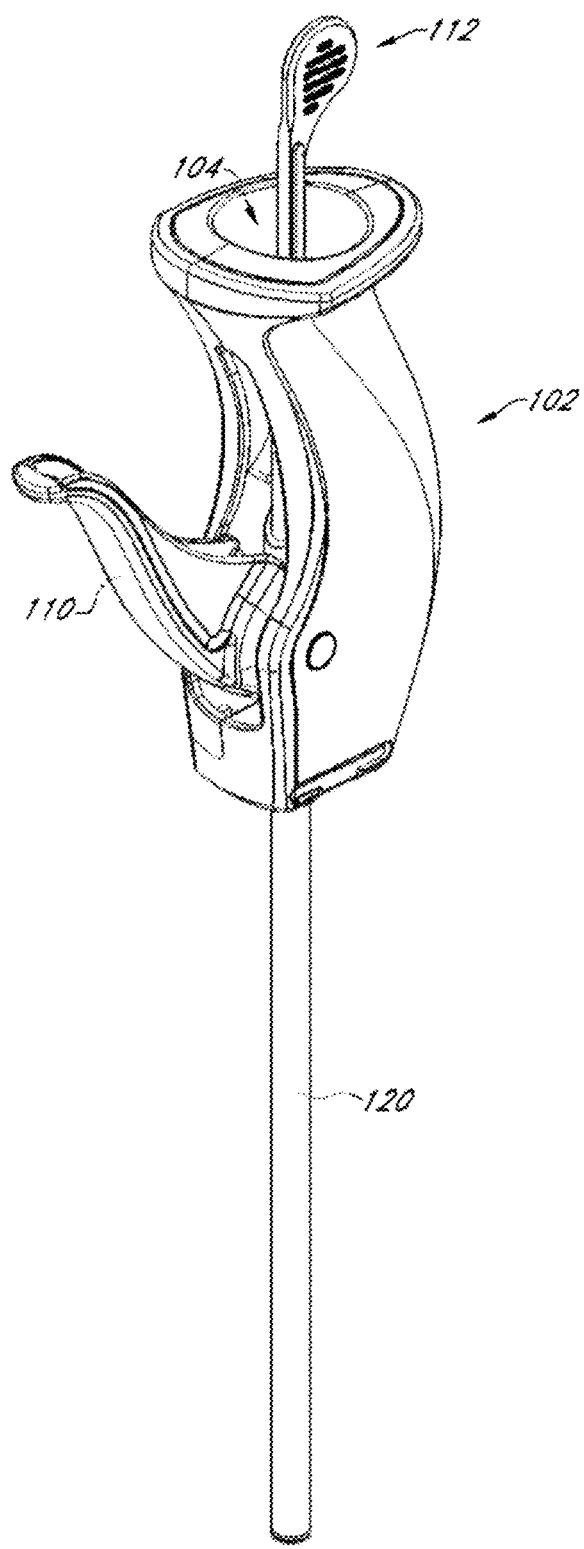
FIGS. 2A and 2B illustrate perspective views of another example embodiment of a bone graft delivery device.
Figure 2B:
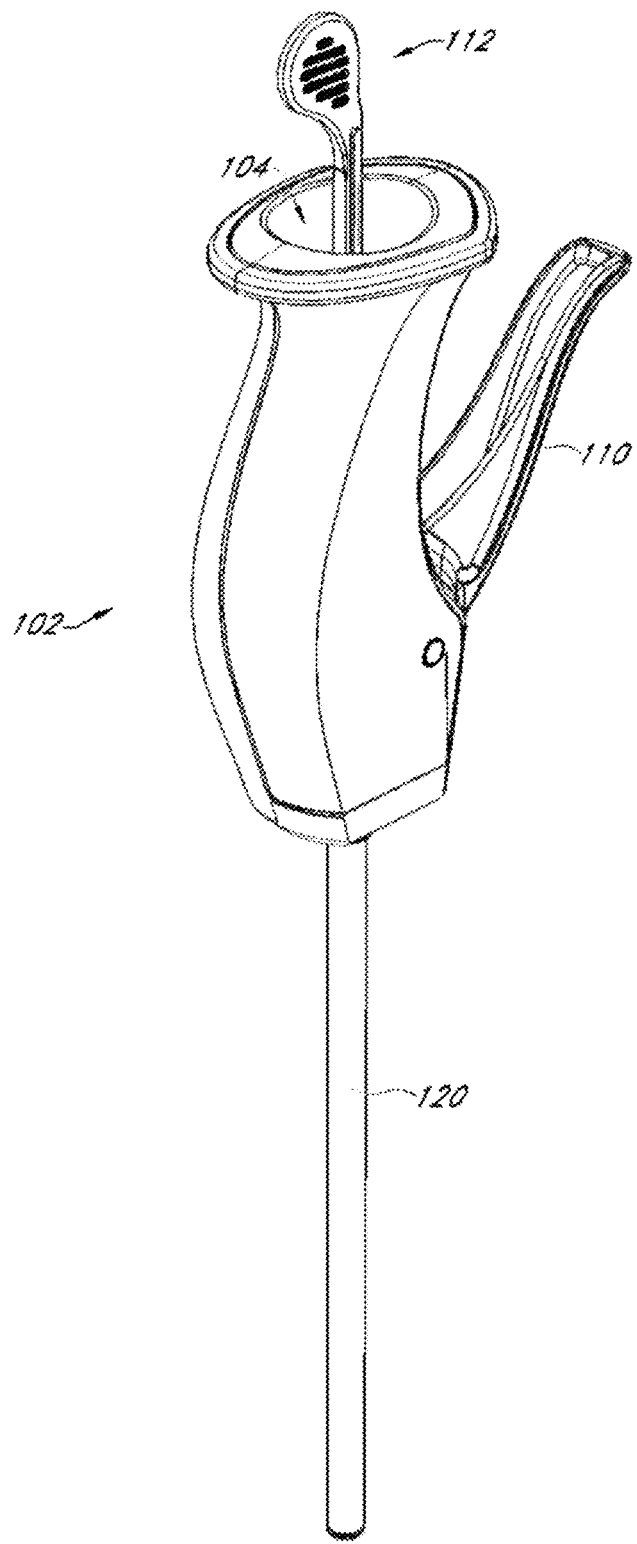

In some embodiments, a portion of the handle 102 can include an opening configured to receive the bone graft material. For example, a base of the handle 102 can include a funnel 104 as shown in FIGS. 2A-2B and 3. In other embodiments, a side or another portion of the handle 102 can include a funnel 104 or other opening configured to receive the bone graft material, for example as shown in FIGS. 2C-2K. Whereas some existing bone graft delivery devices are only compatible with certain, e.g., pre-packaged, bone graft materials, the funnel 104 can be designed to advantageously allow the user to use any bone graft material or combination of bone graft materials he or she wishes or deems appropriate. For example, the user can use synthetic, autologous, stem cell, cellular matrix, demineralized bone matrix (DBM), cadaveric, and/or any other available bone graft material. In some embodiments, the user can use DBM putty. In some embodiments the bone graft materials can include cortical fibers or demineralized cortical fibers. In some embodiments, the bone graft materials can include one or more of hydroxyapatite (HA), tricalcium phosphate (TCP), and bioglass.

The handle 102 can further include a channel or funnel shaft 106 extending therethrough connecting and in fluid communication with the funnel 104 and tube 120. In use, the user can mix the desired bone graft material in the funnel 104, then use the plunger 112 or other means to advance the bone graft material through the channel 106 and into the tube 120 for delivery.

Figure 4A:
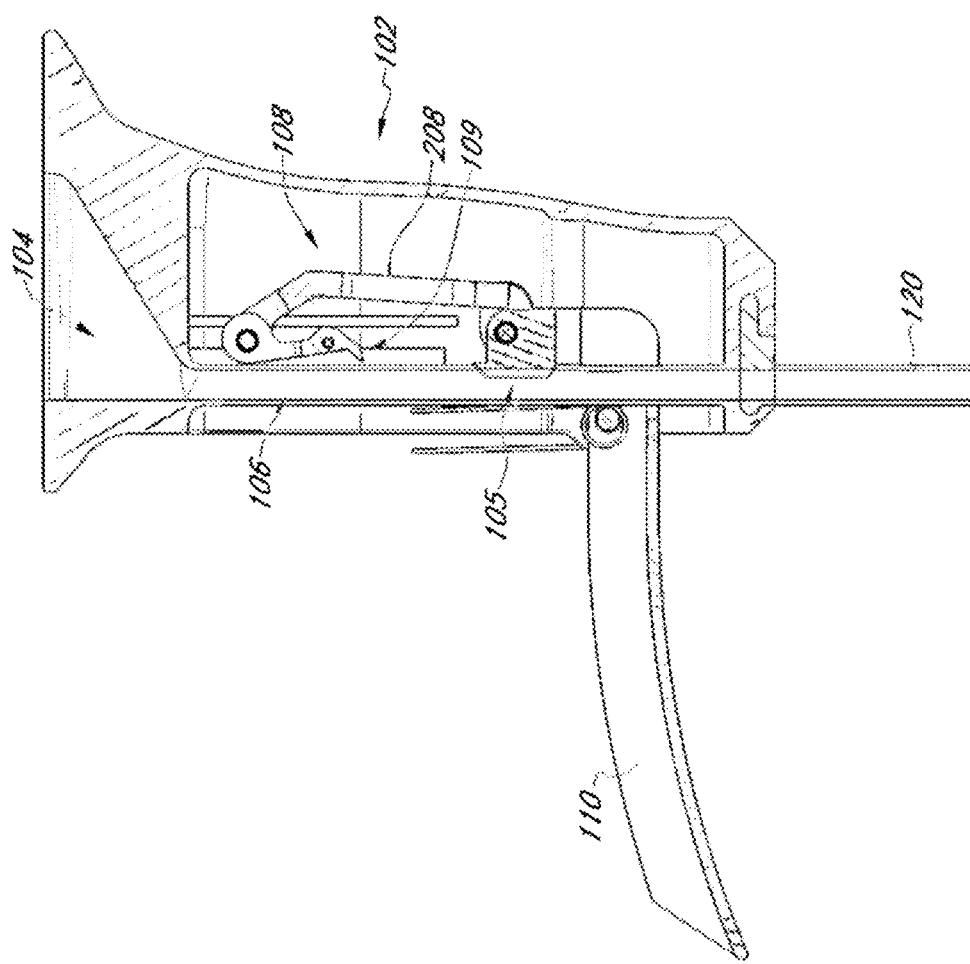
Figure 4B:
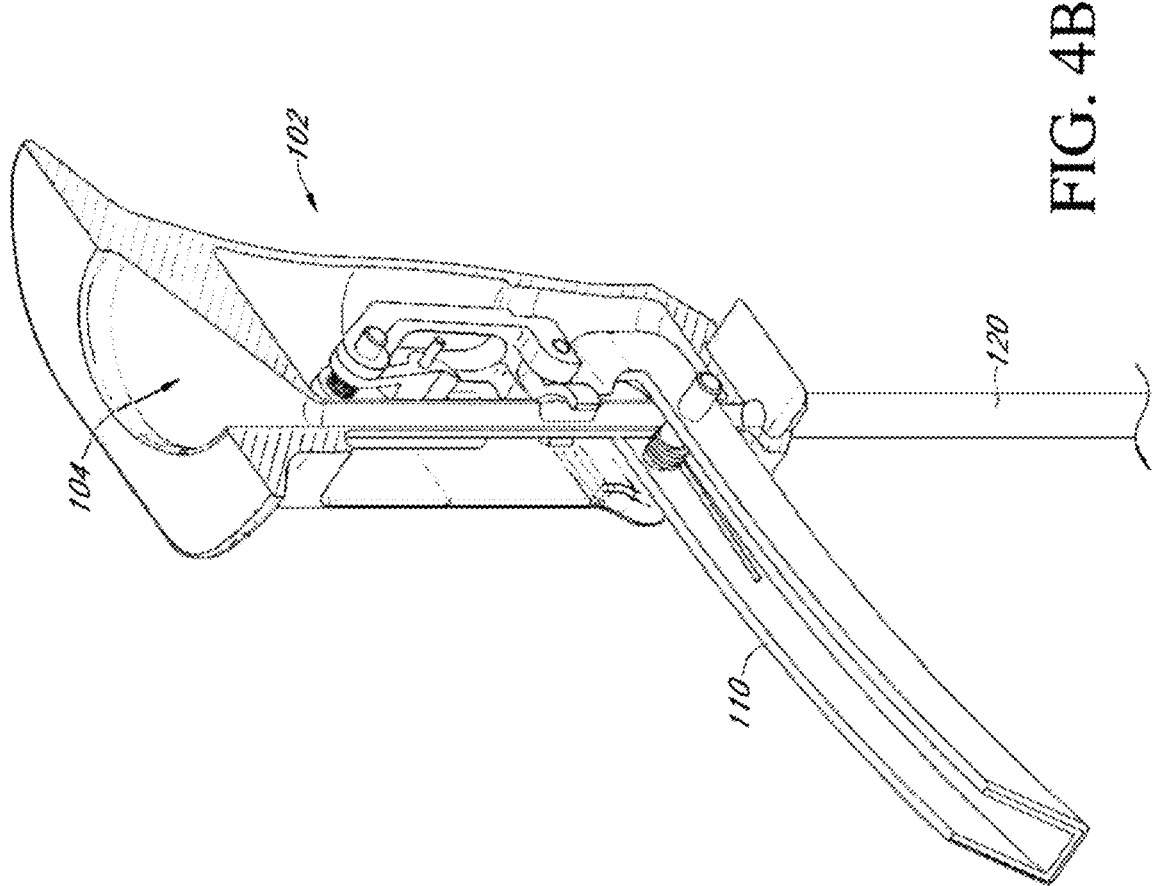
Figure 4C:
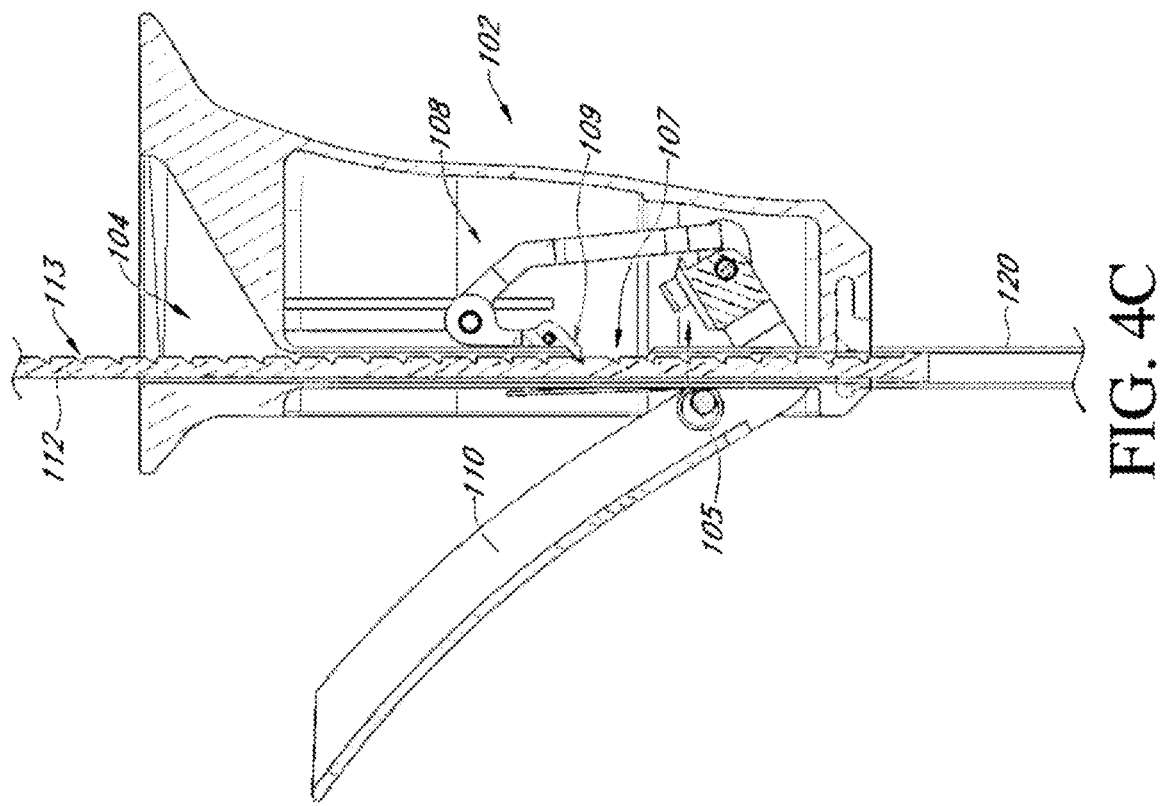
Figure 4E:
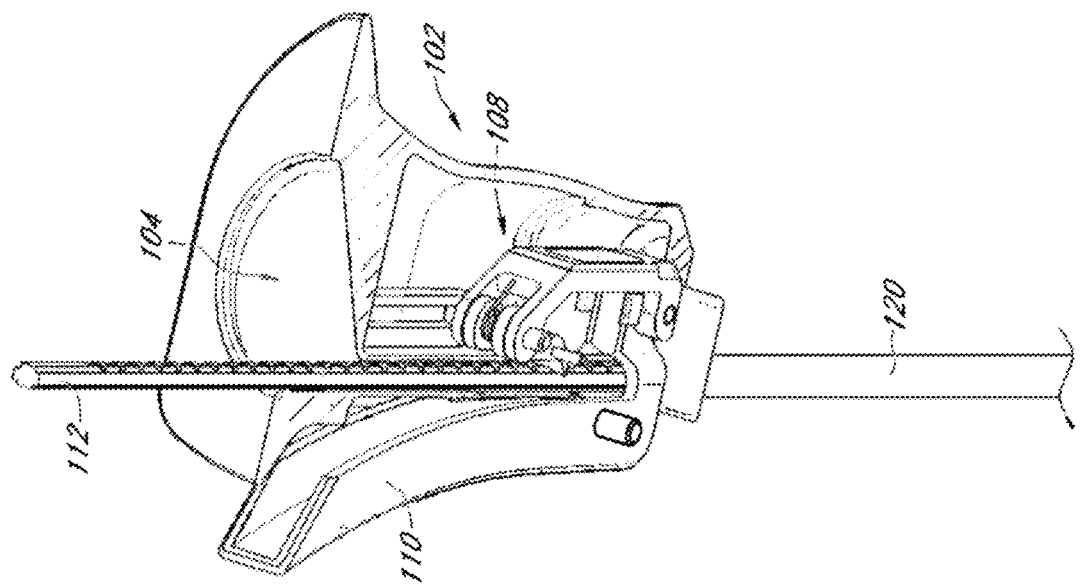
Figure 4F:
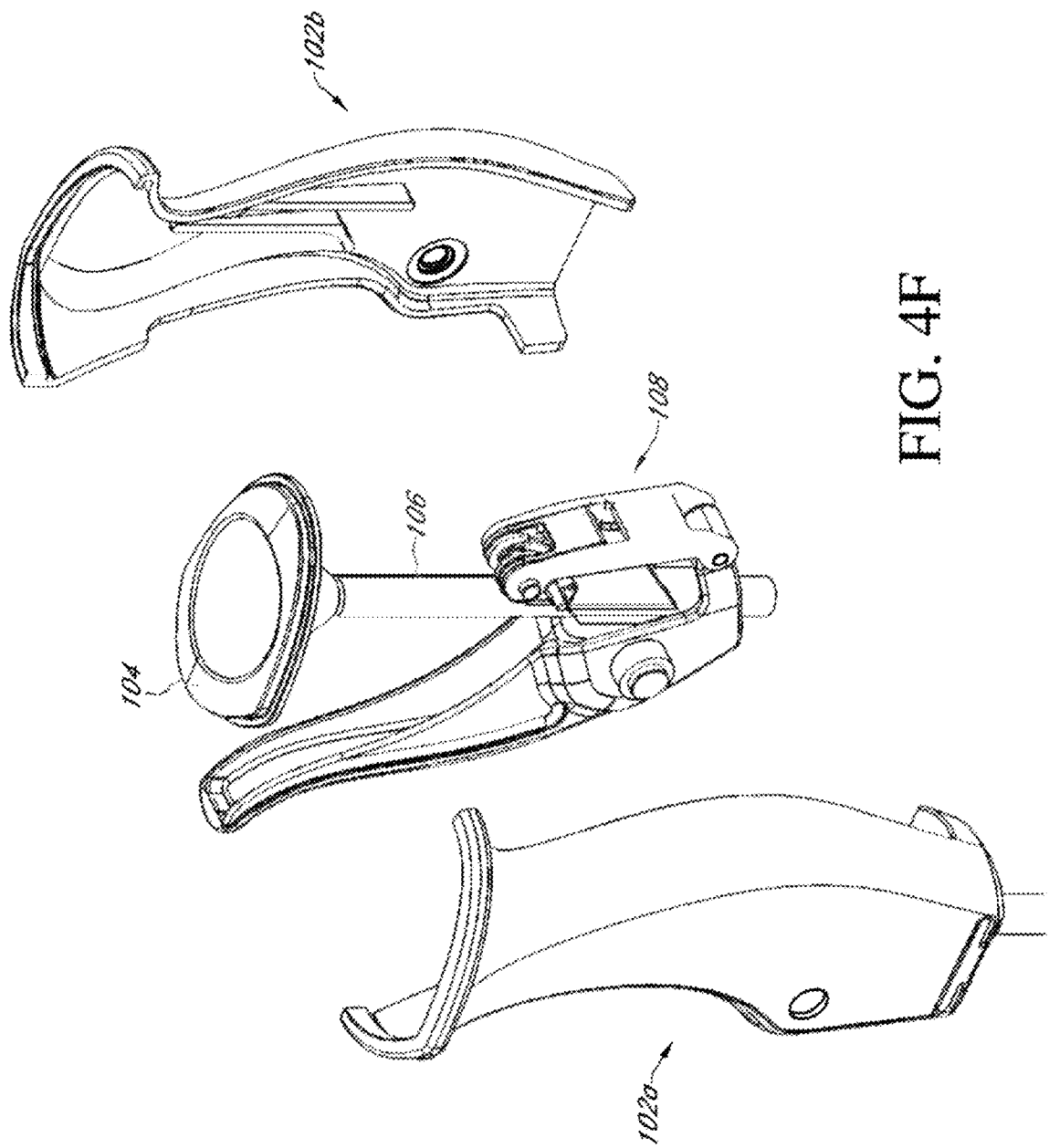
FIGS. 4F and 4G illustrate exploded views of an example embodiment of a bone graft delivery device including a ratcheting mechanism.
Figure 4G:
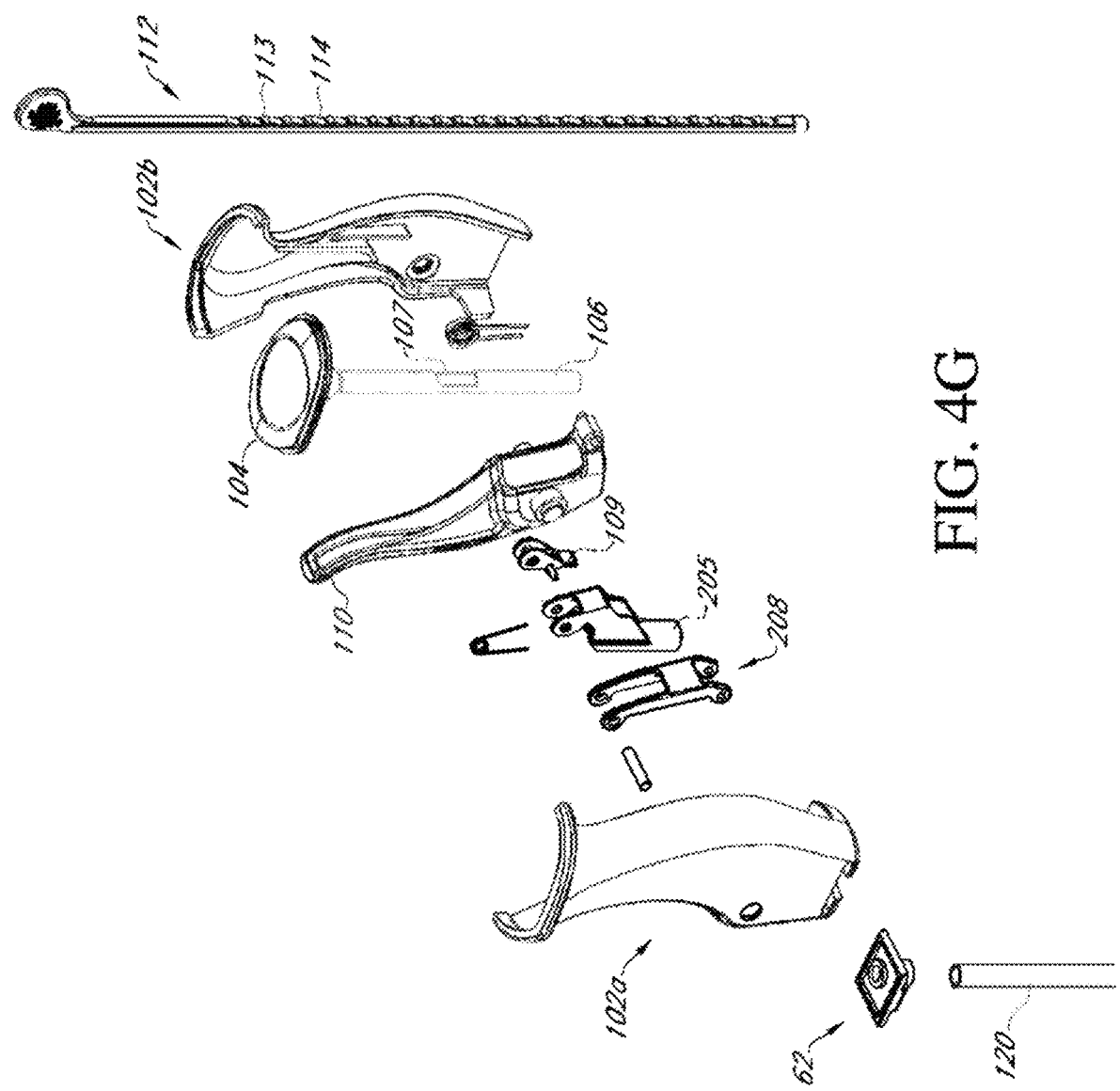

In some embodiments, the handle 102 includes a ratcheting mechanism 108 configured to advance the plunger 112 and bone graft material from the funnel 104 and through the channel 106 and tube 120 for delivery, as shown in FIGS. 4A-4E. The ratcheting mechanism 108 (or any of the ratcheting mechanisms described herein) and plunger 112 can advantageously create pressure on the bone graft material in the tube 120 to improve delivery to the target location. In some embodiments, the plunger 112 fully or substantially seals with the inner diameter of the tube 120. This can create a vacuum within the tube 120 and/or can provide greater pressure on the bone graft material to force the bone graft material through the tube 120 and out of the distal end of the tube 120 or distal tip 130. In some embodiments, the plunger 112 or a portion of the plunger 112 is made of, for example, rubber silicone, which can help improve the seal with the tube 120 and/or can help provide pressure on the bone graft material. In some embodiments, the plunger 112 can be made of a plastic or another material and can include an elastomeric rubber stopper 115 at the distal end, for example as shown in FIG. 4O. The stopper 115 can be dual injection molded or co-molded with the plunger 112 so that the stopper 115 cannot normally be removed from the plunger 112. As shown in FIG. 4X, the stopper 115 can be molded onto or over a barb-shaped distal end of the plunger 112. The plunger 112 and ratcheting mechanism 108 can therefore allow the bone graft delivery device to extrude even highly viscous and/or granular bone graft material.

In the illustrated embodiment, the ratcheting mechanism 108 includes a cover 105 and a pawl 109 coupled to the trigger 110 via an arm 208. The funnel shaft 106 includes a window 107 in a portion of the shaft 106 facing the pawl 109. The plunger 112 can be made of a rigid or flexible material. For example, the plunger 112 can be plastic, carbon fiber, metal, or any other suitable material. The plunger 112 includes a series of teeth 114 and notches 113 located between the teeth 114 and configured to receive the pawl 109. The notches 113 can be generally triangular. As shown, distal edges of the teeth 114 slope proximally toward the outer edge of the plunger 112 to allow the pawl 109 to slide along the distal edges in use. In some embodiments, extending the trigger 110 away from the handle 102, for example to a position perpendicular to the handle 102, causes the cover 105 to rest in and close the window 107 of the funnel shaft 106, as illustrated in FIGS. 4A and 4B, to allow for loading of the bone graft material through the funnel 104 into the channel 106. In this position, the pawl 109 rests proximal to the window 107. The plunger 112 can be inserted into the funnel 104 and channel 106 to advance some or all of the bone graft material past the window 107. Once the bone graft material has been loaded, the trigger 110 can be moved toward the handle 102 to an intermediate position, as shown in FIG. 4C. This moves the pawl 109 distally so that the pawl 109 engages one of the notches 113 on the plunger 112 through the window 107. Movement of the trigger 110 to a final position closest the handle 102 causes the pawl 109 to move distally within the window 107 (or away from the funnel 104 and toward the tube 120), thereby advancing the plunger 112 distally within the channel 106 to force the bone graft material distally within the channel 106 and/or tube 120, as shown in FIGS. 4D and 4E. The trigger 110 can be moved back to the intermediate position to cause the pawl 109 to slide proximally along the plunger 112 and over one of the teeth 114 to engage a more proximal notch 113. The trigger 110 can be moved between the intermediate position and final position multiple times until the pawl 109 has reached the proximal end of the plunger 112. The user can re-load the device 100 as needed during a procedure. The ratcheting mechanism 108 and trigger 110 in combination can advantageously provide a mechanical advantage and allow the user to apply a greater force in operating the bone graft delivery device 100 and/or delivering the bone graft material compared to, for example, a standard syringe used to deliver bone graft material.

Figure 4H:
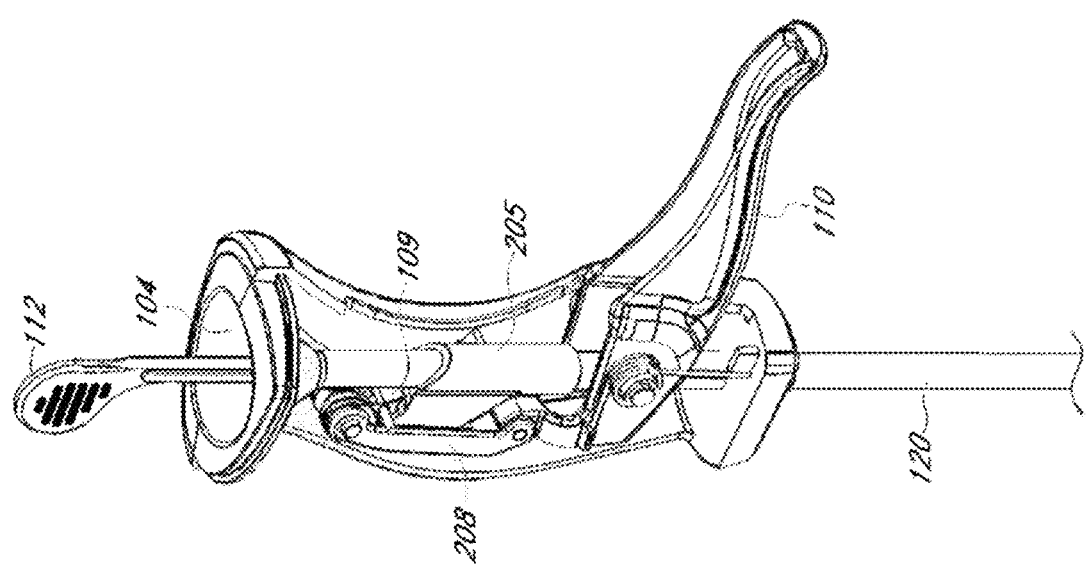
FIGS. 4H-4M illustrate operation of the ratcheting mechanism of the device of FIGS. 4F and 4G.
Figure 4I:
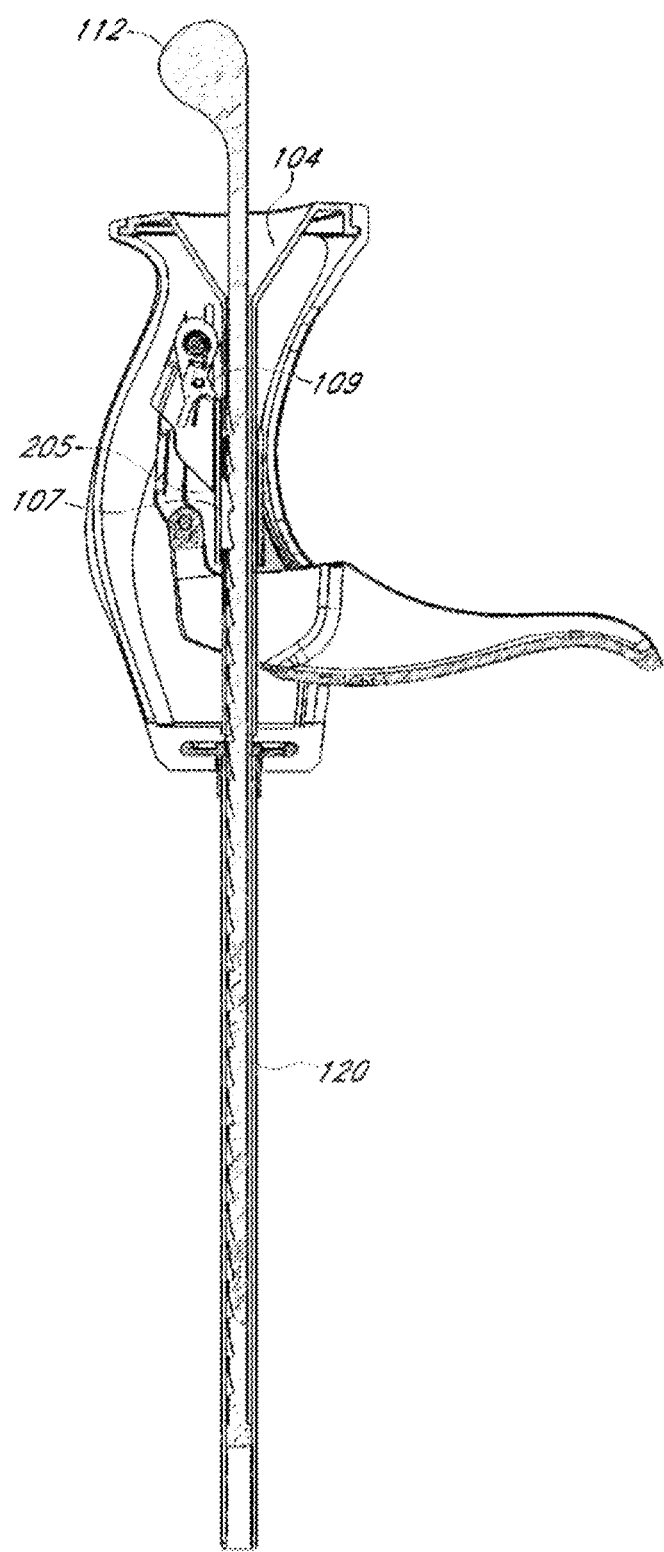
Figure 4J:
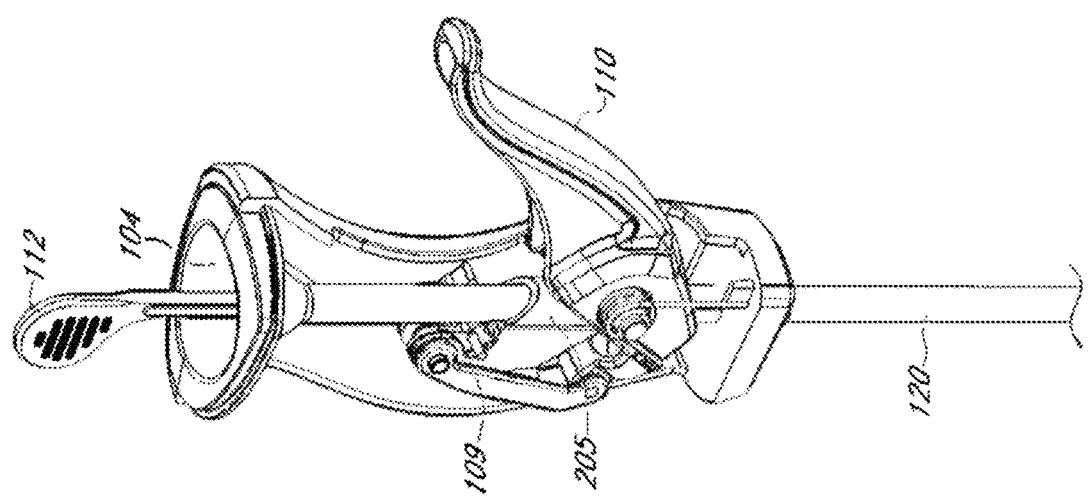
Figure 4K:
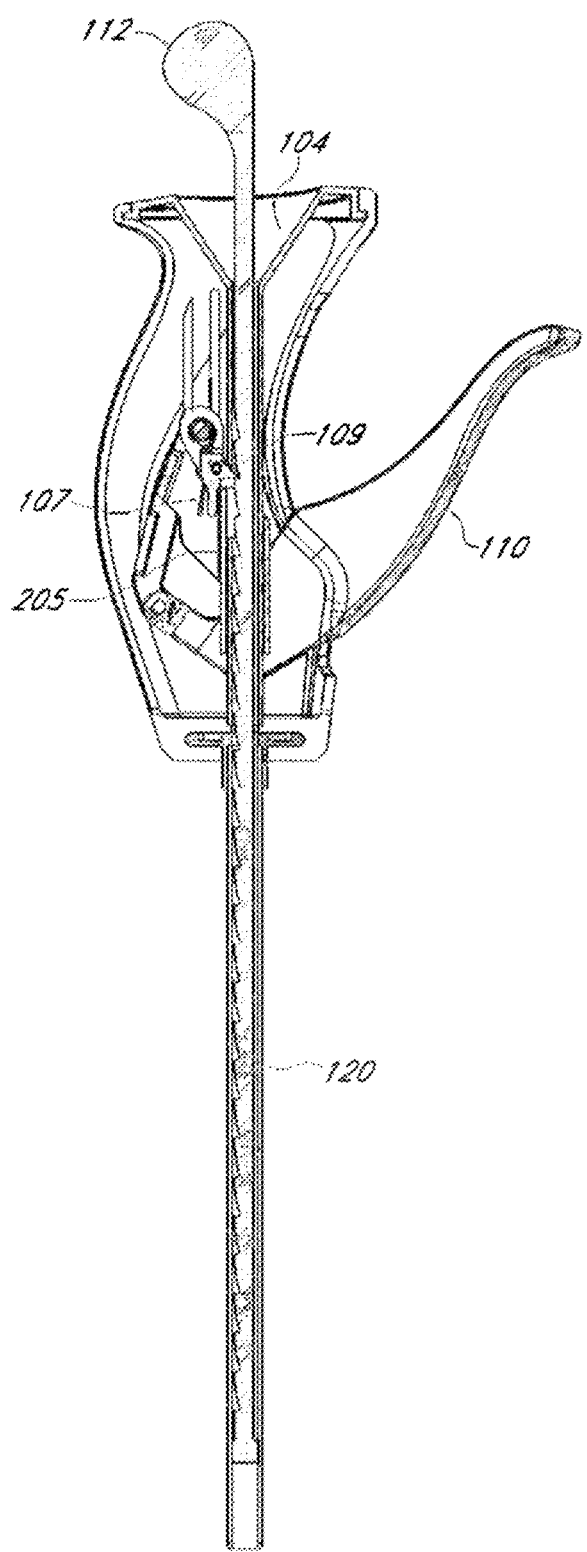
Figure 4L:
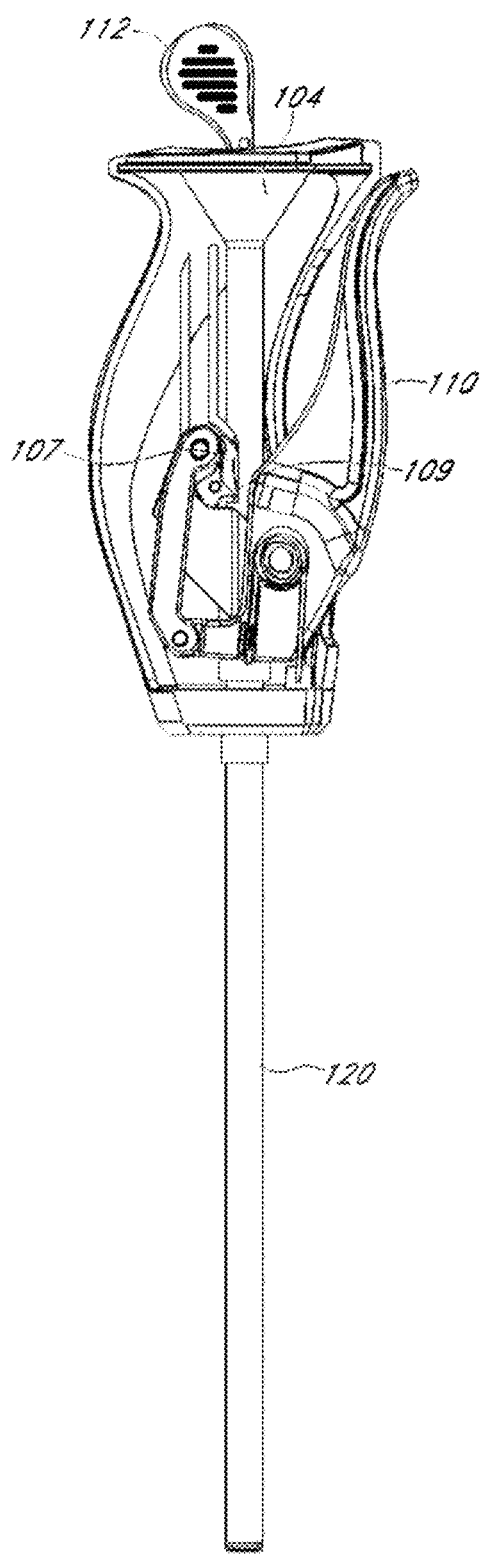
Figure 4M:
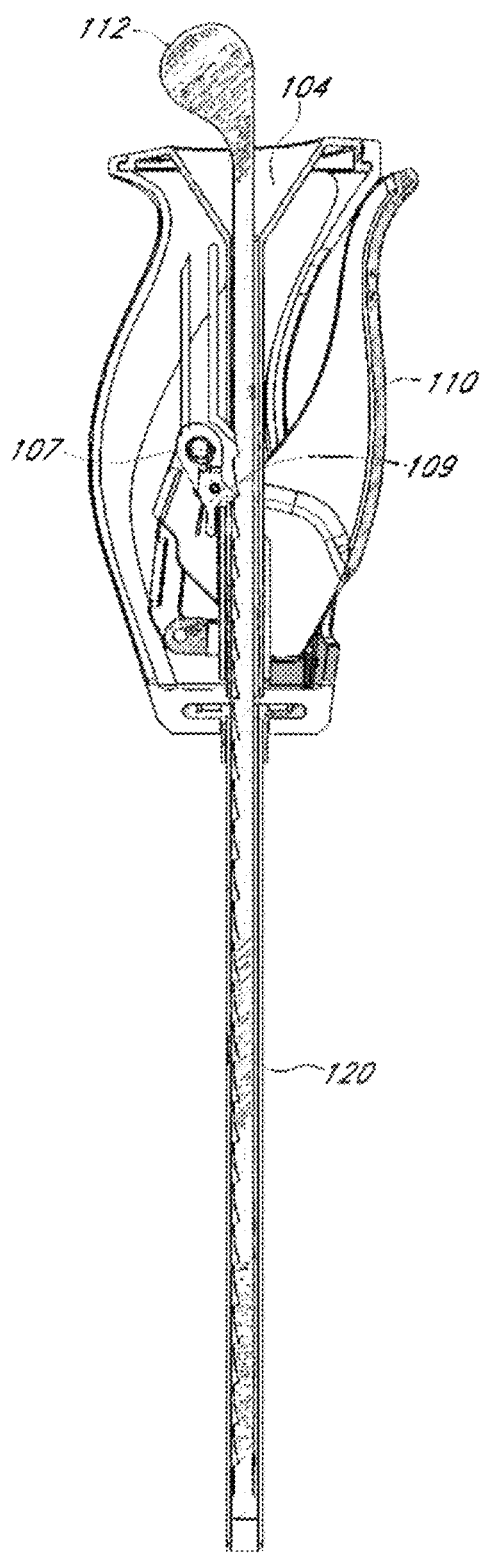
Figure 4N:
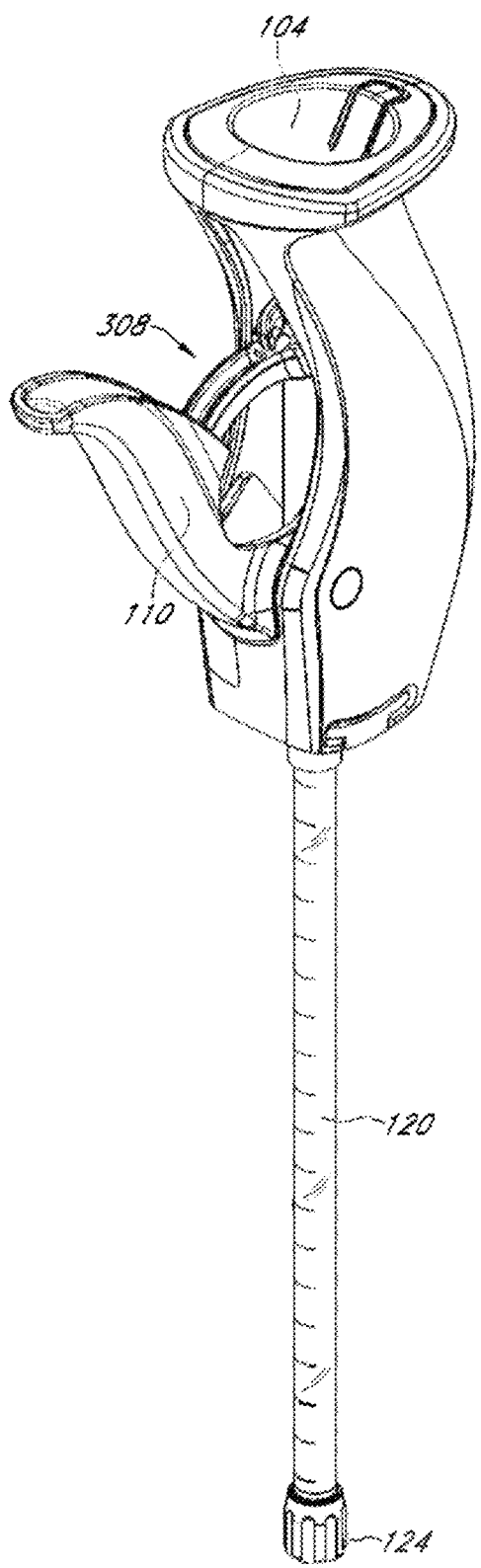
FIG. 4N illustrates a perspective view of an example embodiment of a bone graft delivery device including a ratcheting mechanism.
Figure 40:
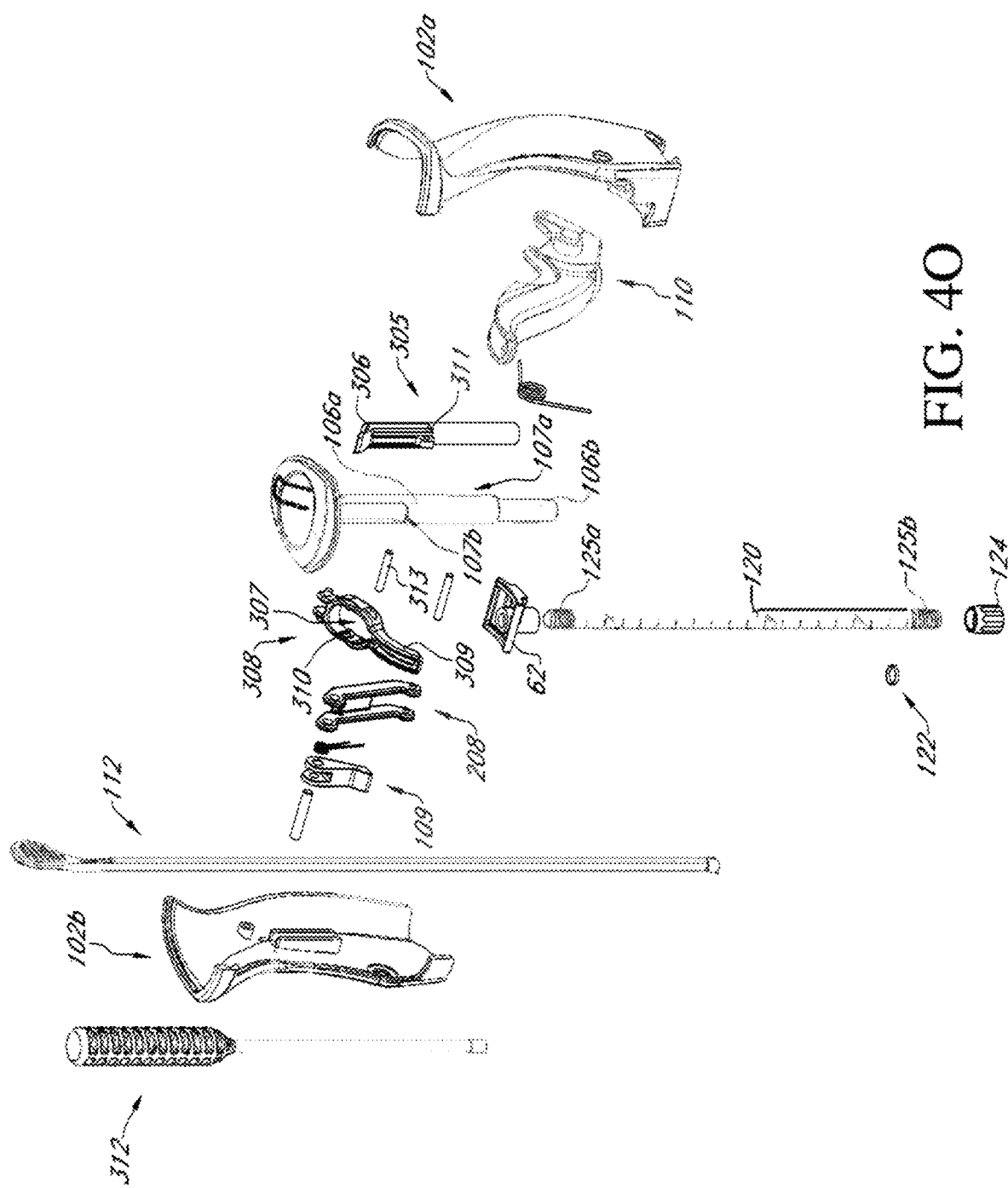
FIG. 40 illustrates a perspective view of an embodiment of a grinder for bone graft material.

Another example embodiment of a handle 102 and ratcheting mechanism 108 is shown in FIGS. 4F-4M. In this embodiment, the handle 102 includes a two-part clamshell housing 102a, 102b that houses the funnel 104, funnel shaft 106, and ratcheting mechanism 108 assembly as shown in the exploded views of FIGS. 4F and 4G. The ratcheting mechanism 108 includes the pawl 109 and a sheath 205 coupled to the trigger 110 via arm 208. The plunger 112 includes a series of sloped teeth 114 alternating with notches 113 that are configured to receive the pawl 109. When the trigger 110 is in the first position, as shown in FIGS. 4H and 4I, the sheath 205 covers the pawl window 107 and the pawl 109 rests proximal to the window 107. Movement of the trigger 110 to the intermediate position causes the sheath 205 and pawl 109 to move distally, exposing the window 107 and allowing the pawl 109 to engage the plunger 112, as shown in FIGS. 4J and 4K. Movement of the trigger 110 to the final position causes the pawl 109 to move distally, advancing the plunger 112 distally, as shown in FIGS. 4L and 4M.

Yet another example embodiment of a handle 102 and ratcheting mechanism 108 is shown in FIGS. 4N-4T. In this embodiment, the funnel shaft 106 includes an upper shaft portion 106a and a lower shaft portion 106b, and the lower shaft portion 106b has an outer diameter smaller than an outer diameter of the upper shaft portion 106a. As shown in FIGS. 4P-4T, the outer diameter of the lower shaft portion 106b can be approximately the same as an inner diameter of the upper shaft portion 106a, and the shaft 106 can include a step 206 (shown in FIG. 4R) at a transition point between the upper shaft portion 106a and lower shaft portion 106b. In the illustrated embodiment, the upper 106a and lower 106b shaft portions are integrally formed. In other embodiments, the upper 106a and lower 106b shaft portions can be separate pieces, and a proximal end of the lower shaft portion 106b can be coupled to an inner perimeter of a distal end of the upper shaft portion 106a. The upper shaft portion 106a includes a first window 107a for the pawl 109 and a second window 107b on an opposite side of the upper shaft portion 106a from the first window 107a. A sheath 305 is disposed within or inside the upper shaft portion 106a, and in the illustrated embodiment, a lever 308 extends from the trigger 110 and engages the sheath 305 through the second window 107b, as shown in FIGS. 4P-4T.

Figure 4P:
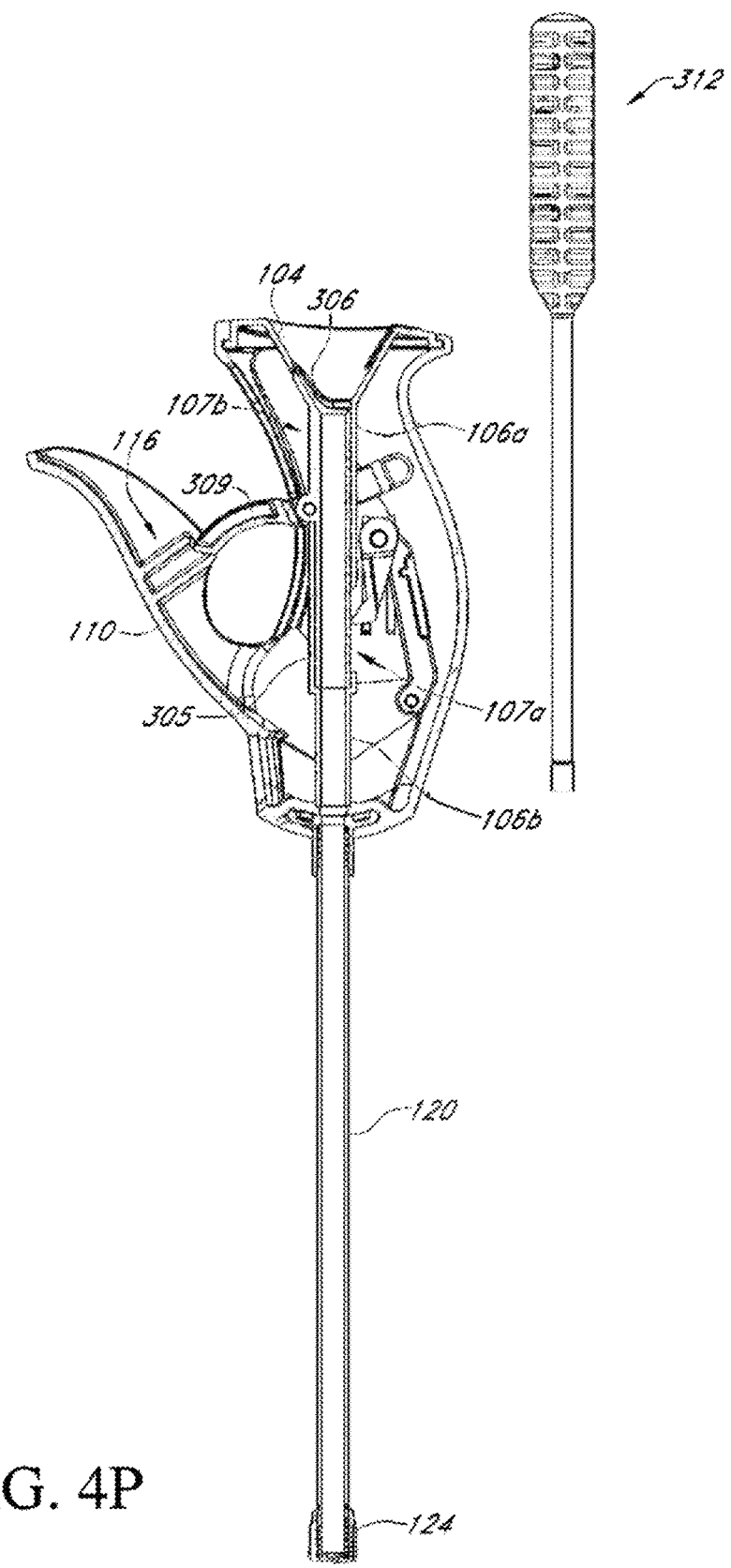
FIGS. 4P-4T are section views illustrating operation of the ratcheting mechanism of the device of FIGS. 4N and 4O.
Figure 4Q:
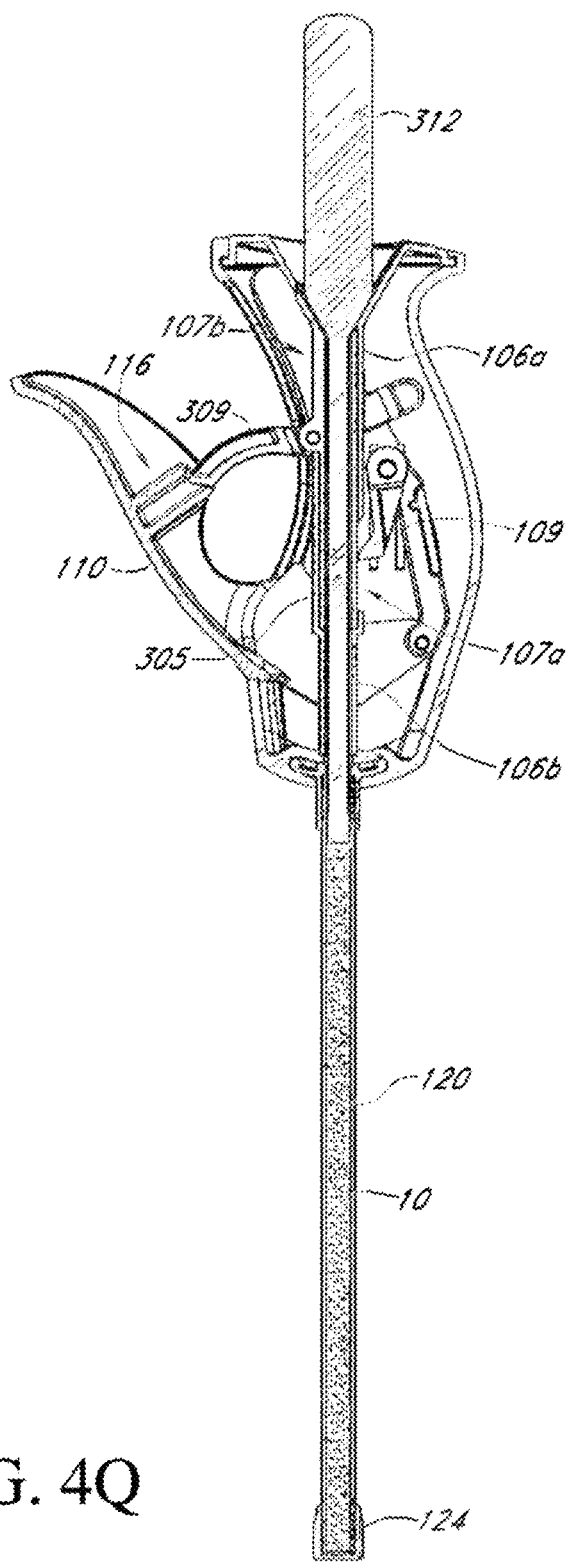

In some embodiments, the lever 308 is integrally formed with the sheath 305. Alternatively, the lever 308 can be coupled to the sheath 305, for example, with a pin 313. In some embodiments, the lever 308 includes a body 310 having a generally circular or ovular aperture 307, and an arm 309 extending from one end of the body 310. The aperture 307 receives the funnel shaft 106 so that the body 310 surrounds the upper shaft portion 106a. The sheath 305 includes a protrusion 311 that can extend through or over the second window 107b when the sheath 305 is disposed in the upper shaft portion 106a. The protrusion 311 is aligned with the lever body 310 with the protrusion 311 disposed in the aperture 307. The pin 313 extends through holes in the body 310 and protrusion 311 to couple the sheath 305 to the lever 308. In some embodiments, the pin 313 is secured to the protrusion 311 and lever body 310 with a weld, glue, or other appropriate means. The free end of the arm 309 of the lever 308 releasably engages the trigger 110. For example, the trigger 110 can include a track 116 configured to releasably receive the arm 309 as shown in FIGS. 4P and 4Q, and the arm 309 can engage the track 116 via, for example, a snap fit. In some embodiments, the trigger 110 is biased or naturally rests at a distance from the handle body that holds the arm 309 in the track 116. The trigger 110 can be flexed or allowed to move slightly away from the handle body to release the arm 309.

In some embodiments, the sheath 305 has an outer diameter about the same and slightly less than the inner diameter of the upper shaft portion 106a and a thickness about the same as a thickness of the lower shaft portion 106b. The sheath 305 can include an upper lip 306, and a length of the sheath 305 can be selected such that in an initial loading position, shown in FIG. 4P, the lip 306 rests against an inner surface of the funnel 104 and a distal end of the sheath 305 rests against the step 206. In the loading position, the sheath 305 covers the first window 107a. The dimensions of the upper shaft portion 106a, lower shaft portion 106b, and sheath 305 advantageously allow the sheath 305 to be substantially flush with an inner surface of the upper shaft portion 106a and step 206 and provide a substantially smooth and constant-diameter inner passageway from the sheath 305 to the lower shaft portion 106b. The bone graft delivery device of FIGS. 4N-4T also includes a pusher rod 312 and a tube end cap 124.

Figure 4R:
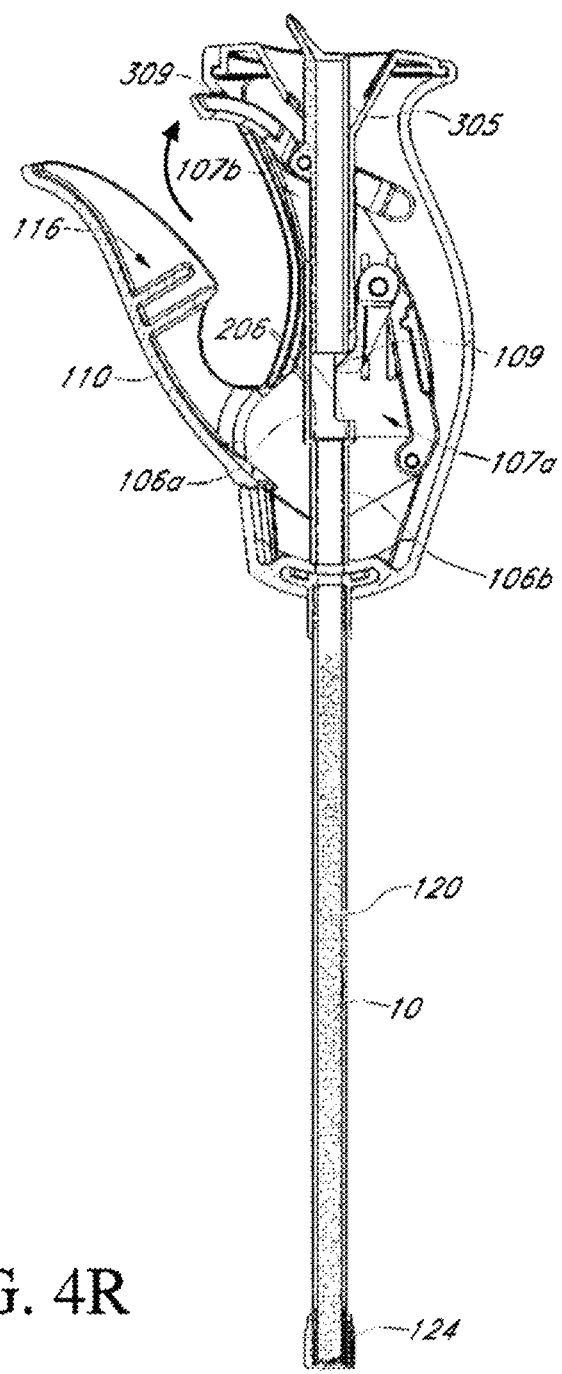
Figure 4S:
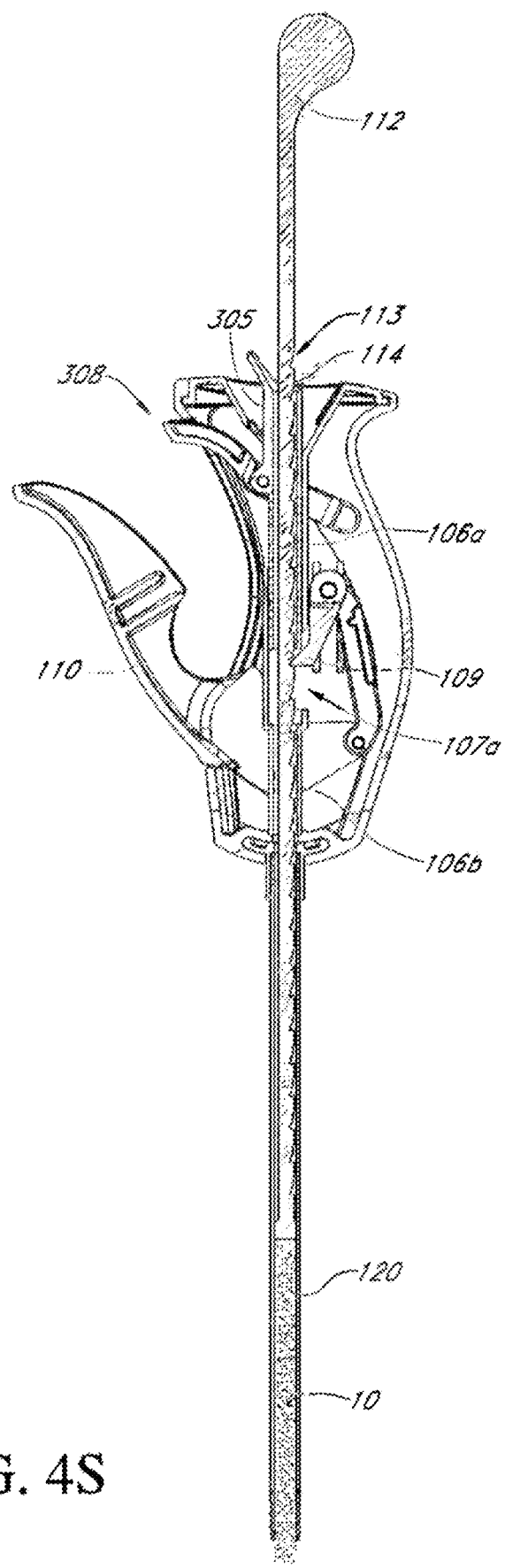
Figure 4T:
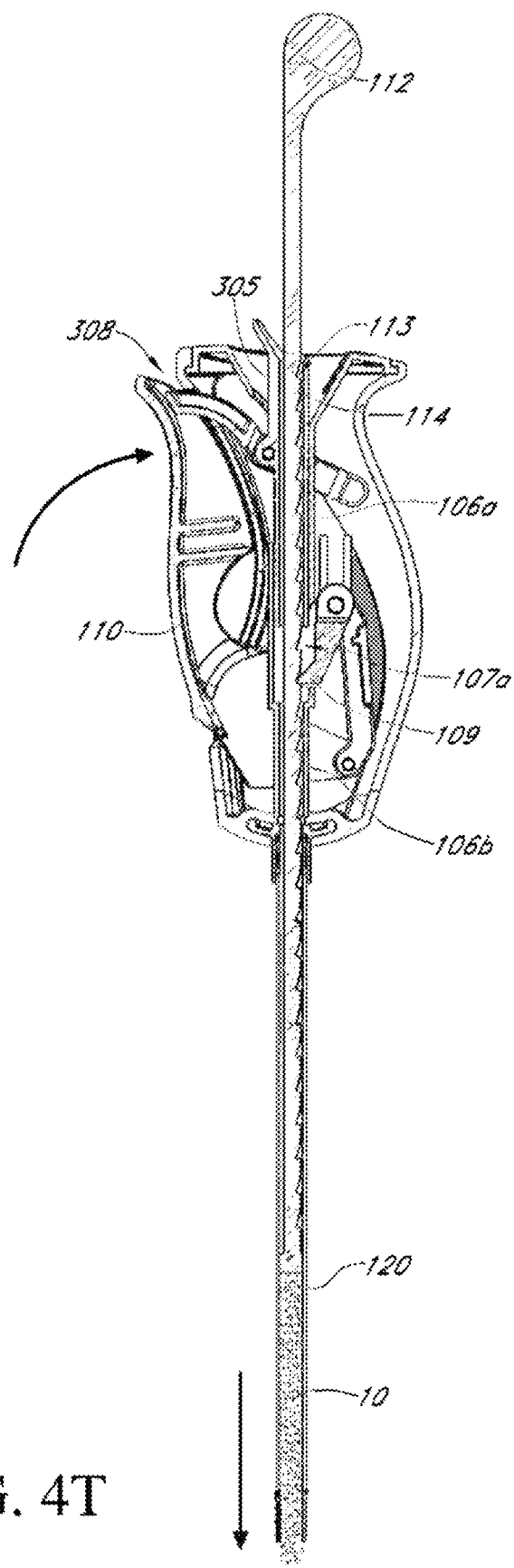
Figure 4U:
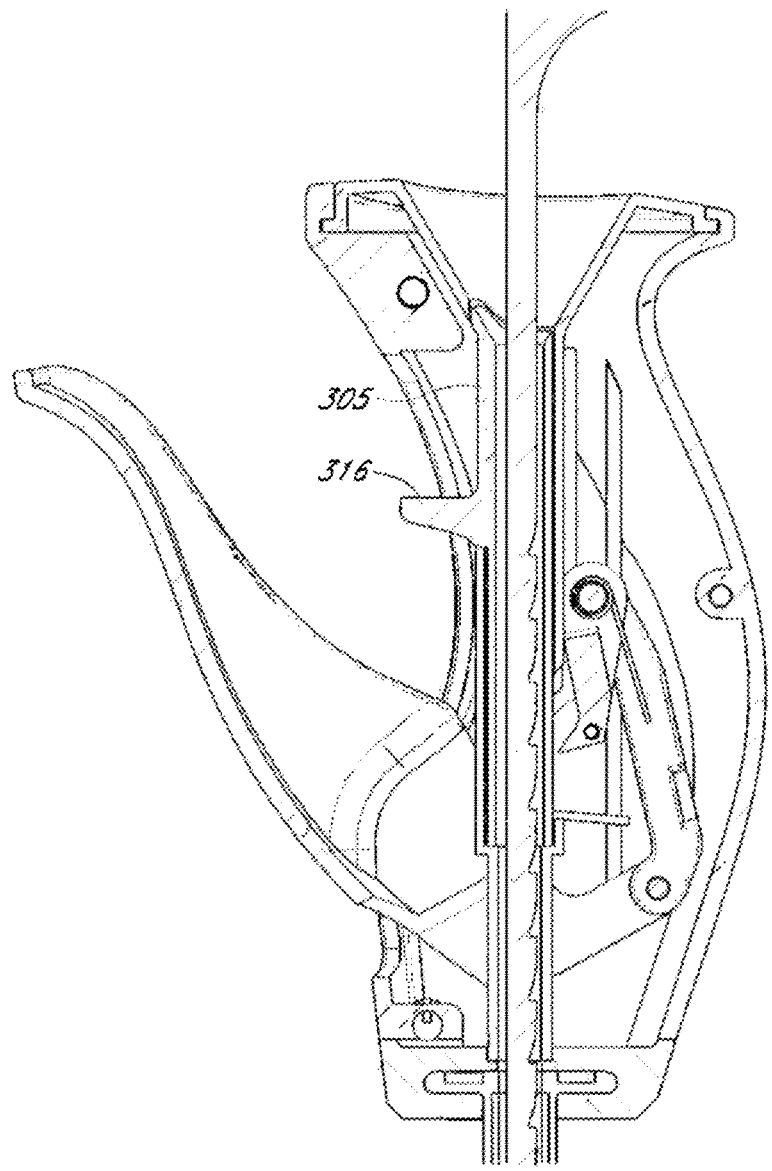
FIGS. 4U and 4V illustrate section views of an example embodiment of a handle of a bone graft delivery device including a ratcheting mechanism.
Figure 4V:
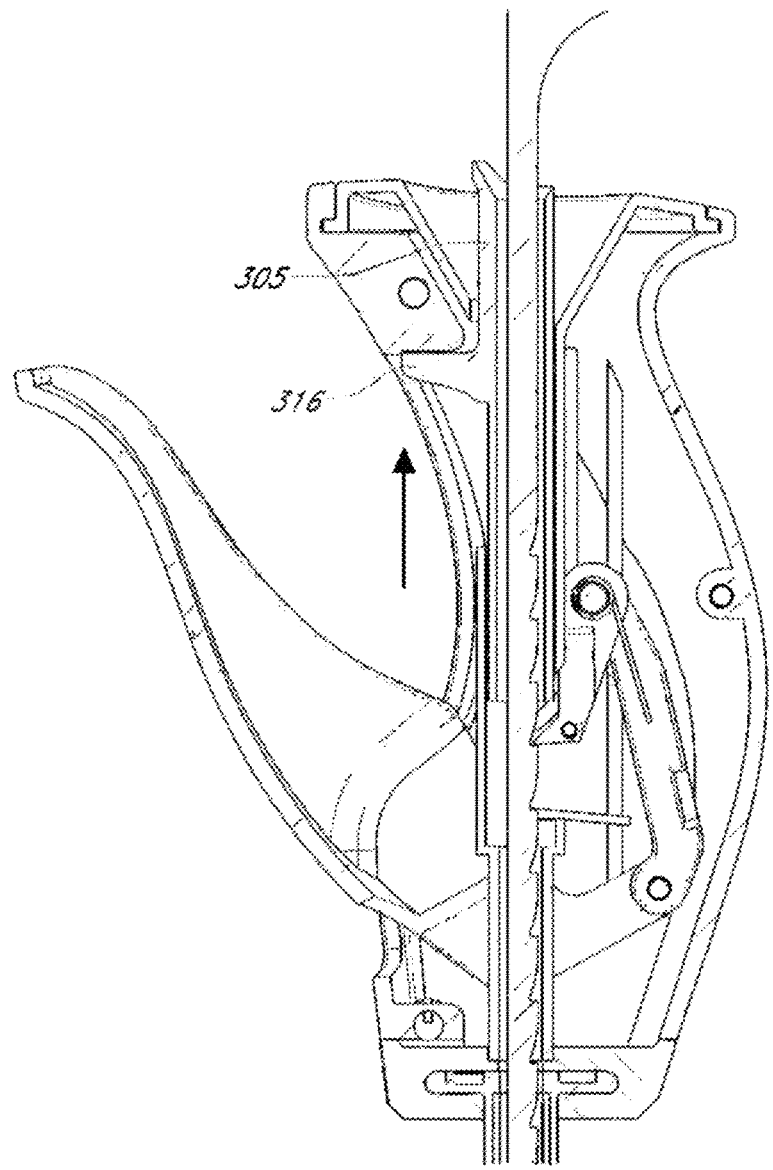
Figure 4X:
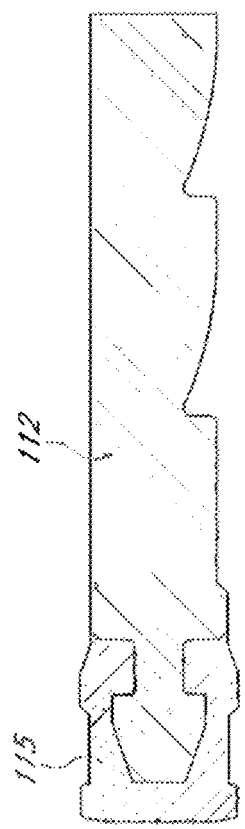
FIG. 4X illustrates a section view of a distal end of a plunger of a bone graft delivery device.

To load bone graft material, the lever 308 is coupled to the trigger 110 so that the sheath 305 sits in the initial loading position shown in FIG. 4P. Bone graft material 10 is loaded into the funnel 104, and the pusher rod 312 can be inserted into the funnel 104 to help urge the bone graft material 10 through the sheath 305 and lower shaft portion 106b and into the tube 120 as shown in FIG. 4Q. In some embodiments, the pusher rod 312 is made of, for example, a glass filled or rigid polymer material. The tube end cap 124 inhibits or prevents the bone graft material 10 from exiting the distal end of the tube 120 during the loading process and until the user wishes to deliver the bone graft material 10. The tube end cap 124 can be attached to the distal end of the tube 120 via a threaded coupling, friction fit, or other suitable means. In the illustrated embodiment, the tube 120 includes external threads 125b at or near the distal end configured to mate with internal threads in the tube end cap 124. Once the bone graft material 10 is loaded, the pusher rod 312 is removed, and the lever 308 is released from the trigger 110 as shown in FIG. 4R. As shown, release of the lever 308 causes or allows the lever to move toward the funnel, thereby also moving the sheath 305 proximally to expose the first window 107a and allow the pawl 109 to enter the shaft 106 through the first window 107a. The plunger 112 can be inserted before or after releasing the lever 308 and extends through the sheath 305, upper shaft portion 106a, and lower shaft portion 106b and into the tube 120 as shown in FIG. 4S. When the plunger 112 is inserted and the lever 308 is released so that the first window 107a is exposed, the pawl 109 engages one of the notches 113 on the plunger 112. The lever 308 can advantageously provide the user with a greater mechanical advantage and/or greater control in moving the sheath 305 proximally to expose the first window 107a. In other embodiments, the sheath includes a protrusion 316 without a lever as shown in FIGS. 4U and 4V. The user can use the protrusion 316 to lift or lower the sheath 305.

The tube end cap 124 is removed when the user wishes to deliver the bone graft material 10 through the tube 120. Movement of the trigger 110 toward the handle causes the pawl 109 to move distally, advancing the plunger 112 distally, as shown in FIG. 4T. The trigger 110 is moved away from and toward the handle to advance the plunger 112 and bone graft material 10 through the tube 120 in discreet increments. Of course, other ratcheting mechanisms and/or other mechanisms for advancing bone graft material through the handle 102 and/or tube 120 are also possible.

In some embodiments, the funnel 104 or other opening for loading of bone graft material can be positioned in the handle 102 in locations other than a proximal end or base of the handle 102. For example, in the example embodiment of FIGS. 2C-2E, the handle 102 is configured such that the trigger 110 and a grip 111 extend from a main body portion 103 of the handle 102. As shown, the funnel 104 is located on an opposite side of the body portion 103 from the grip 111 and trigger 110. A main channel 406 extends through the handle 102 from an opening in a proximal end of the body portion 103 to an opening in a distal end of the body portion 103 and is in fluid communication with the tube 120. The funnel shaft 106 extends from the funnel 104 to intersect the main channel 406 as shown in FIGS. 2D and 2E. In the illustrated embodiment, the funnel 104 and funnel shaft 106 are oriented at an angle 1 relative to the main channel 406. The angle can advantageously help direct bone graft material inserted into the funnel 104 and funnel shaft 106 distally toward the tube 120. The bone graft delivery device can include a pusher rod 312 as shown in FIG. 2E to help urge bone graft material from the funnel 104 through the funnel shaft 106 and into the main channel 406. In some embodiments, the pusher rod 312 can be configured such that when fully inserted into the funnel 104 and funnel shaft 106, a distal end 314 of the pusher rod 312 rests at the intersection of the funnel shaft 106 with the main channel 406 to at least partially or substantially close the main channel 406. The distal end 314 of the pusher rod 312 can be formed at an angle with the angle corresponding to the angle of the funnel shaft 106 so that the distal end 314 is continuous with a wall of the main channel 406 when inserted into the funnel shaft 106. In such embodiments, the pusher rod 312 can be configured to remain in place during delivery of bone graft material.

Figure 2C:
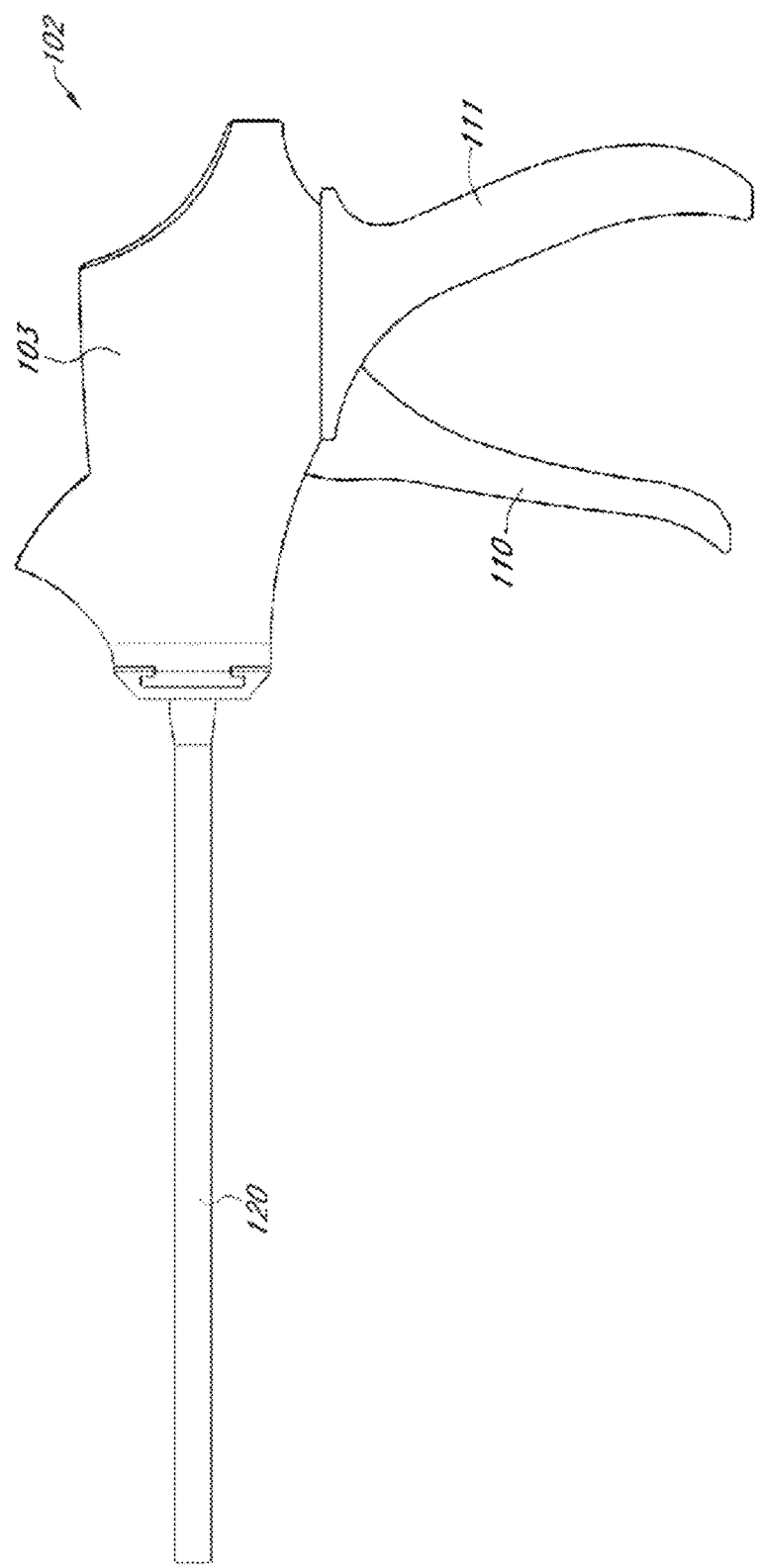
FIG. 2C illustrates a side view of another example embodiment of a bone graft delivery device.
Figure 2D:
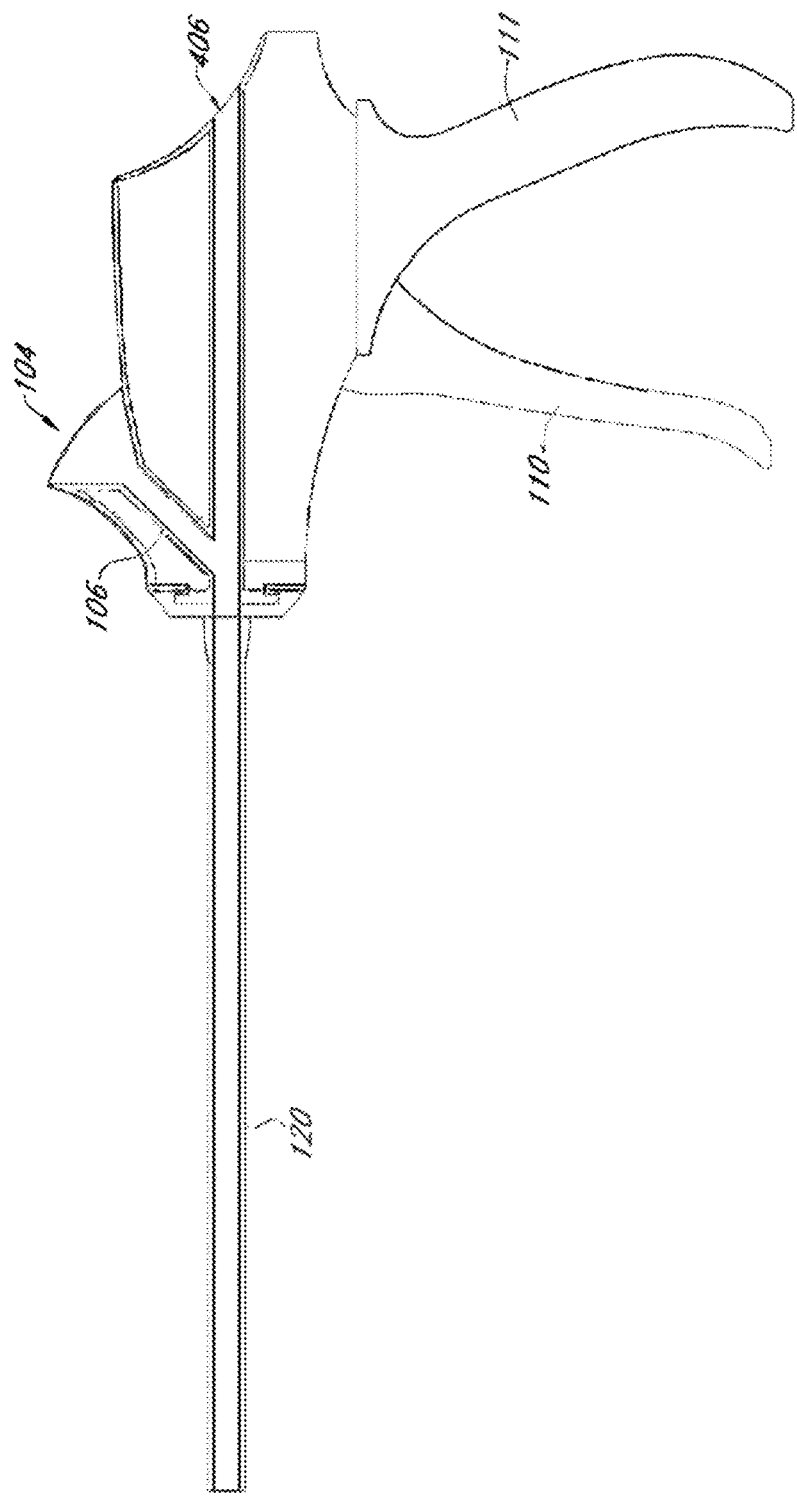
FIG. 2D illustrates a section view of the bone graft delivery device of FIG. 2C.
Figure 2E:
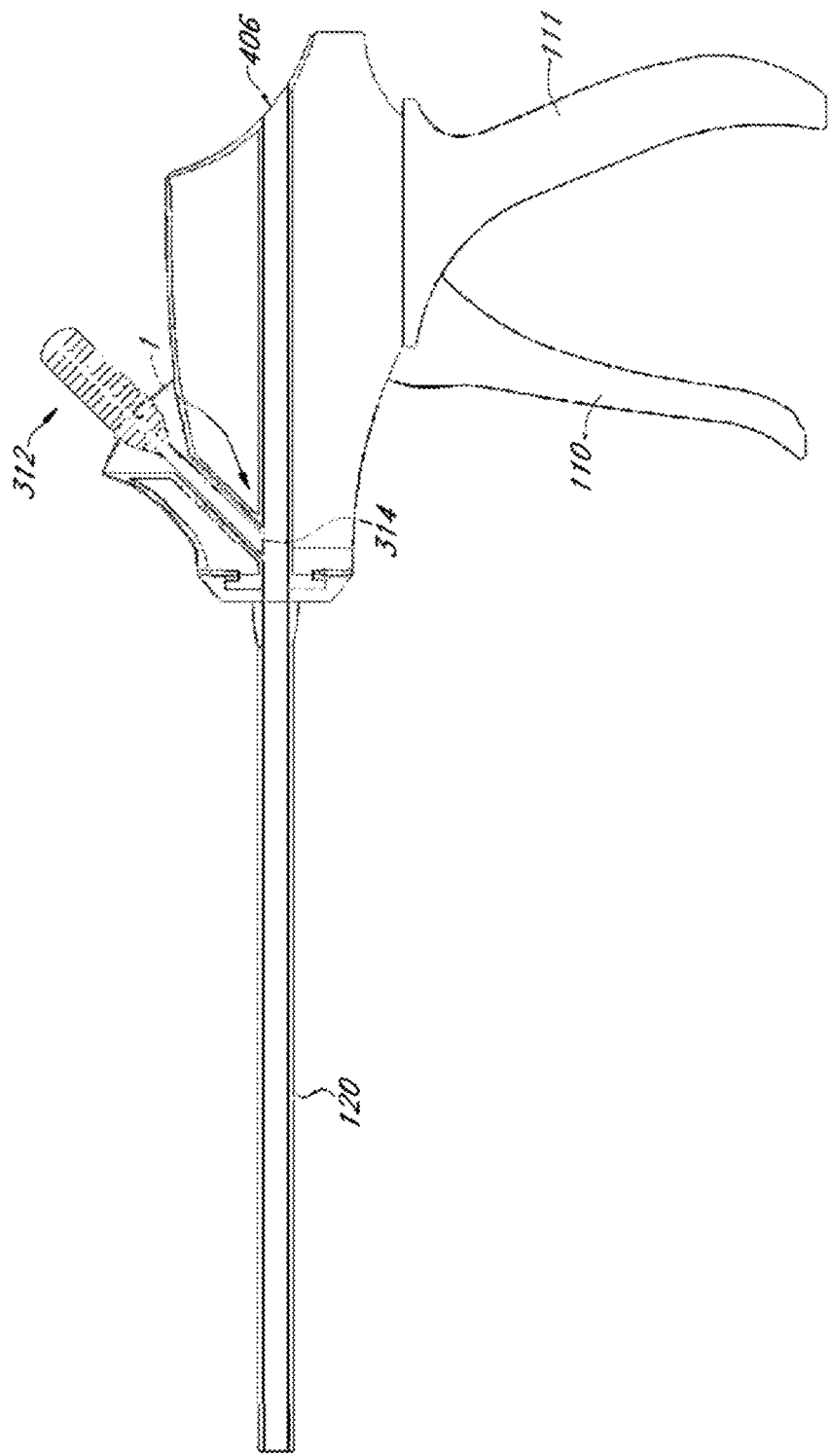
FIG. 2E illustrates a section view of the bone graft delivery device of FIGS. 2C and 2D including a pusher rod.
Figure 3:
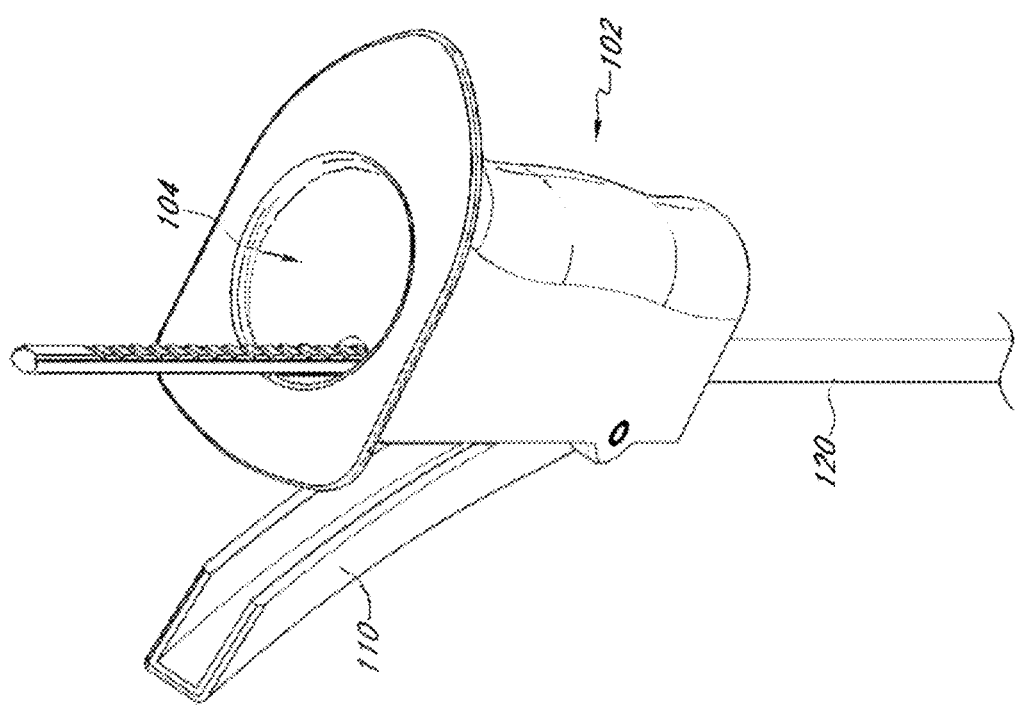
FIG. 3 illustrates a perspective view of a handle of a bone graft delivery device including a funnel for introduction of bone graft.

The handle 102 of FIGS. 2C-2E can include any of the ratcheting mechanisms described herein or any other suitable ratcheting mechanism. In use, once the bone graft material is loaded via the funnel 104, the plunger 112 is inserted from the proximal opening of the main channel 406 through the handle 102 and into the tube 120. The main channel 406 can include a window to allow the pawl to engage notches on the plunger. In use, movement of the trigger 110 toward the grip 111 can cause the pawl to advance the plunger and bone graft material distally in the tube 120. Releasing the trigger 110 to allow the trigger 110 to move away from the grip 111 causes the pawl to slide proximally along the plunger to engage a more proximal notch. If the window is located proximal to the intersection of the funnel shaft 106 with the main channel 406, the cover, sheath, or the like can be omitted from the ratcheting mechanism. In such embodiments, the bone graft material does not pass through the portion of the main channel 406 having the window, so the window can be left uncovered during loading. In some embodiments, the handle 102 of FIGS. 2C-2E does not include a ratcheting mechanism, and a plunger can be inserted into and advanced through the main channel 406 and tube 120 to advance and deliver the bone graft material.

Figure 2F:
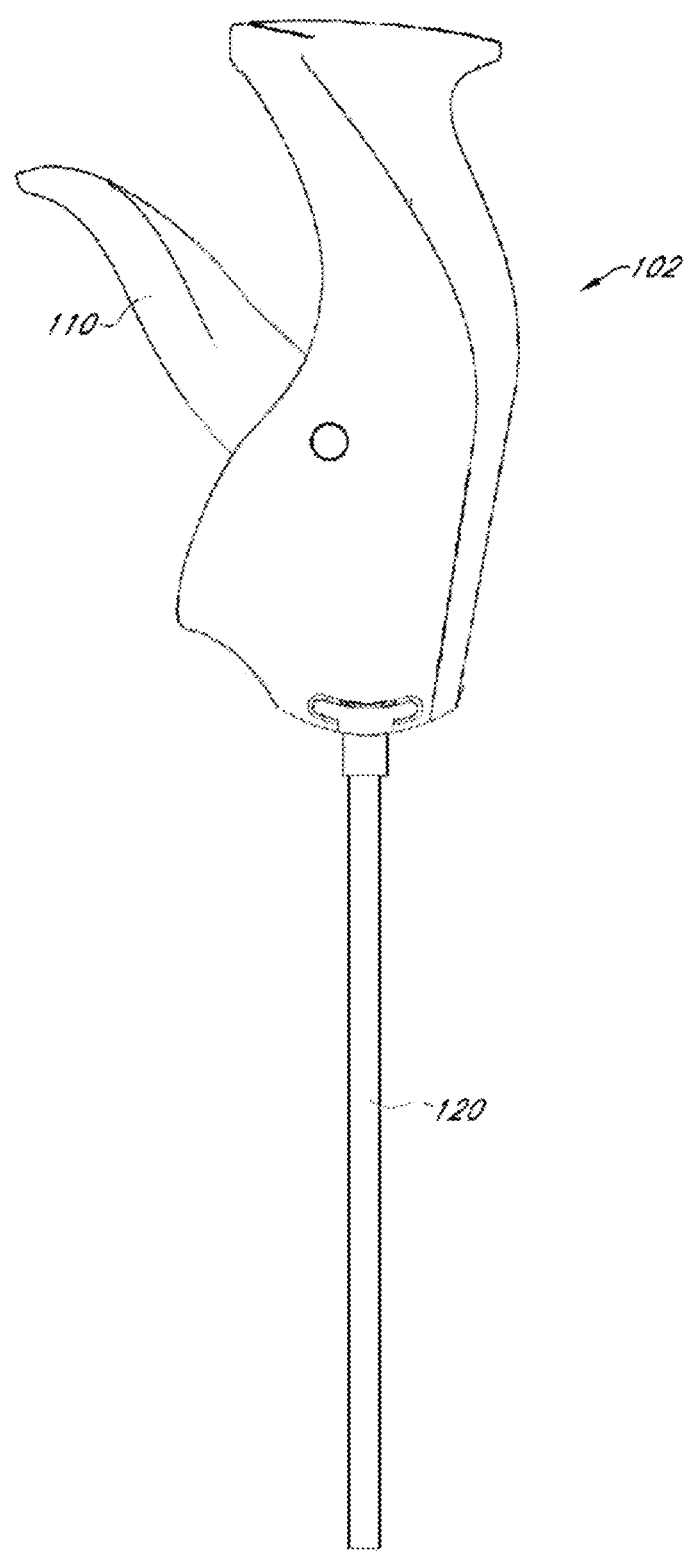
FIG. 2F illustrates a side view of another example embodiment of a bone graft delivery device.
Figure 2G:
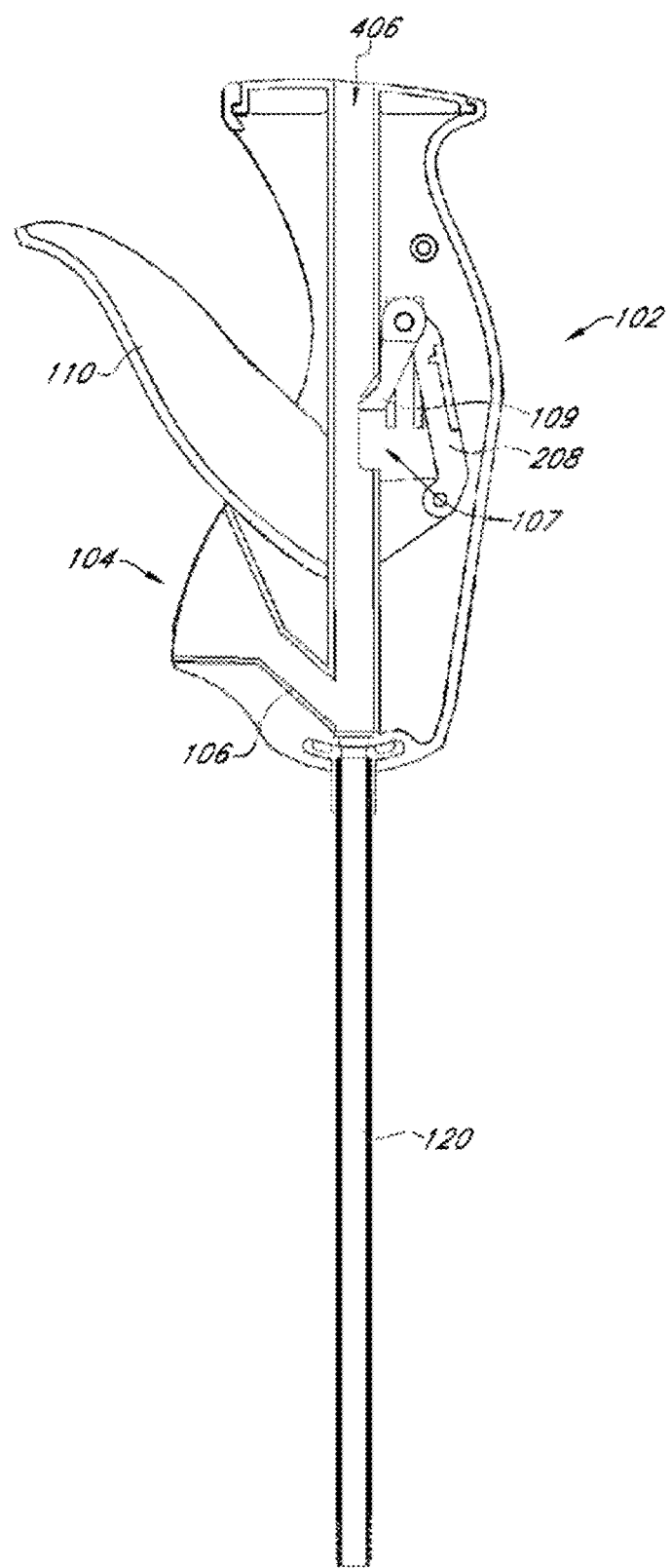
FIG. 2G illustrates a section view of the bone graft delivery device of FIG. 2F.
Figure 2H:
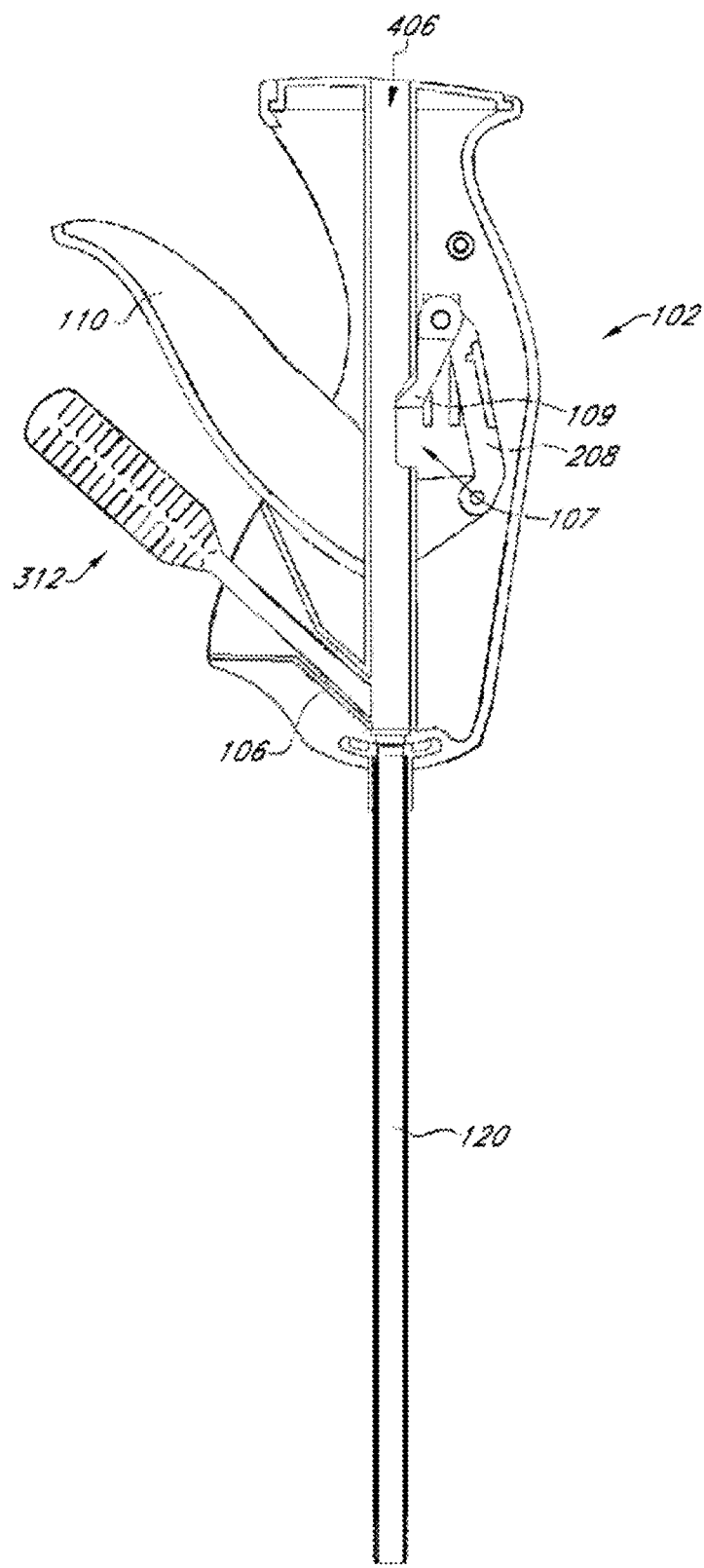
FIG. 2H illustrates a section view of the bone graft delivery device of FIGS. 2F and 2G including a pusher rod.
Figure 2I:
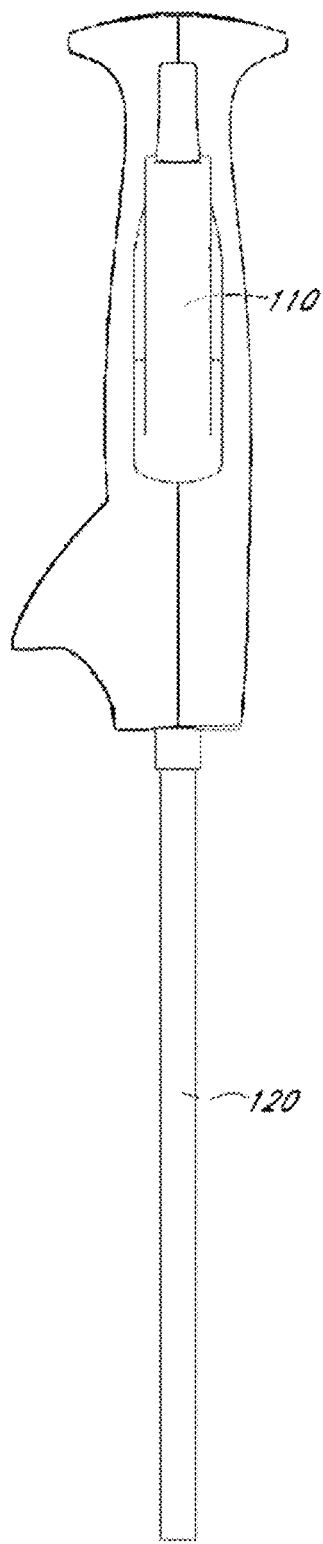
FIG. 2I illustrates a bottom view of another example embodiment of a bone graft delivery device.
Figure 2J:
FIG. 2J illustrates a section view of the bone graft delivery device of FIG. 2I.
Figure 2K:
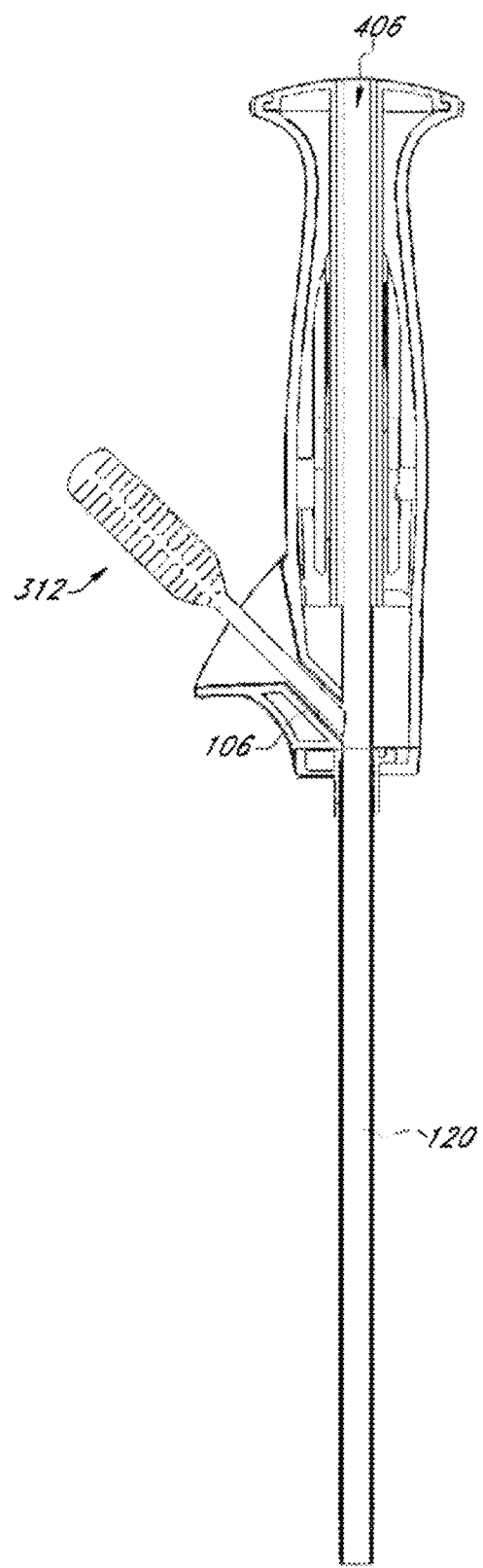
FIG. 2K illustrates a section view of the bone graft delivery device of FIGS. 2I and 2J including a pusher rod.

FIGS. 2F-2H illustrate an alternative embodiment in which the funnel 104 is located on the same side or surface of the handle 102 as the trigger 110. In the illustrated embodiment, the funnel 104 is advantageously located distal to the trigger 110 so that the pusher rod 312, when inserted into the funnel 104, does not interfere with operation of the trigger 110. The embodiment of FIGS. 2F-2H can also include a main channel 406, an angled funnel 104, funnel shaft 106, and distal end 314 of the pusher rod 312, and any suitable ratcheting mechanism similar to the embodiment shown in FIGS. 2C-2E and discussed above. In use, a plunger is inserted into the main channel 406 and tube 120. In the illustrated embodiment, the main channel 406 includes a window 107 to allow the pawl 109 to engage notches on the plunger when the plunger is inserted. Movement of the trigger 110 towards the handle 102 causes the pawl 109 to move distally within the window 107, thereby advancing the plunger and bone graft material. Movement of the trigger 110 away from the handle causes the pawl 109 to slide proximally along the plunger and engage a more proximal notch. In the illustrated embodiment, the window 107 and ratcheting mechanism are located proximal to the intersection of the funnel shaft 106 with the main channel 406, and the ratcheting mechanism does not include a cover or sheath. FIGS. 2I-2K illustrate another alternative embodiment, similar to the embodiment of FIGS. 2F-2H, with the funnel 104 positioned on a side or surface of the handle 102 lateral or generally perpendicular to the trigger 110. In other embodiments, the funnel 104 can be located on any side or surface of the handle 102, for example, opposite the trigger 110, to either side of the trigger, or any other position around the handle 102. The funnel 104 can also be located distal to, even with, or proximal to the trigger 110.

FIGS. 16A-16D illustrate another alternative embodiment of a bone graft delivery device 100 having a handle 102 including a ratcheting mechanism 508. In use, the ratcheting mechanism 508 is used to advance the plunger 112 and bone graft material through the tube 120 for delivery. As shown, the ratcheting mechanism 508 includes a pawl 509 having one or more teeth 514 that are received in the notches 113 of the plunger 112. In the illustrated embodiment, the pawl 509 includes four teeth 514, although more or fewer teeth 514 are also possible. A pawl 509 having multiple teeth 514 can engage multiple notches 113 of the plunger 112 simultaneously, which can advantageously provide a more secure engagement between the ratcheting mechanism 508 and the plunger 112, allow the pawl 509 to apply a greater advancement force on the plunger 112, and/or compensate for possible malfunctioning or manufacturing variances or defects to better ensure at least one tooth 514 engages the plunger 112.

The pawl 509 can be coupled to the trigger 110 via a pivot point 515 and/or a spring 517. The spring 517 can advantageously provide resistance to movement of the trigger 110 relative to the body of the handle 102. In some embodiments, the spring 517 can bias the trigger 110 away from the body of the handle 102 (toward the position shown in FIGS. 16A-16B).

In some embodiments, the handle 102 and tube 120 have a modular construction such that the tube 120 is removably coupleable to the handle 102 as described herein. The tube 120 can be provided preloaded with bone graft or can be loaded with bone graft prior to being coupled to the handle 102 as described in greater detail herein. In some embodiments, a handle 102, for example, a handle 102 including any of the ratcheting mechanisms described herein or another suitable ratcheting or advancement mechanism, need not include a funnel and/or a channel or funnel shaft. In use, a tube 120 loaded with bone graft is coupled to the handle 102, the plunger 112 is inserted through the handle 102 into the tube 120, and the ratcheting mechanism 508 is used to advance the plunger 112 and bone graft material through the tube 120 for delivery.

Figure 16A:
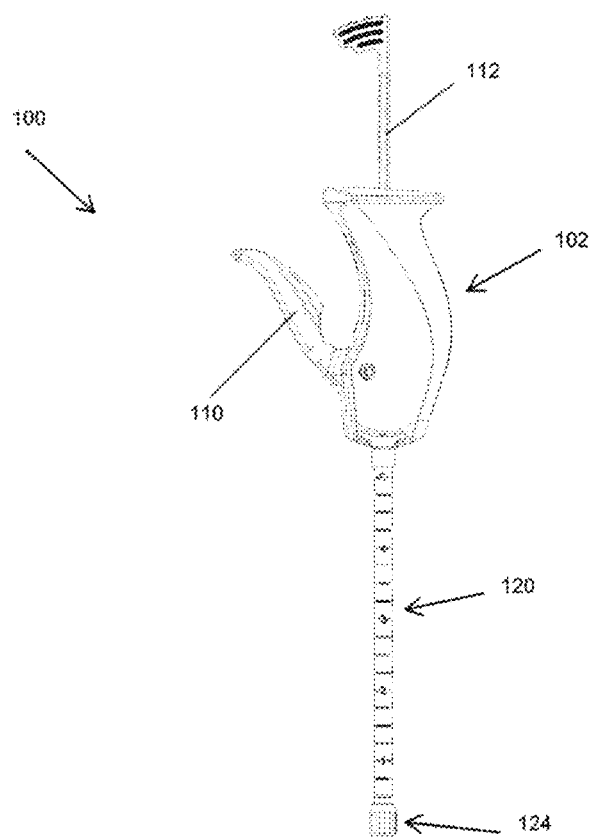
FIG. 16A illustrates a side view of an example embodiment of a bone graft delivery device having a handle including a trigger and a ratcheting mechanism with the trigger in a first position.
Figure 16B:
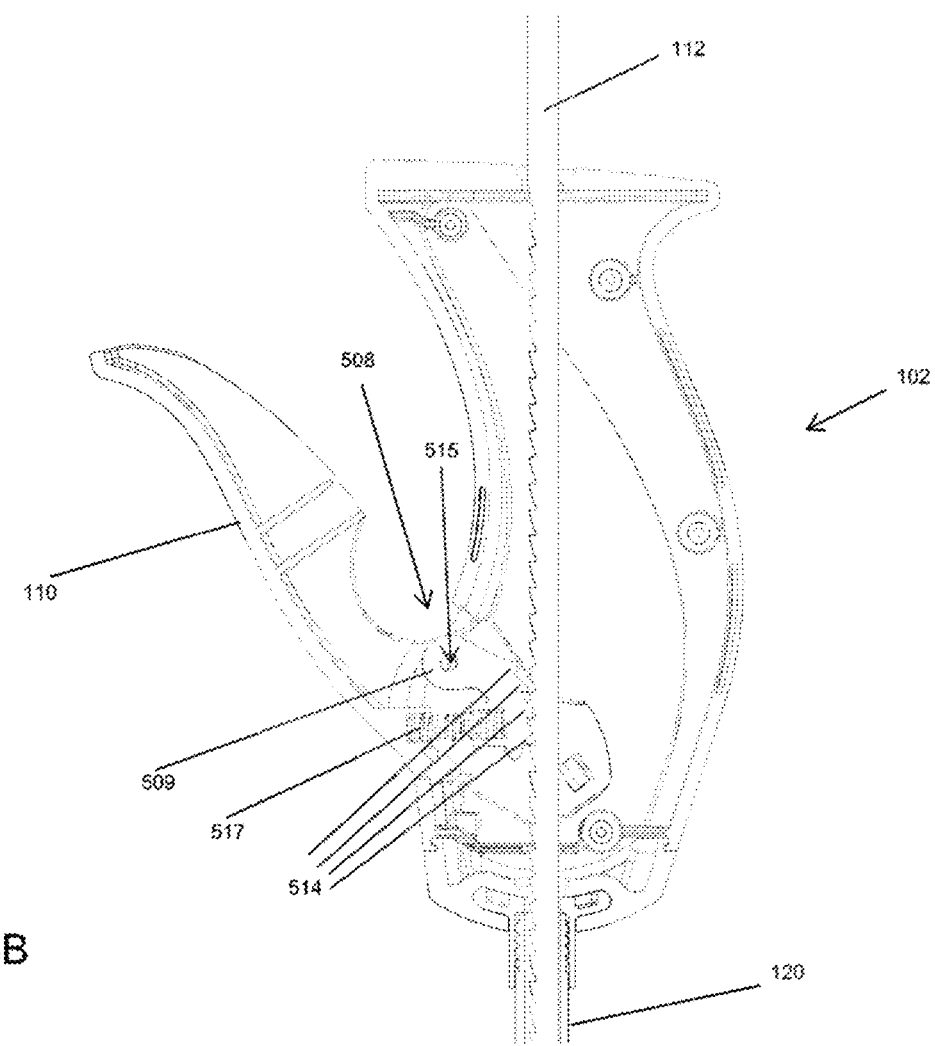
FIG. 16B illustrates a section view of the bone graft delivery device of FIG. 16A.
Figure 16C:
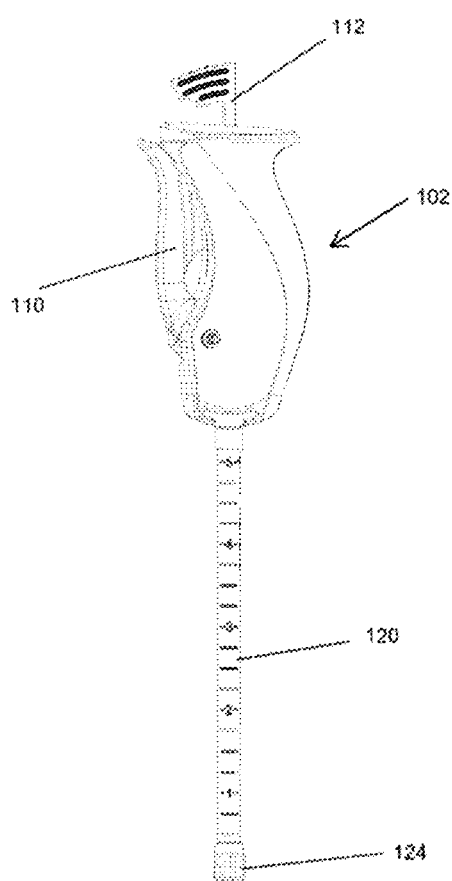
FIG. 16C illustrates a side view of the bone graft delivery device of FIG. 16A with the trigger in a second position.
Figure 16D:
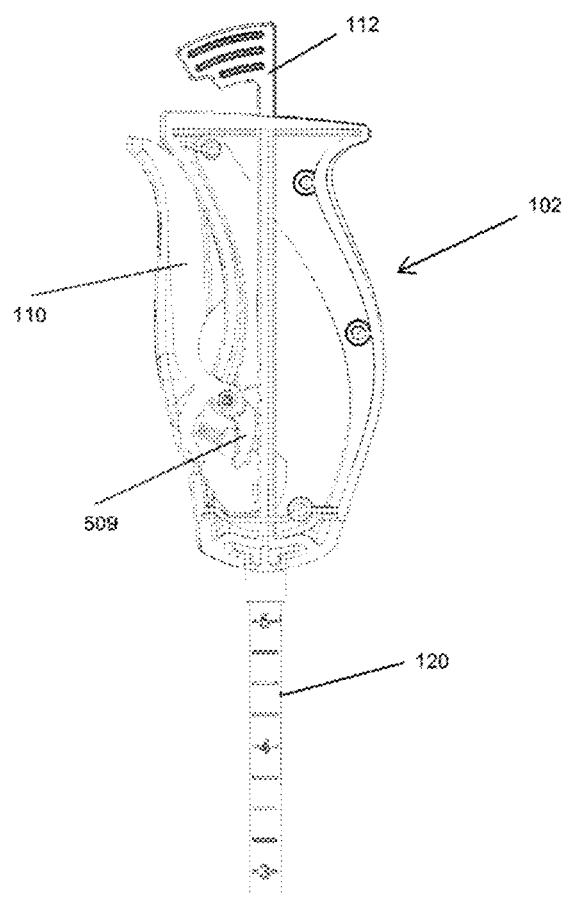
FIG. 16D illustrates a section view of the bone graft delivery device of FIG. 16C.

In use, movement of the trigger 110 from the position shown in FIGS. 16A-16B to the position closest to the handle 102 body shown in FIGS. 16C-16D causes the teeth 514 of the pawl 509 to move distally (toward the tube 120) within the handle 102, thereby advancing the plunger 112 distally within the tube 120 to force the bone graft material distally within the tube 120. Movement of the trigger 110 back to the position shown in FIGS. 16A-16B causes the teeth 514 of the pawl 509 to side proximally along the plunger 112 and over the teeth 114 to engage more proximal notches 113.

In some embodiments, the plunger 112 teeth 114 can be spaced relatively closer together (for example, as shown in FIGS. 16A-16B compared to FIG. 4I). Such closer spacing can allow the ratcheting mechanism 108, 508 to be more reliable such that in the event that the pawl 509 misses a notch 113, the pawl 509 can engage the next notch 113 more quickly, easily, and/or with less backlash. The closer spacing can also allow the user to squeeze the trigger 110 toward the handle 102 body to a lesser extent (for example, only halfway or to another intermediate point) to deliver a smaller amount of bone graft material at a particular time if desired. If the distance between the teeth 114 is less than the displacement of the plunger 112 with a full stroke of the trigger 110 and ratcheting mechanism 108, 508, the pawl 109, 509 can engage a more proximal notch 113 as long as the trigger 110 is moved toward the handle 102 body enough that the plunger 112 is displaced by a distance greater than the distance between adjacent notches 113.

As shown in FIGS. 1A and 1B, the tube 120 of any of the devices described herein can include a permanent bend or curve that may be useful in positioning the device 100 at a desired location, for example, a space between two spinal discs, transverse process, facet joint, lamina, or other target area. Alternatively, the tube 120 may be straight, for example, as shown in FIGS. 2A and 2B, to deliver bone graft material directly into a desired location such as a disc space, transverse process, facet joint, lamina, or other target area. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal. In some embodiments, the tube 120 can be at least partially transparent, which can allow the user to view, for example, the volume or position of the graft material within the tube 120. The tube 120 can also include volume markings to allow the user to monitor the amount of graft material delivered to the target site and remaining in the tube 120, for example, as shown in FIGS. 4N-4O. In some embodiments, the tube 120 includes one or more radiopaque markers to allow for visualization on, for example, x-ray or fluoroscopy. The tube 120 is generally hollow to allow for the passage of bone graft material through the lumen of the tube 120. The tube 120 and lumen can have various diameters, for example, for different applications and/or target locations.

Figure 5A:
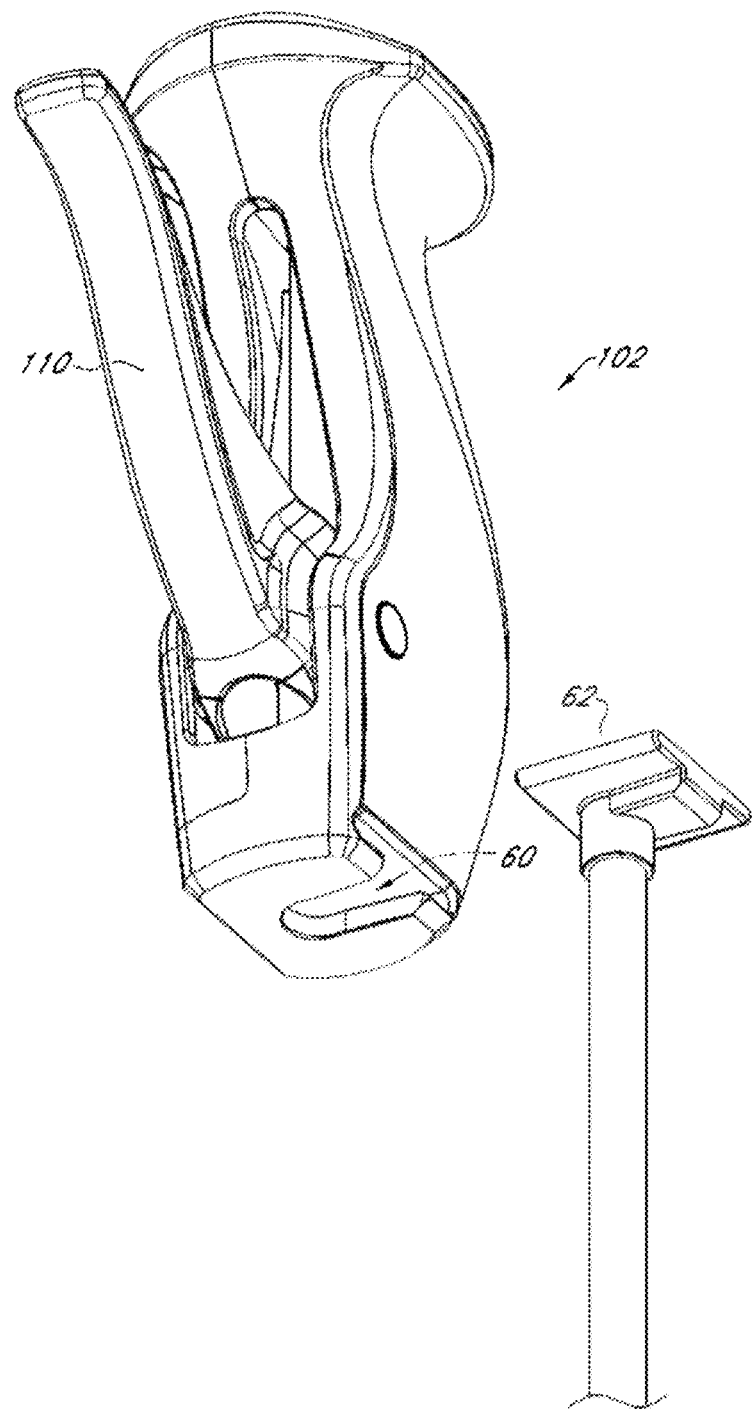
FIGS. 5A and 5B illustrate an example embodiment of a bone graft delivery device having a modular handle and tube construction.
Figure 5B:
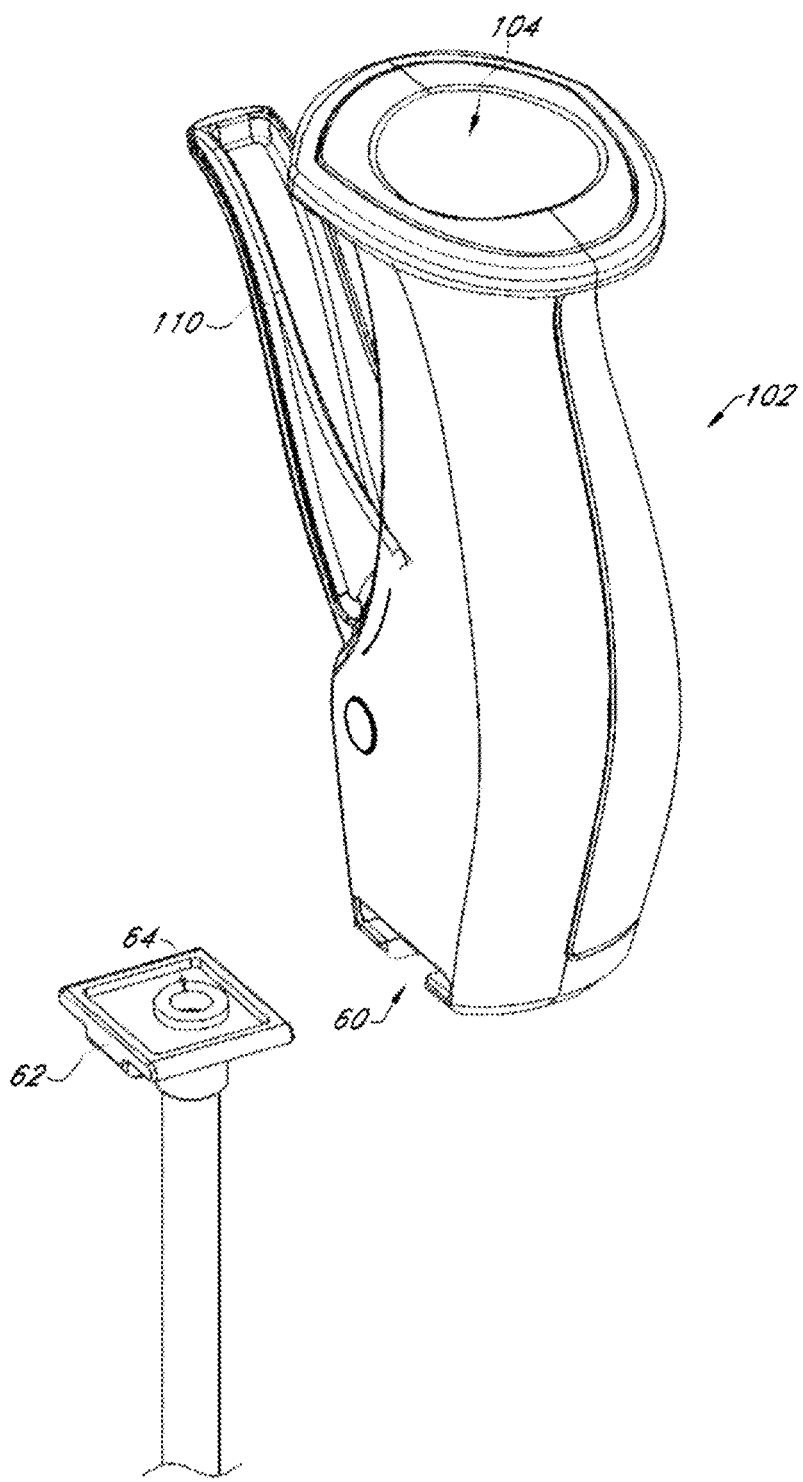

In some embodiments, the tube 120 can be integrally formed with or permanently coupled to the handle 102. In other embodiments, the bone graft delivery device 100 can have a modular construction so that various tubes 120 can be selected and coupled to the handle 102. Such a modular construction can advantageously allow the user to interchange straight and curved handles and/or handles having various other features depending on the target location, particular patient, and/or other factors. As shown in FIGS. 5A and 5B, the distal end of the handle 102 or any of the handles described herein can include a recess 60 configured to receive a base 62 coupled to or integrally formed with the tube 120. The base 62 can be coupled to the tube 120 via a threaded coupling, press fit, or any other suitable means. For example, in the embodiment shown in FIGS. 4N-4T, the tube 120 includes external threads 125a at or near a proximal end of the tube configured to mate with internal threads in the base 62. As shown in FIG. 5B, the base 62 can include an aperture to allow fluid communication between the funnel shaft 106 in the handle 102 and the tube 120. The tube 120 can also be coupled to the handle 102 by any other appropriate means.

Figure 6A:
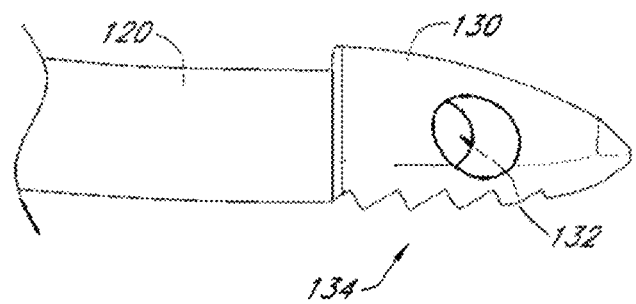
FIGS. 6A-6C illustrate various views of a distal tip of the bone graft delivery device of FIGS. 1A and 1B.
Figure 6B:
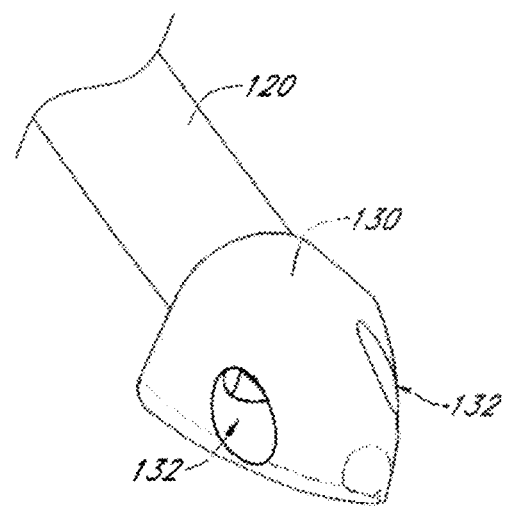
Figure 6C:
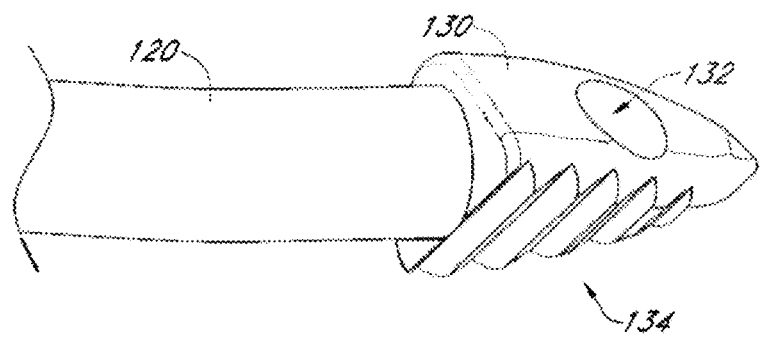
Figure 6D:
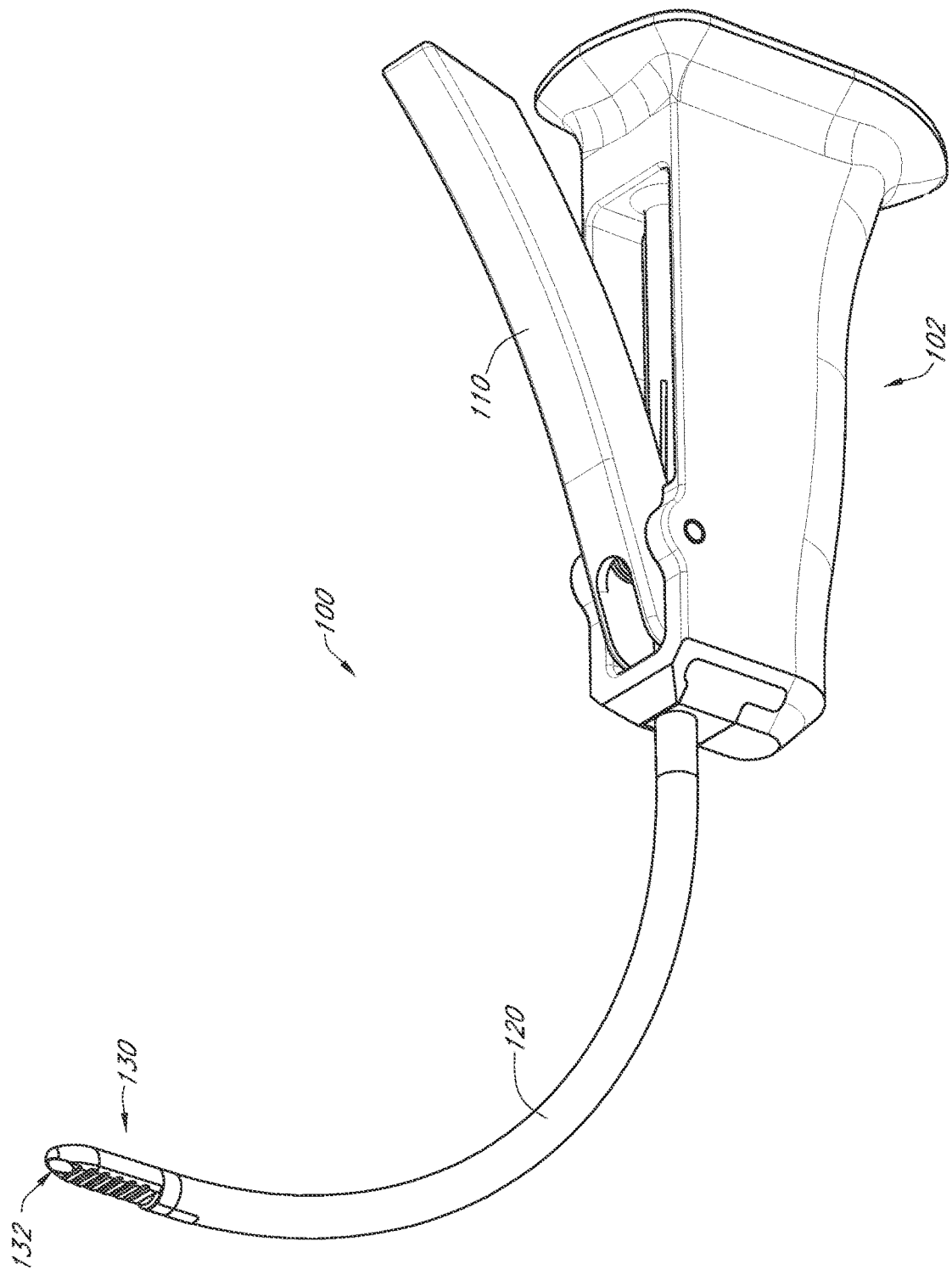
FIG. 6D illustrates a perspective view of an example embodiment of a bone graft delivery device having a curved tube.
Figure 6E:
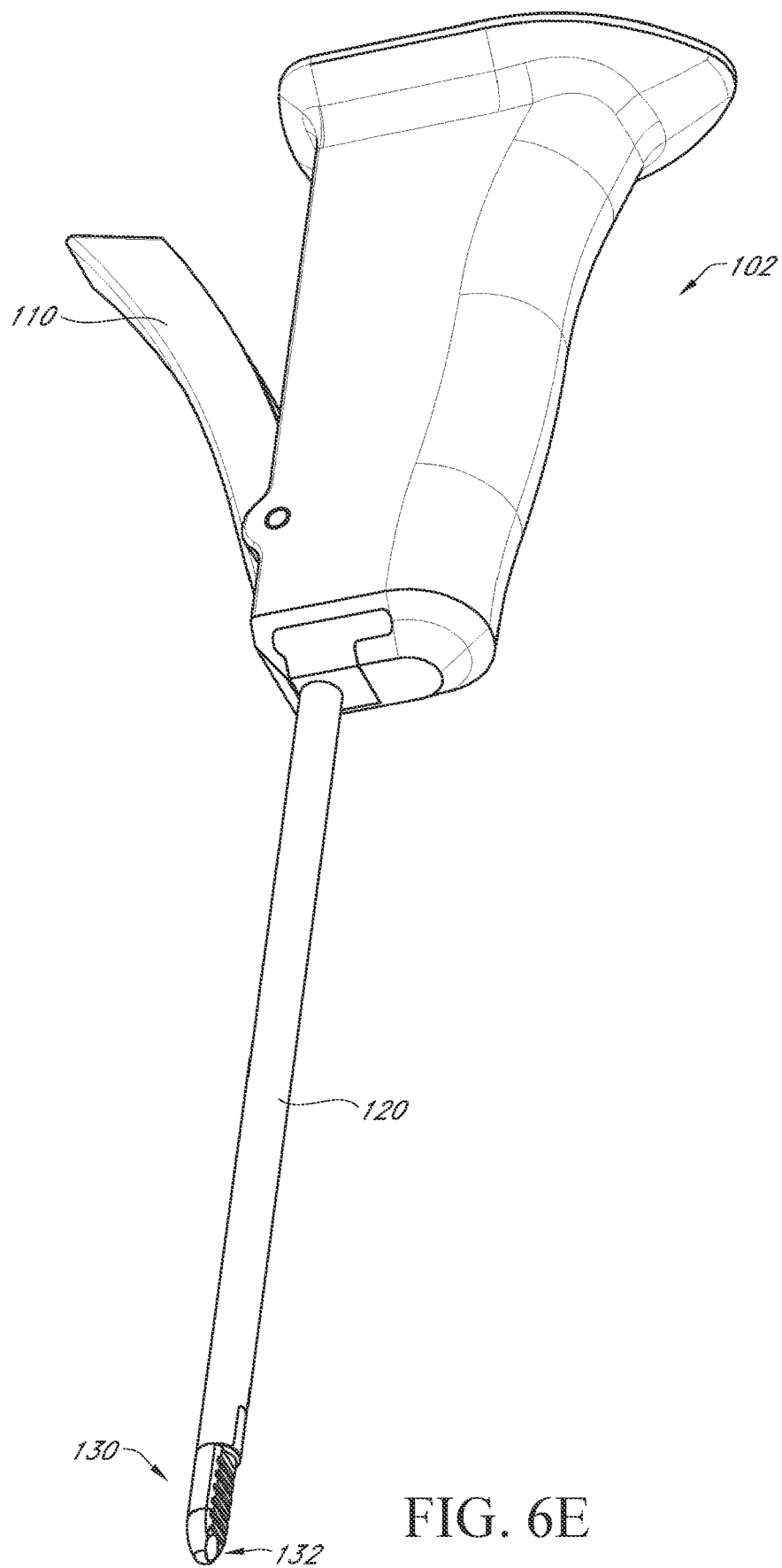
FIG. 6E illustrates a perspective view of an example embodiment of a bone graft delivery device having a straight tube.
Figure 6F:
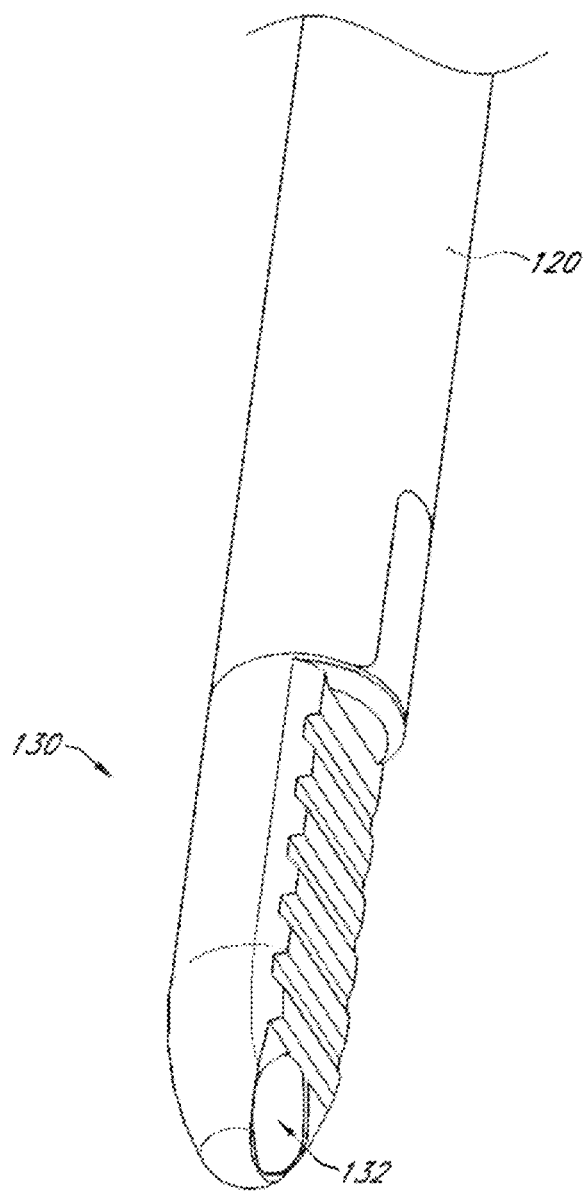
FIG. 6F illustrates an enlarged view of a rasping distal tip of the bone graft delivery device of FIG. 6E.
Figure 6G:
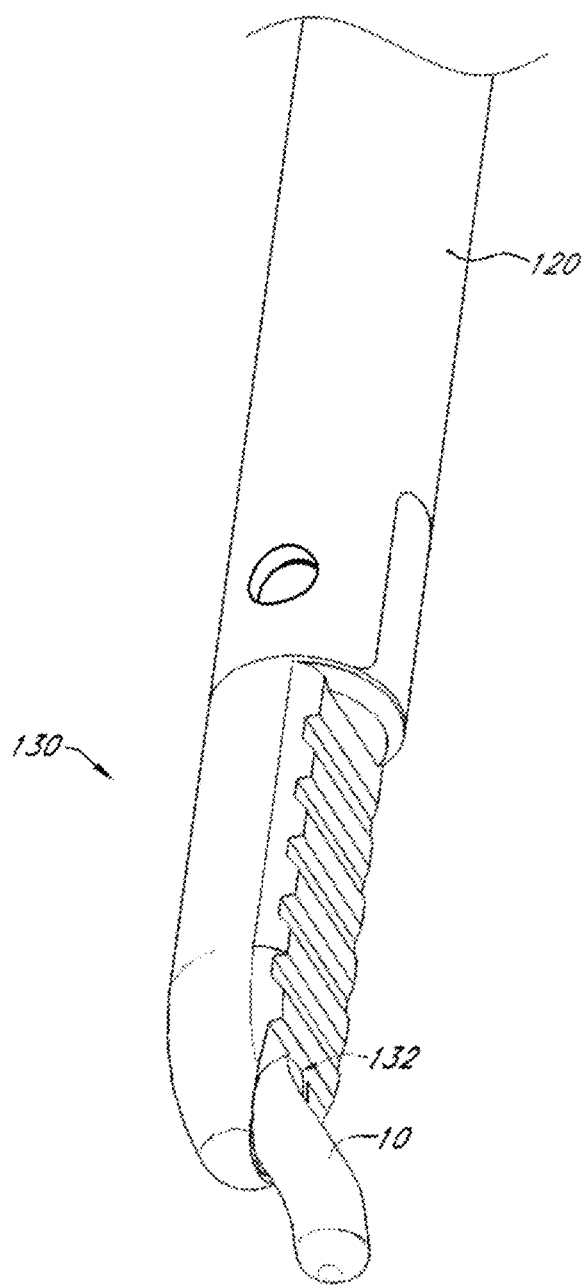
FIG. 6G illustrates the distal tip of FIG. 6F extruding bone graft material.

As shown in FIGS. 6A-6C, a distal end of the tube 120 (which may be any of the tubes described herein) can include a tip 130. The tip 130 can be integrally formed with or coupled, removably or permanently, to the tube 120. In some embodiments, the tube 120 and tip 130 can be a modular system such that different tips can be selected and coupled to the tube 120 for different procedures and/or target locations. The tip 130 can be made of a metallic, radiopaque material to facilitate visualization on, for example, fluoroscopy or x-ray. Alternatively, the tip 130 may be made of another material, for example a durable medical plastic or a composite material, and may include markers to facilitate visualization. In the illustrated embodiment, the tip 130 is somewhat bullet-shaped with a generally triangular cross-section; however, other shapes and configurations are also possible, for example, as shown in FIGS. 20A-D, 25A-26B, and 27A-33C. For example, the tip 130 can be generally flat as shown in the example embodiments of FIGS. 6D-6G. In some embodiments, for example as illustrated in the example embodiment of FIG. 6H-6I, the tip 130 is generally conical. This shape can be beneficial for delivering bone graft material to, for example, a facet joint. In some embodiments, the tip 130 is pointed, bulleted, and/or sharp to dissect or split muscle and tissue as it is advanced through the patient's skin and body to the surgical location. Alternatively, the tip 130 can be blunt to allow for displacement of muscle without risk of cutting of nerves or other tissue. The tip may have a single or multiple openings 132 in fluid communication with the tube 120 lumen and configured to deliver the bone graft material 10 from the tube 120, as shown in FIG. 6G, to the desired location.

Figure 6H:
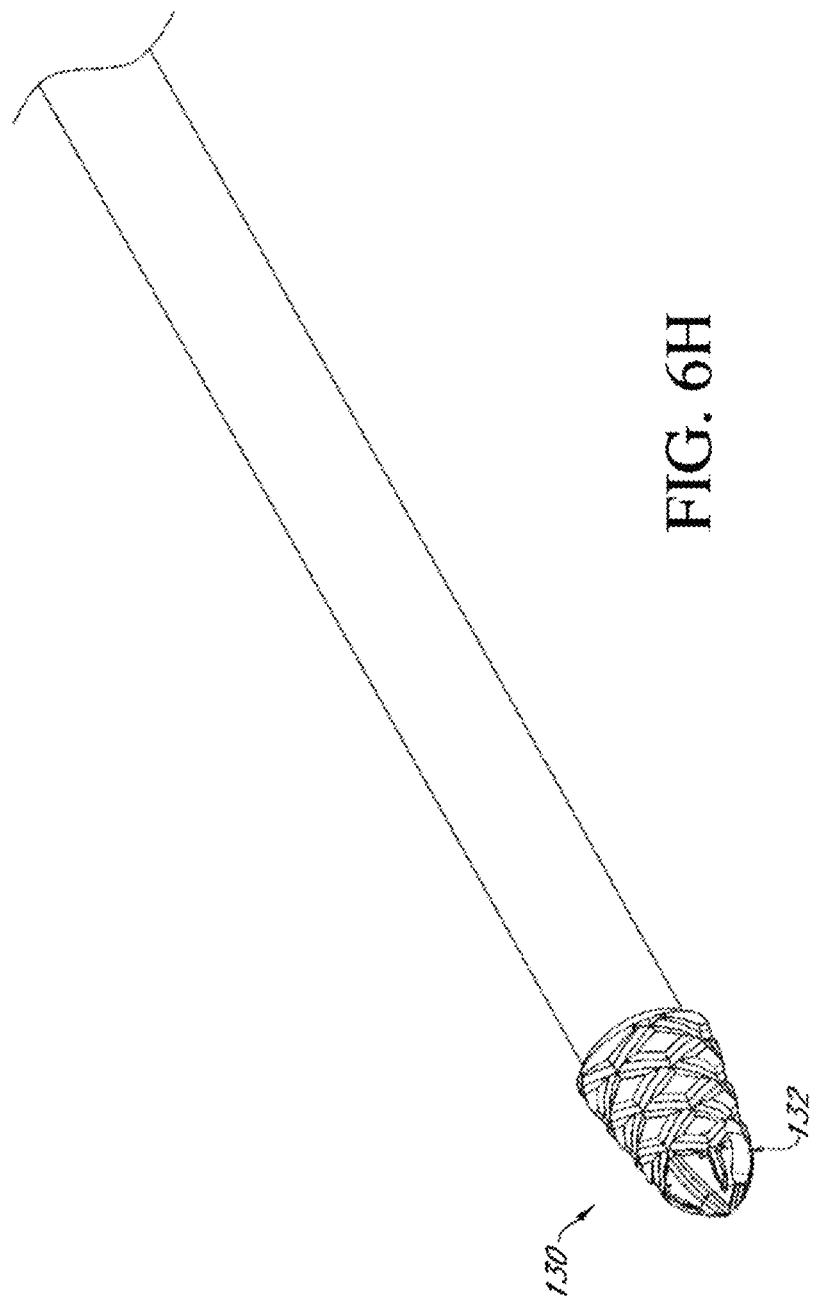
FIG. 6H illustrates an example embodiment of a rasping distal tip coupled to a tube of a bone graft delivery device.
Figure 6I:
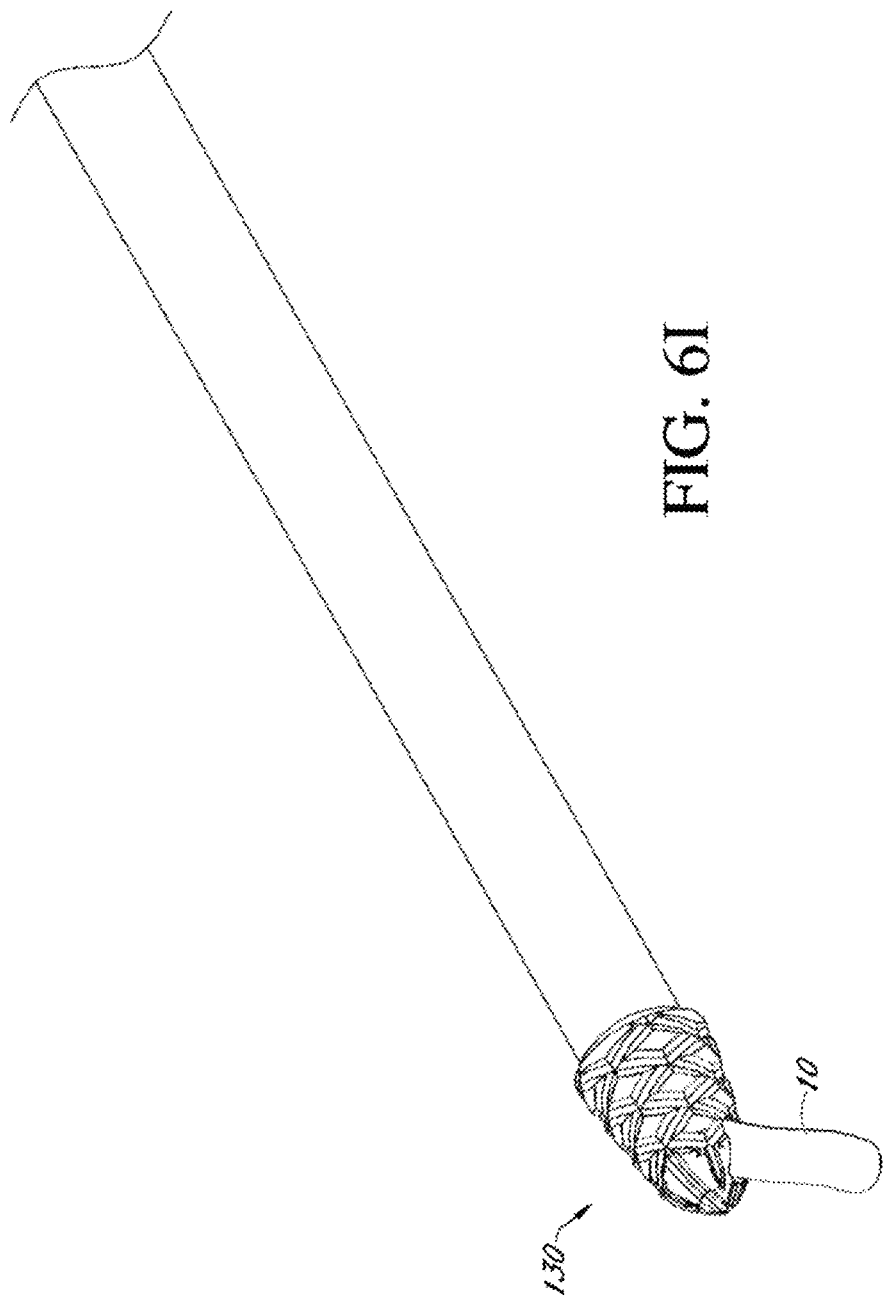
FIG. 6I illustrates the distal tip of FIG. 6H extruding bone graft material.

In some embodiments, at least one side or area of the tip 130 includes a series of jagged edges or other suitable surface 134 configured to serve as a rasp for scraping bone. As shown in FIGS. 6A and 6C, the edges may be triangular in shape, and as shown in in FIGS. 6D-6G, they may be flat. With respect to the embodiment shown in FIGS. 6D-6G, the jagged edges may form a plurality of flat surfaces parallel with each other all within the same plane. In some embodiments, for example as shown in FIGS. 6H-6I, the rasping surface 134 can include a roughened surface extending around an outer surface of the tip. The rasp may be operated manually or by mechanical, battery powered, electric, pneumatic, or any other means of force to allow for decortication of the area to receive the bone graft material. In some embodiments, the opening(s) 132 for delivering bone graft material is located on a side(s) or portion(s) of the tip 130 that does not include a rasping surface, for example as shown in FIGS. 1A-1B and 6A-6C. In some embodiments, the opening(s) 132 is located on a side(s) or portion(s) that does include a rasping surface, for example as shown in FIGS. 6D-6I and 8A.

In some embodiments, the delivery device 100 includes a sleeve slidably or telescopingly disposed over the tip 130. In some embodiments, the sleeve can extend to a proximal end of the tube 120 adjacent the handle 102 so that a user can distally advance or proximally retract the sleeve by manipulating a proximal end of the sleeve. In other embodiments, the sleeve extends over only a portion of the tube 120 or over only the tip 130 and the delivery device 100 includes an actuating mechanism that allows the sleeve to be advanced and retracted. The sleeve can be disposed over the tip 130 during insertion of the tip 130 to the target area to advantageously protect skin, tissue, and/or muscle along the insertion path from damage or injury from the rasping surface 134 and to allow the tip 130 to pass through the skin, tissue, and/or muscle more easily. Once the tip is positioned in the target location, the sleeve can be proximally retracted to expose the rasping surface 134 for decortication of the target area. After decortication and/or after delivery of the bone graft material, the sleeve can be distally advanced to cover the rasping surface 134 for withdrawal of the tip 130 from the body.

Figure 7A:
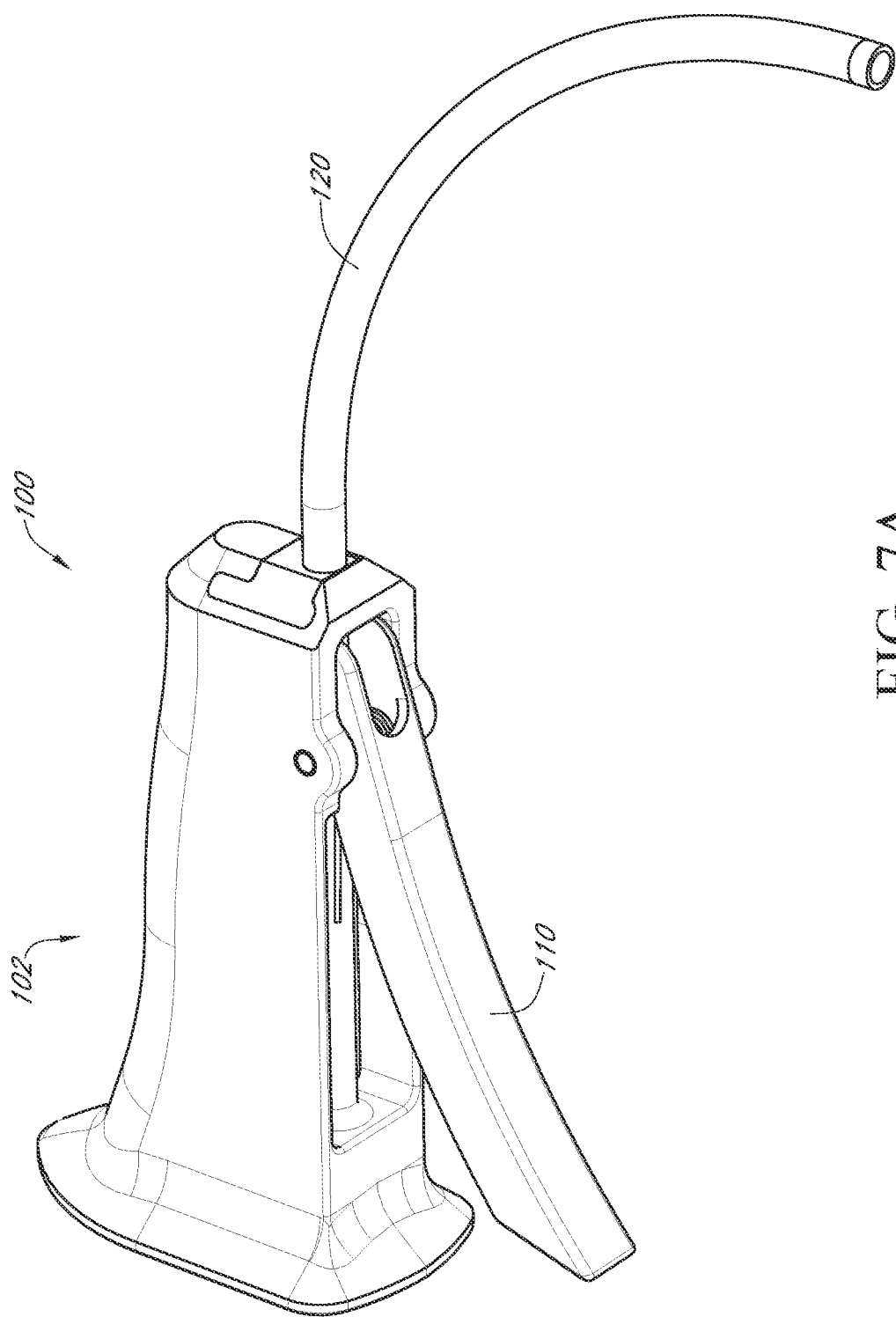
FIG. 7A illustrates a perspective view of an example embodiment of a bone graft delivery device.
Figure 7B:
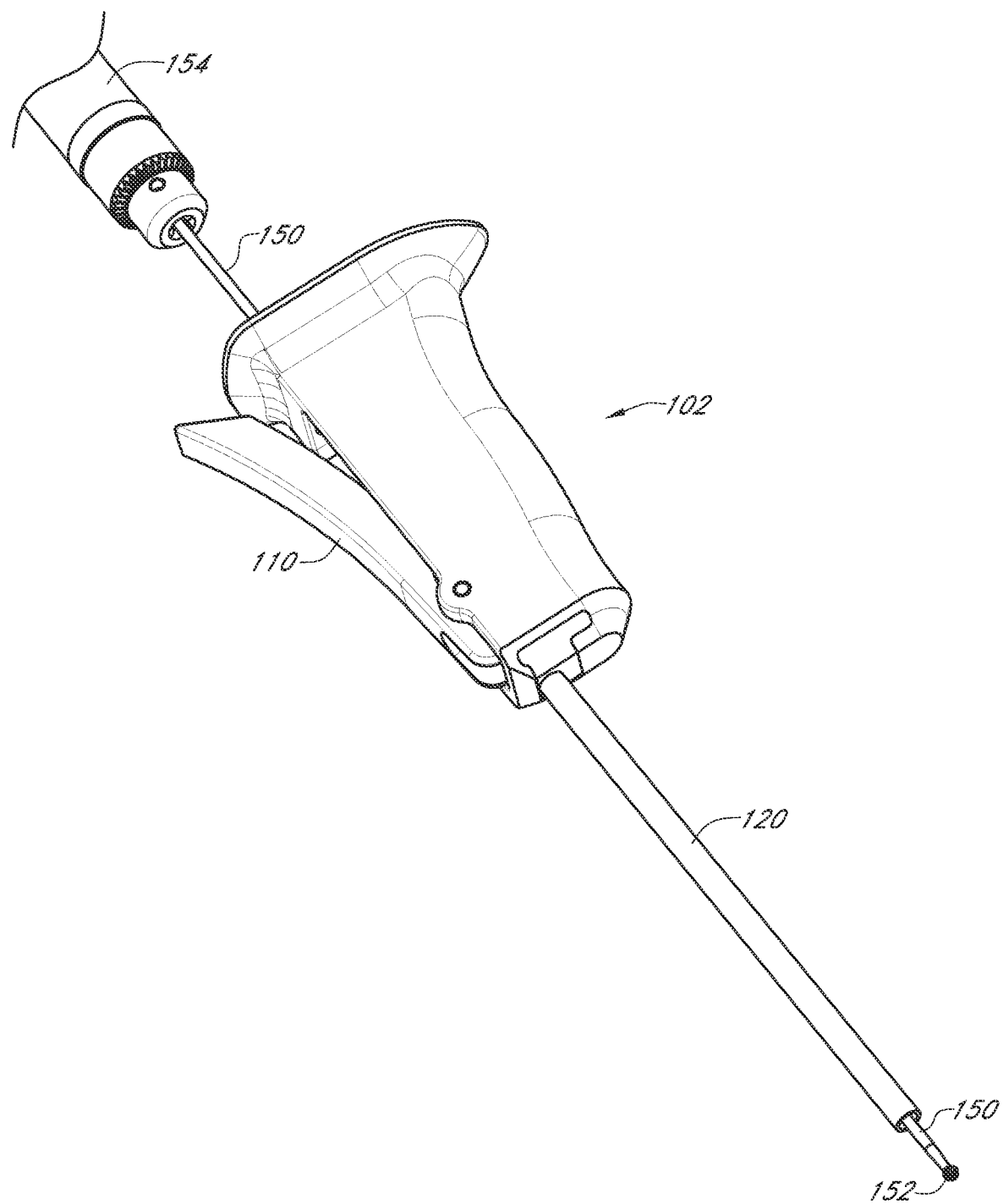
FIG. 7B illustrates a perspective view of an example embodiment of a bone graft delivery device including a shaft having a distal burr disposed therethrough.
Figure 7C:
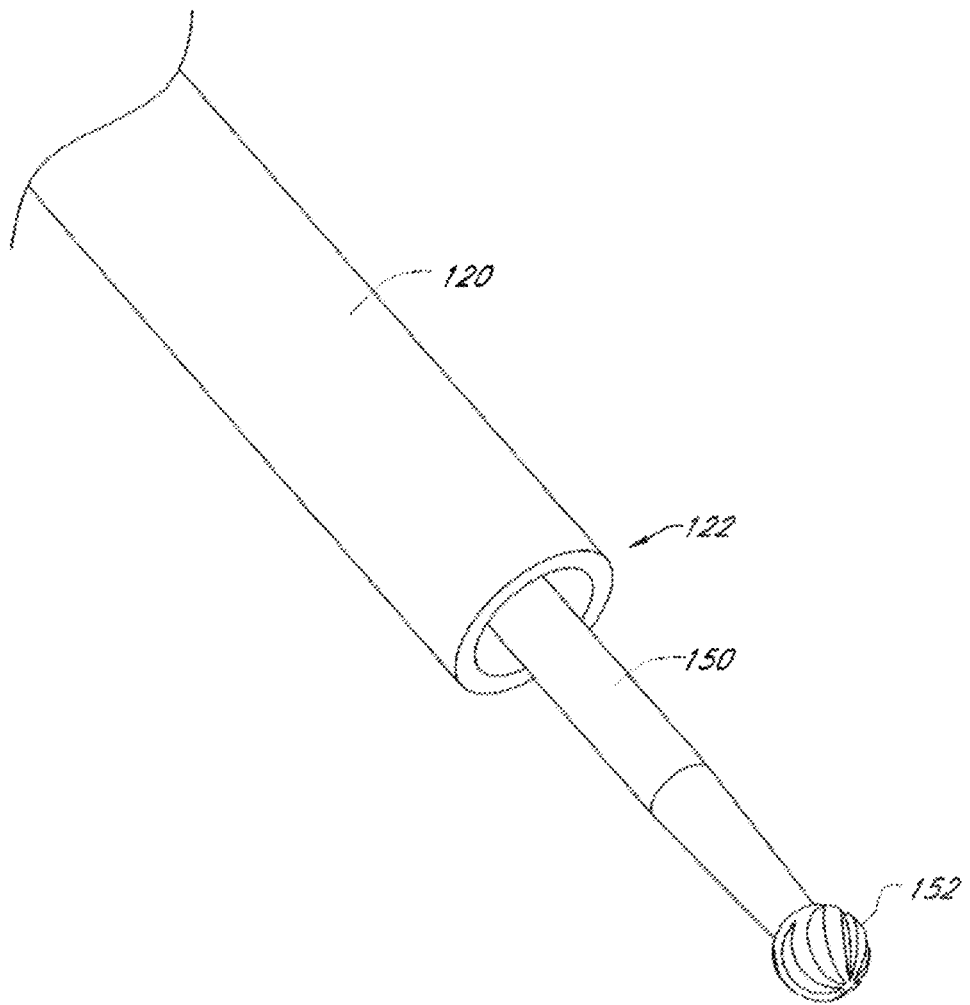
FIG. 7C illustrates an enlarged view of the distal end of the bone graft delivery device of FIG. 7B.

In some embodiments, the distal end of the tube 120 does not include a rasping tip 130, for example as shown in FIGS. 7A-7C. In some such embodiments, an elongate shaft 150 having a burr 152 at a distal end can be inserted through the tube 120 as needed or desired to decorticate a target area, for example as shown in FIGS. 7B and 7C. The burr 152 can have various shapes and configurations, for example, a generally spherical shape as shown in FIGS. 7B and 7C, a bullet shape similar to the distal tip 130 shown in FIGS. 6A-6C, a generally flat shape similar to the distal tip 130 shown in FIGS. 6D-6G, a generally conical shape as shown in FIGS. 6H-6I, or any other suitable shape or configuration. The use of a separate instrument for decortication can advantageously allow the user to select different burrs, rasps, or the like for different patients, target areas, or situations. The elongate shaft 150 and burr 152 can be operated manually. Alternatively, a proximal end of the shaft 150 can be coupled to a drill 154 or another device to provide decortication by mechanical, battery powered, electric, pneumatic, or any other means of force.

Figure 4W:
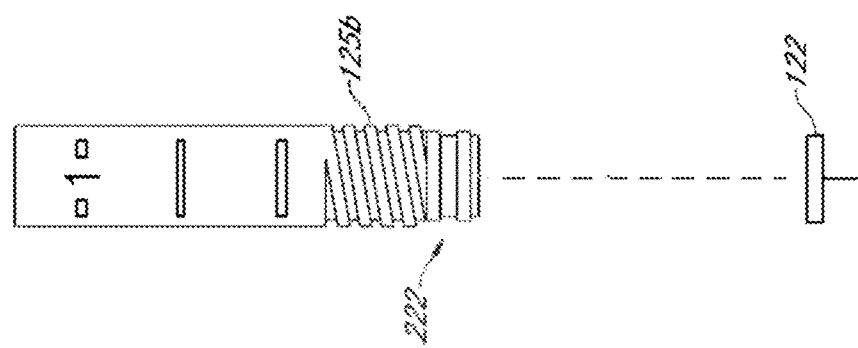
FIG. 4W illustrates a radiopaque ring configured to be placed on a distal end of a tube of a bone graft delivery device.

In some embodiments, the distal end of the tube 120 includes a radiopaque ring or other marker 122 as shown in FIG. 7C to allow for visualization on, for example, x-ray or fluoroscopy. In some embodiments, the radiopaque ring 122 can be used to assist the user in assessing depth during the procedure. In some embodiments, for example as shown in FIG. 4O, the radiopaque ring 122 can be press fit or snapped onto the distal end of the tube 120 during manufacturing and assembly. In some embodiments, for example as shown in FIG. 4W, the radiopaque ring 122 can be press fit or snapped into a groove 222 near a distal end of the tube 120. In the illustrated embodiment, the groove 222 is distal to the threads 125b configured to receive the tube end cap 124 and is therefore covered by the tube end cap 124 when the tube end cap 124 is coupled to the tube 120. In some embodiments, the radiopaque ring 122 can be co-molded with the tube 120 during manufacturing.

In some embodiments in which the handle 102 and tube 120 have a modular construction such that the tube 120 is removably coupleable to the handle 102, the tube 120 can be provided preloaded or can be loaded with a loading device prior to being coupled to the handle 102. FIGS. 17A-19F show example embodiments of loading devices 600, 700, 900 for loading bone graft material into the tube 120. Such loading devices 600, 700, 900 can allow the user to load the tube 120 with any bone graft material or combination of bone graft materials he or she wishes or deems appropriate. For example, the user can use synthetic, autologous, stem cell, cellular matrix, DBM, cortical fibers, demineralized cortical fibers, cadaveric, and/or any other available bone graft material. In some embodiments, the user can use DBM putty. In some embodiments, the bone graft materials can include one or more of hydroxyapatite (HA), tricalcium phosphate (TCP), and bioglass.

As shown in the embodiments of FIGS. 17A-17F, the loading devices 600 include a hollow tube body 602, a plunger shaft 604, a plunger 605, and a cap or coupling 608. In some embodiments, the tube body 602 can hold a volume of about 20 cc, although other sizes and volume are also possible. The tube body 602 can have a smooth or generally smooth inner wall. In some embodiments, the tube body 602 includes measurement markings to allow the user to determine the amount of bone graft material within the tube body 602. The tube body 602 includes a distal tip or end 610. As shown, the distal tip 610 has a smaller diameter than the tube body 602. The tube 120 of a bone graft delivery device 100 such as those described herein is coupled to the distal tip 610 for loading. In some embodiments, the distal tip 610 is internally threaded to receive and engage external threads 125a at or near the proximal end of the tube 120 (shown in FIG. 4O). In some embodiments, the plunger 605 is made in part or entirely of rubber. The plunger 605 is coupled, either removably or permanently, to a distal end of the plunger shaft 604. In some embodiments, the plunger shaft 604 and plunger 605 are integrally molded or formed. The plunger 605 has a greater diameter than the plunger shaft 604 and is sized and shaped to contact and seal against the inner wall of the tube body 102. In some embodiments, the loading device 600 includes a handle 606 that allows the user to better grip the plunger shaft 604. As shown, the handle 606 is integrally molded or formed or coupled, either removably or permanently, to a proximal end of the plunger shaft 604. The handle 606 can have various shapes and configurations, for example as shown in the embodiments of FIGS. 17A-17C and 17D-17F.

As shown, the plunger shaft 604 is externally threaded. The cap or coupling 608 couples to a proximal end of the tube body 602, for example, via a threaded, snap-fit, or other suitable connection. In some embodiments, the cap 608 couples to the tube body 602 via a combined snap fit and rotational coupling mechanism whereby the cap 608 is attached to the tube body 602 by rotating the cap 608 (e.g., clockwise) until the cap 608 snaps into place; the cap 608 can be removed from the tube body 602 by rotating the opposite direction (e.g., counter clockwise) to disengage the snap fit and rotating until the cap 608 fully releases from the tube body 602. The cap 608 has a through-hole that is sized to receive the plunger shaft 604 therethrough and internally threaded to engage the external threads of the plunger shaft 604. The cap 608 can be predisposed on the plunger shaft 604. The cap 608 can be threaded along the plunger shaft 604, but can be retained on the plunger shaft 604, which has a larger diameter than the plunger shaft 604 and therefore a larger diameter than the through-hole in the cap 608 that is sized to engage the plunger shaft 604.

Figure 17A:
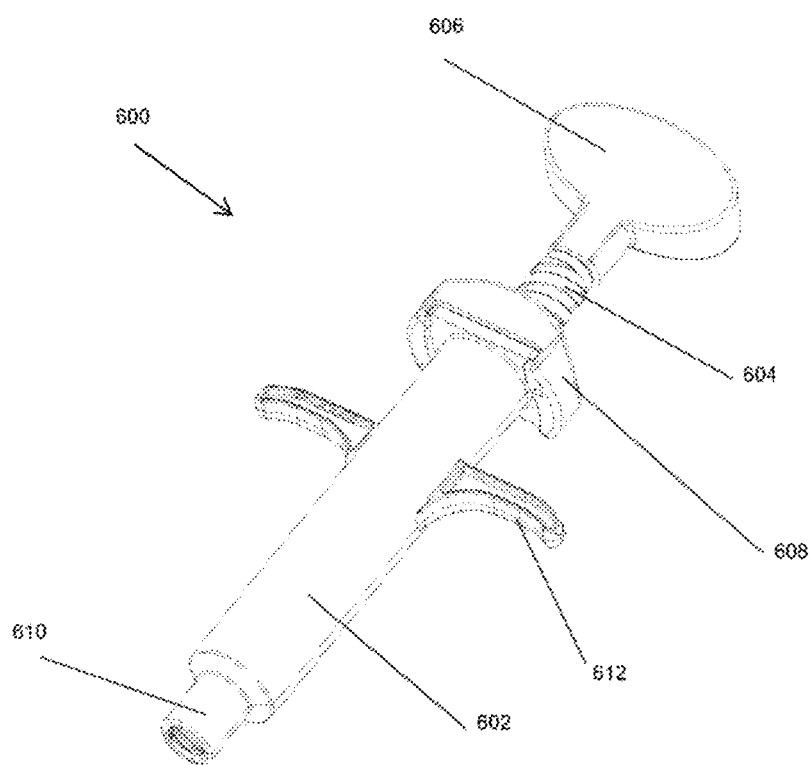
FIG. 17A illustrates a perspective view of an example embodiment of a bone graft loading device.
Figure 17B:
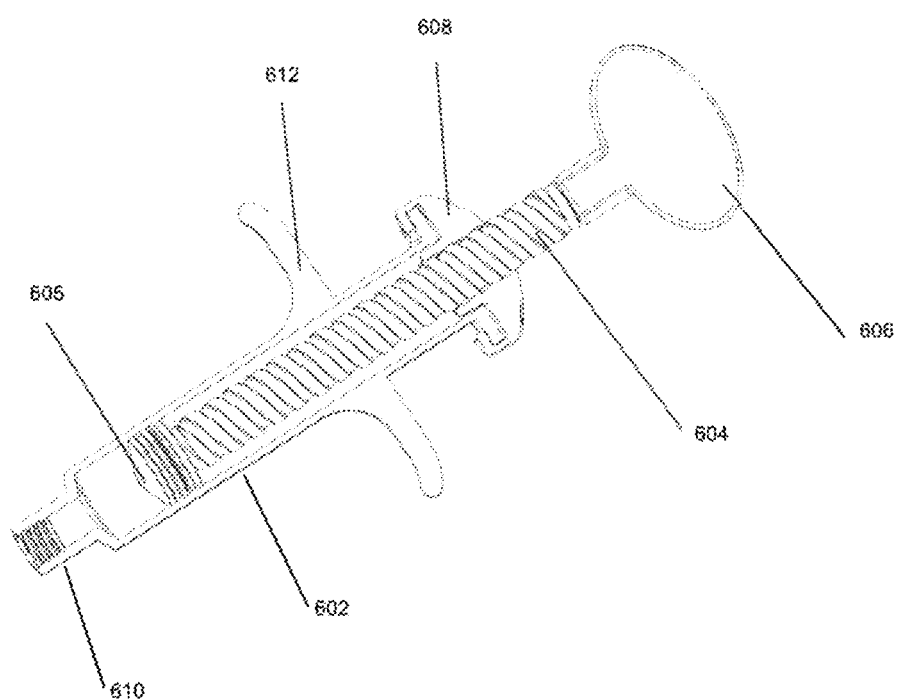
FIG. 17B illustrates a section view of the bone graft loading device of FIG. 17A.
Figure 17C:
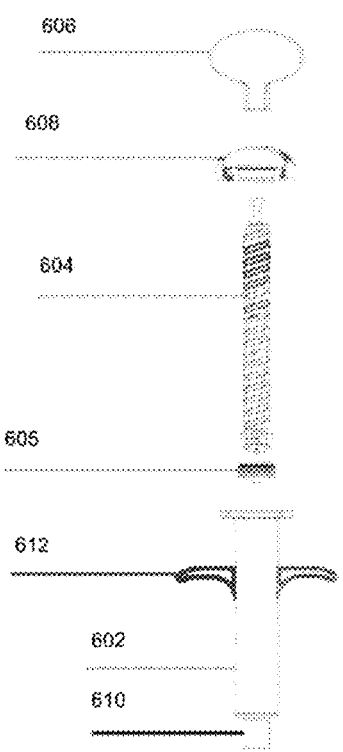
FIG. 17C illustrates an exploded view of the bone graft loading device of FIGS. 17A-17B.
Figure 17D:
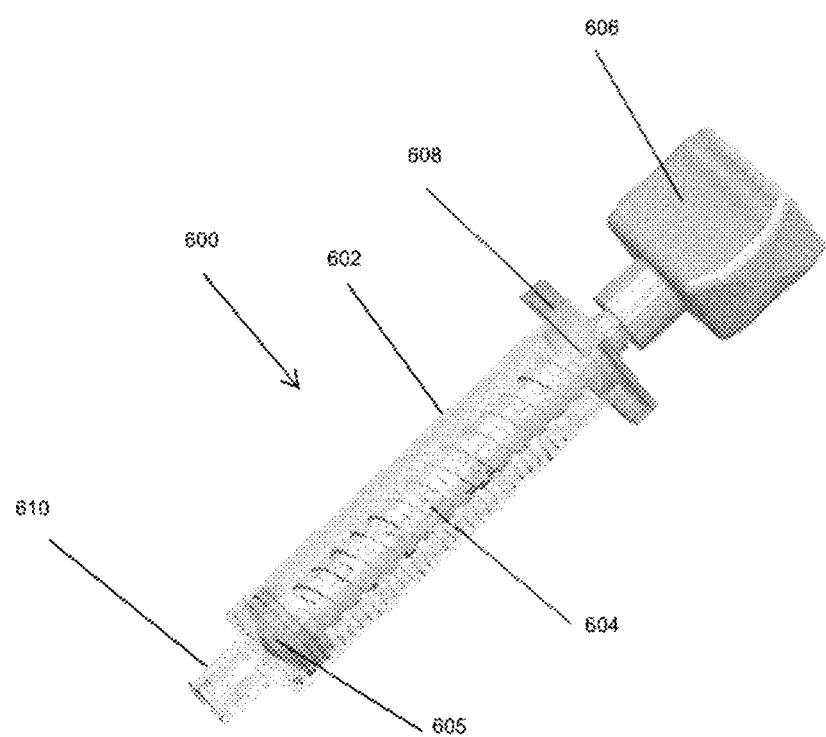
FIG. 17D illustrates a perspective view of another example embodiment of a bone graft loading device.
Figure 17E:
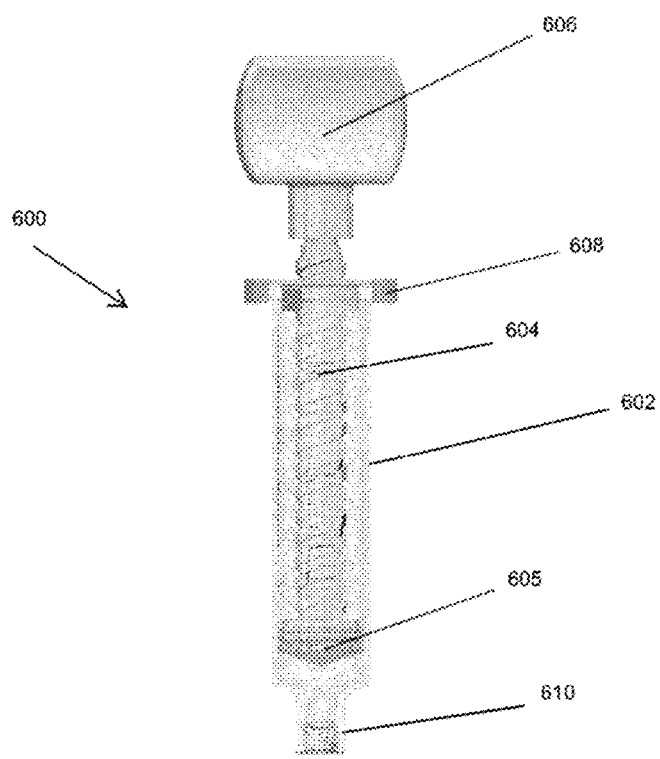
FIG. 17E illustrates a side view of the bone graft loading device of FIG. 17D.
Figure 17F:
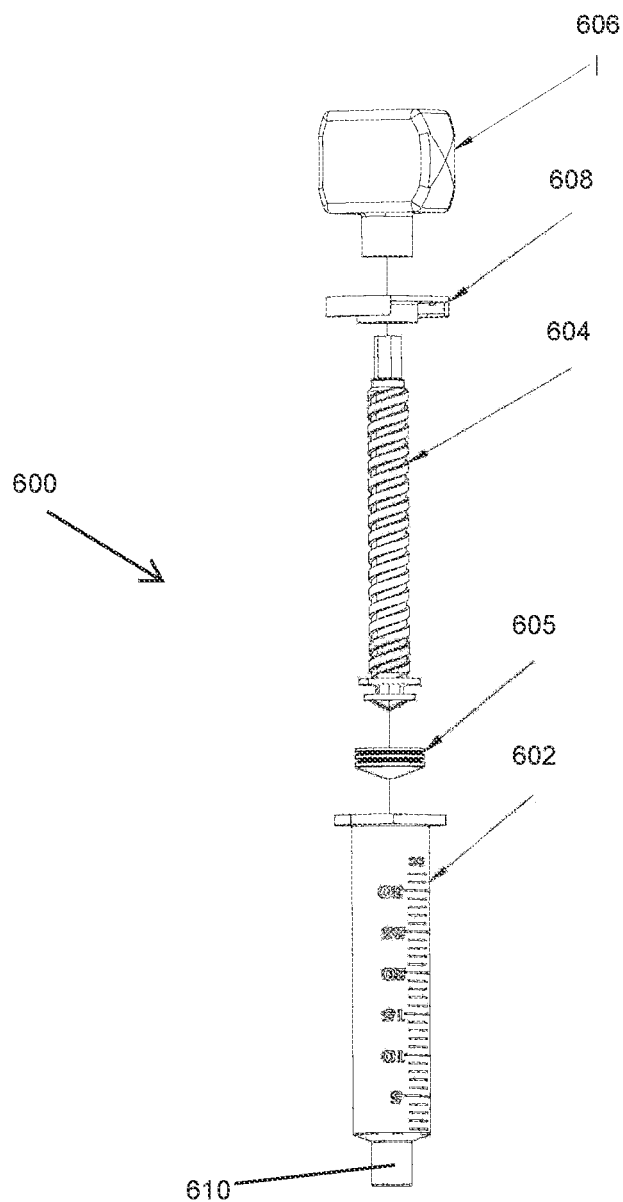
FIG. 17F illustrates an exploded view of the bone graft loading device of FIGS. 17D-17E.

In some embodiments, for example as shown in the embodiment of FIG. 17A-17C, the tube body 602 includes handles or wings 612 extending generally laterally outwardly from the tube body 602. The wings 612 can advantageously allow the user to grip the tube body 602 more easily and securely in use. The wings 612 can have various shapes and configurations as shown.

In use, the user can couple the tube 120 of the bone graft delivery device 100 to the distal tip 610 of the loading device 600 before or after loading the desired bone graft material into the tube body 602. If needed, the user threads the cap 608 to the distal end of the plunger shaft 604 proximate the plunger 605. The user then inserts the plunger 605 into the tube body 602 and couples the cap 608 to the proximal end of the tube body 602. To transfer the bone graft material from the tube body 602 to the tube 120, the user rotates the plunger shaft 604 (e.g., clockwise), for example, by rotating the handle 606, into the cap 608. The internally threaded cap 608 converts the rotational motion of the externally threaded plunger shaft 604 relative to the cap 608 into translational motion of the plunger shaft 604 and plunger 605 distally within the tube body 602. Distal motion of the plunger 605 forces the bone graft material through the distal tip 610 and into the tube 120. The threaded coupling between the plunger 605 and the cap 608 advantageously allows the user to apply greater torque compared to a syringe-type arrangement wherein the plunger is simply pushed distally within the tube body. This greater torque allows the bone graft material to be loaded into the tube 120 more easily. When a desired amount of bone graft material has been loaded into the tube 120, the user can remove the tube 120 from the loading device 600 and couple the tube 120 to a handle 102 for use. If needed during the course of a procedure, the tube 120 can be decoupled from the handle 102, reloaded with the loading device 600, then decoupled from the loading device 600 and recoupled to the handle 102 to continue the procedure.

Figure 18A:
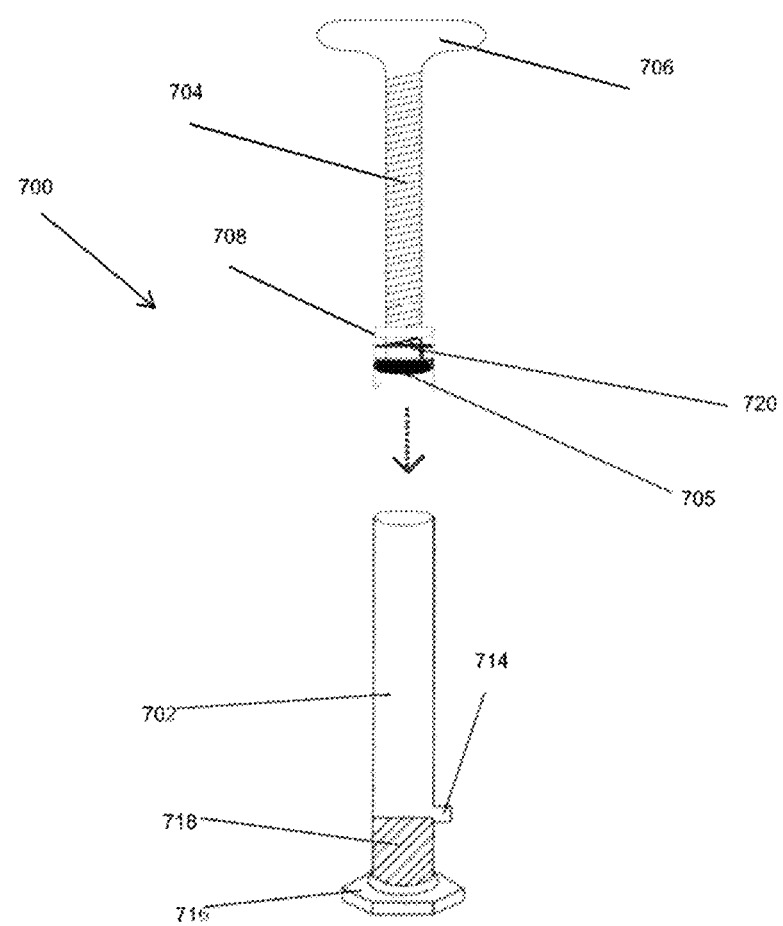
FIG. 18A illustrates an exploded view of another example embodiment of a bone graft loading device.
Figure 18B:
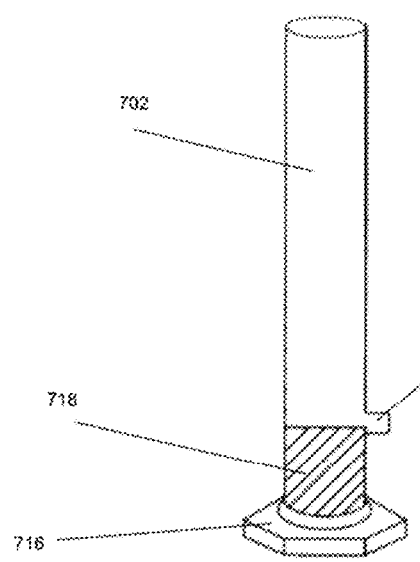
FIG. 18B illustrates a tube body and base of the bone graft loading device of FIG. 18A.
Figure 18C:
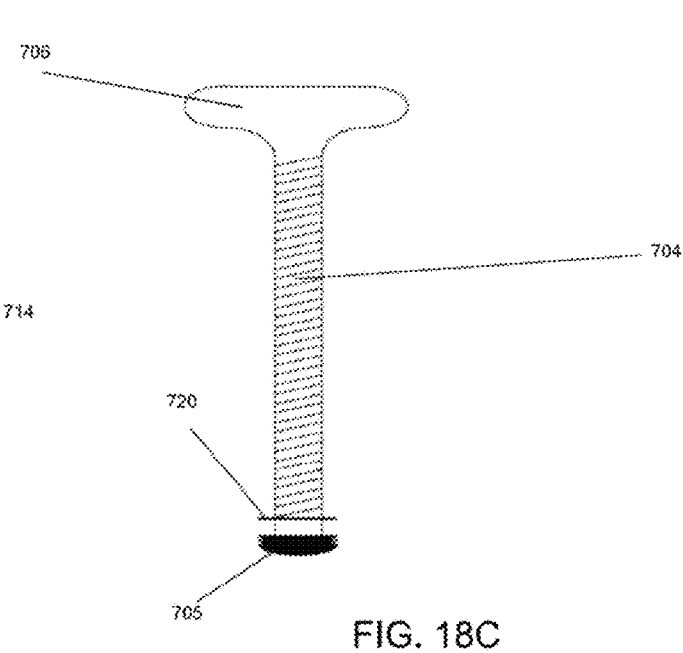
FIG. 18C illustrates a plunger of the bone graft loading device of FIG. 18A.
Figure 18D:
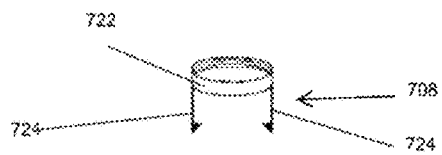
FIG. 18D illustrates a cap or coupling of the bone graft loading device of FIG. 18A.
Figure 19A:
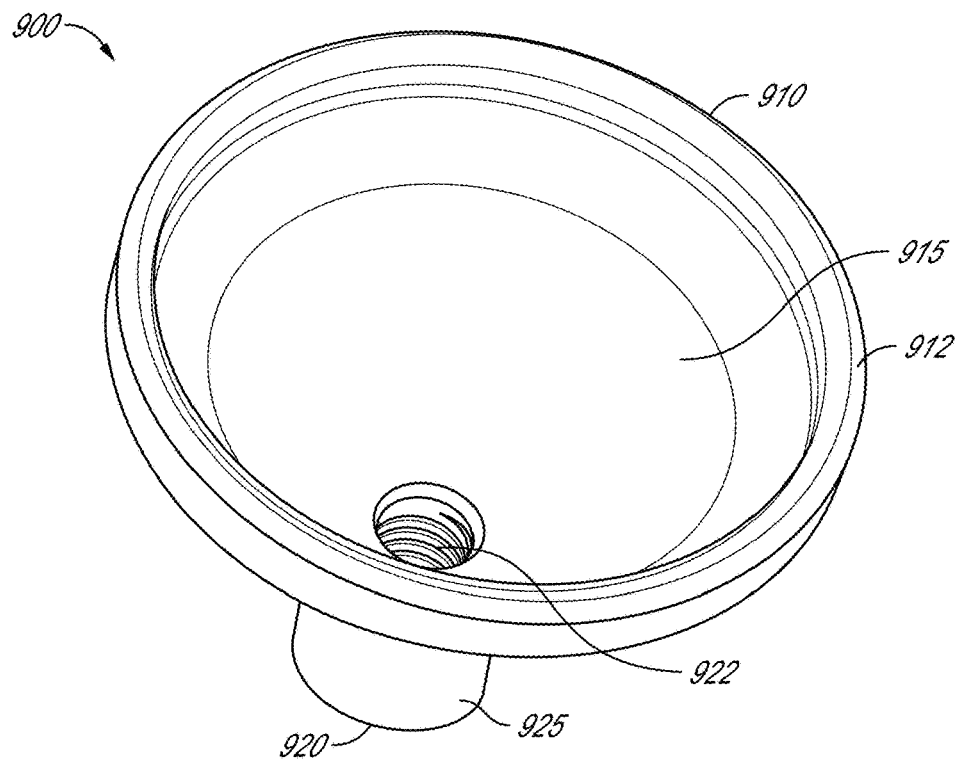
FIG. 19A illustrates a top perspective view of another example embodiment of a bone graft loading device for use with a bone graft delivery device.
Figure 19B:
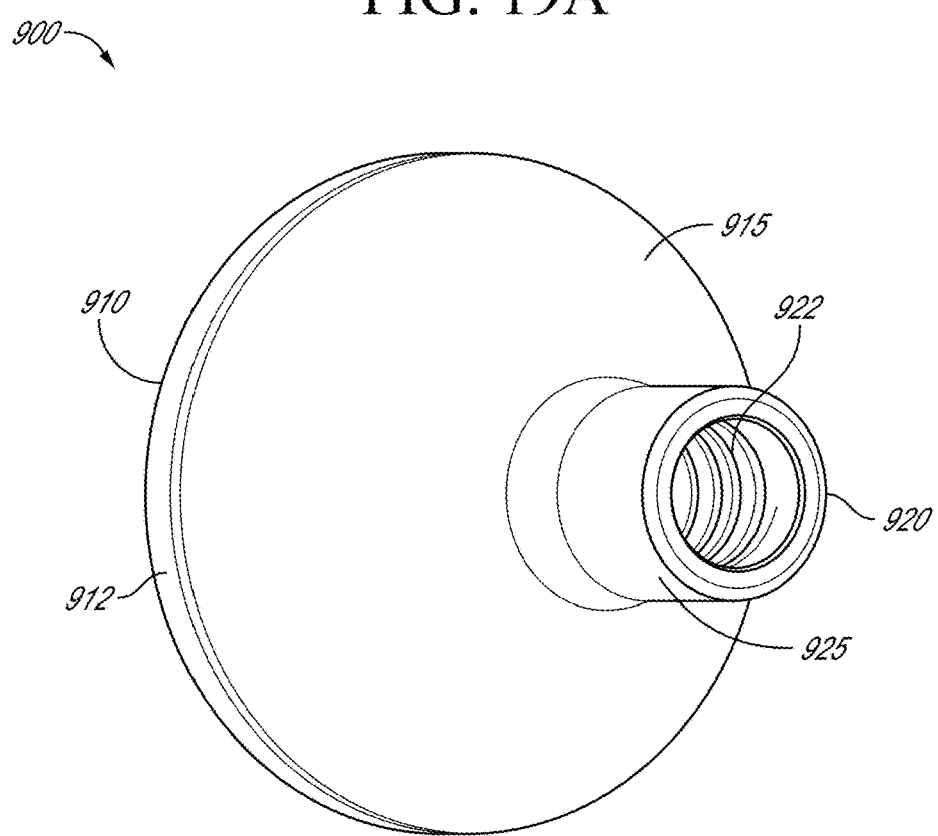
FIG. 19B illustrates a bottom perspective view of the bone graft loading device of FIG. 19A.
Figure 19C:
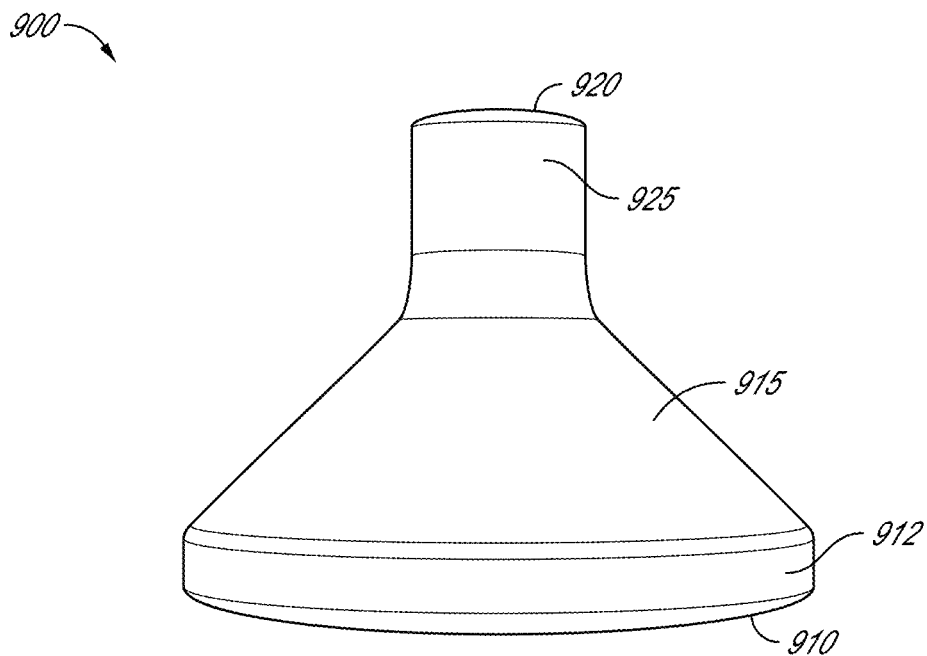
FIG. 19C illustrates a side view of the bone graft loading device of FIG. 19A.
Figure 19D:
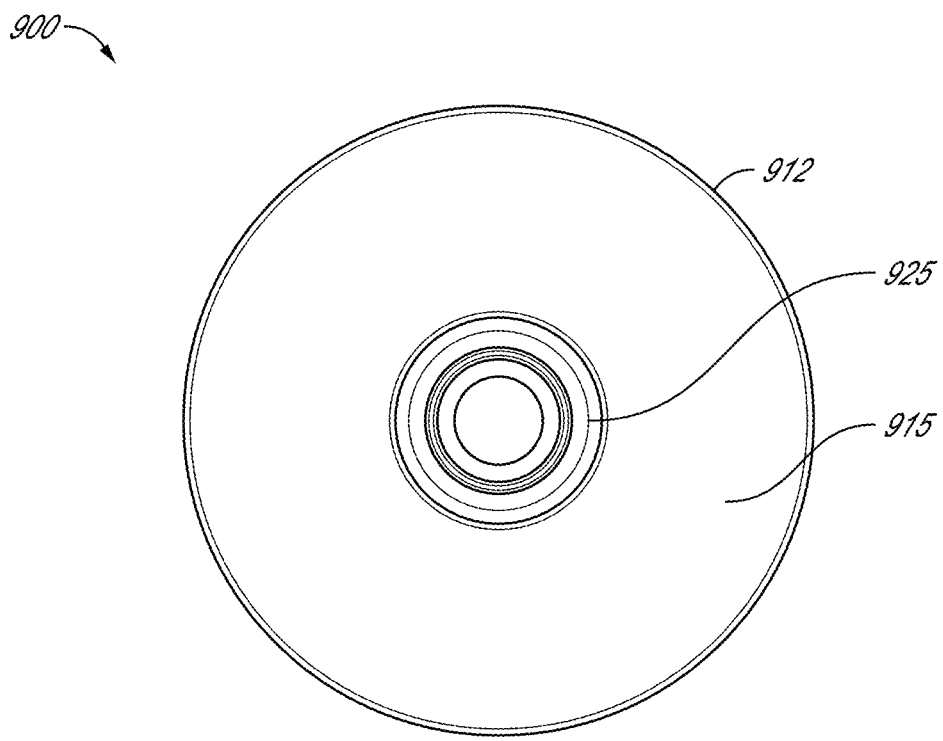
FIG. 19D illustrates a bottom view of the bone graft loading device of FIG. 19A.
Figure 19E:
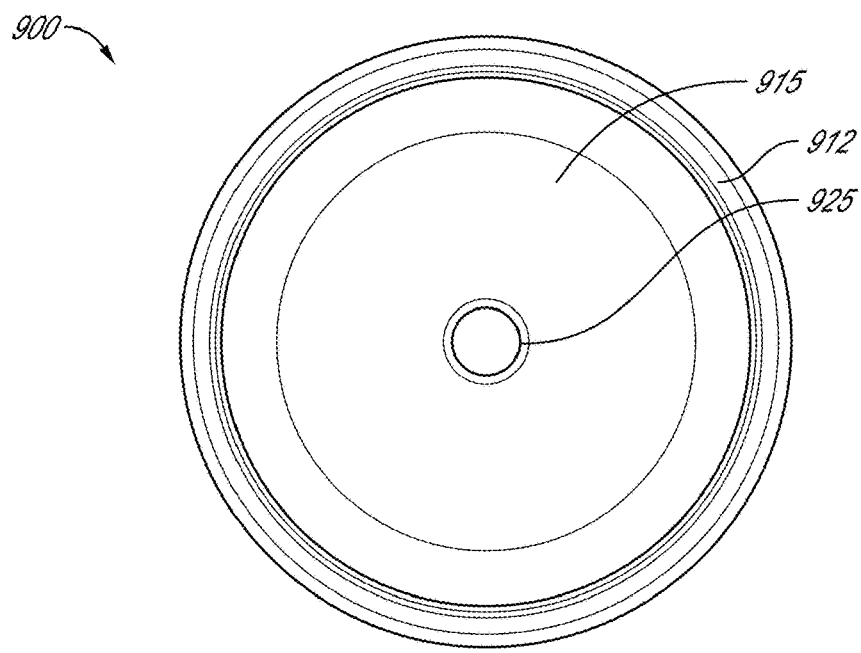
FIG. 19E illustrates a top view of the bone graft loading device of FIG. 19A.
Figure 19F:
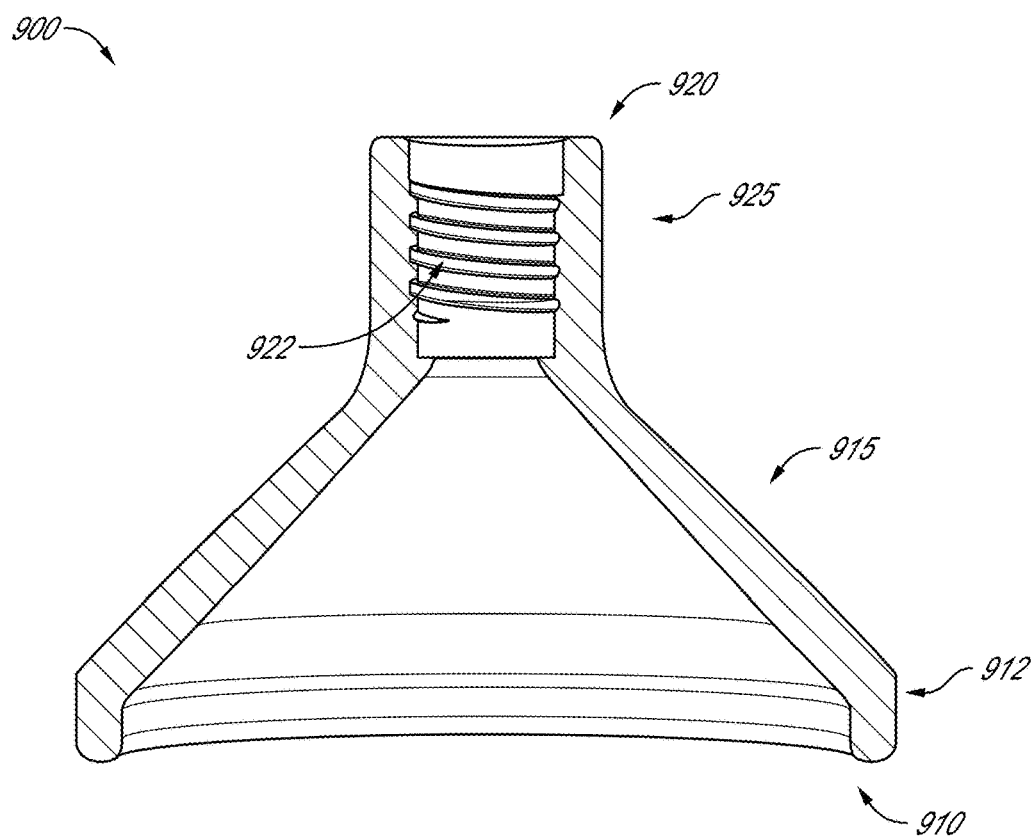
FIG. 19F illustrates a cross-sectional view of the bone graft loading device of FIG. 19A.

FIGS. 18A-18D illustrate an alternative embodiment of a loading device 700. The loading device 700 similarly includes a tube body 702, an externally threaded plunger shaft 704, a plunger 705, and an internally threaded cap or coupling 708 that couples to a proximal end of the tube body 702. As shown in FIG. 18D, the cap 608 can include an internally threaded proximal ring 722 and two arms 724 extending distally from the proximal ring 722 on opposite sides of the proximal ring 722. Distal ends of the arms 724 can include hooks to secure the cap 608 to the tube body 702. Other shapes and configurations for the cap 708 are also possible. As shown in FIG. 18C, a plunger stop 720 can be disposed about the plunger shaft 704 proximate the distal end of the plunger shaft 704 and the plunger 705. As shown in FIG. 18A, the proximal ring 722 of the cap 708 is disposed about the plunger shaft 704 proximal to the plunger stop 720. The plunger stop 720 can help prevent or inhibit the cap 708 from falling off the plunger shaft 704. In the illustrated embodiment, the loading device 700 also includes a handle 706 at the proximal end of the plunger shaft 704. The handle 706 can be integrally formed with the plunger shaft 704 as shown or can be coupled, removably or permanently, to the plunger shaft 704. In the illustrated embodiment, the tube body 702 includes a side spout 714 extending laterally from a side of the tube body 702 and in fluid communication with the internal volume of the tube body 702.

In some embodiments, the loading device 700 includes a base 716, which can advantageously allow the loading device 700 to stand on a table or other support surface before, during, or after use. In some embodiments, the loading device 700 includes a tube stop 718 that fills the internal volume of the tube body 702 between the distal end or bottom of the tube body 702 and the side spout 714. In the illustrated embodiment, the tube stop 718 extends proximally within the tube body 702 to a point proximal to a distal side of the side spout 714. This can help encourage as much bone graft material as possible to travel through the side spout 714 to the tube 120 and reduce potential waste of bone graft material settling into a distal end of the tube body 702 distal to or below the side spout 714. In some embodiments, the tube stop 718 can be made of a material that adds some weight to the bottom of the tube body 702 to advantageously provide the tube body 702 with greater stability when placed on a table or other surface.

The loading device 700 operates similarly to the loading devices 600 described above. However, in this embodiment, the tube 120 of the bone graft delivery device 100 is coupled to the side spout 714 for loading, and advancement of the plunger shaft 704 and plunger 705 distally within the tube body 702 forces the bone graft material within the tube body 702 through the side spout 714 and into the tube 120.

FIGS. 19A-19F illustrate a top perspective view, a bottom perspective view, a side view, a bottom view, a top view, and a cross-sectional view, respectively, of another embodiment of a loading device 900. In the illustrated embodiment, the loading device 900 resembles and/or functions as or similar to a funnel. The loading device or funnel 900 can be provided or used with or in a bone graft delivery system or kit. For example, the funnel 900 can be used to load bone graft material into the tube 120. Such funnels can allow the user to load the tube 120 with any bone graft material or combination of bone graft materials he or she wishes or deems appropriate. For example, the user can use synthetic, autologous, stem cell, cellular matrix, DBM, cortical fibers, demineralized cortical fibers, cadaveric, and/or any other available bone graft material. In some embodiments, the user can use DBM putty. In some embodiments, the bone graft materials can include one or more of hydroxyapatite (HA), tricalcium phosphate (TCP), and bioglass. The funnel 900 can include a first end 910 configured to receive bone graft material and a second end 920 configured to engage the tube 120 and through which bone graft material can pass into the tube 120. In the illustrated embodiment, a first portion 915 of the funnel 900, which includes or is near or adjacent the first end 910, is conical or generally conical. In the illustrated embodiment, the funnel 900 includes a cylindrical edge or rim 912 at or adjacent the first end 910. The cylindrical edge or rim 912 can help prevent or inhibit bone graft material from flowing out of the funnel 900, for example, if the bone graft material is mixed within the funnel 900 and/or during use. The funnel 900 can also or alternatively include an inwardly facing or protruding lip at or near the first end 910. The inwardly facing or protruding lip can prevent or inhibit bone graft material from flowing out of the funnel 900, for example, if the bone graft material is mixed within the funnel 900 and/or during use. In some embodiments, the funnel 900 may include a rubber ring along or near a rim of the first end 910 of the funnel 900. The ring can prevent or inhibit bone graft material from flowing out of the funnel 900, for example, if the bone graft material is mixed within the funnel 900 and/or during use. The ring may be over-molded, glued, adhered, or otherwise attached to the funnel 900. In the illustrated embodiment, a second portion 925 of the funnel 900, which includes or is near or adjacent the second end 920, is cylindrical or generally cylindrical. In some embodiments, at least a portion of the funnel 900 can be internally threaded to receive and engage external threads of the tube 120, such as external threads 125a at or near the proximal end of the tube 120 (shown in FIG. 4O). In the illustrated embodiment, the second portion 925 of the funnel 900 includes internal threads 922 to receive and engage external threads of the tube 120, such as external threads 125a. In use, the user can couple the funnel 900 to the tube 120 (before or after loading the bone graft material or components into the funnel 900 and/or mixing the bone graft material if needed), load the desired bone graft material, or components to mix the desired bone graft material, into the funnel 900, mix the bone graft material if needed, and urge the bone graft material from the funnel 900 into the tube 120. In some embodiments, a pusher rod, such as pusher rod 312, can be used to mix the bone graft material and/or urge the bone graft material from the funnel 900 into the tube 120.

Figure 22:
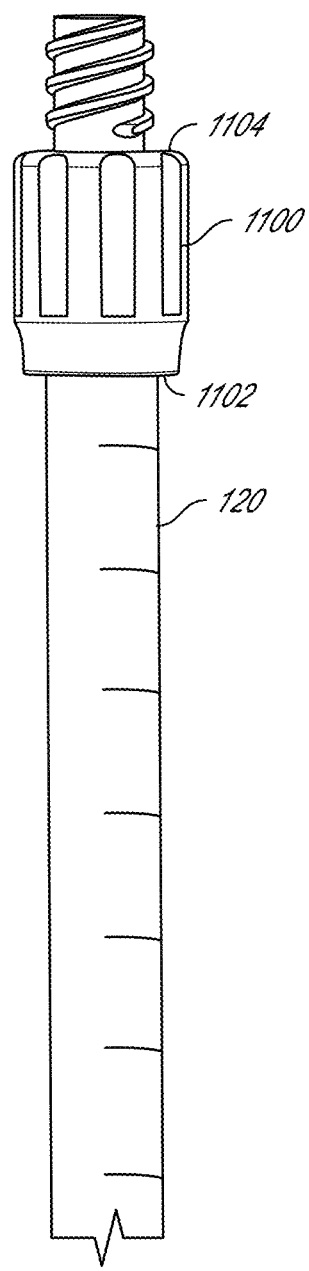
FIG. 22 illustrates a partial front view of an embodiment of an elongate tube, and a connector for use with a bone graft delivery system.
Figure 23:
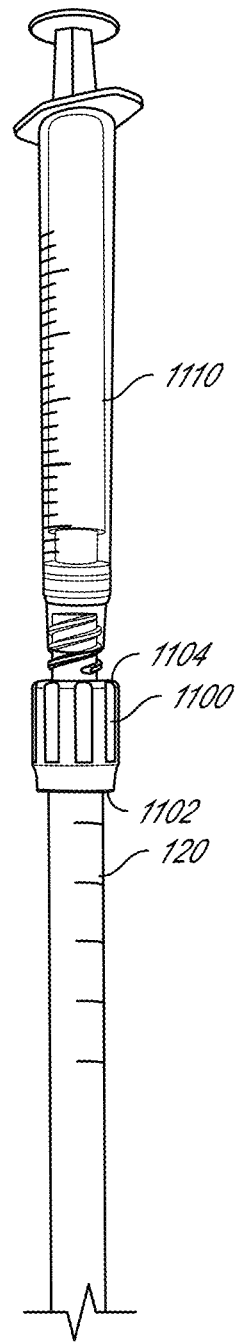
FIG. 23 illustrates a partial front view of embodiment of the elongate tube and connector of FIG. 22 and a syringe for use with a bone graft delivery system.
Figure 24:
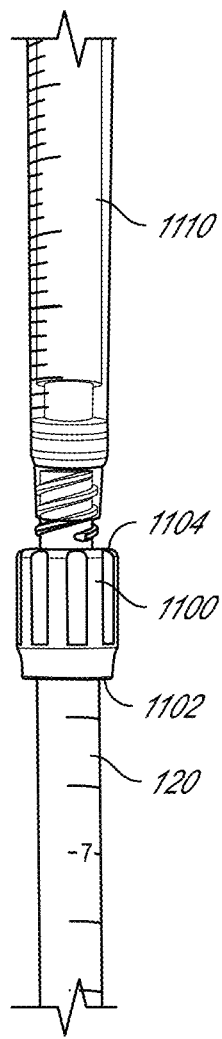
FIG. 24 illustrates a partial front view of the elongate tube, syringe, and connector of FIG. 23.
Figure 25A:
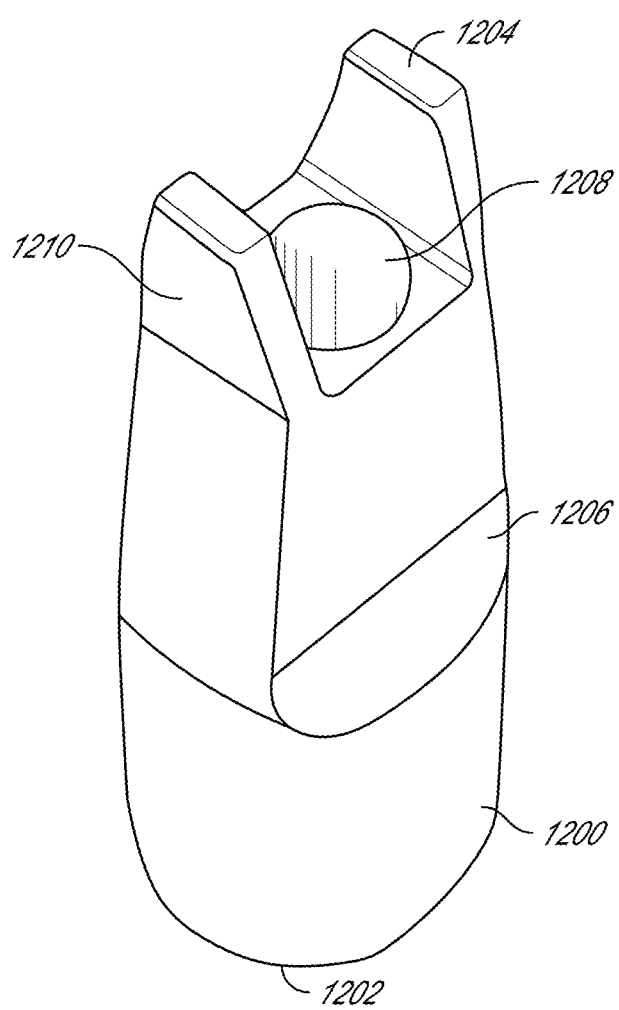
FIG. 25A illustrates a perspective view of an embodiment of a tip of a bone graft delivery system.
Figure 25B:
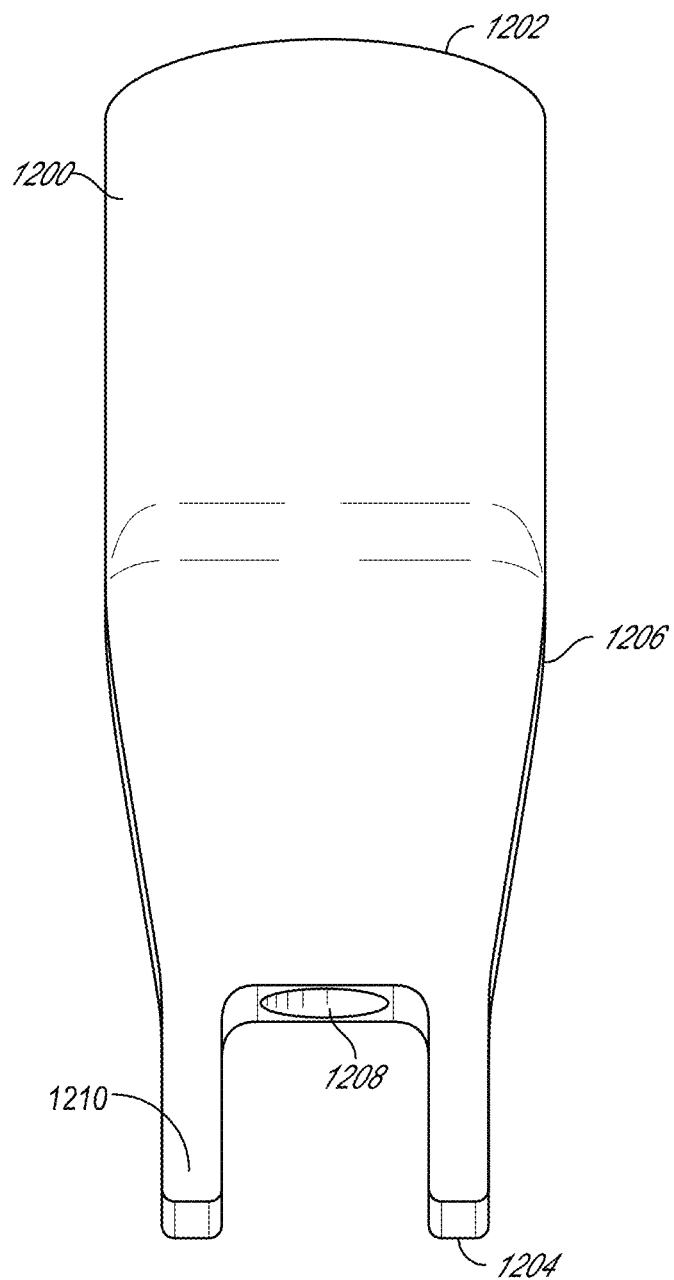
FIG. 25B illustrates another perspective view of the tip of FIG. 25A.
Figure 25C:
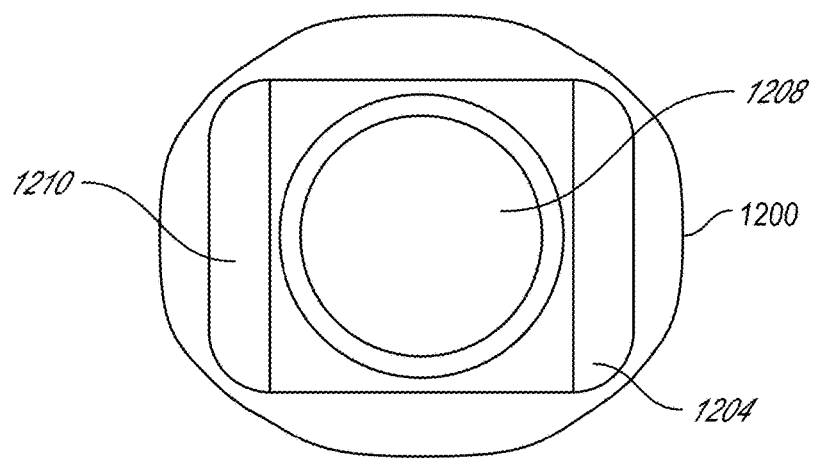
FIG. 25C illustrates a bottom view of the tip of FIG. 25A.
Figure 25D:
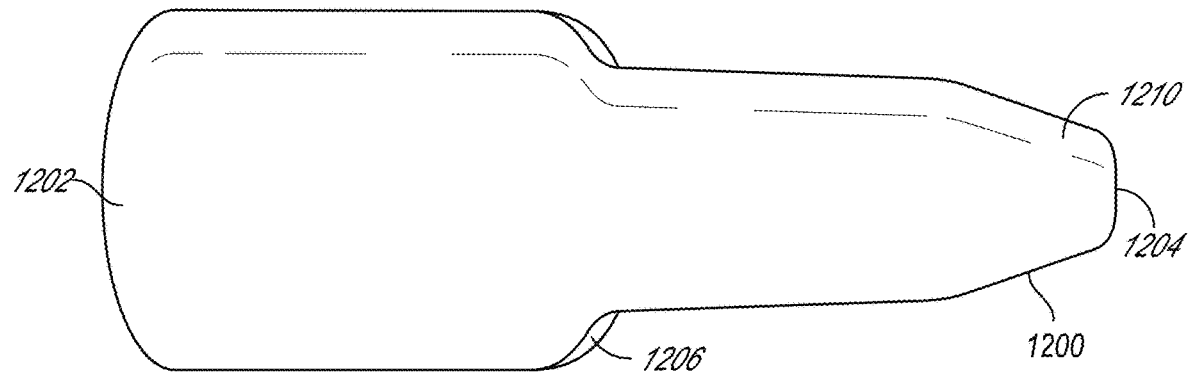
FIG. 25D illustrates a side view of the tip of FIG. 25A.
Figure 25E:
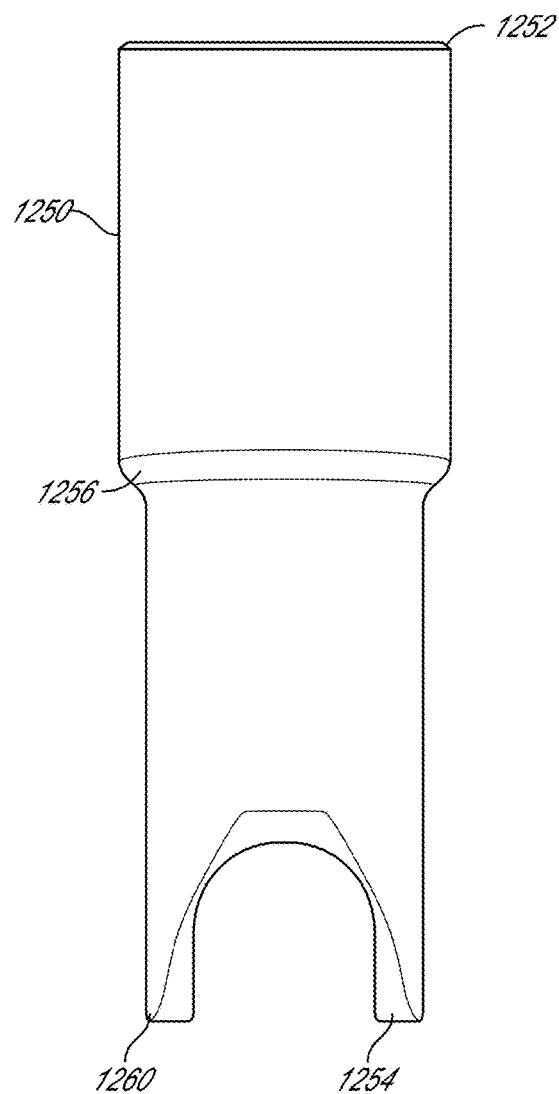
FIG. 25E illustrates a front view of an embodiment of a tip of a bone graft delivery system.
Figure 25F:
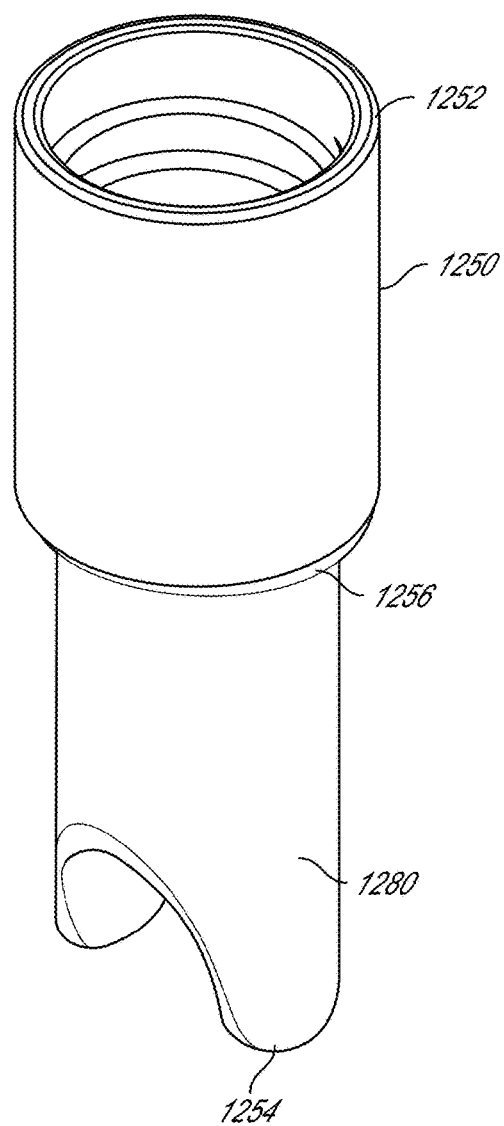
FIG. 25F illustrates a perspective view of the tip of FIG. 25E.
Figure 26A:
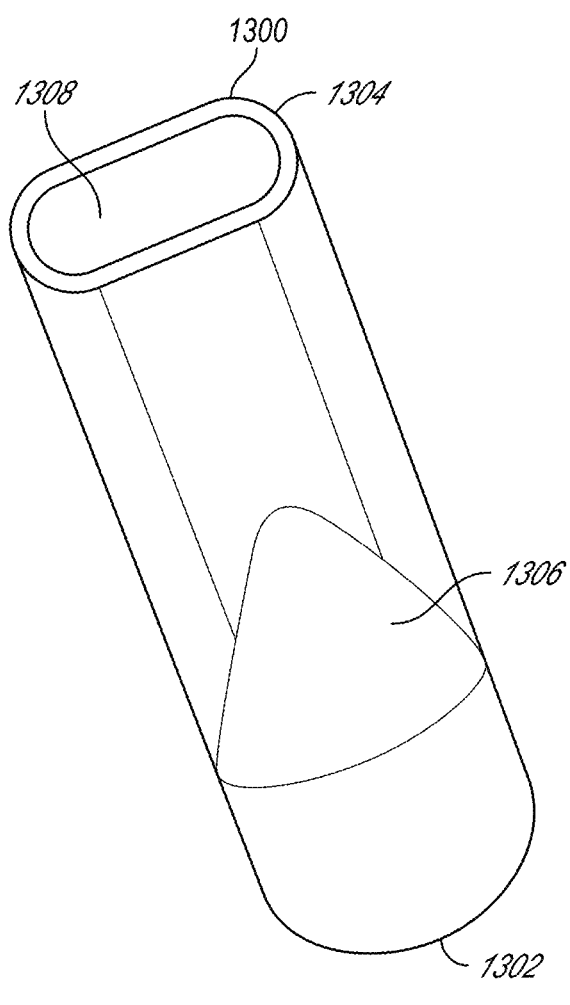
FIG. 26A illustrates a perspective view of an embodiment of a tip of a bone graft delivery system.
Figure 26B:
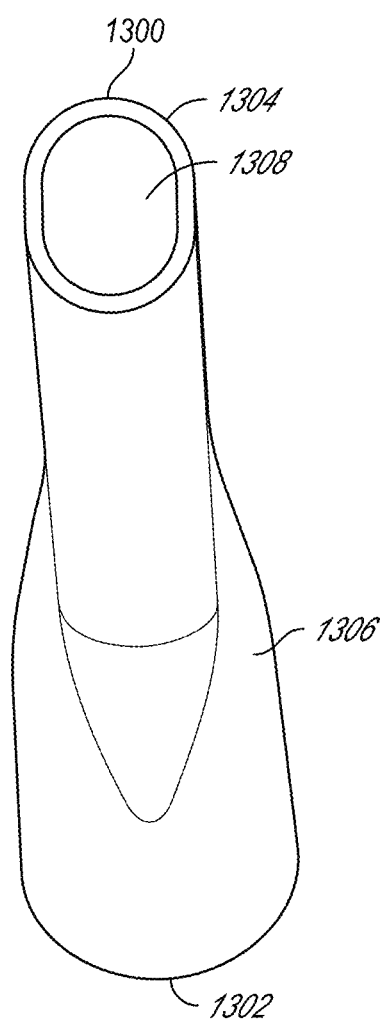
FIG. 26B illustrates another perspective view of the tip of FIG. 26A.
Figure 26C:
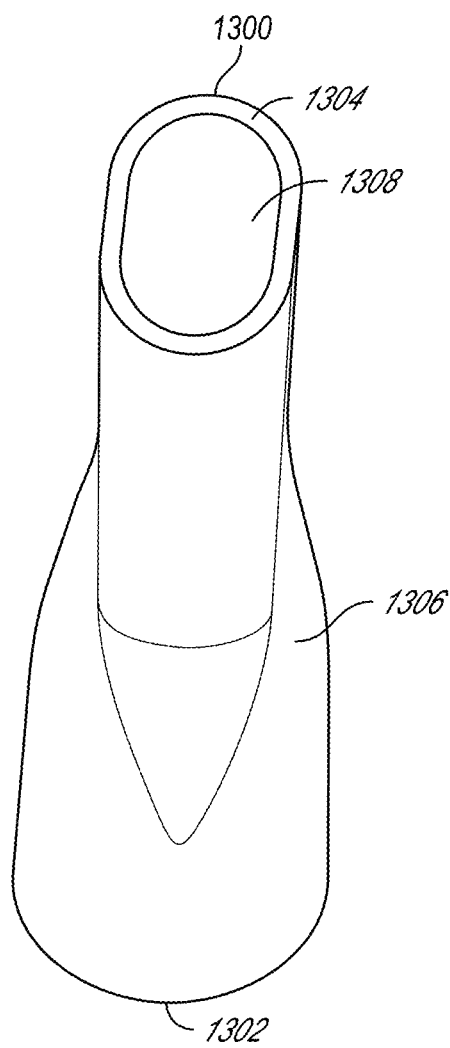
FIG. 26C illustrates another perspective view of the tip of FIG. 26A.
Figure 26D:
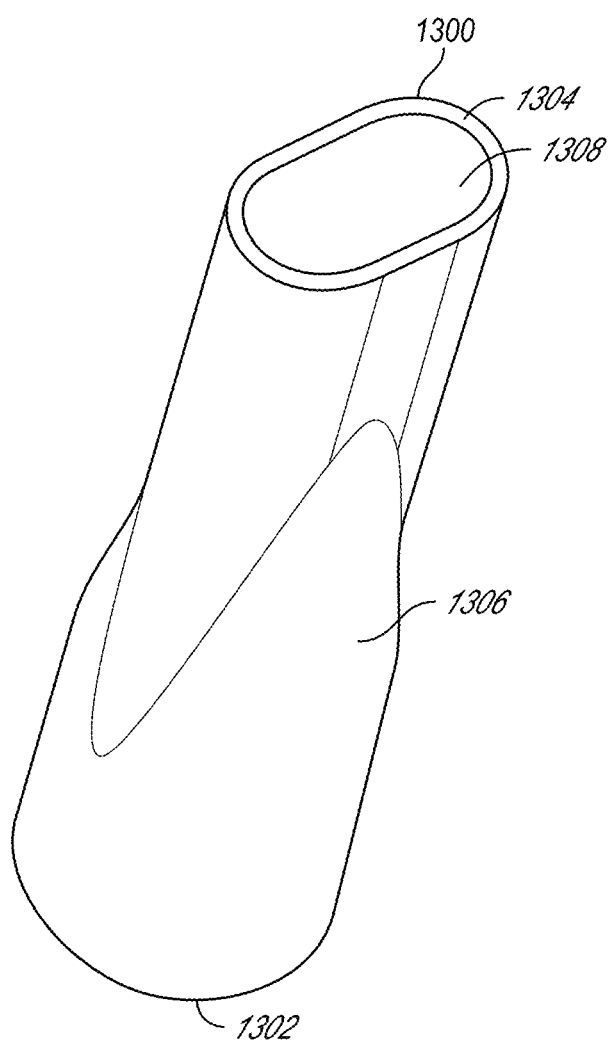
FIG. 26D illustrates another perspective view of the tip of FIG. 26A.
Figure 26E:
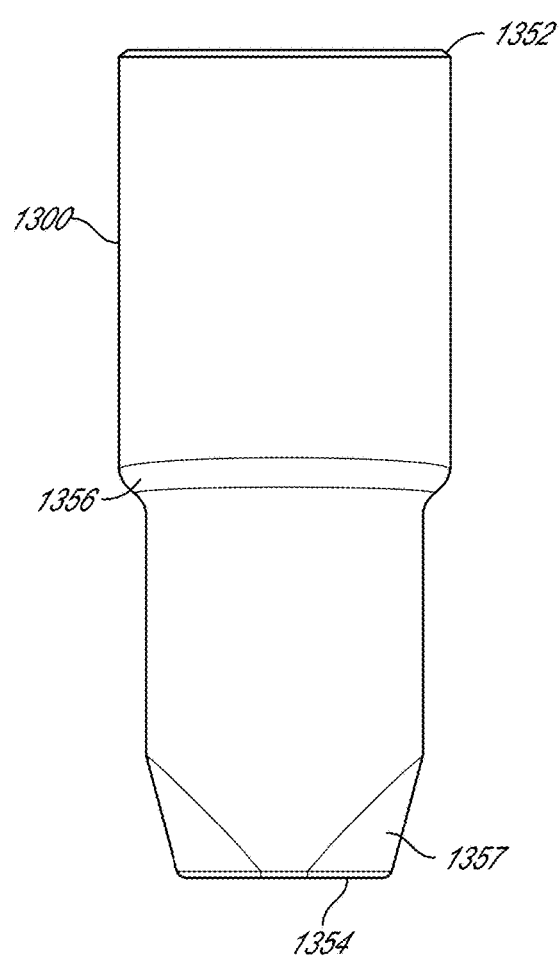
FIG. 26E illustrates a front view of an embodiment of a tip of a bone graft delivery system.
Figure 26F:
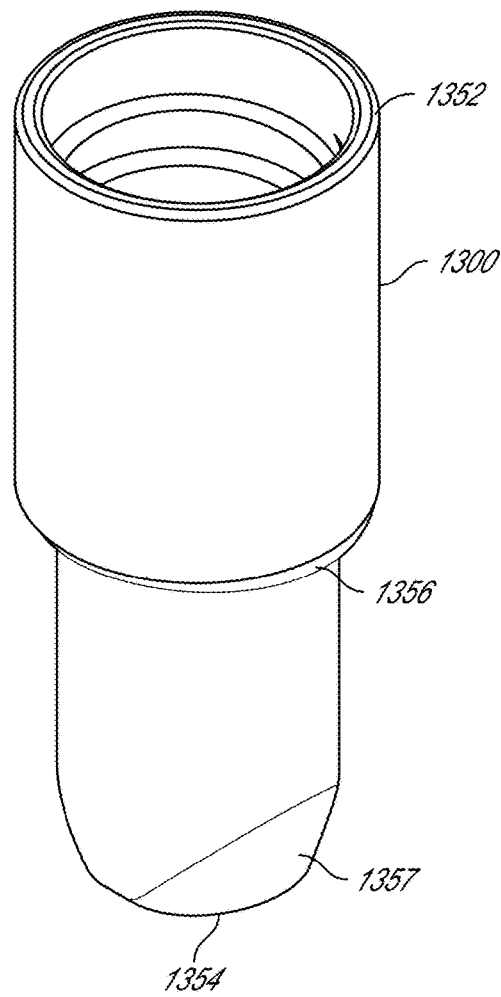
FIG. 26F illustrates a perspective view of the tip of FIG. 26E.

In some embodiments, as shown in FIGS. 22-24, a connector 1100 can be coupled between the tube 120 and a syringe 1110 or a loading device, such as the loading devices 600, 700, 900. A first end 1102 of the connector 1100 can be sized and configured to couple to one end of the tube 120, and a second end 1104 of the connector 1100 can be sized and configured to couple to the syringe 1110 or loading device. In some embodiments, the first end 1102 of the connector 1100 can be internally threaded to engage external threads 125b at the end of the tube 120. In other embodiments, the connector 1100 can couple to the tube 120 via a snap fit or another suitable connection mechanism. In some embodiments, the second end 1104 of the connector 1100 can be externally threaded to engage internal threads of the syringe 1110 or loading device. In other embodiments, the connector 1100 can couple to the syringe 1110 or loading device via a snap fit or any other suitable connection mechanism. In some embodiments, the connector 1100 may have the same thread pattern on each end. In some embodiments, the connector 1100 may have a different thread pattern on each end. In some embodiments, the connector 1100 may be configured to couple to either end of the tube 120. In some embodiments, the connector 1100 can be a luer lock or luer lock style cap. In some embodiments, the connector 1100 can provide a leak-free or substantially leak-free connection between the tube 120 and syringe 1110 or the loading device. In some embodiments, the connector can include a gasket to prevent the leakage of fluid. In some embodiments, the connector 1100 can provide a connection for delivery of one or more of blood, bone marrow aspirate, platelet-rich plasma (PRP), stem cells, or other liquid/fluid with growth factors from the syringe 1110 or loading device into the tube 120, for example, for hydration of cortical fiber and/or bone graft within the tube 120. In other embodiments, blood, bone marrow aspirate, platelet-rich plasma (PRP), stem cells, or other liquid/fluid with growth factors can be introduced into the tube 120 by connecting a syringe 1110 or loading device directly to the tube 120.

In some embodiments, the bone graft delivery device 100 can be configured to deliver bone graft material inside an interbody cage or other interbody device that has been disposed within a disc space. If sufficient bone graft is not applied to a disc space during a fusion procedure, there is a decreased likelihood of fusion and an increased chance of revision surgery. Some interbody implants or cages include an opening or window that can be filled with bone graft. However, this provides for limited surface area for the bone graft to contact the vertebral end plates. In some cases, surgeons use funnels or similar devices to fill the disc space prior to insertion of the implant. However, inserting an interbody cage after delivering bone graft material can disrupt the placement of the bone graft material. Furthermore, it can be difficult to deliver bone graft to the disc space in a controlled manner after the implant has been inserted, and it can be difficult for the surgeon to access the desired area to deliver the bone graft if the implant is already in place. Delivering the bone graft material after inserting the interbody cage and inserting the bone graft material within the interbody cage can help ensure the bone graft material is placed where desired or required. The bone graft delivery device 100 allows for pressurized and controlled delivery of bone graft material into the cage to maximize filling of the cage with the bone graft material.

Figure 14:
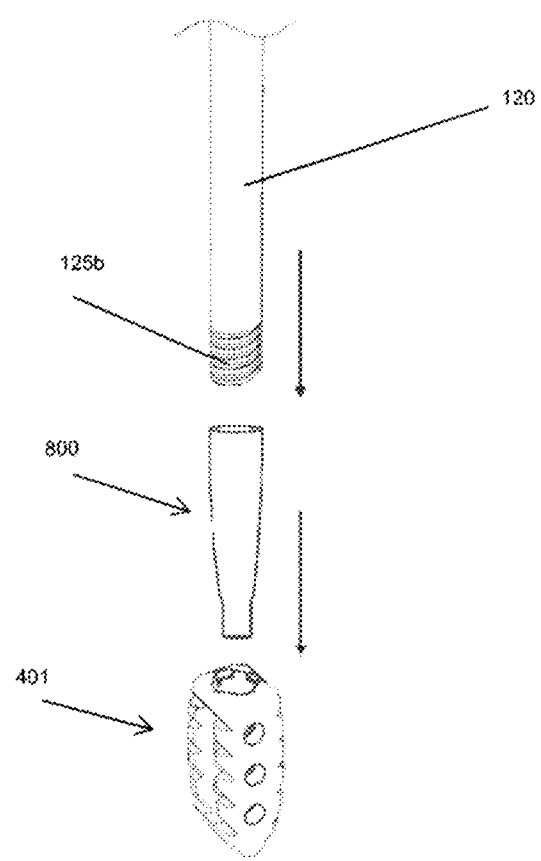
FIG. 14 illustrates an example embodiment of an attachment member coupling a tube of a bone graft delivery device to an interbody cage.

In some embodiments, an attachment member can be provided to couple the distal end of the tube 120 of the bone graft delivery device 100 to the interbody cage. Bone graft material is delivered through the tube 120 and attachment member and into the interbody cage. FIG. 14 illustrates an example embodiment of an adapter or attachment member 800 that can couple the distal end of the tube 120 to an interbody cage 401. A proximal end of the attachment member 800 is sized and configured to couple to the distal end of the tube 120, and the distal end of the attachment member 800 is sized and configured to couple to the interbody cage 401. In some embodiments, the proximal end of the attachment member 800 can be internally threaded to engage external threads 125b at the distal end of the tube 120. In other embodiments, the attachment member 800 can couple to the tube 120 via a snap fit or another suitable connection mechanism. Various attachment members can be manufactured and/or provided for use with various interbody cages or other interbody devices.

Figure 10A:
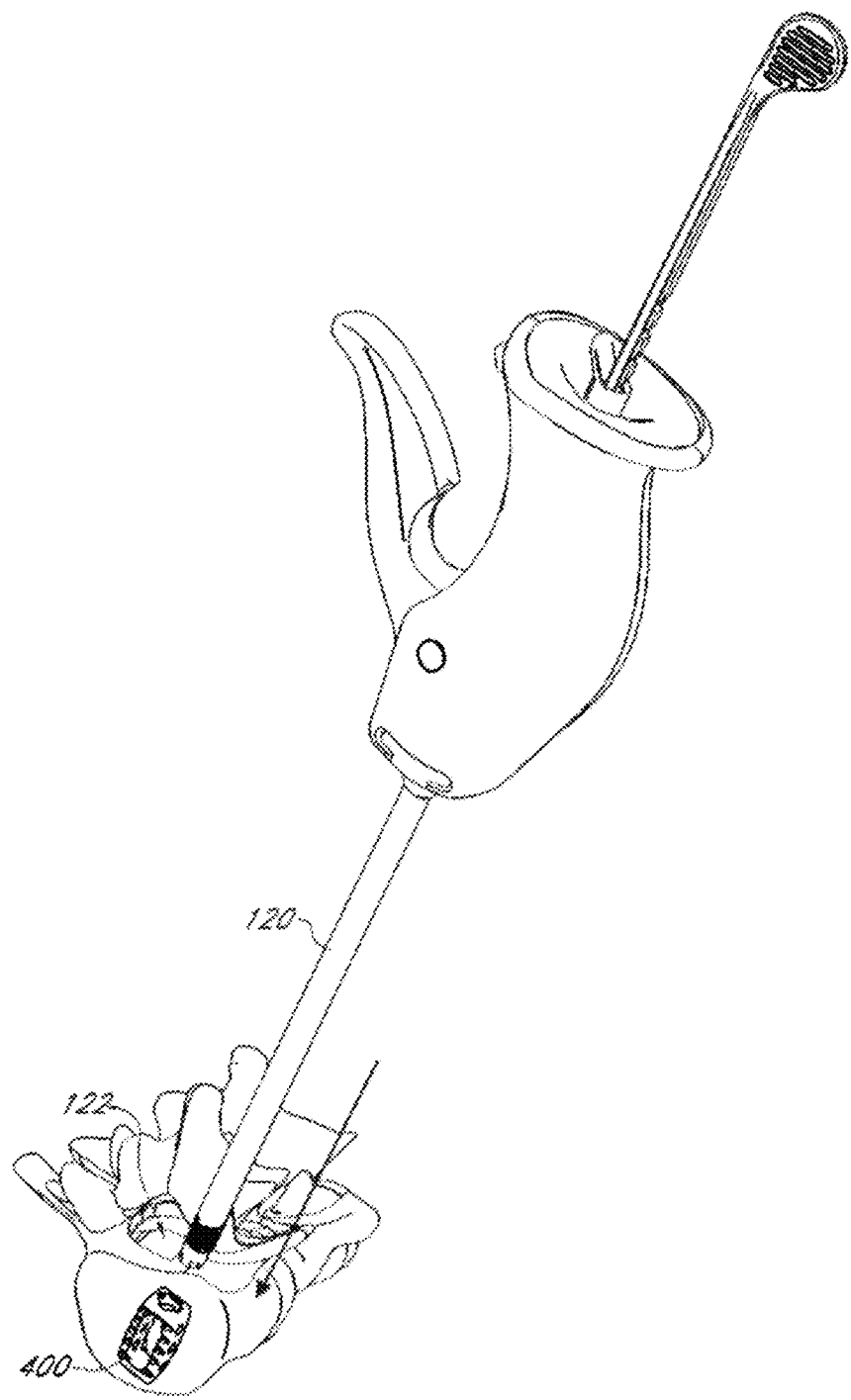
FIGS. 10A-10E illustrate a bone graft delivery device configured to deliver bone graft to an interbody device.
Figure 10B:
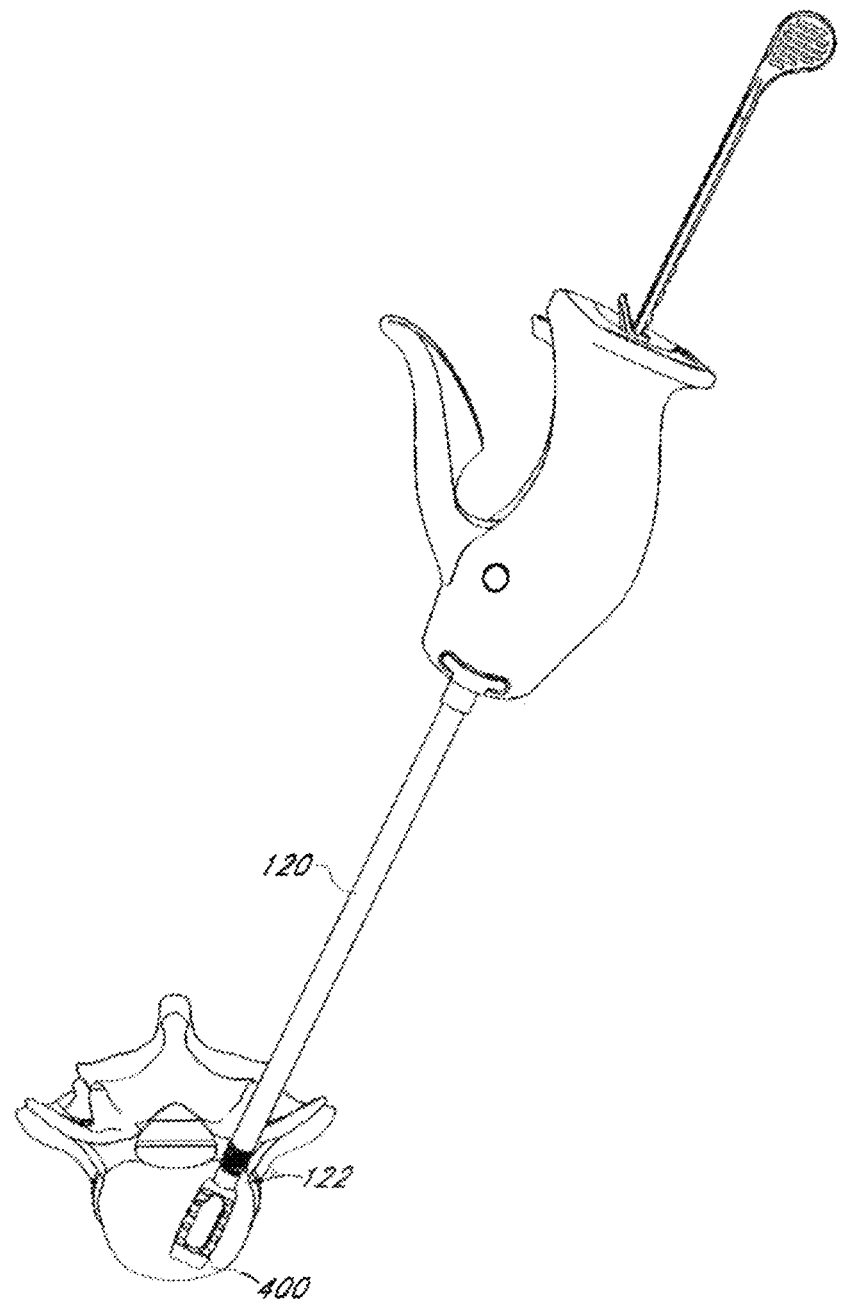
Figure 10C:
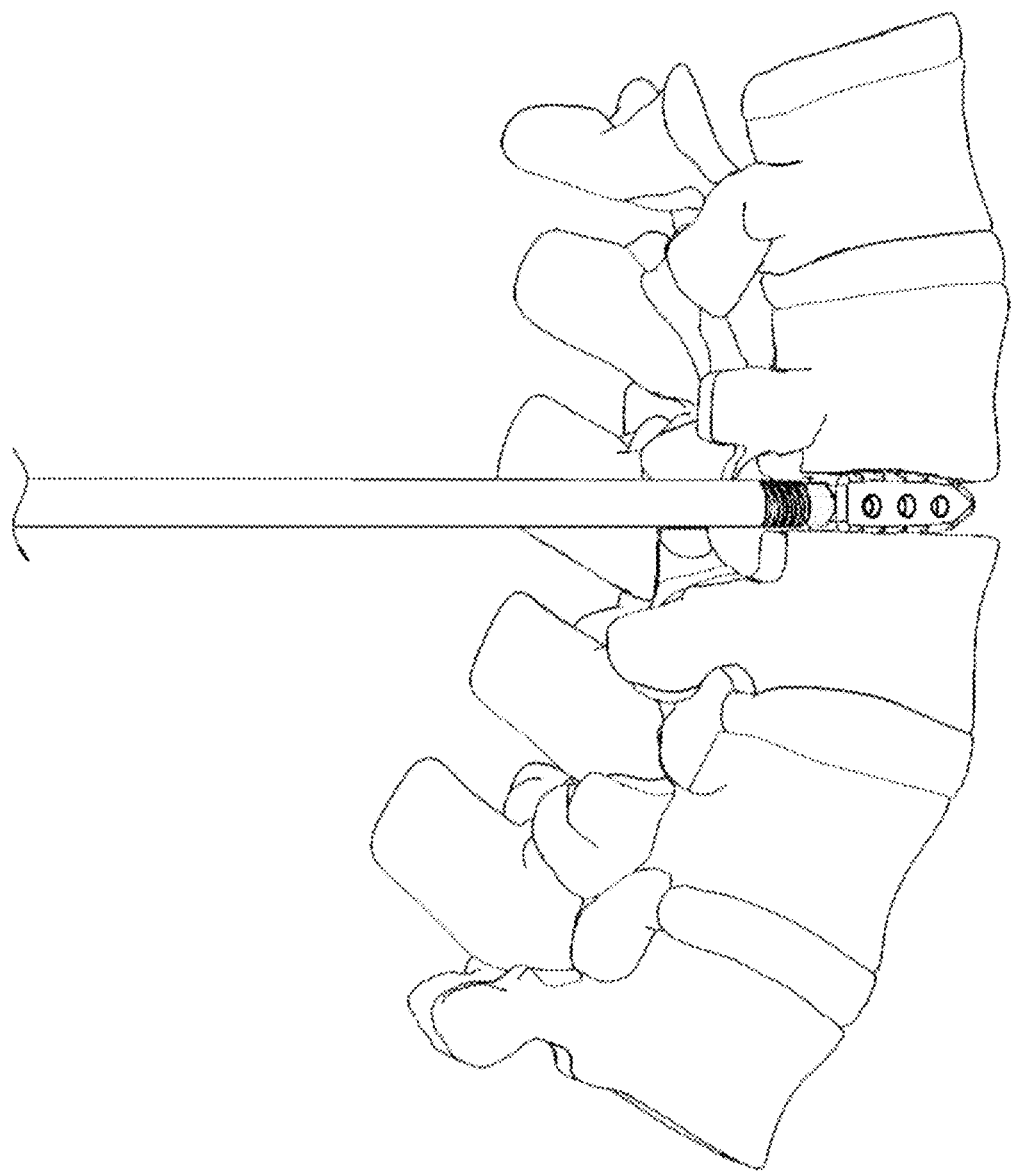
Figure 10D:
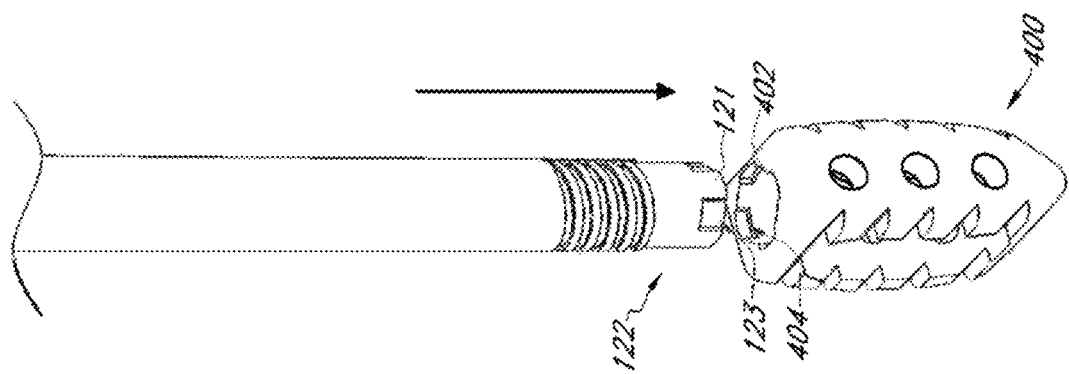
Figure 10E:
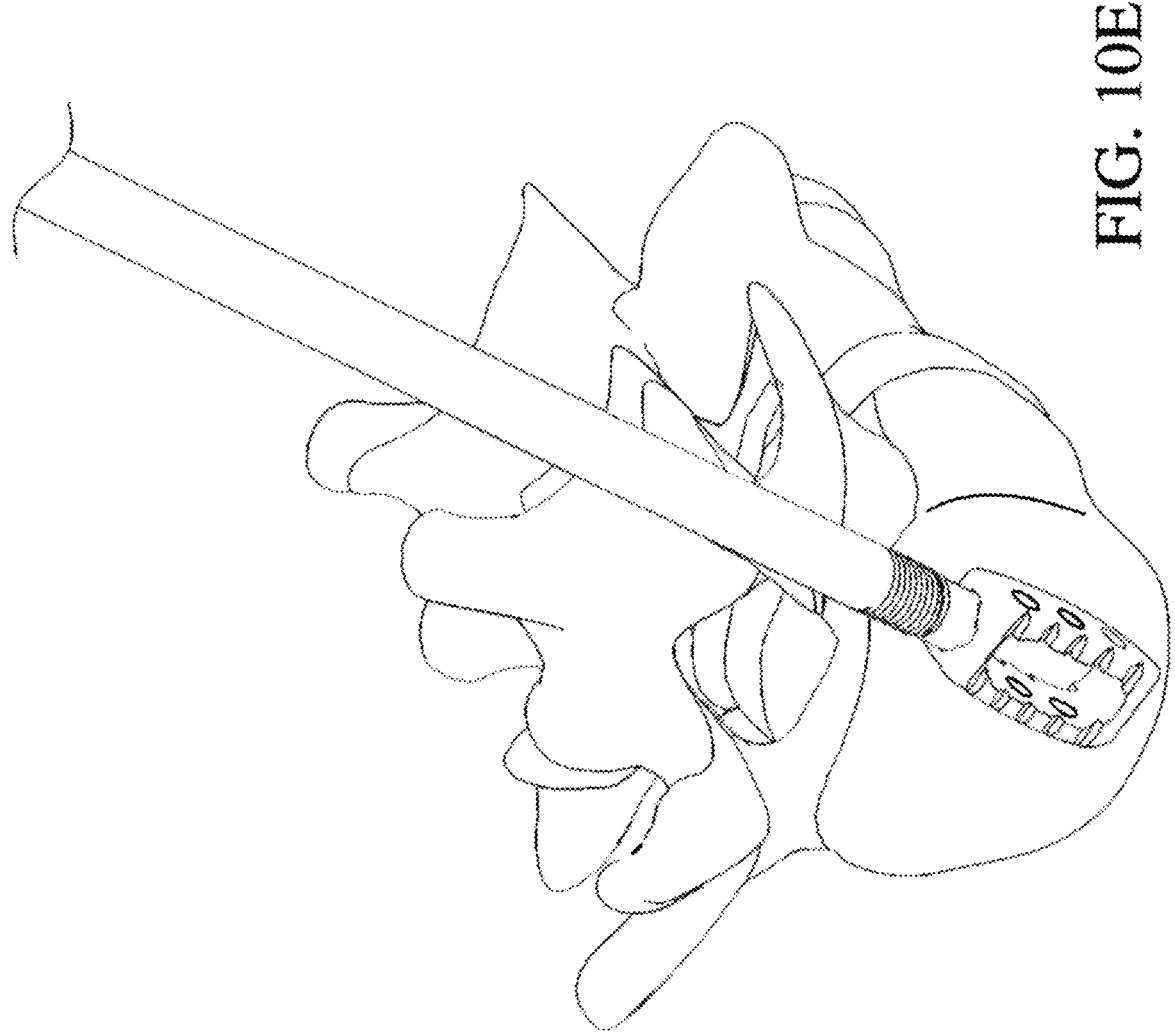

In some embodiments, the distal end of the tube 120 itself includes features configured to engage corresponding features on an interbody device. FIGS. 10A-10E illustrate an example embodiment of a tube 120 having a distal end 122 configured to engage an interbody cage 400. The distal end 122 of the tube 120 can be coupled to the cage 400 after the cage 400 has been placed in the disc space as shown in FIGS. 10A and 10B. As shown in FIG. 10D, the distal end 122 of the tube 120 includes alternating ridges 121 and recesses 123 configured to mate with corresponding recesses 404 and ridges 402 on the cage 400. In some such embodiments, various tubes 120 with different engagement features can be manufactured and/or provided for use with various interbody devices, and the user can select the appropriate tube 120 after selecting the interbody device to be used. In various embodiments, the tubes 120 and/or attachment members can be configured to couple to various cages via threaded connections, snap fit connections, clip-on connections, wedge connections, and/or any other suitable connection mechanism. In some embodiments, the tubes 120 and/or attachment members can be configured to abut one or more cages without such a connection mechanism.

Figure 15A:
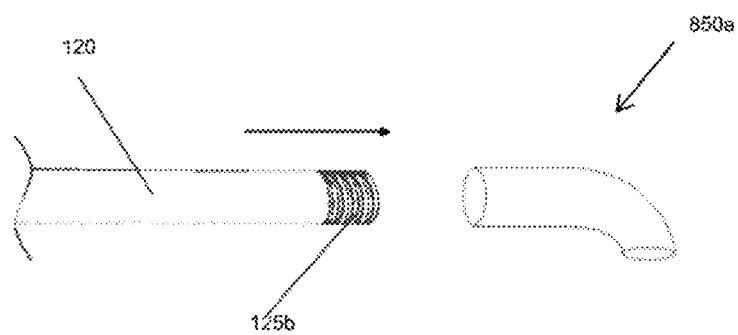
FIGS. 15A-15B illustrate example embodiments of applicators configured to be coupled to a tube of a bone graft delivery device to direct bone graft material in various directions.
Figure 15B:
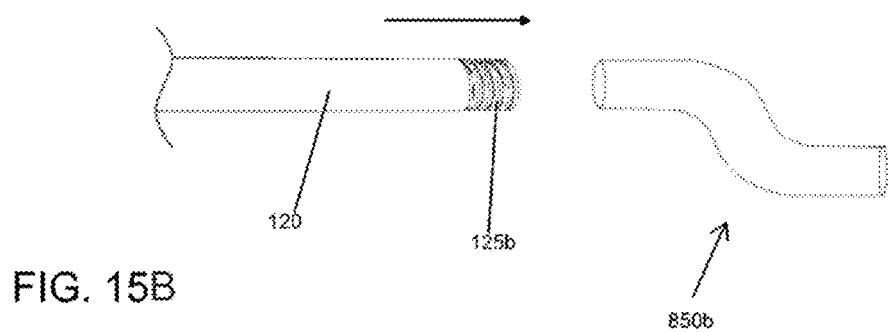

FIGS. 15A-15B illustrate example embodiments of applicators 850a, 850b that can be coupled to the distal end of the tube 120 to direct bone graft in various directions. For example, in some embodiments, the applicators 850a, 850b allow bone graft material to be directed around a cage disposed within the disc space. A proximal end of the applicator 850a, 850b couples to the distal end of the tube 120. In some embodiments, the proximal end of the applicator 850a, 850b is internally threaded to engage external threads 125b at the distal end of the tube 120. In other embodiments, the applicator 850a, 850b can couple to the tube 120 via a snap fit or another suitable connection mechanism. The applicators 850a, 850b can have various shapes. FIG. 15A illustrates an applicator 850a having an approximately 90° curve proximate the distal end such that bone graft material can be extruded in a direction approximately 90° from the distal end of the tube 120. FIG. 15B illustrates an applicator 850b having an S-shape or serpentine shape. In the illustrated embodiment, the applicator 850b allows the bone graft material to be extruded along a direction generally parallel but offset from the distal end of the tube 120. Other shapes and configurations, for example, various curved and/or angular shapes, are also possible.

Figure 11E:
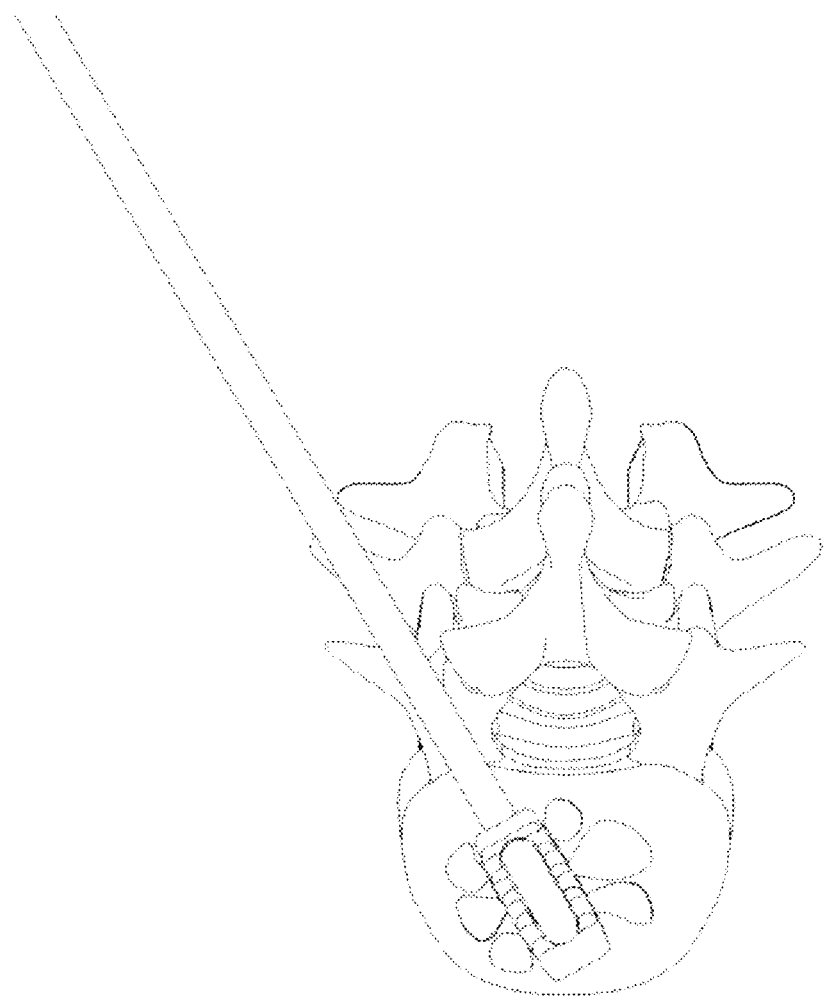
FIG. 11E illustrates a bone graft delivery device coupled to the interbody device of FIGS. 10A-10D disposed within a disc space and bone graft spreading to the surrounding disc space from inside the interbody device.
Figure 12:
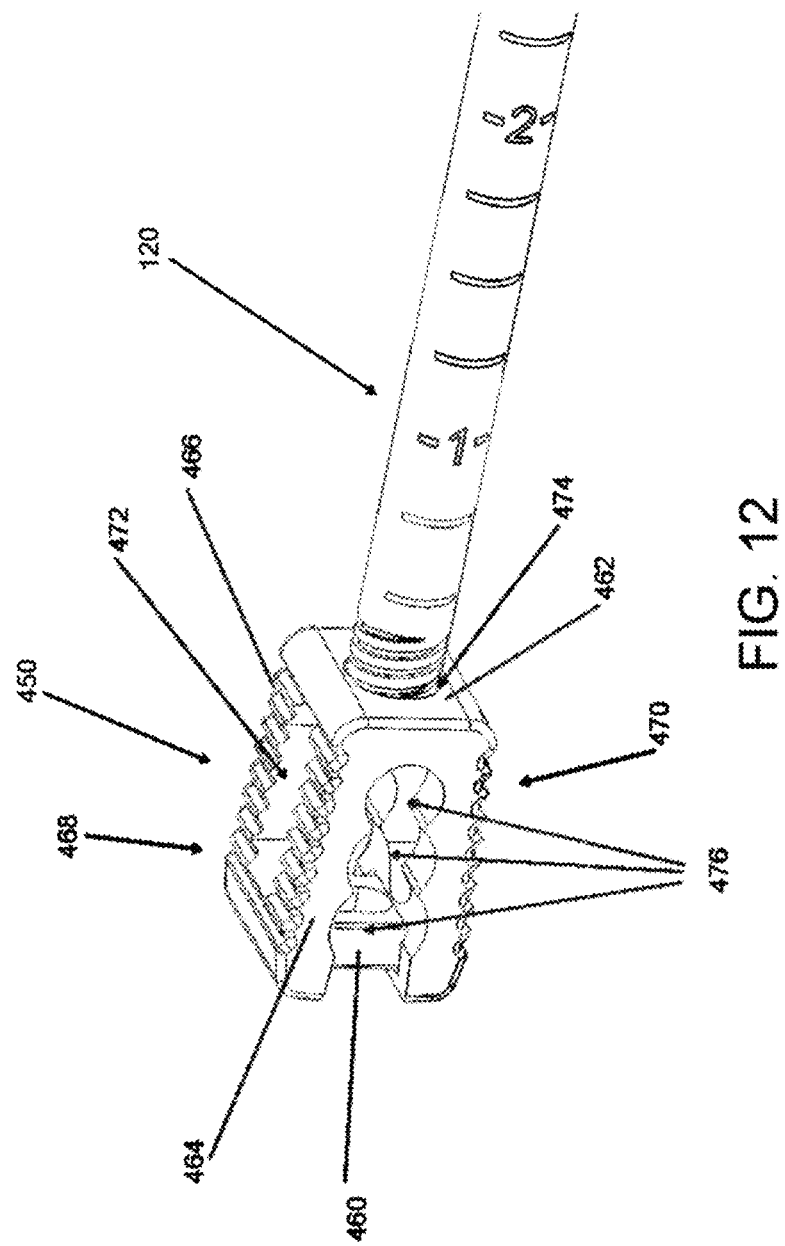
FIG. 12 illustrates an example embodiment of an expandable interbody device coupled to a bone graft delivery device.

Example embodiments of cages that can be used with the bone graft delivery device 100 are illustrated in FIGS. 11A-12. In the embodiment of FIGS. 11A-11D, the cage 400 has a leading end 410, a trailing end 412, and first and second sidewalls 414, 416 extending between the leading end 410 and trailing end 412. In the illustrated embodiment, the leading end 410 is tapered or generally wedge-shaped. The sidewalls 414, 416 have an upper bone contacting surface 418 configured to contact a superior vertebra and a lower bone contacting surface 420 configured to contact an inferior vertebra. The cage 400 also has a central opening 422 bounded by the leading end 410, trailing end 412, and sidewalls 414, 416 and an opening 424 in the trailing end that is in fluid communication with the central opening 422. A perimeter of the opening 424 in the trailing end includes the recesses 404 and ridges 402 configured to mate with the distal end 122 of the tube 120 or attachment member. In other embodiments, the opening 424 can include other engagement features configured to mate with corresponding engagement features on the distal end of the tube 120 or attachment member. The opening 424 is sized to mate with or receive the tube 120 or attachment member and can be larger than openings included in various other cages to mate with insertion instruments. When the distal end 122 of the tube 120 is coupled to the cage 400, the bone graft material can be delivered through the opening 424 into the central opening 422 to promote bone growth into and through the central opening 424 and promote fusion.

As shown, the sidewalls 414, 416 can include holes 426 that are in fluid communication with the central opening 422. The holes 426 allow bone graft material delivered into the central opening 422 from the tube 120 to spread to the surrounding disc space outside of the cage 400, for example as shown in FIG. 11E. In the illustrated embodiment, each of the sidewalls 414, 416 includes three holes 426, although more or fewer holes are also possible. In the illustrated embodiment, the holes 426 have an at least partially conical shape. As shown, a portion of the holes 426 adjacent the central opening 422 and inner surfaces of the sidewalls 414, 416 is generally circular. The perimeter of the holes 426 then flares or tapers outwardly toward outer surfaces of the sidewalls 414, 416, as shown in FIG. 11C. In other embodiments, the perimeter of the holes 426 can be flared or tapered continuously from the inner surfaces of the sidewalls 414, 416 to the outer surfaces of the sidewalls 414, 416. The holes 426 allow bone graft material to spread from inside the central opening 422 to outside of the cage 400 in the surrounding disc space. The tapered shape of the holes 426 allows or promotes dispersal of bone graft material outside of the cage 400 in multiple directions and over a greater area and can allow for a more uniform distribution of bone graft material around the cage 400 in the surrounding disc space to promote fusion.

FIG. 12 illustrates an example embodiment of an expandable cage 450 configured to be coupled to the tube 120 as shown. In some cases in which an expandable cage is used, the surgeon may fill or pack the cage with bone graft before inserting the cage in the patient, then expand the cage within the disc space. However, this then results in excess space within the cage not filled with bone graft material. Coupling the bone graft delivery device 100 to the cage 450 or another expandable cage with the cage in the disc space allows the cage to be filled as it is expanded within the disc space or after it has been expanded to maximize filling of the cage with the bone graft material.

In the illustrated embodiment, the cage 450 has a proximal wall 462, a distal wall 460, and first and second sidewalls 464, 466. The sidewalls 464, 466 have an upper bone contacting surface 468 configured to contact a superior vertebra and a lower bone contacting surface 470 configured to contact an inferior vertebra. The cage 450 also has a central opening 472 and a hole 474 in the proximal wall 462 in fluid communication with the central opening 472 and configured to receive the distal end of the tube 120. The distal end of the tube 120 can be coupled to the proximal wall 462 via a threaded connection as soon or any other suitable mechanism. Similar to the embodiment of FIG. 11A-11D, one or both of the first and second sidewalls 464, 466 can include one or more holes 476 in fluid communication with the central opening 472. In the embodiment of FIG. 12, the holes 476 are connected to one another. In the illustrated embodiment, a distance between the upper bone contacting surface 468 and the lower bone contacting surface 470 is greater adjacent the distal wall 460 than the proximal wall 462, and a height of the cage 450 increases from the proximal wall 462 to the distal wall 460. In some embodiments, the distal wall 460 includes a mechanism that expands the distal end of the cage 450 relative to the proximal end. The distal end of the tube 120 can be coupled to the cage 450 before or after the cage 450 is expanded to allow the cage 450 to be filled with bone graft material as it is being expanded or after it has been expanded.

Figure 8A:
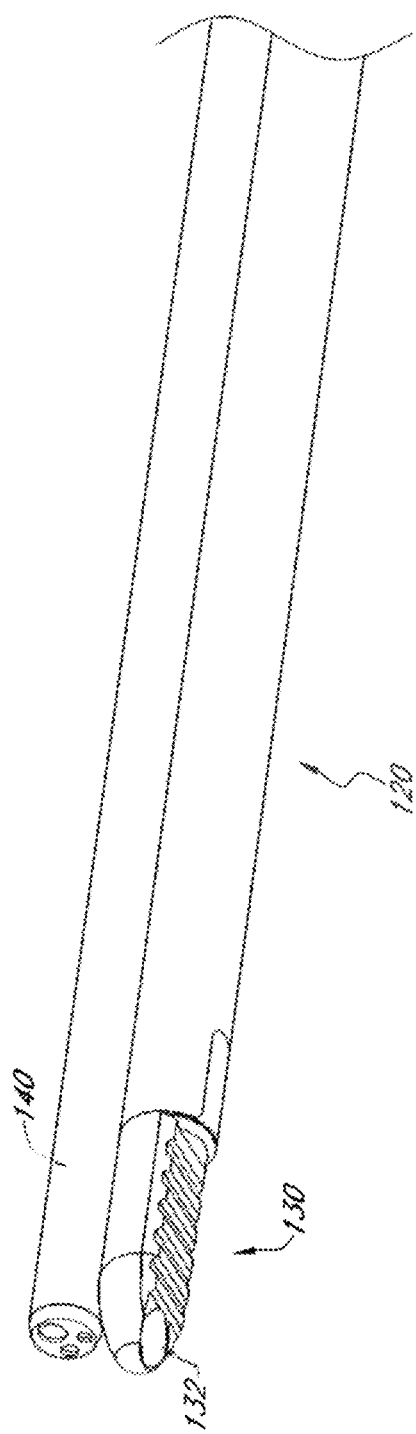
FIG. 8A illustrates a distal section of an example embodiment of a bone graft delivery device including an endoscope.
Figure 8B:
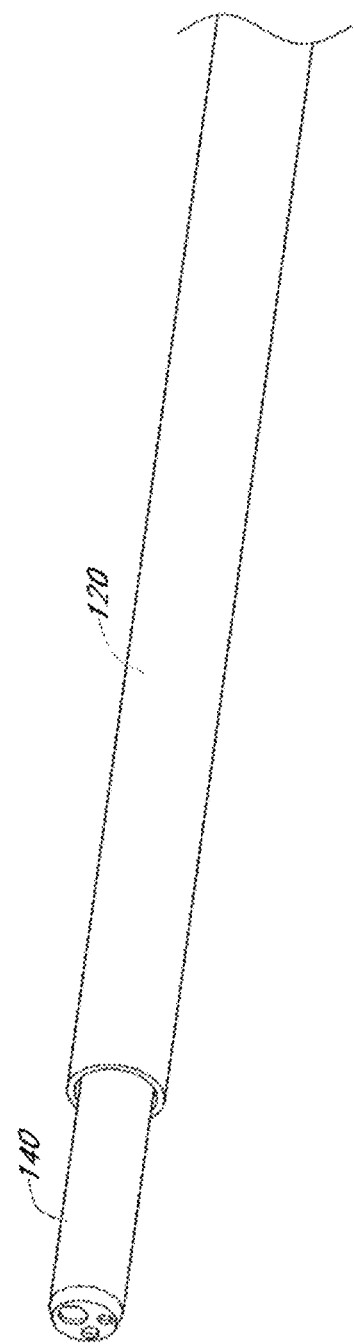
FIG. 8B illustrates a distal section of another example embodiment of a bone graft delivery device including an endoscope.

In some embodiments, the bone graft delivery device 100 can include an endoscope or endoscopic camera to allow for visualization during insertion of the tip 130 to the target area, decortication, and/or delivery of the graft material. This can advantageously allow the physician to visualize muscles, nerves, and other tissue and structures under the skin to help avoid and inhibit damage to sensitive structures. As shown in FIG. 8A, an endoscope 140 can extend along the tube 120 and can be removably or permanently coupled to the tube 120. In some embodiments, the endoscope 140 or camera can extend through the lumen of the tube 120, for example as shown in FIG. 8B.

Figure 9A:
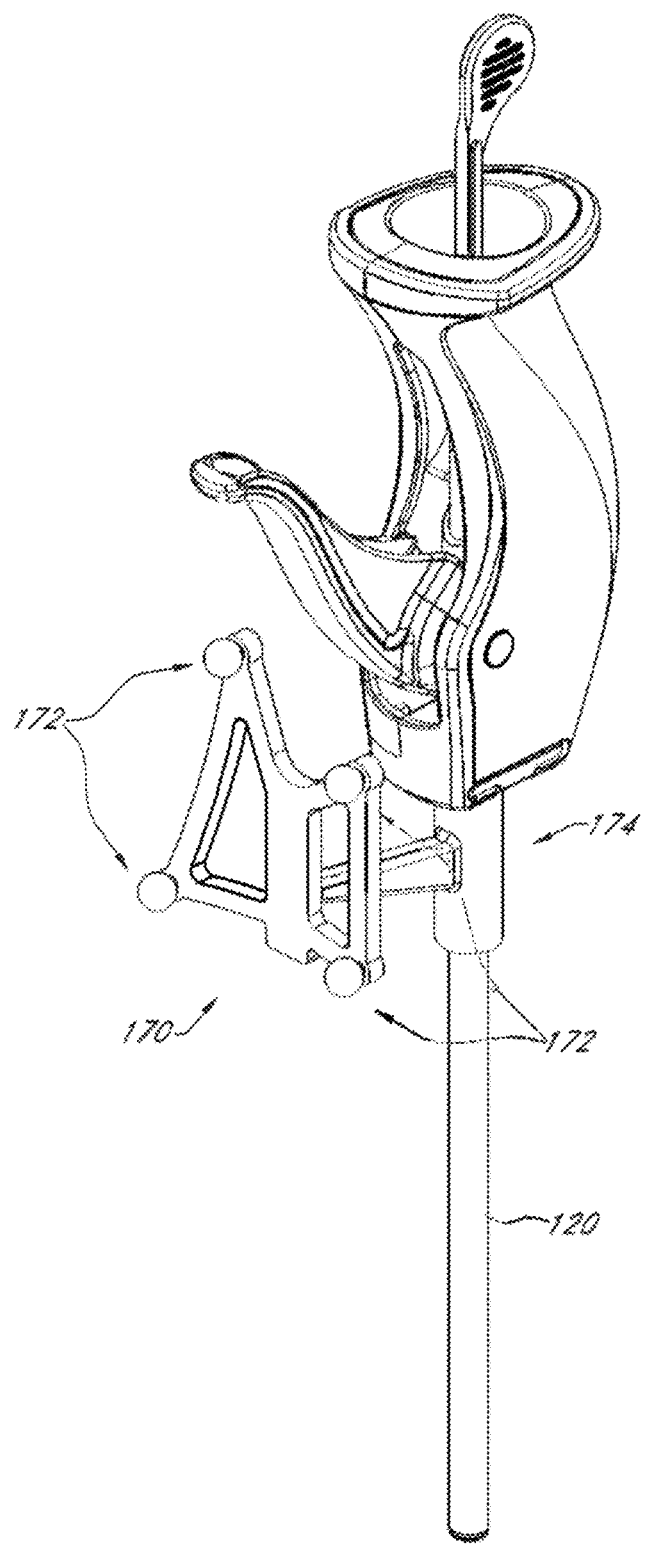
FIGS. 9A and 9B illustrate the bone graft delivery device of FIGS. 2A and 2B with a guide bracket for a surgical navigation system.
Figure 9B:
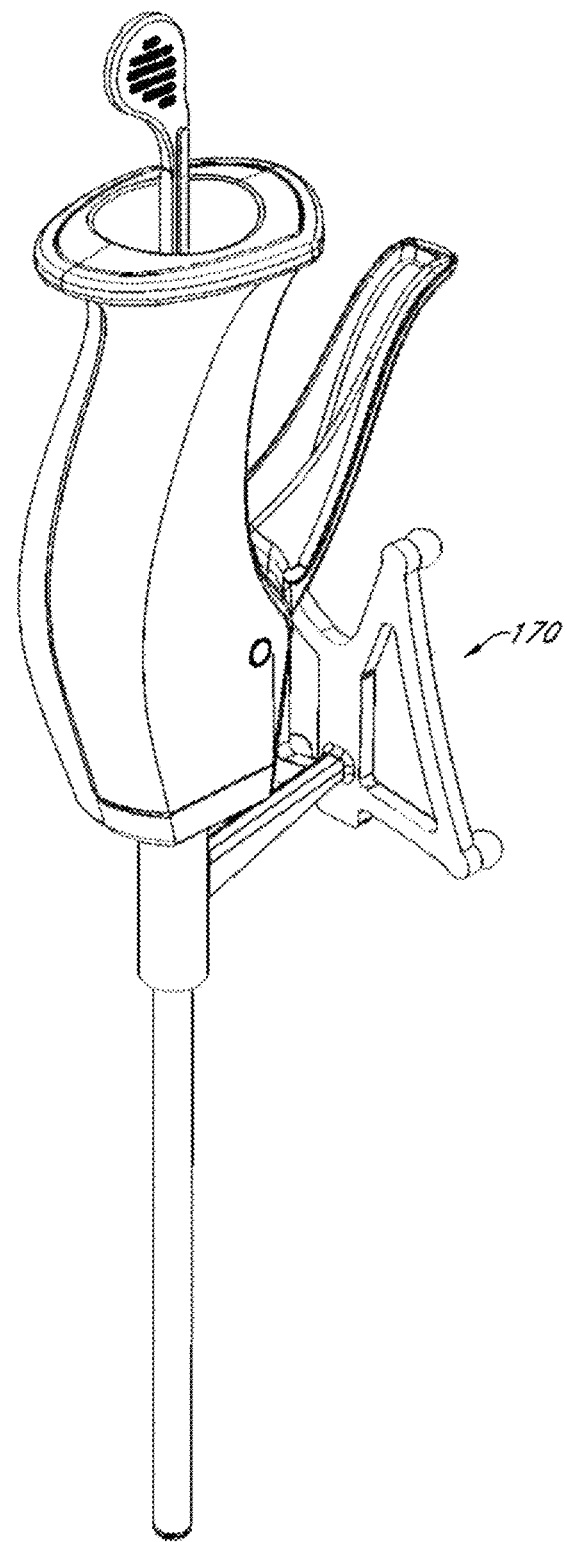

The bone graft delivery device 100 can also or alternatively be used in conjunction with various image-guided surgery systems and devices, such as, for example, StealthStation® Navigation Systems available from Medtronic or other navigation systems. In some embodiments, for example as shown in the example embodiment of FIGS. 9A and 9B, the bone graft delivery device includes a guide 170 having markers 172 configured to be visualized with, for example, fluoroscopy or x-ray. The guide 170 can include a sheath 174 configured to receive the tube 120 to couple the guide 170 to the bone graft delivery device. A surgical navigation system can include an imaging modality, such as an X-ray or CT scanner or fluoroscope, and a camera. In use, during preparation for an image-guided surgical procedure, a reference frame, which can include radiopaque markers, is attached to a pin positioned in a reference location in the patient's spine or other target area. Images are taken, and the image data is transferred to the navigation system for processing and registration. During the procedure, the camera can track the position of the markers 172 on the guide 170 relative to the markers on the reference frame. The navigation system can process images obtained by the camera and/or an imaging modality to display the position of the bone graft delivery device on the pre-operative images. In some embodiments, the navigation system can process images obtained by an endoscopic camera extending alongside or through the tube 120 as described herein.

Figure 20A:
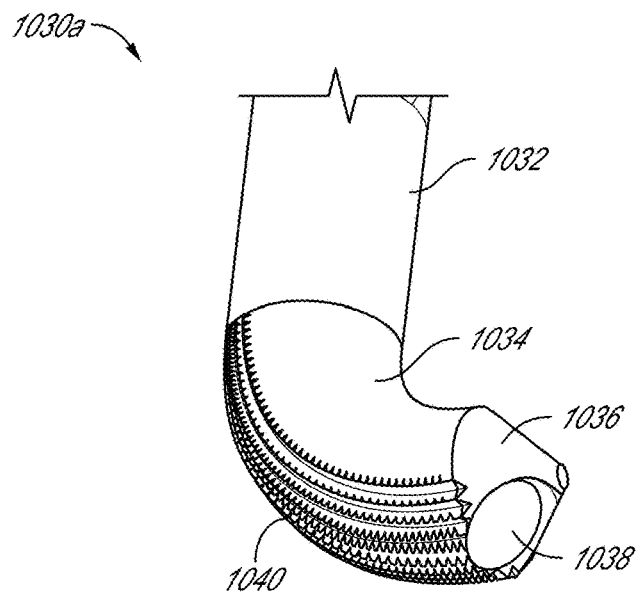
FIG. 20A illustrates a perspective view of an embodiment of a tip of a bone graft delivery device.
Figure 20B:
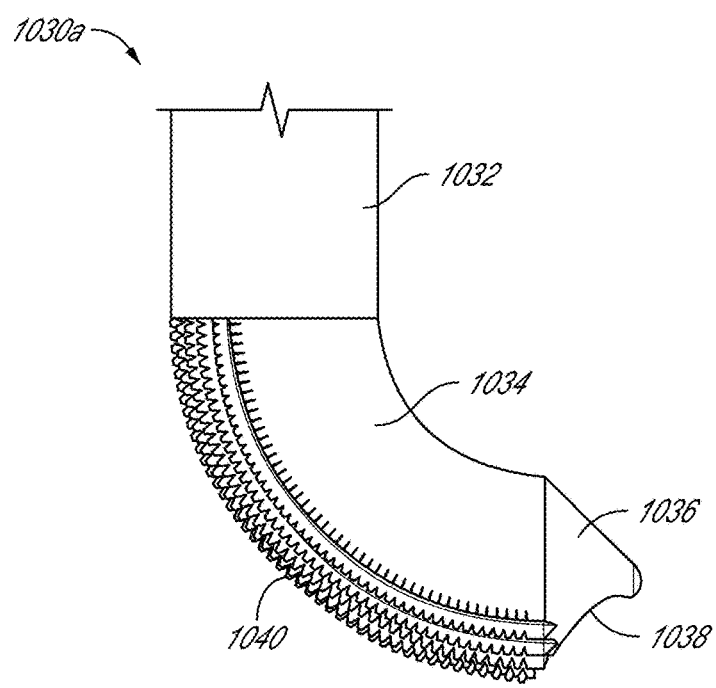
FIG. 20B illustrates a side view of the tip of FIG. 20A.

FIGS. 20A and 20B illustrate a perspective view and a side view, respectively, of an embodiment of a tip or applicator 1030a. In certain embodiments, the tip 1030a can include any of the same or similar functions and features as the distal tip 130 and/or applicators 850a, 850b. In certain embodiments, the tip or applicator 1030a can be used in place of the distal tip 130 and/or applicators 850a, 850b.

In some embodiments, the tip 1030a can be integrally formed with or coupled, removably or permanently, to a bone graft delivery device, such as bone graft delivery device 100 for delivery of bone graft material to a desired location. In certain embodiments, the tip 1030a can be integrally formed with or coupled, removably or permanently to a tube of a bone graft delivery device, such as tube 120. In some embodiments, the tube and tip 1030a can be a modular system such that different tips can be selected and coupled to the tube for different procedures and/or target locations. In certain embodiments, one or more tubes and/or one or more tips 1030a can be part of a bone graft delivery system kit.

The tip 1030a can be made of a metallic, radiopaque material to facilitate visualization on, for example, fluoroscopy or x-ray. Alternatively, the tip 1030a may be made of another material, for example a durable medical plastic or a composite material, and may include markers to facilitate visualization. In the illustrated embodiment, the tip 1030a includes a proximal section 1032, a curved or angled section 1034, and a distal section 1036.

In the illustrated embodiment, the proximal section 1032 is generally cylindrical. In certain embodiments, the proximal section 1032 can include one or more features for coupling to a bone graft delivery device, such as bone graft delivery device 100. In some embodiments, the proximal section 1032 can include one or more features for coupling to a tube of a bone graft delivery device, such as bone graft delivery device 100. For example, the section 1032 can include one or more internal or external threads, grooves, or other connection features configured to couple with corresponding connection features of an elongate tube or attachment member for coupling to a bone graft delivery device. In some embodiments, the proximal section 1032 can couple to the tube or attachment member via a threaded connection, snap fit connection, clip-on connection, wedge connection, and/or any other suitable connection mechanism.

The curved section 1034 may be defined by a 45°, 60°, 75°, 90°, 105°, 120°, or 135° curve. In some embodiments, the curved sections has an angle of curvature between 45° to 135°, between 45° to 90°, between 90° to 135°, between 60° to 120°, between 60° to 90°, between 90° to 135°, between 75° to 105°, between 75° to 90°, between 90° to 105°, or between 85° to 95°.

In the illustrated embodiment, the distal section 1036 is conical or generally conical. This shape can be beneficial for delivering bone graft material to, for example, a facet joint. In some embodiments, the distal section 1036 is pointed, bulleted, and/or sharp to dissect or split muscle and tissue as it is advanced to the surgical location. Alternatively, the distal section 1036 can be blunt to allow for displacement of muscle without risk of cutting of nerves or other tissue.

The tip 1030a may have a single or multiple openings 1038 configured to deliver bone graft material to a desired location. In some embodiments, the one or more openings 1038 are positioned within the distal section 1036. The one or more openings 1038 may be in fluid communication with a bone graft delivery device such as bone graft delivery device 100 when the tip 1030*a* is coupled thereto. In some embodiments, the one or more openings 1038 may be in fluid communication with an elongate tube of a bone graft delivery device, such as tube 120. In some embodiments, the one or more openings 1038 may be offset from a central axis of the distal section 1036. In some embodiments, a distal most point of the distal section 1036 may extend beyond a distal edge of the one or more openings 1038.

In some embodiments, at least one side or area of the tip 1030*a* includes a series of jagged edges or other suitable surface features 1040 configured to serve as a rasp for scraping bone. As shown in FIGS. 20A and 20B, the edges may be triangular in shape. In some embodiments, the edges may be flat. In some embodiments, the jagged edges may form a plurality of flat surfaces parallel with each other all within the same plane. In some embodiments, the rasping surface 1040 can include a roughened surface extending around an outer surface of the tip. In some embodiments, the rasping surface 1040 may be positioned on a portion of the curved section 1034 and/or a portion of the distal section 1036. The rasp may be operated manually or by mechanical, battery powered, electric, pneumatic, or any other means of force to allow for decortication of the area to receive the bone graft material. In some embodiments, at least some of the one or more openings 1038 for delivering bone graft material are located on a side or portion of the tip 1030*a* that does not include a rasping surface. In some embodiments, at least some of the one or more openings 1038 are located on a side or portion that does include a rasping surface.

Figure 20C:
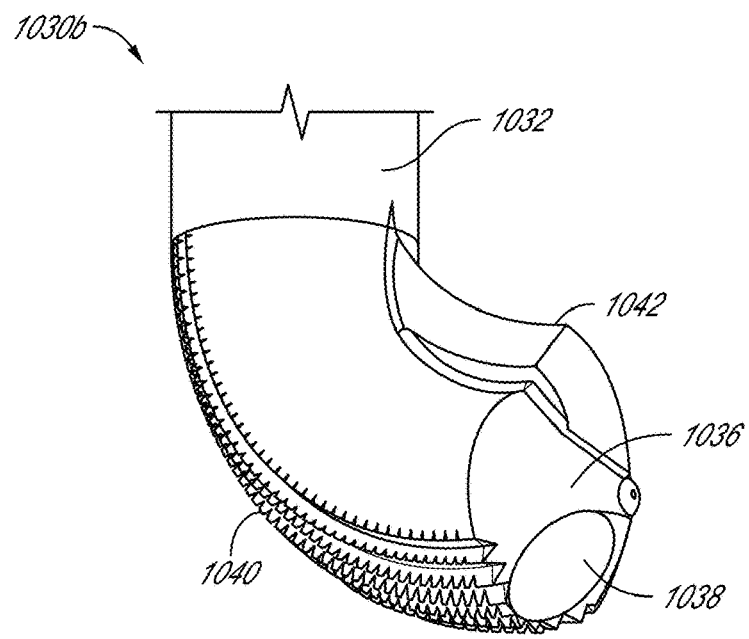
FIG. 20C illustrates a perspective view of an embodiment of a tip of a bone graft delivery device.
Figure 20D:
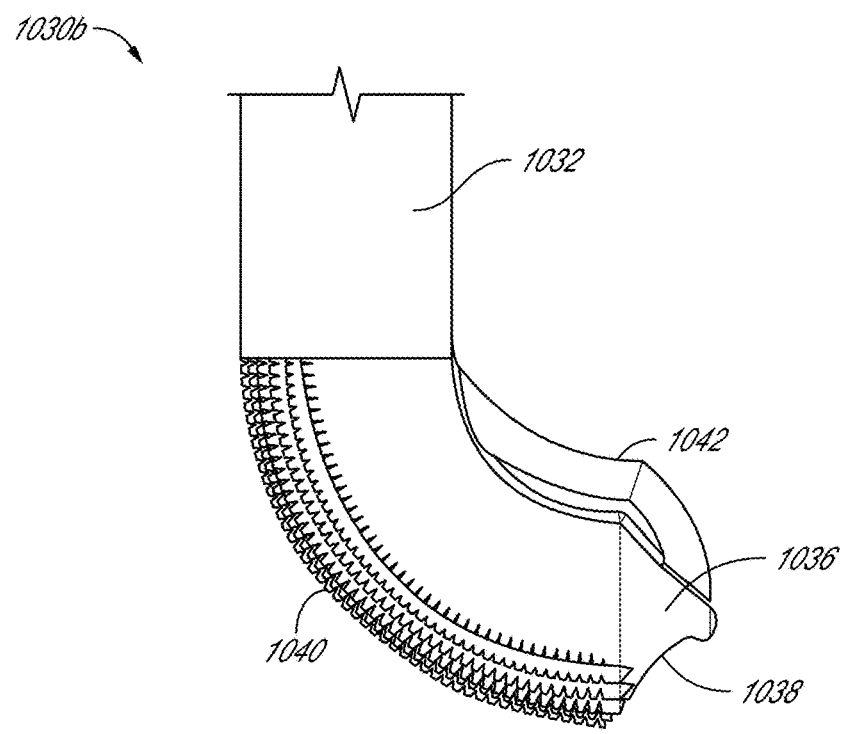
FIG. 20D illustrates a side view of the tip of FIG. 20C.
Figure 21A:
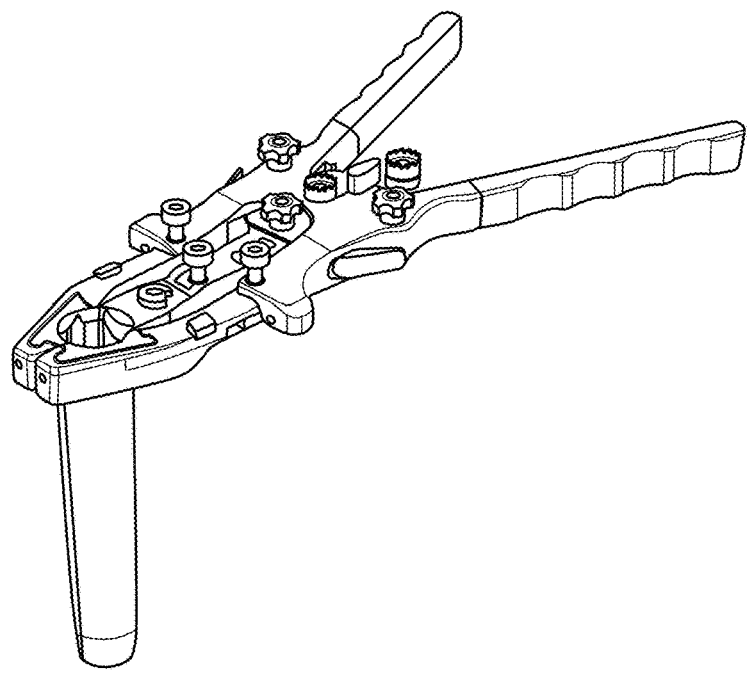
FIG. 21A illustrates a perspective view of an embodiment of a retractor device that can be used with a bone graft delivery system.
Figure 21B:
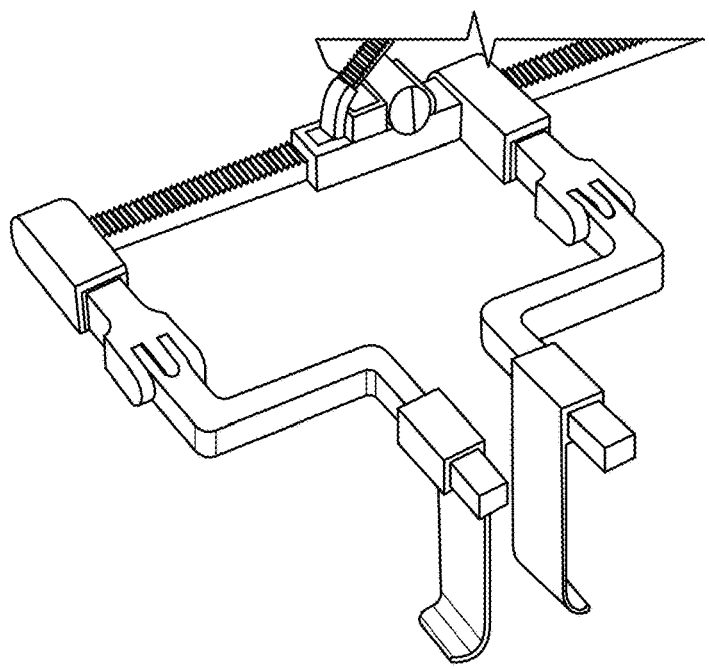
FIG. 21B illustrates a perspective view of another embodiment of a retractor device that can be used with a bone graft delivery system.
Figure 21C:
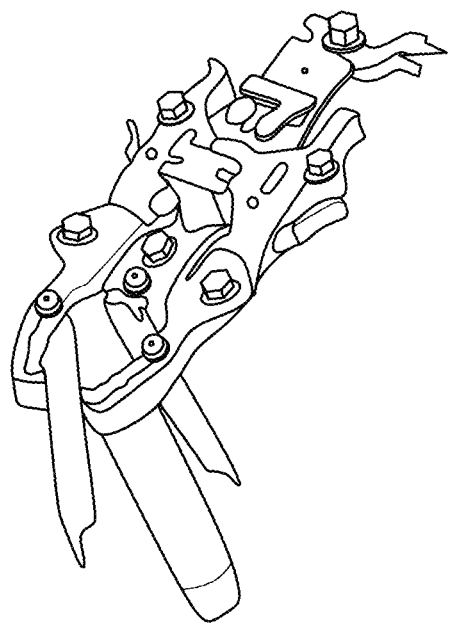
FIG. 21C illustrates a perspective view of another embodiment of a retractor device of a bone graft delivery system.
Figure 21D:
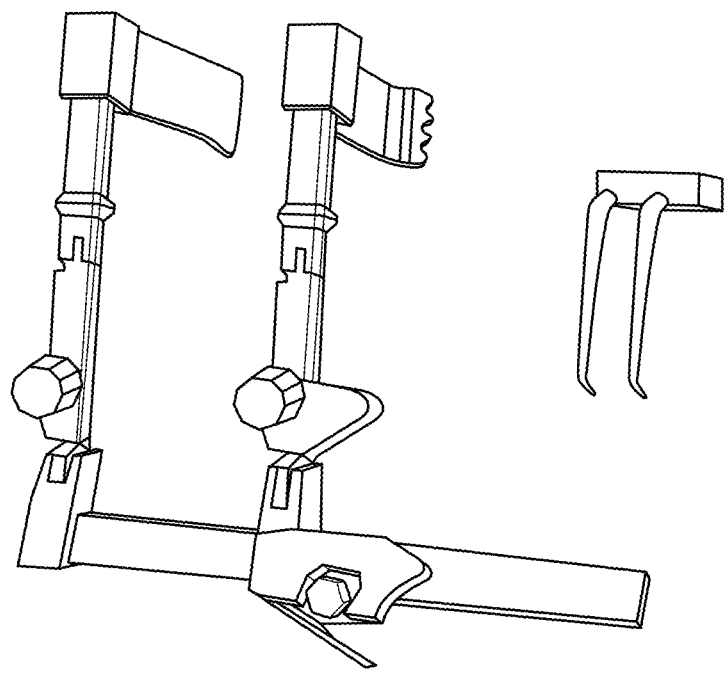
FIG. 21D illustrates a perspective view of another embodiment of a retractor device of a bone graft delivery system.

FIGS. 20C and 20D illustrate a perspective view and a side view, respectively, of an embodiment of a tip or applicator 1030*b*. The tip 1030*b* can include the same or similar features as the tip or applicator 1030*a*. As shown in the illustrated embodiment, the tip 1030*b* can include a sickle or blade 1042 configured to dissect tissue. The sickle 1042 can include one or more edges positioned to dissect tissue as the applicator tip 1030*b* is advanced toward a target location.

Figure 27A:
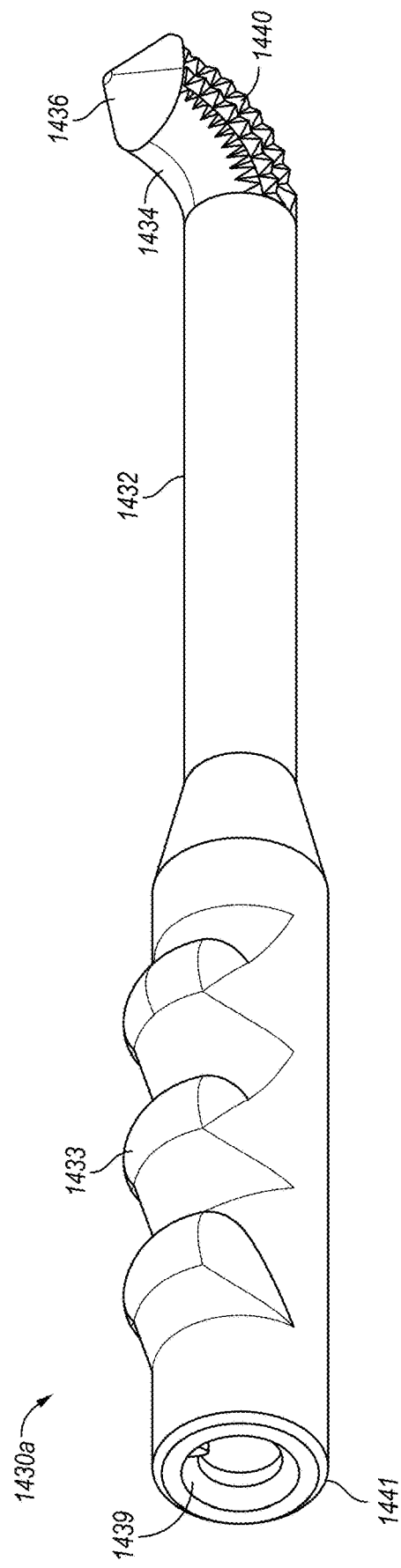
FIG. 27A illustrates a perspective view of an embodiment of a rasp of a bone graft delivery system.
Figure 27B:
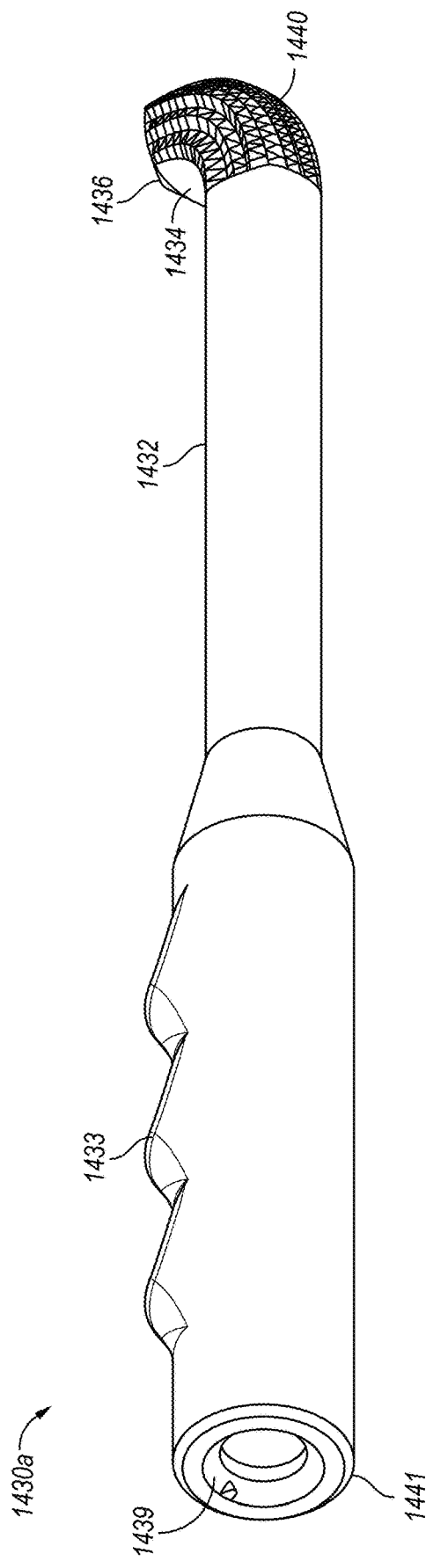
FIG. 27B illustrates a perspective view of the rasp of FIG. 27A.
Figure 27C:
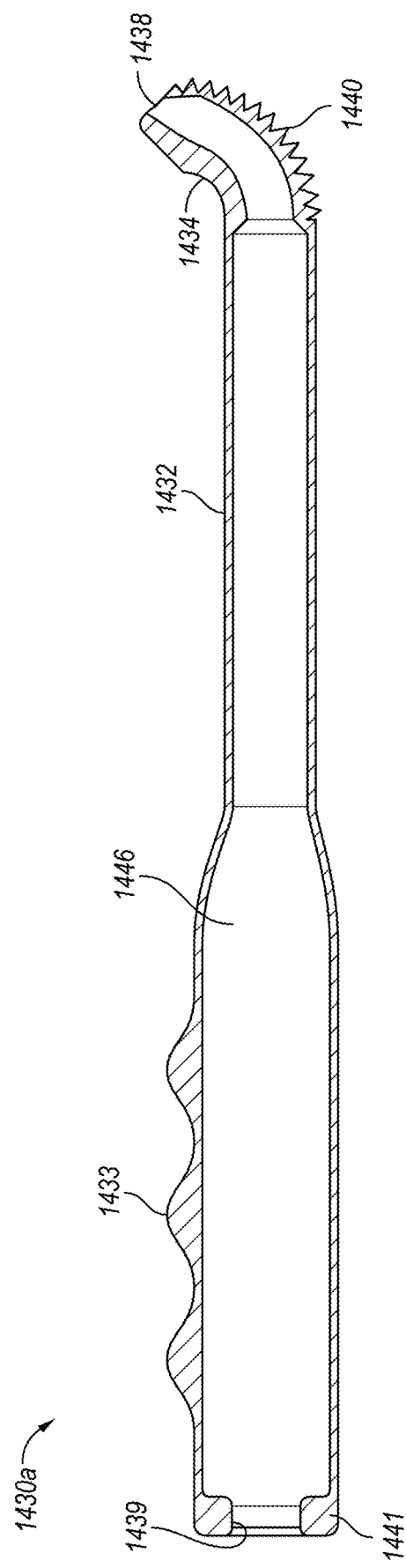
FIG. 27C illustrates a cross-sectional view of the rasp of FIG. 27A.
Figure 31:
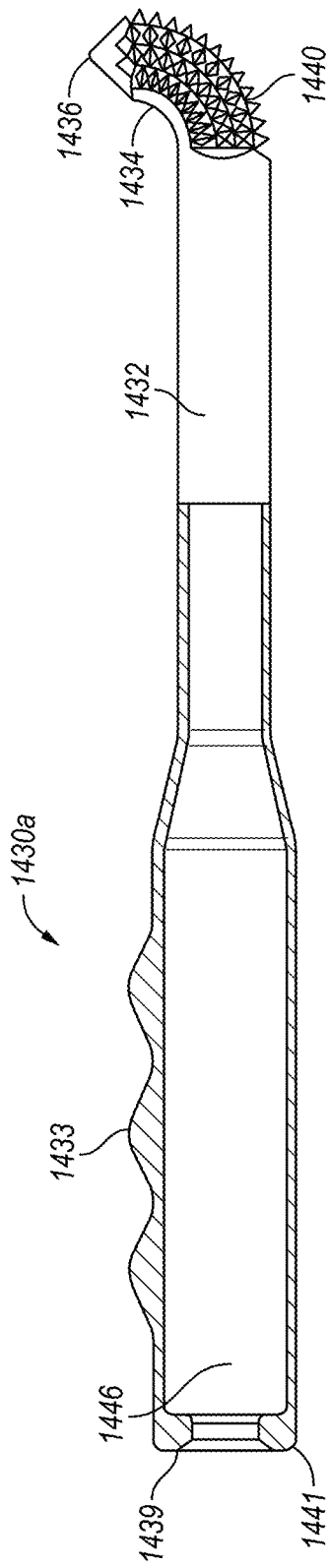
FIG. 31 illustrates a partial cross-sectional view of the rasp of FIG. 29A.

FIGS. 27A and 27B illustrate perspective views of an embodiment of a rasp, tip, or applicator 1430*a*. FIG. 27C illustrates a cross-sectional view of the rasp 1430*a*. FIG. 31 illustrates a partial cross-sectional view of the rasp 1430*a*. In certain embodiments, the rasp 1430*a* can include any of the same or similar functions and features as the distal tip 130, the tip 1030*a*, the tip 1030*b*, and/or applicators 850*a*, 850*b*.

In some embodiments, the rasp 1430*a* can be integrally formed with or coupled, removably or permanently, to a bone graft delivery device, such as bone graft delivery device 100 for delivery of bone graft material to a desired location. In certain embodiments, the rasp 1430*a* can be integrally formed with or coupled, removably or permanently to a tube of a bone graft delivery device, such as tube 120. In some embodiments, the tube and rasp 1430*a* can be a modular system such that different tips can be selected and coupled to the tube for different procedures and/or target locations. In certain embodiments, one or more tubes and/or one or more rasps 1430*a* can be part of a bone graft delivery system kit.

In certain embodiments, the rasp 1430*a* can be integrally formed with or coupled, removably or permanently to a handle of a bone graft delivery device, such as handle 102. In some embodiments, the handle and the rasp 1430*a* can be a modular system such that different rasps can be selected and coupled to the handle for different procedures and/or target locations. In certain embodiments, one or more handles and/or one or more rasps 1430 can be part of a bone graft delivery system kit. In some embodiments, a funnel for delivery of bone graft to the lumen of the rasp 1430*a* can be integrally formed with or coupled, removably or permanently, to the proximal end 1441 and/or handle section 1443 of the rasp 1430*a*. Examples of funnels 900, 900*a*, 900*b*, and 900*c* are described herein. In some embodiments, a lumen of the funnel can extend into a lumen 1446. Bone graft can be loaded into the funnel, either before or after the funnel is coupled to the rasp 1430*a*. Bone graft can be extruded from the lumen of the funnel through the lumen 1446*a* of the rasp 1430*a*, and out of the rasp 1430*a*, for example using a pusher. In some embodiments, the funnel can be formed of a plurality of separate pieces. In other embodiments, the funnel can be monolithically formed.

In certain embodiments a plurality of removable funnels can be used for delivery of bone graft to the lumen of the rasp 1430*a*. In some embodiments, the plurality of funnels can be loaded with bone graft prior to a bone graft delivery procedure. A first funnel can be placed within the lumen of the rasp 1430*a*, and bone graft within the funnel can be extruded into the rasp 1430*a*. Once the bone graft is extruded out of an aperture of the rasp 1430*a*, the first funnel may be removed, and a second funnel having bone graft loaded therein can be placed in the lumen of the rasp 1430*a* to deliver additional bone graft through the rasp 1430*a*. This process can be repeated with additional removable funnels. The use of multiple preloaded funnels can reduce the time required for a bone graft delivery procedure, for example, in comparison to the use of a single funnel, which may need to be reloaded with bone graft during the bone graft delivery procedure.

In some embodiments, a tray or other housing can be coupled to the top of the funnel. The tray can be movably coupled to the top of the funnel to allow the tray to slide back and forth or rotate relative to the funnel to position units of bone graft material over the funnel. In some embodiments, a first unit of bone graft material may be positioned over the funnel and advanced into the funnel, and then a second unit can be positioned over the funnel and advanced into the funnel by repositioning the tray, for example, by sliding or rotation. This method can be repeated until a desired amount of bone graft has been advanced to the surgical location. This mechanism can allow multiple units of bone graft material to be quickly advanced into the lumen of the rasp. This may allow for small amounts of bone graft to be advanced separately from one another, which may prevent clogging. In some embodiments, units of bone graft material can be advanced from the tray or the housing into the funnel using a pusher, as described herein.

In the illustrated embodiment, the rasp 1430*a* includes a handle or grip section 1433, a curved or angled section 1434, and a distal section 1436. In certain embodiments, rasp 1430 can included a connection section 1432 extending between the handle section 1433 and the curved section 1434.

In certain embodiments, one or more of the handle section 1433, connection section 1432, angled section 1434, and distal section 1436 can be integrally formed with one another. In other embodiments, one or more of the handle section 1433, connection section 1432, angled section 1434, and distal section 1436 can be separate components that may be coupled, removably or permanently, to form the rasp 1430*a*.

The curved section 1434 may be defined by a 45°, 60°, 75°, 90°, 105°, 120°, or 135° curve. In some embodiments, the curved sections has an angle of curvature between 45° and 135°, between 45° and 90°, between 90° and 135°, between 60° and 120°, between 60° and 90°, between 90° and 135°, between 75° and 105°, between 75° and 90°, between 90° and 105°, or between 85° and 95°. In some embodiments, an angle between the distal end of the connection section 1432 or the proximal end of the curved section 1434 and the distal tip 1436 can be 45°, 60°, 75°, 90°, 105°, 120°, 135°, between 45° and 135°, between 45° and 90°, between 90° and 135°, between 60° and 120°, between 60° and 90°, between 90° and 135°, between 75° and 105°, between 75° and 90°, between 90° and 105°, between 85° and 95°, or any other suitable angle or range.

In the illustrated embodiment, the distal section 1436 is conical or generally conical. This shape can be beneficial for delivering bone graft material to, for example, a facet joint. In some embodiments, the distal section 1436 is pointed, bulleted, and/or sharp to dissect or split muscle and tissue as it is advanced to the surgical location. Alternatively, the distal section 1436 can be blunt to allow for displacement of muscle without risk of cutting of nerves or other tissue.

The tip 1430*a* may have a single or multiple openings 1438 configured to deliver bone graft material to a desired location. In some embodiments, the one or more openings 1438 are positioned within the distal section 1436. The one or more openings 1438 may be in fluid communication with a bone graft delivery device such as bone graft delivery device 100 when the rasp 1430*a* is coupled thereto. In some embodiments, the one or more openings 1438 may be in fluid communication with an elongate tube of a bone graft delivery device, such as tube 120. In some embodiments, the one or more openings 1438 may be offset from a central axis of the distal section 1436. In some embodiments, a distal most point of the distal section 1436 may extend beyond a distal edge of the one or more openings 1438.

In some embodiments, at least one side or area of the tip 1430*a* includes a series of jagged edges or other suitable surface features 1440 configured to serve as a rasp for scraping bone. The rasping surface 1440 can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In certain embodiments, the rasping surface can be in the shape of a single blade similar to a cheese grater to file the bone down and allow it to bleed.

As shown in FIGS. 27A-C, the edges of the rasping surface 1440 may be triangular in shape. In some embodiments, the edges may be flat. In some embodiments, the jagged edges may form a plurality of flat surfaces parallel with each other all within the same plane. In some embodiments, the rasping surface 1440 can include a roughened surface extending around an outer surface of the tip. In some embodiments, the rasping surface 1440 can include a surface texturing configured to act as an abrasive to roughen the bone and/or remove surfaces of the bone during a rasping procedure. The surface texturing of the rasping surface 1440 can be sprayed on, chemically etched, acid etched, 3D printed, bead blasted or created using any other suitable texturing process. In some embodiments, removing the surface of bone can expose cells and growth factors necessary or advantageous for healing. In some embodiments, the rasping surface 1440 may be positioned on a portion of the curved section 1434 and/or a portion of the distal section 1436. The rasp may be operated manually or by mechanical, battery powered, electric, pneumatic, or any other means of force to allow for decortication of the area to receive the bone graft material. The rasp 1430*a* can be used to decorticate bone in the spine or other regions where orthopedic fusion is needed. In some embodiments, at least some of the one or more openings 1438 for delivering bone graft material are located on a side or portion of the rasp 1430*a* that does not include a rasping surface. In some embodiments, at least some of the one or more openings 1438 are located on a side or portion that does include a rasping surface.

In some embodiments, the rasp 1430*a* can include a sickle or blade configured to dissect tissue, similar to sickle or blade 1042 of tip 1030*b*. In some embodiments, the sickle or blade can include one or more edges positioned to dissect tissue as the rasp 1430*a* is advanced toward a target location.

Figure 28:
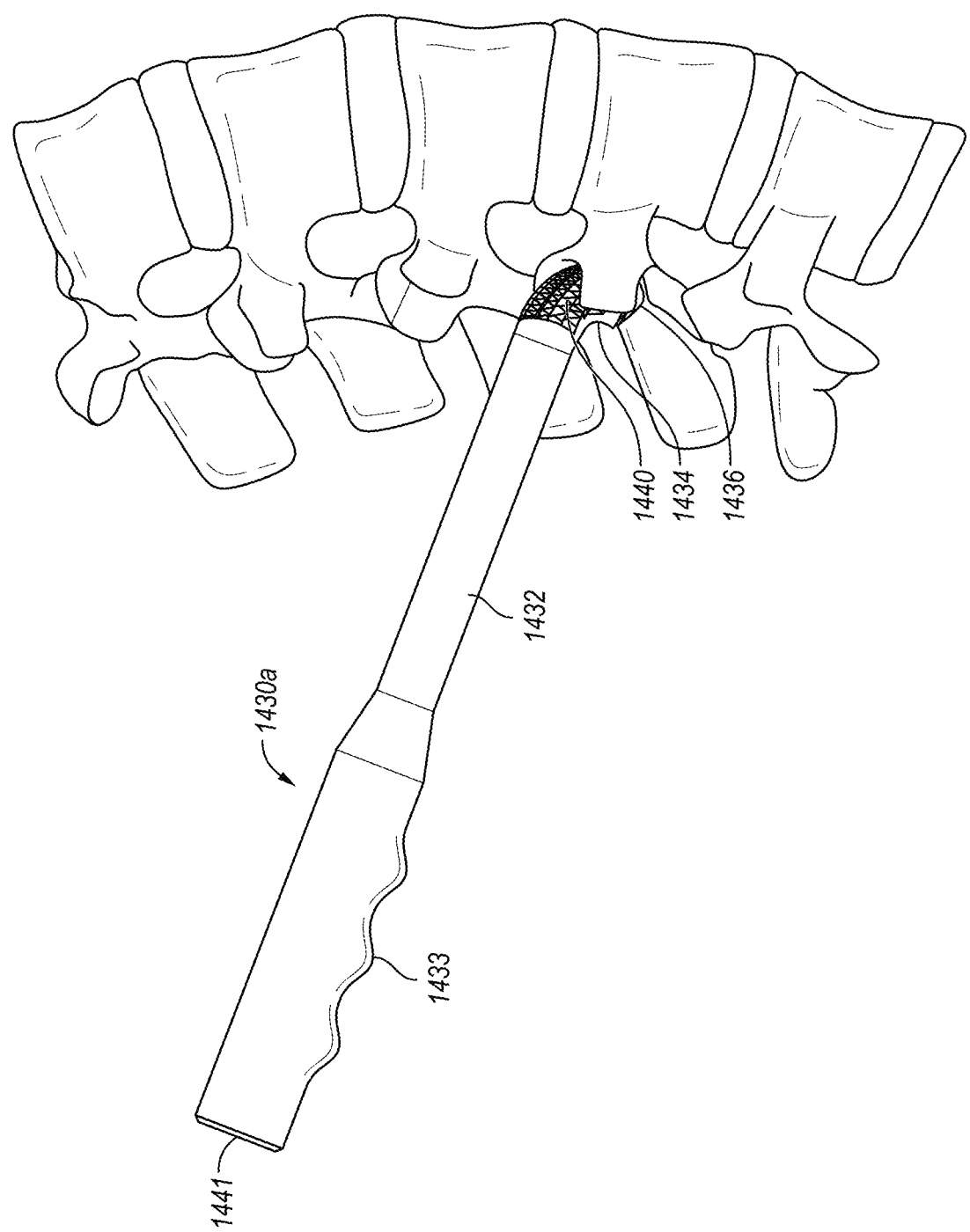
FIG. 28 illustrates an example of a procedure using the rasp of FIG. 27A.

In some embodiments, the handle section 1433 can include one or more finger grips or other surface features configured to facilitate gripping by a user. In use, a user can grasp the handle or finger grips to manipulate the rasp 1430*a* to scrape or decorticate bone. FIG. 28 illustrates an example of the rasp 1430*a* positioned to decorticate bone in a spinal region. In other embodiments, the rasp 1430*a* does not include a handle or grip. In some embodiments, as shown in FIGS. 27A-28, the finger grips or surface features of the handle section 1433 can be aligned with the tip 1436 on the same side of the rasp 1430*a*. In some embodiments, the finger grips or surface features can be positioned on the side of the rasp 1430 relative to which the curved section 1434 extends outwardly. Such an arrangement can provided more control to a user over the distal end 1436 and rasping surface 1440 relative to other arrangements when grasping the handle section 1433.

As shown in FIG. 27C, the rasp 1430*a* can include the lumen 1446. The lumen 1446 can be in fluid communication with the one or more openings 1438 to allow delivery of bone graft therethrough. The lumen 1446 can extend between an opening 1439 and the opening 1438. In some embodiments, bone graft can be delivered into the lumen 1446 through the opening 1439 and then exit through the opening 1438. In certain embodiments, the opening 1439 can be positioned at a proximal end 1441 of the rasp 1430*a*. In some embodiments, a pusher, plunger, or other means may be used to deliver graft through the lumen 1446.

Figure 32A:
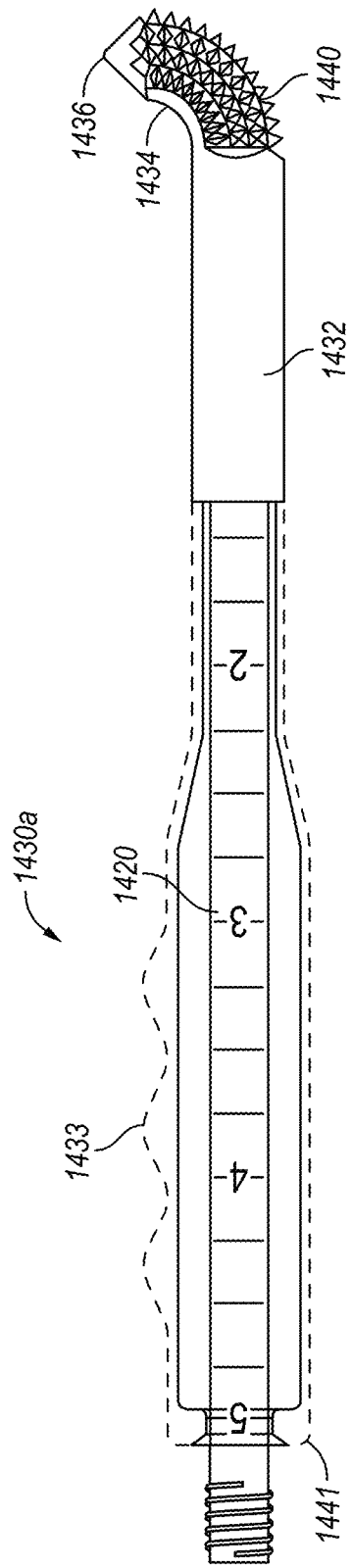
FIG. 32A illustrates a side view of the tube and rasp of FIG. 27A in which a portion of the rasp is shown as transparent.
Figure 32B:
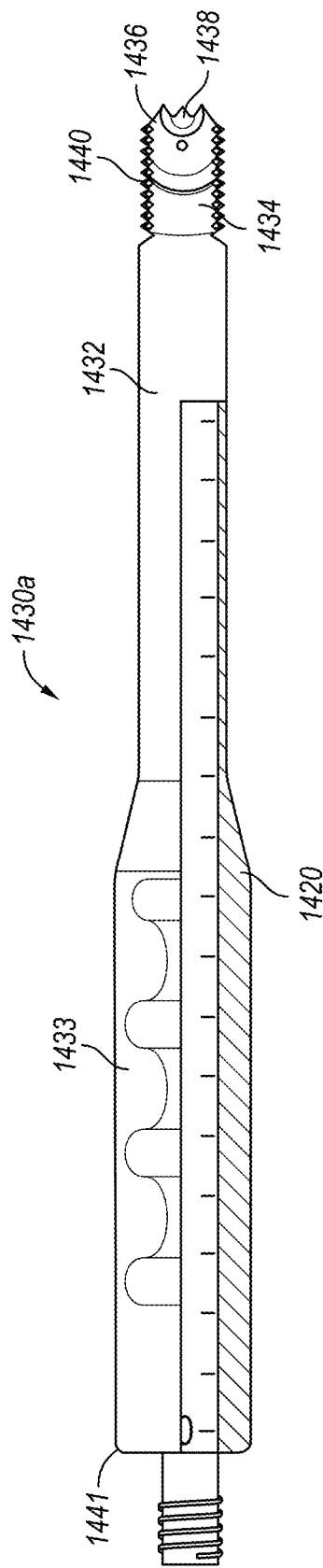
FIG. 32B illustrates a front view of the tube and rasp of FIG. 27A in which a portion of the rasp is removed to show internal features.

In certain embodiments, the lumen 1446 can be dimensioned, shaped, or otherwise configured to receive a tube, such as tube 120. FIGS. 29A-B and 32A-B depict a tube 1420 positioned within the rasp 1430. In FIG. 29A, the rasp 1430 is shown as transparent in dashed lines to show the internal features thereof. FIG. 29B depicts a side view of the rasp 1430 and tube 1420. FIG. 32A depicts a side view of the rasp 1430 and tube 1420 in which a portion of the rasp 1430 is shown as transparent in dashed lines. FIG. 32B depicts a front view of the rasp 1430 and tube 1420 in which a portion of the rasp 1430 has been removed to show the internal features.

The tube 1420 can include any of the same or similar features as the tube 120. In some embodiments, when the tube 1420 is positioned within the lumen 1446, bone graft material can flow through the tube 1420 and out of the opening 1438.

In some embodiments, the rasp 1430*a* can be releasably secured to the tube 1420 when the rasp 1430*a* is positioned over the tube 1420. In some embodiments, the rasp 1430*a* can be securely coupled to the tube 1420 by threads, grooves, bumps, nubs, snap fit, or any other suitable coupling mechanism. In other embodiments, the rasp 1430*a* may only about the tube 1420 without being secured to the tube 1420. Highly flowable bone graft materials, such as DBM putty, may require relatively small amounts of force for extrusion such that extrusion may be possible when without a secure coupling between the tube and the rasp. In certain embodiments, the handle portion 1433 or lumen 1446 can be configured to couple to the tube 1420.

In some embodiments, the rasp 1430a can be used with a graft delivery device, such as graft delivery device 100. In certain embodiments, the rasp 1430a can be used with a bone graft delivery system configured to deliver bone graft through ratcheting, worm gear, rack and pinion, spindle drive, threaded drive or any other suitable delivery mechanism that uses force to extrude graft. In certain embodiments, the bone graft delivery system can be a tube, such as tube 1420, and a plunger, such as plunger 112 or pusher rod 312, a syringe, such as syringe 1110, or a loading device, such as loading devices 600, 700, or 900, configured to cause the flow of bone graft material through the tube.

Figure 30A:
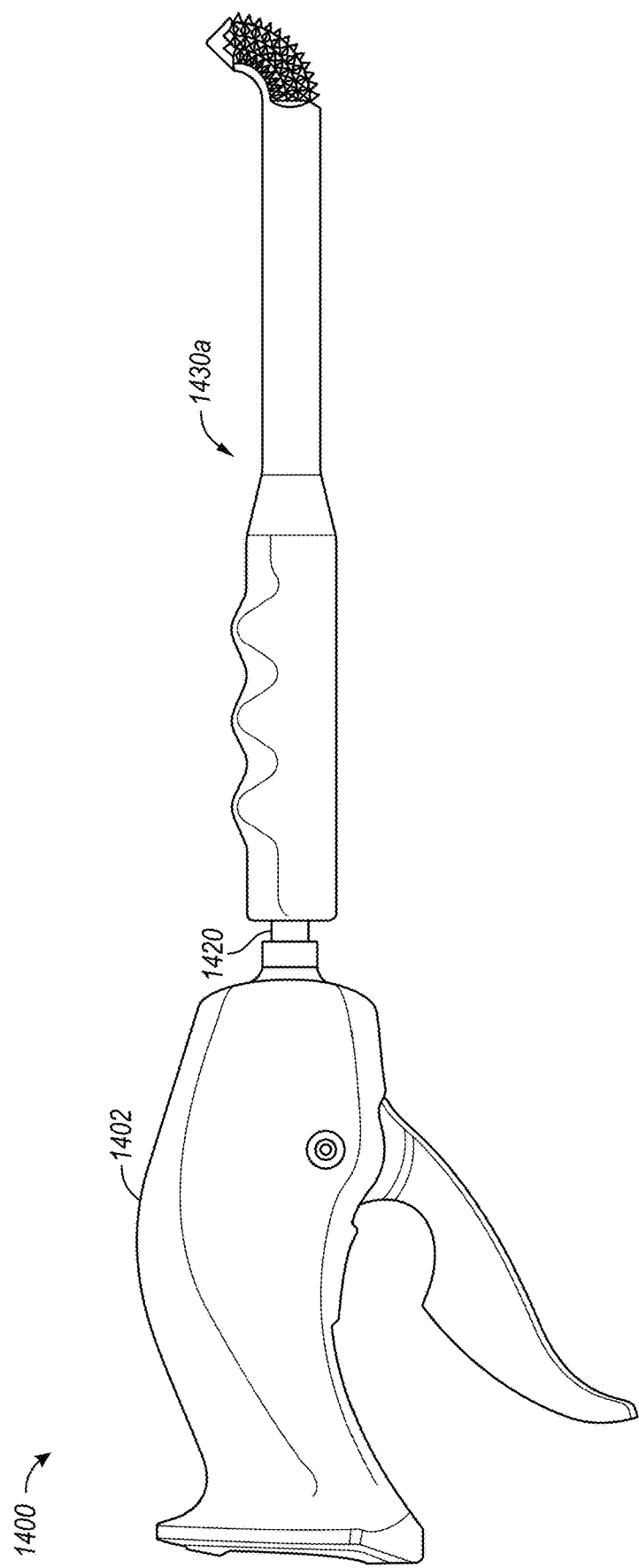
FIG. 30A illustrates a side view of an embodiment of a bone graft delivery system including the tube and rasp of FIG. 29A.
Figure 30B:
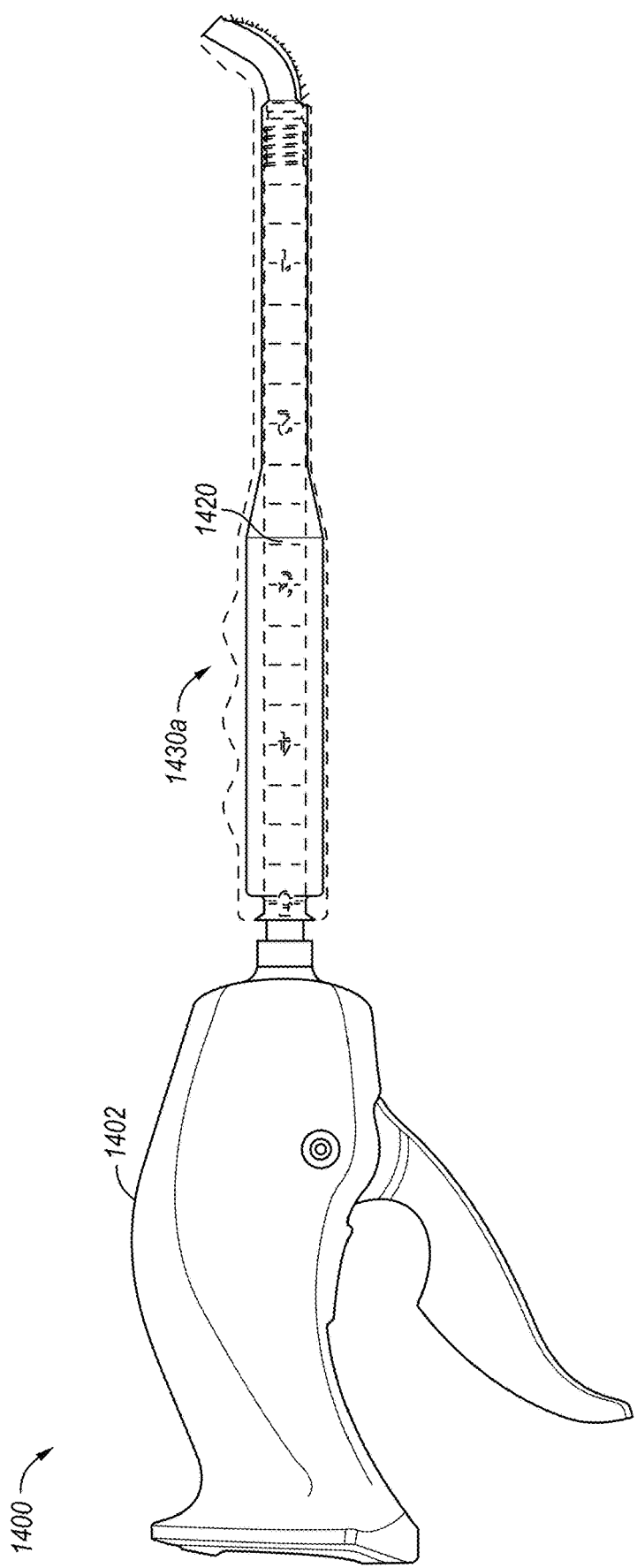
FIG. 30B illustrates a side view of the bone graft delivery system of FIG. 30B in which the rasp is shown as transparent.
Figure 33A:
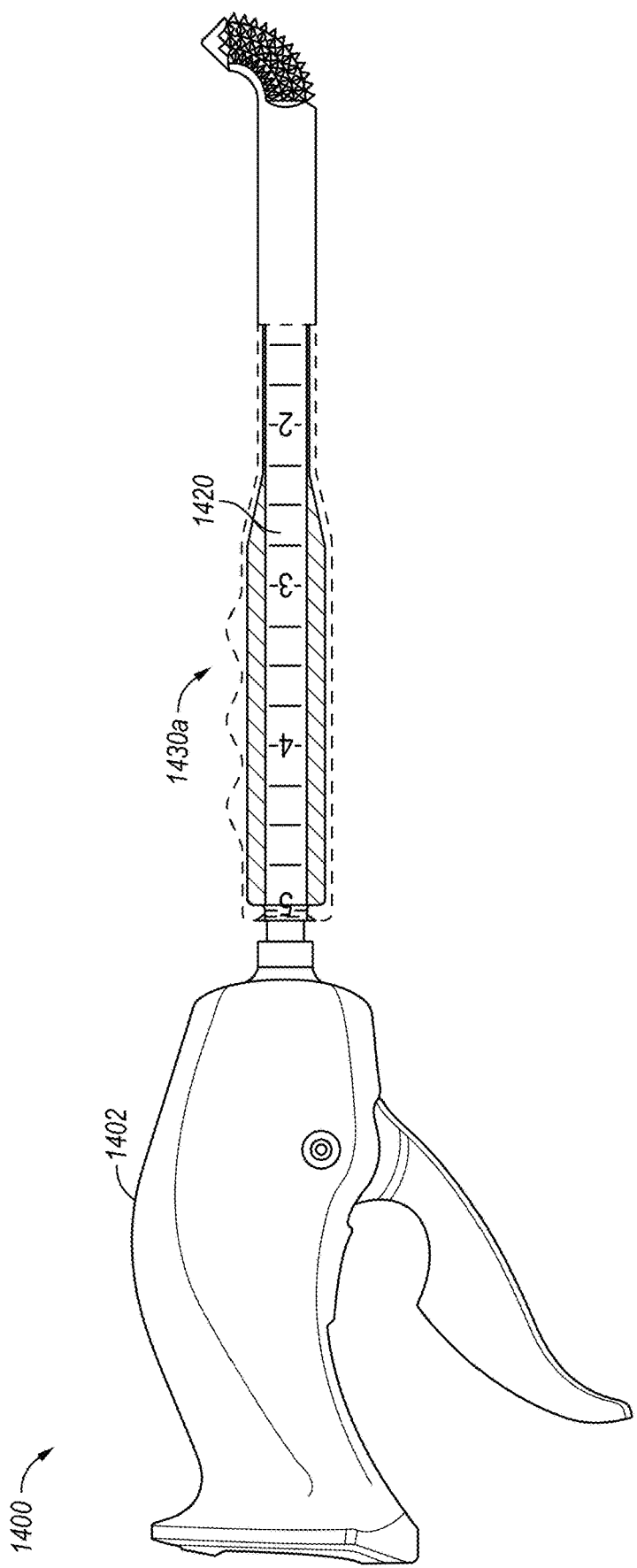
FIG. 33A illustrates a side view of the bone graft delivery system of FIG. 30B in which a portion of the rasp is shown as transparent.
Figure 33B:
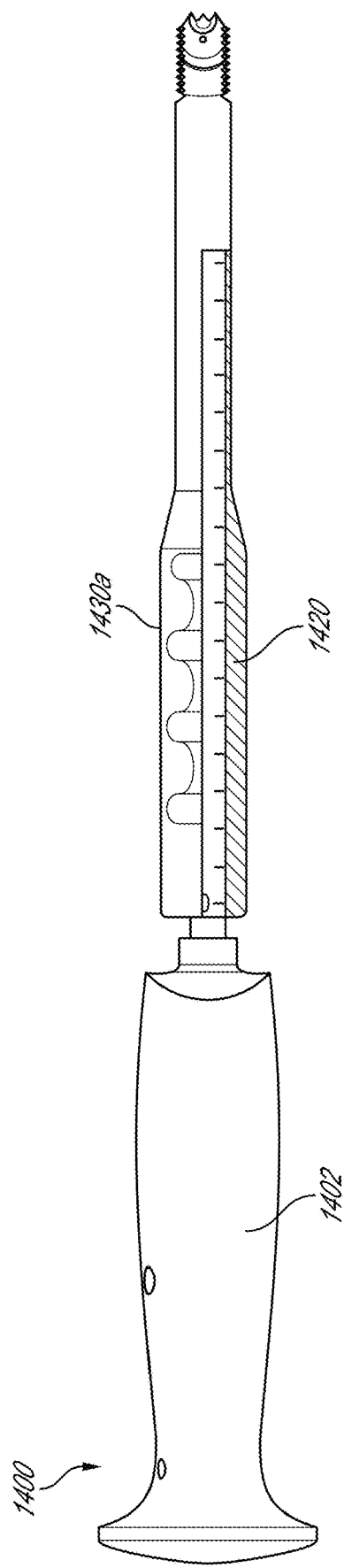
FIG. 33B illustrates a front view of the bone graft delivery system of FIG. 30B in which a portion of the rasp is removed to show internal features.

FIGS. 30A-B and 33A-B depict a bone graft delivery system including a bone graft delivery device 1400 and the rasp 1430. FIGS. 30A and 30B depict a side view and a partial cross-sectional view, respectively, of the bone graft delivery device 1400 and the rasp 1430a. FIG. 33A depicts a side view of the rasp 1430a in use with the bone graft delivery device 1400 showing a portion of the rasp 1430a as transparent using dashed lines. FIG. 33B depicts a front view of the rasp 1430a in use with the bone graft delivery device 1400 in which a section of the 1430a has been removed to show internal features of the rasp 1430a. The bone graft delivery device 1400 can include any of the same or similar features as the bone graft delivery device 100.

In certain embodiments, the rasp 1430a can be coupled to or positioned over a portion of the bone graft delivery device 1400 to allow for the flow of bone graft material from the delivery device 1400 through the rasp 1430a. In certain embodiments, the rasp 1430 can be coupled to the bone graft delivery device 1400 by threads, grooves, bumps, nubs, snap fit, or any other suitable coupling mechanism. In other embodiments, the rasp 1430a may only about the delivery device 1400 without being secured to the delivery device 1400. In some embodiments, the handle portion 1433 or lumen 1446 can be configured to couple to the bone graft delivery device 1400.

In certain embodiments, the delivery device 1400 can include a handle 1402 and the tube 1420. The handle 1402 can include any of the same or similar features or functions as the handle 102. As described herein, in certain embodiments, the rasp 1430a can be configured to couple to the tube 1420. In some embodiments, the rasp 1430a can be coupled to the tube 1420 by one or more threads, grooves, bumps, nubs, snap fit, or any other suitable coupling mechanism. In some embodiments, the rasp 1430a can be configured to couple to the handle 1402. In some embodiments, the rasp 1430a can be coupled to the handle 1402 by threads, grooves, bumps, nubs, snap fit, or any other suitable coupling mechanism. In some embodiments, the handle portion 1433 or lumen 1446 can be configured to couple to the bone graft delivery device 1402.

In some embodiments, the tube 1420 may be configured to rotate freely within the lumen 1446. In other words, in some embodiments, the rasp 1430a may be configured to rotate freely about the tube 1420 and/or relative to the delivery device 1400. Rotation of the rasp 1430a can allow a user to grasp the handle section 1433 from different directions or angles. Rotation of the rasp 1430a can allow the user to choose any angle to insert the graft delivery tube 1440 into the lumen 1446 to deliver graft while rasping bone. In certain embodiments, the rasp 1430a can be configured to engage or secure to the tube 1420 to prevent rotation of the tube within the rasp 1430a, which can provide increased stability and control.

The lumen 1446 and/or the handle 1433 can have a variety of different diameters and/or lengths to accommodate different graft delivery tubes and/or graft delivery systems.

FIGS. 53A and 53B illustrate perspective views of an embodiment of a rasp, tip, or applicator 1430b. FIG. 53C illustrates a side view of the rasp 1430b. FIG. 53D illustrates a cross-sectional view of the rasp 1430b. In certain embodiments, the rasp 1430b can include any of the same or similar functions and features as the rasp 1430a, the distal tip 130, the tip 1030a, the tip 1030b, and/or applicators 850a, 850b.

In some embodiments, at least one side or area of the rasp 1430b includes a rasping surface 1440b configured to serve as a rasp for scraping bone. The rasping surface 1440b can include a series of jagged edges or other suitable surface features. The rasping surface 1440b can have a variety of teeth patterns, sizes, diameters, and/or lengths to allow for rasping of different orthopedic sites including, but not limited to, the transverse process of the spine, facets, SI joint, disc space, tarsals, metatarsals, femur, humeral head, tibial plateau, hip and an array of other locations. In some embodiments, the surface features of the rasping surface 1440b can be patterned (for example, staggered relative to one another), positioned, sized, shaped, and/or otherwise configured to facilitate rasping an entire surface of a bone. In some embodiments, the surface features of the rasping surface 1440b can be patterned (for example, staggered relative to one another), positioned, sized, shaped, and/or otherwise configured to facilitate self-cleaning of the rasping tip. In some embodiments, the surface features of the rasping surface 1440b can be patterned (for example, staggered relative to one another), positioned, sized, shaped, and/or otherwise configured to prevent or restrict tissue from binding to the surface features of the rasping surface 1440b or other portions of the rasp 1430b. In some embodiments, the teeth are staggered when neighboring rows of teeth are offset from one another. Staggering of the teeth can allow the rasp 1430b to contact all or substantially all of the surface of a bone during a rasping procedure. Adversely, in some embodiments, if the teeth are in rows and not staggered some of the cortical bone surface of the bone may not be scraped or rasped to expose growth factors and cells.

As shown in FIGS. 53A-D, the edges of the surface features of the rasping surface 1440b may be triangular in shape. In some embodiments, the edges may be flat. In some embodiments, the jagged edges may form a plurality of flat surfaces parallel with each other all within the same plane. In some embodiments, the rasping surface 1440b can include a roughened surface extending around an outer surface of the tip. In some embodiments, the rasping surface 1440b can include a surface texturing configured to act as an abrasive to roughen the bone during a rasping procedure. The surface texturing can be sprayed on, chemically etched, 3D printed, acid etched, bead blasted or created using any other suitable texturing process. In some embodiments the rasping surface 1440b may be smooth, such as a polished surgical stainless steel surface, for example, to prevent the hang up of soft tissues and muscles on the surface 1440b while passing the rasp 1430b to an orthopedic site for a rasping procedure. In some embodiments, the rasping surface 1440b may be positioned on a portion of the curved section 1434 and/or a portion of the distal section 1436. In some embodiments, as shown in FIGS. 53A-D, the rasping surface 1440b can be a curved surface extending along a bottom portion of the rasp 1430b. In some embodiments, the rasping surface 1440b can extend over the entirety of the bottom portion of the curved section 1434. In other embodiments, the rasping surface 1440b can extend over only a portion of the bottom portion of the curved section 1434, such as for example, 70%, 80%, 90%, or any suitable percentage of the bottom portion of the curved section 1434. In some embodiments, the rasping surface 1440*b* can be positioned at least partially on a side surface of the curved section 1434. The curvature of the rasping surface 1440*b* can prevent muscle or tissue from catching onto the rasp 1430*b* when the rasp 1430*b* passes through the tissue to reach a bone area. The rasp 1430*b* can be used to decorticate bone in the spine or other regions where orthopedic fusion is needed. The curvature of the rasping surface 1440*b* can also facilitate rasping of both a facet and transverse process simultaneously by facilitating contact of the rasping surface with both the facet and transverse process simultaneously. In some embodiments, the curvature of the rasping surface 1440*b* can allow a user to move the rasping surface 1440*b* from one anatomical area to another, for example from a facet to a transverse process or from a transverse process to a facet, without catching the rasping surface 1440*b* on muscle or tissue.

In some embodiments, the rasp 1430*b* can include an expandable exoskeleton or be used together with an apparatus to create a cavity or pocket for bone graft to fill after the rasp is inserted to a desired location. An example of such an apparatus is described with respect to FIGS. 68A-D. Such a cavity can prevent or reduce flow of bone graft from the desired location due to contraction of muscle. In some embodiments, the expandable exoskeleton or apparatus can be deployed or retracted manually, mechanically, electrically, or by any other suitable deployment method. The exoskeleton can move medial, lateral, cephalad, caudad, up, down, or any other direction that may create a pocket for bone graft to pool. A leading edge of the exoskeleton may be blunt or sharp. In some embodiments, a sharp leading edge may be used to dissect muscle with increased efficacy. In some embodiments, the exoskeleton may be part of the rasp 1430*b*, for example as a single piece, or may be removable in one piece or multiple pieces, for example, to assist with cleaning post-surgery. In some embodiments, the exoskeleton may not be expandable, but may slide off of or deploy off of the rasp 1430*b*. In some embodiments, delivering the bone graft into a cavity or pocket within the muscle or tissue can allow the bone graft to maintain its integrity and cohesiveness. In some embodiments, delivering the bone graft into the cavity or pocket can prevent the bone graft from separating. Separation of the bone graft can increase the risk of a non-union fusion.

The rasp may be operated manually or by mechanical, battery powered, electric, pneumatic, or any other means of force to allow for decortication of the area to receive the bone graft material.

In some embodiments, at least some of the one or more openings 1438 for delivering bone graft material are located on a side or portion of the rasp 1430*b* that does not include a rasping surface. In some embodiments, at least some of the one or more openings 1438 are located on a side or portion that does include a rasping surface.

As described above with respect to FIGS. 27A-33B, in some embodiments, the distal section 1436 is pointed, bulleted, and/or sharp to dissect or split muscle and tissue as it is advanced to the surgical location. The overall shape of the rasp 1430*b*, which includes an elongated straight portion defined by the handle section 1433 and the connection section 1432, with the smaller angled section and distal section 1436 can facilitate dissection or splitting of muscle and tissue by providing additional leverage for a user to exert force on the muscle and tissue. Alternatively, the distal section 1436 can be blunt to allow for displacement of muscle without risk of cutting of nerves or other tissue.

In some embodiments, the curved section 1434 can be configured to facilitate a projection of graft and access to an opposite transverse process from a first transverse process without requiring an additional incision. For example, in some embodiments, the rasp 1430*b* can be used to rasp a transverse process of an inferior vertebral body and a transverse process from an adjacent superior vertebral body (for example the L4 and L5 vertebrae) using the same incision. In some embodiments, the rasp 1430*b* can be used to rasp a transverse process of an inferior vertebral body and a transverse process from an adjacent superior vertebral body using the same incision without removal of the rasp 1430*b* from the incision. In some embodiments, a radius of curvature of the curved section 1434 can facilitate the flow of graft through the rasp 1430*b*. Without an appropriate radius of curvature graft may bind in the transition between the straight section of the lumen 1446*b* proximal to the curved section 1434 and the curved section 1434. The binding of the graft may prevent or restrict the flow of the bound graft out of the rasp 1430*b*. In some embodiments, the radius of curvature can facilitate dissection of adjacent transverse processes with minimal repositioning of the rasp 1430*b* and/or within the same incision. For example, a surgeon can use the distal section 1436 to rasp a first transverse process and rotate or move the distal section 1436 while the distal section 1436 is positioned within the body to rasp a second transverse process.

In some embodiments, one or more of the internal diameter of the curved section 1434, the radius of curvature of the curved section 1434, and a curve angle α of the curved section 1434, as shown in FIG. 53D, can be dimensioned to facilitate the advancement of the bone graft through the curved section 1434. In some embodiments, the curve angle α can represent an angle between a longitudinal axis of the lumen 1446*b* at a proximal end of the curved section 1434 and the longitudinal axis of the lumen 1446*b* at the distal end of the curved section 1434. In some embodiments, the internal diameter of the curved section 1434 can be between 2.5 mm and 12 mm. In some embodiments, the radius of curvature of the curved section 1434 can be between 3 mm and 30 mm, between 5 mm and 24 mm, between 10 mm and 15 mm, 10 mm, about 10 mm, 11 mm, about 11 mm, 12 mm, about 12 mm, 13 mm, about 13 mm, 14 mm, about 14 mm, 15 mm, about 15 mm, or any other suitable radius or range. In some embodiments, the curve angle α of the curved section 1434 can be between 0° and 90°. In some embodiments, the curve angle α is preferably between 45° and 70°.

As shown in FIG. 53D, the rasp 1430*b* can include a lumen 1446*b*. The lumen 1446*b* can be in fluid communication with the one or more openings 1438 to allow delivery of bone graft therethrough. The lumen 1446*b* can extend between an opening 1439 and the opening 1438. In some embodiments, bone graft can be delivered into the lumen 1446*b* through the opening 1439 and then exit through the opening 1438. In certain embodiments, the opening 1439 can be positioned at a proximal end 1441 of the rasp 1430*b*. In some embodiments, a pusher, plunger, or other means may be used to deliver graft through the lumen 1446*b*. In some embodiments, the pusher can be straight or generally straight. In other embodiments, the pusher can be curved or flexible so that the pusher can curve within the rasp 1430*b*, for example, within the angled section 1434.

In certain embodiments, the lumen 1446*b* can be dimensioned, shaped, or otherwise configured to receive a tube, such as tube 120 or tube 1420. In some embodiments, when the tube is positioned within the lumen 1446b, bone graft material can flow through the tube and out of the opening 1438.

In some embodiments, the rasp 1430b can be releasably secured to the tube when the rasp 1430b is positioned over the tube. In some embodiments, the rasp 1430b can be securely coupled to the tube by threads, grooves, bumps, nubs, snap fit, or any other suitable coupling mechanism. For example, in the illustrated embodiments, the rasp 1430b includes threads 1437b. The threads 1437b can couple to complementary threads of a tube, such as, for example, threads 125b of the tube 120 as shown in FIG. 14. In some embodiments, securely coupling a tube, such as tube 120 or 1420 with the rasp 1430b can prevent the tube from being pushed out of the lumen 1446b due to back pressure created from the graft when the graft exits the tube. In some embodiments, back pressure can prevent the graft from flowing and potentially bind the graft within the tube. A secure coupling between a tube, such as tube 120 or 1420, and the rasp 1430b can allow a user to exert greater amounts of force to expel bone graft from the tube without the risk of the tube moving within the lumen 1446b or binding of the graft. In other embodiments, the rasp 1430b may receive the tube 1420 without being secured to the tube 1420. Highly flowable bone graft materials, such as DBM putty, may require relatively small amounts of force for extrusion such that extrusion may be possible when without a secure coupling between the tube and the rasp. These types of materials flow well and pose a low risk to binding in the tube or rasp.

As described above with respect to rasp 1430a, in some embodiments, the rasp 1430b can be integrally formed with or coupled, removably or permanently, to a bone graft delivery device, such as bone graft delivery device 100 for delivery of bone graft material to a desired location. In some embodiments, a funnel for delivery of bone graft to the lumen of the rasp 1430b can be integrally formed with or coupled, removably or permanently, to the proximal end 1441 and/or handle section 1443 of the rasp 1430b. In some embodiments, a lumen of the funnel can extend into the lumen 1446b. Bone graft can be loaded into the funnel, either before or after the funnel is coupled to the rasp 1430b. Bone graft can be extruded from the lumen of the funnel through the lumen 1446b of the rasp 1430b, and out of the rasp 1430b, for example using a pusher. In some embodiments, the funnel can be formed of a plurality of separate pieces. In other embodiments, the funnel can be monolithically formed.

FIGS. 54A and 54B illustrate perspective views of an embodiment of a rasp, tip, or applicator 1430c. FIG. 54C illustrates a side view of the rasp 1430c. FIG. 54D illustrates a cross-sectional view of the rasp 1430c. In certain embodiments, the rasp 1430c can include any of the same or similar functions and features as the rasp 1430a, the rasp 1430b, the distal tip 130, the tip 1030a, the tip 1030b, and/or applicators 850a, 850b.

In some embodiments, at least one side or area of the rasp 1430c includes a rasping surface 1440c configured to serve as a rasp for scraping bone. The rasping surface 1440c can include a series of jagged edges or other suitable surface features. The rasping surface 1440c can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In some embodiments, the surface features of the rasping surface 1440c can be patterned (for example, staggered relative to one another), positioned, sized, shaped, and/or otherwise configured to facilitate rasping an entire surface of a bone. In some embodiments, the surface features of the rasping surface 1440c can be patterned (for example, staggered relative to one another), positioned, sized, shaped, and/or otherwise configured to facilitate self-cleaning of the rasping tip. In some embodiments, the surface features of the rasping surface 1440c can be patterned (for example, staggered relative to one another), positioned, sized, shaped, and/or otherwise configured to prevent or restrict tissue from binding to the surface features of the rasping surface 1440c or other portions of the rasp 1430c. In some embodiments, the teeth are staggered when neighboring rows of teeth are offset from one another. Staggering of the teeth can allow the rasp 1430c to contact all or substantially all of the surface of a bone during a rasping procedure.

As shown in FIGS. 54A-D, the edges of the surface features of the rasping surface 1440c may be triangular in shape. In some embodiments, the edges may be flat. In some embodiments, the jagged edges may form a plurality of flat surfaces parallel with each other all within the same plane. In some embodiments, the rasping surface 1440c can include a roughened surface extending around an outer surface of the tip. In some embodiments, the rasping surface 1440c can include a surface texturing configured to act as an abrasive to roughen the bone during a rasping procedure. The surface texturing can be sprayed on, chemically etched, 3D printed, bead blasted or created using any other suitable texturing process. In some embodiments, the rasping surface 1440c may be positioned on a portion of the curved section 1434 and/or a portion of the distal section 1436. In some embodiments, as shown in FIGS. 54-D, the rasping surface 1440c can be a curved surface extending along a bottom portion of the rasp 1430c. The curvature of the rasping surface 1440c can prevent muscle or tissue from catching onto the rasp 1430c when the rasp 1430c passes through the tissue to reach a bone area. The rasp 1430c can be used to decorticate bone in the spine or other regions where orthopedic fusion is needed. The curvature of the rasping surface 1440c can also facilitate rasping of both a facet and transverse process simultaneously by facilitating contact of the rasping surface with both the facet and transverse process simultaneously. In some embodiments, the curvature of the rasping surface 1440c can allow a user to move the rasping surface 1440c from one anatomical area to another, for example from a facet to a transverse process or from a transverse process to a facet, without catching the rasping surface 1440c on muscle or tissue In some embodiments, the rasp 1430c can include an expandable exoskeleton or be used together with an apparatus to create a cavity or pocket for bone graft to fill after the rasp is inserted to a desired location. An example of such an apparatus is described with respect to FIGS. 68A-D. Such a cavity can prevent or reduce flow of bone graft from the desired location due to contraction of muscle. In some embodiments, the expandable exoskeleton or apparatus can be deployed or retracted manually, mechanically, electrically, or by any other suitable deployment process. The exoskeleton can move medial, lateral, cephalad, caudad, up, down, or any other direction that may create a pocket for bone graft to pool. A leading edge of the exoskeleton may be blunt or sharp. In some embodiments, a sharp leading edge may be used to dissect muscle with increased efficacy. In some embodiments, the exoskeleton may be part of the rasp 1430c, for example as a single piece, or may be removable in one piece or multiple pieces, for example, to assist with cleaning post-surgery. In some embodiments, the exoskeleton may not be expandable, but may slide off of or deploy off of the rasp 1430c. In some embodiments, delivering the bone graft into a cavity or pocket within the muscle or tissue can allow the bone graft to maintain its integrity and cohesiveness. In some embodiments, delivering the bone graft into the cavity or pocket can prevent the bone graft from separating. Separation of the bone graft can increase the risk of a non-union fusion.

FIG. 54E depicts illustrates an enlarged cross-sectional view showing a portion of the rasp 1430c including the rasping surface 1440c, the curved section 1434, and the distal section 1436. As shown in FIG. 54E, in some embodiments, the rasping surface 1440c can be removable. In some embodiments, the rasping surface 1440c can be replaceable with another rasping surface 1440c or with a rasping surface having an alternative design. In some embodiments, the rasping surface 1440c can be disposable. As shown in FIG. 54E, the rasping surface 1440c can part of a removable rasping cover or piece 1460c. A rasping surface can become dull over time or may become contaminated. Replacement of a rasping surface, such as rasping surface 1440c allows for a sharp and clean surface 1440c to be used for each patient with the same rasp 1430c. In some embodiments, a rasping surface 1440c can be replaced with a rasping surface 1440c having teeth with different lengths and/or geometries to rasp different bone anatomies.

In some embodiments, the rasp 1430c can include a main body 1431c and the rasping cover 1460c. In some embodiments, as shown in FIGS. 54A-E, the main body 1431c can include the handle section 1433, the connection section 1432, the angled section 1434, and distal section 1436. In certain embodiments, one or more of the handle section 1433, connection section 1432, angled section 1434, and distal section 1436 can be integrally formed with one another. In other embodiments, one or more of the handle section 1433, connection section 1432, angled section 1434, and distal section 1436 can be separate components that may be coupled, removably or permanently, to form the main body 1431c.

In certain embodiments, the rasping cover 1460c can be coupled to the main body 1431c. In some embodiments, the rasping cover 1460c can be configured to couple to the main body 1431c so as to be positioned against or cover an exterior surface 1462c of the rasp 1440c. In some embodiments, the surface 1462c is at least partially formed by an exterior surface of the curved section 1434. In other embodiments, the surface 1462c is at least partially formed by an exterior surface of the connection section 1432.

In some embodiments, the rasping cover 1460c can be coupled to the main body 1431c by one or more fasteners 1464c. For example, as shown in FIG. 54E, the rasping cover 1460c is coupled to the main body 1431c by a screw 1464c. In other embodiments, the cover 1460c can be anchored to the main body 1431c by a plurality of screws and/or by one or more clips, snaps, and/or adhesives. In some embodiments, the screw 1464c can require a specified torque applied using a driver. In other embodiments, the screw 1464c can be applied by hand or other driver without torque. In some embodiments, the cover 1460c can be co-anchored to prevent migration, rotation, and/or other movement. In some embodiments, when the surface features of the rasping surface 1440c are teeth, the teeth can slide into temporary anchor holes until the cover 1460c is fastened to the main body 1431c by the screw 1464c. As shown in FIG. 54J, in some embodiments, the teeth 1440c can be staggered. For example, the pointed ends of the teeth in neighboring rows of teeth 1449a and 1449b are offset from one another.

In some embodiments, the pointed ends of the teeth 1440c in row 1449a can be offset from the pointed ends of the teeth 1440c in the row 1449b such that the pointed ends of the teeth 1440c in the row 1449a are horizontally between the pointed ends of the teeth 1440c in the row 1449b. Staggering of the teeth can allow the rasp 1430c to contact all or substantially all of the surface of a bone during a rasping procedure.

FIG. 54F-G illustrate enlarged exploded views of a section of the rasp 1430c showing the curved section 1434 and distal section 1436 of the main body, the rasping cover 1460c, and the screw 1464c. FIG. 54H illustrates a perspective view of the cover 1460c. FIG. 54I illustrates a top view of the cover 1460c. FIG. 54J illustrates a bottom view of the cover 1460c. FIG. 54K illustrates a first side view of the cover 1460c. FIG. 54L illustrates a second side view of the cover 1460c. FIG. 54M illustrates a front view of the cover 1460c. FIG. 54N illustrates a rear view of the cover 1460c.

In some embodiments, the cover 1460c can include a surface 1466c configured to be positioned against and/or cover the surface 1462c of the main body 1431c when coupled thereto. In some embodiments, the cover 1460c can include a channel 1468c configured to receive the screw 1464c. In some embodiments, the main body 1431c can include a threaded receptacle 1470c configured to receive the screw 1464c. In some embodiments, the channel 1468c and the receptacle 1470c can be configured to align when the surface 1466c of the cover 1460c is positioned against the surface 1462c of the main body 1431c. In some embodiments, the screw 1464c can include a conical head to allow the cover 1460c to align with the main body 1431c. The conical head can align with the body 1431c to prevent cross threading of the screw.

In some embodiments, the cover 1460c can include one or more protrusions or prongs 1472c configured to be received in one or more receptacles 1474c of the main body 1431c. As shown in the illustrated embodiment, the cover 1460c includes a pair of prongs 1472c configured to be received in a pair of receptacles 1474c of the main body 1431c. In some embodiments, the prongs 1472c and receptacles 1474c can align the cover 1460c within the main body 1431c. In some embodiments, the prongs 1472c and receptacles 1474c, in combination with the screw 1464c, can couple the cover 1460c and main body 1431c, for example, by preventing movement of a distal end of the cover 1460c relative to the main body 1431c when the screw 1464c fastens the cover 1460c to the main body 1431c. Engagement of the prongs 1472c with the receptacles 1474c can prevent rotation and posterior gliding movement once the screw 1464c engages the cover 1460c to the main body 1431c. In some embodiments, the cover 1460c can include one or more keels, barbs, teeth, spikes, or any other suitable engagement feature in addition to or instead of the prongs 1472c.

In some embodiments, the rasping cover 1460c can be replaceable with another rasping cover 1460c or with a rasping cover having an alternative design. In some embodiments, the rasping cover 1460c can be disposable.

The rasp may be operated manually or by mechanical, battery powered, electric, pneumatic, or any other means of force to allow for decortication of the area to receive the bone graft material.

In some embodiments, at least some of the one or more openings 1438 for delivering bone graft material are located on a side or portion of the rasp 1430c that does not include a rasping surface. In some embodiments, at least some of the one or more openings 1438 are located on a side or portion that does include a rasping surface. As shown in FIGS.

54A-N, the opening 1438 is positioned on the main body 1431c at a portion uncovered by the cover 1460c.

As described above with respect to FIGS. 27A-33B, in some embodiments, the distal section 1436 is pointed, bulleted, and/or sharp to dissect or split muscle and tissue as it is advanced to the surgical location. The overall shape of the rasp 1430c, which includes an elongated straight portion defined by the handle section 1433 and the connection section 1432, with the smaller angled section and distal section 1436 can facilitate dissection or splitting of muscle and tissue by providing additional leverage for a user to exert force on the muscle and tissue. Alternatively, the distal section 1436 can be blunt to allow for displacement of muscle without risk of cutting of nerves or other tissue.

In some embodiments, the curved section 1434 can be configured to facilitate a projection of graft and access to an opposite transverse process from a first transverse process (for example, adjacent transverse processes of adjacent superior and inferior vertebral bodies) without requiring an additional incision. In some embodiments, a radius of curvature of the curved section 1434 can facilitate the flow of graft through the rasp 1430c. Without an appropriate radius of curvature graft may bind in the transition between the straight section of the lumen 1446c proximal to the curved section 1434 and the curved section 1434. The binding of the graft may prevent or restrict the flow of the bound graft out of the rasp 1430c. In some embodiments, the radius of curvature can facilitate dissection of adjacent transverse processes with minimal repositioning of the rasp 1430c and/or within the same incision. For example, a surgeon can use the distal section 1436 to rasp a first transverse process and rotate or move the distal section 1436 while the distal section 1436 is positioned within the body to rasp a second transverse process.

In some embodiments, one or more of the internal diameter of the curved section 1434, the radius of curvature of the curved section 1434, and a curve angle of the curved section 1434 can be dimensioned to facilitate the advancement of the bone graft through the curved section 1434. In some embodiments, the internal diameter of the curved section 1434 can be between 2.5 mm to 12 mm. In some embodiments, the radius of curvature of the curved section 1434 can be between 5 mm to 24 mm. In some embodiments, the curve angle of the curved section 1434 can be between 0° and 90°. In some embodiments, the curve angle is preferably between 45° and 70°.

FIGS. 54O and 54P depict a perspective view and a side view, respectively, of the rasp 1430c positioned with the rasping surface 1440c placed against a first transverse process.

As shown in FIG. 54D, the rasp 1430c can include a lumen 1446c. The lumen 1446c can be in fluid communication with the one or more openings 1438 to allow delivery of bone graft therethrough. The lumen 1446c can extend between an opening 1439 and the opening 1438. In some embodiments, bone graft can be delivered into the lumen 1446c through the opening 1439 and then exit through the opening 1438. In certain embodiments, the opening 1439 can be positioned at a proximal end 1441 of the rasp 1430c. In some embodiments, a pusher, plunger, or other means may be used to deliver graft through the lumen 1446c. In some embodiments, the pusher can be straight or generally straight. In other embodiments, the pusher can be curved or flexible so that the pusher can curve within the rasp 1430c, for example, within the angled section 1434. In some embodiments, at least a portion of the pusher can be formed of a flexible material, such as cable, tubing, wire, silicone, rubber, any other flexible material sufficient to traverse through the curve. In some embodiments, at least a portion of the pusher can be formed of interlocking shapes that allow for flexing.

In certain embodiments, the lumen 1446c can be dimensioned, shaped, or otherwise configured to receive a tube, such as tube 120 or tube 1420. In some embodiments, when the tube is positioned within the lumen 1446c, bone graft material can flow through the tube and out of the opening 1438.

In some embodiments, the rasp 1430c can be releasably secured to the tube when the rasp 1430c is positioned over the tube. In some embodiments, the rasp 1430c can be securely coupled to the tube by threads, grooves, bumps, nubs, snap fit, or any other suitable coupling mechanism. For example, in the illustrated embodiments, the rasp 1430c includes threads 1437c. The threads 1437c can couple to complementary threads of a tube, such as, for example, threads 125b of the tube 120 as shown in FIG. 14. In some embodiments, securely coupling a tube, such as tube 120 or 1420 with the rasp 1430c can prevent the tube from being pushed out of the lumen 1446c due to back pressure created from the graft when the graft exits the tube. In some embodiments, back pressure can prevent the graft from flowing and potentially bind the graft within the tube. A secure coupling between a tube, such as tube 120 or 1420, and the rasp 1430c can allow a user to exert greater amounts of force to expel bone graft from the tube without the risk of the tube moving within the lumen 1446c or binding of the graft. In other embodiments, the rasp 1430c may only about the tube 1420 without being secured to the tube 1420. Highly flowable bone graft materials, such as DBM putty, may require relatively small amounts of force for extrusion such that extrusion may be possible when without a secure coupling between the tube and the rasp.

As described above with respect to rasp 1430a, in some embodiments, the rasp 1430c can be integrally formed with or coupled, removably or permanently, to a bone graft delivery device, such as bone graft delivery device 100 for delivery of bone graft material to a desired location. In some embodiments, a funnel for delivery of bone graft to the lumen of the rasp 1430c can be integrally formed with or coupled, removably or permanently, to the proximal end 1441 and/or handle section 1443 of the rasp 1430c. In some embodiments, a lumen of the funnel can extend into the lumen 1446c. Bone graft can be loaded into the funnel, either before or after the funnel is coupled to the rasp 1430c. Bone graft can be extruded from the lumen of the funnel through the lumen 1446c of the rasp 1430c, and out of the rasp 1430c, for example using a pusher. In some embodiments, the funnel can be formed of a plurality of separate pieces. In other embodiments, the funnel can be monolithically formed.

FIGS. 55A and 55B illustrate perspective views of an embodiment of a rasp, tip, or applicator 1430d. FIG. 55C illustrates a side view of the rasp 1430d. FIG. 55D illustrates a cross-sectional view of the rasp 1430d. In certain embodiments, the rasp 1430d can include any of the same or similar functions and features as the rasp 1430a, the rasp 1430b, the rasp 1430c, the distal tip 130, the tip 1030a, the tip 1030b, and/or applicators 850a, 850b.

In some embodiments, at least one side or area of the rasp 1430d includes a rasping surface 1440d configured to serve as a rasp for scraping bone. The rasping surface 1440d can include a series of jagged edges or other suitable surface features. The rasping surface 1440d can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In some embodiments, the surface features of the rasping surface 1440*d* can be patterned (for example, staggered relative to one another), positioned, sized, shaped, and/or otherwise configured to facilitate rasping an entire surface of a bone. In some embodiments, the surface features of the rasping surface 1440*d* can be patterned (for example, staggered relative to one another), positioned, sized, shaped, and/or otherwise configured to facilitate self-cleaning of the rasping tip. In some embodiments, the surface features of the rasping surface 1440*d* can be patterned (for example, staggered relative to one another), positioned, sized, shaped, and/or otherwise configured to prevent or restrict tissue from binding to the surface features of the rasping surface 1440*d* or other portions of the rasp 1430*d*. In some embodiments, the teeth are staggered when neighboring rows of teeth are offset from one another. Staggering of the teeth can allow the rasp 1430*d* to contact all or substantially all of the surface of a bone during a rasping procedure.

As shown in FIGS. 55A-D, the edges of the surface features of the rasping surface 1440*d* may be triangular in shape. In some embodiments, the edges may be flat. In some embodiments, the jagged edges may form a plurality of flat surfaces parallel with each other all within the same plane. In some embodiments, the rasping surface 1440*d* can include a roughened surface extending around an outer surface of the tip. In some embodiments, the rasping surface 1440*d* can include a surface texturing configured to act as an abrasive to roughen the bone during a rasping procedure. The surface texturing can be sprayed on, chemically etched, 3D printed, bead blasted or created using any other suitable texturing process. In some embodiments, the rasping surface 1440*d* can be positioned at a distal end of the rasp 1430*d*. In some embodiments, as shown in FIGS. 55A-D, the rasping surface 1440*d* can be a curved surface extending along a bottom portion of the rasp 1430*d*. The curvature of the rasping surface 1440*d* can prevent muscle or tissue from catching onto the rasp 1430*d* when the rasp 1430*d* passes through the tissue to reach a bone area. The rasp 1430*d* can be used to decorticate bone in the spine or other regions where orthopedic fusion is needed. The curvature of the rasping surface 1440*d* can also facilitate rasping of both a facet and transverse process simultaneously by facilitating contact of the rasping surface with both the facet and transverse process simultaneously. In some embodiments, the curvature of the rasping surface 1440*d* can allow a user to move the rasping surface 1440*d* from one anatomical area to another, for example from a facet to a transverse process or from a transverse process to a facet, without catching the rasping surface 1440*d* on muscle or tissue In some embodiments, the rasp 1430*d* can include an expandable exoskeleton or be used together with an apparatus to create a cavity or pocket for bone graft to fill after the rasp is inserted to a desired location. An example of such an apparatus is described with respect to FIGS. 68A-D. Such a cavity can prevent or reduce flow of bone graft from the desired location due to contraction of muscle. In some embodiments, the expandable exoskeleton or apparatus can be deployed or retracted manually, mechanically, electrically, or by any other suitable deployment process. The exoskeleton can move medial, lateral, cephalad, caudad, up, down, or any other direction that may create a pocket for bone graft to pool. A leading edge of the exoskeleton may be blunt or sharp. In some embodiments, a sharp leading edge may be used to dissect muscle with increased efficacy. In some embodiments, the exoskeleton may be part of the rasp 1430*d*, for example as a single piece, or may be removable in one piece or multiple pieces, for example, to assist with cleaning post-surgery. In some embodiments, the exoskeleton may not be expandable, but may slide off of or deploy off of the rasp 1430*d*. In some embodiments, delivering the bone graft into a cavity or pocket within the muscle or tissue can allow the bone graft to maintain its integrity and cohesiveness. In some embodiments, delivering the bone graft into the cavity or pocket can prevent the bone graft from separating. Separation of the bone graft can increase the risk of a non-union fusion.

The rasp may be operated manually or by mechanical, battery powered, electric, pneumatic, or any other means of force to allow for decortication of the area to receive the bone graft material.

As shown in FIGS. 55A-D, in some embodiments, one or more openings 1438*d* for delivering bone graft material are located on a side or portion of the rasp 1430*d* that includes the rasping surface 1440*d*. In other embodiments, at least some of the one or more openings 1438*d* are located on a side or portion of the rasp 1430*d* that does not include a rasping surface. As shown in FIGS. 55A-D, in some embodiments, the rasp 1430*d* can include a single opening 1438*d* extending through a bottom surface of the rasp 1430*d*.

As described above with respect to FIGS. 27A-33B, in some embodiments, the distal section 1436 is pointed, bulleted, and/or sharp to dissect or split muscle and tissue as it is advanced to the surgical location. The overall shape of the rasp 1430*d*, which includes an elongated straight portion defined by the handle section 1433 and the connection section 1432 with a distal section 1436 pointing generally transverse or at an angle to the elongated straight portion can facilitate dissection or splitting of muscle and tissue by providing additional leverage for a user to exert force on the muscle and tissue. Alternatively, the distal section 1436 can be blunt to allow for displacement of muscle without risk of cutting of nerves or other tissue.

As shown in FIG. 55D, the rasp 1430*d* can include a lumen 1446*d*. The lumen 1446*d* can be in fluid communication with the one or more openings 1438 to allow delivery of bone graft therethrough. The lumen 1446*d* can extend between an opening 1439 and the opening 1438. In some embodiments, bone graft can be delivered into the lumen 1446*d* through the opening 1439 and then exit through the opening 1438. In certain embodiments, the opening 1439 can be positioned at a proximal end 1441 of the rasp 1430*d*. In some embodiments, a pusher, plunger, or other means may be used to deliver graft through the lumen 1446*d*. In some embodiments, the pusher can be straight or generally straight. In other embodiments, the pusher can be curved or flexible. In some embodiments, the opening 1438*d* can align with the opening 1439, for example, to allow a rigid instrument, such as a straight pusher, to pass from the opening 1439 through the lumen 1446*d* and to the opening 1438*d* without bending.

In certain embodiments, the lumen 1446*d* can be dimensioned, shaped, or otherwise configured to receive a tube, such as tube 120 or tube 1420. In some embodiments, when the tube is positioned within the lumen 1446*d*, bone graft material can flow through the tube and out of the opening 1438.

In some embodiments, the rasp 1430*d* can be releasably secured to the tube when the rasp 1430*d* is positioned over the tube. In some embodiments, the rasp 1430*d* can be securely coupled to the tube by threads, grooves, bumps, nubs, snap fit, or any other suitable coupling mechanism. For example, in the illustrated embodiments, the rasp 1430d includes threads 1437d. The threads 1437d can couple to complementary threads of a tube, such as, for example, threads 125b of the tube 120 as shown in FIG. 14. In some embodiments, securely coupling a tube, such as tube 120 or 1420 with the rasp 1430d can prevent the tube from being pushed out of the lumen 1446d due to back pressure created from the graft when the graft exits the tube. In some embodiments, back pressure can prevent the graft from flowing and potentially bind the graft within the tube. A secure coupling between a tube, such as tube 120 or 1420, and the rasp 1430d can allow a user to exert greater amounts of force to expel bone graft from the tube without the risk of the tube moving within the lumen 1446d or binding of the graft. In other embodiments, the rasp 1430d may only about the tube 1420 without being secured to the tube 1420. Highly flowable bone graft materials, such as DBM putty, may require relatively small amounts of force for extrusion such that extrusion may be possible when without a secure coupling between the tube and the rasp.

As described above with respect to rasp 1430a, in some embodiments, the rasp 1430d can be integrally formed with or coupled, removably or permanently, to a bone graft delivery device, such as bone graft delivery device 100 for delivery of bone graft material to a desired location. In some embodiments, a funnel for delivery of bone graft to the lumen of the rasp 1430d can be integrally formed with or coupled, removably or permanently, to the proximal end 1441 and/or handle section 1443 of the rasp 1430d. In some embodiments, a lumen of the funnel can extend into the lumen 1446d. Bone graft can be loaded into the funnel, either before or after the funnel is coupled to the rasp 1430d. Bone graft can be extruded from the lumen of the funnel through the lumen 1446d of the rasp 1430d, and out of the rasp 1430d, for example using a pusher. In some embodiments, the funnel can be formed of a plurality of separate pieces. In other embodiments, the funnel can be monolithically formed.

FIGS. 56A and 56B illustrate perspective views of an embodiment of a rasp, tip, or applicator 1430e. FIG. 56C illustrates a side view of the rasp 1430e. FIG. 56D illustrates a cross-sectional view of the rasp 1430e. In certain embodiments, the rasp 1430e can include any of the same or similar functions and features as the rasp 1430a, the rasp 1430b, the rasp 1430c, the rasp 1430d, the distal tip 130, the tip 1030a, the tip 1030b, and/or applicators 850a, 850b.

In some embodiments, at least one side or area of the rasp 1430e includes a rasping surface 1440e configured to serve as a rasp for scraping bone. The rasping surface 1440e can include a series of jagged edges or other suitable surface features. The rasping surface 1440e can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In some embodiments, the surface features of the rasping surface 1440e can be patterned (for example, staggered relative to one another), positioned, sized, shaped, and/or otherwise configured to facilitate rasping an entire surface of a bone. In some embodiments, the surface features of the rasping surface 1440e can be patterned (for example, staggered relative to one another), positioned, sized, shaped, and/or otherwise configured to facilitate self-cleaning of the rasping tip. In some embodiments, the surface features of the rasping surface 1440e can be patterned (for example, staggered relative to one another), positioned, sized, shaped, and/or otherwise configured to prevent or restrict tissue from binding to the surface features of the rasping surface 1440e or other portions of the rasp 1430e. In some embodiments, the teeth are staggered when neighboring rows of teeth are offset from one another. Staggering of the teeth can allow the rasp 1430e to contact all or substantially all of the surface of a bone during a rasping procedure.

As shown in FIGS. 56A-D, the edges of the surface features of the rasping surface 1440e may be triangular in shape. In some embodiments, the edges may be flat. In some embodiments, the jagged edges may form a plurality of flat surfaces parallel with each other all within the same plane. In some embodiments, the rasping surface 1440e can include a roughened surface extending around an outer surface of the tip. In some embodiments, the rasping surface 1440e can include a surface texturing configured to act as an abrasive to roughen the bone during a rasping procedure. The surface texturing can be sprayed on, chemically etched, 3D printed, bead blasted or created using any other suitable texturing process. In some embodiments, the rasping surface 1440e can be positioned at a distal end of the rasp 1430e. In some embodiments, as shown in FIGS. 56A-D, the rasping surface 1440e can be a curved surface extending along a bottom portion of the rasp 1430e. The curvature of the rasping surface 1440e can prevent muscle or tissue from catching onto the rasp 1430e when the rasp 1430e passes through the tissue to reach a bone area. The rasp 1430e can be used to decorticate bone in the spine or other regions where orthopedic fusion is needed. The curvature of the rasping surface 1440e can also facilitate rasping of both a facet and transverse process simultaneously by facilitating contact of the rasping surface with both the facet and transverse process simultaneously. In some embodiments, the curvature of the rasping surface 1440e can allow a user to move the rasping surface 1440e from one anatomical area to another, for example from a facet to a transverse process or from a transverse process to a facet, without catching the rasping surface 1440e on muscle or tissue In some embodiments, the rasp 1430e can include an expandable exoskeleton or be used together with an apparatus to create a cavity or pocket for bone graft to fill after the rasp is inserted to a desired location. An example of such an apparatus is described with respect to FIGS. 68A-D. Such a cavity can prevent or reduce flow of bone graft from the desired location due to contraction of muscle. In some embodiments, the expandable exoskeleton or apparatus can be deployed or retracted manually, mechanically, electrically, or by any other suitable deployment process. The exoskeleton can move medial, lateral, cephalad, caudad, up, down, or any other direction that may create a pocket for bone graft to pool. A leading edge of the exoskeleton may be blunt or sharp. In some embodiments, a sharp leading edge may be used to dissect muscle with increased efficacy. In some embodiments, the exoskeleton may be part of the rasp 1430e, for example as a single piece, or may be removable in one piece or multiple pieces, for example, to assist with cleaning post-surgery. In some embodiments, the exoskeleton may not be expandable, but may slide off of or deploy off of the rasp 1430e. In some embodiments, delivering the bone graft into a cavity or pocket within the muscle or tissue can allow the bone graft to maintain its integrity and cohesiveness. In some embodiments, delivering the bone graft into the cavity or pocket can prevent the bone graft from separating. Separation of the bone graft can increase the risk of a non-union fusion.

FIG. 56E depicts illustrates an enlarged cross-sectional view showing a portion of the rasp 1430e including the rasping surface 1440e and the distal section 1436. As shown in FIG. 56E, in some embodiments, the rasping surface 1440e can be removable. In some embodiments, the rasping surface 1440e can be replaceable with another rasping surface 1440e or with a rasping surface having an alternative design. In some embodiments, the rasping surface 1440e can be disposable. As shown in FIG. 56E, the rasping surface 1440e can part of a removable rasping cover or piece 1460e. A rasping surface can become dull over time or may become contaminated. Replacement of a rasping surface, such as rasping surface 1440e allows for a sharp and clean surface 1440e to be used for each patient with the same rasp 1430e. In some embodiments, a rasping surface 1440e can be replaced with a rasping surface 1440e having teeth with different lengths and/or geometries to rasp different bone anatomies.

In some embodiments, the rasp 1430e can include a main body 1431e and the rasping cover 1460e. In some embodiments, as shown in FIGS. 56A-E, the main body 1431e can include the handle section 1433, the connection section 1432, and distal section 1436. In certain embodiments, one or more of the handle section 1433, connection section 1432, and distal section 1436 can be integrally formed with one another. In other embodiments, one or more of the handle section 1433, connection section 1432, and distal section 1436 can be separate components that may be coupled, removably or permanently, to form the main body 1431e.

In certain embodiments, the rasping cover 1460e can be coupled to the main body 1431e. In some embodiments, the rasping cover 1460e can be configured to couple to the main body 1431e so as to be positioned against or cover an exterior surface 1462e of the rasp 1440e.

In some embodiments, the rasping cover 1460e can be coupled to the main body 1431e by one or more fasteners 1464e. For example, as shown in FIG. 56E, the rasping cover 1460e is coupled to the main body 1431e by a screw 1464e. In other embodiments, the cover 1460e can be anchored to the main body 1431e by a plurality of screws and/or by one or more clips, snaps, and/or adhesives. In some embodiments, the screw 1464e can require a specified torque applied using a driver. In other embodiments, the screw 1464e can be applied by hand or other driver without torque. In some embodiments, the cover 1460e can be co-anchored to prevent migration, rotation, and/or other movement. In some embodiments, when the surface features of the rasping surface 1440e are teeth, the teeth can slide into temporary anchor holes until the cover 1460e is fastened to the main body 1431e by the screw 1464e.

FIG. 56F-G illustrate enlarged exploded views of a section of the rasp 1430e showing the distal section 1436 of the main body, the rasping cover 1460e, and the screw 1464e. FIG. 56H illustrates a perspective view of the cover 1460e. FIG. 56I illustrates a top view of the cover 1460e. FIG. 56J illustrates a bottom view of the cover 1460e. FIG. 56K illustrates a first side view of the cover 1460e. FIG. 56L illustrates a second side view of the cover 1460e. FIG. 56M illustrates a front view of the cover 1460e. FIG. 56N illustrates a rear view of the cover 1460e.

In some embodiments, the cover 1460e can include a surface 1466e configured to be positioned against and/or cover the surface 1462e of the main body 1431e when coupled thereto. In some embodiments, the cover 1460e can include a channel 1468e configured to receive the screw 1464e. In some embodiments, the main body 1431e can include a threaded receptacle 1470e configured to receive the screw 1434e. In some embodiments, the channel 1468e and the receptacle 1470e can be configured to align when the surface 1466e of the cover 1460e is positioned against the surface 1462e of the main body 1431e. In some embodiments, the screw 1464e can include a conical head to allow the cover 1460e to align with the main body 1431e. The conical head can align with the body 1431e to prevent cross threading of the screw.

In some embodiments, the cover 1460e can include one or more protrusions or plugs 1472e configured to be received in one or more receptacles 1474e of the main body 1431e. As shown in the illustrated embodiment, the cover 1460e includes a single plug 1472e configured to be received in a single receptacles 1474e of the main body 1431e. In some embodiments, the plug 1472e and receptacle 1474e can align the cover 1460e within the main body 1431e. In some embodiments, the plug 1472e and receptacles 1474e, in combination with the screw 1434e, can couple the cover 1460e and main body 1431e, for example, by preventing movement of a distal end of the cover 1460e relative to the main body 1431e when the screw 1434e fastens the cover 1460e to the main body 1431e. Engagement of the plug 1472e with the receptacle 1474e can prevent rotation and posterior gliding movement once the screw 1464e engages the cover 1460e to the main body 1431e. In some embodiments, the cover 1460e can include one or more keels, barbs, teeth, spikes, or any other suitable engagement feature in addition to or instead of the one or more plugs 1472e.

In some embodiments, the rasping cover 1460e can be replaceable with another rasping cover 1460e or with a rasping cover having an alternative design. In some embodiments, the rasping cover 1460e can be disposable.

The rasp may be operated manually or by mechanical, battery powered, electric, pneumatic, or any other means of force to allow for decortication of the area to receive the bone graft material.

As shown in FIGS. 56A-N, in some embodiments, the rasp 1430e can include an opening 1438e for delivering bone graft material extending through the cover 1461e. The opening 1438e can align with an opening 1476e in the main body 1431. In some embodiments, the rasp 1431e can include a plurality of openings 1438e and/or 1476e.

As described above with respect to FIGS. 27A-33B, in some embodiments, the distal section 1436 is pointed, bulleted, and/or sharp to dissect or split muscle and tissue as it is advanced to the surgical location. The overall shape of the rasp 1430e, which includes an elongated straight portion defined by the handle section 1433 and the connection section 1432 with a distal section 1436 pointing generally transverse or at an angle to the elongated straight portion can facilitate dissection or splitting of muscle and tissue by providing additional leverage for a user to exert force on the muscle and tissue. Alternatively, the distal section 1436 can be blunt to allow for displacement of muscle without risk of cutting of nerves or other tissue.

As shown in FIG. 56D-E, the rasp 1430e can include a lumen 1446e. The lumen 1446e can be in fluid communication with the one or more openings 1476e and 1438e to allow delivery of bone graft therethrough. The lumen 1446e can extend between an opening 1439 and the opening 1438e. In some embodiments, bone graft can be delivered into the lumen 1446e through the opening 1439 and then exit through the opening 1438e. In certain embodiments, the opening 1439 can be positioned at a proximal end 1441 of the rasp 1430e. In some embodiments, a pusher, plunger, or other means may be used to deliver graft through the lumen 1446e. In some embodiments, the pusher can be straight or generally straight. In other embodiments, the pusher can be curved or flexible. In some embodiments, the opening 1476e and the opening 1438e can align with the opening 1439, for example, to allow a rigid instrument, such as a straight pusher, to pass from the opening 1439 through the lumen 1446e, through the opening 1476e, and to the opening 1438e without bending.

In certain embodiments, the lumen 1446e can be dimensioned, shaped, or otherwise configured to receive a tube, such as tube 120 or tube 1420. In some embodiments, when the tube is positioned within the lumen 1446e, bone graft material can flow through the tube and out of the opening 1438.

In some embodiments, the rasp 1430e can be releasably secured to the tube when the rasp 1430e is positioned over the tube. In some embodiments, the rasp 1430e can be securely coupled to the tube by threads, grooves, bumps, nubs, snap fit, or any other suitable coupling mechanism. For example, in the illustrated embodiments, the rasp 1430e includes threads 1437e. The threads 1437e can couple to complementary threads of a tube, such as, for example, threads 125b of the tube 120 as shown in FIG. 14. In some embodiments, securely coupling a tube, such as tube 120 or 1420 with the rasp 1430e can prevent the tube from being pushed out of the lumen 1446e due to back pressure created from the graft when the graft exits the tube. In some embodiments, back pressure can prevent the graft from flowing and potentially bind the graft within the tube. A secure coupling between a tube, such as tube 120 or 1420, and the rasp 1430e can allow a user to exert greater amounts of force to expel bone graft from the tube without the risk of the tube moving within the lumen 1446e or binding of the graft. In other embodiments, the rasp 1430e may receive the tube 1420 without being secured to the tube 1420. Highly flowable bone graft materials, such as DBM putty, may require relatively small amounts of force for extrusion such that extrusion may be possible when without a secure coupling between the tube and the rasp.

As described above with respect to rasp 1430a, in some embodiments, the rasp 1430e can be integrally formed with or coupled, removably or permanently, to a bone graft delivery device, such as bone graft delivery device 100 for delivery of bone graft material to a desired location. In some embodiments, a bone graft delivery device can be in the form of a funnel. In some embodiments, a funnel for delivery of bone graft to the lumen of the rasp 1430e can be integrally formed with or coupled, removably or permanently, to the proximal end 1441 and/or handle section 1443 of the rasp 1430e. In some embodiments, a lumen of the funnel can extend into the lumen 1446e. Bone graft can be loaded into the funnel, either before or after the funnel is coupled to the rasp 1430e. Bone graft can be extruded from the lumen of the funnel through the lumen 1446e of the rasp 1430e, and out of the rasp 1430e, for example using a pusher. In some embodiments, the funnel can be formed of a plurality of separate pieces. In other embodiments, the funnel can be monolithically formed.

As described above, in some embodiments, a pusher or pushrod can be used to extrude graft through the rasps 1430a-e and/or any tubes positioned within the rasps 1430a-e. For rasps having a straight lumen, such as rasps 1430d and 1430e, in some embodiments, a rasp that is straight or generally straight and/or rigid or generally rigid may be preferable. For rasps having a curved lumen, such as rasps 1430a, 1430b, and 1430c, in some embodiments, a flexible pusher or pusher having a flexible section may be preferable.

FIG. 57A depicts an embodiment of a flexible portion or attachment 1490 of a pusher. The attachment 1490 includes a flexible shaft 1492. The shaft 1492 can be a wire, such as a nitinol wire, a cable, silicone, rubber, interlocking metal pieces that flex, or any other suitable flexible material. The attachment 1490 further includes a ball or head 1494 at a distal end. The head 1494 can be configured to contact bone graft to push the bone graft within a tube or rasp. In some embodiments, the attachment 1490 can be attached to or integrally formed with a pusher or plunger. FIG. 57B depicts the attachment 1490 coupled to a pushrod or plunger 1612a. In some embodiments, the attachment 1490 can be used to push bone graft through curved portions of a rasp or tube, such as the curved section 1434. FIG. 57C depicts the attachment 1490 within the lumen of the rasp 1430c.

FIGS. 58A and 58B depict a perspective view and a cross-section view respectively, of a rasp, tip, or applicator 1430f. In certain embodiments, the rasp 1430f can include any of the same or similar functions and features as the rasp 1430a, the rasp 1430b, the rasp 1430c, the rasp 1430d, rasp 1430e, the distal tip 130, the tip 1030a, the tip 1030b, and/or applicators 850a, 850b.

As shown in FIGS. 58A-B, the rasp 1430f does not include finger grips. Instead the rasp 1430f includes a textured surface 1429 that can be grasped by a user. In some embodiments, the textured surface 1429 can textured by knurling, chemical etching, bead blasting, spray coating, or any other suitable means to create a surface to prevent slippage during a surgical procedure. In other embodiments, the rasp 1430f may not include a textured surface 1429, but may include a smooth outer surface near the proximal end 1441 consistent with adjacent portions of the rasp 1430f.

In some embodiments, the handle section 1433 can include one or more finger grips or other surface features configured to facilitate gripping by a user. In use, a user can grasp the handle or finger grips to manipulate the rasp 1430a to scrape or decorticate bone. In some embodiments, the handle section 1433 and/or finger grips can be formed of the same material as the adjacent portions of the rasp. In other embodiments, the handle section 1433 and/or finger grips can be formed of a different material than adjacent portions of the rasp. For example, in some embodiments, the handle portion 1433 and/or finger grips can be formed of one or more of silicone, rubber, a plastic polymer, a metal, an alloy, and/or any other suitable material. FIG. 28 illustrates an example of the rasp 1430a positioned to decorticate bone in a spinal region. In other embodiments, the rasp 1430a does not include a handle or grip.

As described herein, any of the rasps 1430a-f can be coupled to a bone graft delivery device. In some embodiments, any one of the rasps 1430a-f can be integrally formed with or coupled, removably or permanently to a funnel to receive bone graft therefrom.

FIGS. 59A and 59B depict a perspective view and a cross-sectional view, respectively, of a rasp, tip or applicator 1430g coupled to a funnel 900a. In certain embodiments, the rasp 1430g can include any of the same or similar functions and features as the rasp 1430a, the rasp 1430b, the rasp 1430c, the rasp 1430d, rasp 1430e, the rasp 1430f, the distal tip 130, the tip 1030a, the tip 1030b, and/or applicators 850a, 850b. In certain embodiments, the funnel 900a can include any of the same features or functions as the funnel 900.

As shown in FIG. 59B, the rasp 1430g can include internal threads 1435 configured to couple with external threads 923 of the funnel 900a. The internal threads 1435 can be positioned within a lumen 1446g of the rasp 1430g adjacent the proximal end 1441. In use, bone graft can be delivered through the funnel 900a into the lumen 1446g of the rasp 1430g.

FIGS. 60A and 60B depict a perspective view and a cross-sectional view, respectively, of a rasp 1430*h*. In certain embodiments, the rasp 1430*h* can include any of the same or similar functions and features as the rasp 1430*a*, the rasp 1430*b*, the rasp 1430*c*, the rasp 1430*d*, rasp 1430*e*, the rasp 1430*f*, the rasp 1430*g*, the distal tip 130, the tip 1030*a*, the tip 1030*b*, and/or applicators 850*a*, 850*b*.

As shown in FIGS. 60A and 60B, the rasp 1430*h* is integrally formed with a funnel 900*b*. In certain embodiments, the funnel 900*b* can include any of the same features or functions as the funnel 900 and/or the funnel 900*a*. In use, bone graft can be delivered through the funnel 900*b* into a lumen 1446*h* of the rasp 1430*h*.

FIGS. 61A and 61B depict an embodiment of a funnel 900*c* integrally formed with a tube 120. In certain embodiments, the funnel 900*c* and tube 120 can form a delivery device. In some embodiments, the delivery device can be received within a rasp, such as rasps 1430*a-g*. For example, in some embodiments, the threads 125*b* of the tube 120 of the bone graft delivery device can couple with the threads 1437*b* of the rasp 1430*b*, threads 1437*c* of the rasp 1430*c*, 1437*d* of the rasp 1430*d*, 1437*e* of the rasp 1430*e*, 1437*c* of the rasp 1430*f*, 1437*c* of the rasp 1430*g*, or 1437*c* of the rasp 1430*h*.

In some embodiments, the lumens and or tips of a rasp, such as rasps 1430*a-h* can have a variety of different diameters, for example, to accommodate different graft delivery tubes and/or graft delivery systems. In some embodiments, a diameter of a lumen at a proximal end can be different than a diameter of a lumen at a distal end of the rasp. For example, in some embodiments, if a distal end of the rasp is too large, it can be difficult to pass through tissue in a minimally invasive procedure. It may also destroy muscle and other tissue, and could cause scarring and bleeding. Thus, it may be desirable to have a relatively small lumen at the distal end of the rasp. However, a larger lumen may be desirable at the proximal end of the rasp to facilitate loading of bone graft material or receipt of a bone graft delivery device.

FIG. 62A depicts a cross-sectional view of a rasp 1430*i*. In certain embodiments, the rasp 1430*i* can include any of the same or similar functions and features as the rasp 1430*a*, the rasp 1430*b*, the rasp 1430*c*, the rasp 1430*d*, rasp 1430*e*, the rasp 1430*f*, the rasp 1430*g*, the rasp 1430*h*, the distal tip 130, the tip 1030*a*, the tip 1030*b*, and/or applicators 850*a*, 850*b*. As shown in FIG. 62A, a diameter of a lumen 1446*i* can be generally the same at a proximal section 1425 and at a distal section 1426. In some embodiments, the diameter of the lumen 1446*i* can be 6 mm or about 6 mm at the proximal section 1425 and 6 mm or about 6 mm at the distal section 1426.

FIG. 62B depicts a cross-sectional view of a rasp 1430*j*. In certain embodiments, the rasp 1430*j* can include any of the same or similar functions and features as the rasp 1430*a*, the rasp 1430*b*, the rasp 1430*c*, the rasp 1430*d*, rasp 1430*e*, the rasp 1430*f*, the rasp 1430*g*, the rasp 1430*h*, the rasp 1430*i*, the distal tip 130, the tip 1030*a*, the tip 1030*b*, and/or applicators 850*a*, 850*b*. As shown in FIG. 62B, a diameter of a lumen 1446*j* can be larger at the proximal section 1425 than at the distal section 1426. In some embodiments, the diameter of the lumen 1446*j* can be 8 mm or about 8 mm at the proximal section 1425 and 6 mm or about 6 mm at the distal section 1426.

FIG. 62C depicts a cross-sectional view of a rasp 1430*k*. In certain embodiments, the rasp 1430*j* can include any of the same or similar functions and features as the rasp 1430*a*, the rasp 1430*b*, the rasp 1430*c*, the rasp 1430*d*, rasp 1430*e*, the rasp 1430*f*, the rasp 1430*g*, the rasp 1430*h*, the rasp 1430*i*, the distal tip 130, the tip 1030*a*, the tip 1030*b*, and/or applicators 850*a*, 850*b*. As shown in FIG. 62C, a diameter of a lumen 1446*k* can be larger at the proximal section 1425 than at the distal section 1426. In some embodiments, the diameter of the lumen 1446*k* can be 10 mm, about 10 mm, 12 mm, or about 12 mm at the proximal section 1425 and 6 mm or about 6 mm at the distal section 1426.

In some embodiments, a rasp, such as rasps 1430*a-k*, can be coupled to or used in connection with an apparatus or system for forming a cavity or pocket for bone graft to fill after the rasp is inserted to a desired location. Such a cavity can prevent or reduce flow of bone graft from the desired location due to contraction of muscle.

FIGS. 68A-D illustrate perspective views of an embodiment of a rasping system 2100 having a rasp 1430*l* and a sheath 2150. The rasp 1430*l* can include any of the same or similar features and functions as any of the rasps 1430*a-k*, the distal tip 130, the tip 1030*a*, the tip 1030*b*, and/or applicators 850*a*, 850*b*. FIG. 68E illustrates a perspective view of the sheath 2150.

The sheath 2150 can include a proximal end 2152 and a distal end 2154. The sheath 2150 can include a tubular section 2156 defined by an open distal end 2155 and an open proximal end 2151. The tubular section can be configured to receive at least a portion of the rasp 1430*l* therein. In certain embodiments, the sheath 2150 can include a handle 2143. The handle 2143 can be positioned at the proximal end 2152 of the sheath 2150. In certain embodiments, the sheath 2150 can include a connection section 2153 extending between the handle 2143 and the tubular section 2156.

In certain embodiments, the distal end of the sheath 2150 can include a retractable head 2164 for forming a cavity or pocket in muscle or tissue. The retractable head 2164 can include one or more blades 2157 that can be used to dissect muscle or tissue. As shown in FIGS. 68A-E, the head 2164 can include two blades 2157 coupled by a connector 2159. The blades 2157 can be connected to the tubular section 2156 by a connector 2161 extending between the tubular section and the head 2164. The connector 2161 can dimensioned, shaped, or otherwise configured to be flexible to facilitate movement of the head 2164 between a retracted configuration, as shown in FIGS. 68A-B, and an extended configuration, as shown in FIGS. 68C-D, in which the blades 2157 extend beyond the distal tip 1436 of the rasp 1430*l* in response to movement of the tubular section 2156 along the connection section 1432 of the rasp 1430*l*. Movement of the sheath 2150 about the rasp 1430*l* can be controlled by the handle 2143.

In some embodiments, the head 2164 can be deployed or retracted manually, mechanically, electrically, or by any other suitable deployment process. The head 2164 can move medial, lateral, cephalad, caudad, up, down, or any other direction that may create a pocket for bone graft to pool. A leading edge of the blades 2157 can be blunt or sharp. In some embodiments, a sharp leading edge may be used to dissect muscle with increased efficacy.

The rasp 1430*l* can include a proximal slot at the proximal end 1441. The rasp 1430*l* can further include a slot 2163. At least a portion of the sheath 2150 can extend within the rasp 1430*l* between the proximal slot and the slot 2163. In certain embodiments, at least a portion of the connection section 2153 can be configured to slide within the lumen between the proximal slot and the slot 2163. The connection section 2153 can be configured to slide within the lumen between the proximal slot and the slot 2163. In certain embodiments, at least a portion of the sheath 2150 can extend proximally from the proximal slot. For example, in certain embodiments, the handle 2143 can extend proximally from the proximal slot. As shown in FIGS. 68A-D, the tubular section 2156 can be positioned distally to the slot 2163.

In some embodiments, the rasping system 2100 can be inserted into the body and advanced to a surgical location with the sheath 2150 and head 2164 in the retracted configuration as shown in FIGS. 68A-B. After the rasping system is positioned at the desired location, the head 2164 can be deployed to the extended configuration, as shown in FIGS. 68C-D to create a cavity or pocket within the muscle or tissue at the surgical location. After creation of the cavity or pocket, the head 2164 can be retracted and the rasp 1430/ can be used to fill the cavity or pocket with bone graft material. In some embodiments, delivering the bone graft into a cavity or pocket within the muscle or tissue can allow the bone graft to maintain its integrity and cohesiveness. In some embodiments, delivering the bone graft into the cavity or pocket can prevent the bone graft from separating. Separation of the bone graft can increase the risk of a non-union fusion.

Any of the rasp 1430a-l can be formed of one or more materials including metals, polymers, ceramics, or any other suitable materials. In some embodiments, the rasp may be formed of durable rigid polymer or other suitable materials that are inexpensive and/or disposable. In some embodiments, any of the rasp 1430a-l may be formed of materials of varying rigidity and flexibility to facilitate access, decortication, and/or graft delivery to different areas of the body. In some embodiments, the any of the rasps 1430a-l can be reusable. In other embodiments, any of the rasps 1430a-l can be disposable. In certain embodiments, any of the rasps 1430a-l can be provided in a sterile package for single use by any means of terminal sterilization including, but not limited to EO, E beam, and gamma. In certain embodiments, the components of any of the rasps 1430a-l and any graft delivery system or device may be autoclaved, steam sterilized and reusable. In certain embodiments, the components of the rasp and/or delivery system may be assembled with screws, anchors, clips, glued, or any other suitable means. In certain embodiments, the components of the rasp and/or delivery system or device may be machined in one piece or come in different components. In certain embodiments one or more components of any of the rasps 1430a-l can be 3D printed.

In some embodiments, one or more rasps 1430a-l, one or more delivery systems or devices, one or more dilators, bone graft, one or more guides, one or more burrs, one or more handles, and one or more markers and trackers for image guidance may be packaged together as a kit or individually. In some embodiments, a kit may include one or more rasps 1430a-l, instruments for implanting facet screws, intrafacet implants, facet dowels, pedicle screws, dilators, inserters, drills, drill guides, tamps, facet locators, and/or taps.

In some embodiments, a method for decorticating bone and/or delivering bone graft material to a surgical location includes making an incision in a body of a patient. In certain embodiments, the incision can preferably be between 2 cm and 3.5 cm in length. However, in some procedures, the size of the incision may larger or smaller depending on the number of vertebral levels to be fused. In some embodiments, the size of the incision can be between 1 cm and 9 cm in length. In some embodiments, one or more implants for orthopedic/spinal surgery, such as facet bone dowels, intrafacet screws, intrafacet implants, interspinous plates, cortical screws, lateral plates, SI joint fusion implants and ALIF cage/plates, LLIF lateral cages/plates can be placed in the body through the incision.

FIGS. 63A and 63B depict perspective views of an intrafacet implant 2000. The intrafacet implant 2000 can be in the form of an intrafacet dowel. The implant 2000 includes a proximal end 2002 and a distal end 2004. As shown in FIGS. 63-B, the implant 2000 can include engagement features 2006 in the form of threads extending between the proximal end 2002 and distal end 2004. The intrafacet implant 2000 can be placed within a facet joint, as shown in FIG. 63C. The threads 2006 can engage a portion of a superior articular process of a vertebral body and a portion of an inferior articular process of a vertebral body to secure the facet joint with the implant 2000.

The engagement features 2006 of the implant 2000 may contain helical threads, ridges, recesses, tapered sections, or any other suitable engagement features to allow the implant 2000 to anchor within the facet joint and/or to prevent migration of implant 2000.

The implant 2000 can be formed of titanium, stainless steel, metal/alloy metal, or any other suitable synthetic implant material. The implant 2000 can be cannulated or non-cannulated. The implant 2000 may be textured by bead blasting, chemical etching, acid etching, 3D printing, coating, such as with HA or TCP, or any other suitable texturing method. Texturing of the implant can help with fusion and bony integration. The implant 2000 may be circular, semi-circular, oblong, tapered, triangular, square, rectangular, or any other suitable shape consisting of different angles and geometries. The distal end 2004 can be in the form of a tip. The tip can be bulleted, circular, conical, triangular, self-tapping, or cannulated. The implant can be composed of cortical bone, demineralized cortical bone, cancellous bone or any combination thereof. The proximal end 2002 of the implant 2000 may have an engagement feature to connect to an inserter. The engagement feature may be circular, square, pentagonal, hexagonal, triangular, heptagonal, octagonal, slotted, x-shaped, minus shape or any other shape that could attach to an inserter. In some embodiments, the implant 2000 can may not have an engagement feature. In some embodiments, the implant 2000 can be dropped into the joint without an inserter.

FIGS. 64A, 64B, 64C, and 64D depict a first perspective view, a second perspective view, a side view, and a cross-sectional view, respectively, of an intrafacet implant 2050. The implant 2050 can be in the form of an intrafacet screw. The implant 2050 includes a proximal end 2052 and a distal end 2054. The implant 2050 includes engagement features 2056. The engagement features 2056 can be in the form of threads extending between the proximal end 2052 and the distal end 2054. In some embodiments, the threads can be in the form of helical threads.

In some embodiments, the implant 2050 can be cannulated for minimally invasive surgery. In other embodiments, the implant is non-cannulated. In some embodiments, the intrafacet implant 2050 can be solid and not cannulated. Such embodiments can be useful in an open procedure where a cannulated screw is not necessary.

In some embodiments, the implant 2050 further includes a channel 2058 that can be filled with bone graft material and a plurality of openings 2060 and 2062 for introduction of the bone graft material within the channel 2058 to the facet joint.

The implant 2050 can be configured to be inserted with a driver such as a hex driver, a torx driver, a square driver or any other suitable driver for driving the implant into bone.

In some embodiments, the implant 2050 can be loaded with DBM, cortical fibers, synthetic bone matrix, BMP2 or BMP7, peptide graft, autograft or any combination thereof.

The intrafacet implant 2050 can be placed within the facet joint, as shown in FIG. 64E. The engagement features 2056 can engage a portion of a superior articular process and an inferior articular process to secure the facet joint with the intrafacet implant 2050.

The intrafacet implant 2050 can be formed of titanium, stainless steel, or metal/alloy metal, biocompatible resorbable material, or other any other suitable synthetic implant material.

The implant 2050 may be self tapping or self drilling. The distal end 2054 of the implant 2050 can be in the form of a tip. The tip of the intrafacet implant 2050 can be tapered, round, conical or flat. In some embodiments, the implant 2050 can be tapered throughout the entire length of the implant or a portion of the length. The tapered implant can allow for compression of the facet joint as it is driven in between the superior and inferior articular facets. The tapered design may contain helical threads to create further joint compression and prevent implant migration and back out. The intrafacet implant 2050 can be textured by bead blasting, chemical etching, acid etching, 3D printing, coating such as HA or TCP, or any other suitable mechanism. Texturing of the implant can help with fusion and bony integration.

The windows 2060 and 2062 can allow bone graft to flow through the implant 2050 and contact bone for fusion. The windows 2060 and 2062 can come in a variety of shapes, sizes, and amounts. The windows 2060 and 2062 can include one or more circular windows, square windows, oblong windows and/or windows of any other suitable shape which can be positioned in strategic locations to assist with fusion and graft flow. In some embodiments, there may be only a single window 2060 or 2062. The one or more windows 2062 and 2060 can be strategically placed between/around/through the threads, barbs, blades, teeth, or other engagement features of the implant 2050.

The implant 2050 can monolithic or composed of multiple pieces assembled together. In some embodiments, the implant 2050 can include barbs, blades, or any other suitable deployable/expandable anti-migration elements. These elements can be contained internally in the implant and deploy out of windows 2060 and 2060 via impaction, rotation, tensile or compressive force, or any other suitable other mechanism to allow deployment from inside the implant 2050 into adjacent bone outside the implant 2050 or surfaces of the implant 2050.

In some embodiments, a head 2064 of the implant 2050 may be wider than a shank 2066 of the implant 2050 to prevent the implant 2050 from traversing too far into the joint. Thus, the head 2064 of the implant can act as a stop. In some embodiments, the head 2064 of the implant can have the same diameter as the shank 2066 to facilitate counter-sinking the implant in a pilot hole for improved fixation. In some embodiments, a bottom portion of the implant head 2064 can have undulations or barbs 2068 as shown in FIG. 64 to prevent backout of the implant.

FIGS. 66A, 66B, 66C, and 66D depict a first perspective view, a second perspective view, a side view, and a cross-sectional view, respectively, of an intrafacet implant 2250. The implant 2250 can include any of the same or similar features and functions as the implant 2050. The implant 2250 can be in the form of an intrafacet screw. The implant 2250 includes a proximal end 2252 and a distal end 2254. The implant 2250 includes engagement features 2256. The engagement features 2256 can be in the form of one or more one or more fins, barbs, teeth, or blades extending between the proximal end 2252 and the distal end 2254.

In some embodiments, the engagement features 2256 can be organized in rows or staggered. For example, the engagement features can be organized in 4 rows between the proximal end 2252 and distal end 2254, as shown in FIG. 66. In some embodiments, the engagement features can be organized in more or less than 4 rows. In some embodiments, a higher number of rows of engagement features causes higher pull-out strength.

In some embodiments, the implant 2250 can be cannulated for minimally invasive surgery. In other embodiments, the implant is non-cannulated. In some embodiments, the intrafacet implant 2250 can be solid and not cannulated. Such embodiments can be useful in an open procedure where a cannulated screw is not necessary.

In some embodiments, the implant 2250 further includes a channel 2258 that can be filled with bone graft material and a plurality of openings 2260 for introduction of the bone graft material within the channel 2258 to the facet joint.

In some embodiments, the implant 2250 can be loaded with DBM, cortical fibers, synthetic bone matrix, BMP2 or BMP7, peptide graft, autograft or any combination thereof.

The intrafacet implant 2250 can be placed within a facet joint. The engagement features 2256 can engage a portion of a superior articular process and an inferior articular process to secure the facet joint with the intrafacet implant 2250.

The intrafacet implant 2250 can be formed of titanium, stainless steel, or metal/alloy metal, biocompatible resorbable material, or other any other suitable synthetic implant material.

The implant 2250 may be self tapping or self drilling. The distal end 2254 of the implant 2250 can be in the form of a tip. The tip of the intrafacet implant 2250 can be tapered, round, conical or flat. In some embodiments, the implant 2250 can be tapered throughout the entire length of the implant or a portion of the length. The intrafacet implant 2250 can be textured by bead blasting, chemical etching, acid etching, 3D printing, coating such as HA or TCP, or any other suitable mechanism. Texturing of the implant can help with fusion and bony integration.

The windows 2260 can allow bone graft to flow through the implant 2250 and contact bone for fusion. The windows 2260 can come in a variety of shapes, sizes, and amounts. The windows 2260 can include one or more circular windows, square windows, oblong windows and/or windows of any other suitable shape which can be positioned in strategic locations to assist with fusion and graft flow. In some embodiments, there may be only a single window 2260. The one or more windows 2260 can be strategically placed between/around/through the barbs, blades, teeth, or other engagement features of the implant 2250.

In some embodiments, a head 2264 of the implant 2250 may be wider than a shank 2266 of the implant 2250 to prevent the implant 2250 from traversing too far into the joint. Thus, the head 2264 of the implant can act as a stop. In some embodiments, the head 2264 of the implant can have the same diameter as the shank 2266 to facilitate counter-sinking the implant in a pilot hole for improved fixation. In some embodiments, a bottom portion of the implant head 2264 can have undulations or barbs to prevent backout of the implant.

The implant 2250 can be configured to be inserted with a driver such as a hex driver, a torx driver, a square driver or any other suitable driver for driving the implant into bone. In some embodiments, the implant 2250 can include an engagement feature 2270 for receiving an end of a driver. In some embodiments, the engagement feature 2270 can be in the form of threads. In some embodiments, the implant 2250 can include one or more alignment features 2272 for receive a distal end of a driver.

FIGS. 65A and 65B illustrate a front view and a cross-sectional view, respectively, of a driver or inserter 2800. The inserter 2800 includes a proximal end 2802 and a distal end 2804. The distal end 2804 can be configured to engage the proximal end 2852 of the implant 2250, for example, as shown in FIG. 66E. In some embodiments, the inserter 2800 can be a bone graft delivery device. The inserter 2800 can include a cannula 2808 extending between the proximal end 2802 and the distal end 2804 to deliver bone graft to implant 2250. In some embodiments, the inserter 2800 can include a funnel 2810 connected to the cannula 2808 or forming a portion of the cannula 2808 to receive bone graft. In other embodiments, the funnel 2810 can be a separate component. This may be advantageous so the funnel can be pre-packed, for example on a back operating room table during a surgical procedure. Filling the funnel 2810 separately from the other components of the inserter 2800 can allow for reduced time of surgery. Filling the funnel 2810 separately from the other components of the inserter can also allow for multiple funnels 2810 to be used with the inserter during a single procedure to quickly deliver additional amounts of bone graft. Other types of bone graft delivery systems discussed herein can be used to deliver bone graft into and through the implant 2250. Delivery of bone graft through the implant 2250 can facilitate osteointegration and fusion.

FIGS. 67A, 67B, 67C, and 67D depict a first perspective view, a second perspective view, a side view, and a cross-sectional view, respectively, of an intrafacet implant 2450. The implant 2450 can include any of the same or similar features and functions as the implants 2050 and 2250. The implant 2450 can be in the form of an intrafacet screw. The implant 2450 includes a proximal end 2452 and a distal end 2454. The implant 2450 includes engagement features 2456. The engagement features 2456 can be in the form of one or more one or more fins, barbs, teeth, or blades extending between the proximal end 2442 and the distal end 2454.

In some embodiments, the engagement features 2456 can be organized in rows or staggered. For example, the engagement features 2456 can be organized in staggered pattern as shown in FIG. 67AC. In some embodiments, the engagement features 2456 can be engaged in a staggered helical pattern.

In some embodiments, the implant 2450 can be cannulated for minimally invasive surgery. In other embodiments, the implant is non-cannulated. In some embodiments, the intrafacet implant 2450 can be solid and not cannulated. Such embodiments can be useful in an open procedure where a cannulated screw is not necessary.

In some embodiments, the implant 2450 further includes a channel 2458 that can be filled with bone graft material and a plurality of openings 2460 for introduction of the bone graft material within the channel 2458 to the facet joint.

In some embodiments, the implant 2450 can be loaded with DBM, cortical fibers, synthetic bone matrix, BMP2 or BMP7, peptide graft, autograft or any combination thereof.

The intrafacet implant 2450 can be placed within a facet joint. The engagement features 2456 can engage a portion of a superior articular process and an inferior articular process to secure the facet joint with the intrafacet implant 2450.

The intrafacet implant 2450 can be formed of titanium, stainless steel, or metal/alloy metal, biocompatible resorbable material, or other any other suitable synthetic implant material.

The implant 2450 may be self tapping or self drilling. The distal end 2454 of the implant 2450 can be in the form of a tip. The tip of the intrafacet implant 2450 can be tapered, round, conical or flat. In some embodiments, the implant 2450 can be tapered throughout the entire length of the implant or a portion of the length. In some embodiments, the tapered design can include tapering along the outer diameter of the implant 2450. Tapering along the outer diameter of the implant 2450 can create compression when the implant 2450 driven into the facet joint. The use of threads on the tapered design can allow for further compression and prevent migration and implant back out. The intrafacet implant 2450 can be textured by bead blasting, chemical etching, acid etching, 3D printing, coating such as HA or TCP, or any other suitable mechanism. Texturing of the implant can help with fusion and bony integration.

The windows 2460 can allow bone graft to flow through the implant 2450 and contact bone for fusion. The windows 2460 can come in a variety of shapes, sizes, and amounts. The windows 2460 can include one or more circular windows, square windows, oblong windows and/or windows of any other suitable shape which can be positioned in strategic locations to assist with fusion and graft flow. In some embodiments, there may be only a single window 2460. The one or more windows 2460 can be strategically placed between/around/through the barbs, blades, teeth, or other engagement features of the implant 2450.

In some embodiments, a head 2464 of the implant 2450 may be wider than a shank 2466 of the implant 2450 to prevent the implant 2450 from traversing too far into the joint. Thus, the head 2464 of the implant can act as a stop. In some embodiments, the head 2464 of the implant can have the same diameter as the shank 2466 to facilitate counter-sinking the implant in a pilot hole for improved fixation. In some embodiments, a bottom portion of the implant head 2464 can have undulations or barbs to prevent backout of the implant.

The implant 2450 can be configured to be inserted with a driver such as a hex driver, a torx driver, a square driver or any other suitable driver for driving the implant into bone. In some embodiments, the implant 2450 can couple to the inserter 2800 as shown in FIG. 67E.

FIGS. 69A and 69B depict a first perspective view and a second perspective view of an intrafacet implant 2550. The implant 2550 can include any of the same or similar features and functions as the implants 2050, 2250, and 2450. The implant 2550 can be in the form of an intrafacet screw. The implant 2550 includes a proximal end 2552 and a distal end 2554. The implant 2550 includes engagement features 2556. The engagement features 2556 can be in the form of one or more one or more fins, barbs, teeth, or blades extending between the proximal end 2552 and the distal end 2554.

In some embodiments, the engagement features 2556 can be organized in rows or staggered. For example, the engagement features can be organized in 4 rows between the proximal end 2552 and the distal end 2554 shown in FIG. 69A. In some embodiments, the engagement features can be organized in more or less than 4 rows. In some embodiments, a higher number of rows of engagement features causes higher pull-out strength. In some embodiments the engagement features 2556 can have sharp tips or cutting edges to grip and pierce bone upon rotation of the implant 2550 as shown in FIGS. 69A-B.

In some embodiments, the implant 2550 can be cannulated for minimally invasive surgery. In other embodiments, the implant is non-cannulated. In some embodiments, the intrafacet implant 2550 can be solid and not cannulated. Such embodiments can be useful in an open procedure where a cannulated screw is not necessary.

In some embodiments, the implant 2550 further includes a channel 2558 that can be filled with bone graft material and a plurality of openings 2560 for introduction of the bone graft material within the channel 2558 to the facet joint.

In some embodiments, the implant 2550 can be loaded with DBM, cortical fibers, synthetic bone matrix or putty, BMP2 or BMP7, peptide graft, autograft or any combination thereof.

The intrafacet implant 2550 can be placed within a facet joint. The engagement features 2556 can engage a portion of a superior articular process and an inferior articular process to secure the facet joint with the intrafacet implant 2550.

The intrafacet implant 2550 can be formed of titanium, stainless steel, or metal/alloy metal, biocompatible resorbable material, or other any other suitable synthetic implant material.

The implant 2550 may be self tapping or self drilling. The distal end 2554 of the implant 2050 can be in the form of a tip. The tip of the intrafacet implant 2550 can be tapered, round, conical or flat. In some embodiments, the implant 2550 can be tapered throughout the entire length of the implant or a portion of the length. The intrafacet implant 2550 can be textured by bead blasting, chemical etching, acid etching, 3D printing, coating such as HA or TCP, or any other suitable mechanism. Texturing of the implant can help with fusion and bony integration.

The windows 2560 can allow bone graft to flow through the implant 2550 and contact bone for fusion. The windows 2560 can come in a variety of shapes, sizes, and amounts. The windows 2560 can include one or more circular windows, square windows, oblong windows and/or windows of any other suitable shape which can be positioned in strategic locations to assist with fusion and graft flow. In some embodiments, there may be only a single window 2560. The one or more windows 2560 can be strategically placed between/around/through the barbs, blades, teeth, or other engagement features of the implant 2550.

In some embodiments, a head 2564 of the implant 2550 may be wider than a shank 2566 of the implant 2550 to prevent the implant 2550 from traversing too far into the joint. Thus, the head 2564 of the implant can act as a stop. In some embodiments, the head 2564 of the implant can have the same diameter as the shank 2566 to facilitate counter-sinking the implant in a pilot hole for improved fixation. In some embodiments, a bottom portion of the implant head 2564 can have undulations or barbs to prevent backout of the implant.

The implant 2550 can be configured to be inserted with a driver such as a hex driver, a torx driver, a square driver or any other suitable driver for driving the implant into bone. In some embodiments, the implant 2550 can couple to the inserter 2800.

FIGS. 70A and 70B depict a first perspective view and a second perspective view of an intrafacet implant 2650. The implant 2650 can include any of the same or similar features and functions as the implants 2050, 2250, 2450, and 2550. The implant 2650 can be in the form of an intrafacet screw. The implant 2650 includes a proximal end 2652 and a distal end 2654. The implant 2650 includes engagement features 2656. The engagement features 2656 can be in the form of one or more one or more fins, barbs, teeth, or blades extending between the proximal end 2652 and the distal end 2654.

In some embodiments, the engagement features 2656 can be organized in rows or staggered. For example, the engagement features can be organized in 4 rows extending between the proximal end 2652 and the distal end 2654 as shown in FIG. 70A. In some embodiments, the engagement features can be organized in more or less than 4 rows. In some embodiments, a higher number of rows of engagement features causes higher pull-out strength. In some embodiments the engagement features 2656 can have sharp tips or cutting edges to grip and pierce bone upon rotation of the implant 2650 as shown in FIGS. 70A-B.

In some embodiments, the implant 2650 can be cannulated for minimally invasive surgery. In other embodiments, the implant is non-cannulated. In some embodiments, the intrafacet implant 2650 can be solid and not cannulated. Such embodiments can be useful in an open procedure where a cannulated screw is not necessary.

In some embodiments, the implant 2650 further includes a channel 2658 that can be filled with bone graft material and a plurality of openings 2660 for introduction of the bone graft material within the channel 2658 to the facet joint.

In some embodiments, the implant 2650 can be loaded with DBM, cortical fibers, synthetic bone matrix, BMP2 or BMP7, peptide graft, autograft or any combination thereof.

The intrafacet implant 2650 can be placed within a facet joint. The engagement features 2656 can engage a portion of a superior articular process and an inferior articular process to secure the facet joint with the intrafacet implant 2650.

The intrafacet implant 2650 can be formed of titanium, stainless steel, or metal/alloy metal, biocompatible resorbable material, or other any other suitable synthetic implant material.

The implant 2650 may be self tapping or self drilling. The distal end 2654 of the implant 2650 can be in the form of a tip. The tip of the intrafacet implant 2650 can be tapered, round, conical or flat. In some embodiments, the implant 2650 can be tapered throughout the entire length of the implant or a portion of the length. The intrafacet implant 2650 can be textured by bead blasting, chemical etching, acid etching, 3D printing, coating such as HA or TCP, or any other suitable mechanism. Texturing of the implant can help with fusion and bony integration.

The windows 2660 can allow bone graft to flow through the implant 2650 and contact bone for fusion. The windows 2660 can come in a variety of shapes, sizes, and amounts. The windows 2660 can include one or more circular windows, square windows, oblong windows and/or windows of any other suitable shape which can be positioned in strategic locations to assist with fusion and graft flow. In some embodiments, there may be only a single window 2660. The one or more windows 2660 can be strategically placed between/around/through the barbs, blades, teeth, or other engagement features of the implant 2650.

In some embodiments, a head 2664 of the implant 2650 may be wider than a shank 2666 of the implant 2650 to prevent the implant 2650 from traversing too far into the joint. Thus, the head 2664 of the implant can act as a stop. In some embodiments, the head 2664 of the implant can have the same diameter as the shank 2666 to facilitate counter-sinking the implant in a pilot hole for improved fixation. In some embodiments, a bottom portion of the implant head 2664 can have undulations or barbs to prevent backout of the implant.

The implant 2650 can be configured to be inserted with a driver such as a hex driver, a torx driver, a square driver or any other suitable driver for driving the implant into bone. In some embodiments, the implant 2650 can couple to the inserter 2800.

FIGS. 71A and 71B depict a first perspective view and a second perspective view of an intrafacet implant 2750. The implant 2750 can include any of the same or similar features and functions as the implants 2050, 2250, 2450, 2550, and 2650. The implant 2750 can be in the form of an intrafacet screw. The implant 2750 includes a proximal end 2752 and a distal end 2754. The implant 2750 includes engagement features 2756. The engagement features 2756 can be in the form of one or more one or more fins, barbs, teeth, or blades extending between the proximal end 2752 and the distal end 2754.

In some embodiments, the engagement features 2756 can be organized in rows or staggered. For example, the engagement features can be organized in 2 rows extending between the proximal end 2752 and the distal end 2754 as shown in FIG. 71A. In some embodiments, the engagement features can be organized in more or less than 2 rows. In some embodiments, a higher number of rows of engagement features causes higher pull-out strength. In some embodiments, two rows can make rotate and engagement of bone once implanted easier in comparison to more rows. In some embodiments the engagement features 2756 can have sharp tips or cutting edges to grip and pierce bone upon rotation of the implant 2750.

In some embodiments, the implant 2750 can be cannulated for minimally invasive surgery. In other embodiments, the implant is non-cannulated. In some embodiments, the intrafacet implant 2750 can be solid and not cannulated. Such embodiments can be useful in an open procedure where a cannulated screw is not necessary.

In some embodiments, the implant 2750 further includes a channel 2758 that can be filled with bone graft material and a plurality of openings 2760 for introduction of the bone graft material within the channel 2758 to the facet joint.

In some embodiments, the implant 2750 can be loaded with DBM, cortical fibers, synthetic bone matrix, BMP2 or BMP7, peptide graft, autograft or any combination thereof.

The intrafacet implant 2750 can be placed within a facet joint. The engagement features 2756 can engage a portion of a superior articular process and an inferior articular process to secure the facet joint with the intrafacet implant 2750.

The intrafacet implant 2750 can be formed of titanium, stainless steel, or metal/alloy metal, biocompatible resorbable material, or other any other suitable synthetic implant material.

The implant 2750 may be self tapping or self drilling. The distal end 2754 of the implant 2750 can be in the form of a tip. The tip of the intrafacet implant 2750 can be tapered, round, conical or flat. In some embodiments, the implant 2750 can be tapered throughout the entire length of the implant or a portion of the length. The intrafacet implant 2750 can be textured by bead blasting, chemical etching, acid etching, 3D printing, coating such as HA or TCP, or any other suitable mechanism. Texturing of the implant can help with fusion and bony integration.

The windows 2760 can allow bone graft to flow through the implant 2750 and contact bone for fusion. The windows 2760 can come in a variety of shapes, sizes, and amounts. The windows 2760 can include one or more circular windows, square windows, oblong windows and/or windows of any other suitable shape which can be positioned in strategic locations to assist with fusion and graft flow. In some embodiments, there may be only a single window 2760. The one or more windows 2760 can be strategically placed between/around/through the barbs, blades, teeth, or other engagement features of the implant 2750.

In some embodiments, a head 2764 of the implant 2750 may be wider than a shank 2766 of the implant 2750 to prevent the implant 2750 from traversing too far into the joint. Thus, the head 2764 of the implant can act as a stop. In some embodiments, the head 2764 of the implant can have the same diameter as the shank 2766 to facilitate counter-sinking the implant in a pilot hole for improved fixation. In some embodiments, a bottom portion of the implant head 2764 can have undulations or barbs to prevent backout of the implant.

The implant 2750 can be configured to be inserted with a driver such as a hex driver, a torx driver, a square driver or any other suitable driver for driving the implant into bone. In some embodiments, the implant 2750 can couple to the inserter 2800.

FIGS. 72A, 72B, and 72C depict a first perspective view, a second perspective view, and a side view, respectively, of an intrafacet implant 2850. The implant 2850 can be in the form of an intrafacet screw. The implant 2850 includes a proximal end 2852 and a distal end 2854. The implant 2850 includes engagement features 2856. The engagement features 2856 can be in the form of threads extending between the proximal end 2852 and the distal end 2854. In some embodiments, the threads can be in the form of helical threads. As shown in FIGS. 72A-C, in some embodiments, the engagement features 2856 can include a single start thread. In other embodiments, the engagement features 2856 can include multiple start threads.

In some embodiments, the implant 2850 can be cannulated for minimally invasive surgery. In other embodiments, the implant is non-cannulated. In some embodiments, the intrafacet implant 2850 can be solid and not cannulated. Such embodiments can be useful in an open procedure where a cannulated screw is not necessary.

In some embodiments, the implant 2850 further includes a channel 2858 that can be filled with bone graft material and a plurality of openings 2860 for introduction of the bone graft material within the channel 2858 to the facet joint.

The implant 2850 can be configured to be inserted with a driver such as a hex driver, a torx driver, a square driver or any other suitable driver for driving the implant into bone.

In some embodiments, the implant 2850 can be loaded with DBM, cortical fibers, synthetic bone matrix, BMP2 or BMP7, peptide graft, autograft or any combination thereof.

The intrafacet implant 2850 can be placed within the facet joint. The engagement features 2856 can engage a portion of a superior articular process and an inferior articular process to secure the facet joint with the intrafacet implant 2850.

The intrafacet implant 2850 can be formed of titanium, stainless steel, or metal/alloy metal, biocompatible resorbable material, or other any other suitable synthetic implant material.

The implant 2850 may be self tapping or self drilling. The distal end 2854 of the implant 2850 can be in the form of a tip. The tip of the intrafacet implant 2850 can be tapered, round, conical or flat. As shown in FIGS. 72A-C, the implant 2850 can be tapered throughout the entire length of the shank 2866 implant or a portion of the length. For example, in some embodiments, the implant 2850 can include a taper angle of 5°. The tapered implant can allow for compression of the facet joint as it is driven in between the superior and inferior articular facets. As shown in FIGS. 72A-C, the tapered design can contain helical threads to create further joint compression and prevent implant migration and back out. The intrafacet implant 2850 can be textured by bead blasting, chemical etching, acid etching, 3D printing, coating such as HA or TCP, or any other suitable mechanism. Texturing of the implant can help with fusion and bony integration.

The windows 2860 can allow bone graft to flow through the implant 2850 and contact bone for fusion. The windows 2860 can come in a variety of shapes, sizes, and amounts. The windows 2860 can include one or more circular windows, square windows, oblong windows and/or windows of any other suitable shape which can be positioned in strategic locations to assist with fusion and graft flow. In some embodiments, there may be only a single window 2860. The one or more windows 2862 can be strategically placed between/around/through the threads, barbs, blades, teeth, or other engagement features of the implant 2850.

The implant 2850 can monolithic or composed of multiple pieces assembled together. In some embodiments, the implant 2850 can include barbs, blades, or any other suitable deployable/expandable anti-migration elements. These elements can be contained internally in the implant and deploy out of windows 2860 via impaction, rotation, tensile or compressive force, or any other suitable other mechanism to allow deployment from inside the implant 2850 into adjacent bone outside the implant 2850 or surfaces of the implant 2850.

In some embodiments, a head 2864 of the implant 2850 may be wider than the shank 2866 of the implant 2850 to prevent the implant 2850 from traversing too far into the joint. Thus, the head 2864 of the implant can act as a stop. In some embodiments, the head 2864 of the implant can have the same diameter as the shank 2866 to facilitate counter-sinking the implant in a pilot hole for improved fixation. In some embodiments, a bottom portion of the implant head 2864 can have undulations or barbs to prevent backout of the implant.

FIGS. 73A, 73B, and 73C depict a first perspective view, a second perspective view, and a side view, respectively, of an intrafacet implant 2950. The implant 2950 can be in the form of an intrafacet screw. The implant 2950 includes a proximal end 2952 and a distal end 2954. The implant 2950 includes engagement features 2956. The engagement features 2956 can be in the form of threads extending between the proximal end 2952 and the distal end 2954. In some embodiments, the threads can be in the form of helical threads. As shown in FIGS. 73A-C, in some embodiments, the engagement features 2956 can include a two start threads. In other embodiments, the engagement features 2956 can include a single start thread or more than two start threads.

In some embodiments, the implant 2950 can be cannulated for minimally invasive surgery. In other embodiments, the implant is non-cannulated. In some embodiments, the intrafacet implant 2950 can be solid and not cannulated. Such embodiments can be useful in an open procedure where a cannulated screw is not necessary.

In some embodiments, the implant 2950 further includes a channel 2958 that can be filled with bone graft material and a plurality of openings 2960 for introduction of the bone graft material within the channel 2958 to the facet joint.

The implant 2950 can be configured to be inserted with a driver such as a hex driver, a torx driver, a square driver or any other suitable driver for driving the implant into bone.

In some embodiments, the implant 2950 can be loaded with DBM, cortical fibers, synthetic bone matrix, BMP2 or BMP7, peptide graft, autograft or any combination thereof.

The intrafacet implant 2950 can be placed within the facet joint. The engagement features 2956 can engage a portion of a superior articular process and an inferior articular process to secure the facet joint with the intrafacet implant 2950.

The intrafacet implant 2950 can be formed of titanium, stainless steel, or metal/alloy metal, biocompatible resorbable material, or other any other suitable synthetic implant material.

The implant 2950 may be self tapping or self drilling. The distal end 2954 of the implant 2950 can be in the form of a tip. The tip of the intrafacet implant 2950 can be tapered, round, conical or flat. As shown in FIGS. 73A-C, the implant 2950 can be tapered throughout the entire length of the shank 2966 implant or a portion of the length. For example, in some embodiments, the implant 2950 can include a taper angle of 5°. The tapered implant can allow for compression of the facet joint as it is driven in between the superior and inferior articular facets. As shown in FIGS. 73A-C, the tapered design can contain helical threads to create further joint compression and prevent implant migration and back out. The intrafacet implant 2950 can be textured by bead blasting, chemical etching, acid etching, 3D printing, coating such as HA or TCP, or any other suitable mechanism. Texturing of the implant can help with fusion and bony integration.

The windows 2960 can allow bone graft to flow through the implant 2950 and contact bone for fusion. The windows 2960 can come in a variety of shapes, sizes, and amounts. The windows 2960 can include one or more circular windows, square windows, oblong windows and/or windows of any other suitable shape which can be positioned in strategic locations to assist with fusion and graft flow. In some embodiments, there may be only a single window 2960. The one or more windows 2962 can be strategically placed between/around/through the threads, barbs, blades, teeth, or other engagement features of the implant 2950.

The implant 2950 can monolithic or composed of multiple pieces assembled together. In some embodiments, the implant 2950 can include barbs, blades, or any other suitable deployable/expandable anti-migration elements. These elements can be contained internally in the implant and deploy out of windows 2960 via impaction, rotation, tensile or compressive force, or any other suitable other mechanism to allow deployment from inside the implant 2950 into adjacent bone outside the implant 2950 or surfaces of the implant 2950.

In some embodiments, a head 2964 of the implant 2950 may be wider than the shank 2966 of the implant 2950 to prevent the implant 2950 from traversing too far into the joint. Thus, the head 2964 of the implant can act as a stop. In some embodiments, the head 2964 of the implant can have the same diameter as the shank 2966 to facilitate counter-sinking the implant in a pilot hole for improved fixation. In some embodiments, a bottom portion of the implant head 2964 can have undulations or barbs to prevent backout of the implant.

FIGS. 74A, 74B, and 74C depict a first perspective view, a second perspective view, and a side view, respectively, of an intrafacet implant 3050. The implant 3050 can be in the form of an intrafacet screw. The implant 3050 includes a proximal end 3052 and a distal end 3054. The implant 3050 includes engagement features 3056. The engagement features 3056 can be in the form of threads extending between the proximal end 3052 and the distal end 3054. In some embodiments, the threads can be in the form of helical threads.

In some embodiments, the implant 3050 can be cannulated for minimally invasive surgery. In other embodiments, the implant is non-cannulated. In some embodiments, the intrafacet implant 3050 can be solid and not cannulated. Such embodiments can be useful in an open procedure where a cannulated screw is not necessary.

In some embodiments, the implant 3050 further includes a channel 3058 that can be filled with bone graft material and a plurality of openings 3060 for introduction of the bone graft material within the channel 3058 to the facet joint.

The implant 3050 can be configured to be inserted with a driver such as a hex driver, a torx driver, a square driver or any other suitable driver for driving the implant into bone.

In some embodiments, the implant 3050 can be loaded with DBM, cortical fibers, synthetic bone matrix, BMP2 or BMP7, peptide graft, autograft or any combination thereof.

The intrafacet implant 3050 can be placed within the facet joint. The engagement features 3056 can engage a portion of a superior articular process and an inferior articular process to secure the facet joint with the intrafacet implant 3050.

The intrafacet implant 3050 can be formed of titanium, stainless steel, or metal/alloy metal, biocompatible resorbable material, or other any other suitable synthetic implant material.

The implant 3050 may be self tapping or self drilling. The distal end 3054 of the implant 3050 can be in the form of a tip. As shown in FIGS. 74A-C, the tip of the intrafacet implant 3050 can be flat. In other embodiments, the tip can be tapered, round, or conical. As shown in FIGS. 74A-C, the implant 3050 or a shank 3066 of the implant can be untapered throughout the entire length of the implant or a portion of the length. For example, the shank 3066 can have a uniform cross-section or a generally uniform cross-section. In some embodiments, the threads can extend a uniform distance or generally uniform distance from the shank 3066 throughout the length of the implant 3050. Such untampered embodiments may further prevent or reduce migration or back out of the implant 3050 from a surgical location in comparison to tapered embodiments. The intrafacet implant 3050 can be textured by bead blasting, chemical etching, acid etching, 3D printing, coating such as HA or TCP, or any other suitable mechanism. Texturing of the implant can help with fusion and bony integration.

The windows 3060 can allow bone graft to flow through the implant 3050 and contact bone for fusion. The windows 3060 can come in a variety of shapes, sizes, and amounts. The windows 3060 can include one or more circular windows, square windows, oblong windows and/or windows of any other suitable shape which can be positioned in strategic locations to assist with fusion and graft flow. In some embodiments, there may be only a single window 3060. The one or more windows 3062 can be strategically placed between/around/through the threads, barbs, blades, teeth, or other engagement features of the implant 3050.

The implant 3050 can monolithic or composed of multiple pieces assembled together. In some embodiments, the implant 3050 can include barbs, blades, or any other suitable deployable/expandable anti-migration elements. These elements can be contained internally in the implant and deploy out of windows 3060 via impaction, rotation, tensile or compressive force, or any other suitable other mechanism to allow deployment from inside the implant 3050 into adjacent bone outside the implant 3050 or surfaces of the implant 3050.

In contrast, for example, to the embodiments shown in FIGS. 73A-C, in some embodiments, a head 3064 of the implant 3050 has the same diameter or a similar diameter as the shank 3066 of the implant 3050 to allow the implant 3050 to be countersunk. Thus, the head 3064 of the implant can act as a stop. In some embodiments, the head 3064 of the implant can have the same diameter as the shank 3066 to facilitate counter-sinking the implant in a pilot hole for improved fixation.

In use the engagement features of the implants 2050, 2250, 2450, 2550, 2650, 2750, 2850, 2950, and 3050 can engage bone by twisting or rotating ¹⁄₁₆, ⅛, ¼, ½, ¾, or 1 full turn after the implant is inserted into the bone. The engagement features can be anchored in cortical bone, cancellous bone, or both. In some embodiments, an initial pilot hole can be made using a drill. In some embodiments, a length of implant can be between 6 mm to 12 mm. In some embodiments, a diameter between 4.5 and 8 mm. A broach can be used to make grooves or cuts into the bone to allow the implant to migrate down the pilot hole into the facet joint without breaking the facet joint elements such as the superior articular process and/or the inferior articular process. After the pilot hole is made and the broach is used to create the grooves or cuts for the intrafacet implant. The implant can be dropped into the joint using an inserter, such as inserter 2300. The inserter can then be used to rotate the implant to engage the engagement features into bone to anchor the implant thereto. In some embodiments, the engagement features can act as an anchoring mechanism to prevent the implant from migrating or backing out and to stabilize the joint. In other embodiments, the implants can include alternative anchoring mechanisms or additional anchoring mechanisms to the engagement features. The anchoring mechanisms can include a series, multiple, or single anti-migration elements which prevent the intrafacet implant from backing out and to stabilize the joint. The rotation of the intrafacet implant may be a slight turn or almost a full rotation to engage bone. The anchoring mechanism may be sharp to pierce through bone upon rotation. In some embodiments in which the implant does not require rotation, the implant may be malleted into the pilot hole for a compression fit.

In some embodiments, after the one or more implants are placed, one or more of rasps, such as rasps 1430*a-l*, or rasping systems, such as rasping system 2100, can be used to decorticate bone, such as for example, the facet joints and/or transverse processes. In some embodiments, the one or more rasps or rasping systems can be inserted through the same incision as the one or more implants. Inserting rasps or rasping systems through the same incision can prevent or reduce scarring, blood loss, and/or trauma to the patient. Inserting rasps or rasping systems through the same incision can also decrease time for the surgeon to perform a procedure. Inserting rasps or rasping systems through the same incision can also reduce the risk of infection that would be associated with having another incision. In some embodiments, the shape and the size of the rasp or rasping system can be optimized for accessing the bony area through the same incision. In some embodiments, a surgeon can use one or more dilators, retractors, or other instruments to help mitigate tissue damage. In some embodiments, a retractor may have a light source or illuminator to aid in visualization.

In some embodiments, the one or more rasps can be inserted through a second incision. For example, in some embodiments, it may be preferable to use an alternative incision to reach a target location if it is difficult or impossible to reach the target location through a first incision. In some embodiments, a surgeon may choose to create a larger incision for direct visualization of bony anatomy, for example, if minimally invasive surgery is not performed. In some embodiments, the second incision can be a Wiltse approach or larger incision. In some embodiments, a retractor may be used to assist with tissue retraction. The retractor may be monolithic or contain multiple pieces. In some embodiments, the retractor can be expandable.

In some embodiments, the rasps and rasping systems described herein, such as rasps 1430*a-l* or rasping system 2100, can be used in an open or minimally invasive procedure. One or more rasps or systems can be inserted into any incision suitable for reaching a desired surgical location, such as a facet joint, transverse process, disc space or sacroiliac joint, hip, ankle, tibia etc. In some embodiments, the rasp can include an indicator, such as a line or arrow, for example on the proximal end of the rasp, to indicate the orientation of the distal end of the rasp when the distal end of the rasp is positioned within the body. For example, the in some embodiments, a proximal end 1441 of the rasp can include a line or arrow pointing in the direction of or otherwise indicating the orientation of the distal tip 1436.

In some embodiments, bone graft is the placed in a rasp, such as rasps 1430*a-l*, or rasp systems, such as system 2100, or in a graft tube into a lumen in the rasp to deliver graft in conjunction with implants. In some embodiments, decortication and bone graft delivery on the facets and transverse process provide ancillary fusion to the placed implants. In previous surgical techniques bone graft was only used on the transverse processes when open lumbar fusions were performed due to accessibility issues. A large midline incision was made and the tissue was dissected out to the transverse processes and facets. Using previous methods for minimally invasive lumbar fusions, there is no way to adequately decorticate and deliver bone graft for posterolateral fusions. Attempts with other devices have been made with little to no success. The embodiments of the rasp with in combination with a delivery system of the present application allow a user to decorticate bone and deliver bone graft simultaneously to a targeted site. Under previous methods, these steps are generally done with two separate instruments, for example, a rasp and a bone graft delivery instrument, which can make it difficult for the user to find the decorticated site once the rasp is removed from the incision and the bone graft delivery instrumented is inserted into the incision.

In some embodiments, a physician can dilate to the facet joint, for example using a dilator as described herein, and use any of the following instruments including but not limited to a facet locator, drill guide, broach, tap, drill bit, and/or inserter to implant a facet bone dowel or other intrafacet implant into the facet joint or across the facet joint. These instruments may be used in consecutive order or some of the instruments may be skipped depending on the surgeon's preference. In some embodiments, the surgeon may use all of these instruments or less than all of these instruments.

Once the implant is placed within the body, a rasp, such as rasps 1430*a-l*, can be inserted into the same incision and to the facet joint. In some embodiments, a rasp, such as rasps 1430*a-l*, can be used to rasp the facet joint and then can be maneuvered to rasp the transverse process using the same incision. Such a procedure can prevent scarring, blood loss, trauma and risk of infection. In some embodiments, after decorticating the transverse process, the rasp can be passed under the skin and through the muscle to an adjacent transverse process for decortication.

In some embodiments, the method can include delivering bone graft through the tip of the rasp using a bone graft delivery system, a bone graft delivery device, or a push rod as described herein. In some embodiments, use of a delivery system, such as bone graft delivery devices 100 or 1400, can provide increased control and accuracy while delivery bone graft by allowing a surgeon to estimate how much bone graft is delivered per squeeze, turn, or other means of actuation. In some embodiments, before delivering bone graft, a cavity or pocket can be formed in muscle or tissue, for example, using a rasping system, such as system 2100.

In some embodiments, bone graft compositions, either synthetic, allograft or allogenic, may be used for minimally invasive graft delivery procedures to visualize bone graft under the skin in situ. In some embodiments, bone graft compositions can be radiopaque. In some embodiments, the bone graft may be manufactured to be radiopaque. In some embodiments the graft may be radiopaque in nature, such as cortical bone or synthetic materials. Alternatively, bone graft can be enhanced with a contrast agent at the time of surgery. In some embodiments, cortical allograft fibers, DBM, or synthetic bone graft with wicking effect can provide improved results when adding a contrast agent at the time of surgery. In some embodiments, the contrast agent can include one or more of isovue, omnipaque, iodine, or any other suitable agent. In some embodiments, a carrier or binder material, such as collagen, bioresorbable polymers, or any other suitable carrier material, may provide radiopacity. In such embodiments, the carrier may be used to wick up iodine or other contrast agents and retain those agents until implanted and then resorbed. The radiopacity of the bone graft composition can be important when used in a minimally invasive posterolateral lumbar fusions. In such procedures, a rasp can be used with or without a graft delivery system. In some embodiments, a bone graft composition is loaded into an elongate tube and placed in a rasp or placed directly into rasp lumen. A delivery system or push rod can be used to push the bone graft composition out of the rasp to a decorticated area on the facet joints and/or transverse processes. During this type of minimally invasive procedure, the bone graft cannot be seen under the skin, muscle, and tissue. A surgeon can use the radiopacity of the bone graft composition to ensure bone graft is placed in the proper position.

In some embodiments, after delivery of the bone graft over one or more facets and/or transverse processes, the rasp, such as rasps 1430*a-l*, and/or delivery system may be removed. Following removal of the rasp and/or delivery system, any incisions can be sutured.

Although the methods outlined above are generally described in an order of implanting an implant followed by use of a rasp to decorticate bone and/or deliver bone graft material, in certain embodiments, a rasp may be used first to decorticate bone and/or deliver bone graft material before implantation of an implant. In other embodiments, a method may include implantation of an implant without additionally using a rasp to decorticate bone and/or deliver bone graft material or use of a rasp to decorticate bone and/or deliver bone graft material without implantation of an implant.

Methods for decorticating bone and/or delivering bone graft material to a surgical location using the rasps, such as rasps 1430*a-l*, and delivery systems and devices described herein can provide for a reduced number of incisions, reduced blood loss, reduced scarring, decreased risk for infection, and reduced time in the operating room. In contrast, some conventional techniques involve muscle stripping, facial cutting, and comparatively more blood loss.

In some embodiments, rasps described herein, for example, rasps having a curved section 1434 (such as rasps 1430*a*, 1430*b*, 1430*c*, 1430*f*, 1430*g*, 1430*h*, 1430*i*, 1430*j*, 1430*k*, and 1430*l*, can be used to rasp adjacent transverse processes (for example, a transverse process of an inferior vertebral body and a transverse process of a superior vertebral body adjacent the inferior vertebral body) using a single incision. In some embodiments, the incision is a midline incision. In certain embodiments, the incision can preferably be between 2 cm and 3.5 cm in length. However, in some procedures, the size of the incision may larger or smaller depending on the number of vertebral levels to be fused. In some embodiments, the size of the incision can be between 1 cm and 9 cm in length. The incision can be made about one finger breadth lateral to the facet joint between the superior and inferior vertebral bodies. The rasp can be advanced through the incision to a first transverse process of one of the superior and inferior vertebral bodies. In some embodiments, the rasp is advanced through the musculature and the fascia, for example, to avoid resistance from the fascia during the rasping procedure. In certain embodiments, the rasp can be advanced through the incision to a first transverse process of one of the superior and inferior vertebral bodies with the tip 1436 facing a second transverse process of the other of the superior and inferior vertebral bodies. For example, if the first transverse process is positioned on the inferior vertebral body, the tip 1436 can be pointed in the superior direction. If the first transverse process is positioned on the superior vertebral body the tip 1436 can be pointed in the inferior direction. Orienting the tip towards the second transverse process can facilitate movement of the rasp to the second transverse process by facilitating dissection using the tip 1436 between the two transverse processes without requiring rotation of the rasp. The first transverse process can be rasped laterally and medially and/or cephalad and caudad. After rasping the first transverse process, the rasp can be moved to the second transverse process, for example, without removing the rasp from the incision. The tip 1436 can dissect tissue as the rasp is moved to the second transverse process from the first transverse process. After the rasp is moved to the second transverse process, the second transverse process can be rasped laterally and medially and/or cephalad and caudad. After rasping of the second transverse process, the rasp can be used to deliver bone graft material to the second transverse process. The rasp can be moved back towards the first transverse process while delivering bone graft material to supply bone graft material between the first transverse process and the second transverse process for fusion. After the rasp returns to the first transverse process, the bone graft can be delivered to the first transverse process. In some embodiments, the rasp can be rotated between the second transverse process and the first transverse process while delivering bone graft material to create a wider dispersion of the bone graft material between the first and second transverse processes for fusion of the first and second transverse processes. The curvature and length of the curved section 1434 of the rasp can facilitate a wider dispersion of the bone graft material. For example, in some embodiments, the distal end 1436 of the rasp can extend 10 mm or about 10 mm laterally beyond the edge or diameter of the connection section 1432. In other embodiments the distal end 1436 can extend between 0 mm and 20 mm, between 5 mm and 15 mm, 6 mm, 7 mm, 8 mm, 9 mm, 11 mm, 12 mm, 13 mm, 14 mm, or any other suitable distance or within any other suitable range of distances laterally beyond the edge or diameter of the connection section 1432. The curvature and length of the curved section may also allow for movement between and rasping of the two transverse process with a reduced incision size, reduced force, and/or reduced damage to other tissue in comparison to a rasp in which there is no lateral extension. In some embodiments, the transverse process of the inferior vertebral body can be the first transverse process and the transverse process of the superior vertebral body can be the second transverse process. In some embodiments, the transverse process of the superior vertebral body can be the first transverse process and the transverse process of the inferior vertebral body can be the second transverse process.

In some embodiments, the rasps described herein, such as rasps 1430*a-l*, can be used in mini open or open orthopedic or spine surgeries. For example, in some embodiments, the rasp can be used as an alternative to burrs, cobb elevators, or other conventional rasps. In some embodiments, the rasps described herein, such as rasps 1430*a-l*, have a larger footprint (i.e., can contact a larger surface of the bone), staggered teeth, and bone graft delivery to the decorticated area. In some embodiments, the rasps described herein, such as rasps 1430*a-l*, provide a surgeon with tactile feedback, which can indicate that the bone is being rasped. For example, the surgeon can grip the rasp and feel the grinding of bone during use of the rasp. By feeling the grinding of the bone, the surgeon can detect when a majority or an entirety of a bone surface, such as a transverse process, is cleared from soft tissue to facilitate a larger or maximized area of soft tissue for fusion to be achieved. This case be performed for rasping between in medial and lateral directions and/or cephalad and caudal directions.

In some embodiments, a rasp having a curved section 1434 and a curved lumen, such as rasps 1430*a*, 1430*b*, and 1430*c*, can be advantageous for minimally invasive applications. In some embodiments, a rasp having a straight lumen, such as rasps 1430*d* and 1430*e* can be advantageous for open or mini open applications. In some embodiments, a straight rasp requires a larger incision than a curved rasp due to placement of the aperture (for example, not having aperture at a curved tip).

The rasps 1430*a-l* can be made of a metallic, radiopaque material to facilitate visualization on, for example, fluoroscopy or x-ray. Alternatively, the rasps 1430*a-l* may be made of another material, for example a durable medical plastic or a composite material, and may include markers to facilitate visualization.

In some embodiments, one or more components that act as a register for image guidance can be attached to the bone graft delivery system, bone graft delivery device, or rasp, such as rasps 1430*a-l* to register placement on an imaging modality to allow for tracking of the system, device, or rasp, such as rasps 1430*a-l*.

In some embodiments, the bone graft delivery system or device and/or rasp, such as rasps 1430*a-l*, can be used with a navigation system, such as, for example, Lessray, stealth system O-arm, Excelsius GPS, or a robotic navigation system. In some embodiments, a navigation system can facilitate determination of real time anatomical positioning in relation to the rasp, such as rasps 1430*a-l*, and/or bone graft delivery system or device. In some embodiments, as opposed to traditional fluoroscopy, the navigation system is a three-dimensional navigation system. Fluoroscopy is only two-dimensional as opposed to three-dimensional. In contrast to fluoroscopy, such navigation systems may not require multiple or excessive radiation exposures during surgery.

Figure 34A:
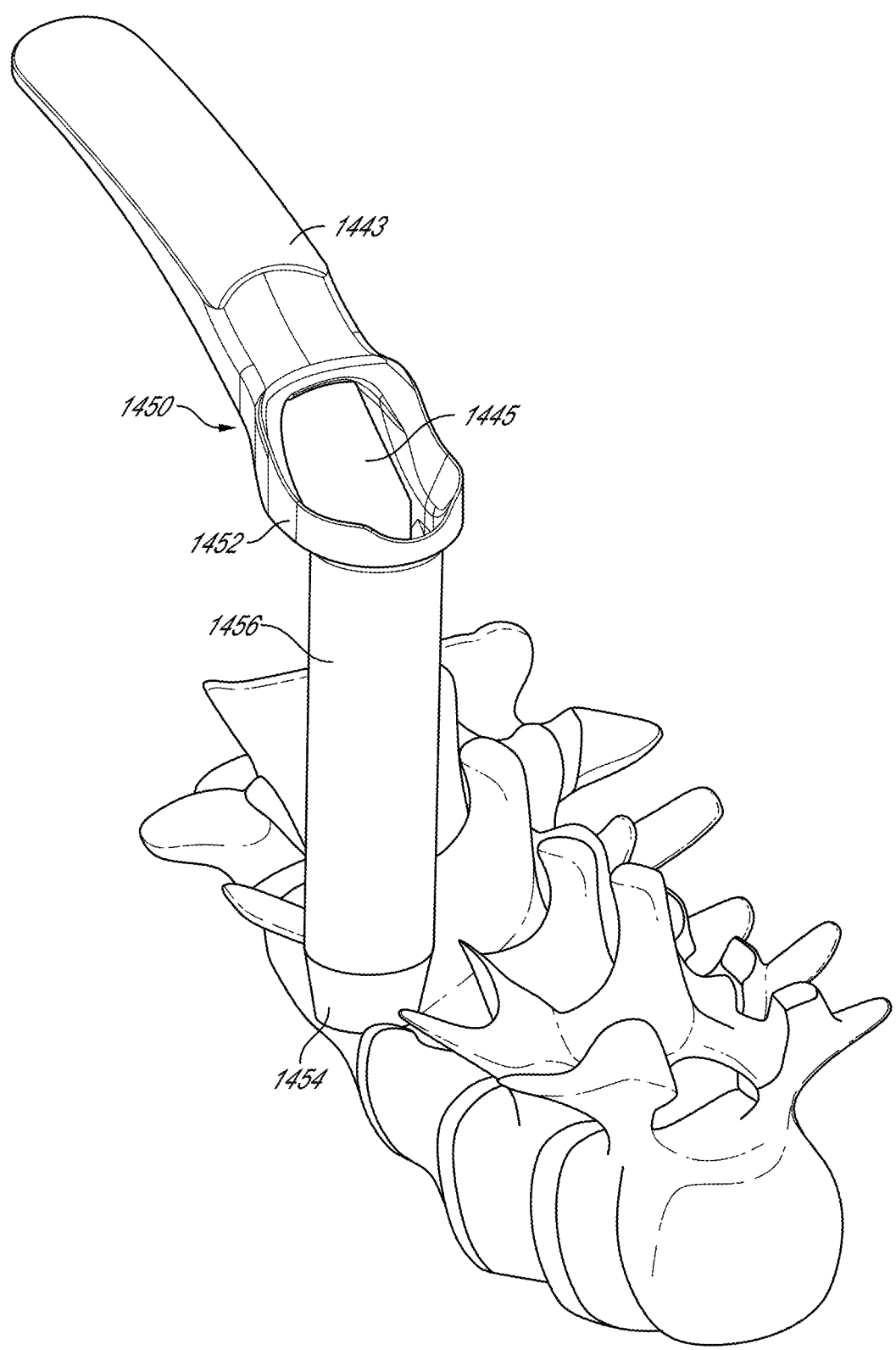
FIG. 34A illustrates a perspective view of an embodiment of a guide of a bone graft delivery system positioned at a surgical location.
Figure 34B:
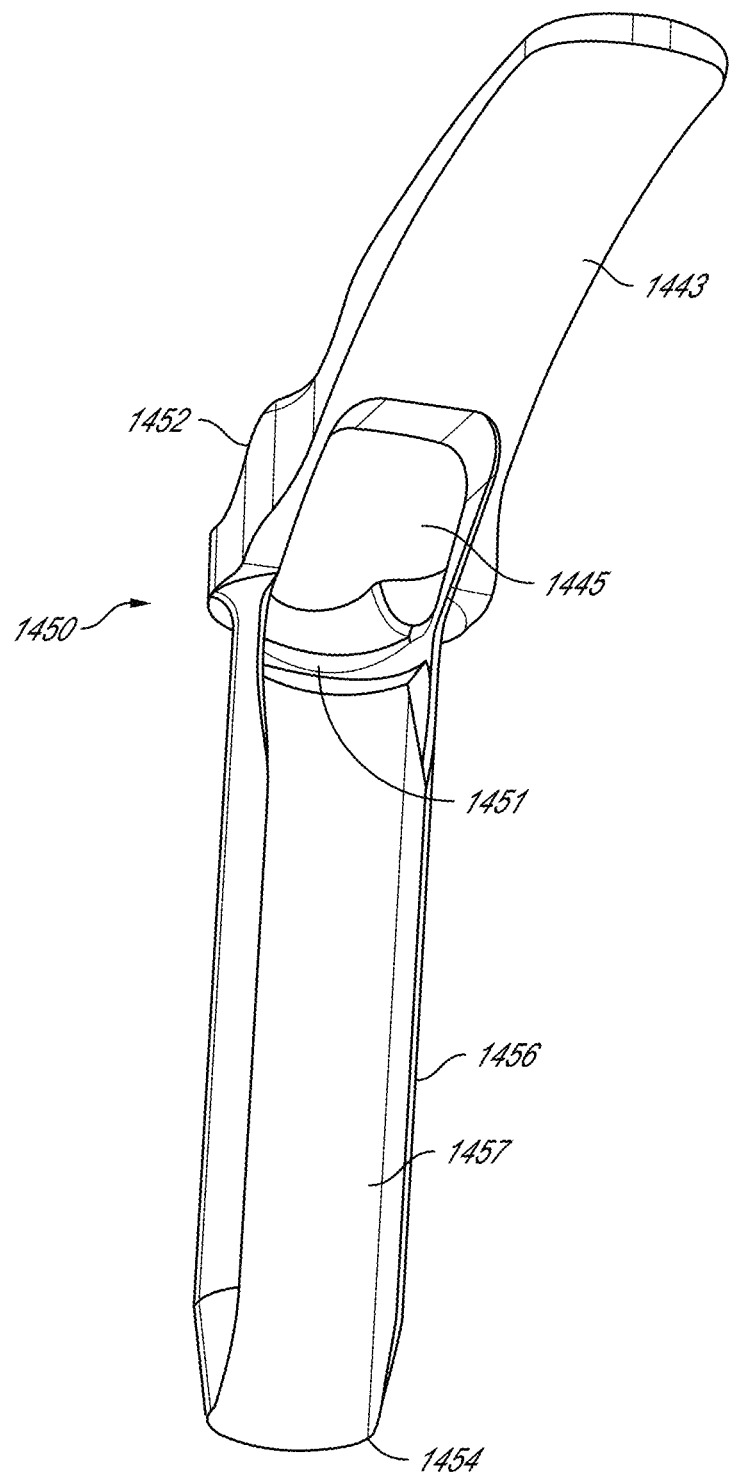
FIG. 34B illustrates a perspective view of the guide of FIG. 34A.
Figure 35A:
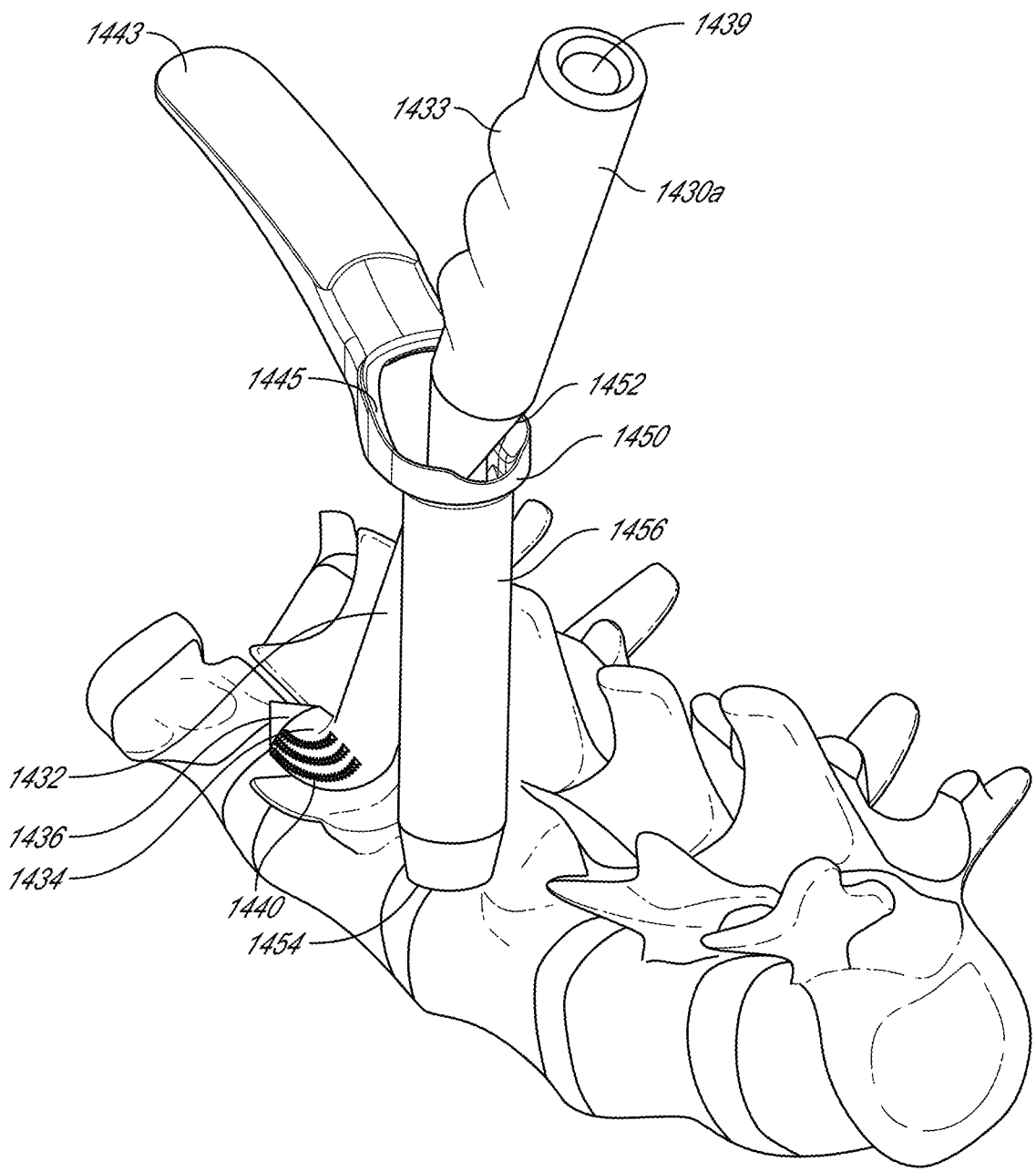
FIG. 35A illustrates a perspective view of the guide of FIG. 34A and an embodiment of a rasp of a bone graft delivery system positioned at a surgical location.
Figure 35B:
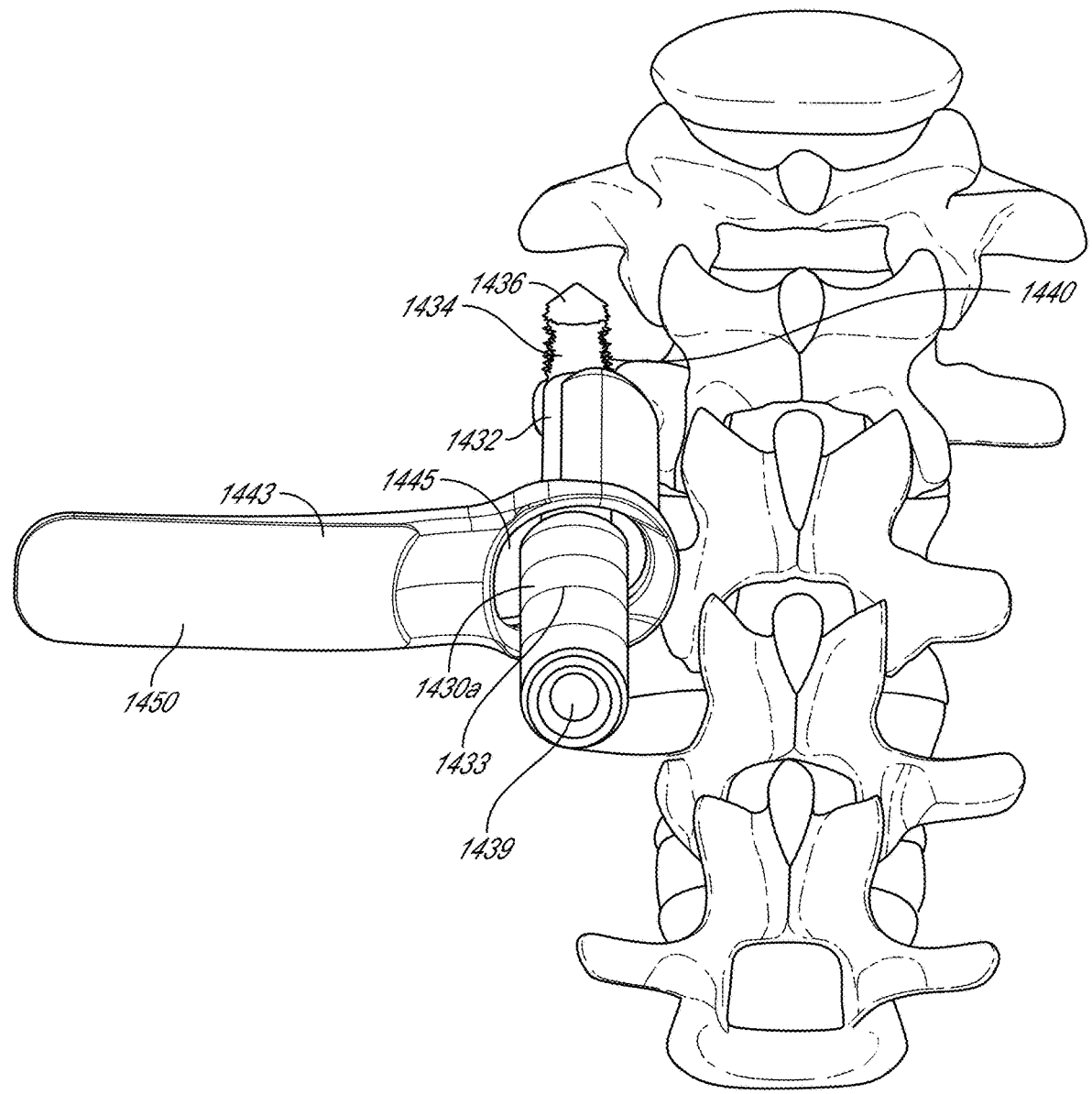
FIG. 35B illustrates a top view of the rasp and guide of FIG. 35A positioned at a surgical location.
Figure 35C:
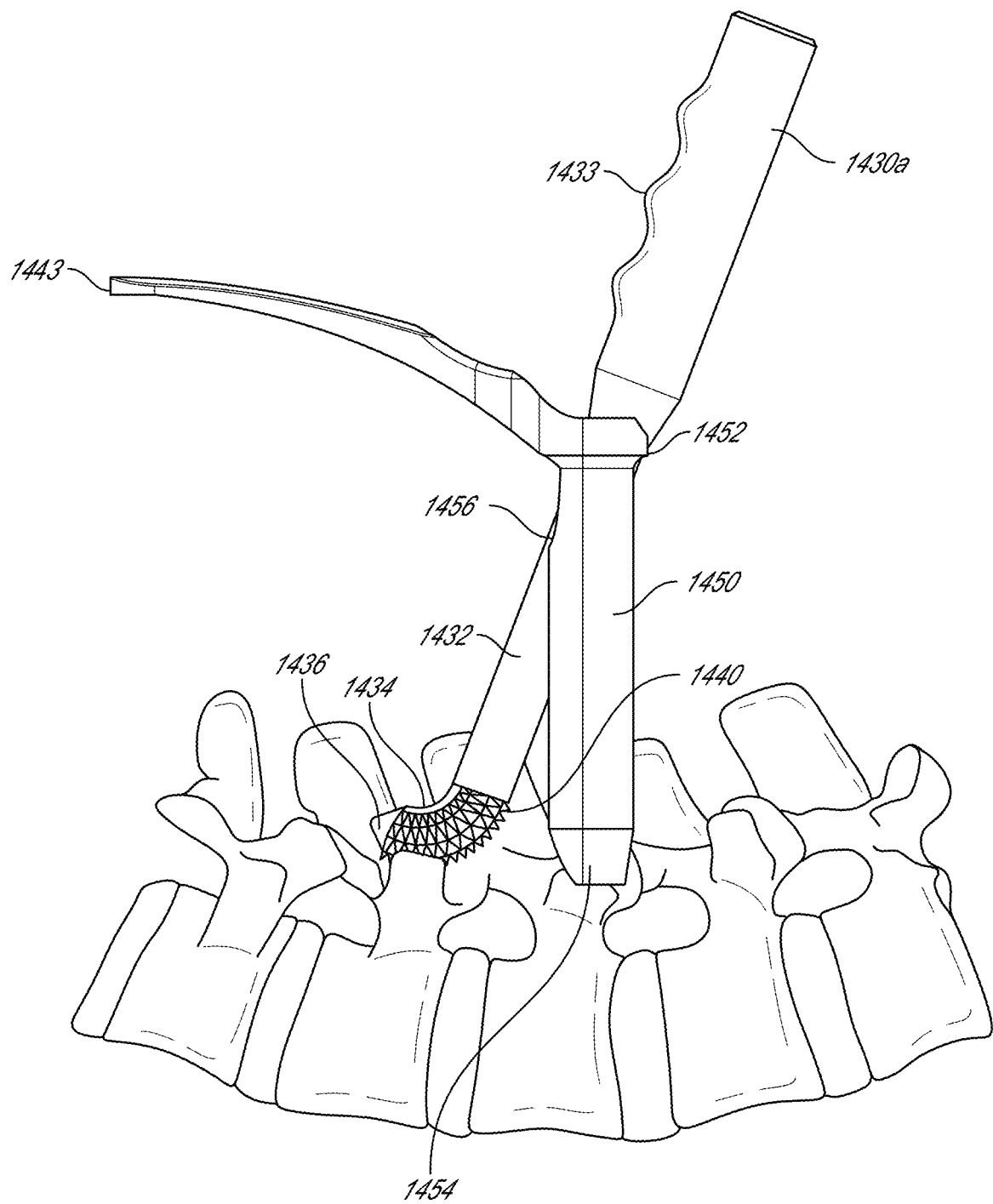
FIG. 35C illustrates a side view of the rasp and guide of FIG. 35A.

In some embodiments, one or more dilators or guides, such as guide 1450, described with respect to FIGS. 34-35C, can be used with a navigation system, such as, for example, Lessray, stealth system O-arm, Excelsius GPS, or a robotic navigation system. In some embodiments, a navigation system can facilitate determination of real time anatomical positioning in relation to the dilators or guides. The navigation system can be used to monitor the dilator or guides within the anatomy of a patient to prevent movement of the dilators or guides into undesired regions of the anatomy, such as, for example, regions in which the dilators or guides would cause unwanted damage to the anatomy.

In some embodiments, navigation spheres are used to track and register surgical instruments used during orthopedic and spine surgery. When decorticating bone using the rasp there are delicate structures such as nerves and blood vessels that surgeons need to stay away from. Because these anatomical bony structures are under the muscle, they are not visible. This can make the procedures described herein, including posterior lateral fusion, dangerous because the surgeon essentially is performing the procedure without visualization or using fluoroscopy which does not provide an accurate depth measurement. Fluoroscopy images may also be blurry or unclear if a patient is overweight or the imaging source is older or not properly calibrated.

In certain embodiments, the spheres or another navigation register can be anchored to the proximal end of a rasp, a delivery tube, a dilator, or a guide as described herein. In certain embodiments, navigation spheres may be too bulky for placement on a distal end of a rasp, tube, dilator, or guide that enters an incision of a patient. Navigation can be performed both active and passively. If active, the register may require batteries or laser capability on a small box or other structure to charge and operate. In some embodiments, in order to function properly, three or more spheres or reflective passive markers must register with the navigation tracking system to provide enough points in space for a reliable signal to proceed. The spheres, markers, or register can be built onto the rasp, graft delivery tube, dilator, or guide or can come as separate modular components that can be snapped, screwed, slid over, clamped or otherwise anchored to the rasp, rasp handle, graft delivery tube, dilator, or guide. The spheres or register can be disposable or reusable. The spheres or register can be formed of different types of reflective materials including metal, plastics, ceramics, polymers, glass, or any other suitable material. Once anchored, the spheres or register may be secured in place permanently or removably. In some embodiments, the spheres or register can include a push button for release or other release mechanism to rotate or remove the device.

In some embodiments, the spheres or register may be preset before a surgery is performed if, for example, a rasp, bone graft delivery system, dilator, or guide is used often. This will ensure the calibration is set properly to reach a desired spot that needs to be decorticated or that requires graft to be delivered for fusion. In other embodiments, the spheres or register can be calibrated during surgery, for example, if the rasp, bone graft delivery system, dilator, or guide are being used for the first time or infrequently.

In some embodiments, once the spheres or register are calibrated, the surgeon can proceed with 3D visualization of the surgical site. Once the surgical site is identified, the surgeon can drop the rasp instrument to an orthopedic site such as a transverse process and begin decortication using a mechanical rasp, file, burr or other object to remove cortical bone and create a bed for bone graft and fusion. The graft can then be delivered by actuating the delivery mechanism to advance bone graft out of the rasp to the desired surgical site.

As technology progress the surgeon may not necessarily have to perform the rasping or delivery. In some embodiments, a robotic arm may perform the rasping for decortication and bone graft delivery. In some embodiments, the robotic arm may grip either the rasp or delivery device to perform to surgery.

In some embodiments, bone graft may be hydrated with iodine or other radiopaque dye prior to loading the rasp, graft delivery device, or tube for visualization in imaging. In certain embodiments, without radiopaque dye the bone graft may be difficult to see after delivery to the surgical site. In certain embodiments, once rasping is complete, it is important that the graft be delivered directly over the decorticated bone for the best chance of creating a fusion. With the radiopaque dye, the surgeon can determine the correct amount of bone graft and ensure the graft is interconnected between the transverse process or other bones to be fused together.

Figure 43B:
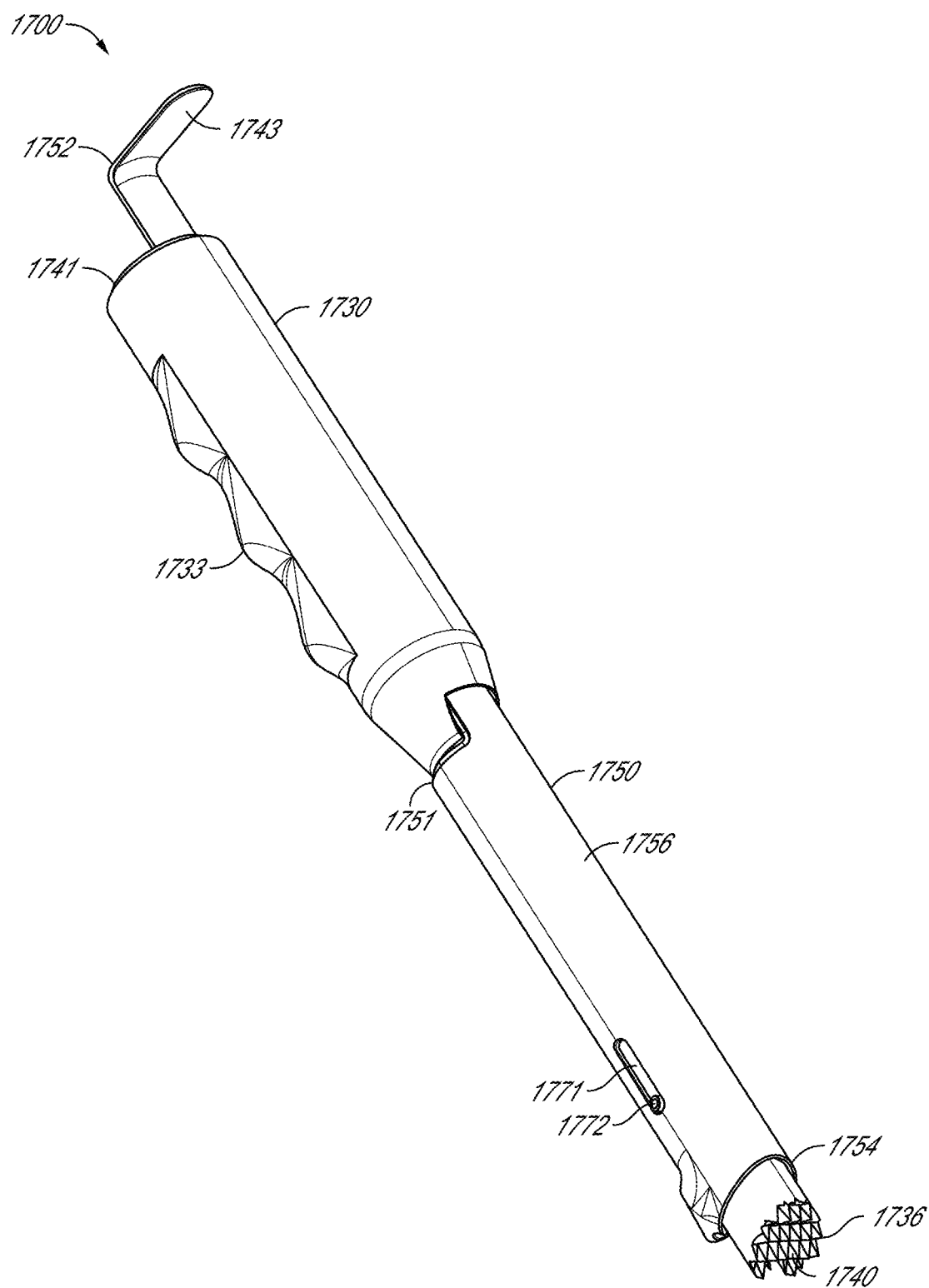
Figure 43C:
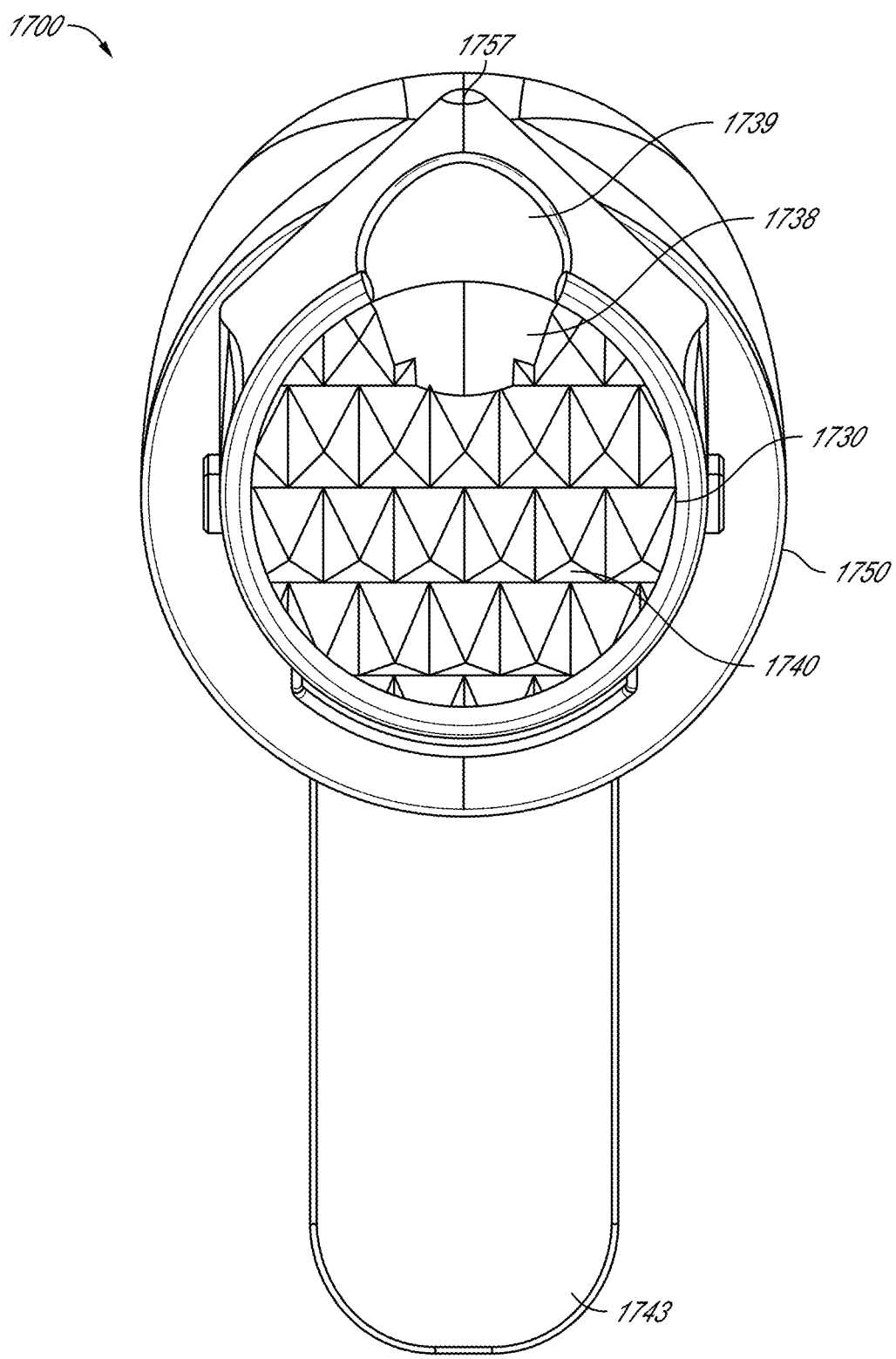

FIGS. 43A and 43B illustrate perspective views of an embodiment of an rasping system 1700 having an applicator, tip, or rasp 1730 and a sheath 1750. FIGS. 43C, 43D, 43E, 43F, and 43G illustrate a bottom view, a top view, a rear view, a front view, and an exploded view, respectively, of the rasping system 1700. FIGS. 44A and 44B show perspective views of the rasp 1730. FIGS. 45A and 45B show perspective views of the sheath 1750.

In certain embodiments, the rasp 1730 can include any of the same or similar functions and features as the distal tip 130, the tip 1030a, the tip 1030b, the applicator 850a, the applicator 850b, the and/or any of the rasps 1430a-l.

In some embodiments, the rasp 1730 can be integrally formed with or coupled, removably or permanently, to a bone graft delivery device, such as bone graft delivery devices 100 and 1400, for delivery of bone graft material to a desired location. In certain embodiments, the rasp 1730 can be integrally formed with or coupled, removably or permanently to a tube of a bone graft delivery device, such as tubes 120 and 1420. In some embodiments, the tube and rasp 1730 can be a modular system such that different tips can be selected and coupled to the tube for different procedures and/or target locations. In certain embodiments, one or more tubes and/or one or more rasps 1730 can be part of a bone graft delivery system kit.

In certain embodiments, the rasp 1730 can be integrally formed with or coupled, removably or permanently to a handle of a bone graft delivery device, such as handle 102. In some embodiments, the handle and the rasp 1730 can be a modular system such that different rasps can be selected and coupled to the handle for different procedures and/or target locations. In certain embodiments, one or more handles and/or one or more rasps 1730 can be part of a bone graft delivery system kit.

In the illustrated embodiment, the rasp 1730 includes a proximal end 1741 and a distal end 1736. The rasp 1730 also includes a handle section 1433.

In certain embodiments, the rasp 1730 may have a single or multiple openings 1738 configured to deliver bone graft material to a desired location. In some embodiments, the one or more openings 1738 are positioned within the distal end 1736. The one or more openings 1738 may be in fluid communication with a bone graft delivery device, such as bone graft delivery devices 100 and 1400, when the rasp 1730 is coupled thereto. In some embodiments, the one or more openings 1738 may be in fluid communication with an elongate tube of a bone graft delivery device, such as tubes 120 and 1420. In some embodiments, the one or more openings 1738 may be offset from a central axis of the distal section 1736.

In some embodiments, at least one side or area of the rasp 1730 includes a series of jagged edges or other suitable surface features 1740 configured to serve as a rasp for scraping bone. The rasping surface 1740 can have a variety of teeth patterns, sizes, diameters, and/or lengths to allow for rasping of different orthopedic sites including, but not limited to, the transverse process of the spine, facets, SI joint, disc space, tibial plateau, hip and an array of other locations. In certain embodiments, the rasping surface 1740 can be in the shape of a single blade similar to a cheese grater to file the bone down and allow it to bleed.

As shown in FIGS. 43A-44B, the edges of the rasping surface 1740 may be triangular in shape. In some embodiments, the edges may be flat. In some embodiments, the jagged edges may form a plurality of flat surfaces parallel with each other all within the same plane. In some embodiments, the rasping surface 1740 can include a roughened surface. In some embodiments, the rasping surface 1740 may be positioned on at the distal end 1736. The rasp 1730 may be operated manually or by mechanical, battery powered, electric, pneumatic, or any other means of force to allow for decortication of the area to receive the bone graft material using the rasping surface 1740. The rasp 1730 can be used to decorticate bone in the spine or other regions where orthopedic fusion is needed. In some embodiments, at least some of the one or more openings 1738 for delivering bone graft material are located on a side or portion of the rasp 1730 that does not include a rasping surface. In some embodiments, at least some of the one or more openings 1738 are located on a side or portion that does include a rasping surface 1740.

In some embodiments, the handle section 1733 can include one or more finger grips or other surface features configured to facilitate gripping by a user. In use, a user can grasp the handle or finger grips to manipulate the rasp 1730 to scrape or decorticate bone. In other embodiments, the rasp 1730 does not include a handle or grip. In some embodiments, the handle section 1733 can be integrally formed with the distal end 1736. In other embodiments, the handle section 1733 and the distal end 1736 can be separate components that may be coupled, removably or permanently to form the rasp 1730.

Figure 43D:
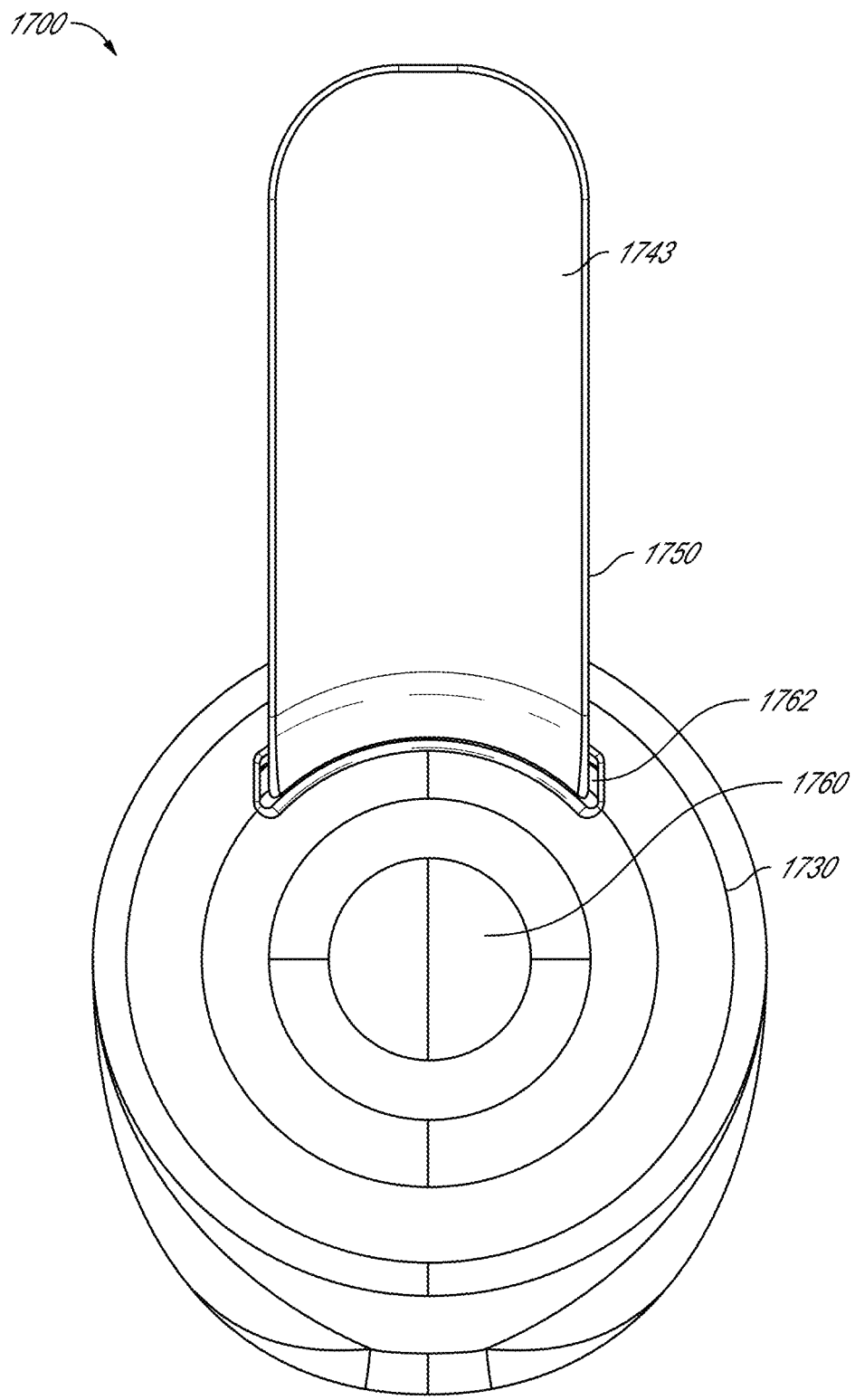
Figure 43E:
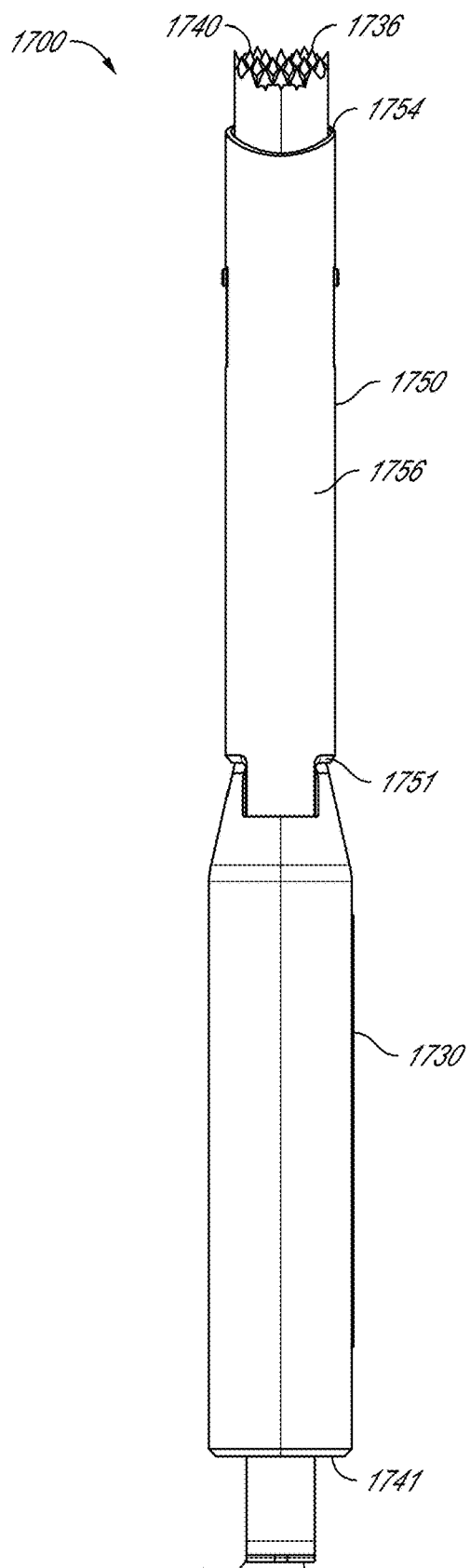
Figure 43F:
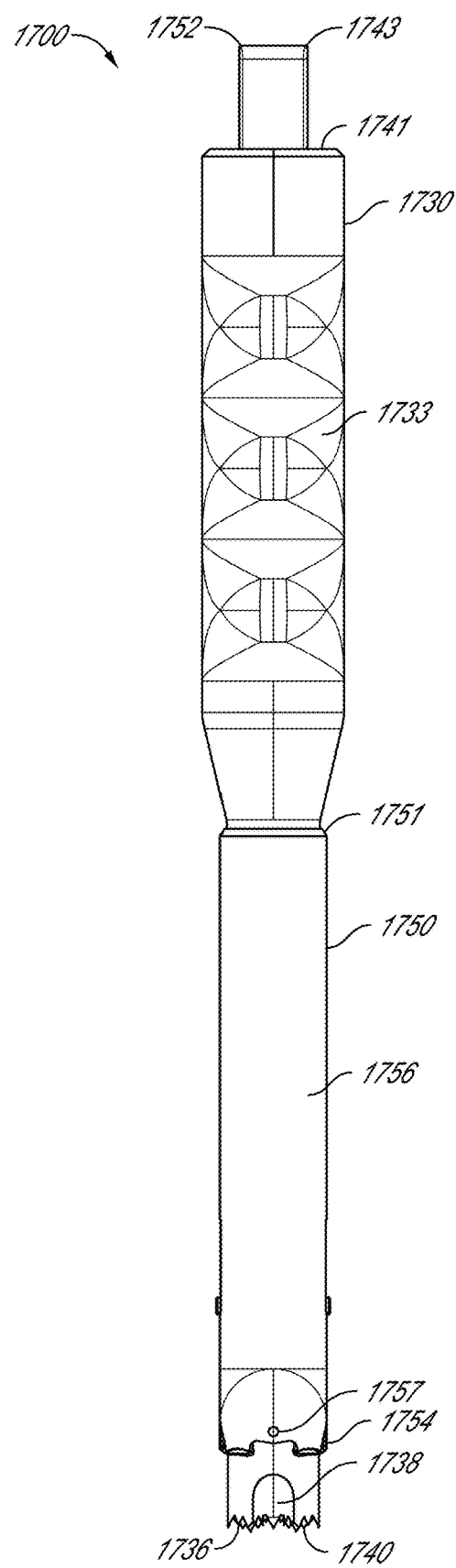
Figure 43G:
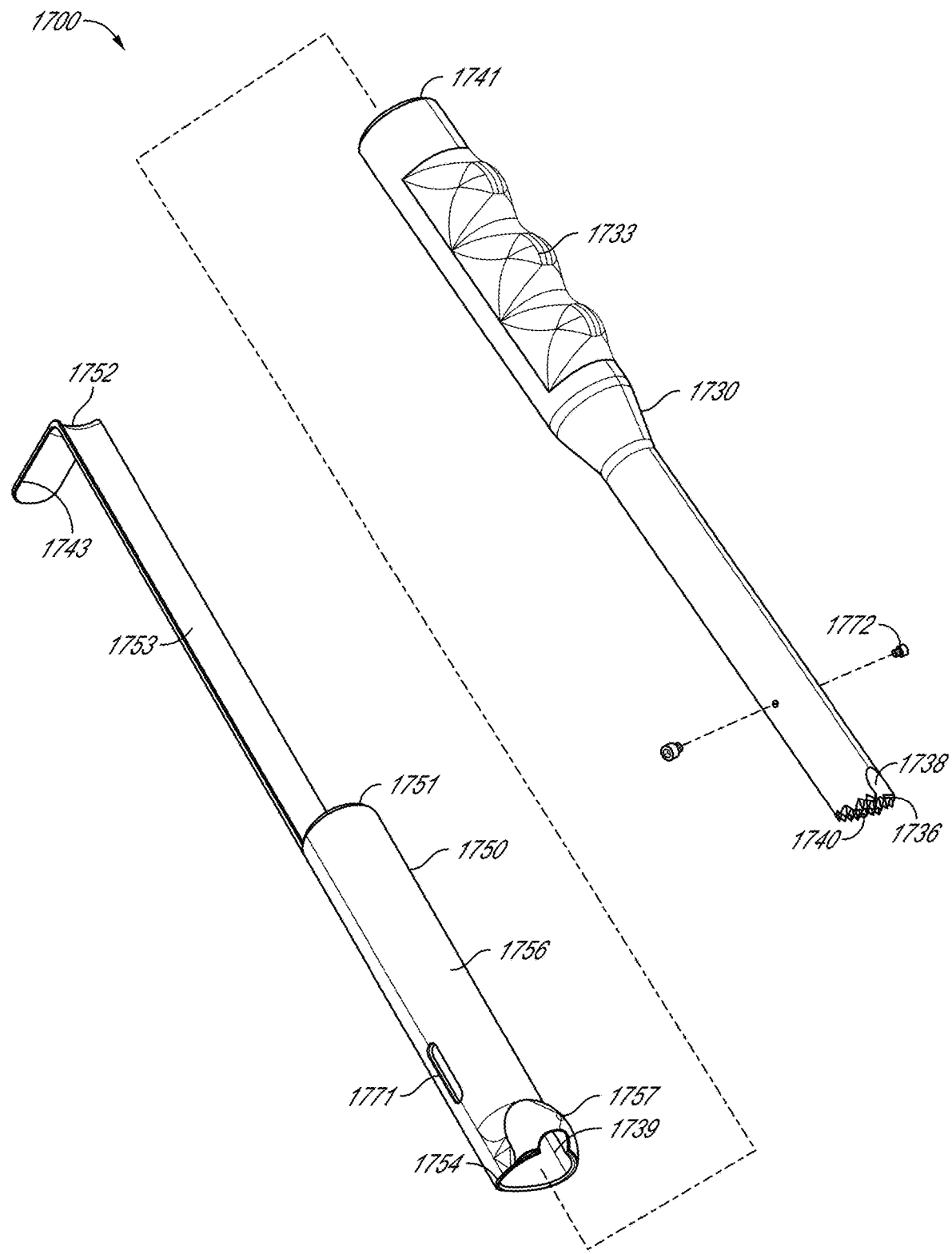

As shown in FIG. 43D, the rasp 1730 can include an opening 1760 at the proximal end 1741. The rasp 1730 can define a lumen between the opening 1760 and the one or more openings 1738 to allow delivery of bone graft therethrough. In some embodiments, bone graft can be delivered into the opening 1760 and then exit through the opening 1738. In some embodiments, a pusher or other means may be used to deliver graft through the lumen of the rasp 1730.

As shown in FIGS. 43A-G and 45A-B, the sheath 1750 can include a proximal end 1752 and a distal end 1754. The sheath 1750 can include a tubular section 1756 defined by an open distal end 1754 and an open proximal end 1751. The tubular section 1756 can be configured to receive at least a portion of the rasp 1730 therein. In certain embodiments, the sheath 1750 can include a handle 1743. The handle 1743 can be positioned at the proximal end 1752 of the sheath 1750. In certain embodiments, the sheath 1750 can include a connection section 1753 extending between the handle 1743 and the tubular section 1756.

In certain embodiments, the distal end 1754 of the sheath 1750 can include an opening 1739. The distal end 1754 can further include a tip 1757. In some embodiments, the tip 1757 at least partially defines the opening 1739. In the illustrated embodiment, the tip 1739 is at least partially conical or generally conical. In some embodiments, the tip 1757 is pointed, bulleted, and/or sharp to dissect or split muscle and tissue as it is advanced to the surgical location. Alternatively, the tip 1757 can be blunt to allow for displacement of muscle without risk of cutting of nerves or other tissue.

As shown in FIG. 43D, the rasp 1730 can include a slot 1762 at the proximal end 1741. As shown in FIG. 44B, the applicator 1740 can further include a slot 1763. At least a portion of the sheath 1750 can extend within the rasp 1730 in a lumen between the slot 1762 and the slot 1763. In certain embodiments, at least a portion of the connection section 1753 can extend within the rasp 1730 in a lumen between the slot 1740 and the slot 1763. The connection section 1753 can be configured to slide within the lumen between the slot 1762 and the slot 1763. In certain embodiments, at least a portion of the sheath 1750 can extend proximally from the slot 1762. For example, in certain embodiments, the handle 1743 can extend proximally from the slot 1762. As shown in FIGS. 43A-F, the tubular section 1756 can be positioned distally to the slot 1763.

The sheath 1750 can be slidably or telescopingly disposed over the rasping surface distal end of the 1736 of the rasp 1730. In some embodiments, a user can distally advance or proximally retract the sheath 1750 relative to the distal end 1736 of the rasp 1730, for example, by manipulating the handle 1743. In some embodiments, the tubular section 1756 of the sheath 1750 can be disposed over the rasping surface 1740 during insertion of the rasp 1730 to the target area to advantageously protect skin, tissue, and/or muscle along the insertion path from damage or injury from the rasping surface 1740 and to allow the rasp 1730 to pass through the skin, tissue, and/or muscle more easily. Once the rasp 1730 is positioned in the target location, the sheath 1750 can be proximally retracted to expose the rasping surface 1730 for decortication of the target area. After decortication and/or after delivery of the bone graft material, the sheath 1750 can be distally advanced to cover the rasping surface 1740 for withdrawal of the rasp 1730 from the body.

In certain embodiments, when the distal end 1736 of the applicator is retracted within the tubular section 1756 of the sheath 1750, the opening 1738 of the rasp 1730 can be aligned with the opening 1739 of the sheath 1750 to allow for delivery of bone graft material.

In some embodiments, the sheath 1750 can include one or more slots 1771. In some embodiments, one or more pins or protrusions 1172 can be coupled to or integrally formed with the rasp 1730 and be configured to engage the slots 1171. In use the pins can extend out of the slots such that the ends of the slots 1771 can prevent further proximal or distal movement of the pins 1772 within the slots so as to limit the range of proximal and distal movement of the sheath 1750 and rasp 1730 relative to one another. In some embodiments, the slots 1772 can be sized, shaped, or otherwise configured to limit or prohibit relative rotation between the sheath 1750 and rasp 1730.

In certain embodiments, the lumen of the rasp 1730 can be dimensioned, shaped, or otherwise configured to receive a tube, such as tubes 120 and 1420. In some embodiments, when a tube is positioned within the lumen of the rasp 1730, bone graft material can flow through the tube and out of the opening 1738.

In some embodiments, the rasp 1730 can be releasably secured to the tube when the rasp 1730 is positioned over the tube. In some embodiments, the rasp 1730 can be securely coupled to the tube by threads, grooves, bumps, nubs, snap fit, or any other suitable coupling mechanism. In other embodiments, the rasp 1730 may only abut the tube without being secured to the tube. In certain embodiments, the handle portion 1733 or lumen of the rasp 1730 can be configured to couple to the tube.

In some embodiments, the rasp 1730 can be used with a bone graft delivery device, such as bone graft delivery device 100 or 1400. In certain embodiments, the rasp 1730 can be used with a bone graft delivery system configured to deliver bone graft through ratcheting, worm gear, rack and pinion, spindle drive, threaded or any other suitable means to extrude bone graft from the delivery device. In certain embodiments, the bone graft delivery system can be a tube, such as tube 120 or 1420, and a plunger, such as plunger 112 or pusher rod 312, a syringe, such as syringe 1110, or a loading device, such as loading devices 600, 700, or 900, configured to cause the flow of bone graft material through the tube.

In certain embodiments, the rasp 1730 can be coupled to or positioned over a portion of a bone graft delivery device, such as delivery devices 100 and 1400, to allow for the flow of bone graft material from the delivery device through the rasp 1730. In certain embodiments, the rasp 1730 can be coupled to the bone graft delivery device by threads, grooves, bumps, nubs, snap fit, or any other suitable coupling mechanism. In other embodiments, the rasp 1730 may only abut the delivery device without being secured to the delivery device. In some embodiments, the handle portion 1733 or lumen of the rasp 1730 can be configured to couple to the bone graft delivery device.

In some embodiments, a tube, such as tubes 120 and 1420, positioned within the rasp 1730 may be configured to rotate freely within the lumen of the rasp 1730. In other words, in some embodiments, the rasp 1730 may be configured to rotate freely about the tube and/or relative to the delivery device. Rotation of the rasp 1730 can allow a user to grasp the handle section 1733 from different directions or angles. Rotation of the rasp 1730 can allow the user to choose any angle to insert the graft delivery tube into the lumen to deliver graft while rasping bone. In certain embodiments, the rasp 1730 can be configured to engage or secure to the tube to prevent rotation of the tube within the rasp 1730, which can provide increased stability and control.

The lumen and/or the handle 1733 of the applicator can have a variety of different diameters and/or lengths to accommodate different graft delivery tubes and/or graft delivery systems.

The rasp 1730 can be formed of one or more materials including metals, polymers, ceramics, or any other suitable materials. In some embodiments, rasp 1730 may be formed of materials of varying rigidity and flexibility to facilitate access, decortication, and/or graft delivery to different areas of the body. In some embodiments, the rasp 1730 can be reusable. In other embodiments, the rasp 1730 can be disposable. In certain embodiments, the rasp 1730 can be provided in a sterile package for single use by any means of terminal sterilization including, but not limited to EO, E beam, and gamma. In certain embodiments, the components of the rasp 1730 and any graft delivery system or device may be autoclaved and reusable. In certain embodiments, the components of the rasp 1730 and/or delivery system may be assembled with screws, anchors, clips, glued, or any other suitable means. In certain embodiments, the components of the rasp 1730 and/or delivery system or device may be machined in one piece or come in different components. In certain embodiments one or more components of the rasp 1730 can be 3D printed.

In some embodiments, one or more applicators 1730, one or more delivery systems or devices, one or more dilators, bone graft, one or more guides, one or more burrs, one or more handles, and one or more markers and trackers for image guidance may be packaged together as a kit or individually.

The rasp 1730 can be made of a metallic, radiopaque material to facilitate visualization on, for example, fluoroscopy or x-ray. Alternatively, the rasp 1730 may be made of another material, for example a durable medical plastic or a composite material, and may include markers to facilitate visualization.

In some embodiments, one or more components that act as a register for image guidance can be attached to the bone graft delivery system or device or the rasp 1730 to register placement on an imaging modality to allow for tracking of the rasp 1730 or bone graft delivery system or device.

In certain embodiments, the rasps, applicators, tubes, bone graft delivery systems, and/or bone graft delivery devices described herein, such as rasps 1430a-l and rasp 1730, can be used with one or more dilators, for example, in methods for minimally invasive surgery. In some embodiments, multiple sequential dilation tubes may be used. In some embodiments, a dilator may act as a guide for the rasps, applicators, tubes, bone graft delivery systems, and/or bone graft delivery devices described herein, such as rasps 1430a-l and rasp 1730. In some embodiments, a final sequential dilator may be used as a guide for the rasps, applicators, tubes, bone graft delivery systems, and/or bone graft delivery devices described herein, such as rasps 1430a-l and rasp 1730.

FIG. 34A illustrates an embodiment of a dilator or guide 1450 positioned within a spine of a patient. 34B illustrates a bottom perspective view of the dilator or guide 1450. FIGS. 35A-C illustrate the guide 1450 and rasp 1430a positioned within a spine of a patient. Although a rasp 1430a is shown in FIGS. 35A-C, it is also contemplated that the guide tube 1450 can be used with any of the rasps 1430b-l or the rasp 1730.

The guide 1450 can include a proximal end 1452, a distal end 1454, and a dilator body 1456 extending therebetween. In certain embodiments, the guide 1450 can be generally cylindrical in shape.

In some embodiments, the guide 1450 is generally hollow to allow for the passage of an elongate tube, such as tube 120 or 1420, and/or rasps 1430a-l or 1730 through a lumen 1451 of the guide 1450 or at least a portion of the lumen 1451 of the guide 1450. The rasp 1430a-l and 1730 and/or tube can be advanced through the lumen 1451 of guide 1450 towards a desired location within a patient. The guide 1450 can be disposed over at least a portion of the rasp 1430a-l or 1730 during insertion of the rasp 1430a-l or 1730 to the target area to advantageously protect skin, tissue, and/or muscle along the insertion path from damage or injury from the rasping surface 1040 and to allow the rasp 1430a-l or 1730 to pass through the skin, tissue, and/or muscle more easily. After decortication and/or after delivery of the bone graft material, the rasp 1430a-l or 1730 can be withdrawn through the lumen of the guide 1450. In some embodiments, the lumen can extend at least partially between the proximal end 1452 and the distal end 1454. In some embodiments, the lumen can be at least partially defined by the body 1456.

In some embodiments, the guide 1450 can include a handle 1443. In some embodiments, the handle 1443 can be positioned at the proximal end 1452 of the guide 1450. In certain embodiments, the handle 1443 can include an elongate opening or slot 1455 at the proximal end of the guide 1450. In some embodiments, the elongate opening 1455 can extend at least partially perpendicularly to a longitudinal axis of the guide 1450. In some embodiments, the elongate opening 1455 can extend beyond the edges of the dilator body 1456, for example, laterally beyond the edges of the dilator body. For example, in some embodiments, the elongate opening 1455 can extend a distance of up to 7 inches from an edge of the dilator body 1456. In some embodiments, the elongate opening 1455 can be partially formed by the dilator body 1456 in addition to the handle 1443 or fully formed by the dilator body 1456. In some embodiments, the elongate opening 1455 can be at least partially recessed within the handle 1443. In some embodiments, the opening 1445 can at least partially define the lumen 1451.

The elongate opening 1455 can be shaped, sized, positioned, and/or otherwise configured to allow for medial/lateral movement, superior/inferior movement, and/or anterior/posterior movement of the rasp 1430*a-l* or 1730 within the patient to adjust a location for decortication and/or delivery of the bone graft material. In some embodiments, the handle 1443 can be configured to facilitate user comfort. The handle 1443 can be dimensioned, shaped, textured, or otherwise configured to facilitate user comfort. In some embodiments, handles 1443 can be provided in different, lengths, widths, thicknesses, and/or textures to facilitate comfort among various users. In some embodiments, the handle 1443 can be removable. In some embodiments, the handle 1443 can be removably coupled to or integrally formed with the body 1456. In some embodiments, the handle 1443 can be rotatable relative to the body 1456. In some embodiments, the handle 1443 can be movable along the length of the body 1456 of the guide 1450. In some embodiments, guides 1450 having handles at different locations along the length of the guide 1450 can be provided.

The guide 1450 can include a slot, opening, or groove extending longitudinally along the body 1456 of the guide 1450. The slot or groove can be shaped, sized, positioned, and/or otherwise configured to allow passage of a curved or angled tube and/or a curved or angled tip through the lumen of the guide 1450. The slot or groove may also be shaped, sized, positioned, and/or otherwise configured to allow for medial/lateral movement, superior/inferior movement, and/or anterior/posterior movement of the rasp 1430*a-l* or 1730 within the patient to adjust a location for decortication and/or delivery of the bone graft material.

In the illustrative embodiment, the guide 1450 includes a slot, opening, or groove 1457 extending distally from the handle 1443 to the distal end 1454 of the guide 1450. In some embodiments, the slot 1457 can extend only partially towards the distal end 1454 of the guide 1450. In some embodiments, the slot 1457 can extend partially between the handle 1443 and the distal end of the guide 1450. In some embodiments, the slot can be defined at least partially by the body 1456. The slot 1457 can be sized and/or shaped to allow passage of a tube and/or rasp 1430*a-l* or 1730 along the slot. In some embodiments, the slot 1457 can be open at the distal end 1454. In some embodiments, the slot 1457 can be closed at the proximal end 1452. In some embodiments, the slot 1457 can extend from the distal end 1454 to the proximal end 1452 and be open at both ends. In some embodiments, the slot 1457 can extend from the distal end 1454 to a point halfway between the proximal end 1452 and the distal end 1454. In some embodiments, guides 1450 having varying slot lengths can be provided to facilitate use of different rasp sizes or use in different procedures.

In some embodiments, the handle 1443 can be positioned at different locations along the guide 1450 with respect to the orientation of the longitudinal slot.

In some embodiments, the handle 1443 may configured to engage with or couple to a table clamp or arm to stabilize the guide 1450 during use. Stabilizing the guide 1450 using a table clamp or arm can allow a surgeon to have both hands free for rasping or bone graft delivery without having to also stabilize the guide 1450.

In some embodiments, the distal end 1454 of the guide 1450 can include one or more teeth, ridges, grooves, and/or any other suitable surface features for anchoring or docking on bone and/or to prevent slipping.

Figure 35D:
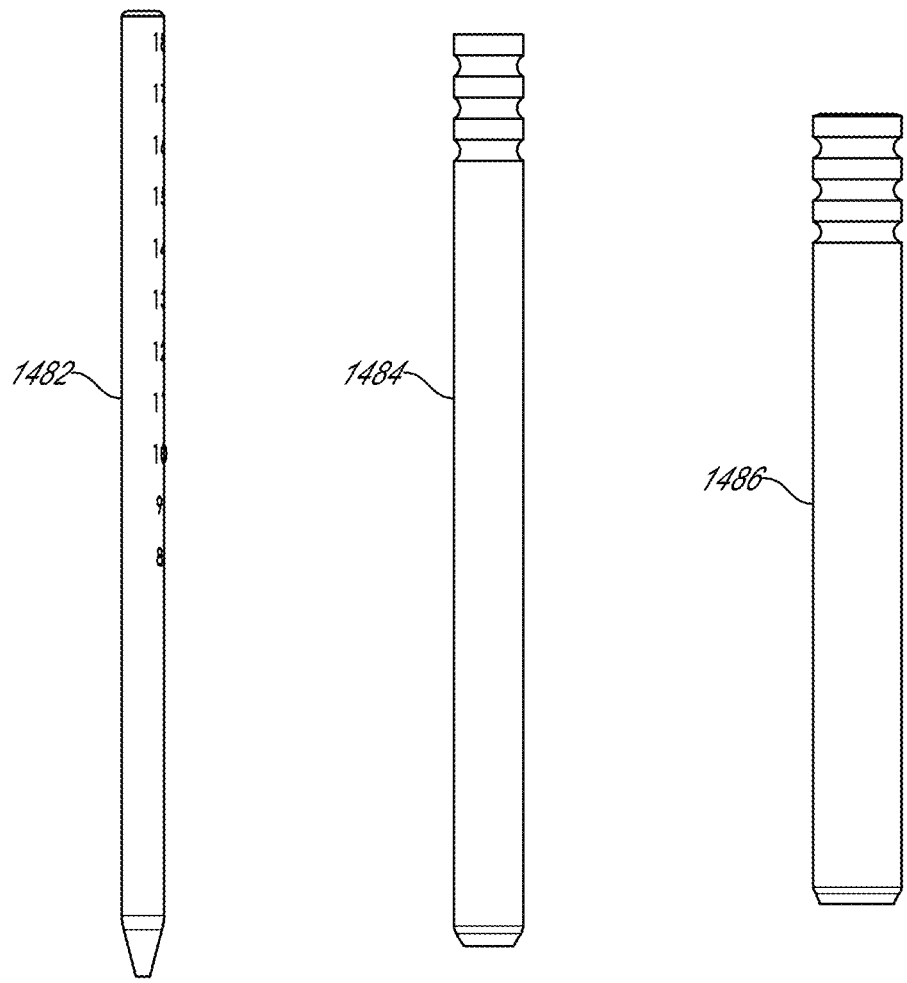
FIG. 35D illustrates embodiments of dilators that can be used in a bone graft delivery system.
Figure 35E:
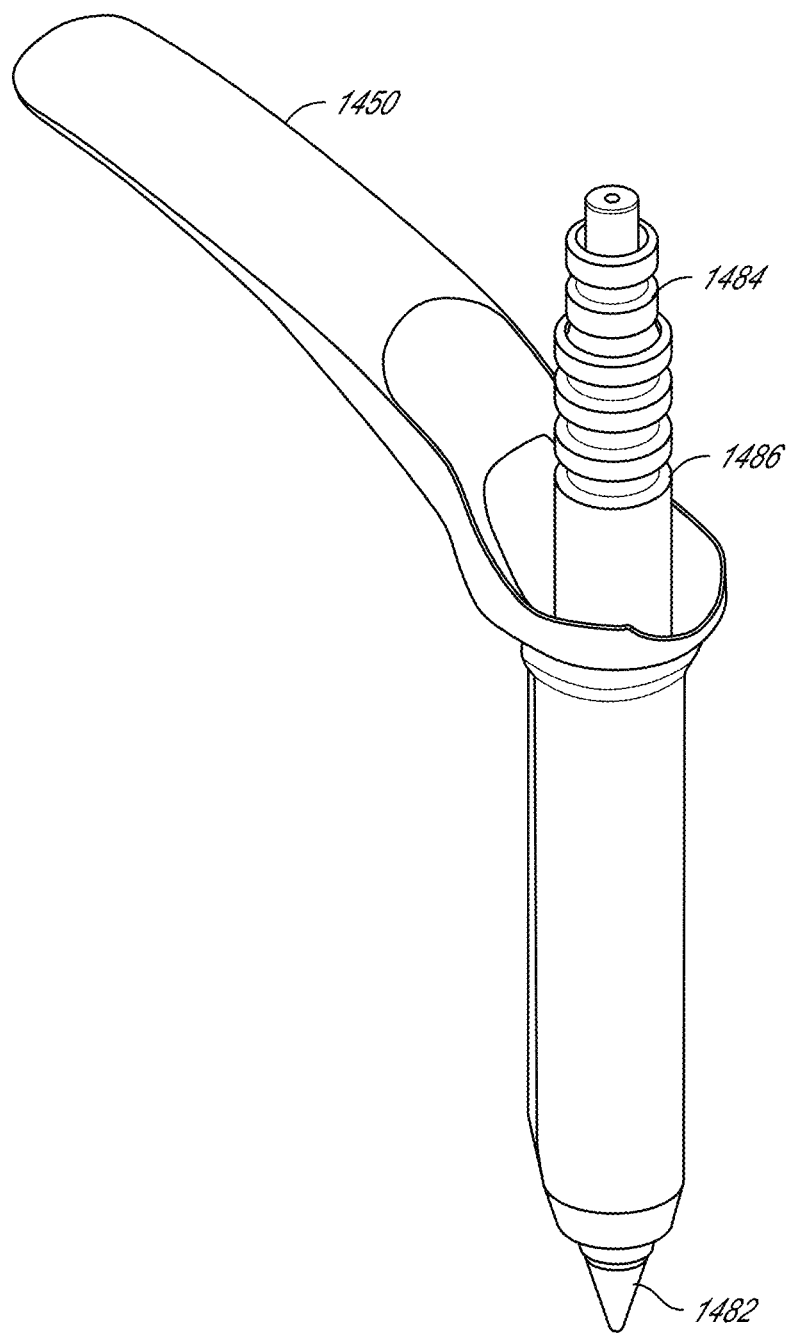
FIG. 35E illustrates the dilators of FIG. 35D positioned within the guide of FIG. 34A.

FIG. 35D depicts examples of sequential dilators 1482, 1484, and 1486 that can be used with the guide 1450. FIG. 35E depicts that sequential dilators 1482, 1484, and 1486 and the guide 1450 together. The dilators 1482, 1484, and 1486 and guide 1450 can be used to create and sequentially enlarge a channel within the body for access to a surgical location. In certain embodiments, the channel can be formed using the dilator 1482. After formation of the channel, the dilator 1484 can be used to expand the channel. The dilator 1486 can be used after the dilator 1484 to further expand the channel. The guide 1482 can then be used to further expand the channel. After the guide 1482 is in place and the dilators 1482, 1484, and 1486 have been be removed, the guide 1482 can be used as a guide for the rasps, applicators, tubes, bone graft delivery systems, and/or bone graft delivery devices described herein.

In some embodiments, a method for decorticating bone and/or delivering bone graft material to a surgical location includes making an incision in a body of a patient. In some embodiments, after an incision is made, a guidewire can be advanced towards the surgical location. In some embodiments, a retractor can be introduced into the incision to retract the tissue. Examples of retractors that can be used in the embodiments described herein are shown in FIG. 21A-D. One or more dilators, such as dilators 1482, 1484, 1486, or guide 1450, can be advanced along the guidewire towards the surgical location. The dilators can be used to dilate muscle or tissue to allow access to bony structures. In some embodiments, after a final dilator, such as guide 1450, is positioned within the patient, an elongate tube, such as elongate tube 120 or tube 1420, and a tip, such as tip 1030*b* or rasp 1430*a-l* or 1730, can be advanced through a lumen of the dilator towards the surgical location. In some embodiments, the tip or rasp can be advanced out of the slotted dilator and traversed through muscle or tissue to other bony structures, such as a transverse process. In some embodiments, the method further includes decorticating or rasping bone, such as the transverse process, with the tip or rasp. In some embodiments, the method further includes delivering bone graft material through the elongate tube and the tip or rasp. In some embodiments, the method further includes adjusting the lateral position of the tip or rasp while the elongate tube is positioned within the dilator. After decortication and/or delivery of bone graft material, the elongate tube and tip or rasp can be retracted through the slotted dilator and/or removed from the slotted dilator. The dilators, tubes, tips, rasps, retractors, bone graft delivery devices, and bone graft delivery systems, described herein can be used in medical procedures including posterior lateral fusion procedures, sacroiliac joint fusion procedures, subtalar fusion procedures, hip revision procedures, knee revision procedures, and Charcot joint procedures.

It should be recognized that the guide 1450 can be used with any of the tubes and/or tips described herein. In certain embodiments, one or more guides 1450 may be part of a bone graft delivery system kit as described herein with one or more elongate tubes and/or tips.

In certain embodiments, one or more caps can be coupled to the ends of a delivery tube, such as tube 120 or tube 1420.

In some embodiments, the caps can include openings, channels, or other connections to facilitate the flow of fluid into or out of the delivery tube, for example, as described herein with respect to connector 1100. Further examples of such caps and tubes are shown in FIGS. 36A-B and 37A-B.

Figure 36A:
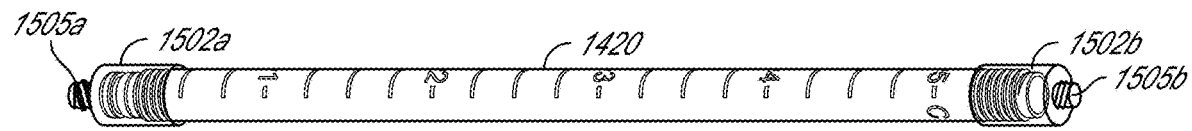
FIG. 36A illustrates a perspective view an embodiment of a tube of a bone graft delivery system with caps of a bone graft delivery system.
Figure 36B:
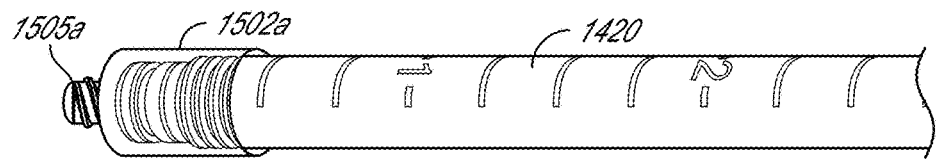
FIG. 36B illustrates a partial view of the tube of FIG. 36A.

FIG. 36A depicts the tube 1420 with a cap 1502*a* coupled to the first end of the tube and a cap 1502*b* positioned on a second end of the tube 1420. In certain embodiments, the caps 1502*a* and 1502*b* can include any of the same or similar features or functions as the connector 1100. In certain embodiments, the caps 1502*a* and 1502*b* can be luer locks or luer lock style caps. In some embodiments, only one of the caps 1502*a* or 1502*b* can be positioned on a single end of the tube 1420.

The caps 1502*a* and 1502*b* can have tips or connection portions 1505*a* and 1505*b* having channels to facilitate the transmission of fluid into and out of the tube 1420. For example, in certain embodiments, the connection portions 1505*a* and 1505*b* can facilitate the delivery of fluid into the tube 1420 for rehydration of bone graft within the tube 1420. In some embodiments, the connection portions 1505*a* and 1505*b* can be luer lock style connection portions sized, shaped, or otherwise configured to couple to a syringe, such as syringe 1110, or loading or a loading device, such as loading devices 600, 700, or 900.

Figure 38A:
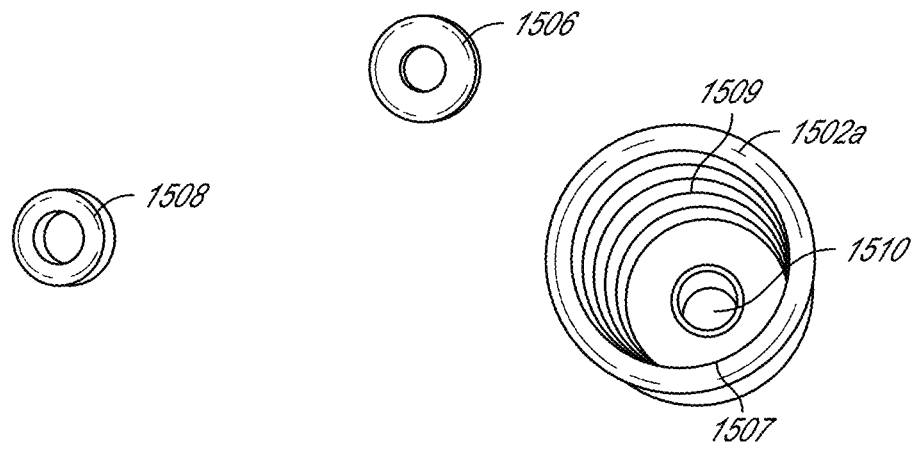
FIG. 38A illustrates a perspective view of one of the caps of FIG. 36A and gaskets for use with a tube of a bone graft delivery system.
Figure 38B:
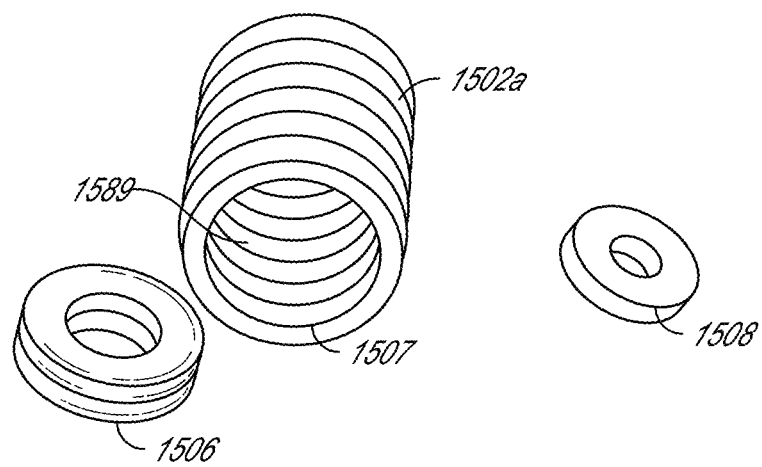
FIG. 38B illustrates a perspective view of the cap and gaskets of FIG. 38A.

In some embodiments, the caps 1502*a* and 1502*b* may contain one or more gaskets or seals 1506 and 1508 as seen FIGS. 38A-B to prevent leakage of fluids when dispensing the fluids into the tube under pressure. in some embodiments, the caps 1502*a* and 1502*b* includes an opening 1507 sized, shaped, or otherwise configured to receive an end of the tube 1420. The caps 1502*a* and 1502*b* also include an opening 1510 sized, shaped, or otherwise configured to facilitate the flow of fluid into and/or out of the tube 1420. The opening 1510 can be sized, shaped, or otherwise configured to receive an end of a syringe for the delivery of fluid into the tube 1420.

In some embodiments, the caps 1502*a* and 1502*b* can thread, snap, slide, push on and/or otherwise couple to the tube 1420. In some embodiments, the caps 1502*a* and 1502*b* can include a threaded portion 1509 configured to releasably secure to complementary threads of the tube 1420.

Figure 39A:
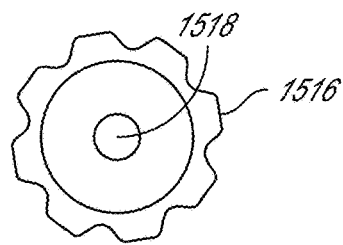
FIG. 39A illustrates a top view of an embodiment of a cap for use with a tube of a bone graft delivery system.
Figure 39B:
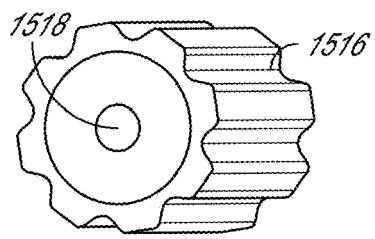
FIG. 39B illustrates a perspective view of the cap of FIG. 39A.
Figure 40:
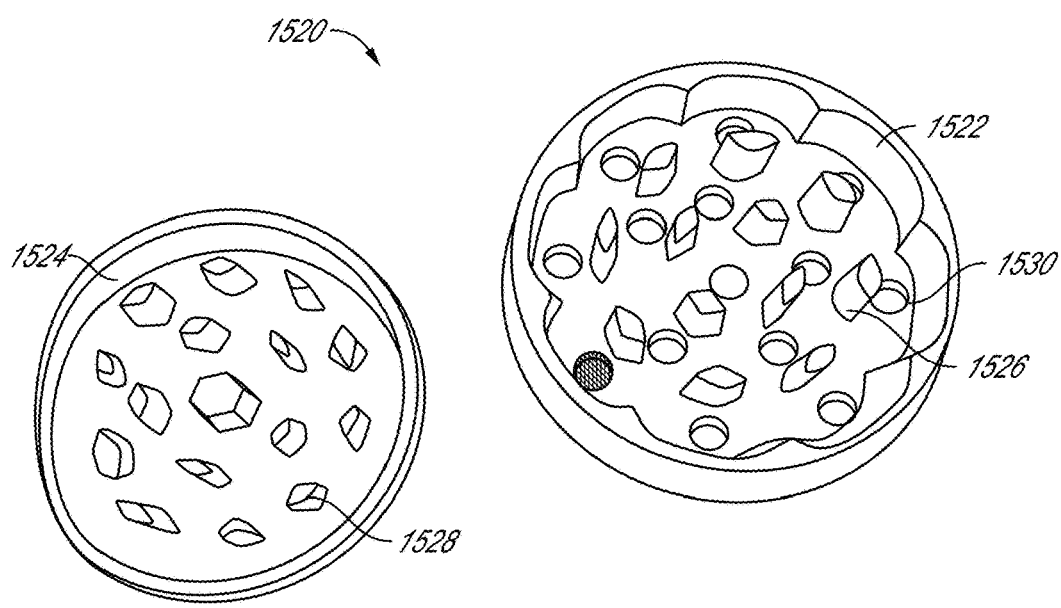

FIGS. 39A-B depict an embodiment of a cap 1516 that can be used one or both ends of a tube, such as tube 120 or tube 1420. In some embodiments, the cap 1516 can include any of the same or similar features as the connector 1100 and/or the caps 1502*a* and 1502*b*. The cap 1516 includes a hole 1518 to facilitate the flow of fluid into or out of the tube, for example, for rehydration of bone graft within the tube. In some embodiments, the cap 1516 can be formed by creating a hole in a standard cap design to close the ends of a tube, such as tube 120 or tube 1420.

In some embodiments a hole 1518 can be sized, shaped, or otherwise configured to engage a syringe, such as syringe 1110, or loading or a loading device, such as loading devices 600, 700, or 900, to facilitate the delivery of fluid from the syringe or loading device into the tube. In some embodiments, the cap 1516 can thread, snap, slide, push on and/or otherwise couple to the tube. For example, in some embodiments, the cap 1516 can include inner threads configured to couple to complementary threads of the tube.

A syringe or loading device can be used to dispense a wide variety of fluids or liquids into a tube, such as tube 120 or tube 1420, for rehydration or mixing of bone graft. Examples of fluids or liquids that may be used with the tube include PRP, bone marrow aspirate, stem cells, blood, saline, water, iodine or contrast (to aide in visualization on imaging).

In some embodiments, the connector or connectors 1100, cap or caps 1502*a*, 1502*b*, and/or 1516 at one or both ends of the tube can be used to hydrate bone graft materials including, but not limited to DBM putty, cellular matrix, cortical fibers, synthetic graft, cancellous sponges, synthetic foam or other suitable bone graft materials that can wick blood.

Bench tests were performed using a syringe to direct fluid into a single cap on one end of a bone graft delivery tube, such as tube 120 or tube 1420. In the bench tests with a single cap on one end of the tube, fluid or liquid did not flow completely from one end of the tube to the other end of the tube because graft became trapped in the tube, even with the exertion of large amounts of force on the syringe. Similar tests were also performed with a luer lock style cap, such as connector 1100 and caps 1502*a* and 1502*b*, on each end. With a luer lock cap on each end, fluid flowed through the tube with multiple types of porous or fibrous bone graft.

Figure 37A:
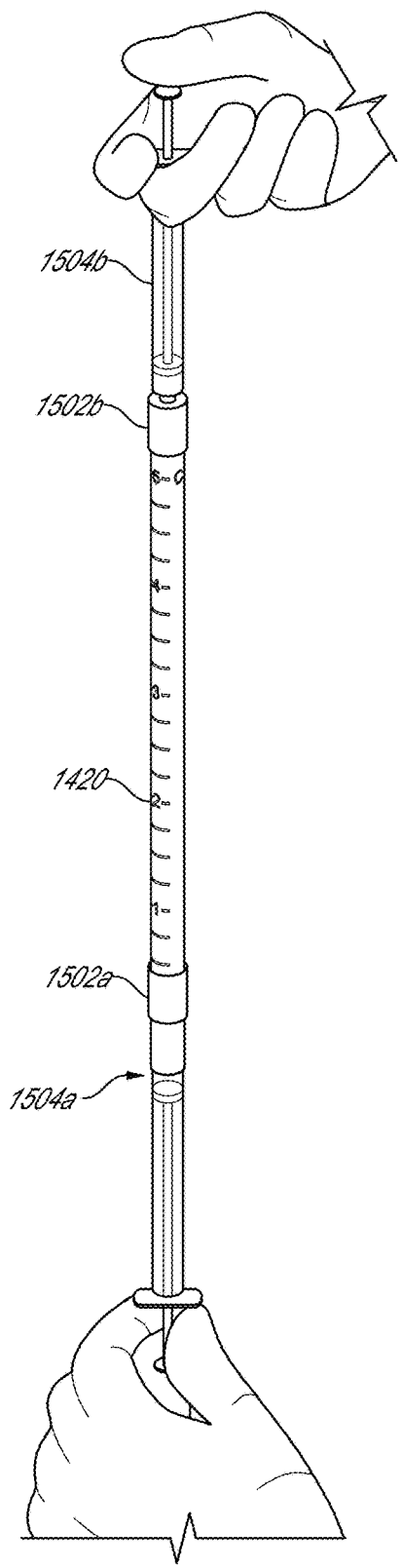
FIG. 37A illustrates an example of a procedure for hydrating graft within the tube of FIG. 36A.
Figure 37B:
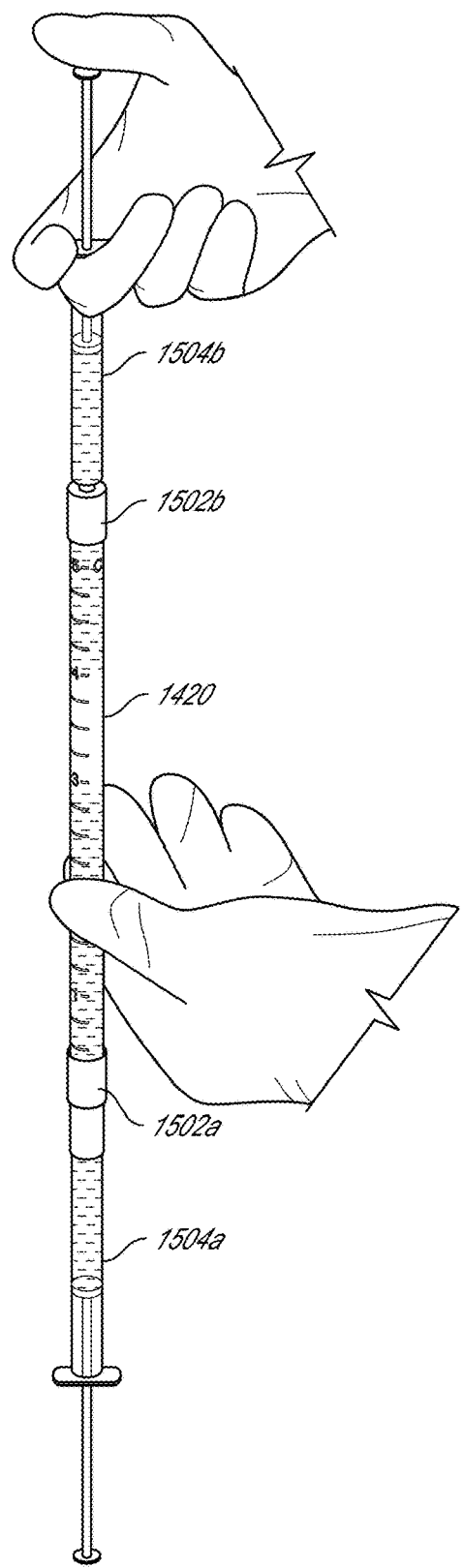
FIG. 37B illustrates an example of a procedure for hydrating graft within the tube of FIG. 36A.
Figure 37C:
FIG. 37C illustrates an example of a procedure for hydrating graft within the tube of FIG. 36A.
Figure 37D:
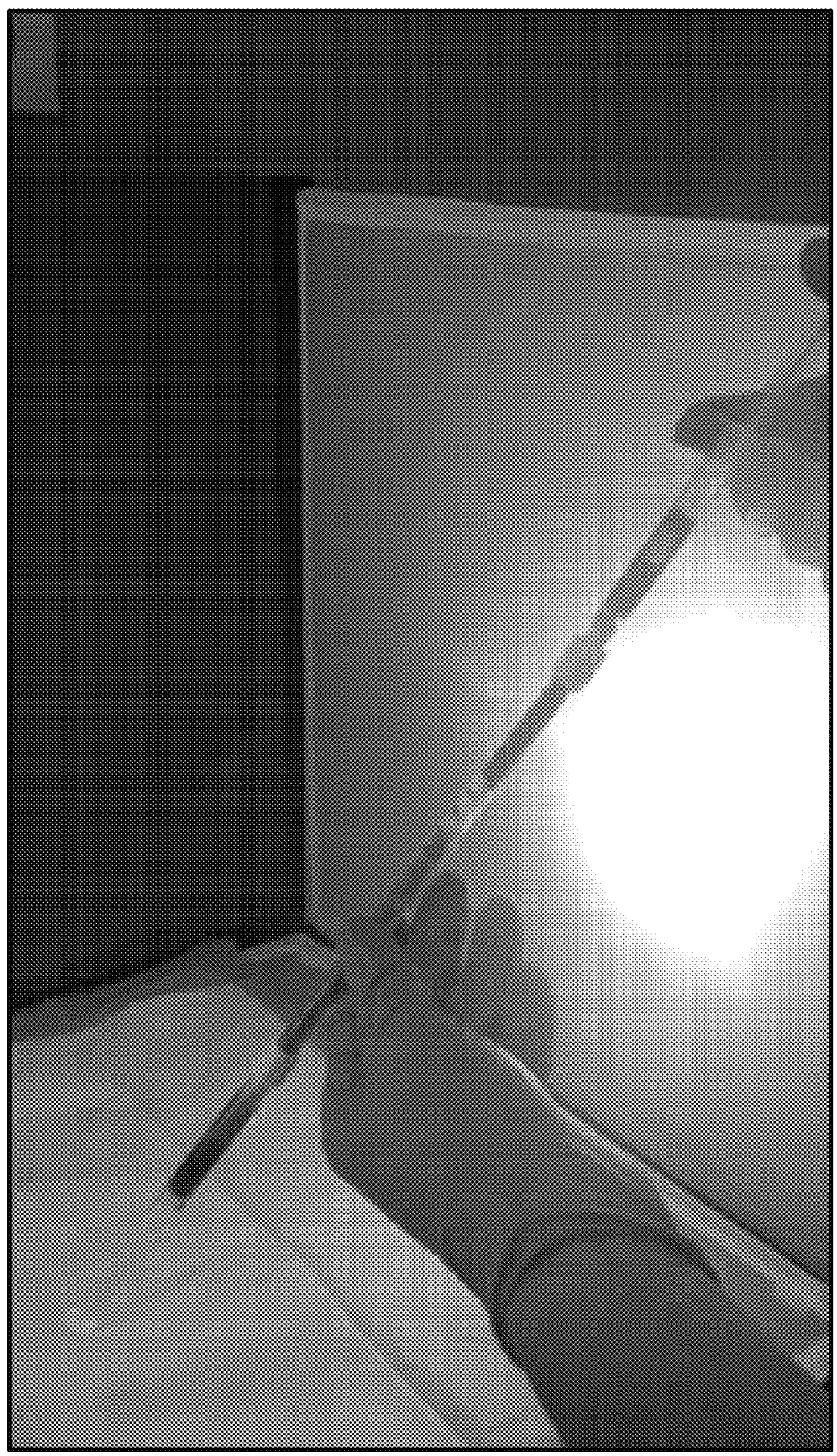
FIG. 37D illustrates an example of a procedure for hydrating graft within the tube of FIG. 36A.

As shown in FIGS. 37A-B, in some embodiments, a first syringe 1504*a* can be used to deliver fluid through a first cap 1502*a* and a second syringe 1504*b* can be used to deliver fluid through a second cap 1502*b*. The syringes 1504*a* and 1504*b* can have any of the same or similar features and functions as the syringe 1110 and/or the loading devices 600, 700, and/or 900. In some embodiments, the first syringe 1504*a* can be used to deliver fluid through the first cap 1502*a* and the second syringe 1504*b* can be used to create suction through the other cap 1502*b* or vice versa, for example, to push and pull thick graft within the tube 1420. FIGS. 37C and 37D are photographs corresponding to FIGS. 37A and 37B, respectively.

Delivering fluid through both ends of the tube 1420 can also facilitate even hydration of the graft. In bench testing, it was determined that a contiguous opening from one side of the tube 1420 to the other enhances the flow of air and fluid. It was noticed that with only one luer lock cap 1502*a* or 1502*b*, graft within the tube became over hydrated on the end of the tube 1420 adjacent the luer lock cap 1502*a* or 1502*b* and dry at the opposite end of the tube 1420.

Bench tests were also performed with a luer lock cap 1502*a* or 1502*b* on one end of a tube, such as tube 120 and tube 1420, and a cap 1516 with hole 1518 on the other end of the tube. Some types of grafts were hydrated effectively using a luer lock cap 1502*a* or 1502*b* on one end and a cap 1516 with a hole 1518 on the other end. The hole 1518 in the cap 1516 can allow venting and fluid to flow through.

In use, once bone graft is hydrated, the two caps 1502*a*, 1502*b*, and/or 1516 coupled to the tube can be removed, and the tube can be connected to a delivery system, such as delivery systems 100 and 1400, for extrusion into an orthopedic void or site such as hip, femur, spine, tibia, or any other suitable site.

Hydrating the graft in the tube can allow for a method of bone graft delivery in which the bone graft is never touched by anyone or anything external to the tube on the surgical field to reduce risk of cross-contamination. As more external sources come into contact with the bone graft, risk of contamination increases. Traditionally, bone graft is loaded in a tissue bank, sterilized, filled with fluid, and then implanted directly into the patient. Current methods require handling and mixing with latex gloves and/or other instruments before placing the bone graft in a reusable metal funnel for delivery.

In contrast, the tubes described herein, such as tubes 120 and 1420, can be coupled to a bone graft delivery device, such as bone graft delivery device 100 and 1440, after hydration to deliver bone graft to a delivery site or can be delivered using a plunger, rod, or pusher, such as plunger 112 and pusher 312, inserted directly into the tube. As described herein, the tube may be connected to an array of metallic or plastic tips, applicators, or adapters, such as tips 130, 1030*a*, and 1030*b*, applicators 850*a* and 850*b*, and adapter 800, a, to aid in delivery to tight spaces.

In bench testing, a variety of bone grafts were loaded into tubes and used to test rehydration as described above. The bone grafts included a variety of different consistencies and configurations including granular bone graft, wafers, fibers, and round particles. Several of the tested bone grafts bound tightly or balled up to create barrier or wall restricting fluid flow. It was found that for certain grafts, such as cortical fibers, a grinder or morselizer can be used to reduce the size of the fiber pieces.

An embodiment of a grinder 1520 is shown in FIG. 4O. The grinder 1520 includes a top 1524 and a bottom 1522. The top includes a plurality of grinding surfaces 1528. As shown in FIG. 4O, the grinding surfaces 1528 can be projections. The bottom includes a plurality of grinding surfaces 1526. As show in FIG. 4O, the grinding surfaces 1526 can be projections. The bottom 1522 can further include a plurality of openings 1530 for ground fibers can pass. In use, bone graft, such as cortical fibers can be placed in the bottom 1522 between the grinding surfaces 1526. The top 1524 can then be coupled to the bottom 1522 and rotated such that the grinding surfaces 1526 and 1528 grind the bone graft. After grinding to a smaller size, the fibers could be packed into a tube, such as tubes 120 and 1420, for example, using a funnel, such as funnel 104, and a plunger or pusher rod, such as plunger 112 and pushrod 312. In bench testing, after the tube was full to a desired volume, full rehydration of the fibers was possible.

For certain bone graft materials, rehydration can be important for proper function, which can maximize bone growth. Bone marrow aspirate, platelet Rich plasma, stem cells, blood, or other fluids carry essentials growth factors or stem cells that when attached to bone graft can help regenerate bone. If these fluids do not bind to the bone graft, the effectiveness of the graft may decline.

Figure 41A:
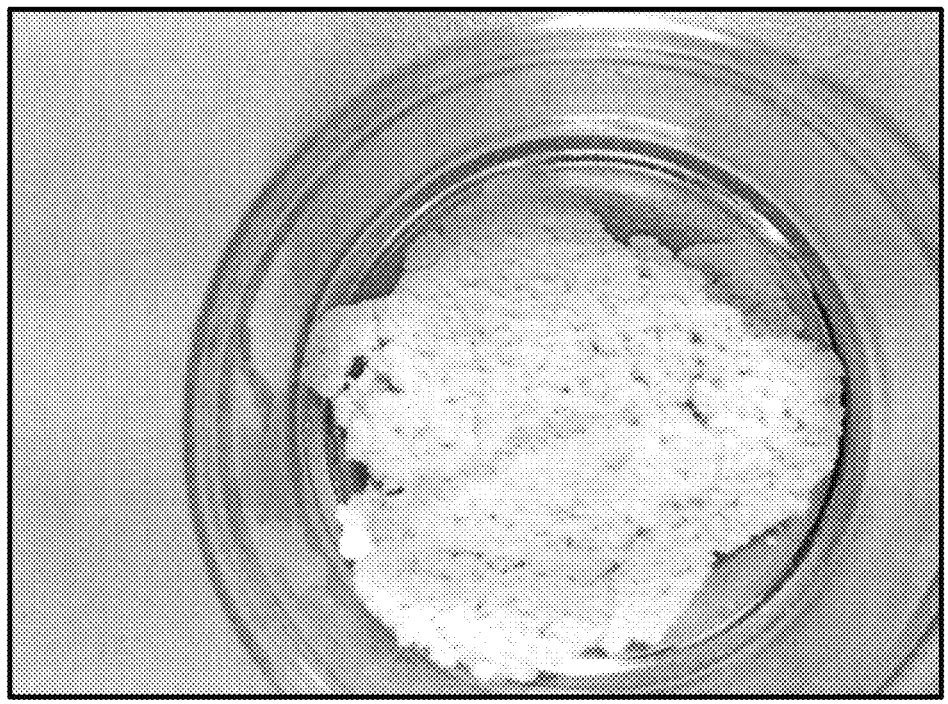
Figure 41B:
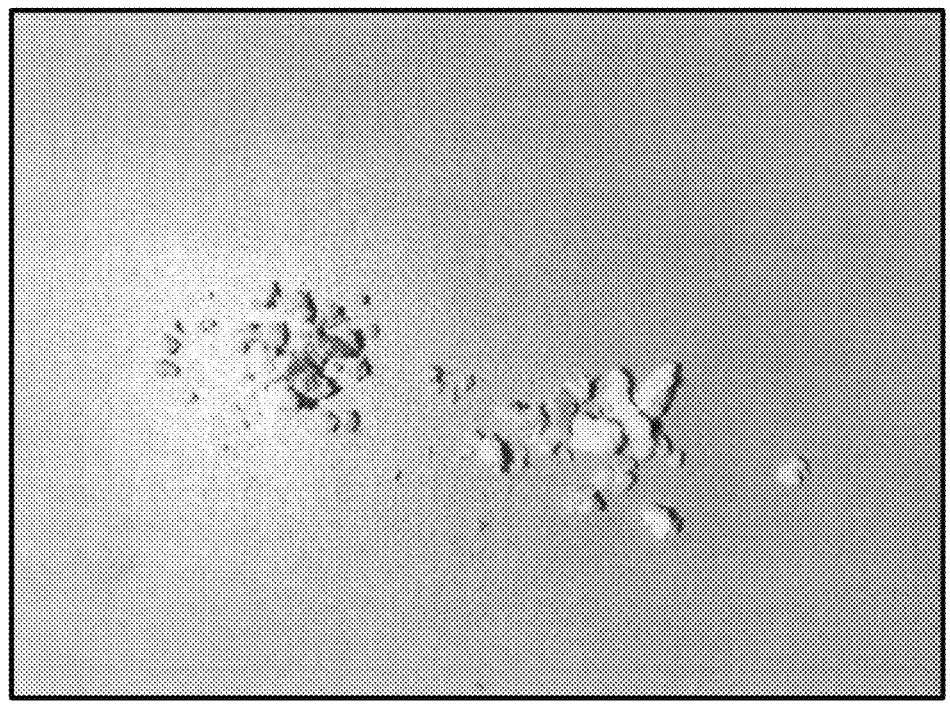

In some embodiments, cortical fibers are used as a bone graft material. Cortical fibers can be formed as wafers or sheets in lengths between 5 mm to 25 mm as shown in FIG. 41A. However, cortical fibers may come in many different lengths, widths and diameters depending on manufacturing techniques. As previously described, in certain embodiments, cortical fibers may be ground to fit in a tube and allow for porosity for fluid or blood to properly hydrate bone graft.

In bench testing, it was determined that cortical fibers having at least two of the three axis lengths (X, Y, or Z) within a range of 0.5 mm to 9 mm provided improved hydration. In certain embodiments, the third axis length may be unrestricted. The 0.5 mm to 9 mm range allows the fibers to be sufficiently small to fit within the graft tube and allow fluid porosity while being sufficiently large so that the fibers do not pack together to form a barrier to fluid flow. One of skill in the art would understand that sizes of the cortical fibers may vary depending on the size of bone graft delivery tube.

The elongate tube containing bone graft, such as tubes 120 and 1420, may be made of numerous types of material including medical grade polymer, metals, plastic, or any other suitable materials. The tubes described herein, such as tubes 120 and 1420, may come in a variety of lengths between 30 mm and 300 mm. The wall thickness of the tubes can be between 0.5 mm and 9 mm.

In certain embodiments, a metallic marker may be positioned at an end of the tube to help aid in visualization on imaging.

In certain embodiments, the tubes described herein, such as tubes 120 and 1420, can be provided in a sterile package with one or more luer lock caps 1502*a* and 1502*b*, one or more caps 1516, and/or one or more solid caps on each end. In some embodiments, the tubes can be provided with solid caps to prevent bone graft from falling out of the tube during packaging and/or transport. One or more of the solid caps can be replaced with luer lock caps 1502*a* and 1502*b* and/or caps 1516 prior to rehydration of the bone graft.

In certain embodiments, after hydration of the bone graft, the tube can be coupled to a bone graft delivery device as described herein, such as bone graft delivery devices 100 and 1400, to extrude bone graft from the tube.

Figure 42A:
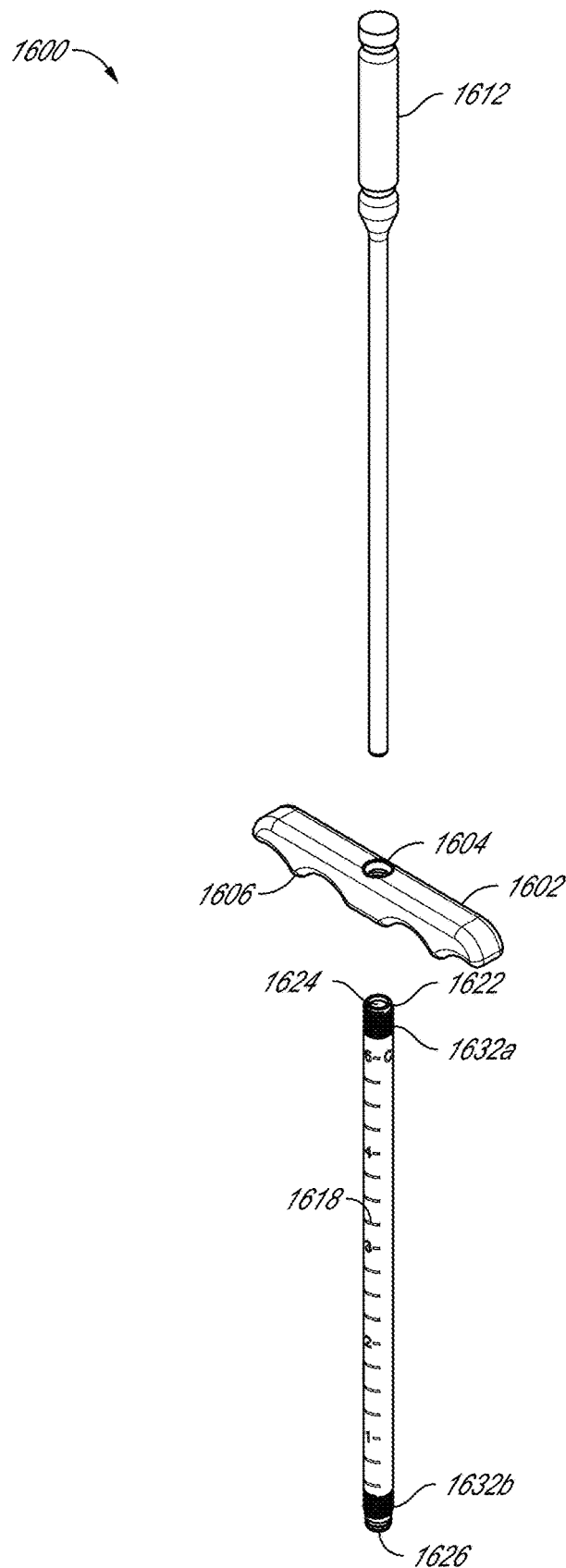
Figure 42B:
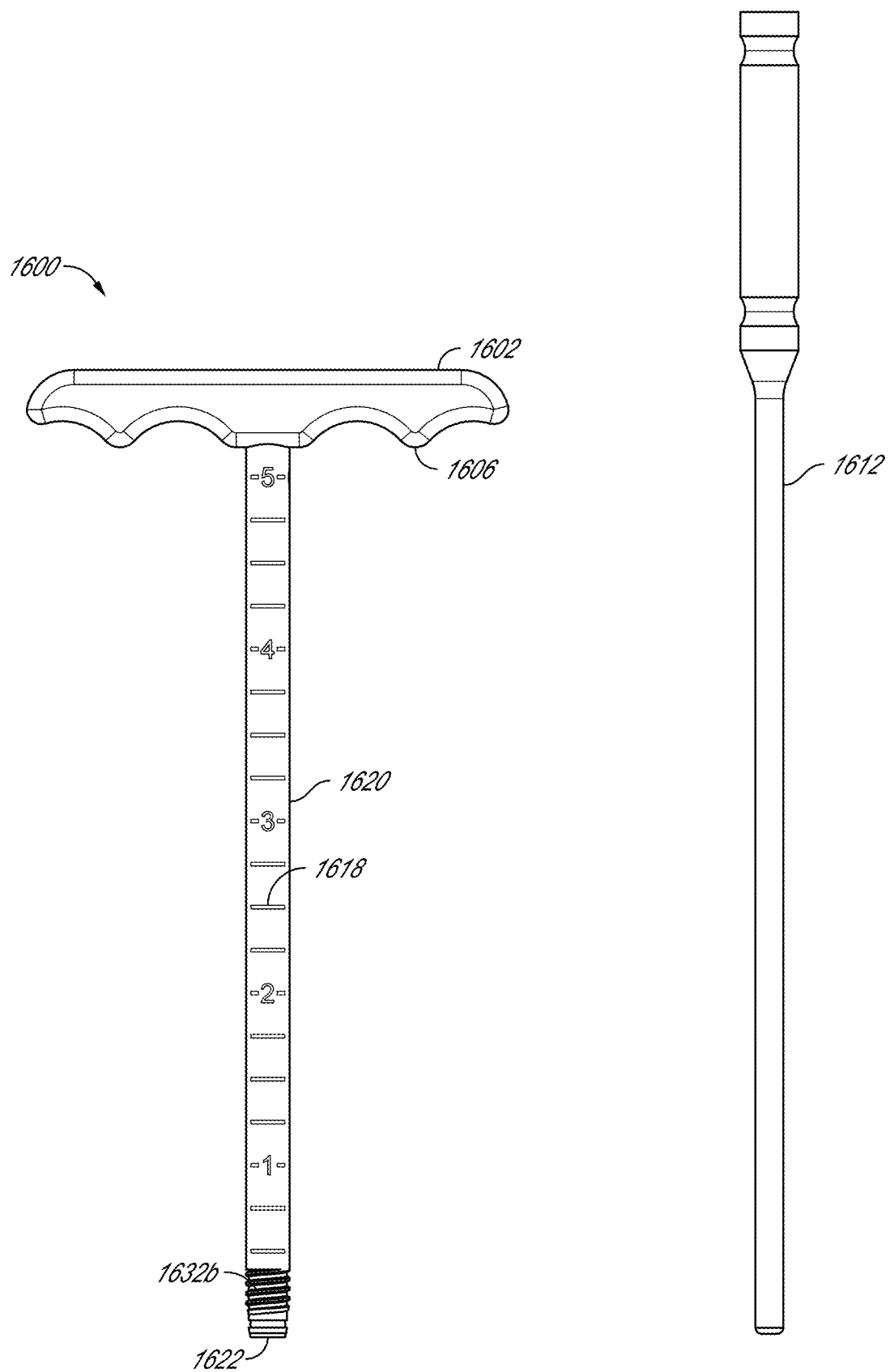
Figure 42C:
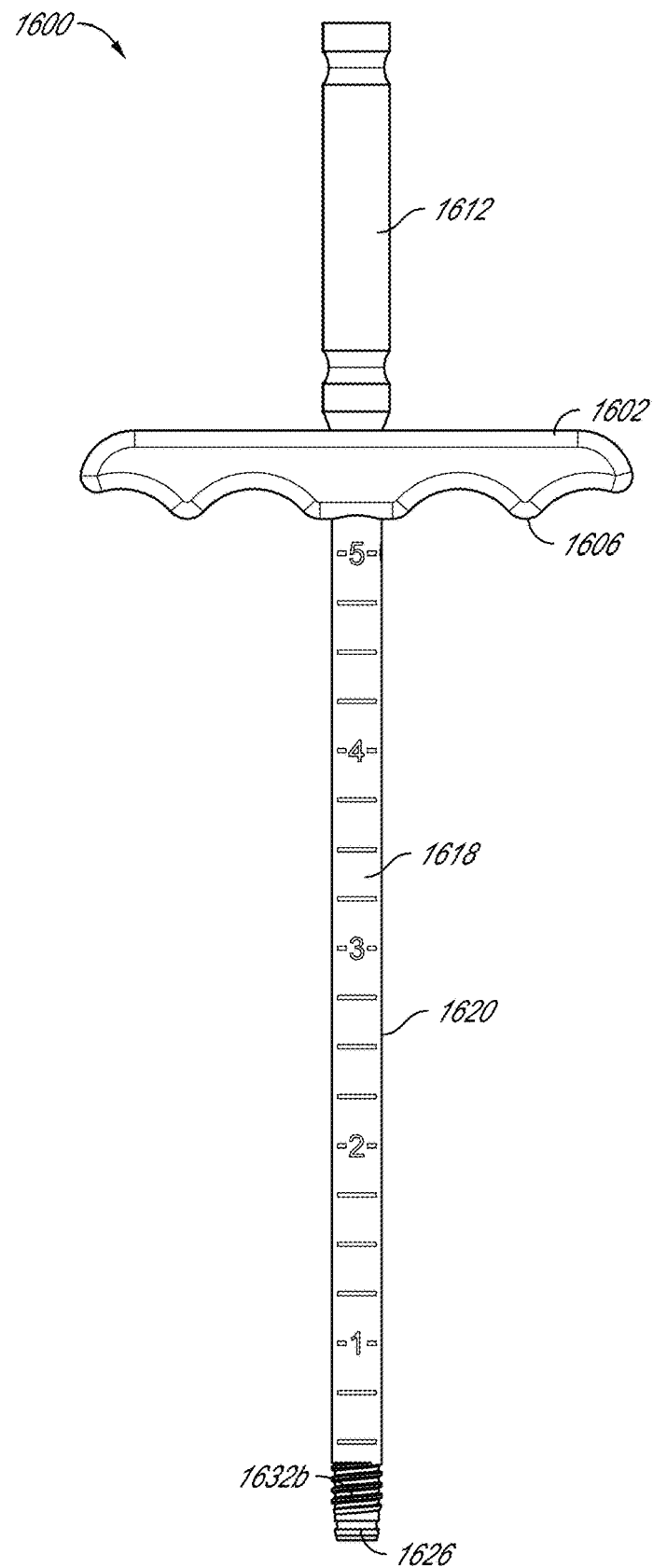

FIGS. 42A-C depict an embodiment of a bone graft delivery system 1600 having a tube 1620. The tube 1620 can include any of the same or similar features and/or functions of the tubes 120 and 1420 described herein. Further, in some embodiments, the tube 1620 can be used in any of the same procedures or with any of the same components as the tubes 120 and 1420. As shown in FIGS. 42A-C, the tube 1620 includes a first end 1622 and a second end 1626, each end including an opening. The tube 1620 can define a channel between the first end 1622 and the second end 1626. In certain embodiments, the ends 1622 and 1626 can include coupling features 1632*a* and 1632*b*. The coupling features 1632*a* and/or 1632*b* can be configured to couple to one or more bone graft delivery devices, such as devices 100 and 1400, caps or connectors, such as caps 124, 1502*a*, 1502*b*, and 1516 and connector 1110 or tips, adapters, or applicators, such as tips 130, 1030*a*, 1030*b*, applicators 850*a* and 850*b*, and adapter 800. In certain embodiments, the coupling features 1632*a* can be threads. In certain embodiments, the tube 1620 can couple to one or more bone raft delivery devices, caps, connectors, tips, adapters, or applicators by grooves, bumps, nubs, snap fit, or any other suitable coupling mechanism.

In certain embodiments, the bone graft delivery system 1600 can include a pushrod or plunger 1612. The plunger 1612 can have any of the same or similar features as the plunger 112 or the pushrod 312. In certain embodiments, the pushrod or plunger 1612 can be used as a bone graft delivery device. In certain embodiments, the pushrod or plunger 1612 can be inserted into the opening 1624 at the end 1622 of the tube 1620 to cause bone graft to flow out of the opening at the end 1626. In certain embodiments, the plunger 1612 can be inserted into the end 1626 of the tube 1620 to cause bone graft to flow out of the end 1622.

In certain embodiments, the bone graft delivery system can include a handle 1602. In certain embodiments, the handle 1602 can be a bone graft delivery device or part of a bone graft delivery device. The handle 1602 can be removably coupled to the elongate tubular body 1620. In certain embodiments, the handle 1602 can be configured to couple to one of the ends 1622 and 1626 of the elongate tubular body 120. For example, in certain embodiments, the handle 1602 can include complementary coupling features, such as complementary threads, configured to couple to the coupling features 1632*a* or 1632*b* of the tube 1620. In certain embodiments, the handle 1602 can couple to the tube 1612 by a threaded connection, snap fit connection, clip-on connection, wedge connection, and/or any other suitable connection mechanism. In certain embodiments, the handle 1602 and tube 1620 can be coupled to form a bone graft delivery device.

In certain embodiments, the handle 1602 can include a channel 1604 configured to align with the opening 1624 when the handle 1602 is coupled to the end 1622 or the end 1626, respectively. The channel 1604 can be configured to receive the pushrod or plunger 1612. In use the pushrod or plunger 1612 can be inserted through the channel 1604 and lumen of the elongate tubular body 1620 to cause the flow of bone graft material out of the elongate tubular body 1620. In certain embodiments, the plunger 1612, handle 1602 and elongate tubular body 1620 can form a bone graft delivery device.

In certain embodiments, the handle 1602 can be gripped for support and stability during use of the bone graft delivery system 1600. In certain embodiments, the handle 1602 can be manipulated by a user to position the tube 1620. In certain embodiments, the handle 202 can include one or more finger grips or other surface features 1606 to facilitate gripping by a user.

In some embodiments, the bone graft delivery system 1600 may be operated without the handle 1602. In certain embodiments, the pushrod 1612 may be used without the handle to extrude bone graft from the tube 1620, for example, in minimally invasive applications or for delivery to tight spaces. In certain embodiments, the pushrod 1612 and the elongate tubular body 1620 can act together as a bone graft delivery device.

In some embodiments, after hydration of the bone graft, the tube can be connected to an adapter, such as adapter 800, to connect to a spinal or orthopedic implant cage or screw for post-filling. In some embodiments, the adapter can include a sleeve that can mate with the elongate tube. In some embodiments, a tube can thread, snap, or otherwise attach to an adapter that may be designed to mate to a particular implant. In some embodiments, a delivery system, pusher rod or plunger as described herein, can extrude graft out of the tube and into the spinal or orthopedic implant. In some embodiments, the tube may be placed against the implant to post-fill using the flowable bone graft after implantation into the body.

In the orthopedic field, there are many shapes and sizes of implants that are used to aid in bone fusion. It is common in the field to pre-fill these implants with bone graft materials prior to implantation to improve the chance of fusion. Due to the variability between implants, it can be difficult to fill implants by hand.

In certain embodiments, implants can be manufactured using 3D printing. This manufacturing process allows for more complex designs, which can result in difficulty filling some regions of the implant with bone graft. In certain embodiments, filling devices can be used to apply pressure to cause bone graft to completely, nearly completely, or substantially fill the crevices of an implant.

FIGS. 46 and 47 depict an embodiment of a filling system 1800. The filling system 1800 includes a filling container 1840. The filling container 1840 can have a clamshell type design with a top section 1844 and a bottom section 1846 that pivot relative to one another to open and close the container. In some embodiments, the container 1840 can closed and secured via a latch 1847. In other embodiments, threads, pins, snap fits, or any other suitable coupling feature can be used to close the container 1840.

As shown in FIGS. 46 and 47, the container 1840 can include a shaft 1842 configured to couple to a graft delivery device to allow for the delivery of bone graft into the container 1840. As shown in FIG. 46, in certain embodiments, the container 1840 can couple to a tube 1820 that can be used to deliver bone graft material into the container 1840. The tube 1820 can have any of the same or similar functions and features as the tubes 120, 1420, and 1620 described herein. In certain embodiments, the container 1840 can couple to a loading device such as loading devices 600, 700, and 900 or delivery device such as delivery devices 100 and 1400 as described herein.

In use, a delivery device, such as the tube 1820, can be used to expel graft into the container 1840 through the shaft 1842 into the container 1840 to create enough pressure to fill an implant with bone graft. In certain embodiments, a threaded plunger, a plunger with a ratchet, hydraulics, or any method can be employed in conjunction with the tube 1820 or another delivery or loading device to create sufficient force to pressurize the container 1840 to fill an implant within. An embodiment of an implant 1850 that can be filled using the filling system 1800 is shown FIG. 47.

In certain embodiments, the tube 1820 or another delivery or loading device can couple to the shaft 1842 via a threaded connection, press-fit connection, snap fit connection, clip-on connection, wedge connection, and/or any other suitable connection mechanism.

FIG. 48 depicts an embodiment of a filling system 1900 for filing an implant 1850. The filling system 1900 can include a container 1910 having a bottom 1912 and defining volume for receiving the implant 1950 and bone graft material. In certain embodiments, an arm 1904 can be rigidly coupled to or integrally formed with the container 1910.

The filling system 1900 can further include an arm 1902 movably coupled to the container 1910. For example, in some embodiments, the arm 1902 can be hingedly connected to the container 1910 by a hinge 1906. The arm 1902 can be rigidly coupled to or integrally formed with a press 1914 having a pressing surface 1908. The press 1914 can be shaped, sized, positioned, and/or otherwise configured to align with and be received within the container 1910.

In use, the implant 1850 and bone graft material can be placed within the container 1910 and the arms 1902 and 1904 can be manipulated so that the press 1914 enters the chamber 1910 and the pressing surface 1908 exerts a force in the direction of the bottom surface 1912 of the container 1910 to create sufficient pressure between the pressing surface 1908 and the bottom surface 1912 of the container 1910 to cause the bone graft to fill the implant.

FIGS. 49A-D depict an embodiment of a filling container 2240. The filling container 2240 includes a top section 2244 and a bottom section 2246 having a chamber 2248. As shown in FIGS. 49A-D, the bottom section 2246 can include one or more posts 2249, and the top section 2244 can include one or more hollow shafts 2247 configured to align with and receive the posts 2249. In some embodiments, top section 2244 and the bottom section 2246 can include one or more coupling features configured to releasably secure the top section 2244 and the bottom section 2246 together. For example, in some embodiments, the posts 2249 and shafts 2247 can include one or more coupling features configured to releasably secure the top section 2244 and the bottom section 2246 together. In some embodiments, latches, threads, pins, snap fits, or any other suitable feature can be used to releasably secure the top section 2244 and the bottom section 2246 together. As shown in FIGS. 49A-D, in some embodiments, the posts 2249 can include one or more surface features 2243 configured to couple with complementary surface features of the shafts 2247 to releasably secure the top section 2244 and the bottom section 2246 together.

In some embodiments, the container 2240 can include a channel 2242 configured to facilitate delivery of bone graft into the chamber 2248. In certain embodiments, the channel 2242 can be configured to receive bone graft material from a tube, such as tubes 120, 1420, and 1620, a loading device, such as loading devices 600, 700, and 900, or a delivery device, such as delivery devices 100 and 1400. In some embodiments, the channel 2242 can be configured to couple to a tube, a loading device, or a bone graft delivery device for delivery of bone graft material into the chamber 2248. In some embodiments, the channel 2242 can include one or more coupling features 2243 to couple to a tube, a loading device, or a bone graft delivery device. As shown in FIG. 49A, in certain embodiments, the coupling features 2243 can be threads. In other embodiments, the coupling features 2243 can include pins, grooves, bumps, nubs, snap fits, or any other suitable coupling mechanism.

In use, a tube, loading device, or delivery device, can be used to expel graft into the container 2240 through the channel 2242 to create enough pressure to fill an implant within the chamber 2248 with bone graft. In certain embodiments, a threaded plunger, a plunger with a ratchet, hydraulics, or any method can be employed in conjunction with a tube or another delivery device or loading device to create sufficient force to pressurize the container 2240 to fill an implant within. In certain embodiments, the container 2240 can be used to fill an implant such as implant 1850.

FIGS. 50A-D depict an embodiment of an adapter 2300 that can be used to pre-fill an implant before implantation or post-fill an implant after implantation. As shown in FIGS. 50A-B, the adapter 2300 can be used to fill an implant 2350. The adapter 2300 can have any of the same or similar features as the adapter 800.

As shown in FIGS. 50A-B, the adapter 2300 can include a proximal end 2302 shaped, sized, or otherwise configured to receive bone graft from a tube, such as tubes 120, 1420, and 1620, a loading device, such as loading devices 600, 700, and 900, or a delivery device, such as delivery devices 100 and 1400, and a distal end 2304 sized, shaped, or otherwise configured to deliver bone graft to the implant 2350. In some embodiments, the proximal end 2302 can be shaped, sized, or otherwise configured to couple to the tube, loading device, or delivery device. In some embodiments, the distal end is sized, shaped, or otherwise configured to couple to the implant 2350. The adapter 2300 also includes one or more coupling features 2308 for coupling to a bone graft delivery device, tube, or loading device. As shown in FIG. 50B, the coupling features 2308 can be threads configured to couple to complimentary threads of a bone graft delivery device. In other embodiments, the coupling features 2308 can be grooves, bumps, nubs, snap fit, or any other suitable coupling features.

The adapter 2300 can include a tapered region 2306 having one or more ramps or tapers between the proximal end 2302 and the distal end 2304 such that the adapter 2300 narrows between the proximal end 2302 and the distal end 2304.

FIG. 50C depicts a cross-section of the adapter 2300 and implant 2350. FIG. 50D depicts an enlarged view showing a section of the cross-section of the adapter 2300 and implant 2350. As shown in FIGS. 50C and 50D, the implant 2350 can include a channel 2352. The channel 2352 can include threads or other coupling features 2354. The threads 2354 can be configured to couple to a tube, delivery device, or other device used to implant the implant 2350 within a surgical location. A portion 2307 of the adapter 2300 can be sized, shaped, or otherwise configured to extend through the channel 2352 so that the distal end 2304 is positioned within the implant 2350 beyond the threads 2354 of the channel 2352. In some embodiments, it is preferable to position the distal end 2304 within the implant 2305 beyond the threads 2354 to prevent bone graft from being exposed to and binding to the threads 2354 so as to maintain the flowability of the bone graft into the body of the implant 2305. In some embodiments, the section 2307 of the adapter 2300 can include complementary threads configured to couple to the threads 2354 of the channel 2352. In other embodiments, the channel 2352 and section 2307 of the adapter 2300 can be sized, shaped, or otherwise configured to provide an amount of resistance to removal of the section 2307 of the adapter 2300 but also allow for insertion of the distal end 2304 within the interior of the implant 2305.

In certain embodiments, a bone graft can become lodged in a delivery tube, such as tubes 120, 1420, and 1620. In such embodiments, a plunger or pushrod, such as plungers 112 and 1612 and pushrod 312, can be advanced through the body of a delivery device and/or lumen of a delivery tube to dislodge the graft. In some embodiments, the plunger or pushrod can be used in combination with a mallet to dislodge the graft.

FIGS. 51A and 51B depict a pushrod or plunger 2012 positioned within an embodiment of the bone graft delivery device 100 and a mallet 2014. The plunger 2012 can have any of the same or similar features as the plungers 112 and 1612 or the pushrod 2012. In certain embodiments, the plunger 2012 can be made of metal, polymer, or any other material suitable for malleting. In certain embodiments, the mallet 2014 can be used to cause the plunger 2012 to advance within the handle 102 and tube 120, or any other delivery device and tube described herein, such as the tubes 1420 and 1620 and the delivery device 1400. The mallet 2014 can impart a force to a proximal end 2016 of the plunger 2012 to cause a distal end 2018 of the plunger 2012 to impart a suitable force on the lodged bone graft material to cause the lodged bone graft material to dislodge or break up and advance through the body 102 and/or tube 120. In some embodiments, the plunger 2012 may have a knob or other malleting surface 2020 on the proximal end 2016. In some embodiments, the malleting surface 2020 can be wider and/or have a greater circumference than the rest of the plunger 2012 to provide greater surface area for malleting.

In some embodiments, the plunger 2012 can include teeth or notches similar to the plunger 112 to allow for advancement of the plunger 2012 using the trigger 110 after the bone graft is dislodged using the mallet. In other embodiments, the plunger 2012 does not include teeth or notches. In some embodiments, the plunger 2012 may have a smooth exterior. In some embodiments, the plunger 2012 may have a uniform diameter from the proximal end 2016 to the distal end 2020. In other embodiments, the plunger 2012 may be tapered. In some embodiments, the plunger 2012 may be of a sufficient length so that the distal end 2020 of the pushrod can be advanced to the distal end of the tube 120 to advance bone graft material out of the tube 120.

In some embodiments, a bone graft delivery system can include a plurality of plungers and/or pushrods. For example, in some embodiments, a bone graft delivery system can include one or more plungers suitable for advancing bone graft material through a delivery device and/or tube and one or more plungers suitable for use with a mallet, such as mallet 2014. As an example, in some embodiments, a user may begin delivering graft with a first plunger that may not be suitable for use with the mallet 2014, and then remove and replace the first plunger with a second plunger suitable for use with the mallet 2014, such as the plunger 2012, if bone graft material becomes lodged within a delivery device and/or tube.

In some embodiments, a delivery system may include only a pushrod or plunger, such as plunger 2012, suitable for use with a mallet, such as mallet 2014. For example, a user may use only a pushrod or plunger suitable for use with a mallet if the user utilizes graft that tends to bind on a regular basis.

In some embodiments, the delivery systems described herein can be used to post-fill screws, such as sacroiliac screws used in sacroiliac joint fusion procedures. Sacroiliac joint fusion can be performed to stabilize the joint with the implant while the graft fuses the sacrum and ilium to prevent movement over time.

FIG. 52 depicts an embodiment of a distal end of the tube 120 of the delivery device 100 coupled to a screw 2135. The screw 2135 can be cannulated and can include one or more fenestrations or holes 2137 for dispensing bone graft material. In some embodiments, the fenestrations or holes 2317 can be positioned along side walls of the screw 2135. The fenestrations or holes 2317 can be single fenestrations or holes or multiple window fenestrations or holes.

In some embodiments, the screw 2135 can be a sacroiliac joint screw. In some embodiments, the screw 2135 can be used for facet fusion, as a longbone screw, or as a screw in any other orthopedic procedure that requires post-filling with bone graft material after implantation. In some embodiments, the screw 2135 can be used to treat humeral fractions, tibial fractures, or any other bone fracture.

In some embodiments, the screw 2135 can include one or more coupling features, such as internal threads, configured to couple to the distal end of the tube 120. In certain embodiments, a separate attachment member may be used to mate the tube 120 and the screw 2135. In some embodiments, the screw 2135 can be used with any of the tubes described herein, such as tubes 1420 and 1620.

In some embodiments, the screw 2135 can be generally triangular in shape and/or cross-section or have any other shape and/or size suitable for post-filling with bone graft material after implantation. In some embodiments, the screw 2135 can have external threads 2136. In other embodiments, the screw 2135 may not have external threads.

In certain embodiments, the delivery systems described herein can be used to post-fill an expandable interspinous implant. In certain embodiments, the implant can be placed in between the interspinous process and expanded. Graft can be used to fill the void remaining after expansion of the implant. In some embodiments, the delivery systems described herein can mate to the interspinous implant directly or via an attachment member. In some embodiments, the interspinous implant may be non-expandable and post-filled with the delivery system. In some embodiments, the interspinous implant can be filled so that graft contact is maximized between the adjacent spinous processes.

In some embodiments, one or more handles 102, 1402, and/or 1602, of a bone graft delivery device can be provided in a system or kit with one or more tips 130, tips 1030*a*, tips 1030*b*, rasps 1430*a*-*l*, rasps 1730, tubes 120, tubes 1420, tubes 1620, tubes 1820 and/or other instruments. The kit can allow a surgeon or other medical personnel to select an appropriate tube or and/or tip for the particular patient, procedure, and/or treatment location. As described above, certain tip configurations can be suited for certain target locations. For some procedures, the surgeon may select a curved or straight tube to help improve access to the particular target location and/or may select from two or more tubes having different lengths. In some embodiments, the kit can include an endoscopic camera. In some embodiments, the kit can include one or more separate rasping instruments. In some embodiments, the kit can include one or more bone graft loading devices, for example, one or more of the bone graft loading devices shown in FIGS. 17A-19F. The kit can include various other instruments that might be used during an orthopedic procedure. For example, the kit may include one or more dilators, such as guide 1450, one or more retractors, light sources, one of more fasteners, such as titanium facet screws or facet bone dowels, one or more guidewires, one or more mallets, such as mallet 2014. In some embodiments, titanium facet screws or bone dowels may be used in a posterior lateral fusion procedure. In some embodiments, the kit may include one or more cortical bone implants, one or more pedicle screws, one or more spinous process fixation devices, and/or one or more sacroiliac fixation devices, such as sacroiliac joint screw 2135. In some embodiments, the kit may include one or more caps or connectors, such as caps 124, 1502*a*, 1502*b*, 1516, and connector 1100. In some embodiments, the kit can include one or more plungers or pushrods, such as plungers 112, 1612, 2012, and pushrod 312. In some embodiments, the kit can include one or more interbody devices or implants, such as interbody devices 400, 401, and 450 and implants 1850, 1950, and 2350. In some embodiments, the kit can include one or more implant filling systems or containers, such as implant filling system 1900 and implant filling containers 1840 and 2240. In some embodiments, the kit can include one or more implant adapters for implant filling, such as adapter 800 and adapter 2300.

Figure 13:
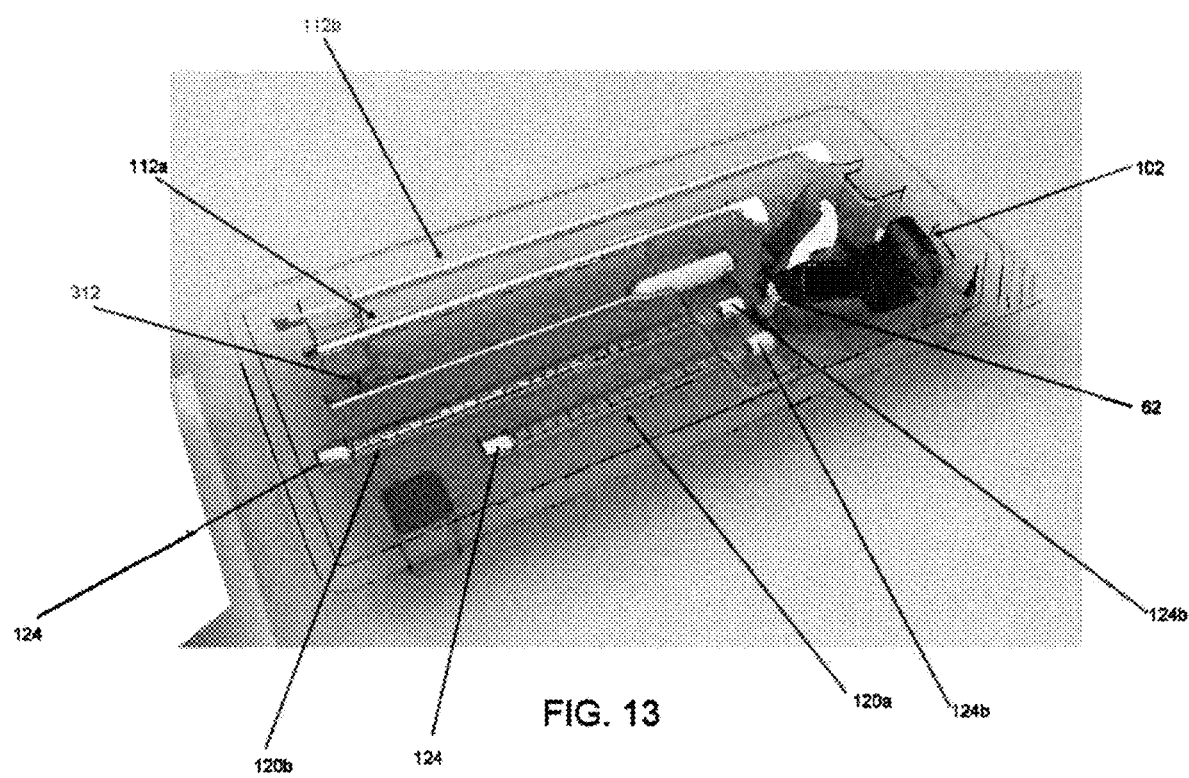
FIG. 13 illustrates an example embodiment of a bone graft delivery system kit.

FIG. 13 illustrates an example embodiment of a kit that can be provided to a surgeon in a tray. In the illustrated embodiment, the kit includes a handle 102, a relatively shorter tube 120*a* and corresponding relatively shorter plunger 112*a*, a relatively longer tube 120*b* and corresponding relatively longer plunger 112*b*, and a pusher rod 312. The kit can include more or fewer tubes 120 and/or plungers 112. As shown, each tube 120*a*, 120*b* includes a tube end cap 124 on its distal end. Each tube also includes a proximal end cap 124*b* on its proximal end for shipping and storage. For use, the surgeon or other medical professional selects the desired tube 120*a*, 120*b*, removes the proximal end cap 124*b*, and couples the proximal end of the selected tube 120*a*, 120*b* to the base 62 of the handle 102. In the case of a handle 102 having a funnel 104, the surgeon or other medical professional can then proceed to load bone graft into the handle 102, use the pusher rod 312 to urge the bone graft material into the tube 120*a*, 120*b*, then remove the pusher rod 312 and select the appropriate plunger 112*a*, 112*b* for use in delivering the bone graft material using the bone graft delivery device 100. The pusher rod 312 can be inserted into the handle 102, into the tube 120, and/or into a bone graft loading device such as a funnel in connection with the tube 120 to urge bone graft material into the tube 120. In some embodiments, one or more of the tubes 120*a*, 120*b* and/or handle 102 can be provided pre-loaded with bone graft material.

In some embodiments, a kit includes a handle 102, one or more prefilled tubes 120, and one or more plungers 112. For example, the kit can include one or more tubes 120 prefilled with a synthetic bone graft material. In some embodiments, the synthetic bone graft material prefilled in the tube(s) 120 has a composition of about 40-95% calcium phosphate and about 5-60% collagen. As another example, the kit can include one or more tubes 120 prefilled with a demineralized bone matrix material. In some embodiments, the kit can include one or more tubes 120 prefilled with cortical fibers or demineralized cortical fibers. Any prefilled tubes can be sealed in the kit or other package for shipment and storage to preserve the integrity of the bone graft material. In some embodiments, a kit can be provided including a handle 102, one or more tubes 120, one or more plungers 112, and one or more bone graft loading devices, such as loading devices 600, 700, 900. The loading device 600, 700, 900 can be used to load the tube(s) 120 with any appropriate bone graft material the surgeon desires or requires. In some embodiments, the kit can further include one or more types of bone graft material.

In some embodiments, a kit includes one or more elongate tubes 120, 1420, and/or 1620, one or more tips, such as tip 130, tip 1030a, tip 1030b, rasps 1430a-l, and/or rasp 1730, and one or more guides 1450. In some embodiments, the kit can include one or more retractors, light sources, one of more fasteners, such as titanium facet screws of facet bone dowels, and/or one or more guidewires. As described herein, at least one of the one or more elongated tubes can be preloaded with a bone graft material, such as, for example, a synthetic bone graft material, demineralized bone matrix, cortical fibers, demineralized cortical fibers, a cellular bone graft material, or an allogeneic bone graft material. In some embodiments, the tubes can be preloaded with DBM putty. Any prefilled tubes can be sealed in the kit or other package for shipment and storage to preserve the integrity of the bone graft material.

Additional embodiments of tips that can be used with or in a bone graft delivery system or kit are provided in FIGS. 25A-26B. FIGS. 25A-25D depict an embodiment of a tip 1200 that can be provided or used with or in a bone graft delivery system or kit. FIGS. 25E-F depict an embodiment of a tip 1250 that can be provided or used with or in a bone graft delivery system or kit. FIGS. 26A-D depict an embodiment of a tip 1300 that can be provided or used with or in a bone graft delivery system or kit. FIGS. 26E-F depict an embodiment of a tip 1350 that can be provided or used with or in a bone graft delivery system or kit.

The tip 1200 includes an opening 1208 for delivering bone graft material. The tip 1200 narrows from a proximal end 1202 configured to couple with a tube of a bone graft delivery device to a distal end 1204. The tip 1200 include a tapered or ramped section 1206 between the proximal end 1202 and distal end 1204. The tapered or ramped section 1206 can have one or more tapers or ramps. The distal end 1204 can be sized and/or shaped to enter narrow bone voids or disc spaces. The tapered or ramped shape of the tip 1200 can allow for distraction of tissue surrounding the tip 1200 by advancing the tip further into the bone void or disc space. The tip 1200 can be advanced by application of a force to a bone graft delivery device coupled to the tip, for example, by malleting a portion of the bone graft delivery device.

The tip 1200 includes a pair of prongs 1210 positioned at a distal end of the tip 1200. In certain embodiments, the prongs 1210 can facilitate distraction in a disc space or bone void that is more narrow than a desired cross-section of a lumen of the tip 1200.

The tip 1250 narrows from a proximal end 1252 configured to couple with a tube of a bone graft delivery device to a distal end 1254. The tip 1200 include a tapered or ramped section 1256 between the proximal end 1252 and distal end 1254. The tapered or ramped section 1256 can have one or more tapers or ramps. The distal end 1254 can be sized and/or shaped to enter narrow bone voids or disc spaces. The tapered or ramped shape of the tip 1250 can allow for distraction of tissue surrounding the tip 1250 by advancing the tip further into the bone void or disc space. The tip 1250 can be advanced by application of a force to a bone graft delivery device coupled to the tip, for example, by malleting a portion of the bone graft delivery device.

The tip 1250 includes a pair of prongs 1260 positioned at a distal end of the tip 1250. In certain embodiments, the prongs 1260 can facilitate distraction in a disc space or bone void that is more narrow than a desired cross-section of a lumen of the tip 1250.

The tip 1300 includes an opening 1308 for delivering bone graft material. The tip 1300 narrows from a proximal end 1302 configured to couple with a tube of a bone graft delivery device to a distal end 1304. The tip 1300 include a tapered or ramped section 1306 between the proximal end 1302 and distal end 1304. The tapered or ramped section 1306 can have one or more tapers or ramps. The distal end 1304 can be sized and/or shaped to enter narrow bone voids or disc spaces. The tapered or ramped shape of the tip 1300 can allow for distraction of tissue surrounding the tip 1300 by advancing the tip further into the bone void or disc space. The tip 1300 can be advanced by application of a force to a bone graft delivery device coupled to the tip, for example, by malleting a portion of the bone graft delivery device.

The tip 1350 narrows from a proximal end 1352 configured to couple with a tube of a bone graft delivery device to a distal end 1354. The tip 1350 include a tapered or ramped section 1356 between the proximal end 1302 and distal end 1304. The tapered or ramped section 1356 can have one or more tapers or ramps. The tip 1350 further includes a tapered section 1357 at the distal end 1354 such that the tip 1350 is narrowest at the distal end 1354. The distal end 1354 can be sized and/or shaped to enter narrow bone voids or disc spaces. The tapered or ramped shape of the tip 1350 can allow for distraction of tissue surrounding the tip 1350 by advancing the tip further into the bone void or disc space. The tip 1350 can be advanced by application of a force to a bone graft delivery device coupled to the tip, for example, by malleting a portion of the bone graft delivery device.

The tips 1200, 1250, 1300, and 1350 can include any of the same or similar features and functions as the tips 130, 1030a, and 1030b as described herein. The tips 1200, 1250, 1300, and 1350 can be metallic, plastic polymer, ceramic, or any other suitable material. In some embodiments the tips 1200, 1250, 1300, and 1350 can be formed of medical grade plastic. In some embodiments, the tips 1200, 1250, 1300 and 1350 can be formed by 3D printing or CNC machining. Any of the tips 1200, 1250, 1300 and 1350 can be formed of 3D printed metal or CNC machined metal. In some embodiments, the 3D printing metal facilitates the formation of smooth curvature that would not be achievable through other methods.

In some embodiments, a diameter at the distal end of the tip 1200, the tip 1250, the tip 1300, or the tip 1350 can be between 3 mm to 5 mm or about 3 mm to 5 mm. In some embodiments, a diameter at the distal end of the tip 1200 or tip 1300 can be 6 mm or about 6 mm. In some embodiments, a diameter at the proximal end of the tip 1200 or tip 1300 can be between 8 mm to 9 mm or about 8 mm to 9 mm.

In one embodiment, the devices described herein, such as the device 100 and device 1400, may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, lamina, or facet joints, through one of these small incisions. The devices described herein can be sized to be delivered through a minimally invasive opening made in the patient's skin (e.g., through a skin incision of 4 cm or less), and configured so that the tip can be positioned adjacent a pedicle screw or other desired location. The optional curvature of the tubes described herein, such as tubes 120, 1420, and 1620, can facilitate positioning of the tips, such as tips 130, 1030a, 1030b, rasps, such as rasps 1430a-l and 1730, or applicators, such as applicators 850a and 850b, at desired spinal locations and allows, for example, insertion of the device through an incision over one vertebra, and positioning of the tip at an adjacent vertebra. Alternatively, the device can be delivered through any desired opening made in the patient's skin (e.g., minimally invasive, mini-open, or open). If needed, the optional jagged edges or other decortication surfaces on the device can be used to decorticate desired bone locations, causing bleeding of the bone and creating a surface that promotes bone fusion. In some embodiments, a trigger, such as trigger 110, or other actuation mechanism can then be actuated to deliver bone graft material through the tube lumen and openings in the tip to promote fusion of the bone.

In some embodiments, an endoscope or camera can be inserted through the tubes described herein, such as tubes 120, 1420, and 1620, and used to help guide the physician or other medical professional to the target location and/or to allow the physician to evaluate the area. If the physician wants to decorticate the bone, the physician can remove the endoscope or camera, insert the shaft 150 having the burr 152 or another suitable rasping instrument, and decorticate the target area. In some embodiments, the tube can be inserted into the patient with the shaft 150 or other rasping instrument already inserted or with a rasping tip 130 attached and the physician can use an endoscope, camera, navigation system, or the like placed alongside, adjacent, or proximal the tube to navigate to and/or evaluate the target area. Once the target location is ready, the physician can remove the shaft 150 or other rasping instrument if present and deliver the bone graft material, for example, using the trigger 110.

Although use of the devices has been described with respect to an example spinal procedure, the devices described herein can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible. For example, a bone graft delivery device can include a handle and tube and may or may not include a distal rasping tip. The tube can be integrally formed with the handle and/or a distal rasping tip and/or any or all of the components can have a modular configuration such that various tubes and/or distal tips can be selected and exchanged as desired by the surgeon or other user. A bone graft delivery device can have a curved or straight tube. A distal tip can have any suitable configuration, including bullet-shaped, flat, conical, or any other configuration. A bone graft delivery device can be configured to received and/or supplied with various endoscopes, other cameras or imaging equipment, and/or guide brackets for imaging equipment. A bone graft delivery device can include any suitable ratcheting mechanism to advance bone graft material through the device for delivery and may include a plunger and/or pusher rod. Certain embodiments of the invention are encompassed in the claim set listed below.

What is claimed is:

1. A method for bone graft delivery comprising:
   making an incision;
   inserting an intrafacet implant through the incision, the intrafacet implant comprising:
     a body extending from a proximal end to a distal end of the intrafacet implant; and
     a plurality of threads extending from the body from the proximal end to the distal end of the intrafacet implant;
   advancing the intrafacet implant through the incision to a facet joint;
   implanting the intrafacet implant within the facet joint;
   inserting a rasp through the incision;
   advancing the rasp to a transverse process;
   rasping the transverse process using the rasp; and
   delivering bone graft material to the transverse process.

2. The method of claim 1, wherein the transverse process is a first transverse process, wherein advancing the intrafacet implant through the incision to the facet joint comprises advancing the intrafacet implant using an inserter coupled to the intrafacet implant, the method further comprising delivering bone graft material to a channel within the intrafacet implant through a lumen of the inserter.

3. The method of claim 1, further comprising delivering bone graft material to the facet joint.

4. The method of claim 1, further comprising rasping the facet joint using the rasp.

5. The method of claim 1, wherein the intrafacet implant comprises a channel configured to receive bone graft material and a plurality of openings between the proximal end and the distal end of the intrafacet implant, the plurality of openings being in communication with the channel.

6. The method of claim 1, wherein the body of the implant comprises a uniform cross-section between the proximal end and the distal end of the intrafacet implant.

7. The method of claim 1, wherein a diameter of the proximal end of the intrafacet implant does not exceed a diameter of the distal end of the intrafacet implant.

8. A method for bone graft delivery comprising:
   making an incision;
   inserting an intrafacet implant through the incision,
   advancing the intrafacet implant through the incision to a facet joint;
   implanting the intrafacet implant within the facet joint;
   inserting a rasp through the incision, the rasp comprising a removable rasping surface;
   advancing the rasp to a facet;
   rasping the facet using the rasp; and
   delivering bone graft material to the facet.

9. The method of claim 8, wherein the intrafacet implant comprises:
   a body extending from a proximal end to a distal end of the intrafacet implant; and
   a plurality of threads extending from the body from the proximal end to the distal end of the intrafacet implant.

10. The method of claim 9, wherein the body of the implant comprises a uniform cross-section between the proximal end and the distal end of the intrafacet implant.

11. The method of claim 8, wherein the rasp comprises an elongate body extending between a proximal end and a distal end, the elongate body comprising a curved portion.

12. The method of claim 11, wherein the removable rasping surface is positioned on the curved portion of the elongate body.

13. The method of claim 11, wherein the elongate body comprises a straight portion extending between the proximal end and the curved portion, wherein the curved portion extends laterally relative to the straight portion beyond a diameter of the straight portion.

14. The method of claim 8, wherein the rasp comprises a distal tip, the method comprising dissecting tissue using the distal tip.

* * * * *